(12) United States Patent
Hasskarl et al.

(10) Patent No.: US 12,263,190 B2
(45) Date of Patent: Apr. 1, 2025

(54) METHODS AND COMBINATIONS FOR TREATMENT AND T CELL MODULATION

(71) Applicant: Juno Therapeutics, Inc., Seattle, WA (US)

(72) Inventors: Jens Hasskarl, Boudry (CH); Stanley R. Frankel, Summit, NJ (US); Michael Ports, Seattle, WA (US); Michael Pourdehnad, Summit, NJ (US); Heidi Jessup, Seattle, WA (US); Yue Jiang, Seattle, WA (US); Jim Shi Xiang Qin, Seattle, WA (US); Neha Soni, Seattle, WA (US); Melissa Works, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 925 days.

(21) Appl. No.: 17/292,363

(22) PCT Filed: Nov. 7, 2019

(86) PCT No.: PCT/US2019/060367
§ 371 (c)(1),
(2) Date: May 7, 2021

(87) PCT Pub. No.: WO2020/097403
PCT Pub. Date: May 14, 2020

(65) Prior Publication Data
US 2022/0008477 A1 Jan. 13, 2022

Related U.S. Application Data

(60) Provisional application No. 62/826,928, filed on Mar. 29, 2019, provisional application No. 62/757,755, filed on Nov. 8, 2018.

(51) Int. Cl.
| | |
|---|---|
| *A61K 35/28* | (2015.01) |
| *A61K 39/00* | (2006.01) |
| *A61P 35/02* | (2006.01) |
| *A61P 43/00* | (2006.01) |
| *C07K 16/28* | (2006.01) |
| *C12N 5/0783* | (2010.01) |

(52) U.S. Cl.
CPC .......... *A61K 35/28* (2013.01); *A61K 39/4611* (2023.05); *A61K 39/4631* (2023.05); *A61K 39/464412* (2023.05); *A61K 39/464417* (2023.05); *A61P 35/02* (2018.01); *A61P 43/00* (2018.01); *C07K 16/2809* (2013.01); *C07K 16/2866* (2013.01); *C07K 16/2896* (2013.01); *C12N 5/0636* (2013.01); *A61K 2239/31* (2023.05); *A61K 2239/38* (2023.05); *A61K 2239/48* (2023.05)

(58) Field of Classification Search
CPC .......... A61K 35/28; A61K 39/00; A61P 35/02; A61P 43/00; C12N 5/0783; C07K 16/28
See application file for complete search history.

(56) References Cited

U.S. PATENT DOCUMENTS

| | | | |
|---|---|---|---|
| 4,235,871 | A | 11/1980 | Papahadjopoulos et al. |
| 4,452,773 | A | 6/1984 | Molday |
| 4,501,728 | A | 2/1985 | Geho et al. |
| 4,690,915 | A | 9/1987 | Rosenberg |
| 4,795,698 | A | 1/1989 | Owen et al. |
| 4,837,028 | A | 6/1989 | Allen |
| 5,019,369 | A | 5/1991 | Presant et al. |
| 5,200,084 | A | 4/1993 | Liberti et al. |
| 5,219,740 | A | 6/1993 | Miller et al. |
| 5,635,517 | A | 6/1997 | Muller et al. |
| 5,712,291 | A | 1/1998 | D'Amato |
| 5,798,368 | A | 8/1998 | Muller et al. |

(Continued)

FOREIGN PATENT DOCUMENTS

| | | |
|---|---|---|
| EP | 0 452 342 | 11/1994 |
| EP | 2 537 416 | 12/2012 |

(Continued)

OTHER PUBLICATIONS

US 8,252,592 B2, 08/2012, Sadelain (withdrawn)

(Continued)

*Primary Examiner* — Erich A Leeser
(74) *Attorney, Agent, or Firm* — MORRISON & FOERSTER LLP

(57) ABSTRACT

The present disclosure relates in some aspects to methods, compositions and uses involving immunotherapies, such as adoptive cell therapy, e.g., T cell therapy, and an immunomodulatory compound, such as a structural or functional analog or derivative of thalidomide and/or an inhibitor of E3-ubiquitin ligase. The provided methods, compositions and uses include those for combination therapies involving the administration or use of one or more immunomodulatory compounds in conjunction with a T cell therapy, such as a genetically engineered T cell therapy involving cells engineered with a recombinant receptor, such as chimeric antigen receptor (CAR)-expressing T cells. Also provided are compositions, methods of administration to subjects, articles of manufacture and kits for use in the methods. In some aspects, features of the methods and cells provide for increased or improved activity, efficacy, persistence, expansion and/or proliferation of T cells for adoptive cell therapy or endogenous T cells recruited by immunotherapeutic agents.

33 Claims, 150 Drawing Sheets
Specification includes a Sequence Listing.

(56) References Cited

U.S. PATENT DOCUMENTS

| | | | |
|---|---|---|---|
| 6,040,177 | A | 3/2000 | Riddell et al. |
| 6,207,453 | B1 | 3/2001 | Maass et al. |
| 6,281,230 | B1 | 8/2001 | Muller et al. |
| 6,316,471 | B1 | 11/2001 | Muller et al. |
| 6,335,349 | B1 | 1/2002 | Muller et al. |
| 6,380,239 | B1 | 4/2002 | Muller et al. |
| 6,395,754 | B1 | 5/2002 | Muller et al. |
| 6,403,613 | B1 | 6/2002 | Man et al. |
| 6,410,319 | B1 | 6/2002 | Raubitschek et al. |
| 6,451,995 | B1 | 9/2002 | Cheung et al. |
| 6,458,810 | B1 | 10/2002 | Muller et al. |
| 6,476,052 | B1 | 11/2002 | Muller et al. |
| 7,070,995 | B2 | 7/2006 | Jensen |
| 7,091,353 | B2 | 8/2006 | Robarge et al. |
| 7,244,759 | B2 | 7/2007 | Muller et al. |
| 7,265,209 | B2 | 9/2007 | Jensen |
| 7,320,991 | B2 | 1/2008 | Figg et al. |
| 7,354,762 | B2 | 4/2008 | Jensen |
| 7,446,179 | B2 | 11/2008 | Jensen et al. |
| 7,446,190 | B2 | 11/2008 | Sadelain et al. |
| 7,446,191 | B2 | 11/2008 | Jensen |
| 8,324,353 | B2 | 12/2012 | Jensen |
| 8,339,645 | B2 | 12/2012 | Nakawaki |
| 8,389,282 | B2 | 3/2013 | Sadelain et al. |
| 8,479,118 | B2 | 7/2013 | Lindersay |
| 8,716,315 | B2 | 5/2014 | Figg et al. |
| 8,802,374 | B2 | 8/2014 | Jensen |
| 8,822,647 | B2 | 9/2014 | Jensen |
| 8,911,993 | B2 | 12/2014 | June et al. |
| 9,221,788 | B2 | 12/2015 | Cohen et al. |
| 9,629,849 | B2 | 4/2017 | Cohen et al. |
| 9,765,342 | B2 | 9/2017 | Kochenderfer |
| 9,828,361 | B2 | 11/2017 | Man et al. |
| 10,080,801 | B2 | 9/2018 | Parikh et al. |
| 2002/0045643 | A1 | 4/2002 | Muller et al. |
| 2002/0131960 | A1 | 9/2002 | Sadelain et al. |
| 2003/0045552 | A1 | 3/2003 | Robarge et al. |
| 2003/0096841 | A1 | 5/2003 | Robarge et al. |
| 2003/0170238 | A1 | 9/2003 | Gruenberg et al. |
| 2007/0116690 | A1 | 5/2007 | Yang et al. |
| 2011/0003380 | A1 | 1/2011 | Miltenyi et al. |
| 2013/0149337 | A1 | 6/2013 | Cooper et al. |
| 2013/0287748 | A1 | 10/2013 | June et al. |
| 2014/0045843 | A1 | 2/2014 | Schafer et al. |
| 2014/0046057 | A1 | 2/2014 | Cohen et al. |
| 2014/0162282 | A1 | 6/2014 | Schafer et al. |
| 2014/0271635 | A1 | 9/2014 | Brogdon et al. |
| 2015/0283178 | A1 | 10/2015 | June et al. |
| 2016/0017286 | A1 | 1/2016 | Albelda et al. |
| 2016/0051530 | A1 | 2/2016 | Thakurta et al. |
| 2016/0159768 | A1 | 6/2016 | Man et al. |
| 2016/0313300 | A1 | 10/2016 | Trotter et al. |
| 2017/0051035 | A1 | 2/2017 | Payne et al. |
| 2018/0360880 | A1 | 12/2018 | Brentjens et al. |
| 2019/0084924 | A1 | 3/2019 | Traverse |
| 2020/0078404 | A1 | 3/2020 | Ports et al. |
| 2022/0401483 | A1 | 12/2022 | Ports et al. |
| 2023/0165872 | A1 | 6/2023 | Ports et al. |

FOREIGN PATENT DOCUMENTS

| | | |
|---|---|---|
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1998/003502 | 1/1998 |
| WO | WO 1998/054170 | 12/1998 |
| WO | WO 1999/018129 | 4/1999 |
| WO | WO 1999/060120 | 11/1999 |
| WO | WO 2000/014257 | 3/2000 |
| WO | WO 2002/059106 | 8/2002 |
| WO | WO 2002/068414 | 9/2002 |
| WO | WO 2003/020763 | 3/2003 |
| WO | WO 2004/033685 | 4/2004 |
| WO | WO 2006/000830 | 1/2006 |
| WO | WO 2008/039489 | 4/2008 |
| WO | WO 2008/154252 | 12/2008 |
| WO | WO 2009/072003 | 6/2009 |
| WO | WO 2010/033140 | 3/2010 |
| WO | WO 2010/104949 | 9/2010 |
| WO | WO 2011/044186 | 4/2011 |
| WO | WO 2011/100380 | 8/2011 |
| WO | WO 2012/129514 | 9/2012 |
| WO | WO 2013/071154 | 5/2013 |
| WO | WO 2013/123061 | 8/2013 |
| WO | WO 2013/126726 | 8/2013 |
| WO | WO 2013/166321 | 11/2013 |
| WO | WO 2014/031687 | 2/2014 |
| WO | WO 2014/055668 | 4/2014 |
| WO | WO 2015/105522 | 7/2015 |
| WO | WO 2016/014530 | 1/2016 |
| WO | WO 2016/014789 | 1/2016 |
| WO | WO 2016/046724 | 3/2016 |
| WO | WO 2016/090320 | 6/2016 |
| WO | WO 2016/090327 | 6/2016 |
| WO | WO 2016/094304 | 6/2016 |
| WO | WO 2016/164580 | 10/2016 |
| WO | WO 2016/187349 | 11/2016 |
| WO | WO 2016/210129 | 12/2016 |
| WO | WO 2016/210262 | 12/2016 |
| WO | WO 2017/025038 | 2/2017 |
| WO | WO 2017/058754 | 4/2017 |
| WO | WO 2017/096024 | 8/2017 |
| WO | WO 2017/173256 | 10/2017 |
| WO | WO 2017/176289 | 10/2017 |
| WO | WO 2017/214207 | 12/2017 |
| WO | WO 2018/023100 | 2/2018 |
| WO | WO 2018/071873 | 4/2018 |
| WO | WO 2018/085690 | 5/2018 |
| WO | WO 2018/085731 | 5/2018 |
| WO | WO 2018/093591 | 5/2018 |
| WO | WO 2018/102785 | 6/2018 |
| WO | WO 2018/102786 | 6/2018 |
| WO | WO 2018/102787 | 6/2018 |
| WO | WO 2018/075820 * 7/2018 ............ A61K 47/68 |
| WO | WO 2018/183842 | 10/2018 |
| WO | WO 2018/204427 | 11/2018 |
| WO | WO 2018/223101 | 12/2018 |
| WO | WO 2019/014100 | 1/2019 |
| WO | WO 2019/108900 | 6/2019 |
| WO | WO 2019/109053 | 6/2019 |
| WO | WO 2019/226761 | 11/2019 |
| WO | WO 2020/014333 | 1/2020 |
| WO | WO 2020/092848 | 5/2020 |
| WO | WO 2020/097403 | 5/2020 |
| WO | WO 2020/210418 | 10/2020 |
| WO | WO 2021/091978 | 5/2021 |
| WO | WO 2021/092498 | 5/2021 |
| WO | WO 2021/222330 | 11/2021 |
| WO | WO 2022/212384 | 10/2022 |
| WO | WO 2022/221726 | 10/2022 |

OTHER PUBLICATIONS

Brittain, "X-ray Diffraction III: Pharmaceutical Applications of X-ray Powder Diffraction," Spectroscopy (2001) 16(7):14-18, p. 15.

U.S. Appl. No. 18/284,800, filed Mar. 29, 2022, by Trede et al. (Copy not provided). Copy not submitted herewith pursuant to the waiver of 37 C.F. R. § 1.98(a)(2)(iii) issued by the Office on Sep. 21, 2004).

Anonymous, "Safety and Efficacy of bb2121 (lde-cel) Combinations in Multiple Myeloma-Full Text View-ClinicalTrials.gov", Apr. 22, 2021, XP055952059, 12 pages.

Brahmandam et al. "106 Treatment with CC-99282 enhances antitumor function of the anti-CD19 Car T cell therapy lisocabtagene maraleucel (liso-cel)." J Immunother Cancer (2021) 9(Suppl 2):A117, 1 page.

Database PUBCHEM: Golcadeomide hydrochloride, XP055938424, Database Accession No. 163203519, Created May 12, 2022, 10 pages.

Legarda et al., "Recent Advances in the Treatment of Patients with Multiple Myeloma," Cancers (Basel). (2020) 12(12):3576, 22 pages.

(56) References Cited

OTHER PUBLICATIONS

Li et al. "PiggyBac-Generated CAR19-T Cells Plus Lenalidomide Cause Durable Complete Remission of Triple-Hit Refractory/Relapsed DLBCL: A Case Report." *Frontiers in Immunology* (2021) 12:599493, 9 pages.
Li et al., "Mechanisms of failure of chimeric antigen receptor T-cell therapy," Curr Opin Hematol. (Nov. 2019);26(6):427-433.
Lopez-Girona et al., "CC-92480 is a Novel Cerebion E3 Ligase Modulator with Enhanced Tumoricidal and Immunomodulatory Activity Against Sensitive and Resistant Multiple Myeloma Cells," Blood (2019) 134 (Supplement_1): 1812, 3 pages.
Maude et al., "Tisagenlecleucel in Children and Young Adults with B-Cell Lymphoblastic Leukemia," N Engl J Med (2018) 378(5):439-448.
Michot et al. "Clinical Activity of CC-99282, a Novel, Oral Small Molecule Cereblon E3 Ligase Modulator (CELMoD) Agent, in Patients (Pts) with Relapsed or Refractory Non-Hodgkin Lymphoma (R/R NHL)-First Results from a Phase 1, Open-Label Study." Blood (2021) 138:3574-3576.
Munshi et al., "Idecabtagene Vicleucel in Relapsed and Refractory Multiple Myeloma," N Engl J Med (2021) 384(8):705-716.
Qin et al, "Treatment with Iberdomide Enhances Antitumor Function of the Anti-CD19 Chimeric Antigen Receptor (CAR) T Cell Therapy Lisocabtagene Maraleucel (liso-cel)," Cancer-Immunotherapy (2020) 28: 4S1: Abstract 1158, p. 497.
Qin et al, "Treatment with Iberdomide Enhances Antitumor Function of the Anti-CD19 Chimeric Antigen Receptor (CAR) T Cell Therapy Lisocabtagene Maraleucel (liso-cel)," Poster: Presented at the 23rd Annual Meeting of the American Society of Gene & Cell Therapy (ASGCT); May 12-15, 2020, 1 page.
Raje et al. "KarMMa-7, a Phase 1/2, Dose-Finding and Dose-Expansion Study of Combination Therapies with Idecabtagene Vicleucel (ide-cel, bb2121), a BCMA-Directed CAR T Cell Therapy for Relapsed/Refractory Multiple Myeloma (RRMM)." Blood (2021) 138: 4830-4832.
Steiner et al., "CAR-T cells in multiple myeloma: current status," Magazine of European Medical Oncology. (2020) 13:43-49.
Abramson et al., "High CR rates in relapsed/refractory (R/R) aggressive B-NHL treated with the CD19-directed CAR T cell product JCAR017 (Transcend NHL 001)," Presented at 14th International Conference on Malignant Lymphoma; Jun. 14-17, 2017; Lugano, Switzerland. Abstract 128.
Abramson et al., "High Durable CR Rates in R/R Aggressive B-NHL Treated with JCAR017 (Transcend NHL 001): Defined Composition CD19-Directed CAR T Cell Product Allows for Dose Finding and Definition of Pivotal Cohort," Presented Dec. 7, 2017 at ASH 2017.
Abramson et al., "High Durable CR Rates in Relapsed/Refractory (R/R) Aggressive B-NHL Treated with the CD19-Directed CAR T Cell Product JCAR 017 (Transcend NHL001): Defined Composition Allows for Dose-Finding and Definition of Pivotal Cohort," Blood (2017) 130:581 Abstract.
Abramson et al., "Transcend NHL 001: Immunotherapy with the CD19-directed CAR T-cell Product JCAR017 Results in High Complete Response Rates in Relapsed or Refractory B-Cell Non-Hodgkin Lymphoma," Blood (2016) 128:4192 Abstract.
Actemra [Package Insert]. South San Francisco, CA: Genentech Inc, a Member of the Roche Group. 2019. Available from: https://www.accessdata.fda.gov/drugsatfda_docs/label/2019/125276s127,125472s040lbl.pdf.
Actemra® [Prescribing Information]. South San Francisco, USA: Genentech Inc. Available from: https://www.accessdata.fda.gov/drugsatfda_docs/label/2013/125276s092lbl.pdf.
Alonso-Camino et al., "CARbodies: Human Antibodies Against Cell Surface Tumor Antigens Selected From Repertoires Displayed on T Cell Chimeric Antigen Receptors," Mol Ther Nucleic Acids (2013) 2(5):e93.
Amatangelo et al. "Iberdomide (CC-220) has synergistic anti-tumor and immunostimulatory activity against multiple myeloma in combination with both bortezomib and dexamethasone, or in combination with daratumumab in vitro." *Blood* 132 (2018): 1935.
Amatangelo et al. "PF559 Iberdomide (CC-220) is Pharmacodynamically Active and Has Dose-Dependent Immunostimulatory Activity in Relapsed/Refractory Multiple Myeloma Patients Irrespective of Prior Imid Drug Treatment." *HemaSphere* 3.S1 (2019): 231-232.
Attal et al. "Isatuximab plus pomalidomide and low-dose dexamethasone versus pomalidomide and low-dose dexamethasone in patients with relapsed and refractory multiple myeloma (ICARIA-MM): a randomised, multicentre, open-label, phase 3 study." *The Lancet* 394.10214 (2019): 2096-2107.
Avet-Loiseau et al. "Evaluation of minimal residual disease (MRD) in relapsed/refractory multiple myeloma (RRMM) patients treated with daratumumab in combination with lenalidomide plus dexamethasone or bortezomib plus dexamethasone." *Blood* 128.22 (2016): 246.
Balaian et al., "Selective expansion of regulatory T cells during lenalidomide treatment of myelodysplastic syndrome with isolated deletion 5q," Ann Hematol. (2016) 95(11): 1805-10.
Barrett et al., "Chimeric Antigen Receptor Therapy for Cancer," Annual Review of Medicine (2014) 65:333-347.
Benedetti et al. "OP0204 Emapalumab, an interferon gamma (IFN-Y)-Blocking monoclonal antibody, in patients with macrophage activation syndrome (MAS) complicating systemic juvenile idiopathic arthritis (SJIA)." (2019): 178-178.
Bertilaccio et al., "Low-Dose Lenalidomide Improves CAR-Based Immunotherapy In CLL By Reverting T-Cell Defects In Vivo," Blood (2013) 122:4171.
Bjorklund et al. "CC-122 is a cereblon modulating agent that is active in lenalidomide-resistant and lenalidomide/dexamethasone-double-resistant multiple myeloma pre-clinical models." *Blood* 128. 22 (2016): 1592.
Bjorklund et al. "Iberdomide (CC-220) is a potent cereblon E3 ligase modulator with antitumor and immunostimulatory activities in lenalidomide-and pomalidomide-resistant multiple myeloma cells with dysregulated CRBN." *Leukemia* 34.4 (2020): 1197-1201.
Bjorklund et al. "Rate of CRL4 CRBN substrate Ikaros and Aiolos degradation underlies differential activity of lenalidomide and pomalidomide in multiple myeloma cells by regulation of c-Myc and IRF4." *Blood cancer journal* 5.10 (2015): e354-e354.
Boris-Lawrie et al., "Recent advances in retrovirus vector technology," Current Opinion in Genetics & Development (1993) 3(1):102-109.
Botta et al. "Network meta-analysis of randomized trials in multiple myeloma: efficacy and safety in relapsed/refractory patients." *Blood advances* 1.7 (2017): 455-466.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Brentjens et al., "Safety and persistence of adoptively transferred autologous CD19-targeted T cells in patients with relapsed or chemotherapy refractory B-cell leukemias," Blood (2011) 118(18):4817-4828.
Bringhen et al. "Efficacy and safety of once-weekly bortezomib in multiple myeloma patients." *Blood, The Journal of the American Society of Hematology* 116.23 (2010): 4745-4753.
Brudno et al., "Toxicities of chimeric antigen receptor T cells: recognition and management." *Blood, The Journal of the American Society of Hematology* 127.26 (2016): 3321-3330.
Buenrostro et al., "Transposition of Native Chromatin for Fast and Sensitive Epigenomic Profiling of Open Chromatin, DNA-binding Proteins and Nucleosome Position," Nat Methods (2013) 10(12):1213-1218.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Busch et al., "Role of memory T cell subsets for adoptive immunotherapy," Semin Immunol (2016) 28(1):28-34.

(56) References Cited

OTHER PUBLICATIONS

Busch et al., "Treatment with lenalidomide induces immunoactivating and counter-regulatory immunosuppressive changes in myeloma patients," Clin Exp Immunol. (2014) 177(2): 439-453.
Cairo et al., "Tumour lysis syndrome: new therapeutic strategies and classification," Br J Haematol (2004) 127(1):3-11.
Carlens et al., "Ex vivo T lymphocyte expansion for retroviral transduction: influence of serum-free media on variations in cell expansion rates and lymphocyte subset distribution," Exp Hematol (2000) 28(10): 1137-1146.
Carpenter et al., "B-cell maturation antigen is a promising target for adoptive T-cell therapy of Multiple Myeloma," Clin Cancer Res (2013) 19(8):2048-2060.
Carrillo et al., "The Multiple Sequence Alignment Problem in Biology," Siam J Appl Math (1988) 48(5):1073-1082.
Cavaletti et al., "Chemotherapy-induced peripheral neurotoxicity," Nature Reviews Neurology (2010) 6:657-666.
Cavalieri et al., "Human T lymphocytes transduced by lentiviral vectors in the absence of TCR activation maintain an intact immune competence," Blood (2003) 102(2): 497-505.
Challita et al., "Multiple Modifications in Cis Elements of the Long Terminal Repeat of Retroviral Vectors Lead to Increased Expression and Decreased DNA Methylation in Embryonic Carcinoma Cells," J Virol (1995) 69(2): 748-55.
Chamberlain et al. "Structure of the human Cereblon-DDB1-lenalidomide complex reveals basis for responsiveness to thalidomide analogs." *Nature structural & molecular biology* 21.9 (2014): 803-809.
Chari et al. "Daratumumab plus pomalidomide and dexamethasone in relapsed and/or refractory multiple myeloma." *Blood, The Journal of the American Society of Hematology* 130.8 (2017): 974-981.
Chari et al. "Oral selinexor-dexamethasone for triple-class refractory multiple myeloma." *New England Journal of Medicine* 381.8 (2019): 727-738.
Cheadle et al., "Chimeric antigen receptors for T-cell based therapy," Methods Mol Biol. (2012);907:645-66.
Chervin et al., "Engineering higher affinity T cell receptors using a T cell display system," J Immunol Methods (2008) 339(2):175-184.
Cheson et al., "Recommendations for initial evaluation, staging, and response assessment of Hodgkin and non-Hodgkin lymphoma: the Lugano classification," J Clin Oncol (2014) 20(27):3059-3068.
Chicaybam et al., "An efficient low cost method for gene transfer to T lymphocytes," PLoS One (2013) 8(3): e60298.
Cho et al., "A Small Molecule Inhibitor of ITK and RLK Impairs Th1 Differentiation and Prevents Colitis Disease Progression," J Immunol (2015) 195:4822-4831.
Chothia et al., "The outline structure of the T-cell alpha beta receptor," EMBO J (1988) 7(12):3745-3755.
Clambey et al., "The Ikaros Transcription Factor Regulates Responsiveness to IL-12 and Expression of IL-2 Receptor Alpha in Mature, Activated CD8 T Cells," PLOS One, (2013) 8(2): e57435.
Clinicaltrials.gov Identifier NCT02315612. First posted Dec. 12, 2014. Last updated Oct. 9, 2019.
Cohen et al., "Recognition of fresh human tumor by human peripheral blood lymphocytes transduced with a bicistronic retroviral vector encoding a murine anti-p53 TCR," J Immunol. (2005) 175:5799-5808.
Collins et al., "Chemical approaches to targeted protein degradation through modulation of the ubiquitin-proteasome pathway," Biochem J. (2017) 474(7): 1127-1147.
Cooper et al., "T-cell clones can be rendered specific for CD19: toward the selective augmentation of the graft-versus-B-lineage leukemia effect," Blood (2003) 101:1637-1644.
Corral et al. "Differential cytokine modulation and T cell activation by two distinct classes of thalidomide analogues that are potent inhibitors of TNF-α." *The Journal of Immunology* 163.1 (1999): 380-386.
Couzin et al., "As Gelsinger case ends, gene therapy suffers another blow." (2005): 1028-1028.

Cowan et al. "Efficacy and safety of fully human Bcma CAR T cells in combination with a gamma secretase inhibitor to increase Bcma surface expression in patients with relapsed or refractory multiple myeloma." (2019): 204-204.
Crayne et al. "The immunology of macrophage activation syndrome." Frontiers in immunology 10 (2019): 119.
Crump et al., "Outcomes in refractory diffuse large B-cell lymphoma: results from the international Scholar-1 study," Blood (2017) 130(16):1800-1808.
Darzalex Faspro™. [Package Insert]. Horsham, PA: Janssen Biotech, Inc; 2020. Available from: https://www.janssenlabels.com/package-insert/product-monograph/prescribing-information/DARZALEX+Faspro-pi.pdf.
Darzalex®. [Package Insert]. Horsham, PA: Janssen Biotech, Inc; 2020. Available from: https://www.janssenmd.com/pdf/darzalex/darzalex_pi.pdf.
Davies et al. "Thalidomide and immunomodulatory derivatives augment natural killer cell cytotoxicity in multiple myeloma." *Blood, The Journal of the American Society of Hematology* 98.1 (2001): 210-216.
Davila et al., "CD19 CAR-Targeted T Cells Induce Long-Term Remission and B Cell Aplasia in an Immunocompetent Mouse Model of B Cell Acute Lymphoblastic Leukemia," PLOS One (2013) 8(4):e61338.
Davila et al., "Efficacy and toxicity management of 19-28z CAR T cell therapy in B cell acute lymphoblastic leukemia," Sci Transl Med (2014) 6:224ra25.
Davila et al., "How do CARs work?: Early insights from recent clinical studies targeting CD19," Oncoimmunology (2012) 1(9):1577-1583.
De Felipe et al., "Targeting of Proteins Derived from Self-Processing Polyproteins Containing Multiple Signal Sequences," Traffic (2004) 5(8):616-626.
De Felipe, "Skipping the co-expression problem: the new 2A "Chysel" technology," Genet Vaccines Ther (2004) 2:13.
Deniger et al., "A Pilot Trial of the Combination of Vemurafenib with Adoptive Cell Therapy in Patients with Metastatic Melanoma." Clin Cancer Res. Jan. 2017; 23(2): 351-362.
Dimopoulos et al. "Carfilzomib and dexamethasone versus bortezomib and dexamethasone for patients with relapsed or refractory multiple myeloma (Endeavor): a randomised, phase 3, open-label, multicentre study." *The Lancet Oncology* 17.1 (2016): 27-38.
Dimopoulos et al. "Daratumumab, lenalidomide, and dexamethasone for multiple myeloma." *New England Journal of Medicine* 375.14 (2016): 1319-1331.
Dimopoulos et al. "Pomalidomide+ Bortezomib+ low-dose dexamethasone vs bortezomib+ low-dose dexamethasone as second-line treatment in patients with lenalidomide-pretreated multiple myeloma: a subgroup analysis of the phase 3 optimismm trial." *Blood* 132 (2018): 3278.
Donahue et al. "Helper virus induced T cell lymphoma in nonhuman primates after retroviral mediated gene transfer." The Journal of experimental medicine 176.4 (1992): 1125-1135.
Dudley et al., "Cancer regression and autoimmunity in patients after clonal repopulation with antitumor lymphocytes," Science (2002) 298(5594):850-854.
Dumortier et al. "Ikaros regulates neutrophil differentiation." *Blood, The Journal of the American Society of Hematology* 101.6 (2003): 2219-2226.
Durie et al. "A clinical staging system for multiple myeloma correlation of measured myeloma cell mass with presenting clinical features, response to treatment, and survival." *Cancer* 36.3 (1975): 842-854.
Even et al. "Notch pathway inhibition with LY3039478 in adenoid cystic carcinoma (ACC)." (2017): 6024-6024.
Facon et al. "Daratumumab in combination with pomalidomide and dexamethasone for relapsed and/or refractory multiple myeloma (RRMM) patients with 2 prior lines of therapy: updated analysis of MMY1001." (2017): 1824-1824.
Fedorov et al., "PD-1- and CTLA-4-Based Inhibitory Chimeric Antigen Receptors (iCARs) Divert Off-Target Immunotherapy Responses," Science Translational Medicine (2013) 5(215):215ra172.

(56) References Cited

OTHER PUBLICATIONS

Ferguson et al. "Immunomodulatory drug CC-4047 is a cell-type and stimulus-selective transcriptional inhibitor of cyclooxygenase 2." *Journal of clinical immunology* 27.2 (2007): 210-220.
Fischer et al. "Structure of the DDB1-CRBN E3 ubiquitin ligase in complex with thalidomide." *Nature* 512.7512 (2014): 49-53.
Fraietta et al., "Ibrutinib enhances chimeric antigen receptor T-cell engraftment and efficacy in leukemia." Blood. Mar. 3, 2016;127(9):1117-27.
Frey et al. "Cytokine release syndrome with chimeric antigen receptor T cell therapy." Biology of Blood and Marrow Transplantation 25.4 (2019): e123-e127.
Frey. "Cytokine release syndrome: who is at risk and how to treat." *Best Practice & Research Clinical Haematology* 30.4 (2017): 336-340.
Gandhi et al. "Immunomodulatory agents lenalidomide and pomalidomide co-stimulate T cells by inducing degradation of T cell repressors I karos and A iolos via modulation of the E 3 ubiquitin ligase complex CRL 4 CRBN." *British journal of haematology* 164.6 (2014): 811-821.
Gandhi et al. "Outcomes of patients with multiple myeloma refractory to CD38-targeted monoclonal antibody therapy." *Leukemia* 33.9 (2019): 2266-2275.
Gardner et al., "Intent-to-treat leukemia remission by CD19 CAR T cells of defined formulation and dose in children and young adults," Blood (2017) 129(25):3322-3331.
Gattinoni et al., "Moving T memory stem cells to the clinic," Blood. 2013 121(4): 567-568.
Godin et al., "Microfluidics and photonics for Bio-System-on-a-Chip: a review of advancements in technology towards a microfluidic flow cytometry chip," J Biophotonics (2008) 1(5):355-376.
Gorgun et al., "Immunomodulatory Effects of Lenalidomide and Pomalidomide on Interaction of Tumor and Bone Marrow Accessory Cells in Multiple Myeloma," Blood (2010) 116(17): 3227-3237.
Greipp et al. "International staging system for multiple myeloma." *Journal of clinical oncology* 23.15 (2005): 3412-3420.
Grupp et al., "Chimeric antigen receptor-modified T cells for acute lymphoid leukemia," N. Engl. J. Med. (2013) 368:1509-1518.
Gust et al. "Endothelial activation and blood-brain barrier disruption in neurotoxicity after adoptive immunotherapy with CD19 CAR-T cells." *Cancer discovery* 7.12 (2017): 1404-1419.
Hacein-Bey-Abina et al. "LMO2-associated clonal T cell proliferation in two patients after gene therapy for SCID-X1." *science* 302.5644 (2003): 415-419.
Hagner et al., "CC-122, a pleiotropic pathway modifier, mimics an interferon response and has antitumor activity in DLBCL," Blood (2015) 126(6):770-789.
Han et al., "Chimeric antigen receptor-engineered T cells for cancer immunotherapy: progress and challenges," J Hematology & Oncology (2013) 6:47.
Haslett et al., "Thalidomide costimulates primary human T lymphocytes, preferentially inducing proliferation, cytokine production, and cytotoxic responses in the CD8+ subset," J Exp Med. (1998) 187(11):1885-1892.
Hay et al. "Kinetics and biomarkers of severe cytokine release syndrome after CD19 chimeric antigen receptor-modified T-cell therapy." *Blood, The Journal of the American Society of Hematology* 130.21 (2017): 2295-2306.
Heipel et al., "Pharmacokinetic, Pharmacodynamic and Blood Analytes Associated with Clinical response and Safety in Relapsed/ Refractory Aggressive B-NHL Patients Treated with JCAR017," Blood (2017) 130 (Suppl 1):2835.
Herman et al., "The Bruton tyrosine kinase (BTK) inhibitor acalabrutinib demonstrates potent on-target effects and efficacy in two mouse models of chronic lymphocytic leukemia," Clin Cancer Res. (2017)23: 2831-2841.
Holler et al., "In vitro evolution of a T cell receptor with high affinity for peptide/MHC," PNAS (2000) 97(10):5387-5392.
Holler et al., "TCRs with high affinity for foreign pMHC show self-reactivity," Nat Immunol (2003) 4(1):55-62.
Howlader et al., SEER Cancer Statistics Review, 1975-2017, National Cancer Institute. Bethesda, MD, https://seer.cancer.gov/csr/1975_2017/, based on Nov. 2019 SEER data submission, posted to the SEER web site, Apr. 2020.
Huang et al., "DNA transposons for modification of human primary T lymphocytes," Methods Mol Biol (2009) 506:115-126.
Hudecek et al., "Receptor affinity and extracellular domain modifications affect tumor recognition by ROR1-specific chimeric antigen receptor T cells," Clin Cancer Res (2013) 19(12):3153-3164.
Hudecek et al., "The nonsignaling extracellular spacer domain of chimeric antigen receptors is decisive for in vivo antitumor activity," Cancer Immunol Res (2015) 3(2):125-135.
Ito et al., "Identification of a primary target of thalidomide teratogenicity," Science (2010) 327(5971): 1345-50.
Janeway et al., Immunobiology: The Immune System in Health and Disease, 3rd ED., Current Biology Publications (1997), p. 4:33.
Jensen et al., "Antitransgene rejection responses contribute to attenuated persistence of adoptively transferred CD20/CD19-specific chimeric antigen receptor redirected T cells in humans," Biol Blood Marrow Transplant (2010) 16(9):1245-1256.
Jessup et al., "Avadomide (CC-122) Improves Effector Function and Reverses Exhaustion in Chronically Stimulated Lisocabtagene Maraleucel (JCAR017) Drug Product," Immunology (2019) Abstract 2320.
Jessup et al., "Avadomide (CC-122) Improves Effector Function and Reverses Exhaustion in Chronically Stimulated Lisocabtagene Maraleucel (JCAR017) Drug Product," Poster 2320, Presented at the 2019 AACR Annual Meeting; Mar. 29-Apr. 3, 2019; Atlanta, GA.
Jiang et al., "T-cell exhaustion in the tumor microenvironment," Cell Death Dis (2015) 6:e1792.
Johnston, "Biolistic transformation: microbes to mice," Nature (1990) 346:776-777.
Jores et al., "Resolution of hypervariable regions in T-cell receptor beta chains by a modified Wu-Kabat index of amino acid diversity.," PNAS (1990) 87(23):9138-9142.
Kalos et al., "T cells with chimeric antigen receptors have potent antitumor effects and can establish memory in patients with advanced leukemia," Sci Transl Med (2011) 3(95):95ra73.
Karakike et al. "Macrophage activation-like syndrome: a distinct entity leading to early death in sepsis." *Frontiers in immunology* 10 (2019): 55.
Kawano, et al. "Targeting the bone marrow microenvironment in multiple myeloma." *Immunological reviews* 263.1 (2015): 160-172.
Khalil et al., "The Future of Cancer Treatment: Immunomodulation, CARs and Combination Therapy." Nat. Rev. Clin. Oncol. Mar. 2016; 13(5): 273-290.
Klebanoff et al., "Sorting through subsets: Which T cell populations mediate highly effective adoptive immunotherapy?" J Immunother (2012) 35(9):651-660.
Kochenderfer et al., "B-cell depletion and remissions of malignancy along with cytokine-associated toxicity in a clinical trial of anti-CD19 chimeric-antigen-receptor-transduced T cells," Blood (2012) 119:2709-2720.
Kochenderfer et al., "Chemotherapy-refractory diffuse large B-cell lymphoma and indolent B-cell malignancies can be effectively treated with autologous T cells expressing an anti-CD19 chimeric antigen receptor," J Clin Oncol (2015) 33(6):540-549.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nat Rev Clin Oncol (2013) 10(5):267-276.
Koste et al., "T-cell receptor transfer into human T cells with ecotropic retroviral vectors," Gene Therapy (2014) 21:533-538.
Kotb et al., "Bacterial pyrogenic exotoxins as superantigens," Clinical Microbiology Reviews (1995) 8:411-426.
Kotla et al., "Mechanism of action of lenalidomide in hematological malignancies." J Hematol Oncol. (2009) 2:36.

(56) References Cited

OTHER PUBLICATIONS

Krejcik et al. "Daratumumab depletes CD38+ immune regulatory cells, promotes T-cell expansion, and skews T-cell repertoire in multiple myeloma." *Blood, The Journal of the American Society of Hematology* 128.3 (2016): 384-394.

Kronke et al., "Lenalidomide causes selective degradation of IKZF1 and IKZF3 in multiple myeloma cells," Science (2014) 343(6168):301-305.

Kronke et al., "Lenalidomide induces ubiquitination and degradation of CK1α in del(5q) MDS," Nature. (2015) 523(7559): 183-188.

Kumar et al. "Correlation of bone marrow angiogenesis and response to thalidomide dexamethasone in multiple myeloma." *Journal of Clinical Oncology* 24.18_suppl (2006): 7621-7621.

Kumar et al. "International Myeloma Working Group consensus criteria for response and minimal residual disease assessment in multiple myeloma." *The lancet oncology* 17.8 (2016): e328-e346.

Kumar et al. "Risk of progression and survival in multiple myeloma relapsing after therapy with IMiDs and bortezomib: a multicenter international myeloma working group study." *Leukemia* 26.1 (2012): 149-157.

Kumar, et al. "Natural history of relapsed myeloma, refractory to immunomodulatory drugs and proteasome inhibitors: a multicenter IMWG study." *Leukemia* 31.11 (2017): 2443-2448.

Kuramitsu et al., "Lenalidomide enhances the function of chimeric antigen receptor T cells against the epidermal growth factor receptor variant III by enhancing immune synapses," Cancer Gene Therapy (2015) 22(10):487-495.

Kurucz et al., "A bacterially expressed single-chain Fv construct from the 2B4 T-cell receptor," PNAS (1993) 90(9):3830-3834.

Lamers et al., "Immune responses to transgene and retroviral vector in patients treated with ex vivo-engineered T cells," Blood (2011) 117(1):72-82.

Landgren et al. "Role of MRD status in relation to clinical outcomes in newly diagnosed multiple myeloma patients: a meta-analysis." Bone marrow transplantation 51.12 (2016): 1565-1568.

Larocca et al. "Emerging drugs and combinations to treat multiple myeloma." *Oncotarget* 8.36 (2017): 60656.

Laurent et al. "γ-Secretase directly sheds the survival receptor BCMA from plasma cells." *Nature communications* 6.1 (2015): 1-12.

Lee et al., "A predictive probability design for phase II cancer clinical trials." *Clinical Trials* 5.2 (2008): 93-106.

Lee et al. "ASTCT consensus grading for cytokine release syndrome and neurologic toxicity associated with immune effector cells." *Biology of Blood and Marrow Transplantation* 25.4 (2019): 625-638.

Lee et al. Bayesian efficacy monitoring via predictive probability. PID:901;v1.1.1.1. 2019b. Available from: https://trialdesign.org/one-page-shell.html#BEMPR.

Lee et al., "Current concepts in the diagnosis and management of cytokine release syndrome," Blood. (2014) 124(2):188-95.

Lee et al., "Evaluation of B Cell Maturation Antigen as a Target for Antibody Drug Conjugate Mediated Cytotoxicity in Multiple Myeloma," Br J Haematol (2016) 174(6): 911-22.

Lee et al., "T cells expressing CD19 chimeric antigen receptors for acute lymphoblastic leukaemia in children and yound adults: a phase 1 dose escalation trial," The Lancet (2015) 385(9967): 517-528.

Lefranc et al., "IMGT unique numbering for immunoglobulin and T cell receptor variable domains and Ig superfamily V-like domains," Dev Comp Immunol (2003) 27(1):55-77.

Lehmberg, et al. "Consensus recommendations for the diagnosis and management of hemophagocytic lymphohistiocytosis associated with malignancies." *Haematologica* 100.8 (2015): 997.

Leleu et al. "Role of proteasome inhibitors in relapsed and/or refractory multiple myeloma." *Clinical Lymphoma Myeloma and Leukemia* 19.1 (2019): 9-22.

Li et al. "Murine leukemia induced by retroviral gene marking." *Science* 296.5567 (2002): 497-497.

Li et al., "Directed evolution of human T-cell receptors with picomolar affinities by phage display," Nat Biotechnol (2005) 23(3):349-354.

Ling et al. (1987). "Leucocyte typing III," 302.

Liu et al. "Bayesian optimal interval designs for phase I clinical trials." *Journal of the Royal Statistical Society: Series C: Applied Statistics* (2015): 507-523.

Liu et al., "Inclusion of Strep-tag II in design of antigen receptors for T-cell immunotherapy," Nat Biotechnol (2016) 34(4):430-434.

Locke et al. "Preliminary results of prophylactic tocilizumab after axicabtageneciloleucel (axi-cel; KTE-C19) treatment for patients with refractory, aggressive non-Hodgkin lymphoma (NHL)." (2017): 1547-1547.

Locke et al., "Abstract CT020: Immune signatures of cytokine release syndrome and neurologic events in a multicenter registrational trial (ZUMA-1) in subjects with refractory diffuse large B cell lymphoma treated with axicabtagene ciloleucel," Cancer Res (2017) 77(13_Supplement):CT020.

Lonial et al. "Belantamab mafodotin for relapsed or refractory multiple myeloma (DREAMM-2): a two-arm, randomised, open-label, phase 2 study." *The lancet oncology* 21.2 (2020): 207-221.

Lonial et al. "Daratumumab monotherapy in patients with treatment-refractory multiple myeloma (SIRIUS): an open-label, randomised, phase 2 trial." *The Lancet* 387.10027 (2016): 1551-1560.

Lonial et al. "Elotuzumab therapy for relapsed or refractory multiple myeloma." *New England Journal of Medicine* 373.7 (2015): 621-631.

Lonial et al. "First clinical (phase 1b/2a) study of iberdomide (CC-220; IBER), a CELMoD, in combination with dexamethasone (DEX) in patients (pts) with relapsed/refractory multiple myeloma (RRMM)." (2019): 8006-8006.

Lonial et al. "Translational and clinical evidence of a differentiated profile for the novel CELMoD, iberdomide (CC-220)." (2019): 3119-3119.

Lopez-Girona et al., "Cereblon is a direct protein target for immunomodulatory and antiproliferative activities of lenalidomide and pomalidomide," Leukemia. (2012) 26(11): 2326-35.

Lu et al. "The myeloma drug lenalidomide promotes the cereblon-dependent destruction of Ikaros proteins." *Science* 343.6168 (2014): 305-309.

Lupton et al., "Dominant positive and negative selection using a hygromycin phosphotransferase-thymidine kinase fusion gene," Mol and Cell Biol (1991) 11(6):3374-3378.

Maloney et al., "Preliminary Safety Profile of the CD19-Directed Defined Composition CAR T Cell Product JCAR017 in Relapsed/Refractory Aggressive B-NHL Patients: Potential for Outpatient Administration," Blood (2017) 130(Supplement 1):1552.

Maloney et al., "Safety Profile of the CD19-Directed Defined Composition CAR T Cell Product JCAR017 (lisocabtagene maraleucel; liso-cel) in Relapsed/Refractory Aggressive B-NHL Patients: Potential for Outpatient Administration," Poster Presentation 1552 at American Society of Hematology 2017, Dec. 9-12, 2017, Atlanta, Georgia.

Manuri et al., "piggyBac Transposon/Transposase System to Generate CD19-Specific T Cells for the Treatment of B-Lineage Malignancies," Hum Gene Ther (2010) 21(4):427-437.

Martin et al., "Correlation of tumor BCMA expression with response and acquired resistance to idecabtagene vicleucel in the KarMMa study in relapsed and refractory multiple myeloma." HemaSphere https://doi.org/10.1097/HS9 404 (2020).

Matyskiela et al. "A cereblon modulator (CC-220) with improved degradation of Ikaros and Alolos." Journal of medicinal chemistry 61.2 (2018): 535-542.

Maude et al. "Managing cytokine release syndrome associated with novel T cell-engaging therapies." *Cancer journal* (Sudbury, Mass.) 20.2 (2014): 119.

Maude et al., "Chimeric antigen receptor T cells for sustained remissions in leukemia," N Engl J Med. Oct. 16, 2014;371(16):1507-17.

McDaniel, J.M., "Lenalidomide targets the T-cell co-stimulatory pathway to mediate immune modulation." Ph.D. Dissertation, University of South Florida, Aug. 24, 2012, Retrieved from https://

(56) References Cited

OTHER PUBLICATIONS scholarcommons.usf.edu/cgi/viewcontent.cgi?referer=&httpsredir=1&article=5563&context=etd retrieved on May 7, 2019.

McGarrity et al. "Patient monitoring and follow-up in lentiviral clinical trials." *The journal of gene medicine* 15.2 (2013): 78-82.

Miller et al., "Improved retroviral vectors for gene transfer and expression," Biotechniques (1989) 7(9):980-990.

Miller, "Retrovirus packaging cells," Hum Gene Ther (1990) 1(1):5-14.

Millrine et al., "A Brighter Side to Thalidomide: Its Potential Use in Immunological Disorders," Trends Mol Med. Apr. 2017;23(4):348-361.

Mitsiades, et al. "Apoptotic signaling induced by immunomodulatory thalidomide analogs in human multiple myeloma cells: therapeutic implications." *Blood, The Journal of the American Society of Hematology* 99.12 (2002): 4525-4530.

Modlich et al. "Leukemias following retroviral transfer of multidrug resistance 1 (MDR1) are driven by combinatorial insertional mutagenesis." *Blood* 105.11 (2005): 4235-4246.

Moreau et al. "Multiple myeloma: ESMO Clinical Practice Guidelines for diagnosis, treatment and follow-up." *Annals of oncology* 28 (2017): iv52-iv61.

Moreau et al. "Oral ixazomib, lenalidomide, and dexamethasone for multiple myeloma." *New England Journal of Medicine* 374.17 (2016): 1621-1634.

Mullen et al., "Transfer of the bacterial gene for cytosine deaminase to mammalian cells confers lethal sensitivity to 5-fluorocytosine: A negative selection system," Proc Natl Acad Sci U.S.A (1992) 89:33-37.

Munshi et al. "Idecabtagene vicleucel (ide-cel; bb2121), a BCMA-targeted CAR T-cell therapy, in patients with relapsed and refractory multiple myeloma (RRMM): Initial KarMMa results." (2020): 8503-8503.

Muranski et al., "Increased intensity lymphodepletion and adoptive immunotherapy—how far can we go?" Nat Clin Pract Oncol (2006) 3(12):668-681.

Neelapu et al. "Chimeric antigen receptor T-cell therapy-assessment and management of toxicities." *Nature reviews Clinical oncology* 15.1 (2018): 47-62.

Neelapu et al., "Axicabtagene Ciloleucel CAR T-Cell Therapy in Refractory Large B- Cell Lymphoma," N Engl J Med (2017) 377(26):2531-2544.

Nijhof et al. "Preclinical evidence for the therapeutic potential of CD38-targeted immuno-chemotherapy in multiple myeloma patients refractory to lenalidomide and bortezomib." *Clinical cancer research* 21.12 (2015): 2802-2810.

Nooka et al. "Clinical efficacy of daratumumab, pomalidomide, and dexamethasone in patients with relapsed or refractory myeloma: Utility of re-treatment with daratumumab among refractory patients." *Cancer* 125.17 (2019): 2991-3000.

Oken et al., "Toxicity and response criteria of the Eastern Cooperative Oncology Group," Am J Clin Oncol (1982) 5(6):649-655.

Oshima et al., "Immunomodulatory drugs (IMiDs)," Nihon Rinsho. (2014) 72(6): 1130-5.

Otahal et al., "Lenalidomide enhances antitumor functions of chimeric antigen receptor modified T cells," Oncoimmunology (2015) 5(4):e1115940.

Overdijk et al. "Antibody-mediated phagocytosis contributes to the anti-tumor activity of the therapeutic antibody daratumumab in lymphoma and multiple myeloma." mAbs (2015) 7(2):311-320.

Paiva et al. "The prognostic value of multiparameter flow cytometry minimal residual disease assessment in relapsed multiple myeloma." *Haematologica* 100.2 (2015): e53.

Palumbo et al. "Daratumumab, bortezomib, and dexamethasone for multiple myeloma." *New England Journal of Medicine* 375.8 (2016): 754-766.

Park et al., "Adoptive transfer of chimeric antigen receptor re-directed cytolytic T lymphocyte clones in patients with neuroblastoma," Mol Ther (2007) 15(4):825-833.

Park et al., "Treating cancer with genetically engineered T cells," Trends Biotechnol (2011) 29(11):550-557.

Park. Managing cytokine release syndrome [slides]. Clinical Care Options Oncol. 2017. Available from: https://www.clinicaloptions.com/oncology/programs/managing-aes/modules/managing-_crs_slides.

Parkhurst et al., "Characterization of genetically modified T-cell receptors that recognize the CEA:691-699 peptide in the context of HLA-A2.1 on human colorectal cancer cells." Clin Cancer Res. (2009) 15:169-180.

Pomalyst®. [Package Insert]. Summit, NJ: Celgene Corporation;2019.

Pont et al. "γ-Secretase inhibition increases efficacy of BCMA-specific chimeric antigen receptor T cells in multiple myeloma." *Blood* 134.19 (2019): 1585-1597.

Porter et al., "Chimeric antigen receptor T cells persist and induce sustained remissions in relapsed refractory chronic lymphocytic leukemia," Sci Transl Med (2015) 7(303):303ra139.

Quach et al., "Mechanism of action of immunomodulatory drugs (IMiDS) in multiple myeloma." Leukemia. 2010 24(1):22-32.

Raje et al. "Anti-BCMA CAR T-cell therapy bb2121 in relapsed or refractory multiple myeloma." *New England Journal of Medicine* 380.18 (2019): 1726-1737.

Rajkumar et al., "Multiple myeloma: diagnosis and treatment." Mayo Clinic Proceedings (2016) 91(1):101-119.

Ramos-Casals et al. "Adult haemophagocytic syndrome." *The Lancet* 383.9927 (2014): 1503-1516.

Ramsay et al., "Multiple inhibitory ligands induce impaired T-cell immunologic synapse function in chronic lymphocytic leukemia that can be blocked with lenalidomide: establishing a reversible immune evasion mechanism in human cancer," Blood. Aug. 16, 2012;120(7):1412-21.

Ramsborg et al., "JCAR017 Is a Defined Composition CAR T Cell Product with Product and Process Controls That Deliver Precise Doses of CD4 and CD8 Car T Cell to Patients with NHL," Blood (2017) 130(Suppl_1):4471.

Ramsborg et al., "JCAR017(lisocabtagene maraleucel; liso-cel) is a Defined Composition CAR T Cell Product with Product and Process Controls That Deliver Precise Doses of CD4 and CD8 CAR T Cells to Patients With NHL," Poster Presentation 4471 at American Society of Hematology 2017, Dec. 9-12, 2017, Atlanta, Georgia.

Reddy et al. "Immunomodulatory drugs stimulate natural killer-cell function, alter cytokine production by dendritic cells, and inhibit angiogenesis enhancing the anti-tumour activity of rituximab in vivo." *British journal of haematology* 140.1 (2008): 36-45.

Reeder et al. "Once-versus twice-weekly bortezomib induction therapy with CyBorD in newly diagnosed multiple myeloma." *Blood, The Journal of the American Society of Hematology* 115.16 (2010): 3416-3417.

Richardson et al. "Extended follow-up of a phase 3 trial in relapsed multiple myeloma: final time-to-event results of the APEX trial." *Blood, The Journal of the American Society of Hematology* 110.10 (2007): 3557-3560.

Richardson et al. "Pomalidomide, bortezomib, and dexamethasone for patients with relapsed or refractory multiple myeloma previously treated with lenalidomide (OPTIMISMM): a randomised, open-label, phase 3 trial." *The Lancet Oncology* 20.6 (2019): 781-794.

Riddell et al., "Phase I Study of Cellular Adoptive Immunotherapy Using Genetically Modified CD8+ HIV-Specific T Cells for HIV Seropositive Patients Undergoing Allogeneic Bone Marrow Transplant," Human Gene Therapy (1992) 3:319-338.

RoActemra® [Summary of Product Characteristics]. Welwyn Garden City, United Kingdom: Roche Products Limited, 2019.

Rosenberg et al., "Durable Complete Responses in Heavily Pretreated Patients with Metastatic Melanoma Using T-Cell Transfer Immunotherapy," Clin Cancer Res (2011) 17(13):4550-4557.

Rosenberg, "Cell transfer immunotherapy for metastatic solid cancer—what clinicians need to know," Nat Rev Clin Oncol (2011) 8(10):577-585.

Rothe et al. "Biosafety challenges for use of lentiviral vectors in gene therapy." *Current gene therapy* 13.6 (2013): 453-468.

(56) References Cited

OTHER PUBLICATIONS

Sadelain et al., "The basic principles of chimeric antigen receptor (CAR) design," Cancer Discov (2013) 3(4):388-398.
Sanchez et al. "The role of B-cell maturation antigen in the biology and management of, and as a potential therapeutic target in, multiple myeloma." *Targeted oncology* 13.1 (2018): 39-47.
San-Miguel et al. "Panobinostat plus bortezomib and dexamethasone versus placebo plus bortezomib and dexamethasone in patients with relapsed or relapsed and refractory multiple myeloma: a multicentre, randomised, double-blind phase 3 trial." *The lancet oncology* 15.11 (2014): 1195-1206.
San-Miguel et al., New approaches to myeloma treatment in 2017. Hematology Education: the Education Program for the Annual Congress of the European Hematology Association. (2017)11(1):9-12.
Savoldo et al., "CD28 costimulation improves expansion and persistence of chimeric antigen receptor-modified T cells in lymphoma patients," J Clin Invest (2011) 121(5):1822-1826.
Scarpa et al., "Characterization of recombinant helper retroviruses from Moloney-based vectors in ecotropic and amphotropic packaging cell lines," Virology (1991) 180(2):849-852.
Schlueter et al., "Specificity and Binding Properties of a Single-chain T Cell Receptor," J Mol Biol (1996) 256(5):859-869.
Scholler et al. "Decade-long safety and function of retroviral-modified chimeric antigen receptor T cells." *Science translational medicine* 4.132 (2012): 132ra53-132ra53.
Schuler et al., "SYFPEITHI: database for searching and T-cell epitope prediction," Methods Mol Biol. (2007) 409: 75-93.
Schulert et al. "Pathogenesis of macrophage activation syndrome and potential for cytokine-directed therapies." *Annual review of medicine* 66 (2015): 145-159.
Schuster et al. "Primary analysis of Juliet: a global, pivotal, phase 2 trial of CTL019 in adult patients with relapsed or refractory diffuse large B-cell lymphoma." Blood (2017) 130(Supplement 1):577.
Seckinger et al. "Target expression, generation, preclinical activity, and pharmacokinetics of the BCMA-T cell bispecific antibody EM801 for multiple myeloma treatment." *Cancer cell* 31.3 (2017): 396-410.
Sharma et al., "Efficient Sleeping Beauty DNA Transposition From DNA Minicircles," Molec Ther Nucl Acids (2013) 2:e74.
Siddiqi et al., "Patient Characteristics and Pre-Infusion Biomarkers of Inflammation Correlate with Clinical Outcomes after Treatment with the Defined Composition, CD19-Targeted Car T Cell Product, JCAR017," Oral Presentation 193 at American Society of Hematology 2017, Dec. 9-12, 2017, Atlanta, Georgia.
Siddiqi, et al. Patient Characteristics and Pre-Infusion Biomarkers of Inflammation Correlate with Clinical Outcomes after Treatment with the Defined Composition, CD19-Targeted Car T Cell Product, JCAR017. Presented at ASH 2017.Blood. 2017; 130(1): Abstract 193.
Siegel et al. "Pomalidomide, dexamethasone, and daratumumab in relapsed refractory multiple myeloma after lenalidomide treatment." *Leukemia* 34.12 (2020): 3286-3297.
Siegel et all. "Cancer statistics, 2020." *CA: a cancer journal for clinicians* 70.1 (2020): 7-30.
Singh et al., "ProPred: prediction of HLA-DR binding sites," Bioinformatics (2001) 17(12):1236-1237.
Sommermeyer et al., "Chimeric antigen receptor-modified T cells derived from defined CD8+ and CD4+ subsets confer superior antitumor reactivity in vivo," Leukemia (2016) 30(2):492-500.
Song et al. "Real-world treatment patterns, comorbidities, and disease-related complications in patients with multiple myeloma in the United States." *Current medical research and opinion* 32.1 (2016): 95-103.
Soni et al. "Iberdomide Increases the Potency of the Anti-BCMA CAR T Cell Product Orvacabtagene Autoleucel (Orva-Cel)." Molecular Therapy. vol. 28. No. 4. 50 Hampshire St, Floor 5, Cambridge, MA 02139 USA: Cell Press, 2020.

Sonneveld et al. "How have evolutions in strategies for the treatment of relapsed/refractory multiple myeloma translated into improved outcomes for patients?." *Critical reviews in oncology/hematology* 112 (2017): 153-170.
Soo Hoo et al., "Characterization of a single-chain T-cell receptor expressed in *Escherichia coli*," PNAS (1992) 89(10):4759-4763.
Stewart et al. "Carfilzomib, lenalidomide, and dexamethasone for relapsed multiple myeloma." *New England Journal of Medicine* 372.2 (2015): 142-152.
Swerdlow et al., "The 2016 Revision of the World Health Organization Classification of Lymphoid Neoplasms," Blood (2016) 127(20): 2375-2390.
Szoka et al., "Comparative properties and methods of preparation of lipid vesicles (liposomes)," Annu Rev Biophys Bioeng. (1980) 9:467-508.
Teachey et al. "Identification of predictive biomarkers for cytokine release syndrome after chimeric antigen receptor T-cell therapy for acute lymphoblastic leukemia." *Cancer discovery* 6.6 (2016): 664-679.
Terakura et al., "Generation of CD19-chimeric antigen receptor modified CD8+ T cells derived from virus-specific central memory T cells," Blood (2012) 119(1):72-82.
Themeli et al., "Generation of tumor-targeted human T lymphocytes from induced pluripotent stem cells for cancer therapy," Nat Biotechnol (2013) 31(10):928-933.
Thompson et al. "Markers of initial and long-term responses to idecabtagene vicleucel (Ide-Cel; bb2121) in the CRB-401 Study in Relapsed/Refractory Multiple Myeloma." (2019): 4328-4328.
Tsukahara et al., "CD19 target-engineered T-cells accumulate at tumor lesions in human B-cell lymphoma xenograft mouse models," Biochem Biophys Res Commun (2013) 438(1):84-89.
Turtle et al., "Engineered T cells for anti-cancer therapy," Engineered T cells for anti-cancer therapy, Curr Opin Immunol (2012) 24(5):633-639.
Turtle et al., "Immunotherapy of non-Hodgkin's lymphoma with a defined ratio of CD8+ and CD4+ CD19-specific chimeric antigen receptor-modified T cells," Sci Transl Med (2016) 8(355):355ra116.
Turtle et al., "Rate of durable complete response in ALL, NHL, and CLL after immunotherapy with optimized lymphodepletion and defined composition CD19 CAR-T cells," J Clin Oncol (2016) 34(15 Suppl): 102.
Turtle et al., "CD19 CAR-T cells of defined CD4+:CD8+ composition in adult B cell ALL patients," J Clin Invest. 2016;126(6):2123-2138.
Ullenhag et al., "Clinical and immune effects of lenalidomide in combination with gemcitabine in patients with advanced pancreatic cancer," PLOS One (2017) 12(1):e0169736.
Usmani et al. "Analysis of real-world data on overall survival in multiple myeloma patients with> 3 prior lines of therapy including a proteasome inhibitor (PI) and an immunomodulatory drug (IMID), or double refractory to a PI and an IMiD." *The oncologist* 21.11 (2016): 1355.
Van Den Neste et al., "Outcome of patients with relapsed diffuse large B-cell lymphoma who fail second-line salvage regimens in the International CORAL study," Bone Marrow Transplant (2016) 51(1):51-7.
Van Tendeloo et al., "High-level transgene expression in primary human T lymphocytes and adult bone marrow CD34+ cells via electroporation-mediated gene delivery," Gene Therapy (2000) 7(16): 1431-1437.
Varela-Rohena et al., "Control of HIV-1 immune escape by CD8 T cells expressing enhanced T-cell receptor," Nat Med. (2008) 14:1390-1395.
Velcade. [Summary of Product Characteristics]. Beerse, Belgium: Janssen-Cilag International NV; 2019. Available from: http://www.ema.europa.eu/docs/en_GB/document_library/EPAR_-_Product_Information/human/000539/WC500048471.pdf.
Velcade®. [Package Insert]. Cambridge, MA: Millennium Pharmaceuticals, Inc.; 2019. Available from: https://www.accessdata.fda.gov/drugsatfda_docs/label/2017/021602s043lbl.pdf.
Verhoeyen et al., "Lentiviral vector gene transfer into human T cells," Methods Mol Biol (2009) 506:97-114.

(56) References Cited

OTHER PUBLICATIONS

Wang et al. "Analysis of lentiviral vector integration in HIV+ study subjects receiving autologous infusions of gene modified CD4+ T cells." *Molecular therapy* 17.5 (2009): 844-850.
Wang et al., "Lenalidomide Enhances the Function of CS1 Chimeric Antigen Receptor Redirected-T Cells Against Multiple Myeloma." Blood. Dec. 2016; 128:812.
Wang et al., "Lenalidomide Enhances the Function of CS1 Chimeric Antigen Receptor Redirected-T Cells Against Multiple Myeloma." Clin. Cancer Res. (2018) 24(1):106-119.
Wang et al., "Phenotypic and Functional Attributes of Lentivirus Modified CD19-specific Human CD8+ Central Memory T Cells Manufactured at Clinical Scale," J Immunother (2012) 35(9):689-701.
Wigler et al., "Transfer of Purified Herpes Virus Thymidine Kinase Gene to Cultured Mouse Cells." Cell (1997) 2:223.
Works et al., "Lenalidomide Enhances Anti-BCMA Chimeric Antigen Receptor T Cell Function Against Multiple Myeloma," Blood (2017) 130:1794.
Works et al., "Lenalidomide Enhances Anti-BCMA Chimeric Antigen Receptor T Cell Function Against Multiple Myeloma," Poster Presentation at American Society of Hematology 2017, Dec. 9-12, 2017, Atlanta, Georgia.
Wu et al., "Acalabrutinib (ACP-196): a selective second-generation BTK inhibitor," Journal of Hematology & Oncology (2016) 9:Article No. 21.
Wu et al., "Adoptive T-cell therapy using autologous tumor-infiltrating lymphocytes for metastatic melanoma: current status and future outlook," Cancer J (2012) 18(2):160-175.
Wulfing et al., "Correctly folded T-cell receptor fragments in the periplasm of *Escherichia coli*. Influence of folding catalysts," J Mol Biol (1994) 242(5):655-669.
Xu et al., "Cytokine release syndrome in cancer immunotherapy with chimeric antigen receptor engineered T cells," Cancer Letters (2014) 343:172-78.
Yong et al. "Multiple myeloma: patient outcomes in real-world practice." *British journal of haematology* 175.2 (2016): 252-264.
Yuan et al. "Bayesian optimal interval design: a simple and well-performing design for phase I oncology trials." *Clinical Cancer Research* 22.17 (2016): 4291-4301.
Yuen et al. "Abstract CT048: population pharmacokinetics and pharmacodynamics for an oral Notch inhibitor, LY3039478, in the first-in-man study." Cancer Research (2016) 76(14_Supplement): CT048.
Zamagni et al. "PET/CT improves the definition of complete response and allows to detect otherwise unidentifiable skeletal progression in multiple myeloma." *Clinical Cancer Research* 21.19 (2015): 4384-4390.
Zhao et al., "Structural Design of Engineered Costimulation Determines Tumor Rejection Kinetics and Persistence of CAR T Cells," Cancer Cell (2015) 28(4):415-428.
Zheng et al., "Enhancing adoptive cell therapy of cancer through targete delivery of small-molecule immunomodulators to internalizing or noninternalizing receptors," ACS NANO (2017) 11(3):3089-3100.
Zhu et al. "Cereblon expression is required for the antimyeloma activity of lenalidomide and pomalidomide." *Blood, The Journal of the American Society of Hematology* 118.18 (2011): 4771-4779.

\* cited by examiner

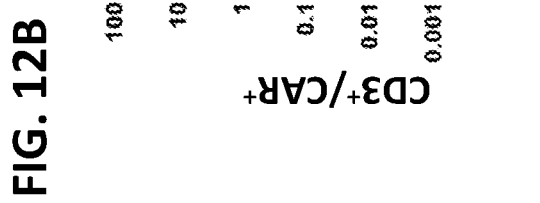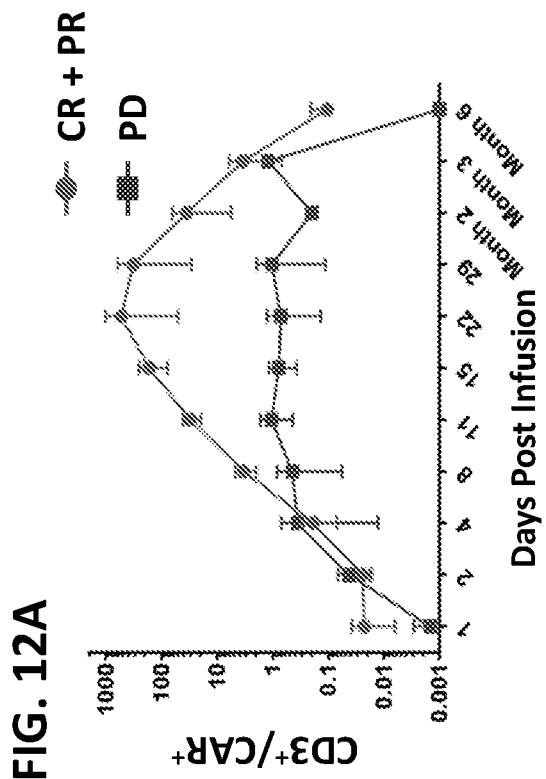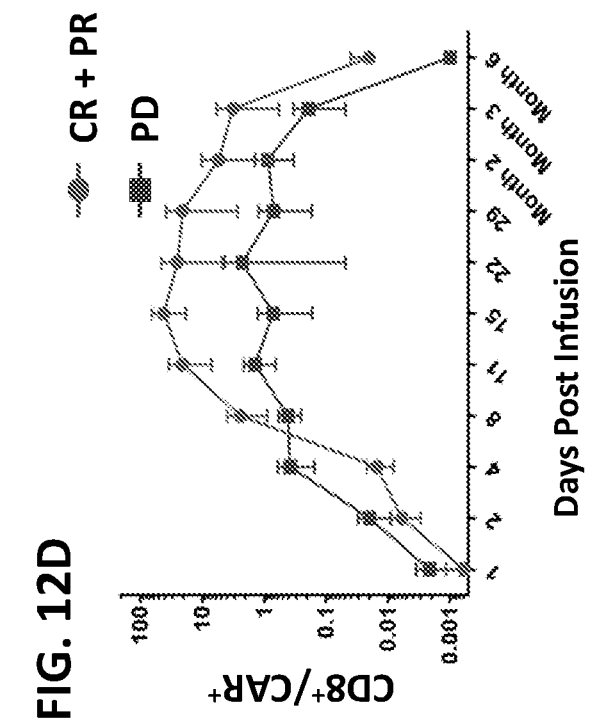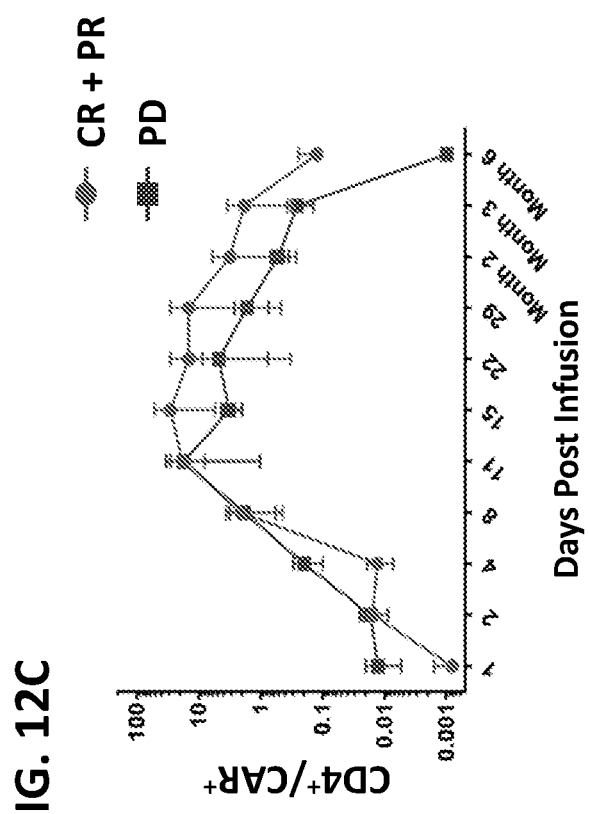

FIG. 18A
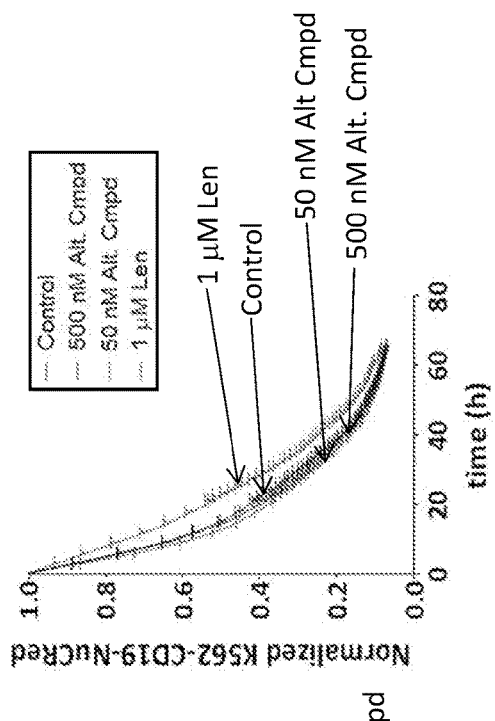
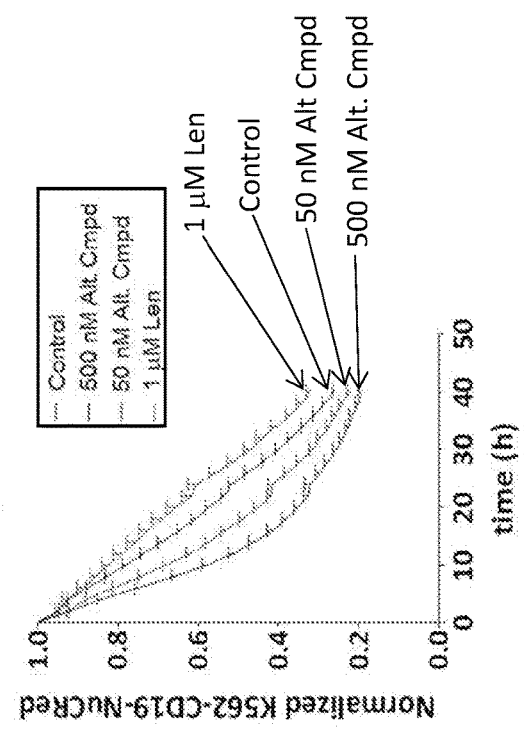
2nd Stimulation
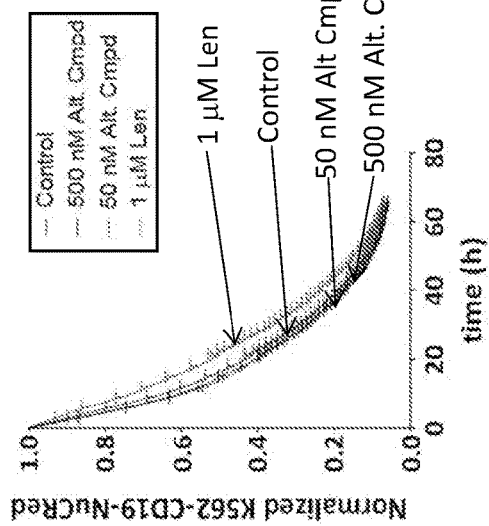
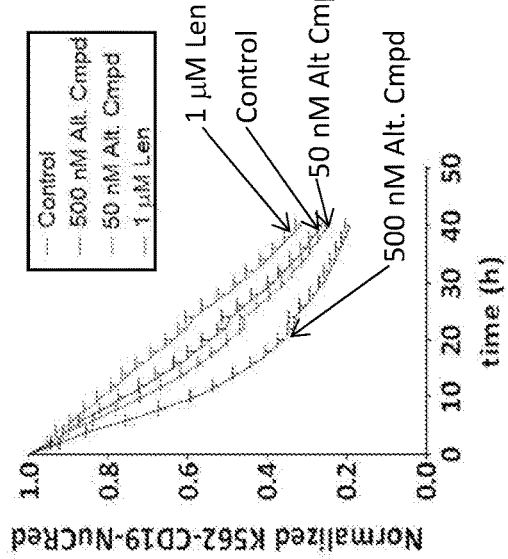
4th Stimulation

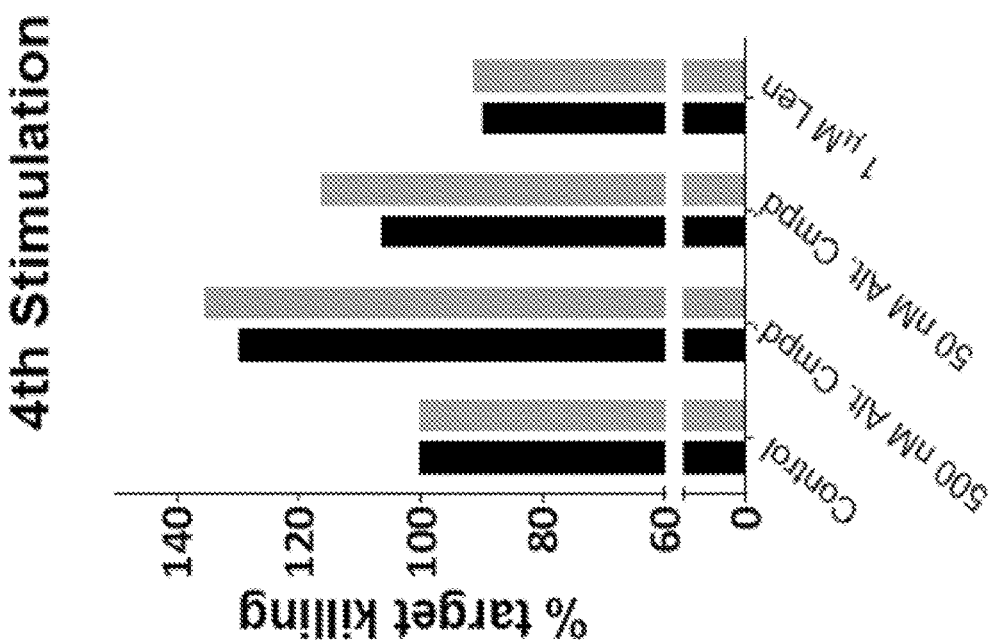
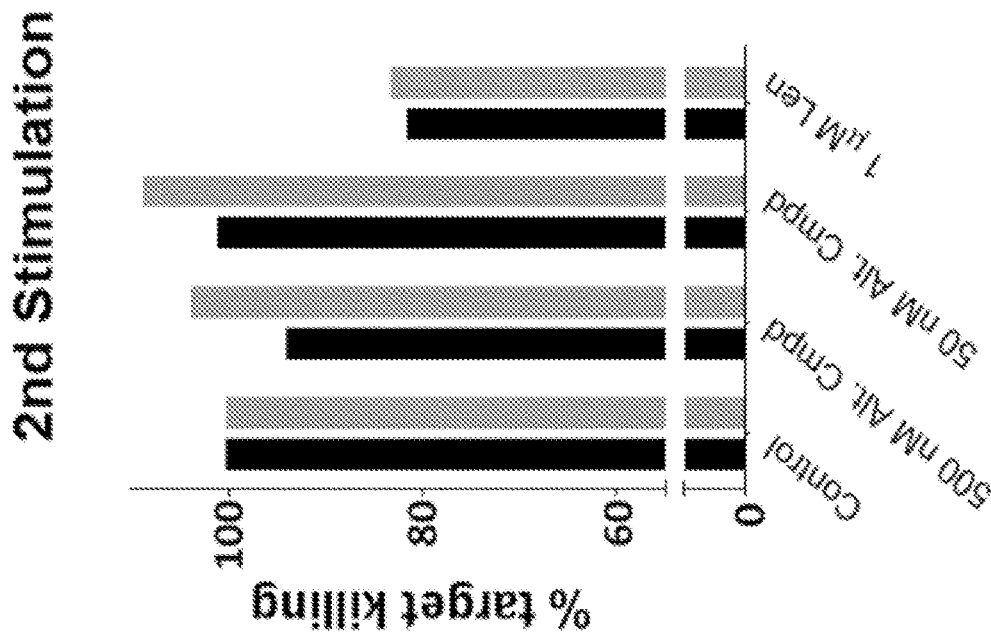
FIG. 18B

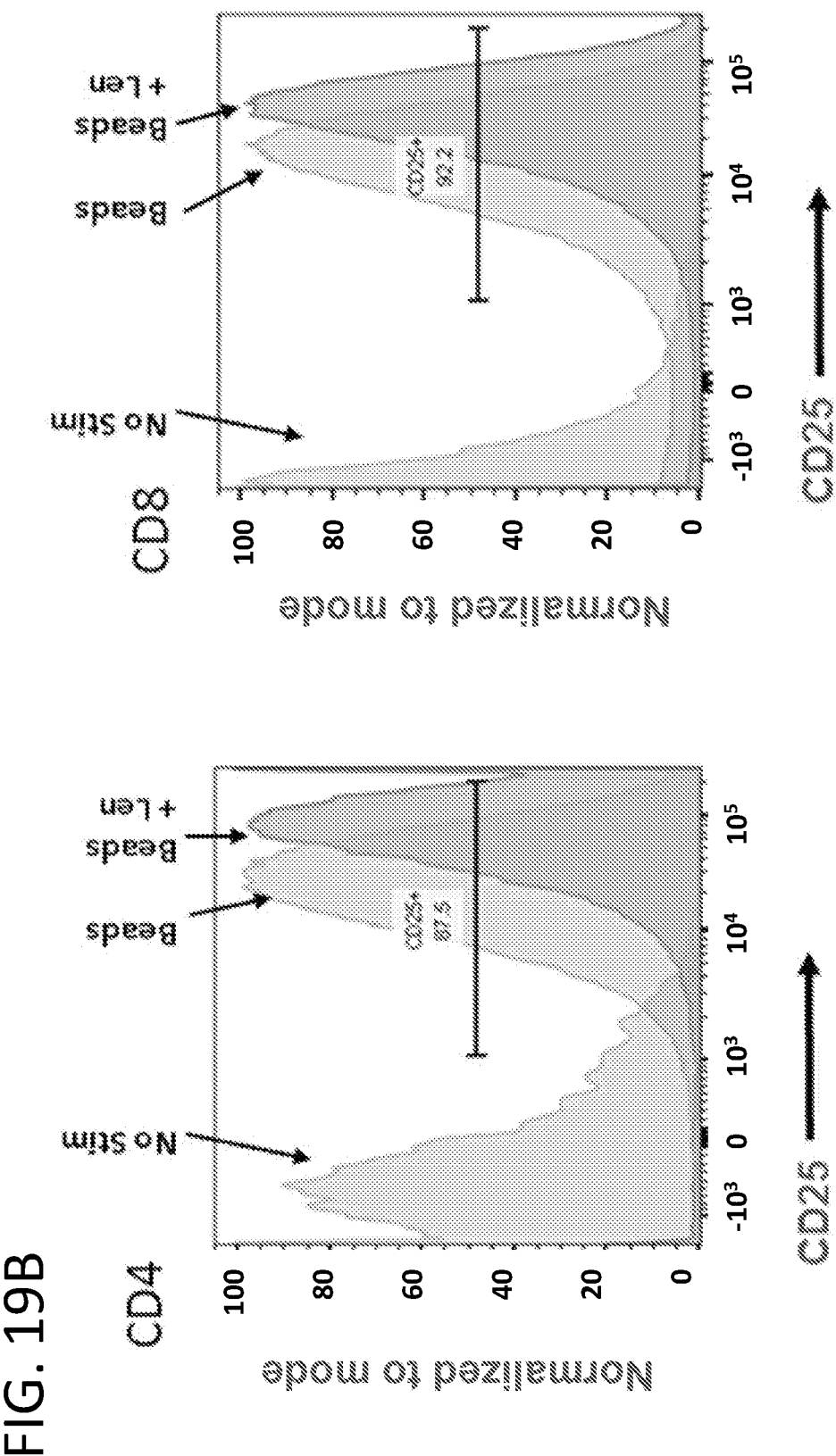

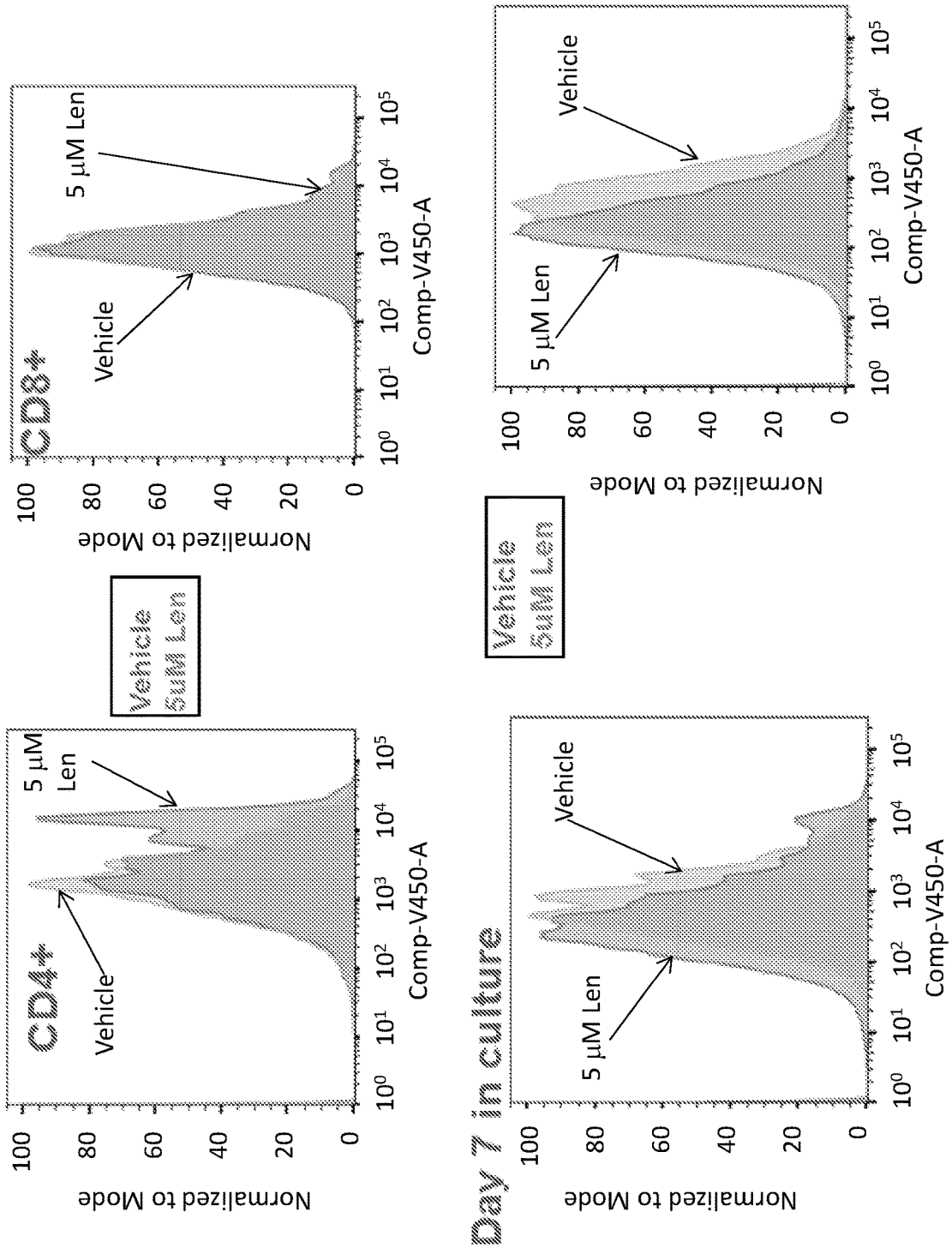
FIG. 21G Day 4 in culture Cell trace violet dye dilution assay

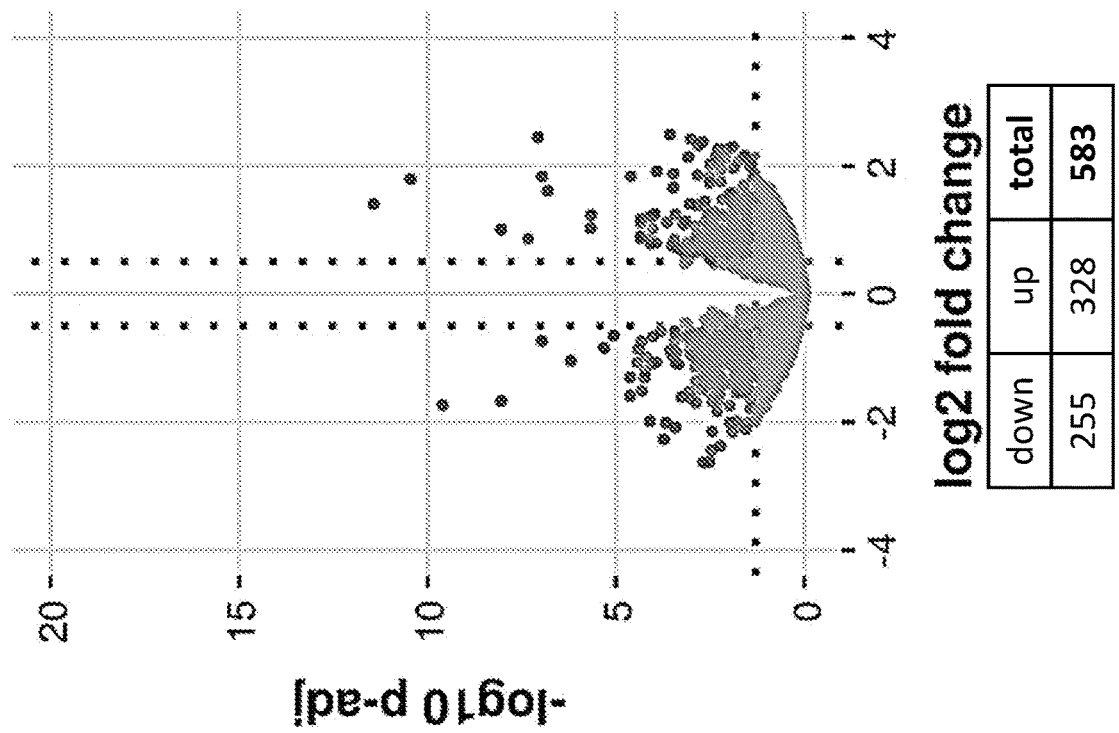
FIG. 27A  24hr: Len/Vehicle
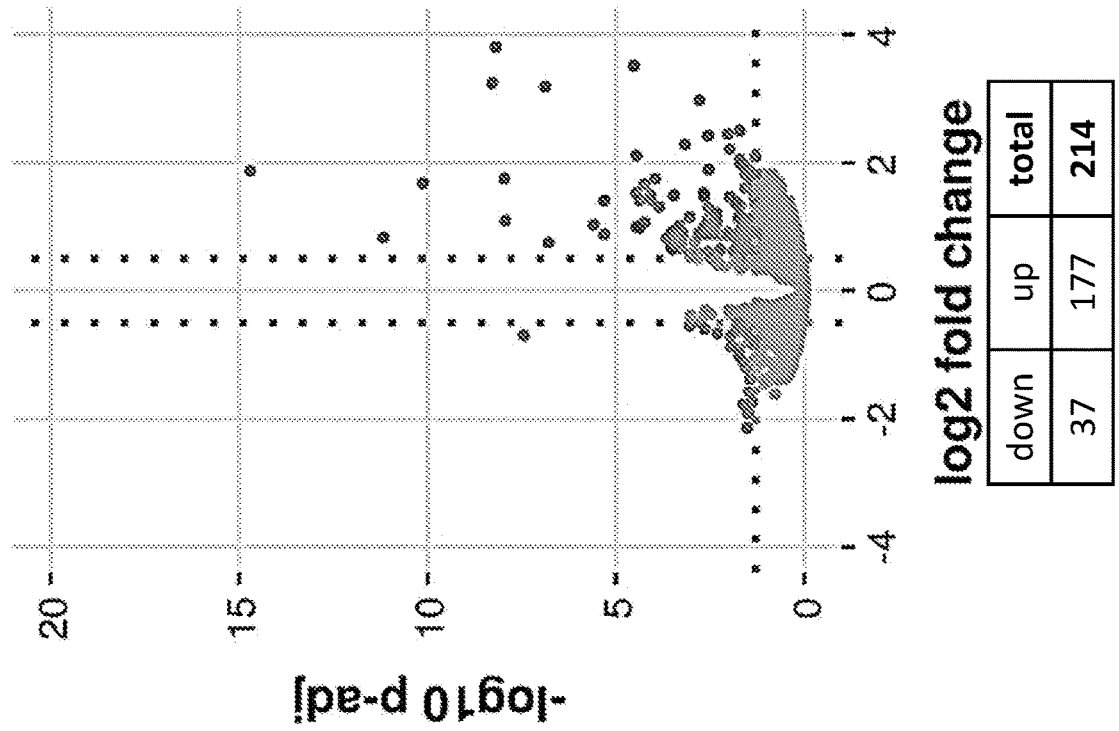
FIG. 27B  d7: Len/Vehicle

FIG. 30

| Motif Name | Motif | Log P-value | % of Target Sequences with Motif |
|---|---|---|---|
| Atf3(bZIP)/GBM-ATF3 | ssATGASTCAtss | -7.66E+01 | 61.90% |
| BATF(bZIP)/Th17-BATF | ssATGASTCAt | -7.54E+01 | 61.56% |
| Fra1(bZIP)/BT549-Fra1 | ssATGASTCAts | -7.39E+01 | 58.50% |
| AP-1(bZIP)/ThioMac-PU.1 | sTGASTCAs | -7.33E+01 | 62.24% |
| JunB(bZIP)/DendriticCells-Junb | ssTGASTCAt | -7.17E+01 | 58.16% |
| FosI2(bZIP)/3T3L1-Fosl2 | ssATGASTCAtss | -6.18E+01 | 46.94% |
| Jun-AP1(bZIP)/K562-cJun | ssATGASTCAtss | -5.14E+01 | 39.12% |
| Smad3(MAD)/NPC-Smad3 | sTGTCTs | -4.50E+01 | 56.46% |
| NFkB-p65(RHD)/GM12787-p65 | sGGGATTTCCC | -4.41E+01 | 29.59% |
| RUNX1(Runt)/Jurkat-RUNX1 | sAACCACAs | -4.04E+01 | 50.00% |
| RUNX(Runt)/HPC7-Runx1 | sAAACCACAs | -3.77E+01 | 41.16% |
| Bach2(bZIP)/OCILy7-Bach2 | TGCTGAGTCA | -3.62E+01 | 26.53% |

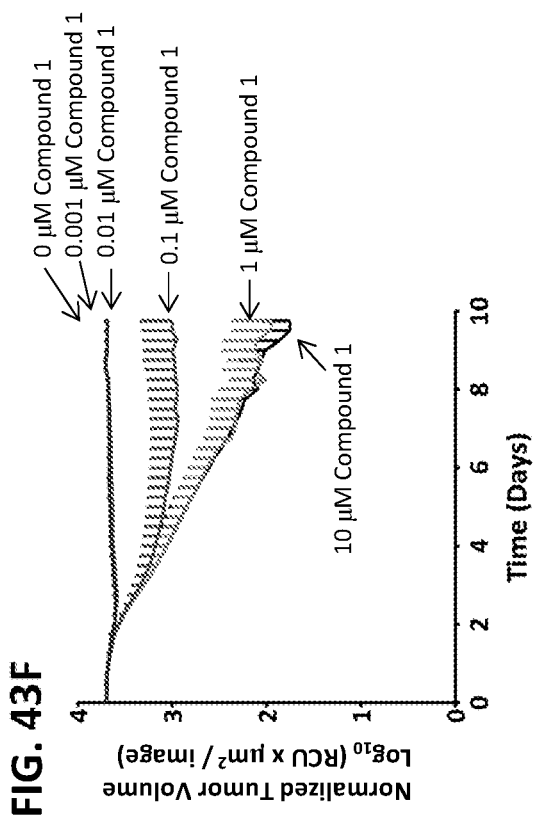
FIG. 43F
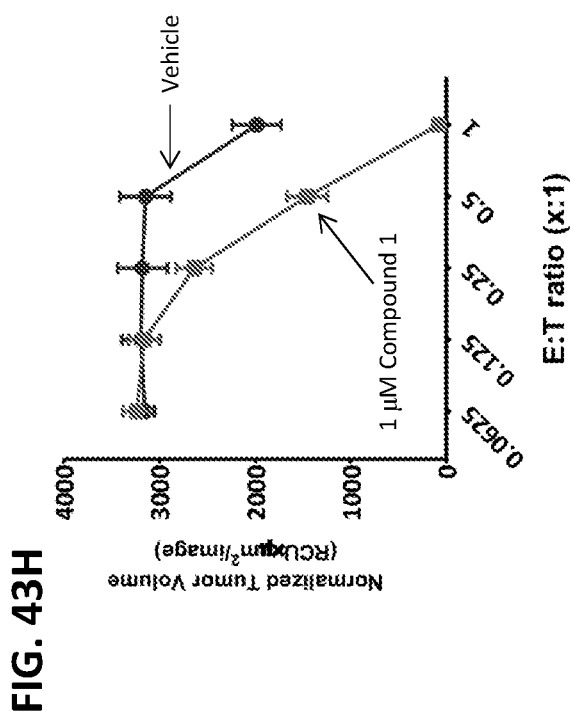
FIG. 43H
FIG. 43G

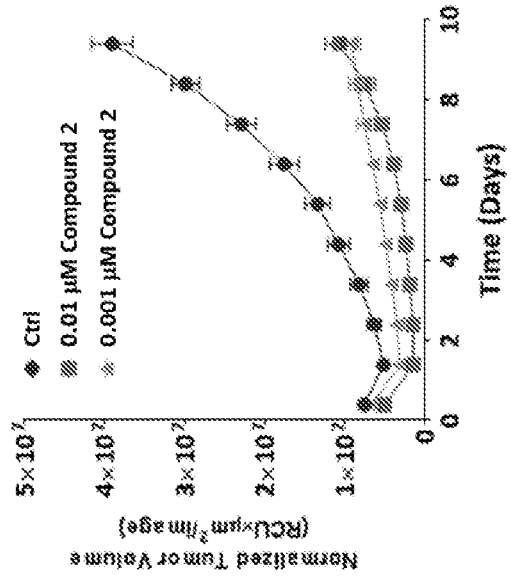
FIG. 48C
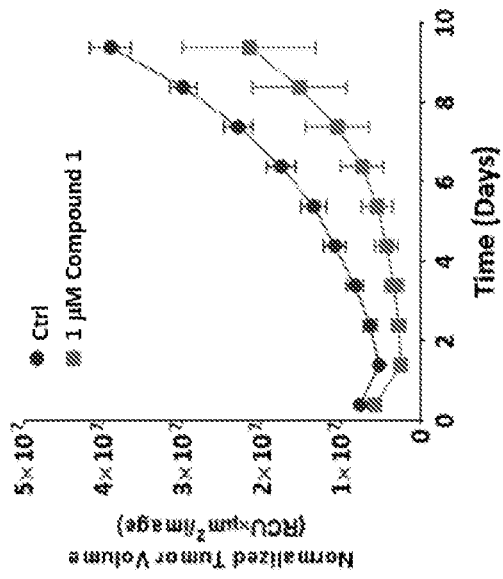
FIG. 48D
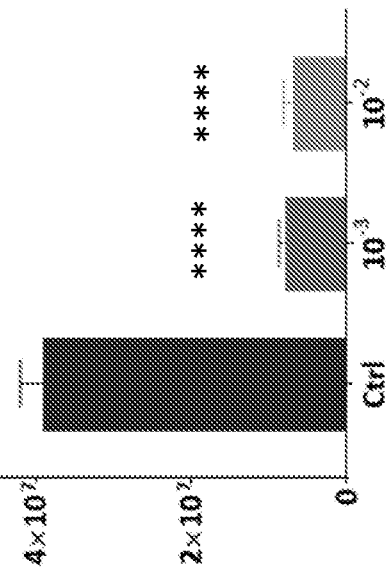

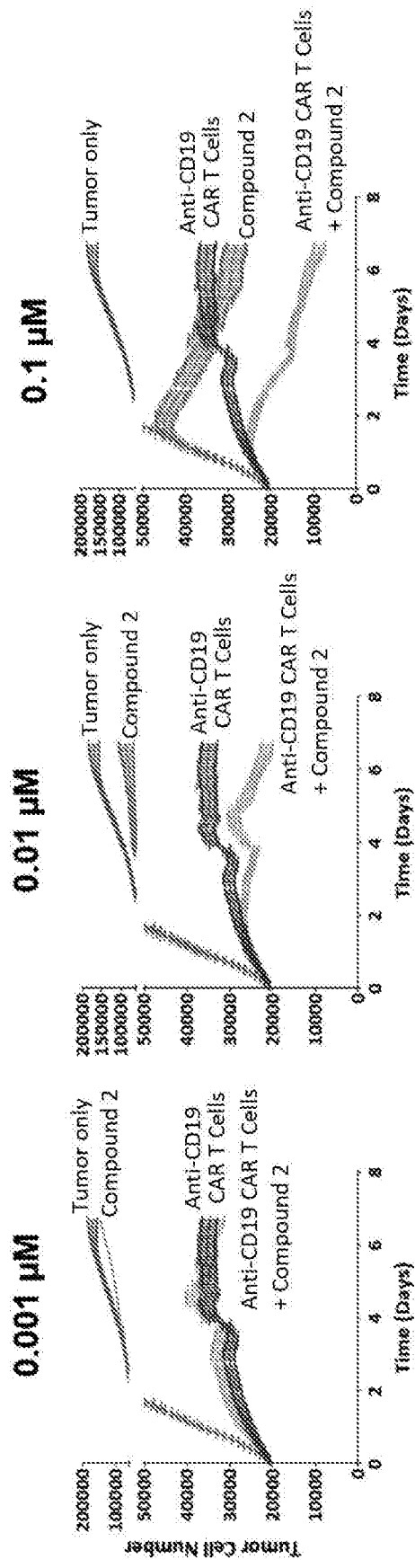
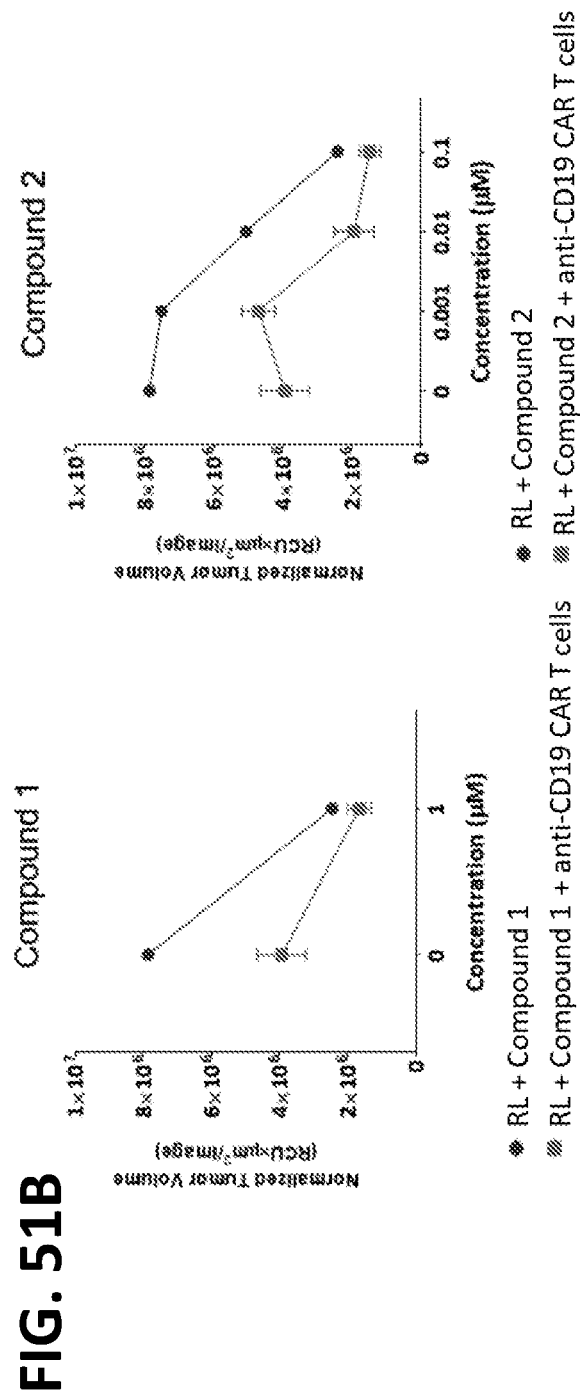
FIG. 51A
FIG. 51B

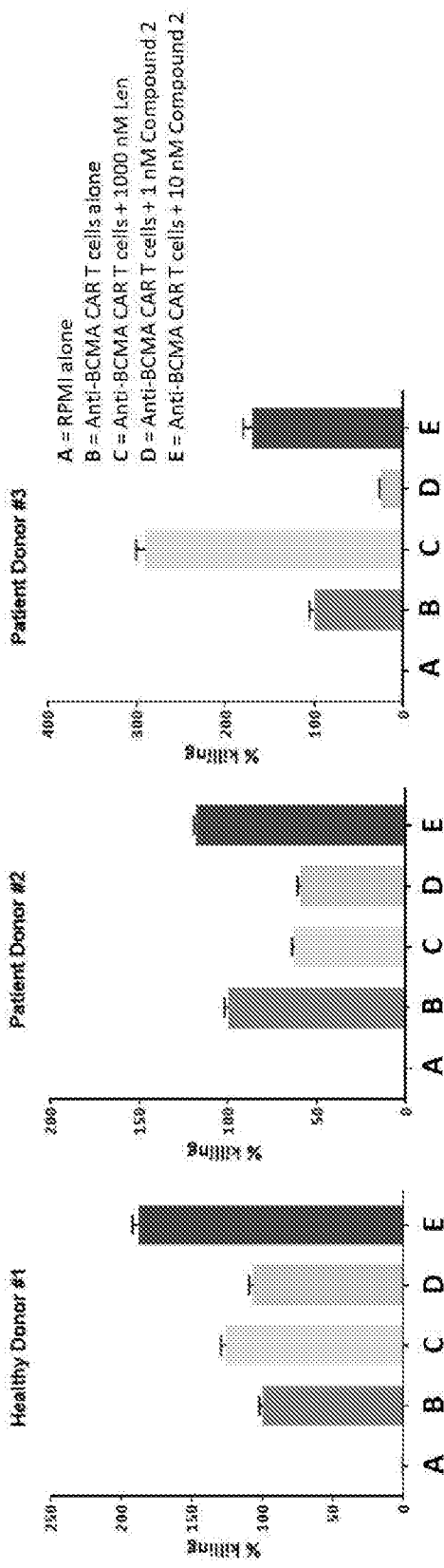
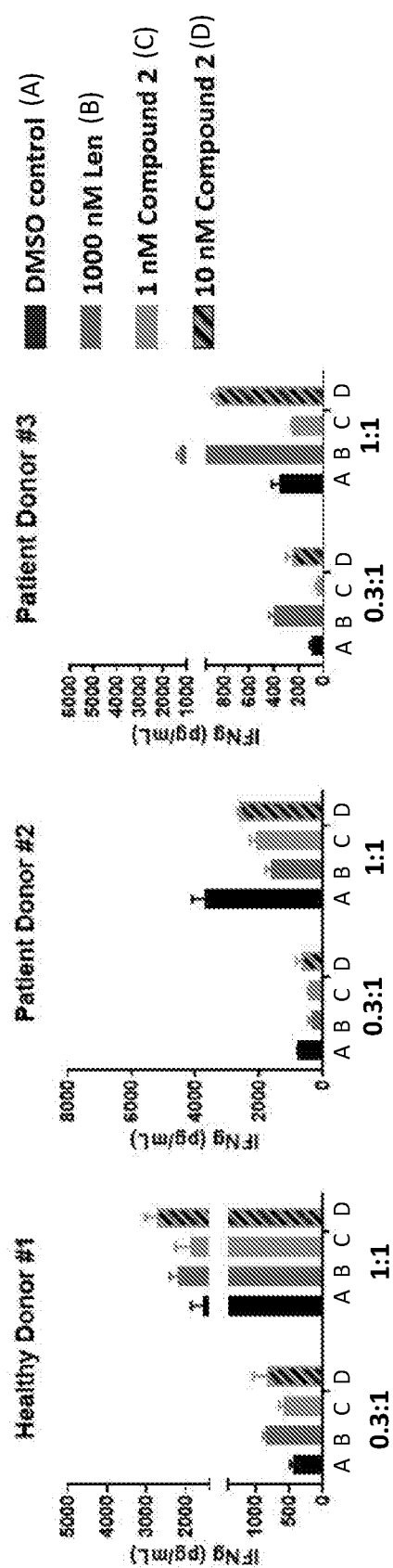
FIG. 53A
FIG. 53B

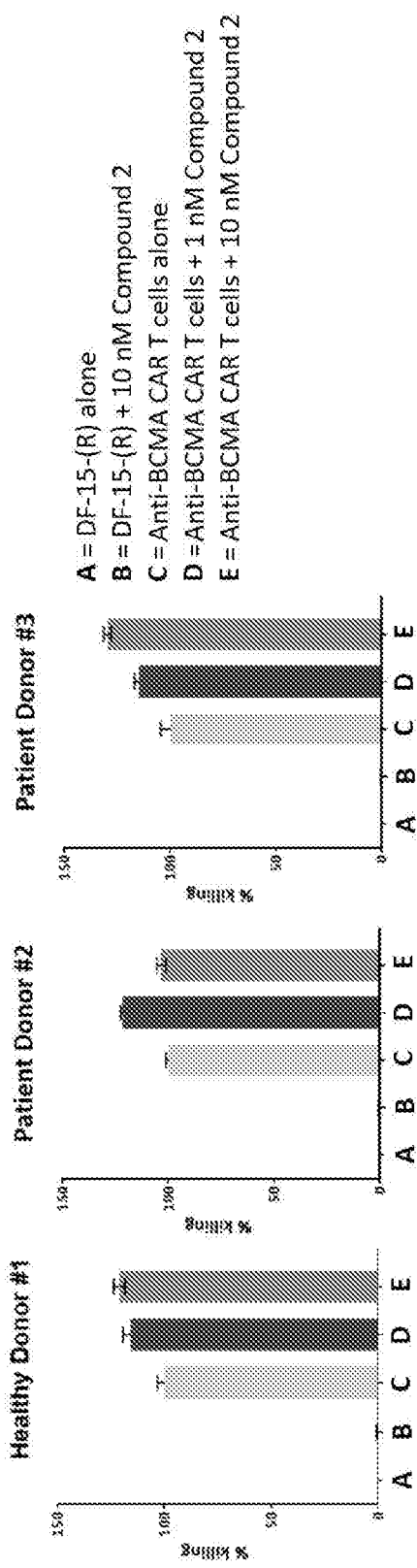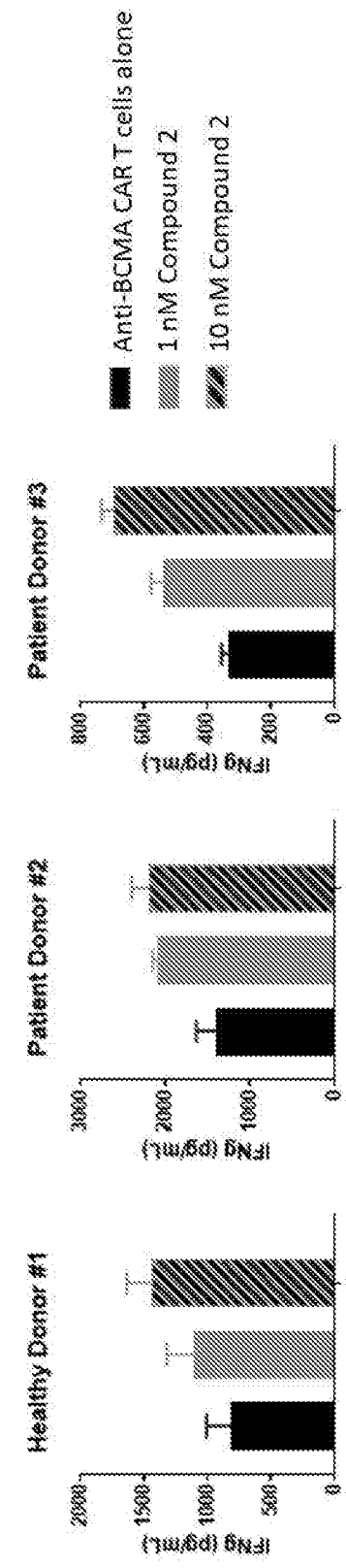
FIG. 55A
FIG. 55B

SEQUENCE LISTING

<160> NUMBER OF SEQ ID NOS: 189

<210> SEQ ID NO 1
<211> LENGTH: 12
<212> TYPE: PRT
<213> ORGANISM: Homo sapiens
<220> FEATURE:
<223> OTHER INFORMATION: spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: spacer (IgG4hinge)

<400> SEQUENCE: 2
gaatctaagt acggaccgcc ctgccccct tgccct                                  36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Gln Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

```
Ser Gln Glu Asp Pro Glu Val Gln Phe Asn Trp Tyr Val Asp Gly Val
 50                  55                  60

Glu Val His Asn Ala Lys Thr Lys Pro Arg Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
                180                 185                 190

Thr Val Asp Lys Ser Arg Trp Gln Gln Gly Asn Val Phe Ser Cys Ser
                195                 200                 205

Val Met His Glu Ala Leu His Asn His Tyr Thr Gln Lys Ser Leu Ser
210                 215                 220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
 1               5                   10                  15

Gln Pro Gln Ala Glu Gly Ser Leu Ala Lys Ala Thr Thr Ala Pro Ala
                 20                  25                  30

Thr Thr Arg Asn Thr Gly Arg Gly Gly Glu Glu Lys Lys Lys Glu Lys
             35                  40                  45

Glu Lys Glu Glu Gln Glu Glu Arg Glu Thr Lys Thr Pro Glu Cys Pro
 50                  55                  60

Ser His Thr Gln Pro Leu Gly Val Tyr Leu Leu Thr Pro Ala Val Gln
 65                  70                  75                  80

Asp Leu Trp Leu Arg Asp Lys Ala Thr Phe Thr Cys Phe Val Val Gly
                 85                  90                  95

Ser Asp Leu Lys Asp Ala His Leu Thr Trp Glu Val Ala Gly Lys Val
                100                 105                 110

Pro Thr Gly Gly Val Glu Glu Gly Leu Leu Glu Arg His Ser Asn Gly
            115                 120                 125

Ser Gln Ser Gln His Ser Arg Leu Thr Leu Pro Arg Ser Leu Trp Asn
        130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175
```

```
Leu Ser Leu Asn Leu Leu Ala Ser Ser Asp Pro Pro Glu Ala Ala Ser
                180                 185                 190

Trp Leu Leu Cys Glu Val Ser Gly Phe Ser Pro Pro Asn Ile Leu Leu
            195                 200                 205

Met Trp Leu Glu Asp Gln Arg Glu Val Asn Thr Ser Gly Phe Ala Pro
    210                 215                 220

Ala Arg Pro Pro Gln Pro Gly Ser Thr Thr Phe Trp Ala Trp Ser
225                 230                 235                 240

Val Leu Arg Val Pro Ala Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
            275                 280

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 7
<211> LENGTH: 335
<212> TYPE: PRT
<213> ORGANISM: Artificial Sequence
<220> FEATURE:
<223> OTHER INFORMATION: tEGFR

<400> SEQUENCE: 7

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
```

```
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
            210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
            275                 280                 285

Pro Asn Cys Thr Tyr Gly Cys Thr Gly Pro Gly Leu Glu Gly Cys Pro
            290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 8
<211> LENGTH: 27
<212> TYPE: PRT
<213> ORGANISM: Homo sapiens
<220> FEATURE:
<223> OTHER INFORMATION: CD28 (amino acids 153-179 of Accession No.
      P10747)

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<223> OTHER INFORMATION: CD28 (amino acids 114-179 of Accession No.
      P10747)

<400> SEQUENCE: 9

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
        50                  55                  60

Trp Val
65

<210> SEQ ID NO 10
<211> LENGTH: 41
<212> TYPE: PRT
```

```
<213> ORGANISM: Homo sapiens
<220> FEATURE:
<223> OTHER INFORMATION: CD28 (amino acids 180-220 of P10747)

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 11
<211> LENGTH: 41
<212> TYPE: PRT
<213> ORGANISM: Homo sapiens
<220> FEATURE:
<223> OTHER INFORMATION: CD28 (LL to GG)

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 12
<211> LENGTH: 42
<212> TYPE: PRT
<213> ORGANISM: Homo sapiens
<220> FEATURE:
<223> OTHER INFORMATION: 4-1BB (amino acids 214-255 of Q07011.1)

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
```

```
                     85                  90                  95

Thr Lys Asp Thr Tyr Asp Ala Leu His Met Gln Ala Leu Pro Pro Arg
                100                 105                 110

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 16
<211> LENGTH: 29
<212> TYPE: PRT
<213> ORGANISM: Artificial Sequence
<220> FEATURE:
<223> OTHER INFORMATION: Linker

<400> SEQUENCE: 16

Pro Gly Gly Gly Ser Gly Gly Gly Ser Gly Gly Gly Gly Ser Gly
1               5                   10                  15
```

Gly Gly Gly Ser Gly Gly Gly Ser Gly Gly Gly
            20                  25

<210> SEQ ID NO 17
<211> LENGTH: 17
<212> TYPE: PRT
<213> ORGANISM: Artificial Sequence
<220> FEATURE:
<223> OTHER INFORMATION: Linker

<400> SEQUENCE: 17

Gly Ser Ala Asp Asp Ala Lys Lys Asp Ala Ala Lys Lys Asp Gly Lys
1               5                   10                  15

Ser

<210> SEQ ID NO 18
<211> LENGTH: 54
<212> TYPE: PRT
<213> ORGANISM: Homo sapiens
<220> FEATURE:
<223> OTHER INFORMATION: Extracellular domain of human BCMA (GenBank No.
      NP_001183.2)

<400> SEQUENCE: 18

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50

<210> SEQ ID NO 19
<211> LENGTH: 5
<212> TYPE: PRT
<213> ORGANISM: Artificial Sequence
<220> FEATURE:
<223> OTHER INFORMATION: Linker sequence

<400> SEQUENCE: 19

Gly Gly Gly Gly Ser
1               5

<210> SEQ ID NO 20
<211> LENGTH: 231
<212> TYPE: PRT
<213> ORGANISM: Artificial Sequence
<220> FEATURE:
<223> OTHER INFORMATION: Modified Human IgG1 Fc

<400> SEQUENCE: 20

Pro Lys Ser Ser Asp Lys Thr His Thr Cys Pro Pro Cys Pro Ala Pro
1               5                   10                  15

Glu Ala Glu Gly Ala Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

```
Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ser Ser Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 21
<211> LENGTH: 16
<212> TYPE: PRT
<213> ORGANISM: Artificial Sequence
<220> FEATURE:
<223> OTHER INFORMATION: CD33 Signal peptide

<400> SEQUENCE: 21

Met Pro Leu Leu Leu Leu Leu Pro Leu Leu Trp Ala Gly Ala Leu Ala
1               5                   10                  15

<210> SEQ ID NO 22
<211> LENGTH: 306
<212> TYPE: PRT
<213> ORGANISM: Artificial Sequence
<220> FEATURE:
<223> OTHER INFORMATION: BCMA-Fc construct

<400> SEQUENCE: 22

Met Pro Leu Leu Leu Leu Leu Pro Leu Leu Trp Ala Gly Ala Leu Ala
1               5                   10                  15

Met Leu Gln Met Ala Gly Gln Cys Ser Gln Asn Glu Tyr Phe Asp Ser
            20                  25                  30

Leu Leu His Ala Cys Ile Pro Cys Gln Leu Arg Cys Ser Ser Asn Thr
        35                  40                  45

Pro Pro Leu Thr Cys Gln Arg Tyr Cys Asn Ala Ser Val Thr Asn Ser
    50                  55                  60

Val Lys Gly Thr Asn Ala Gly Gly Gly Ser Pro Lys Ser Ser Asp
65                  70                  75                  80

Lys Thr His Thr Cys Pro Pro Cys Pro Ala Pro Glu Ala Glu Gly Ala
                85                  90                  95

Pro Ser Val Phe Leu Phe Pro Pro Lys Pro Lys Asp Thr Leu Met Ile
            100                 105                 110

Ser Arg Thr Pro Glu Val Thr Cys Val Val Val Asp Val Ser His Glu
        115                 120                 125

Asp Pro Glu Val Lys Phe Asn Trp Tyr Val Asp Gly Val Glu Val His
```

-continued

```
              130                 135                 140
Asn Ala Lys Thr Lys Pro Arg Glu Glu Gln Tyr Asn Ser Thr Tyr Arg
145                 150                 155                 160

Val Val Ser Val Leu Thr Val Leu His Gln Asp Trp Leu Asn Gly Lys
                165                 170                 175

Glu Tyr Lys Cys Lys Val Ser Asn Lys Ala Leu Pro Ser Ser Ile Glu
                180                 185                 190

Lys Thr Ile Ser Lys Ala Lys Gly Gln Pro Arg Glu Pro Gln Val Tyr
                195                 200                 205

Thr Leu Pro Pro Ser Arg Asp Glu Leu Thr Lys Asn Gln Val Ser Leu
                210                 215                 220

Thr Cys Leu Val Lys Gly Phe Tyr Pro Ser Asp Ile Ala Val Glu Trp
225                 230                 235                 240

Glu Ser Asn Gly Gln Pro Glu Asn Asn Tyr Lys Thr Thr Pro Pro Val
                245                 250                 255

Leu Asp Ser Asp Gly Ser Phe Phe Leu Tyr Ser Lys Leu Thr Val Asp
                260                 265                 270

Lys Ser Arg Trp Gln Gln Gly Asn Val Phe Ser Cys Ser Val Met His
                275                 280                 285

Glu Ala Leu His Asn His Tyr Thr Gln Lys Ser Leu Ser Leu Ser Pro
                290                 295                 300

Gly Lys
305
```

```
<210> SEQ ID NO 23
<211> LENGTH: 18
<212> TYPE: PRT
<213> ORGANISM: Artificial Sequence
<220> FEATURE:
<223> OTHER INFORMATION: T2A

<400> SEQUENCE: 23

Glu Gly Arg Gly Ser Leu Leu Thr Cys Gly Asp Val Glu Glu Asn Pro
1               5                   10                  15

Gly Pro
```

```
<210> SEQ ID NO 24
<211> LENGTH: 22
<212> TYPE: PRT
<213> ORGANISM: Artificial Sequence
<220> FEATURE:
<223> OTHER INFORMATION: P2A

<400> SEQUENCE: 24

Gly Ser Gly Ala Thr Asn Phe Ser Leu Leu Lys Gln Ala Gly Asp Val
1               5                   10                  15

Glu Glu Asn Pro Gly Pro
            20
```

```
<210> SEQ ID NO 25
<211> LENGTH: 19
<212> TYPE: PRT
<213> ORGANISM: Artificial Sequence
<220> FEATURE:
<223> OTHER INFORMATION: P2A

<400> SEQUENCE: 25

Ala Thr Asn Phe Ser Leu Leu Lys Gln Ala Gly Asp Val Glu Glu Asn
1               5                   10                  15
```

Pro Gly Pro

<210> SEQ ID NO 26
<211> LENGTH: 20
<212> TYPE: PRT
<213> ORGANISM: Artificial Sequence
<220> FEATURE:
<223> OTHER INFORMATION: E2A

<400> SEQUENCE: 26

Gln Cys Thr Asn Tyr Ala Leu Leu Lys Leu Ala Gly Asp Val Glu Ser
1               5                   10                  15

Asn Pro Gly Pro
            20

<210> SEQ ID NO 27
<211> LENGTH: 22
<212> TYPE: PRT
<213> ORGANISM: Artificial Sequence
<220> FEATURE:
<223> OTHER INFORMATION: F2A

<400> SEQUENCE: 27

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 28
<211> LENGTH: 335
<212> TYPE: PRT
<213> ORGANISM: Artificial Sequence
<220> FEATURE:
<223> OTHER INFORMATION: tEGFR

<400> SEQUENCE: 28

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

```
Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
            275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335
```

<210> SEQ ID NO 29
<211> LENGTH: 228
<212> TYPE: PRT
<213> ORGANISM: Homo sapiens
<220> FEATURE:
<223> OTHER INFORMATION: Hinge-CH2-CH3 spacer

<400> SEQUENCE: 29

```
Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
            195                 200                 205

Met His Glu Ala Leu His Asn His Tyr Thr Gln Lys Ser Leu Ser Leu
    210                 215                 220
```

Ser Leu Gly Lys
225

```
<210> SEQ ID NO 30
<211> LENGTH: 117
<212> TYPE: PRT
<213> ORGANISM: Artificial Sequence
<220> FEATURE:
<223> OTHER INFORMATION: Variable heavy (VH) Anti-BCMA
```

<400> SEQUENCE: 30

Gln Ile Gln Leu Val Gln Ser Gly Pro Glu Leu Lys Lys Pro Gly Glu
1               5                  10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115

```
<210> SEQ ID NO 31
<211> LENGTH: 111
<212> TYPE: PRT
<213> ORGANISM: Artificial Sequence
<220> FEATURE:
<223> OTHER INFORMATION: Variable light (VL) Anti-BCMA
```

<400> SEQUENCE: 31

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

```
<210> SEQ ID NO 32
<211> LENGTH: 122
<212> TYPE: PRT
<213> ORGANISM: Artificial Sequence
<220> FEATURE:
<223> OTHER INFORMATION: Variable heavy (VH) Anti-BCMA
```

<400> SEQUENCE: 32

-continued

```
Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr Asn Phe
            20                  25                  30

Gly Met Asn Trp Val Lys Gln Ala Pro Gly Lys Gly Phe Lys Trp Met
        35                  40                  45

Ala Trp Ile Asn Thr Tyr Thr Gly Glu Ser Tyr Phe Ala Asp Asp Phe
    50                  55                  60

Lys Gly Arg Phe Ala Phe Ser Val Glu Thr Ser Ala Thr Thr Ala Tyr
65                  70                  75                  80

Leu Gln Ile Asn Asn Leu Lys Thr Glu Asp Thr Ala Thr Tyr Phe Cys
                85                  90                  95

Ala Arg Gly Glu Ile Tyr Tyr Gly Tyr Asp Gly Gly Phe Ala Tyr Trp
            100                 105                 110

Gly Gln Gly Thr Leu Val Thr Val Ser Ala
            115                 120

<210> SEQ ID NO 33
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 33

Asp Val Val Met Thr Gln Ser His Arg Phe Met Ser Thr Ser Val Gly
1               5                   10                  15

Asp Arg Val Ser Ile Thr Cys Arg Ala Ser Gln Asp Val Asn Thr Ala
            20                  25                  30

Val Ser Trp Tyr Gln Gln Lys Pro Gly Gln Ser Pro Lys Leu Leu Ile
        35                  40                  45

Phe Ser Ala Ser Tyr Arg Tyr Thr Gly Val Pro Asp Arg Phe Thr Gly
    50                  55                  60

Ser Gly Ser Gly Ala Asp Phe Thr Leu Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Asp Ile Lys
            100                 105

<210> SEQ ID NO 34
<211> LENGTH: 116
<212> TYPE: PRT
<213> ORGANISM: Artificial Sequence
<220> FEATURE:
<223> OTHER INFORMATION: Variable heavy (VH) Anti-BCMA

<400> SEQUENCE: 34

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly His Val Thr Ile Ser Ala Asp Lys Ser Ile Ser Thr Ala Tyr
65                  70                  75                  80
```

```
Leu Gln Trp Ser Ser Leu Lys Ala Ser Asp Thr Ala Met Tyr Tyr Cys
                85                  90                  95

Ala Arg Tyr Ser Gly Ser Phe Asp Asn Trp Gly Gln Gly Thr Leu Val
            100                 105                 110

Thr Val Ser Ser
        115

<210> SEQ ID NO 35
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 35

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly
            100                 105                 110

<210> SEQ ID NO 36
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 36

Glu Val Gln Leu Val Gln Ser Gly Ala Glu Met Lys Lys Pro Gly Ala
1               5                   10                  15

Ser Leu Lys Leu Ser Cys Lys Ala Ser Gly Tyr Thr Phe Ile Asp Tyr
            20                  25                  30

Tyr Val Tyr Trp Met Arg Gln Ala Pro Gly Gln Gly Leu Glu Ser Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Ser Gln Arg Asp Gly Tyr Met Asp Tyr Trp Gly Gln Gly Thr
            100                 105                 110

Leu Val Thr Val Ser Ser
        115

<210> SEQ ID NO 37
<211> LENGTH: 105
<212> TYPE: PRT
```

```
<213> ORGANISM: Artificial Sequence
<220> FEATURE:
<223> OTHER INFORMATION: Variable light (VL) Anti-BCMA

<400> SEQUENCE: 37

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly
            100                 105

<210> SEQ ID NO 38
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 38

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Ser Lys Ser Ile Val Ser Tyr Met Asp Tyr Trp
            100                 105                 110

Gly Gln Gly Thr Leu Val Thr Val Ser Ser
            115                 120

<210> SEQ ID NO 39
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 39

Leu Pro Val Leu Thr Gln Pro Pro Ser Thr Ser Gly Pro Gly Gln
1               5                   10                  15

Arg Val Thr Val Ser Cys Ser Gly Ser Ser Asn Ile Gly Ser Asn
            20                  25                  30

Val Val Phe Trp Tyr Gln Gln Leu Pro Gly Thr Ala Pro Lys Leu Val
        35                  40                  45
```

Ile Tyr Arg Asn Asn Gln Arg Pro Ser Gly Val Pro Asp Arg Phe Ser
            50                  55                  60

Val Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Tyr Val Phe Gly Thr Gly Thr Lys Val Thr Val Leu Gly
            100                 105                 110

<210> SEQ ID NO 40
<211> LENGTH: 120
<212> TYPE: PRT
<213> ORGANISM: Artificial Sequence
<220> FEATURE:
<223> OTHER INFORMATION: Variable heavy (VH) Anti-BCMA

<400> SEQUENCE: 40

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Arg Ile Ile Pro Ile Leu Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Gly Tyr Gly Ser Tyr Arg Trp Glu Asp Ser Trp Gly Gln
            100                 105                 110

Gly Thr Leu Val Thr Val Ser Ser
        115                 120

<210> SEQ ID NO 41
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 41

Gln Ala Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Ser Asn
             20                  25                  30

Tyr Val Phe Trp Tyr Gln Gln Leu Pro Gly Thr Ala Pro Lys Leu Leu
         35                  40                  45

Ile Tyr Ser Asn Asn Gln Arg Pro Ser Gly Val Pro Asp Arg Phe Ser
     50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Ala Ser Tyr Val Phe Gly Thr Gly Thr Lys Val Thr Val Leu Gly
            100                 105                 110

```
<210> SEQ ID NO 42
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 42
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Arg Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Ile Thr Val Thr Arg Asp Thr Ser Asn Thr Gly Tyr
65                  70                  75                  80

Met Glu Leu Thr Arg Leu Arg Ser Asp Asp Thr Ala Val Tyr Tyr Cys
                85                  90                  95

Ala Arg Ser Pro Tyr Ser Gly Val Leu Asp Lys Trp Gly Gln Gly Thr
            100                 105                 110

Leu Val Thr Val Ser Ser
        115

```
<210> SEQ ID NO 43
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 43
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

```
<210> SEQ ID NO 44
<211> LENGTH: 5
<212> TYPE: PRT
<213> ORGANISM: Artificial Sequence
<220> FEATURE:
<223> OTHER INFORMATION: FMC63 CDR H1

<400> SEQUENCE: 44
```

Asp Tyr Gly Val Ser
1               5

```
<210> SEQ ID NO 45
```

```
<211> LENGTH: 16
<212> TYPE: PRT
<213> ORGANISM: Artificial Sequence
<220> FEATURE:
<223> OTHER INFORMATION: FMC63 CDR H2

<400> SEQUENCE: 45

Val Ile Trp Gly Ser Glu Thr Thr Tyr Tyr Asn Ser Ala Leu Lys Ser
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: FMC63 CDR H3

<400> SEQUENCE: 46

Tyr Ala Met Asp Tyr Trp Gly
1               5

<210> SEQ ID NO 47
<211> LENGTH: 12
<212> TYPE: PRT
<213> ORGANISM: Artificial Sequence
<220> FEATURE:
<223> OTHER INFORMATION: FMC63 HC-CDR3

<400> SEQUENCE: 47

His Tyr Tyr Tyr Gly Gly Ser Tyr Ala Met Asp Tyr
1               5                   10

<210> SEQ ID NO 48
<211> LENGTH: 11
<212> TYPE: PRT
<213> ORGANISM: Artificial Sequence
<220> FEATURE:
<223> OTHER INFORMATION: FMC63 CDR L1

<400> SEQUENCE: 48

Arg Ala Ser Gln Asp Ile Ser Lys Tyr Leu Asn
1               5                   10

<210> SEQ ID NO 49
<211> LENGTH: 7
<212> TYPE: PRT
<213> ORGANISM: Artificial Sequence
<220> FEATURE:
<223> OTHER INFORMATION: FMC63 CDR L2

<400> SEQUENCE: 49

Ser Arg Leu His Ser Gly Val
1               5

<210> SEQ ID NO 50
<211> LENGTH: 7
<212> TYPE: PRT
<213> ORGANISM: Artificial Sequence
<220> FEATURE:
<223> OTHER INFORMATION: FMC63 LC-CDR2

<400> SEQUENCE: 50

His Thr Ser Arg Leu His Ser
1               5

<210> SEQ ID NO 51
<211> LENGTH: 9
```

```
<212> TYPE: PRT
<213> ORGANISM: Artificial Sequence
<220> FEATURE:
<223> OTHER INFORMATION: FMC63 CDR L3

<400> SEQUENCE: 51

Gly Asn Thr Leu Pro Tyr Thr Phe Gly
1               5

<210> SEQ ID NO 52
<211> LENGTH: 9
<212> TYPE: PRT
<213> ORGANISM: Artificial Sequence
<220> FEATURE:
<223> OTHER INFORMATION: FMC63 LC-CDR3

<400> SEQUENCE: 52

Gln Gln Gly Asn Thr Leu Pro Tyr Thr
1               5

<210> SEQ ID NO 53
<211> LENGTH: 120
<212> TYPE: PRT
<213> ORGANISM: Artificial Sequence
<220> FEATURE:
<223> OTHER INFORMATION: FMC63 VH

<400> SEQUENCE: 53

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 54
<211> LENGTH: 107
<212> TYPE: PRT
<213> ORGANISM: Artificial Sequence
<220> FEATURE:
<223> OTHER INFORMATION: FMC63 VL

<400> SEQUENCE: 54

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60
```

```
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr
            100                 105
```

<210> SEQ ID NO 55
<211> LENGTH: 245
<212> TYPE: PRT
<213> ORGANISM: Artificial Sequence
<220> FEATURE:
<223> OTHER INFORMATION: FMC63 scFv

<400> SEQUENCE: 55

```
Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile Ser Lys Tyr
                 20                  25                  30

Leu Asn Trp Tyr Gln Gln Lys Pro Asp Gly Thr Val Lys Leu Leu Ile
             35                  40                  45

Tyr His Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
210                 215                 220

Tyr Tyr Gly Gly Ser Tyr Ala Met Asp Tyr Trp Gly Gln Gly Thr Ser
225                 230                 235                 240

Val Thr Val Ser Ser
            245
```

<210> SEQ ID NO 56
<211> LENGTH: 11
<212> TYPE: PRT
<213> ORGANISM: Artificial Sequence
<220> FEATURE:
<223> OTHER INFORMATION: SJ25C1 CDR L1

<400> SEQUENCE: 56

```
Lys Ala Ser Gln Asn Val Gly Thr Asn Val Ala
  1               5                  10
```

-continued

```
<210> SEQ ID NO 57
<211> LENGTH: 7
<212> TYPE: PRT
<213> ORGANISM: Artificial Sequence
<220> FEATURE:
<223> OTHER INFORMATION: SJ25C1 CDR L2

<400> SEQUENCE: 57

Ser Ala Thr Tyr Arg Asn Ser
1               5

<210> SEQ ID NO 58
<211> LENGTH: 9
<212> TYPE: PRT
<213> ORGANISM: Artificial Sequence
<220> FEATURE:
<223> OTHER INFORMATION: SJ25C1 CDR L3

<400> SEQUENCE: 58

Gln Gln Tyr Asn Arg Tyr Pro Tyr Thr
1               5

<210> SEQ ID NO 59
<211> LENGTH: 5
<212> TYPE: PRT
<213> ORGANISM: Artificial Sequence
<220> FEATURE:
<223> OTHER INFORMATION: SJ25C1 CDR H1

<400> SEQUENCE: 59

Ser Tyr Trp Met Asn
1               5

<210> SEQ ID NO 60
<211> LENGTH: 17
<212> TYPE: PRT
<213> ORGANISM: Artificial Sequence
<220> FEATURE:
<223> OTHER INFORMATION: SJ25C1 CDR H2

<400> SEQUENCE: 60

Gln Ile Tyr Pro Gly Asp Gly Asp Thr Asn Tyr Asn Gly Lys Phe Lys
1               5                   10                  15

Gly

<210> SEQ ID NO 61
<211> LENGTH: 13
<212> TYPE: PRT
<213> ORGANISM: Artificial Sequence
<220> FEATURE:
<223> OTHER INFORMATION: SJ25C1 CDR H3

<400> SEQUENCE: 61

Lys Thr Ile Ser Ser Val Val Asp Phe Tyr Phe Asp Tyr
1               5                   10

<210> SEQ ID NO 62
<211> LENGTH: 122
<212> TYPE: PRT
<213> ORGANISM: Artificial Sequence
<220> FEATURE:
<223> OTHER INFORMATION: SJ25C1 VH

<400> SEQUENCE: 62

Glu Val Lys Leu Gln Gln Ser Gly Ala Glu Leu Val Arg Pro Gly Ser
```

```
                1               5                      10                      15
            Ser Val Lys Ile Ser Cys Lys Ala Ser Gly Tyr Ala Phe Ser Ser Tyr
                                20                      25                      30

Trp Met Asn Trp Val Lys Gln Arg Pro Gly Gln Gly Leu Glu Trp Ile
                                35                      40                      45

Gly Gln Ile Tyr Pro Gly Asp Gly Asp Thr Asn Tyr Asn Gly Lys Phe
                                50                      55                      60

Lys Gly Gln Ala Thr Leu Thr Ala Asp Lys Ser Ser Thr Ala Tyr
             65                 70                      75                      80

Met Gln Leu Ser Gly Leu Thr Ser Glu Asp Ser Ala Val Tyr Phe Cys
                                85                      90                      95

Ala Arg Lys Thr Ile Ser Ser Val Val Asp Phe Tyr Phe Asp Tyr Trp
                                100                     105                     110

Gly Gln Gly Thr Thr Val Thr Val Ser Ser
                                115                     120

<210> SEQ ID NO 63
<211> LENGTH: 108
<212> TYPE: PRT
<213> ORGANISM: Artificial Sequence
<220> FEATURE:
<223> OTHER INFORMATION: SJ25C1 VL

<400> SEQUENCE: 63

Asp Ile Glu Leu Thr Gln Ser Pro Lys Phe Met Ser Thr Ser Val Gly
             1               5                      10                      15

Asp Arg Val Ser Val Thr Cys Lys Ala Ser Gln Asn Val Gly Thr Asn
                                20                      25                      30

Val Ala Trp Tyr Gln Gln Lys Pro Gly Gln Ser Pro Lys Pro Leu Ile
                                35                      40                      45

Tyr Ser Ala Thr Tyr Arg Asn Ser Gly Val Pro Asp Arg Phe Thr Gly
                                50                      55                      60

Ser Gly Ser Gly Thr Asp Phe Thr Leu Thr Ile Thr Asn Val Gln Ser
             65                 70                      75                      80

Lys Asp Leu Ala Asp Tyr Phe Cys Gln Gln Tyr Asn Arg Tyr Pro Tyr
                                85                      90                      95

Thr Ser Gly Gly Gly Thr Lys Leu Glu Ile Lys Arg
                                100                     105

<210> SEQ ID NO 64
<211> LENGTH: 15
<212> TYPE: PRT
<213> ORGANISM: Artificial Sequence
<220> FEATURE:
<223> OTHER INFORMATION: Linker

<400> SEQUENCE: 64

Gly Gly Gly Gly Ser Gly Gly Gly Gly Ser Gly Gly Gly Gly Ser
             1               5                      10                      15

<210> SEQ ID NO 65
<211> LENGTH: 245
<212> TYPE: PRT
<213> ORGANISM: Artificial Sequence
<220> FEATURE:
<223> OTHER INFORMATION: SJ25C1 scFv

<400> SEQUENCE: 65

Glu Val Lys Leu Gln Gln Ser Gly Ala Glu Leu Val Arg Pro Gly Ser
             1               5                      10                      15
```

```
Ser Val Lys Ile Ser Cys Lys Ala Ser Gly Tyr Ala Phe Ser Ser Tyr
             20                  25                  30

Trp Met Asn Trp Val Lys Gln Arg Pro Gly Gln Gly Leu Glu Trp Ile
         35                  40                  45

Gly Gln Ile Tyr Pro Gly Asp Gly Asp Thr Asn Tyr Asn Gly Lys Phe
     50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                 85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly
            115                 120                 125

Gly Gly Gly Ser Gly Gly Gly Ser Asp Ile Glu Leu Thr Gln Ser
130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
            195                 200                 205

Thr Leu Thr Ile Thr Asn Val Gln Ser Lys Asp Leu Ala Asp Tyr Phe
    210                 215                 220

Cys Gln Gln Tyr Asn Arg Tyr Pro Tyr Thr Ser Gly Gly Gly Thr Lys
225                 230                 235                 240

Leu Glu Ile Lys Arg
                245

<210> SEQ ID NO 66
<211> LENGTH: 12
<212> TYPE: PRT
<213> ORGANISM: Artificial Sequence
<220> FEATURE:
<223> OTHER INFORMATION: FMC63 HC-CDR3

<400> SEQUENCE: 66

His Tyr Tyr Tyr Gly Gly Ser Tyr Ala Met Asp Tyr
1               5                   10

<210> SEQ ID NO 67
<211> LENGTH: 7
<212> TYPE: PRT
<213> ORGANISM: Artificial Sequence
<220> FEATURE:
<223> OTHER INFORMATION: FMC63 LC-CDR2

<400> SEQUENCE: 67

His Thr Ser Arg Leu His Ser
1               5

<210> SEQ ID NO 68
<211> LENGTH: 9
<212> TYPE: PRT
<213> ORGANISM: Artificial Sequence
<220> FEATURE:
<223> OTHER INFORMATION: FMC63 LC-CDR3
```

```
<400> SEQUENCE: 68

Gln Gln Gly Asn Thr Leu Pro Tyr Thr
1               5

<210> SEQ ID NO 69
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 69
gacatccaga tgacccagac cacctccagc ctgagcgcca gcctgggcga ccgggtgacc      60
atcagctgcc gggccagcca ggacatcagc aagtacctga actggtatca gcagaagccc     120
gacggcaccg tcaagctgct gatctaccac accagccggc tgcacagcgg cgtgcccagc     180
cggtttagcg gcagcggctc cggcaccgac tacagcctga ccatctccaa cctggaacag     240
gaagatatcg ccacctactt tgccagcag ggcaacacac tgcccta cac ctttggcggc      300 ggaacaaagc tggaaatcac cggcagcacc tccggcagcg gcaagcctgg cagcggcgag     360
ggcagcacca agggcgaggt gaagctgcag gaaagcggcc ctggcctggt ggcccccagc     420
cagagcctga gcgtgacctg caccgtgagc ggcgtgagcc tgcccgacta cggcgtgagc     480
tggatccggc agcccccag gaagggcctg gaatggctgg gcgtgatctg gggcagcgag     540
accacctact acaacagcgc cctgaagagc cggctgacca tcatcaagga caacagcaag     600
agccaggtgt tcctgaagat gaacagcctg cagaccgacg acaccgccat ctactactgc     660
gccaagcact actactacgg cggcagctac gccatggact actggggcca gggcaccagc     720
gtgaccgtga gcagc                                                     735

<210> SEQ ID NO 70
<211> LENGTH: 18
<212> TYPE: PRT
<213> ORGANISM: Artificial Sequence
<220> FEATURE:
<223> OTHER INFORMATION: Linker

<400> SEQUENCE: 70

Gly Ser Thr Ser Gly Ser Gly Lys Pro Gly Ser Gly Glu Gly Ser Thr
1               5                   10                  15

Lys Gly

<210> SEQ ID NO 71
<211> LENGTH: 4
<212> TYPE: PRT
<213> ORGANISM: Artificial Sequence
<220> FEATURE:
<223> OTHER INFORMATION: Linker

<400> SEQUENCE: 71

Gly Gly Gly Ser
1

<210> SEQ ID NO 72
<211> LENGTH: 15
<212> TYPE: PRT
<213> ORGANISM: Artificial Sequence
<220> FEATURE:
<223> OTHER INFORMATION: Linker

<400> SEQUENCE: 72
```

Gly Gly Gly Gly Ser Gly Gly Gly Ser Gly Gly Gly Ser
1               5                   10                  15

<210> SEQ ID NO 73
<211> LENGTH: 18
<212> TYPE: PRT
<213> ORGANISM: Artificial Sequence
<220> FEATURE:
<223> OTHER INFORMATION: Linker

<400> SEQUENCE: 73

Gly Ser Thr Ser Gly Ser Gly Lys Pro Gly Ser Gly Glu Gly Ser Thr
1               5                   10                  15

Lys Gly

<210> SEQ ID NO 74
<211> LENGTH: 21
<212> TYPE: PRT
<213> ORGANISM: Artificial Sequence
<220> FEATURE:
<223> OTHER INFORMATION: Linker

<400> SEQUENCE: 74

Ser Arg Gly Gly Gly Gly Ser Gly Gly Gly Gly Ser Gly Gly Gly Gly
1               5                   10                  15

Ser Leu Glu Met Ala
            20

<210> SEQ ID NO 75
<211> LENGTH: 21
<212> TYPE: PRT
<213> ORGANISM: Artificial Sequence
<220> FEATURE:
<223> OTHER INFORMATION: CD8a signal peptide

<400> SEQUENCE: 75

Met Ala Leu Pro Val Thr Ala Leu Leu Leu Pro Leu Ala Leu Leu Leu
1               5                   10                  15

His Ala Ala Arg Pro
            20

<210> SEQ ID NO 76
<211> LENGTH: 20
<212> TYPE: PRT
<213> ORGANISM: Artificial Sequence
<220> FEATURE:
<223> OTHER INFORMATION: signal peptide

<400> SEQUENCE: 76

Met Glu Thr Asp Thr Leu Leu Leu Trp Val Leu Leu Leu Trp Val Pro
1               5                   10                  15

Gly Ser Thr Gly
            20

<210> SEQ ID NO 77
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 77

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ala Glu Met Gly Ala Val Phe Asp Ile Trp Gly Gln Gly Thr
            100                 105                 110

Met Val Thr Val Ser Ser
            115

<210> SEQ ID NO 78
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 78

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ile Ser Trp Pro Phe
                85                  90                  95

Thr Phe Gly Gly Gly Thr Lys Val Glu Ile Lys
            100                 105

<210> SEQ ID NO 79
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 79

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                    85                  90                  95

Ala Arg Asp Gly Thr Tyr Leu Gly Gly Leu Trp Tyr Phe Asp Leu Trp
            100                 105                 110

Gly Arg Gly Thr Leu Val Thr Val Ser Ser
            115                 120

<210> SEQ ID NO 80
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 80

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gly Leu Pro Leu Thr Phe Gly Gly Gly Thr Lys Val Glu Ile Lys
            100                 105                 110

<210> SEQ ID NO 81
<211> LENGTH: 116
<212> TYPE: PRT
<213> ORGANISM: Artificial Sequence
<220> FEATURE:
<223> OTHER INFORMATION: Variable heavy (VH) Anti-BCMA

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Gly Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
            100                 105                 110

Thr Val Ser Ser
        115

<210> SEQ ID NO 82
<211> LENGTH: 106
<212> TYPE: PRT
<213> ORGANISM: Artificial Sequence
<220> FEATURE:
```

<223> OTHER INFORMATION: Variable light (VL) Anti-BCMA

<400> SEQUENCE: 82

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ala Ala Tyr Pro Thr
                85                  90                  95

Phe Gly Gly Gly Thr Lys Val Glu Ile Lys
            100                 105
```

<210> SEQ ID NO 83
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 83

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Arg Gly Tyr Ala Thr Ser Leu Ala Phe Asp Ile Trp
            100                 105                 110

Gly Gln Gly Thr Met Val Thr Val Ser Ser
        115                 120
```

<210> SEQ ID NO 84
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 84

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
```

```
                   50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg His Val Trp Pro Pro
                     85                  90                  95

Thr Phe Gly Gly Gly Thr Lys Val Glu Ile Lys
                100                 105

<210> SEQ ID NO 85
<211> LENGTH: 119
<212> TYPE: PRT
<213> ORGANISM: Artificial Sequence
<220> FEATURE:
<223> OTHER INFORMATION: Variable heavy (VH) Anti-BCMA

<400> SEQUENCE: 85

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Thr Ile Ser Ser Ser Ser Thr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Gln Glu His Leu Ile Phe Asp Tyr Trp Gly Gln Gly
                100                 105                 110

Thr Leu Val Thr Val Ser Ser
            115

<210> SEQ ID NO 86
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 86

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Arg Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Phe Tyr Tyr Pro Trp
                 85                  90                  95

Thr Phe Gly Gly Gly Thr Lys Val Glu Ile Lys
                100                 105

<210> SEQ ID NO 87
<211> LENGTH: 122
```

```
<212> TYPE: PRT
<213> ORGANISM: Artificial Sequence
<220> FEATURE:
<223> OTHER INFORMATION: Variable heavy (VH) Anti-BCMA

<400> SEQUENCE: 87

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Phe Trp Ser Gly Ser Pro Pro Gly Leu Asp Tyr Trp
            100                 105                 110

Gly Gln Gly Thr Leu Val Thr Val Ser Ser
        115                 120

<210> SEQ ID NO 88
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 88

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Tyr Thr Phe Pro Phe
                85                  90                  95

Thr Phe Gly Gly Gly Thr Lys Val Glu Ile Lys
            100                 105

<210> SEQ ID NO 89
<211> LENGTH: 126
<212> TYPE: PRT
<213> ORGANISM: Artificial Sequence
<220> FEATURE:
<223> OTHER INFORMATION: Variable heavy (VH) Anti-BCMA

<400> SEQUENCE: 89

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
```

```
                35                  40                  45
Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Glu Tyr Ser Ser Ile Trp His Tyr Tyr Tyr Gly
            100                 105                 110

Met Asp Val Trp Gly Gln Gly Thr Thr Val Thr Val Ser Ser
        115                 120                 125

<210> SEQ ID NO 90
<211> LENGTH: 113
<212> TYPE: PRT
<213> ORGANISM: Artificial Sequence
<220> FEATURE:
<223> OTHER INFORMATION: Variable light (VL) Anti-BCMA

<400> SEQUENCE: 90

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Ala His Thr Pro Phe Thr Phe Gly Gly Gly Thr Lys Val Glu Ile
            100                 105                 110

Lys

<210> SEQ ID NO 91
<211> LENGTH: 123
<212> TYPE: PRT
<213> ORGANISM: Artificial Sequence
<220> FEATURE:
<223> OTHER INFORMATION: Variable heavy (VH) Anti-BCMA

<400> SEQUENCE: 91

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Asp Tyr Gly Met Asp Val
```

100                 105                 110

Trp Gly Gln Gly Thr Thr Val Thr Val Ser Ser
        115                 120

<210> SEQ ID NO 92
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 92

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His His Val Trp Pro Leu
                85                  90                  95

Thr Phe Gly Gly Gly Thr Lys Val Glu Ile Lys
            100                 105

<210> SEQ ID NO 93
<211> LENGTH: 121
<212> TYPE: PRT
<213> ORGANISM: Artificial Sequence
<220> FEATURE:
<223> OTHER INFORMATION: Variable heavy (VH) Anti-BCMA

<400> SEQUENCE: 93

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Ser His Asp Met Trp Ser Glu Asp Trp Gly
            100                 105                 110

Gln Gly Thr Leu Val Thr Val Ser Ser
        115                 120

<210> SEQ ID NO 94
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 94

```
Leu Pro Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Ser Asn
            20                  25                  30

Ser Val Asn Trp Tyr Arg Gln Leu Pro Gly Ala Ala Pro Lys Leu Leu
        35                  40                  45

Ile Tyr Ser Asn Asn Gln Arg Pro Gly Val Pro Val Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Thr Tyr Tyr Cys Ala Thr Trp Asp Asp Asn Leu
                85                  90                  95

Asn Val His Tyr Val Phe Gly Thr Gly Thr Lys Val Thr Val Leu Gly
            100                 105                 110
```

<210> SEQ ID NO 95
<211> LENGTH: 117
<212> TYPE: PRT
<213> ORGANISM: Artificial Sequence
<220> FEATURE:
<223> OTHER INFORMATION: Variable heavy (VH) Anti-BCMA

<400> SEQUENCE: 95

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
        35                  40                  45

Gly Trp Ile Asn Thr Glu Thr Arg Glu Pro Ala Tyr Ala Tyr Asp Phe
    50                  55                  60

Arg Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Ser Tyr Ala Met Asp Tyr Trp Gly Gln Gly Thr Leu
            100                 105                 110

Val Thr Val Ser Ser
        115
```

<210> SEQ ID NO 96
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 96

```
Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
```

```
                65                  70                  75                  80
Ser Leu Gln Ala Glu Asp Ala Ala Ile Tyr Tyr Cys Leu Gln Ser Arg
                    85                  90                  95

Ile Phe Pro Arg Thr Phe Gly Gln Gly Thr Lys Leu Glu Ile Lys
                100                 105                 110
```

<210> SEQ ID NO 97
<211> LENGTH: 115
<212> TYPE: PRT
<213> ORGANISM: Artificial Sequence
<220> FEATURE:
<223> OTHER INFORMATION: Variable heavy (VH) Anti-BCMA

<400> SEQUENCE: 97

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
                20                  25                  30

Gly Met Ser Trp Val Arg Arg Ala Pro Gly Lys Gly Leu Glu Trp Val
            35                  40                  45

Ser Gly Ile Val Tyr Ser Gly Ser Thr Tyr Tyr Ala Ala Ser Val Lys
        50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
                100                 105                 110

Val Ser Ser
        115
```

<210> SEQ ID NO 98
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 98

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
                100                 105
```

<210> SEQ ID NO 99
<211> LENGTH: 120
<212> TYPE: PRT
<213> ORGANISM: Artificial Sequence
<220> FEATURE:

<223> OTHER INFORMATION: Variable heavy (VH) Anti-BCMA

<400> SEQUENCE: 99

```
Gln Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Ser Asn Tyr
            20                  25                  30
Ala Met Ser Trp Val Arg Gln Ala Pro Gly Lys Gly Leu Gly Trp Val
        35                  40                  45
Ser Gly Ile Ser Arg Ser Gly Glu Asn Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Asp Glu Asp Thr Ala Val Tyr Tyr Cys
                85                  90                  95
Ala Arg Ser Pro Ala His Tyr Tyr Gly Gly Met Asp Val Trp Gly Gln
            100                 105                 110
Gly Thr Thr Val Thr Val Ser Ser
        115                 120
```

<210> SEQ ID NO 100
<211> LENGTH: 109
<212> TYPE: PRT
<213> ORGANISM: Artificial Sequence
<220> FEATURE:
<223> OTHER INFORMATION: Variable light (VL) Anti-BCMA

<400> SEQUENCE: 100

```
Asp Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Ile Ser Ser Ser
            20                  25                  30
Phe Leu Ala Trp Tyr Gln Gln Lys Pro Gly Gln Ala Pro Arg Leu Leu
        35                  40                  45
Ile Tyr Gly Ala Ser Arg Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Ser Ala Val Tyr Tyr Cys Gln Gln Tyr His Ser Ser Pro
                85                  90                  95
Ser Trp Thr Phe Gly Gln Gly Thr Lys Leu Glu Ile Lys
            100                 105
```

<210> SEQ ID NO 101
<211> LENGTH: 115
<212> TYPE: PRT
<213> ORGANISM: Artificial Sequence
<220> FEATURE:
<223> OTHER INFORMATION: Variable heavy (VH) Anti-BCMA

<400> SEQUENCE: 101

```
Gln Val Gln Leu Val Glu Ser Gly Gly Gly Leu Val Gln Pro Gly Gly
1               5                   10                  15
Ser Leu Arg Leu Ser Cys Ala Val Ser Gly Phe Ala Leu Ser Asn His
            20                  25                  30
Gly Met Ser Trp Val Arg Arg Ala Pro Gly Lys Gly Leu Glu Trp Val
        35                  40                  45
Ser Gly Ile Val Tyr Ser Gly Ser Thr Tyr Tyr Ala Ala Ser Val Lys
```

```
                    50                  55                  60
Gly Arg Phe Thr Ile Ser Arg Asp Asn Ser Arg Asn Thr Leu Tyr Leu
 65                  70                  75                  80

Gln Met Asn Ser Leu Arg Pro Glu Asp Thr Ala Ile Tyr Tyr Cys Ser
                    85                  90                  95

Ala His Gly Gly Glu Ser Asp Val Trp Gly Gln Gly Thr Thr Val Thr
                100                 105                 110

Val Ser Ser
        115

<210> SEQ ID NO 102
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 102

Asp Ile Arg Leu Thr Gln Ser Pro Ser Pro Leu Ser Ala Ser Val Gly
  1               5                  10                  15

Asp Arg Val Thr Ile Thr Cys Gln Ala Ser Glu Asp Ile Asn Lys Phe
                 20                  25                  30

Leu Asn Trp Tyr His Gln Thr Pro Gly Lys Ala Pro Lys Leu Leu Ile
             35                  40                  45

Tyr Asp Ala Ser Thr Leu Gln Thr Gly Val Pro Ser Arg Phe Ser Gly
 50                  55                  60

Ser Gly Ser Gly Thr Asp Phe Thr Leu Thr Ile Asn Ser Leu Gln Pro
 65                  70                  75                  80

Glu Asp Ile Gly Thr Tyr Tyr Cys Gln Gln Tyr Glu Ser Leu Pro Leu
                 85                  90                  95

Thr Phe Gly Gly Gly Thr Lys Val Glu Ile Lys
                100                 105

<210> SEQ ID NO 103
<211> LENGTH: 115
<212> TYPE: PRT
<213> ORGANISM: Artificial Sequence
<220> FEATURE:
<223> OTHER INFORMATION: Variable heavy (VH) Anti-BCMA

<400> SEQUENCE: 103

Glu Val Gln Leu Val Glu Ser Gly Gly Gly Leu Val Gln Pro Gly Gly
  1               5                  10                  15

Ser Leu Arg Leu Ser Cys Ala Val Ser Gly Phe Ala Leu Ser Asn His
                 20                  25                  30

Gly Met Ser Trp Val Arg Ala Pro Gly Lys Gly Leu Glu Trp Val
             35                  40                  45

Ser Gly Ile Val Tyr Ser Gly Ser Thr Tyr Tyr Ala Ala Ser Val Lys
 50                  55                  60

Gly Arg Phe Thr Ile Ser Arg Asp Asn Ser Arg Asn Thr Leu Tyr Leu
 65                  70                  75                  80

Gln Met Asn Ser Leu Arg Pro Glu Asp Thr Ala Ile Tyr Tyr Cys Ser
                 85                  90                  95

Ala His Gly Gly Glu Ser Asp Val Trp Gly Gln Gly Thr Thr Val Thr
                100                 105                 110

Val Ser Ser
        115
```

```
<210> SEQ ID NO 104
<211> LENGTH: 109
<212> TYPE: PRT
<213> ORGANISM: Artificial Sequence
<220> FEATURE:
<223> OTHER INFORMATION: Variable light (VL) Anti-BCMA

<400> SEQUENCE: 104
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Gly Ser Ser
            20                  25                  30

Ser Leu Ala Trp Tyr Gln Gln Lys Pro Gly Gln Ala Pro Arg Leu Leu
        35                  40                  45

Met Tyr Gly Ala Ser Ser Arg Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Gly Ser Pro
                85                  90                  95

Pro Phe Thr Phe Gly Gln Gly Thr Lys Val Glu Ile Lys
            100                 105

```
<210> SEQ ID NO 105
<211> LENGTH: 117
<212> TYPE: PRT
<213> ORGANISM: Artificial Sequence
<220> FEATURE:
<223> OTHER INFORMATION: Variable heavy (VH) Anti-BCMA

<400> SEQUENCE: 105
```

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg His Tyr
            20                  25                  30

Ser Met Asn Trp Val Lys Gln Ala Pro Gly Lys Gly Leu Lys Trp Met
        35                  40                  45

Gly Arg Ile Asn Thr Glu Ser Gly Val Pro Ile Tyr Ala Asp Asp Phe
    50                  55                  60

Lys Gly Arg Phe Ala Phe Ser Val Glu Thr Ser Ala Ser Thr Ala Tyr
65                  70                  75                  80

Leu Val Ile Asn Asn Leu Lys Asp Glu Asp Thr Ala Ser Tyr Phe Cys
                85                  90                  95

Ser Asn Asp Tyr Leu Tyr Ser Leu Asp Phe Trp Gly Gln Gly Thr Ala
            100                 105                 110

Leu Thr Val Ser Ser
        115

```
<210> SEQ ID NO 106
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 106
```

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu

```
                     20                  25                  30
Gly Ser His Leu Ile Tyr Trp Tyr Gln Gln Lys Pro Gly Gln Pro Pro
            35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 107
<211> LENGTH: 117
<212> TYPE: PRT
<213> ORGANISM: Artificial Sequence
<220> FEATURE:
<223> OTHER INFORMATION: Variable heavy (VH) Anti-BCMA

<400> SEQUENCE: 107

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
                20                  25                  30

Ser Met Asn Trp Val Lys Gln Ala Pro Gly Lys Gly Leu Lys Trp Met
            35                  40                  45

Gly Arg Ile Asn Thr Glu Thr Gly Glu Pro Leu Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Val Ile Asn Asn Leu Lys Asn Glu Asp Thr Ala Thr Phe Phe Cys
                85                  90                  95

Ser Asn Asp Tyr Leu Tyr Ser Cys Asp Tyr Trp Gly Gln Gly Thr Thr
            100                 105                 110

Leu Thr Val Ser Ser
        115

<210> SEQ ID NO 108
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 108

Asp Ile Val Leu Thr Gln Ser Pro Ala Ser Leu Ala Met Ser Leu Gly
1               5                   10                  15

Lys Arg Ala Thr Ile Ser Cys Arg Ala Ser Glu Ser Val Ser Val Ile
                20                  25                  30

Gly Ala His Leu Ile His Trp Tyr Gln Gln Lys Pro Gly Gln Pro Pro
            35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Asp
65                  70                  75                  80

Pro Val Glu Glu Asp Asp Val Ala Ile Tyr Ser Cys Leu Gln Ser Arg
                85                  90                  95
```

```
Ile Phe Pro Arg Thr Phe Gly Gly Gly Thr Lys Leu Glu Ile Lys
            100                 105                 110
```

<210> SEQ ID NO 109
<211> LENGTH: 119
<212> TYPE: PRT
<213> ORGANISM: Artificial Sequence
<220> FEATURE:
<223> OTHER INFORMATION: Variable heavy (VH) Anti-BCMA

<400> SEQUENCE: 109

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
50                  55                  60

Thr Gly Arg Val Thr Met Thr Arg Asp Thr Ser Ile Asn Thr Ala Tyr
65                  70                  75                  80

Met Glu Leu Ser Ser Leu Thr Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser
        115
```

<210> SEQ ID NO 110
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 110

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Ser Gln Ser
                85                  90                  95

Ser Ile Tyr Pro Trp Thr Phe Gly Gln Gly Thr Lys Leu Glu Ile Lys
            100                 105                 110
```

<210> SEQ ID NO 111
<211> LENGTH: 119
<212> TYPE: PRT
<213> ORGANISM: Artificial Sequence
<220> FEATURE:
<223> OTHER INFORMATION: Variable heavy (VH) Anti-BCMA

<400> SEQUENCE: 111

```
Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Ser Phe Pro Asp Tyr
                20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
                100                 105                 110

Thr Met Val Thr Val Ser Ser
        115
```

<210> SEQ ID NO 112
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 112

```
Asp Ile Val Met Thr Gln Thr Pro Leu Ser Leu Ser Val Thr Pro Gly
1               5                   10                  15

Glu Pro Ala Ser Ile Ser Cys Lys Ser Ser Gln Ser Leu Val His Ser
                20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Ala Asp Phe Thr Leu Lys Ile
65                  70                  75                  80

Ser Arg Val Glu Ala Glu Asp Val Gly Val Tyr Tyr Cys Ala Glu Thr
                85                  90                  95

Ser His Val Pro Trp Thr Phe Gly Gln Gly Thr Lys Leu Glu Ile Lys
                100                 105                 110
```

<210> SEQ ID NO 113
<211> LENGTH: 122
<212> TYPE: PRT
<213> ORGANISM: Artificial Sequence
<220> FEATURE:
<223> OTHER INFORMATION: Anti-BCMA sdAb

<400> SEQUENCE: 113

```
Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
                20                  25                  30

Ala Ile Gly Trp Phe Arg Gln Ala Pro Gly Lys Glu Arg Glu Gly Val
        35                  40                  45

Ile Cys Ile Ser Arg Ser Asp Gly Ser Thr Tyr Tyr Ala Asp Ser Val
    50                  55                  60

Lys Gly Arg Phe Thr Ile Ser Arg Asp Asn Ala Lys Lys Thr Val Tyr
65                  70                  75                  80
```

```
Leu Gln Met Ile Ser Leu Lys Pro Glu Asp Thr Ala Ala Tyr Tyr Cys
                85                  90                  95

Ala Ala Gly Ala Asp Cys Ser Gly Tyr Leu Arg Asp Tyr Glu Phe Arg
            100                 105                 110

Gly Gln Gly Thr Gln Val Thr Val Ser Ser
        115                 120

<210> SEQ ID NO 114
<211> LENGTH: 39
<212> TYPE: PRT
<213> ORGANISM: Artificial Sequence
<220> FEATURE:
<223> OTHER INFORMATION: CD28 spacer

<400> SEQUENCE: 114

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 115
<211> LENGTH: 25
<212> TYPE: PRT
<213> ORGANISM: Artificial Sequence
<220> FEATURE:
<223> OTHER INFORMATION: CD8a TM

<400> SEQUENCE: 115

Ile Tyr Ile Trp Ala Pro Leu Ala Gly Thr Cys Gly Val Leu Leu Leu
1               5                   10                  15

Ser Leu Val Ile Thr Leu Tyr Cys Asn
            20                  25

<210> SEQ ID NO 116
<211> LENGTH: 30
<212> TYPE: PRT
<213> ORGANISM: Artificial Sequence
<220> FEATURE:
<223> OTHER INFORMATION: CD28 spacer (truncated)

<400> SEQUENCE: 116

Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30

<210> SEQ ID NO 117
<211> LENGTH: 46
<212> TYPE: PRT
<213> ORGANISM: Artificial Sequence
<220> FEATURE:
<223> OTHER INFORMATION: CD8a hinge

<400> SEQUENCE: 117

Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
            20                  25                  30

Gly Gly Ala Val His Thr Arg Gly Leu Asp Phe Ala Cys Asp
        35                  40                  45
```

<210> SEQ ID NO 118
<211> LENGTH: 45
<212> TYPE: PRT
<213> ORGANISM: Artificial Sequence
<220> FEATURE:
<223> OTHER INFORMATION: CD8a hinge

<400> SEQUENCE: 118

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 119
<211> LENGTH: 55
<212> TYPE: PRT
<213> ORGANISM: Artificial Sequence
<220> FEATURE:
<223> OTHER INFORMATION: CD8a hinge

<400> SEQUENCE: 119

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 120
<211> LENGTH: 39
<212> TYPE: PRT
<213> ORGANISM: Artificial Sequence
<220> FEATURE:
<223> OTHER INFORMATION: CTLA4 hinge

<400> SEQUENCE: 120

Asp Thr Gly Leu Tyr Ile Cys Lys Val Glu Leu Met Tyr Pro Pro Pro
1               5                   10                  15

Tyr Tyr Leu Gly Ile Gly Asn Gly Thr Gln Ile Tyr Val Ile Asp Pro
            20                  25                  30

Glu Pro Cys Pro Asp Ser Asp
        35

<210> SEQ ID NO 121
<211> LENGTH: 24
<212> TYPE: PRT
<213> ORGANISM: Artificial Sequence
<220> FEATURE:
<223> OTHER INFORMATION: CTLA4 TM

<400> SEQUENCE: 121

Phe Leu Leu Trp Ile Leu Ala Ala Val Ser Ser Gly Leu Phe Phe Tyr
1               5                   10                  15

Ser Phe Leu Leu Thr Ala Val Ser
            20

<210> SEQ ID NO 122
<211> LENGTH: 38

```
<212> TYPE: PRT
<213> ORGANISM: Artificial Sequence
<220> FEATURE:
<223> OTHER INFORMATION: PD-1 hinge

<400> SEQUENCE: 122

Gln Ile Lys Glu Ser Leu Arg Ala Glu Leu Arg Val Thr Glu Arg Arg
1               5                   10                  15

Ala Glu Val Pro Thr Ala His Pro Ser Pro Ser Pro Arg Pro Ala Gly
            20                  25                  30

Gln Phe Gln Thr Leu Val
        35

<210> SEQ ID NO 123
<211> LENGTH: 21
<212> TYPE: PRT
<213> ORGANISM: Artificial Sequence
<220> FEATURE:
<223> OTHER INFORMATION: PD-1 TM

<400> SEQUENCE: 123

Val Gly Val Val Gly Gly Leu Leu Gly Ser Leu Val Leu Leu Val Trp
1               5                   10                  15

Val Leu Ala Val Ile
            20

<210> SEQ ID NO 124
<211> LENGTH: 16
<212> TYPE: PRT
<213> ORGANISM: Artificial Sequence
<220> FEATURE:
<223> OTHER INFORMATION: FcγRIIIa hinge

<400> SEQUENCE: 124

Gly Leu Ala Val Ser Thr Ile Ser Ser Phe Phe Pro Pro Gly Tyr Gln
1               5                   10                  15

<210> SEQ ID NO 125
<211> LENGTH: 231
<212> TYPE: PRT
<213> ORGANISM: Artificial Sequence
<220> FEATURE:
<223> OTHER INFORMATION: IgG1 hinge

<400> SEQUENCE: 125

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125
```

Glu Pro Gln Val Tyr Thr Leu Pro Pro Ser Arg Asp Glu Leu Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230

<210> SEQ ID NO 126
<211> LENGTH: 457
<212> TYPE: PRT
<213> ORGANISM: Artificial Sequence
<220> FEATURE:
<223> OTHER INFORMATION: anti-BCMA CAR

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Glu Met Gly Ala Val Phe Asp Ile Trp Gly Gln Gly Thr
            100                 105                 110

Met Val Thr Val Ser Ser Gly Ser Thr Ser Gly Ser Gly Lys Pro Gly
        115                 120                 125

Ser Gly Glu Gly Ser Thr Lys Gly Glu Ile Val Leu Thr Gln Ser Pro
130                 135                 140

Ala Thr Leu Ser Leu Ser Pro Gly Glu Arg Ala Thr Leu Ser Cys Arg
145                 150                 155                 160

Ala Ser Gln Ser Val Ser Arg Tyr Leu Ala Trp Tyr Gln Gln Lys Pro
                165                 170                 175

Gly Gln Ala Pro Arg Leu Leu Ile Tyr Asp Ala Ser Asn Arg Ala Thr
            180                 185                 190

Gly Ile Pro Ala Arg Phe Ser Gly Ser Gly Ser Gly Thr Asp Phe Thr
        195                 200                 205

Leu Thr Ile Ser Ser Leu Glu Pro Glu Asp Phe Ala Val Tyr Tyr Cys
    210                 215                 220

Gln Gln Arg Ile Ser Trp Pro Phe Thr Phe Gly Gly Gly Thr Lys Val
225                 230                 235                 240

Glu Ile Lys Arg Ala Ala Ala Leu Asp Asn Glu Lys Ser Asn Gly Thr
                245                 250                 255

-continued

Ile Ile His Val Lys Gly Lys His Leu Cys Pro Ser Pro Leu Phe Pro
            260                 265                 270

Gly Pro Ser Lys Pro Phe Trp Val Leu Val Val Gly Gly Val Leu
            275                 280                 285

Ala Cys Tyr Ser Leu Leu Val Thr Val Ala Phe Ile Ile Phe Trp Val
290                 295                 300

Arg Ser Lys Arg Ser Arg Leu Leu His Ser Asp Tyr Met Asn Met Thr
305                 310                 315                 320

Pro Arg Arg Pro Gly Pro Thr Arg Lys His Tyr Gln Pro Tyr Ala Pro
            325                 330                 335

Pro Arg Asp Phe Ala Ala Tyr Arg Ser Arg Val Lys Phe Ser Arg Ser
            340                 345                 350

Ala Asp Ala Pro Ala Tyr Gln Gln Gly Gln Asn Gln Leu Tyr Asn Glu
            355                 360                 365

Leu Asn Leu Gly Arg Arg Glu Glu Tyr Asp Val Leu Asp Lys Arg Arg
            370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
            405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala
            435                 440                 445

Leu His Met Gln Ala Leu Pro Pro Arg
450                 455

<210> SEQ ID NO 127
<211> LENGTH: 457
<212> TYPE: PRT
<213> ORGANISM: Artificial Sequence
<220> FEATURE:
<223> OTHER INFORMATION: anti-BCMA CAR

<400> SEQUENCE: 127

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Ser Trp Pro Phe
            85                  90                  95

Thr Phe Gly Gly Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
            115                 120                 125

Gln Leu Leu Glu Ser Gly Gly Gly Leu Val Gln Pro Gly Gly Ser Leu
            130                 135                 140

Arg Leu Ser Cys Ala Ala Ser Gly Phe Thr Phe Ser Ser Tyr Ala Met
145                 150                 155                 160

```
Ser Trp Val Arg Gln Ala Pro Gly Lys Gly Leu Glu Trp Val Ser Ala
            165                 170                 175

Ile Ser Gly Ser Gly Gly Ser Thr Tyr Tyr Ala Asp Ser Val Lys Gly
        180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Arg
    210                 215                 220

Ala Glu Met Gly Ala Val Phe Asp Ile Trp Gly Gln Gly Thr Met Val
225                 230                 235                 240

Thr Val Ser Ser Ala Ala Ala Leu Asp Asn Glu Lys Ser Asn Gly Thr
                245                 250                 255

Ile Ile His Val Lys Gly Lys His Leu Cys Pro Ser Pro Leu Phe Pro
            260                 265                 270

Gly Pro Ser Lys Pro Phe Trp Val Leu Val Val Val Gly Gly Val Leu
        275                 280                 285

Ala Cys Tyr Ser Leu Leu Val Thr Val Ala Phe Ile Ile Phe Trp Val
    290                 295                 300

Arg Ser Lys Arg Ser Arg Leu Leu His Ser Asp Tyr Met Asn Met Thr
305                 310                 315                 320

Pro Arg Arg Pro Gly Pro Thr Arg Lys His Tyr Gln Pro Tyr Ala Pro
                325                 330                 335

Pro Arg Asp Phe Ala Ala Tyr Arg Ser Arg Val Lys Phe Ser Arg Ser
            340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala
        435                 440                 445

Leu His Met Gln Ala Leu Pro Pro Arg
    450                 455

<210> SEQ ID NO 128
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 128

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Thr Tyr Leu Gly Gly Leu Trp Tyr Phe Asp Leu Trp
            100                 105                 110

Gly Arg Gly Thr Leu Val Thr Val Ser Ser Gly Ser Thr Ser Gly Ser
        115                 120                 125

Gly Lys Pro Gly Ser Gly Glu Gly Ser Thr Lys Gly Asp Ile Val Met
    130                 135                 140

Thr Gln Ser Pro Leu Ser Leu Pro Val Thr Pro Gly Glu Pro Ala Ser
145                 150                 155                 160

Ile Ser Cys Arg Ser Ser Gln Ser Leu Leu His Ser Asn Gly Tyr Asn
                165                 170                 175

Tyr Leu Asp Trp Tyr Leu Gln Lys Pro Gly Gln Ser Pro Gln Leu Leu
            180                 185                 190

Ile Tyr Leu Gly Ser Asn Arg Ala Ser Gly Val Pro Asp Arg Phe Ser
        195                 200                 205

Gly Ser Gly Ser Gly Thr Asp Phe Thr Leu Lys Ile Ser Arg Val Glu
    210                 215                 220

Ala Glu Asp Val Gly Val Tyr Tyr Cys Met Gln Gly Leu Gly Leu Pro
225                 230                 235                 240

Leu Thr Phe Gly Gly Gly Thr Lys Val Glu Ile Lys Arg Ala Ala Ala
                245                 250                 255

Leu Asp Asn Glu Lys Ser Asn Gly Thr Ile Ile His Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465
```

-continued

```
<210> SEQ ID NO 129
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 129
```

| | | | | | | | | | | | | | | |
|---|---|---|---|---|---|---|---|---|---|---|---|---|---|---|
| Asp | Ile | Val | Met | Thr | Gln | Ser | Pro | Leu | Ser | Leu | Pro | Val | Thr | Pro | Gly |
| 1 | | | | 5 | | | | | 10 | | | | | 15 | |

| Glu | Pro | Ala | Ser | Ile | Ser | Cys | Arg | Ser | Ser | Gln | Ser | Leu | Leu | His | Ser |
|---|---|---|---|---|---|---|---|---|---|---|---|---|---|---|---|
| | | | 20 | | | | | 25 | | | | | 30 | | |

| Asn | Gly | Tyr | Asn | Tyr | Leu | Asp | Trp | Tyr | Leu | Gln | Lys | Pro | Gly | Gln | Ser |
|---|---|---|---|---|---|---|---|---|---|---|---|---|---|---|---|
| | | 35 | | | | | 40 | | | | | 45 | | | |

| Pro | Gln | Leu | Leu | Ile | Tyr | Leu | Gly | Ser | Asn | Arg | Ala | Ser | Gly | Val | Pro |
|---|---|---|---|---|---|---|---|---|---|---|---|---|---|---|---|
| | 50 | | | | | 55 | | | | | 60 | | | | |

| Asp | Arg | Phe | Ser | Gly | Ser | Gly | Ser | Gly | Thr | Asp | Phe | Thr | Leu | Lys | Ile |
|---|---|---|---|---|---|---|---|---|---|---|---|---|---|---|---|
| 65 | | | | | 70 | | | | | 75 | | | | | 80 |

| Ser | Arg | Val | Glu | Ala | Glu | Asp | Val | Gly | Val | Tyr | Tyr | Cys | Met | Gln | Gly |
|---|---|---|---|---|---|---|---|---|---|---|---|---|---|---|---|
| | | | | 85 | | | | | 90 | | | | | 95 | |

| Leu | Gly | Leu | Pro | Leu | Thr | Phe | Gly | Gly | Gly | Thr | Lys | Val | Glu | Ile | Lys |
|---|---|---|---|---|---|---|---|---|---|---|---|---|---|---|---|
| | | | 100 | | | | | 105 | | | | | 110 | | |

| Arg | Gly | Ser | Thr | Ser | Gly | Ser | Gly | Lys | Pro | Gly | Ser | Gly | Glu | Gly | Ser |
|---|---|---|---|---|---|---|---|---|---|---|---|---|---|---|---|
| | | 115 | | | | | 120 | | | | | 125 | | | |

| Thr | Lys | Gly | Gln | Val | Gln | Leu | Val | Glu | Ser | Gly | Gly | Val | Val | Gln |
|---|---|---|---|---|---|---|---|---|---|---|---|---|---|---|
| | 130 | | | | | 135 | | | | | 140 | | | |

| Pro | Gly | Arg | Ser | Leu | Arg | Leu | Ser | Cys | Ala | Ala | Ser | Gly | Phe | Thr | Phe |
|---|---|---|---|---|---|---|---|---|---|---|---|---|---|---|---|
| 145 | | | | | 150 | | | | | 155 | | | | | 160 |

| Ser | Ser | Tyr | Gly | Met | His | Trp | Val | Arg | Gln | Ala | Pro | Gly | Lys | Gly | Leu |
|---|---|---|---|---|---|---|---|---|---|---|---|---|---|---|---|
| | | | | 165 | | | | | 170 | | | | | 175 | |

| Glu | Trp | Val | Ala | Val | Ile | Ser | Tyr | Asp | Gly | Ser | Asn | Lys | Tyr | Tyr | Ala |
|---|---|---|---|---|---|---|---|---|---|---|---|---|---|---|---|
| | | | 180 | | | | | 185 | | | | | 190 | | |

| Asp | Ser | Val | Lys | Gly | Arg | Phe | Thr | Ile | Ser | Arg | Asp | Asn | Ser | Lys | Asn |
|---|---|---|---|---|---|---|---|---|---|---|---|---|---|---|---|
| | | 195 | | | | | 200 | | | | | 205 | | | |

| Thr | Leu | Tyr | Leu | Gln | Met | Asn | Ser | Leu | Arg | Ala | Glu | Asp | Thr | Ala | Val |
|---|---|---|---|---|---|---|---|---|---|---|---|---|---|---|---|
| | 210 | | | | | 215 | | | | | 220 | | | | |

| Tyr | Tyr | Cys | Ala | Arg | Asp | Gly | Thr | Tyr | Leu | Gly | Leu | Trp | Tyr | Phe |
|---|---|---|---|---|---|---|---|---|---|---|---|---|---|---|
| 225 | | | | | 230 | | | | | 235 | | | | | 240 |

| Asp | Leu | Trp | Gly | Arg | Gly | Thr | Leu | Val | Thr | Val | Ser | Ser | Ala | Ala | Ala |
|---|---|---|---|---|---|---|---|---|---|---|---|---|---|---|---|
| | | | | 245 | | | | | 250 | | | | | 255 | |

| Leu | Asp | Asn | Glu | Lys | Ser | Asn | Gly | Thr | Ile | Ile | His | Val | Lys | Gly | Lys |
|---|---|---|---|---|---|---|---|---|---|---|---|---|---|---|---|
| | | | 260 | | | | | 265 | | | | | 270 | | |

| His | Leu | Cys | Pro | Ser | Pro | Leu | Phe | Pro | Gly | Pro | Ser | Lys | Pro | Phe | Trp |
|---|---|---|---|---|---|---|---|---|---|---|---|---|---|---|---|
| | | 275 | | | | | 280 | | | | | 285 | | | |

| Val | Leu | Val | Val | Val | Gly | Gly | Val | Leu | Ala | Cys | Tyr | Ser | Leu | Leu | Val |
|---|---|---|---|---|---|---|---|---|---|---|---|---|---|---|---|
| | 290 | | | | | 295 | | | | | 300 | | | | |

| Thr | Val | Ala | Phe | Ile | Ile | Phe | Trp | Val | Arg | Ser | Lys | Arg | Ser | Arg | Leu |
|---|---|---|---|---|---|---|---|---|---|---|---|---|---|---|---|
| 305 | | | | | 310 | | | | | 315 | | | | | 320 |

| Leu | His | Ser | Asp | Tyr | Met | Asn | Met | Thr | Pro | Arg | Arg | Pro | Gly | Pro | Thr |
|---|---|---|---|---|---|---|---|---|---|---|---|---|---|---|---|
| | | | | 325 | | | | | 330 | | | | | 335 | |

| Arg | Lys | His | Tyr | Gln | Pro | Tyr | Ala | Pro | Pro | Arg | Asp | Phe | Ala | Ala | Tyr |
|---|---|---|---|---|---|---|---|---|---|---|---|---|---|---|---|
| | | | 340 | | | | | 345 | | | | | 350 | | |

| Arg | Ser | Arg | Val | Lys | Phe | Ser | Arg | Ser | Ala | Asp | Ala | Pro | Ala | Tyr | Gln |
|---|---|---|---|---|---|---|---|---|---|---|---|---|---|---|---|
| | | 355 | | | | | 360 | | | | | 365 | | | |

| Gln | Gly | Gln | Asn | Gln | Leu | Tyr | Asn | Glu | Leu | Asn | Leu | Gly | Arg | Arg | Glu |

```
            370                 375                 380
Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
                420                 425                 430

Glu Arg Arg Arg Gly Lys Gly His Asp Gly Leu Tyr Gln Gly Leu Ser
                435                 440                 445

Thr Ala Thr Lys Asp Thr Tyr Asp Ala Leu His Met Gln Ala Leu Pro
            450                 455                 460

Pro Arg
465

<210> SEQ ID NO 130
<211> LENGTH: 454
<212> TYPE: PRT
<213> ORGANISM: Artificial Sequence
<220> FEATURE:
<223> OTHER INFORMATION: anti-BCMA CAR

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Gly Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
                100                 105                 110

Thr Val Ser Ser Gly Ser Thr Ser Gly Ser Gly Lys Pro Gly Ser Gly
            115                 120                 125

Glu Gly Ser Thr Lys Gly Glu Ile Val Met Thr Gln Ser Pro Ala Thr
        130                 135                 140

Leu Ser Val Ser Pro Gly Glu Arg Ala Thr Leu Ser Cys Arg Ala Ser
145                 150                 155                 160

Gln Ser Val Ser Ser Asn Leu Ala Trp Tyr Gln Gln Lys Pro Gly Gln
                165                 170                 175

Ala Pro Arg Leu Leu Ile Tyr Gly Ala Ser Thr Arg Ala Thr Gly Ile
                180                 185                 190

Pro Ala Arg Phe Ser Gly Ser Gly Ser Gly Thr Glu Phe Thr Leu Thr
            195                 200                 205

Ile Ser Ser Leu Gln Ser Glu Asp Phe Ala Val Tyr Tyr Cys Gln Gln
        210                 215                 220

Tyr Ala Ala Tyr Pro Thr Phe Gly Gly Gly Thr Lys Val Glu Ile Lys
225                 230                 235                 240

Arg Ala Ala Ala Leu Asp Asn Glu Lys Ser Asn Gly Thr Ile Ile His
                245                 250                 255

Val Lys Gly Lys His Leu Cys Pro Ser Pro Leu Phe Pro Gly Pro Ser
```

```
                    260                 265                 270
Lys Pro Phe Trp Val Leu Val Val Gly Gly Val Leu Ala Cys Tyr
                275                 280                 285

Ser Leu Leu Val Thr Val Ala Phe Ile Ile Phe Trp Val Arg Ser Lys
                290                 295                 300

Arg Ser Arg Leu Leu His Ser Asp Tyr Met Asn Met Thr Pro Arg Arg
305                 310                 315                 320

Pro Gly Pro Thr Arg Lys His Tyr Gln Pro Tyr Ala Pro Pro Arg Asp
                325                 330                 335

Phe Ala Ala Tyr Arg Ser Arg Val Lys Phe Ser Arg Ser Ala Asp Ala
                340                 345                 350

Pro Ala Tyr Gln Gln Gly Gln Asn Gln Leu Tyr Asn Glu Leu Asn Leu
                355                 360                 365

Gly Arg Arg Glu Glu Tyr Asp Val Leu Asp Lys Arg Arg Gly Arg Asp
            370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
                420                 425                 430

Gln Gly Leu Ser Thr Ala Thr Lys Asp Thr Tyr Asp Ala Leu His Met
                435                 440                 445

Gln Ala Leu Pro Pro Arg
            450

<210> SEQ ID NO 131
<211> LENGTH: 454
<212> TYPE: PRT
<213> ORGANISM: Artificial Sequence
<220> FEATURE:
<223> OTHER INFORMATION: anti-BCMA CAR

<400> SEQUENCE: 131

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
                35                  40                  45

Tyr Gly Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ala Ala Tyr Pro Thr
                85                  90                  95

Phe Gly Gly Gly Thr Lys Val Glu Ile Lys Arg Gly Ser Thr Ser Gly
                100                 105                 110

Ser Gly Lys Pro Gly Ser Gly Glu Gly Ser Thr Lys Gly Gln Val Gln
            115                 120                 125

Leu Val Gln Ser Gly Ala Glu Val Lys Lys Pro Gly Ala Ser Val Lys
            130                 135                 140

Val Ser Cys Lys Ala Ser Gly Tyr Thr Phe Thr Ser Tyr Tyr Met His
145                 150                 155                 160

Trp Val Arg Gln Ala Pro Gly Gln Gly Leu Glu Trp Met Gly Ile Ile
```

```
                165                 170                 175
Asn Pro Gly Gly Gly Ser Thr Ser Tyr Ala Gln Lys Phe Gln Gly Arg
            180                 185                 190

Val Thr Met Thr Arg Asp Thr Ser Thr Val Tyr Met Glu Leu
            195                 200                 205

Ser Ser Leu Arg Ser Glu Asp Thr Ala Val Tyr Tyr Cys Ala Arg Glu
        210                 215                 220

Ser Trp Pro Met Asp Val Trp Gly Gln Gly Thr Thr Val Thr Val Ser
225                 230                 235                 240

Ser Ala Ala Leu Asp Asn Glu Lys Ser Asn Gly Thr Ile Ile His
            245                 250                 255

Val Lys Gly Lys His Leu Cys Pro Ser Pro Leu Phe Pro Gly Pro Ser
            260                 265                 270

Lys Pro Phe Trp Val Leu Val Val Gly Gly Val Leu Ala Cys Tyr
            275                 280                 285

Ser Leu Leu Val Thr Val Ala Phe Ile Ile Phe Trp Val Arg Ser Lys
        290                 295                 300

Arg Ser Arg Leu Leu His Ser Asp Tyr Met Asn Met Thr Pro Arg Arg
305                 310                 315                 320

Pro Gly Pro Thr Arg Lys His Tyr Gln Pro Tyr Ala Pro Pro Arg Asp
            325                 330                 335

Phe Ala Ala Tyr Arg Ser Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
            355                 360                 365

Gly Arg Arg Glu Glu Tyr Asp Val Leu Asp Lys Arg Arg Gly Arg Asp
            370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
            435                 440                 445

Gln Ala Leu Pro Pro Arg
            450

<210> SEQ ID NO 132
<211> LENGTH: 461
<212> TYPE: PRT
<213> ORGANISM: Artificial Sequence
<220> FEATURE:
<223> OTHER INFORMATION: anti-BCMA CAR

<400> SEQUENCE: 132

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
```

```
                65                  70                  75                  80
            Ser Leu Lys Leu Ser Ser Val Thr Ala Ala Asp Thr Ala Val Tyr Tyr
                                85                  90                  95

Cys Ala Arg Gly Arg Gly Tyr Ala Thr Ser Leu Ala Phe Asp Ile Trp
                            100                 105                 110

Gly Gln Gly Thr Met Val Thr Val Ser Ser Gly Ser Thr Ser Gly Ser
                        115                 120                 125

Gly Lys Pro Gly Ser Gly Glu Gly Ser Thr Lys Gly Glu Ile Val Leu
                    130                 135                 140

Thr Gln Ser Pro Ala Thr Leu Ser Leu Ser Pro Gly Glu Arg Ala Thr
            145                 150                 155                 160

Leu Ser Cys Arg Ala Ser Gln Ser Val Ser Ser Tyr Leu Ala Trp Tyr
                            165                 170                 175

Gln Gln Lys Pro Gly Gln Ala Pro Arg Leu Leu Ile Tyr Asp Ala Ser
                        180                 185                 190

Asn Arg Ala Thr Gly Ile Pro Ala Arg Phe Ser Gly Ser Gly Ser Gly
                    195                 200                 205

Thr Asp Phe Thr Leu Thr Ile Ser Ser Leu Glu Pro Glu Asp Phe Ala
            210                 215                 220

Val Tyr Tyr Cys Gln Gln Arg His Val Trp Pro Thr Phe Gly Gly Gly
            225                 230                 235                 240

Gly Thr Lys Val Glu Ile Lys Arg Ala Ala Ala Leu Asp Asn Glu Lys
                            245                 250                 255

Ser Asn Gly Thr Ile Ile His Val Lys Gly Lys His Leu Cys Pro Ser
                        260                 265                 270

Pro Leu Phe Pro Gly Pro Ser Lys Pro Phe Trp Val Leu Val Val Val
                    275                 280                 285

Gly Gly Val Leu Ala Cys Tyr Ser Leu Leu Val Thr Val Ala Phe Ile
            290                 295                 300

Ile Phe Trp Val Arg Ser Lys Arg Ser Arg Leu Leu His Ser Asp Tyr
            305                 310                 315                 320

Met Asn Met Thr Pro Arg Arg Pro Gly Pro Thr Arg Lys His Tyr Gln
                            325                 330                 335

Pro Tyr Ala Pro Pro Arg Asp Phe Ala Ala Tyr Arg Ser Arg Val Lys
                        340                 345                 350

Phe Ser Arg Ser Ala Asp Ala Pro Ala Tyr Gln Gln Gly Gln Asn Gln
                    355                 360                 365

Leu Tyr Asn Glu Leu Asn Leu Gly Arg Arg Glu Glu Tyr Asp Val Leu
            370                 375                 380

Asp Lys Arg Arg Gly Arg Asp Pro Glu Met Gly Gly Lys Pro Arg Arg
            385                 390                 395                 400

Lys Asn Pro Gln Glu Gly Leu Tyr Asn Glu Leu Gln Lys Asp Lys Met
                            405                 410                 415

Ala Glu Ala Tyr Ser Glu Ile Gly Met Lys Gly Glu Arg Arg Arg Gly
                        420                 425                 430

Lys Gly His Asp Gly Leu Tyr Gln Gly Leu Ser Thr Ala Thr Lys Asp
                    435                 440                 445

Thr Tyr Asp Ala Leu His Met Gln Ala Leu Pro Pro Arg
            450                 455                 460

<210> SEQ ID NO 133
<211> LENGTH: 461
<212> TYPE: PRT
<213> ORGANISM: Artificial Sequence
```

<220> FEATURE:
<223> OTHER INFORMATION: anti-BCMA CAR

<400> SEQUENCE: 133

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg His Val Trp Pro Pro
                85                  90                  95

Thr Phe Gly Gly Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Leu
        115                 120                 125

Gln Leu Gln Glu Ser Gly Pro Gly Leu Val Lys Pro Ser Glu Thr Leu
    130                 135                 140

Ser Leu Thr Cys Thr Val Ser Gly Gly Ser Ile Ser Ser Ser Ser Tyr
145                 150                 155                 160

Tyr Trp Gly Trp Ile Arg Gln Pro Pro Gly Lys Gly Leu Glu Trp Ile
                165                 170                 175

Gly Ser Ile Ser Tyr Ser Gly Ser Thr Tyr Tyr Asn Pro Ser Leu Lys
            180                 185                 190

Ser Arg Val Thr Ile Ser Val Asp Thr Ser Lys Asn Gln Phe Ser Leu
        195                 200                 205

Lys Leu Ser Ser Val Thr Ala Ala Asp Thr Ala Val Tyr Tyr Cys Ala
    210                 215                 220

Arg Gly Arg Gly Tyr Ala Thr Ser Leu Ala Phe Asp Ile Trp Gly Gln
225                 230                 235                 240

Gly Thr Met Val Thr Val Ser Ser Ala Ala Ala Leu Asp Asn Glu Lys
                245                 250                 255

Ser Asn Gly Thr Ile Ile His Val Lys Gly Lys His Leu Cys Pro Ser
            260                 265                 270

Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
290                 295                 300

Ile Phe Trp Val Arg Ser Lys Arg Ser Arg Leu Leu His Ser Asp Tyr
                305                 310                 315                 320

Met Asn Met Thr Pro Arg Arg Pro Gly Pro Thr Arg Lys His Tyr Gln
            325                 330                 335

Pro Tyr Ala Pro Pro Arg Asp Phe Ala Ala Tyr Arg Ser Arg Val Lys
        340                 345                 350

Phe Ser Arg Ser Ala Asp Ala Pro Ala Tyr Gln Gln Gly Gln Asn Gln
    355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400
```

```
Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 134
<211> LENGTH: 458
<212> TYPE: PRT
<213> ORGANISM: Artificial Sequence
<220> FEATURE:
<223> OTHER INFORMATION: anti-BCMA CAR

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Thr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gln Glu His Leu Ile Phe Asp Tyr Trp Gly Gln Gly
            100                 105                 110

Thr Leu Val Thr Val Ser Ser Gly Ser Thr Ser Gly Ser Gly Lys Pro
        115                 120                 125

Gly Ser Gly Glu Gly Ser Thr Lys Gly Glu Ile Val Leu Thr Gln Ser
130                 135                 140

Pro Ala Thr Leu Ser Leu Ser Pro Gly Glu Arg Ala Thr Leu Ser Cys
145                 150                 155                 160

Arg Ala Ser Gln Ser Val Ser Arg Tyr Leu Ala Trp Tyr Gln Gln Lys
                165                 170                 175

Pro Gly Gln Ala Pro Arg Leu Leu Ile Tyr Asp Ala Ser Asn Arg Ala
            180                 185                 190

Thr Gly Ile Pro Ala Arg Phe Ser Gly Ser Gly Ser Gly Thr Asp Phe
        195                 200                 205

Thr Leu Thr Ile Ser Ser Leu Glu Pro Glu Asp Phe Ala Val Tyr Tyr
    210                 215                 220

Cys Gln Gln Arg Phe Tyr Tyr Pro Trp Thr Phe Gly Gly Gly Thr Lys
225                 230                 235                 240

Val Glu Ile Lys Arg Ala Ala Ala Leu Asp Asn Glu Lys Ser Asn Gly
                245                 250                 255

Thr Ile Ile His Val Lys Gly Lys His Leu Cys Pro Ser Pro Leu Phe
            260                 265                 270

Pro Gly Pro Ser Lys Pro Phe Trp Val Leu Val Val Val Gly Gly Val
        275                 280                 285

Leu Ala Cys Tyr Ser Leu Leu Val Thr Val Ala Phe Ile Ile Phe Trp
    290                 295                 300
```

```
Val Arg Ser Lys Arg Ser Arg Leu Leu His Ser Asp Tyr Met Asn Met
305                 310                 315                 320

Thr Pro Arg Arg Pro Gly Pro Thr Arg Lys His Tyr Gln Pro Tyr Ala
            325                 330                 335

Pro Pro Arg Asp Phe Ala Ala Tyr Arg Ser Arg Val Lys Phe Ser Arg
            340                 345                 350

Ser Ala Asp Ala Pro Ala Tyr Gln Gln Gly Gln Asn Gln Leu Tyr Asn
            355                 360                 365

Glu Leu Asn Leu Gly Arg Arg Glu Glu Tyr Asp Val Leu Asp Lys Arg
370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
            405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg
    450                 455

<210> SEQ ID NO 135
<211> LENGTH: 458
<212> TYPE: PRT
<213> ORGANISM: Artificial Sequence
<220> FEATURE:
<223> OTHER INFORMATION: anti-BCMA CAR

<400> SEQUENCE: 135

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Tyr Tyr Pro Trp
            85                  90                  95

Thr Phe Gly Gly Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Thr Phe Ser Ser Tyr Ser Met
145                 150                 155                 160

Asn Trp Val Arg Gln Ala Pro Gly Lys Gly Leu Glu Trp Val Ser Thr
            165                 170                 175

Ile Ser Ser Ser Ser Ser Thr Ile Tyr Tyr Ala Asp Ser Val Lys Gly
        180                 185                 190

Arg Phe Thr Ile Ser Arg Asp Asn Ala Lys Asn Ser Leu Tyr Leu Gln
    195                 200                 205
```

```
Met Asn Ser Leu Arg Ala Glu Asp Thr Ala Val Tyr Tyr Cys Ala Arg
    210                 215                 220

Gly Ser Gln Glu His Leu Ile Phe Asp Tyr Trp Gly Gln Gly Thr Leu
225                 230                 235                 240

Val Thr Val Ser Ser Ala Ala Ala Leu Asp Asn Glu Lys Ser Asn Gly
                245                 250                 255

Thr Ile Ile His Val Lys Gly Lys His Leu Cys Pro Ser Pro Leu Phe
            260                 265                 270

Pro Gly Pro Ser Lys Pro Phe Trp Val Leu Val Val Val Gly Gly Val
            275                 280                 285

Leu Ala Cys Tyr Ser Leu Leu Val Thr Val Ala Phe Ile Ile Phe Trp
        290                 295                 300

Val Arg Ser Lys Arg Ser Arg Leu Leu His Ser Asp Tyr Met Asn Met
305                 310                 315                 320

Thr Pro Arg Arg Pro Gly Pro Thr Arg Lys His Tyr Gln Pro Tyr Ala
                325                 330                 335

Pro Pro Arg Asp Phe Ala Ala Tyr Arg Ser Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro Arg
    450                 455

<210> SEQ ID NO 136
<211> LENGTH: 461
<212> TYPE: PRT
<213> ORGANISM: Artificial Sequence
<220> FEATURE:
<223> OTHER INFORMATION: anti-BCMA CAR

<400> SEQUENCE: 136

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Phe Trp Ser Gly Ser Pro Pro Gly Leu Asp Tyr Trp
            100                 105                 110
```

Gly Gln Gly Thr Leu Val Thr Val Ser Ser Gly Ser Thr Gly Ser
            115                 120                 125

Gly Lys Pro Gly Ser Gly Glu Gly Ser Thr Lys Gly Asp Ile Gln Leu
        130                 135                 140

Thr Gln Ser Pro Ser Ser Val Ser Ala Ser Val Gly Asp Arg Val Thr
145                 150                 155                 160

Ile Thr Cys Arg Ala Ser Gln Gly Ile Ser Ser Trp Leu Ala Trp Tyr
                165                 170                 175

Gln Gln Lys Pro Gly Lys Ala Pro Lys Leu Leu Ile Tyr Gly Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ile Tyr Thr Phe Pro Phe Thr Phe Gly Gly
225                 230                 235                 240

Gly Thr Lys Val Glu Ile Lys Arg Ala Ala Ala Leu Asp Asn Glu Lys
                245                 250                 255

Ser Asn Gly Thr Ile Ile His Val Lys Gly Lys His Leu Cys Pro Ser
            260                 265                 270

Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
    290                 295                 300

Ile Phe Trp Val Arg Ser Lys Arg Ser Arg Leu Leu His Ser Asp Tyr
305                 310                 315                 320

Met Asn Met Thr Pro Arg Arg Pro Gly Pro Thr Arg Lys His Tyr Gln
                325                 330                 335

Pro Tyr Ala Pro Pro Arg Asp Phe Ala Ala Tyr Arg Ser Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 137
<211> LENGTH: 461
<212> TYPE: PRT
<213> ORGANISM: Artificial Sequence
<220> FEATURE:
<223> OTHER INFORMATION: anti-BCMA CAR

<400> SEQUENCE: 137

Asp Ile Gln Leu Thr Gln Ser Pro Ser Ser Val Ser Ala Ser Val Gly
1               5                   10                  15

-continued

```
Asp Arg Val Thr Ile Thr Cys Arg Ala Ser Gln Gly Ile Ser Ser Trp
         20                  25                  30
Leu Ala Trp Tyr Gln Gln Lys Pro Gly Lys Ala Pro Lys Leu Leu Ile
         35                  40                  45
Tyr Gly Ala Ser Ser Leu Gln Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ile Tyr Thr Phe Pro Phe
                 85                  90                  95
Thr Phe Gly Gly Gly Thr Lys Val Glu Ile Lys Arg Gly Ser Thr Ser
             100                 105                 110
Gly Ser Gly Lys Pro Gly Ser Gly Glu Gly Ser Thr Lys Gly Gln Val
         115                 120                 125
Gln Leu Val Glu Ser Gly Gly Val Val Gln Pro Gly Arg Ser Leu
130                 135                 140
Arg Leu Ser Cys Ala Ala Ser Gly Phe Thr Phe Ser Ser Tyr Gly Met
145                 150                 155                 160
His Trp Val Arg Gln Ala Pro Gly Lys Gly Leu Glu Trp Val Ala Val
                 165                 170                 175
Ile Ser Tyr Asp Gly Ser Asn Lys Tyr Tyr Ala Asp Ser Val Lys Gly
             180                 185                 190
Arg Phe Thr Ile Ser Arg Asp Asn Ser Lys Asn Thr Leu Tyr Leu Gln
         195                 200                 205
Met Asn Ser Leu Arg Ala Glu Asp Thr Ala Val Tyr Tyr Cys Ala Arg
 210                 215                 220
Thr Asp Phe Trp Ser Gly Ser Pro Pro Gly Leu Asp Tyr Trp Gly Gln
225                 230                 235                 240
Gly Thr Leu Val Thr Val Ser Ser Ala Ala Leu Asp Asn Glu Lys
                 245                 250                 255
Ser Asn Gly Thr Ile Ile His Val Lys Gly Lys His Leu Cys Pro Ser
             260                 265                 270
Pro Leu Phe Pro Gly Pro Ser Lys Pro Phe Trp Val Leu Val Val Val
         275                 280                 285
Gly Gly Val Leu Ala Cys Tyr Ser Leu Leu Val Thr Val Ala Phe Ile
 290                 295                 300
Ile Phe Trp Val Arg Ser Lys Arg Ser Arg Leu Leu His Ser Asp Tyr
305                 310                 315                 320
Met Asn Met Thr Pro Arg Arg Pro Gly Pro Thr Arg Lys His Tyr Gln
                 325                 330                 335
Pro Tyr Ala Pro Pro Arg Asp Phe Ala Ala Tyr Arg Ser Arg Val Lys
             340                 345                 350
Phe Ser Arg Ser Ala Asp Ala Pro Ala Tyr Gln Gln Gly Gln Asn Gln
         355                 360                 365
Leu Tyr Asn Glu Leu Asn Leu Gly Arg Arg Glu Glu Tyr Asp Val Leu
 370                 375                 380
Asp Lys Arg Arg Gly Arg Asp Pro Glu Met Gly Gly Lys Pro Arg Arg
385                 390                 395                 400
Lys Asn Pro Gln Glu Gly Leu Tyr Asn Glu Leu Gln Lys Asp Lys Met
                 405                 410                 415
Ala Glu Ala Tyr Ser Glu Ile Gly Met Lys Gly Glu Arg Arg Arg Gly
             420                 425                 430
```

```
Lys Gly His Asp Gly Leu Tyr Gln Gly Leu Ser Thr Ala Thr Lys Asp
            435                 440                 445

Thr Tyr Asp Ala Leu His Met Gln Ala Leu Pro Pro Arg
    450                 455                 460

<210> SEQ ID NO 138
<211> LENGTH: 471
<212> TYPE: PRT
<213> ORGANISM: Artificial Sequence
<220> FEATURE:
<223> OTHER INFORMATION: anti-BCMA CAR

<400> SEQUENCE: 138

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Glu Tyr Ser Ser Ser Ile Trp His Tyr Tyr Tyr Gly
            100                 105                 110

Met Asp Val Trp Gly Gln Gly Thr Thr Val Thr Val Ser Ser Gly Ser
        115                 120                 125

Thr Ser Gly Ser Gly Lys Pro Gly Ser Gly Glu Gly Ser Thr Lys Gly
    130                 135                 140

Asp Ile Val Met Thr Gln Ser Pro Asp Ser Leu Ala Val Ser Leu Gly
145                 150                 155                 160

Glu Arg Ala Thr Ile Asn Cys Lys Ser Ser Gln Ser Val Leu Tyr Ser
                165                 170                 175

Ser Asn Asn Lys Asn Tyr Leu Ala Trp Tyr Gln Gln Lys Pro Gly Gln
            180                 185                 190

Pro Pro Lys Leu Leu Ile Tyr Trp Ala Ser Thr Arg Glu Ser Gly Val
        195                 200                 205

Pro Asp Arg Phe Ser Gly Ser Gly Ser Gly Thr Asp Phe Thr Leu Thr
    210                 215                 220

Ile Ser Ser Leu Gln Ala Glu Asp Val Ala Val Tyr Tyr Cys Gln Gln
225                 230                 235                 240

Phe Ala His Thr Pro Phe Thr Phe Gly Gly Gly Thr Lys Val Glu Ile
                245                 250                 255

Lys Arg Ala Ala Ala Leu Asp Asn Glu Lys Ser Asn Gly Thr Ile Ile
            260                 265                 270

His Val Lys Gly Lys His Leu Cys Pro Ser Pro Leu Phe Pro Gly Pro
        275                 280                 285

Ser Lys Pro Phe Trp Val Leu Val Val Val Gly Gly Val Leu Ala Cys
    290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335
```

Arg Pro Gly Pro Thr Arg Lys His Tyr Gln Pro Tyr Ala Pro Pro Arg
                340                 345                 350

Asp Phe Ala Ala Tyr Arg Ser Arg Val Lys Phe Ser Arg Ser Ala Asp
            355                 360                 365

Ala Pro Ala Tyr Gln Gln Gly Gln Asn Gln Leu Tyr Asn Glu Leu Asn
        370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
                405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
        435                 440                 445

Tyr Gln Gly Leu Ser Thr Ala Thr Lys Asp Thr Tyr Asp Ala Leu His
450                 455                 460

Met Gln Ala Leu Pro Pro Arg
465                 470

<210> SEQ ID NO 139
<211> LENGTH: 471
<212> TYPE: PRT
<213> ORGANISM: Artificial Sequence
<220> FEATURE:
<223> OTHER INFORMATION: anti-BCMA CAR

<400> SEQUENCE: 139

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Ala His Thr Pro Phe Thr Phe Gly Gly Gly Thr Lys Val Glu Ile
            100                 105                 110

Lys Arg Gly Ser Thr Ser Gly Ser Gly Lys Pro Gly Ser Gly Glu Gly
        115                 120                 125

Ser Thr Lys Gly Gln Val Gln Leu Val Gln Ser Gly Ala Glu Val Lys
    130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Gly Ile Ile Pro Ile Phe Gly Thr Ala Asn Tyr
            180                 185                 190

Ala Gln Lys Phe Gln Gly Arg Val Thr Ile Thr Ala Asp Glu Ser Thr
        195                 200                 205

Ser Thr Ala Tyr Met Glu Leu Ser Ser Leu Arg Ser Glu Asp Thr Ala
    210                 215                 220

Val Tyr Tyr Cys Ala Arg Thr Pro Glu Tyr Ser Ser Ile Trp His
225                 230                 235                 240

Tyr Tyr Tyr Gly Met Asp Val Trp Gly Gln Gly Thr Thr Val Thr Val
            245                 250                 255

Ser Ser Ala Ala Ala Leu Asp Asn Glu Lys Ser Asn Gly Thr Ile Ile
        260                 265                 270

His Val Lys Gly Lys His Leu Cys Pro Ser Pro Leu Phe Pro Gly Pro
            275                 280                 285

Ser Lys Pro Phe Trp Val Leu Val Val Gly Val Leu Ala Cys
290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
            325                 330                 335

Arg Pro Gly Pro Thr Arg Lys His Tyr Gln Pro Tyr Ala Pro Pro Arg
            340                 345                 350

Asp Phe Ala Ala Tyr Arg Ser Arg Val Lys Phe Ser Arg Ser Ala Asp
            355                 360                 365

Ala Pro Ala Tyr Gln Gln Gly Gln Asn Gln Leu Tyr Asn Glu Leu Asn
370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
            405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
        450                 455                 460

Met Gln Ala Leu Pro Pro Arg
465                 470

<210> SEQ ID NO 140
<211> LENGTH: 462
<212> TYPE: PRT
<213> ORGANISM: Artificial Sequence
<220> FEATURE:
<223> OTHER INFORMATION: anti-BCMA CAR

<400> SEQUENCE: 140

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Asp Tyr Gly Met Asp Val
            100                 105                 110

```
Trp Gly Gln Gly Thr Thr Val Thr Val Ser Ser Gly Ser Thr Ser Gly
            115                 120                 125

Ser Gly Lys Pro Gly Ser Gly Glu Gly Ser Thr Lys Gly Glu Ile Val
        130                 135                 140

Met Thr Gln Ser Pro Ala Thr Leu Ser Val Ser Pro Gly Glu Arg Ala
145                 150                 155                 160

Thr Leu Ser Cys Arg Ala Ser Gln Ser Val Ser Ser Asn Leu Ala Trp
                165                 170                 175

Tyr Gln Gln Lys Pro Gly Gln Ala Pro Arg Leu Leu Ile Tyr Ser Ala
            180                 185                 190

Ser Thr Arg Ala Thr Gly Ile Pro Ala Arg Phe Ser Gly Ser Gly Ser
        195                 200                 205

Gly Thr Glu Phe Thr Leu Thr Ile Ser Ser Leu Gln Ser Glu Asp Phe
    210                 215                 220

Ala Val Tyr Tyr Cys Gln Gln His His Val Trp Pro Leu Thr Phe Gly
225                 230                 235                 240

Gly Gly Thr Lys Val Glu Ile Lys Arg Ala Ala Ala Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 141
<211> LENGTH: 462
<212> TYPE: PRT
<213> ORGANISM: Artificial Sequence
<220> FEATURE:
<223> OTHER INFORMATION: anti-BCMA CAR

<400> SEQUENCE: 141

Glu Ile Val Met Thr Gln Ser Pro Ala Thr Leu Ser Val Ser Pro Gly
1               5                   10                  15
```

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His His Val Trp Pro Leu
                85                  90                  95

Thr Phe Gly Gly Gly Thr Lys Val Glu Ile Lys Arg Gly Ser Thr Ser
                100                 105                 110

Gly Ser Gly Lys Pro Gly Ser Gly Glu Gly Ser Thr Lys Gly Gln Val
            115                 120                 125

Gln Leu Val Glu Ser Gly Gly Val Val Gln Pro Gly Arg Ser Leu
        130                 135                 140

Arg Leu Ser Cys Ala Ala Ser Gly Phe Thr Phe Ser Ser Tyr Gly Met
145                 150                 155                 160

His Trp Val Arg Gln Ala Pro Gly Lys Gly Leu Glu Trp Val Ala Val
                165                 170                 175

Ile Ser Tyr Asp Gly Ser Asn Lys Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Val Lys
210                 215                 220

Gly Pro Leu Gln Glu Pro Pro Tyr Asp Tyr Gly Met Asp Val Trp Gly
225                 230                 235                 240

Gln Gly Thr Thr Val Thr Val Ser Ser Ala Ala Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys

```
            435                 440                 445
Asp Thr Tyr Asp Ala Leu His Met Gln Ala Leu Pro Pro Arg
    450                 455                 460
```

<210> SEQ ID NO 142
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 142

```
Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Ser Leu Glu Met Ala Glu Val
            115                 120                 125

Gln Leu Val Gln Ser Gly Ala Glu Met Lys Lys Pro Gly Ala Ser Leu
        130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
    210                 215                 220

Ser Gln Arg Asp Gly Tyr Met Asp Tyr Trp Gly Gln Gly Thr Leu Val
225                 230                 235                 240

Thr Val Ser Ser Ala Ala Ala Ile Glu Val Met Tyr Pro Pro Pro Tyr
                245                 250                 255

Leu Asp Asn Glu Lys Ser Asn Gly Thr Ile Ile His Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
```

```
                340                 345                 350
Arg Ser Arg Val Lys Phe Ser Arg Ser Ala Asp Ala Pro Ala Tyr Gln
            355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
            435                 440                 445

Thr Ala Thr Lys Asp Thr Tyr Asp Ala Leu His Met Gln Ala Leu Pro
            450                 455                 460

Pro Arg
465

<210> SEQ ID NO 143
<211> LENGTH: 473
<212> TYPE: PRT
<213> ORGANISM: Artificial Sequence
<220> FEATURE:
<223> OTHER INFORMATION: anti-BCMA CAR

<400> SEQUENCE: 143

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
    130                 135                 140

Lys Lys Pro Gly Ala Ser Val Lys Val Ser Cys Lys Ala Ser Gly Tyr
145                 150                 155                 160

Thr Phe Thr Asp Tyr Tyr Met His Trp Val Arg Gln Ala Pro Gly Gln
                165                 170                 175

Arg Leu Glu Trp Met Gly Trp Ile Asn Pro Asn Ser Gly Gly Thr Asn
            180                 185                 190

Tyr Ala Gln Lys Phe Gln Asp Arg Ile Thr Val Thr Arg Asp Thr Ser
        195                 200                 205

Ser Asn Thr Gly Tyr Met Glu Leu Thr Arg Leu Arg Ser Asp Asp Thr
    210                 215                 220

Ala Val Tyr Tyr Cys Ala Arg Ser Pro Tyr Ser Gly Val Leu Asp Lys
```

```
            225                 230                 235                 240
    Trp Gly Gln Gly Thr Leu Val Thr Val Ser Ser Ala Ala Ile Glu
                    245                 250                 255
    Val Met Tyr Pro Pro Tyr Leu Asp Asn Glu Lys Ser Asn Gly Thr
                    260                 265                 270
    Ile Ile His Val Lys Gly Lys His Leu Cys Pro Ser Pro Leu Phe Pro
                275                 280                 285
    Gly Pro Ser Lys Pro Phe Trp Val Leu Val Val Val Gly Gly Val Leu
            290                 295                 300
    Ala Cys Tyr Ser Leu Leu Val Thr Val Ala Phe Ile Ile Phe Trp Val
    305                 310                 315                 320
    Arg Ser Lys Arg Ser Arg Leu Leu His Ser Asp Tyr Met Asn Met Thr
                    325                 330                 335
    Pro Arg Arg Pro Gly Pro Thr Arg Lys His Tyr Gln Pro Tyr Ala Pro
                    340                 345                 350
    Pro Arg Asp Phe Ala Ala Tyr Arg Ser Arg Val Lys Phe Ser Arg Ser
                    355                 360                 365
    Ala Asp Ala Pro Ala Tyr Gln Gln Gly Gln Asn Gln Leu Tyr Asn Glu
            370                 375                 380
    Leu Asn Leu Gly Arg Arg Glu Glu Tyr Asp Val Leu Asp Lys Arg Arg
    385                 390                 395                 400
    Gly Arg Asp Pro Glu Met Gly Gly Lys Pro Arg Arg Lys Asn Pro Gln
                    405                 410                 415
    Glu Gly Leu Tyr Asn Glu Leu Gln Lys Asp Lys Met Ala Glu Ala Tyr
                    420                 425                 430
    Ser Glu Ile Gly Met Lys Gly Glu Arg Arg Arg Gly Lys Gly His Asp
                    435                 440                 445
    Gly Leu Tyr Gln Gly Leu Ser Thr Ala Thr Lys Asp Thr Tyr Asp Ala
            450                 455                 460
    Leu His Met Gln Ala Leu Pro Pro Arg
    465                 470

<210> SEQ ID NO 144
<211> LENGTH: 470
<212> TYPE: PRT
<213> ORGANISM: Artificial Sequence
<220> FEATURE:
<223> OTHER INFORMATION: anti-BCMA CAR

<400> SEQUENCE: 144

Ser Tyr Glu Leu Thr Gln Pro Pro Ser Ala Ser Gly Thr Pro Gly Gln
    1               5                   10                  15
    Arg Val Thr Met Ser Cys Ser Gly Thr Ser Ser Asn Ile Gly Ser His
                    20                  25                  30
    Ser Val Asn Trp Tyr Gln Gln Leu Pro Gly Thr Ala Pro Lys Leu Leu
                35                  40                  45
    Ile Tyr Thr Asn Asn Gln Arg Pro Ser Gly Val Pro Asp Arg Phe Ser
            50                  55                  60
    Gly Ser Lys Ser Gly Thr Ser Ala Ser Leu Ala Ile Ser Gly Leu Gln
    65                  70                  75                  80
    Ser Glu Asp Glu Ala Asp Tyr Tyr Cys Ala Ala Trp Asp Gly Ser Leu
                    85                  90                  95
    Asn Gly Leu Val Phe Gly Gly Gly Thr Lys Leu Thr Val Leu Gly Ser
                    100                 105                 110
    Arg Gly Gly Gly Gly Ser Gly Gly Gly Gly Ser Gly Gly Gly Gly Ser
```

```
                    115                 120                 125
Leu Glu Met Ala Glu Val Gln Leu Val Gln Ser Gly Ala Glu Val Lys
    130                 135                 140
Lys Pro Gly Glu Ser Leu Lys Ile Ser Cys Lys Gly Ser Gly Tyr Ser
145                 150                 155                 160
Phe Thr Ser Tyr Trp Ile Gly Trp Val Arg Gln Met Pro Gly Lys Gly
                165                 170                 175
Leu Glu Trp Met Gly Ile Ile Tyr Pro Gly Asp Ser Asp Thr Arg Tyr
            180                 185                 190
Ser Pro Ser Phe Gln Gly His Val Thr Ile Ser Ala Asp Lys Ser Ile
        195                 200                 205
Ser Thr Ala Tyr Leu Gln Trp Ser Ser Leu Lys Ala Ser Asp Thr Ala
    210                 215                 220
Met Tyr Tyr Cys Ala Arg Tyr Ser Gly Ser Phe Asp Asn Trp Gly Gln
225                 230                 235                 240
Gly Thr Leu Val Thr Val Ser Ser Ala Ala Ile Glu Val Met Tyr
                245                 250                 255
Pro Pro Pro Tyr Leu Asp Asn Glu Lys Ser Asn Gly Thr Ile Ile His
            260                 265                 270
Val Lys Gly Lys His Leu Cys Pro Ser Pro Leu Phe Pro Gly Pro Ser
        275                 280                 285
Lys Pro Phe Trp Val Leu Val Val Gly Gly Val Leu Ala Cys Tyr
    290                 295                 300
Ser Leu Leu Val Thr Val Ala Phe Ile Ile Phe Trp Val Arg Ser Lys
305                 310                 315                 320
Arg Ser Arg Leu Leu His Ser Asp Tyr Met Asn Met Thr Pro Arg Arg
                325                 330                 335
Pro Gly Pro Thr Arg Lys His Tyr Gln Pro Tyr Ala Pro Pro Arg Asp
            340                 345                 350
Phe Ala Ala Tyr Arg Ser Arg Val Lys Phe Ser Arg Ser Ala Asp Ala
        355                 360                 365
Pro Ala Tyr Gln Gln Gly Gln Asn Gln Leu Tyr Asn Glu Leu Asn Leu
    370                 375                 380
Gly Arg Arg Glu Glu Tyr Asp Val Leu Asp Lys Arg Arg Gly Arg Asp
385                 390                 395                 400
Pro Glu Met Gly Gly Lys Pro Arg Arg Lys Asn Pro Gln Glu Gly Leu
                405                 410                 415
Tyr Asn Glu Leu Gln Lys Asp Lys Met Ala Glu Ala Tyr Ser Glu Ile
            420                 425                 430
Gly Met Lys Gly Glu Arg Arg Arg Gly Lys Gly His Asp Gly Leu Tyr
        435                 440                 445
Gln Gly Leu Ser Thr Ala Thr Lys Asp Thr Tyr Asp Ala Leu His Met
    450                 455                 460
Gln Ala Leu Pro Pro Arg
465                 470

<210> SEQ ID NO 145
<211> LENGTH: 476
<212> TYPE: PRT
<213> ORGANISM: Artificial Sequence
<220> FEATURE:
<223> OTHER INFORMATION: anti-BCMA CAR

<400> SEQUENCE: 145

Leu Pro Val Leu Thr Gln Pro Pro Ser Ala Ser Gly Thr Pro Gly Gln
```

-continued

```
1               5                   10                  15
Arg Val Thr Ile Ser Cys Ser Gly Arg Ser Ser Asn Ile Gly Ser Asn
                20                  25                  30
Ser Val Asn Trp Tyr Arg Gln Leu Pro Gly Ala Ala Pro Lys Leu Leu
                35                  40                  45
Ile Tyr Ser Asn Asn Gln Arg Pro Pro Gly Val Pro Val Arg Phe Ser
                50                  55                  60
Gly Ser Lys Ser Gly Thr Ser Ala Ser Leu Ala Ile Ser Gly Leu Gln
65                  70                  75                  80
Ser Glu Asp Glu Ala Thr Tyr Tyr Cys Ala Thr Trp Asp Asp Asn Leu
                85                  90                  95
Asn Val His Tyr Val Phe Gly Thr Gly Thr Lys Val Thr Val Leu Gly
                100                 105                 110
Ser Arg Gly Gly Gly Ser Gly Gly Gly Ser Gly Gly Gly Gly
                115                 120                 125
Ser Leu Glu Met Ala Gln Val Gln Leu Val Gln Ser Gly Ala Glu Val
                130                 135                 140
Lys Lys Pro Gly Ser Ser Val Lys Val Ser Cys Lys Ala Ser Gly Gly
145                 150                 155                 160
Thr Phe Ser Ser Tyr Ala Ile Ser Trp Val Arg Gln Ala Pro Gly Gln
                165                 170                 175
Gly Leu Glu Trp Met Gly Arg Ile Ile Pro Ile Leu Gly Ile Ala Asn
                180                 185                 190
Tyr Ala Gln Lys Phe Gln Gly Arg Val Thr Ile Thr Ala Asp Lys Ser
                195                 200                 205
Thr Ser Thr Ala Tyr Met Glu Leu Ser Ser Leu Arg Ser Glu Asp Thr
                210                 215                 220
Ala Val Tyr Tyr Cys Ala Arg Gly Gly Tyr Tyr Ser His Asp Met Trp
225                 230                 235                 240
Ser Glu Asp Trp Gly Gln Gly Thr Leu Val Thr Val Ser Ser Ala Ala
                245                 250                 255
Ala Ile Glu Val Met Tyr Pro Pro Tyr Leu Asp Asn Glu Lys Ser
                260                 265                 270
Asn Gly Thr Ile Ile His Val Lys Gly Lys His Leu Cys Pro Ser Pro
                275                 280                 285
Leu Phe Pro Gly Pro Ser Lys Pro Phe Trp Val Leu Val Val Val Gly
                290                 295                 300
Gly Val Leu Ala Cys Tyr Ser Leu Leu Val Thr Val Ala Phe Ile Ile
305                 310                 315                 320
Phe Trp Val Arg Ser Lys Arg Ser Arg Leu Leu His Ser Asp Tyr Met
                325                 330                 335
Asn Met Thr Pro Arg Arg Pro Gly Pro Thr Arg Lys His Tyr Gln Pro
                340                 345                 350
Tyr Ala Pro Pro Arg Asp Phe Ala Ala Tyr Arg Ser Arg Val Lys Phe
                355                 360                 365
Ser Arg Ser Ala Asp Ala Pro Ala Tyr Gln Gln Gly Gln Asn Gln Leu
370                 375                 380
Tyr Asn Glu Leu Asn Leu Gly Arg Arg Glu Glu Tyr Asp Val Leu Asp
385                 390                 395                 400
Lys Arg Arg Gly Arg Asp Pro Glu Met Gly Gly Lys Pro Arg Arg Lys
                405                 410                 415
Asn Pro Gln Glu Gly Leu Tyr Asn Glu Leu Gln Lys Asp Lys Met Ala
                420                 425                 430
```

```
Glu Ala Tyr Ser Glu Ile Gly Met Lys Gly Glu Arg Arg Gly Lys
        435                 440                 445

Gly His Asp Gly Leu Tyr Gln Gly Leu Ser Thr Ala Thr Lys Asp Thr
    450                 455                 460

Tyr Asp Ala Leu His Met Gln Ala Leu Pro Pro Arg
465                 470                 475

<210> SEQ ID NO 146
<211> LENGTH: 475
<212> TYPE: PRT
<213> ORGANISM: Artificial Sequence
<220> FEATURE:
<223> OTHER INFORMATION: anti-BCMA CAR

<400> SEQUENCE: 146

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Phe Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Ala Ala Trp Asp Asp Ser Leu
                85                  90                  95

Ser Ala Ser Tyr Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Gln Val Gln Leu Val Gln Ser Gly Ala Glu Val
    130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Thr Ala Asn
            180                 185                 190

Tyr Ala Gln Lys Phe Gln Gly Arg Val Thr Ile Thr Ala Asp Glu Ser
        195                 200                 205

Thr Ser Thr Ala Tyr Met Glu Leu Ser Ser Leu Arg Ser Glu Asp Thr
    210                 215                 220

Ala Val Tyr Tyr Cys Ala Arg Ser Gly Tyr Gly Ser Tyr Arg Trp Glu
225                 230                 235                 240

Asp Ser Trp Gly Gln Gly Thr Leu Val Thr Val Ser Ser Ala Ala Ala
                245                 250                 255

Ile Glu Val Met Tyr Pro Pro Tyr Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
    290                 295                 300

Val Leu Ala Cys Tyr Ser Leu Leu Val Thr Val Ala Phe Ile Ile Phe
305                 310                 315                 320
```

-continued

```
Trp Val Arg Ser Lys Arg Ser Arg Leu Leu His Ser Asp Tyr Met Asn
            325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
            355                 360                 365

Arg Ser Ala Asp Ala Pro Ala Tyr Gln Gln Gly Gln Asn Gln Leu Tyr
            370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
            405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
            435                 440                 445

His Asp Gly Leu Tyr Gln Gly Leu Ser Thr Ala Thr Lys Asp Thr Tyr
            450                 455                 460

Asp Ala Leu His Met Gln Ala Leu Pro Pro Arg
465                 470                 475
```

<210> SEQ ID NO 147
<211> LENGTH: 482
<212> TYPE: PRT
<213> ORGANISM: Artificial Sequence
<220> FEATURE:
<223> OTHER INFORMATION: anti-BCMA CAR

<400> SEQUENCE: 147

```
Leu Pro Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Ser Asn
            20                  25                  30

Ser Val Asn Trp Tyr Arg Gln Leu Pro Gly Ala Ala Pro Lys Leu Leu
            35                  40                  45

Ile Tyr Ser Asn Asn Gln Arg Pro Pro Gly Val Pro Val Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Thr Tyr Tyr Cys Ala Thr Trp Asp Asp Asn Leu
            85                  90                  95

Asn Val His Tyr Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
            115                 120                 125

Ser Leu Glu Met Ala Gln Val Gln Leu Val Gln Ser Gly Ala Glu Val
            130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
            165                 170                 175

Gly Leu Glu Trp Met Gly Arg Ile Ile Pro Ile Leu Gly Ile Ala Asn
            180                 185                 190

Tyr Ala Gln Lys Phe Gln Gly Arg Val Thr Ile Thr Ala Asp Lys Ser
            195                 200                 205
```

```
Thr Ser Thr Ala Tyr Met Glu Leu Ser Ser Leu Arg Ser Glu Asp Thr
    210                 215                 220

Ala Val Tyr Tyr Cys Ala Arg Gly Gly Tyr Tyr Ser His Asp Met Trp
225                 230                 235                 240

Ser Glu Asp Trp Gly Gln Gly Thr Leu Val Thr Val Ser Ser Ala Ala
                245                 250                 255

Ala Pro Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
        275                 280                 285

Ala Gly Gly Ala Val His Thr Arg Gly Leu Asp Phe Ala Cys Asp Ile
290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Asn Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Glu Pro Pro Ala Tyr Gln
370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 148
<211> LENGTH: 476
<212> TYPE: PRT
<213> ORGANISM: Artificial Sequence
<220> FEATURE:
<223> OTHER INFORMATION: anti-BCMA CAR

<400> SEQUENCE: 148

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
                20                  25                  30

Ser Val Asn Trp Tyr Gln Gln Leu Pro Gly Thr Ala Pro Lys Leu Leu
            35                  40                  45

Ile Tyr Thr Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80
```

```
Ser Glu Asp Glu Ala Asp Tyr Tyr Cys Ala Trp Asp Gly Ser Leu
                 85                  90                  95

Asn Gly Leu Val Phe Gly Gly Thr Lys Leu Thr Val Leu Gly Ser
            100                 105                 110

Arg Gly Gly Gly Ser Gly Gly Gly Ser Gly Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly His Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Tyr Ser Gly Ser Phe Asp Asn Trp Gly Gln
225                 230                 235                 240

Gly Thr Leu Val Thr Val Ser Ser Ala Ala Ala Pro Thr Thr Thr Pro
                245                 250                 255

Ala Pro Arg Pro Pro Thr Pro Ala Pro Thr Ile Ala Ser Gln Pro Leu
            260                 265                 270

Ser Leu Arg Pro Glu Ala Cys Arg Pro Ala Ala Gly Gly Ala Val His
        275                 280                 285

Thr Arg Gly Leu Asp Phe Ala Cys Asp Ile Tyr Ile Trp Ala Pro Leu
    290                 295                 300

Ala Gly Thr Cys Gly Val Leu Leu Leu Ser Leu Val Ile Thr Leu Tyr
305                 310                 315                 320

Cys Asn Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
            340                 345                 350

Arg Phe Pro Glu Glu Glu Glu Gly Gly Cys Glu Leu Arg Val Lys Phe
        355                 360                 365

Ser Arg Ser Ala Glu Pro Pro Ala Tyr Gln Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
        435                 440                 445

Gly His Asp Gly Leu Tyr Gln Gly Leu Ser Thr Ala Thr Lys Asp Thr
    450                 455                 460

Tyr Asp Ala Leu His Met Gln Ala Leu Pro Pro Arg
465                 470                 475

<210> SEQ ID NO 149
<211> LENGTH: 481
<212> TYPE: PRT
```

<213> ORGANISM: Artificial Sequence
<220> FEATURE:
<223> OTHER INFORMATION: anti-BCMA CAR

<400> SEQUENCE: 149

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Phe Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Ser Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
        115                 120                 125

Ser Leu Glu Met Ala Gln Val Gln Leu Val Gln Ser Gly Ala Glu Val
    130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Thr Ala Asn
            180                 185                 190

Tyr Ala Gln Lys Phe Gln Gly Arg Val Thr Ile Thr Ala Asp Glu Ser
        195                 200                 205

Thr Ser Thr Ala Tyr Met Glu Leu Ser Ser Leu Arg Ser Glu Asp Thr
    210                 215                 220

Ala Val Tyr Tyr Cys Ala Arg Ser Gly Tyr Gly Ser Tyr Arg Trp Glu
225                 230                 235                 240

Asp Ser Trp Gly Gln Gly Thr Leu Val Thr Val Ser Ser Ala Ala Ala
                245                 250                 255

Pro Thr Thr Thr Pro Ala Pro Arg Pro Pro Thr Pro Ala Pro Thr Ile
            260                 265                 270

Ala Ser Gln Pro Leu Ser Leu Arg Pro Glu Ala Cys Arg Pro Ala Ala
        275                 280                 285

Gly Gly Ala Val His Thr Arg Gly Leu Asp Phe Ala Cys Asp Ile Tyr
    290                 295                 300

Ile Trp Ala Pro Leu Ala Gly Thr Cys Gly Val Leu Leu Leu Ser Leu
305                 310                 315                 320

Val Ile Thr Leu Tyr Cys Asn Lys Arg Gly Arg Lys Lys Leu Leu Tyr
                325                 330                 335

Ile Phe Lys Gln Pro Phe Met Arg Pro Val Gln Thr Thr Gln Glu Glu
            340                 345                 350

Asp Gly Cys Ser Cys Arg Phe Pro Glu Glu Glu Glu Gly Gly Cys Glu
        355                 360                 365

Leu Arg Val Lys Phe Ser Arg Ser Ala Glu Pro Pro Ala Tyr Gln Gln
    370                 375                 380

Gly Gln Asn Gln Leu Tyr Asn Glu Leu Asn Leu Gly Arg Arg Glu Glu
```

```
385                 390                 395                 400

Tyr Asp Val Leu Asp Lys Arg Gly Arg Asp Pro Glu Met Gly Gly
                405                 410                 415

Lys Pro Arg Arg Lys Asn Pro Gln Glu Gly Leu Tyr Asn Glu Leu Gln
                420                 425                 430

Lys Asp Lys Met Ala Glu Ala Tyr Ser Glu Ile Gly Met Lys Gly Glu
                435                 440                 445

Arg Arg Arg Gly Lys Gly His Asp Gly Leu Tyr Gln Gly Leu Ser Thr
450                 455                 460

Ala Thr Lys Asp Thr Tyr Asp Ala Leu His Met Gln Ala Leu Pro Pro
465                 470                 475                 480

Arg

<210> SEQ ID NO 150
<211> LENGTH: 479
<212> TYPE: PRT
<213> ORGANISM: Artificial Sequence
<220> FEATURE:
<223> OTHER INFORMATION: anti-BCMA CAR

<400> SEQUENCE: 150

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Phe Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
                100                 105                 110

Ser Arg Gly Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
        130                 135                 140

Lys Lys Pro Gly Ala Ser Val Lys Val Ser Cys Lys Ala Ser Gly Tyr
145                 150                 155                 160

Thr Phe Thr Asp Tyr Tyr Met His Trp Val Arg Gln Ala Pro Gly Gln
                165                 170                 175

Arg Leu Glu Trp Met Gly Trp Ile Asn Pro Asn Ser Gly Gly Thr Asn
                180                 185                 190

Tyr Ala Gln Lys Phe Gln Asp Arg Ile Thr Val Thr Arg Asp Thr Ser
            195                 200                 205

Ser Asn Thr Gly Tyr Met Glu Leu Thr Arg Leu Arg Ser Asp Asp Thr
    210                 215                 220

Ala Val Tyr Tyr Cys Ala Arg Ser Pro Tyr Ser Gly Val Leu Asp Lys
225                 230                 235                 240

Trp Gly Gln Gly Thr Leu Val Thr Val Ser Ser Ala Ala Pro Thr
                245                 250                 255

Thr Thr Pro Ala Pro Arg Pro Pro Thr Pro Ala Pro Thr Ile Ala Ser
                260                 265                 270
```

```
Gln Pro Leu Ser Leu Arg Pro Glu Ala Cys Arg Pro Ala Ala Gly Gly
            275                 280                 285

Ala Val His Thr Arg Gly Leu Asp Phe Ala Cys Asp Ile Tyr Ile Trp
    290                 295                 300

Ala Pro Leu Ala Gly Thr Cys Gly Val Leu Leu Leu Ser Leu Val Ile
305                 310                 315                 320

Thr Leu Tyr Cys Asn Lys Arg Gly Arg Lys Lys Leu Leu Tyr Ile Phe
                325                 330                 335

Lys Gln Pro Phe Met Arg Pro Val Gln Thr Thr Gln Glu Glu Asp Gly
            340                 345                 350

Cys Ser Cys Arg Phe Pro Glu Glu Glu Glu Gly Cys Glu Leu Arg
                355                 360                 365

Val Lys Phe Ser Arg Ser Ala Glu Pro Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
            435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475

<210> SEQ ID NO 151
<211> LENGTH: 472
<212> TYPE: PRT
<213> ORGANISM: Artificial Sequence
<220> FEATURE:
<223> OTHER INFORMATION: anti-BCMA CAR

<400> SEQUENCE: 151

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Ser Leu Glu Met Ala Glu Val
        115                 120                 125

Gln Leu Val Gln Ser Gly Ala Glu Met Lys Lys Pro Gly Ala Ser Leu
    130                 135                 140

Lys Leu Ser Cys Lys Ala Ser Gly Tyr Thr Phe Ile Asp Tyr Tyr Val
145                 150                 155                 160
```

Tyr Trp Met Arg Gln Ala Pro Gly Gln Gly Leu Glu Ser Met Gly Trp
            165                 170                 175

Ile Asn Pro Asn Ser Gly Gly Thr Asn Tyr Ala Gln Lys Phe Gln Gly
        180                 185                 190

Arg Val Thr Met Thr Arg Asp Thr Ser Ile Ser Thr Ala Tyr Met Glu
    195                 200                 205

Leu Ser Arg Leu Arg Ser Asp Asp Thr Ala Met Tyr Tyr Cys Ala Arg
210                 215                 220

Ser Gln Arg Asp Gly Tyr Met Asp Tyr Trp Gly Gln Gly Thr Leu Val
225                 230                 235                 240

Thr Val Ser Ser Ala Ala Ala Pro Thr Thr Thr Pro Ala Pro Arg Pro
            245                 250                 255

Pro Thr Pro Ala Pro Thr Ile Ala Ser Gln Pro Leu Ser Leu Arg Pro
        260                 265                 270

Glu Ala Cys Arg Pro Ala Ala Gly Gly Ala Val His Thr Arg Gly Leu
    275                 280                 285

Asp Phe Ala Cys Asp Ile Tyr Ile Trp Ala Pro Leu Ala Gly Thr Cys
        290                 295                 300

Gly Val Leu Leu Leu Ser Leu Val Ile Thr Leu Tyr Cys Asn Lys Arg
305                 310                 315                 320

Gly Arg Lys Lys Leu Leu Tyr Ile Phe Lys Gln Pro Phe Met Arg Pro
            325                 330                 335

Val Gln Thr Thr Gln Glu Glu Asp Gly Cys Ser Cys Arg Phe Pro Glu
        340                 345                 350

Glu Glu Glu Gly Gly Cys Glu Leu Arg Val Lys Phe Ser Arg Ser Ala
    355                 360                 365

Glu Pro Pro Ala Tyr Gln Gln Gly Gln Asn Gln Leu Tyr Asn Glu Leu
370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
            405                 410                 415

Gly Leu Tyr Asn Glu Leu Gln Lys Asp Lys Met Ala Glu Ala Tyr Ser
        420                 425                 430

Glu Ile Gly Met Lys Gly Glu Arg Arg Arg Gly Lys Gly His Asp Gly
    435                 440                 445

Leu Tyr Gln Gly Leu Ser Thr Ala Thr Lys Asp Thr Tyr Asp Ala Leu
450                 455                 460

His Met Gln Ala Leu Pro Pro Arg
465                 470

<210> SEQ ID NO 152
<211> LENGTH: 472
<212> TYPE: PRT
<213> ORGANISM: Artificial Sequence
<220> FEATURE:
<223> OTHER INFORMATION: anti-BCMA CAR

<400> SEQUENCE: 152

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

```
Thr Leu Leu Ile Gln Leu Ala Ser Asn Val Gln Thr Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Glu Asp Asp Val Ala Val Tyr Tyr Cys Leu Gln Ser Arg
                 85                  90                  95

Thr Ile Pro Arg Thr Phe Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240

Ser Val Thr Val Ser Ser Ala Ala Ala Thr Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460
```

```
His Met Gln Ala Leu Pro Pro Arg
465                 470
```

<210> SEQ ID NO 153
<211> LENGTH: 472
<212> TYPE: PRT
<213> ORGANISM: Artificial Sequence
<220> FEATURE:
<223> OTHER INFORMATION: anti-BCMA CAR

<400> SEQUENCE: 153

```
Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Val Gln Leu Val Gln Ser Gly Ser Glu Leu Lys Lys Pro Gly
    130                 135                 140

Ala Ser Val Lys Val Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205

Tyr Leu Gln Ile Ser Ser Leu Lys Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

Leu Val Thr Val Ser Ser Ala Ala Ala Thr Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350
```

Glu Glu Glu Gly Gly Cys Glu Leu Arg Val Lys Phe Ser Arg Ser Ala
            355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
            435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470

<210> SEQ ID NO 154
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 154

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Val Gln Leu Val Gln Ser Gly Ser Glu Leu Lys Lys Pro Gly
    130                 135                 140

Ala Ser Val Lys Val Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205

Tyr Leu Gln Ile Ser Ser Leu Lys Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

```
Leu Val Thr Val Ser Ser Ala Ala Asp Thr Gly Leu Tyr Ile Cys
                245                 250                 255

Lys Val Glu Leu Met Tyr Pro Pro Tyr Tyr Leu Gly Ile Gly Asn
            260                 265                 270

Gly Thr Gln Ile Tyr Val Ile Asp Pro Glu Pro Cys Pro Asp Ser Asp
            275                 280                 285

Phe Leu Leu Trp Ile Leu Ala Ala Val Ser Ser Gly Leu Phe Phe Tyr
290                 295                 300

Ser Phe Leu Leu Thr Ala Val Ser Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Gln
            355                 360                 365

Gln Gly Gln Asn Gln Leu Tyr Asn Glu Leu Asn Leu Gly Arg Arg Glu
            370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
            435                 440                 445

Thr Ala Thr Lys Asp Thr Tyr Asp Ala Leu His Met Gln Ala Leu Pro
            450                 455                 460

Pro Arg
465

<210> SEQ ID NO 155
<211> LENGTH: 464
<212> TYPE: PRT
<213> ORGANISM: Artificial Sequence
<220> FEATURE:
<223> OTHER INFORMATION: anti-BCMA CAR

<400> SEQUENCE: 155

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125
```

-continued

```
Gly Gln Val Gln Leu Val Gln Ser Gly Ser Glu Leu Lys Lys Pro Gly
    130                 135                 140

Ala Ser Val Lys Val Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205

Tyr Leu Gln Ile Ser Ser Leu Lys Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

Leu Val Thr Val Ser Ser Ala Ala Gln Ile Lys Glu Ser Leu Arg
                245                 250                 255

Ala Glu Leu Arg Val Thr Glu Arg Arg Ala Glu Val Pro Thr Ala His
                260                 265                 270

Pro Ser Pro Ser Pro Arg Pro Ala Gly Gln Phe Gln Thr Leu Val Val
            275                 280                 285

Gly Val Val Gly Gly Leu Leu Gly Ser Leu Val Leu Leu Val Trp Val
290                 295                 300

Leu Ala Val Ile Cys Ser Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Gln Gln Gly
        355                 360                 365

Gln Asn Gln Leu Tyr Asn Glu Leu Asn Leu Gly Arg Arg Glu Glu Tyr
    370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
        435                 440                 445

Thr Lys Asp Thr Tyr Asp Ala Leu His Met Gln Ala Leu Pro Pro Arg
    450                 455                 460
```

<210> SEQ ID NO 156
<211> LENGTH: 653
<212> TYPE: PRT
<213> ORGANISM: Artificial Sequence
<220> FEATURE:
<223> OTHER INFORMATION: anti-BCMA CAR

<400> SEQUENCE: 156

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30
```

-continued

```
Tyr Met Ser Trp Ile Arg Gln Ala Pro Gly Lys Gly Leu Glu Trp Val
         35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Asp Gly Asp Tyr Thr Glu Asp Tyr Trp Gly Gln Gly Thr
                100                 105                 110

Leu Val Thr Val Ser Ser Gly Gly Gly Gly Ser Gly Gly Gly Gly Ser
        115                 120                 125

Gly Gly Gly Gly Ser Gln Ser Ala Leu Thr Gln Pro Ala Ser Val Ser
130                 135                 140

Gly Ser Pro Gly Gln Ser Ile Thr Ile Ser Cys Thr Gly Ser Ser Ser
145                 150                 155                 160

Asp Val Gly Lys Tyr Asn Leu Val Ser Trp Tyr Gln Gln Pro Pro Gly
                165                 170                 175

Lys Ala Pro Lys Leu Ile Ile Tyr Asp Val Asn Lys Arg Pro Ser Gly
                180                 185                 190

Val Ser Asn Arg Phe Ser Gly Ser Lys Ser Gly Asn Thr Ala Thr Leu
        195                 200                 205

Thr Ile Ser Gly Leu Gln Gly Asp Asp Glu Ala Asp Tyr Tyr Cys Ser
210                 215                 220

Ser Tyr Gly Gly Ser Arg Ser Tyr Val Phe Gly Thr Gly Thr Lys Val
225                 230                 235                 240

Thr Val Leu Glu Ser Lys Tyr Gly Pro Pro Cys Pro Pro Cys Pro Ala
                245                 250                 255

Pro Pro Val Ala Gly Pro Ser Val Phe Leu Phe Pro Pro Lys Pro Lys
                260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Gln Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
                340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
```

```
                450            455            460
Leu Ser Leu Ser Leu Gly Lys Met Phe Trp Val Leu Val Val Gly
465                 470                475                480

Gly Val Leu Ala Cys Tyr Ser Leu Leu Val Thr Val Ala Phe Ile Ile
                    485                490                495

Phe Trp Val Lys Arg Gly Arg Lys Lys Leu Leu Tyr Ile Phe Lys Gln
                500                505                510

Pro Phe Met Arg Pro Val Gln Thr Thr Gln Glu Glu Asp Gly Cys Ser
            515                520                525

Cys Arg Phe Pro Glu Glu Glu Glu Gly Gly Cys Glu Leu Arg Val Lys
        530                535                540

Phe Ser Arg Ser Ala Asp Ala Pro Ala Tyr Gln Gln Gly Gln Asn Gln
545                 550                555                560

Leu Tyr Asn Glu Leu Asn Leu Gly Arg Arg Glu Glu Tyr Asp Val Leu
                565                570                575

Asp Lys Arg Arg Gly Arg Asp Pro Glu Met Gly Gly Lys Pro Arg Arg
            580                585                590

Lys Asn Pro Gln Glu Gly Leu Tyr Asn Glu Leu Gln Lys Asp Lys Met
        595                600                605

Ala Glu Ala Tyr Ser Glu Ile Gly Met Lys Gly Glu Arg Arg Arg Gly
610                 615                620

Lys Gly His Asp Gly Leu Tyr Gln Gly Leu Ser Thr Ala Thr Lys Asp
625                 630                635                640

Thr Tyr Asp Ala Leu His Met Gln Ala Leu Pro Pro Arg
                645                650

<210> SEQ ID NO 157
<211> LENGTH: 650
<212> TYPE: PRT
<213> ORGANISM: Artificial Sequence
<220> FEATURE:
<223> OTHER INFORMATION: anti-BCMA CAR

<400> SEQUENCE: 157

Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Lys Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ala Phe Leu
    130                 135                 140

Ser Ala Ser Val Gly Asp Arg Val Thr Val Thr Cys Arg Ala Ser Gln
145                 150                 155                 160

Gly Ile Ser Asn Tyr Leu Ala Trp Tyr Gln Gln Lys Pro Gly Asn Ala
```

-continued

```
                165                 170                 175
Pro Arg Leu Leu Ile Tyr Ser Ala Ser Thr Leu Gln Ser Gly Val Pro
            180                 185                 190

Ser Arg Phe Arg Gly Thr Gly Tyr Gly Thr Glu Phe Ser Leu Thr Ile
            195                 200                 205

Asp Ser Leu Gln Pro Glu Asp Phe Ala Thr Tyr Tyr Cys Gln Gln Ser
        210                 215                 220

Tyr Thr Ser Arg Gln Thr Phe Gly Pro Gly Thr Arg Leu Asp Ile Lys
225                 230                 235                 240

Glu Ser Lys Tyr Gly Pro Pro Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Gln Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys Met Phe Trp Val Leu Val Val Gly Gly Val Leu
465                 470                 475                 480

Ala Cys Tyr Ser Leu Leu Val Thr Val Ala Phe Ile Ile Phe Trp Val
                485                 490                 495

Lys Arg Gly Arg Lys Lys Leu Leu Tyr Ile Phe Lys Gln Pro Phe Met
            500                 505                 510

Arg Pro Val Gln Thr Thr Gln Glu Glu Asp Gly Cys Ser Cys Arg Phe
        515                 520                 525

Pro Glu Glu Glu Glu Gly Gly Cys Glu Leu Arg Val Lys Phe Ser Arg
    530                 535                 540

Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
                565                 570                 575

Arg Gly Arg Asp Pro Glu Met Gly Gly Lys Pro Arg Arg Lys Asn Pro
            580                 585                 590
```

```
Gln Glu Gly Leu Tyr Asn Glu Leu Gln Lys Asp Lys Met Ala Glu Ala
            595                 600                 605

Tyr Ser Glu Ile Gly Met Lys Gly Glu Arg Arg Arg Gly Lys Gly His
        610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
                645                 650

<210> SEQ ID NO 158
<211> LENGTH: 651
<212> TYPE: PRT
<213> ORGANISM: Artificial Sequence
<220> FEATURE:
<223> OTHER INFORMATION: anti-BCMA CAR

<400> SEQUENCE: 158

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Ser Tyr Val Leu Thr Gln Pro Pro Ser Val Ser
    130                 135                 140

Val Ala Pro Gly Gln Thr Ala Arg Ile Thr Cys Gly Ala Asn Asn Ile
145                 150                 155                 160

Gly Ser Lys Ser Val His Trp Tyr Gln Gln Lys Pro Gly Gln Ala Pro
                165                 170                 175

Met Leu Val Val Tyr Asp Asp Asp Arg Pro Ser Gly Ile Pro Glu
            180                 185                 190

Arg Phe Ser Gly Ser Asn Ser Gly Asn Thr Ala Thr Leu Thr Ile Ser
        195                 200                 205

Gly Val Glu Ala Gly Asp Glu Ala Asp Tyr Phe Cys His Leu Trp Asp
    210                 215                 220

Arg Ser Arg Asp His Tyr Val Phe Gly Thr Gly Thr Lys Leu Thr Val
225                 230                 235                 240

Leu Glu Ser Lys Tyr Gly Pro Pro Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
    290                 295                 300
```

Glu Val His Asn Ala Lys Thr Lys Pro Arg Glu Gln Phe Gln Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
            355                 360                 365

Gln Val Tyr Thr Leu Pro Pro Ser Gln Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
            435                 440                 445

Val Met His Glu Ala Leu His Asn His Tyr Thr Gln Lys Ser Leu Ser
450                 455                 460

Leu Ser Leu Gly Lys Met Phe Trp Val Leu Val Val Val Gly Gly Val
465                 470                 475                 480

Leu Ala Cys Tyr Ser Leu Leu Val Thr Val Ala Phe Ile Ile Phe Trp
            485                 490                 495

Val Lys Arg Gly Arg Lys Lys Leu Leu Tyr Ile Phe Lys Gln Pro Phe
            500                 505                 510

Met Arg Pro Val Gln Thr Thr Gln Glu Glu Asp Gly Cys Ser Cys Arg
            515                 520                 525

Phe Pro Glu Glu Glu Glu Gly Gly Cys Glu Leu Arg Val Lys Phe Ser
530                 535                 540

Arg Ser Ala Asp Ala Pro Ala Tyr Gln Gln Gly Gln Asn Gln Leu Tyr
545                 550                 555                 560

Asn Glu Leu Asn Leu Gly Arg Arg Glu Glu Tyr Asp Val Leu Asp Lys
            565                 570                 575

Arg Arg Gly Arg Asp Pro Glu Met Gly Gly Lys Pro Arg Arg Lys Asn
            580                 585                 590

Pro Gln Glu Gly Leu Tyr Asn Glu Leu Gln Lys Asp Lys Met Ala Glu
            595                 600                 605

Ala Tyr Ser Glu Ile Gly Met Lys Gly Glu Arg Arg Arg Gly Lys Gly
            610                 615                 620

His Asp Gly Leu Tyr Gln Gly Leu Ser Thr Ala Thr Lys Asp Thr Tyr
625                 630                 635                 640

Asp Ala Leu His Met Gln Ala Leu Pro Pro Arg
            645                 650

<210> SEQ ID NO 159
<211> LENGTH: 658
<212> TYPE: PRT
<213> ORGANISM: Artificial Sequence
<220> FEATURE:
<223> OTHER INFORMATION: anti-BCMA CAR

<400> SEQUENCE: 159

Ser Tyr Glu Leu Thr Gln Pro Pro Ser Ala Ser Gly Thr Pro Gly Gln
1               5                   10                  15

```
Arg Val Thr Met Ser Cys Ser Gly Thr Ser Ser Asn Ile Gly Ser His
                20                  25                  30

Ser Val Asn Trp Tyr Gln Gln Leu Pro Gly Thr Ala Pro Lys Leu Leu
            35                  40                  45

Ile Tyr Thr Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Thr Lys Leu Thr Val Leu Gly Ser
                100                 105                 110

Arg Gly Gly Gly Gly Ser Gly Gly Gly Ser Gly Gly Gly Gly Ser
            115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly His Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Tyr Ser Gly Ser Phe Asp Asn Trp Gly Gln
225                 230                 235                 240

Gly Thr Leu Val Thr Val Ser Ser Glu Ser Lys Tyr Gly Pro Pro Cys
                245                 250                 255

Pro Pro Cys Pro Ala Pro Pro Val Ala Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Asp Val Ser Gln Glu Asp Pro Glu Val Gln Phe
    290                 295                 300

Asn Trp Tyr Val Asp Gly Val Glu Val His Asn Ala Lys Thr Lys Pro
305                 310                 315                 320

Arg Glu Glu Gln Phe Gln Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Gly Leu Pro Ser Ile Glu Lys Thr Ile Ser Lys Ala
        355                 360                 365

Lys Gly Gln Pro Arg Glu Pro Gln Val Tyr Thr Leu Pro Pro Ser Gln
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430
```

```
Phe Phe Leu Tyr Ser Arg Leu Thr Val Asp Lys Ser Arg Trp Gln Glu
            435                 440                 445

Gly Asn Val Phe Ser Cys Ser Val Met His Glu Ala Leu His Asn His
450                 455                 460

Tyr Thr Gln Lys Ser Leu Ser Leu Ser Leu Gly Lys Met Phe Trp Val
465                 470                 475                 480

Leu Val Val Val Gly Val Leu Ala Cys Tyr Ser Leu Leu Val Thr
                485                 490                 495

Val Ala Phe Ile Ile Phe Trp Val Lys Arg Gly Arg Lys Lys Leu Leu
            500                 505                 510

Tyr Ile Phe Lys Gln Pro Phe Met Arg Pro Val Gln Thr Thr Gln Glu
            515                 520                 525

Glu Asp Gly Cys Ser Cys Arg Phe Pro Glu Glu Glu Glu Gly Gly Cys
530                 535                 540

Glu Leu Arg Val Lys Phe Ser Arg Ser Ala Asp Ala Pro Ala Tyr Gln
545                 550                 555                 560

Gln Gly Gln Asn Gln Leu Tyr Asn Glu Leu Asn Leu Gly Arg Arg Glu
                565                 570                 575

Glu Tyr Asp Val Leu Asp Lys Arg Arg Gly Arg Asp Pro Glu Met Gly
            580                 585                 590

Gly Lys Pro Arg Arg Lys Asn Pro Gln Glu Gly Leu Tyr Asn Glu Leu
            595                 600                 605

Gln Lys Asp Lys Met Ala Glu Ala Tyr Ser Glu Ile Gly Met Lys Gly
            610                 615                 620

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
                645                 650                 655

Pro Arg

<210> SEQ ID NO 160
<211> LENGTH: 654
<212> TYPE: PRT
<213> ORGANISM: Artificial Sequence
<220> FEATURE:
<223> OTHER INFORMATION: anti-BCMA CAR

<400> SEQUENCE: 160

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Ser Leu Glu Met Ala Glu Val
        115                 120                 125

Gln Leu Val Gln Ser Gly Ala Glu Met Lys Lys Pro Gly Ala Ser Leu
```

-continued

```
            130                 135                 140
Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
                180                 185                 190

Arg Val Thr Met Thr Arg Asp Thr Ser Ile Ser Thr Ala Tyr Met Glu
                195                 200                 205

Leu Ser Arg Leu Arg Ser Asp Asp Thr Ala Met Tyr Tyr Cys Ala Arg
210                 215                 220

Ser Gln Arg Asp Gly Tyr Met Asp Tyr Trp Gly Gln Gly Thr Leu Val
225                 230                 235                 240

Thr Val Ser Ser Glu Ser Lys Tyr Gly Pro Pro Cys Pro Pro Cys Pro
                245                 250                 255

Ala Pro Pro Val Ala Gly Pro Ser Val Phe Leu Phe Pro Pro Lys Pro
                260                 265                 270

Lys Asp Thr Leu Met Ile Ser Arg Thr Pro Glu Val Thr Cys Val Val
                275                 280                 285

Val Asp Val Ser Gln Glu Asp Pro Glu Val Gln Phe Asn Trp Tyr Val
290                 295                 300

Asp Gly Val Glu Val His Asn Ala Lys Thr Lys Pro Arg Glu Glu Gln
305                 310                 315                 320

Phe Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
                340                 345                 350

Leu Pro Ser Ser Ile Glu Lys Thr Ile Ser Lys Ala Lys Gly Gln Pro
                355                 360                 365

Arg Glu Pro Gln Val Tyr Thr Leu Pro Pro Ser Gln Glu Glu Met Thr
                370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Arg Leu Thr Val Asp Lys Ser Arg Trp Gln Glu Gly Asn Val Phe
                435                 440                 445

Ser Cys Ser Val Met His Glu Ala Leu His Asn His Tyr Thr Gln Lys
                450                 455                 460

Ser Leu Ser Leu Ser Leu Gly Lys Met Phe Trp Val Leu Val Val Val
465                 470                 475                 480

Gly Gly Val Leu Ala Cys Tyr Ser Leu Leu Val Thr Val Ala Phe Ile
                485                 490                 495

Ile Phe Trp Val Lys Arg Gly Arg Lys Lys Leu Leu Tyr Ile Phe Lys
                500                 505                 510

Gln Pro Phe Met Arg Pro Val Gln Thr Thr Gln Glu Glu Asp Gly Cys
                515                 520                 525

Ser Cys Arg Phe Pro Glu Glu Glu Gly Gly Cys Glu Leu Arg Val
                530                 535                 540

Lys Phe Ser Arg Ser Ala Asp Ala Pro Ala Tyr Gln Gln Gly Gln Asn
545                 550                 555                 560
```

```
Gln Leu Tyr Asn Glu Leu Asn Leu Gly Arg Arg Glu Tyr Asp Val
                565                 570                 575

Leu Asp Lys Arg Arg Gly Arg Asp Pro Glu Met Gly Gly Lys Pro Arg
            580                 585                 590

Arg Lys Asn Pro Gln Glu Gly Leu Tyr Asn Glu Leu Gln Lys Asp Lys
        595                 600                 605

Met Ala Glu Ala Tyr Ser Glu Ile Gly Met Lys Gly Glu Arg Arg Arg
    610                 615                 620

Gly Lys Gly His Asp Gly Leu Tyr Gln Gly Leu Ser Thr Ala Thr Lys
625                 630                 635                 640

Asp Thr Tyr Asp Ala Leu His Met Gln Ala Leu Pro Pro Arg
                645                 650

<210> SEQ ID NO 161
<211> LENGTH: 653
<212> TYPE: PRT
<213> ORGANISM: Artificial Sequence
<220> FEATURE:
<223> OTHER INFORMATION: anti-BCMA CAR

<400> SEQUENCE: 161

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Ser Leu Glu Met Ala Glu Val
        115                 120                 125

Gln Leu Val Gln Ser Gly Ala Glu Met Lys Lys Pro Gly Ala Ser Leu
    130                 135                 140

Lys Leu Ser Cys Lys Ala Ser Gly Tyr Thr Phe Ile Asp Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
    210                 215                 220

Ser Gln Arg Asp Gly Tyr Met Asp Tyr Trp Gly Gln Gly Thr Leu Val
225                 230                 235                 240

Thr Val Ser Ser Glu Ser Lys Tyr Gly Pro Pro Cys Pro Pro Cys Pro
                245                 250                 255

Ala Pro Pro Val Ala Gly Pro Ser Val Phe Leu Phe Pro Pro Lys Pro
            260                 265                 270
```

```
Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Gln Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

Arg Glu Pro Gln Val Tyr Thr Leu Pro Pro Ser Gln Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Glu Gly Asn Val Phe
        435                 440                 445

Ser Cys Ser Val Met His Glu Ala Leu His Asn His Tyr Thr Gln Lys
    450                 455                 460

Ser Leu Ser Leu Ser Leu Gly Lys Met Phe Trp Val Leu Val Val Val
465                 470                 475                 480

Gly Gly Val Leu Ala Cys Tyr Ser Leu Leu Val Thr Val Ala Phe Ile
                485                 490                 495

Ile Phe Trp Val Arg Ser Lys Arg Ser Arg Leu Leu His Ser Asp Tyr
            500                 505                 510

Met Asn Met Thr Pro Arg Arg Pro Gly Pro Thr Arg Lys His Tyr Gln
        515                 520                 525

Pro Tyr Ala Pro Pro Arg Asp Phe Ala Ala Tyr Arg Ser Arg Val Lys
    530                 535                 540

Phe Ser Arg Ser Ala Asp Ala Pro Ala Tyr Gln Gln Gly Gln Asn Gln
545                 550                 555                 560

Leu Tyr Asn Glu Leu Asn Leu Gly Arg Arg Glu Glu Tyr Asp Val Leu
                565                 570                 575

Asp Lys Arg Arg Gly Arg Asp Pro Glu Met Gly Gly Lys Pro Arg Arg
            580                 585                 590

Lys Asn Pro Gln Glu Gly Leu Tyr Asn Glu Leu Gln Lys Asp Lys Met
        595                 600                 605

Ala Glu Ala Tyr Ser Glu Ile Gly Met Lys Gly Glu Arg Arg Arg Gly
    610                 615                 620

Lys Gly His Asp Gly Leu Tyr Gln Gly Leu Ser Thr Ala Thr Lys Asp
625                 630                 635                 640

Thr Tyr Asp Ala Leu His Met Gln Ala Leu Pro Pro Arg
                645                 650

<210> SEQ ID NO 162
<211> LENGTH: 462
<212> TYPE: PRT
<213> ORGANISM: Artificial Sequence
<220> FEATURE:
```

<223> OTHER INFORMATION: anti-BCMA CAR

<400> SEQUENCE: 162

```
Glu Val Gln Leu Val Glu Ser Gly Gly Gly Leu Val Gln Pro Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Ser Gly Gly Arg Ala Ser Gly
        115                 120                 125

Gly Gly Gly Ser Asp Ile Gln Leu Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Tyr Thr Phe Gly Gln Gly Thr Lys Val Glu Ile Lys Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Ile Tyr Ile Trp
        275                 280                 285

Ala Pro Leu Ala Gly Thr Cys Gly Val Leu Leu Leu Ser Leu Val Ile
    290                 295                 300

Thr Leu Tyr Cys Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Gly Gly Cys Glu Leu Arg Val
            340                 345                 350

Lys Phe Ser Arg Ser Ala Asp Ala Pro Ala Tyr Lys Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400
```

-continued

```
Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 163
<211> LENGTH: 469
<212> TYPE: PRT
<213> ORGANISM: Artificial Sequence
<220> FEATURE:
<223> OTHER INFORMATION: anti-BCMA CAR

<400> SEQUENCE: 163

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Ser Arg Ser Gly Glu Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Ser Pro Ala His Tyr Tyr Gly Gly Met Asp Val Trp Gly Gln
            100                 105                 110

Gly Thr Thr Val Thr Val Ser Ala Ser Gly Gly Gly Gly Ser Gly
        115                 120                 125

Gly Arg Ala Ser Gly Gly Gly Ser Asp Ile Val Leu Thr Gln Ser
    130                 135                 140

Pro Gly Thr Leu Ser Leu Ser Pro Gly Glu Arg Ala Thr Leu Ser Cys
145                 150                 155                 160

Arg Ala Ser Gln Ser Ile Ser Ser Ser Phe Leu Ala Trp Tyr Gln Gln
                165                 170                 175

Lys Pro Gly Gln Ala Pro Arg Leu Leu Ile Tyr Gly Ala Ser Arg Arg
            180                 185                 190

Ala Thr Gly Ile Pro Asp Arg Phe Ser Gly Ser Gly Ser Gly Thr Asp
        195                 200                 205

Phe Thr Leu Thr Ile Ser Arg Leu Glu Pro Glu Asp Ser Ala Val Tyr
    210                 215                 220

Tyr Cys Gln Gln Tyr His Ser Ser Pro Ser Trp Thr Phe Gly Gln Gly
225                 230                 235                 240

Thr Lys Leu Glu Ile Lys Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
        275                 280                 285

Ala Cys Asp Ile Tyr Ile Trp Ala Pro Leu Ala Gly Thr Cys Gly Val
    290                 295                 300
```

```
Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
            325                 330                 335

Thr Gln Glu Glu Asp Gly Cys Ser Cys Arg Phe Pro Glu Glu Glu Glu
        340                 345                 350

Gly Gly Cys Glu Leu Arg Val Lys Phe Ser Arg Ser Ala Asp Ala Pro
        355                 360                 365

Ala Tyr Lys Gln Gly Gln Asn Gln Leu Tyr Asn Glu Leu Asn Leu Gly
    370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
            405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
            435                 440                 445

Gly Leu Ser Thr Ala Thr Lys Asp Thr Tyr Asp Ala Leu His Met Gln
    450                 455                 460

Ala Leu Pro Pro Arg
465

<210> SEQ ID NO 164
<211> LENGTH: 462
<212> TYPE: PRT
<213> ORGANISM: Artificial Sequence
<220> FEATURE:
<223> OTHER INFORMATION: anti-BCMA CAR

<400> SEQUENCE: 164

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
            85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
        115                 120                 125

Gly Gly Gly Ser Asp Ile Arg Leu Thr Gln Ser Pro Ser Pro Leu Ser
    130                 135                 140

Ala Ser Val Gly Asp Arg Val Thr Ile Thr Cys Gln Ala Ser Glu Asp
145                 150                 155                 160

Ile Asn Lys Phe Leu Asn Trp Tyr His Gln Thr Pro Gly Lys Ala Pro
            165                 170                 175

Lys Leu Leu Ile Tyr Asp Ala Ser Thr Leu Gln Thr Gly Val Pro Ser
            180                 185                 190
```

```
Arg Phe Ser Gly Ser Gly Ser Gly Thr Asp Phe Thr Leu Thr Ile Asn
            195                 200                 205

Ser Leu Gln Pro Glu Asp Ile Gly Thr Tyr Tyr Cys Gln Gln Tyr Glu
    210                 215                 220

Ser Leu Pro Leu Thr Phe Gly Gly Gly Thr Lys Val Glu Ile Lys Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
            260                 265                 270

Ala Val His Thr Arg Gly Leu Asp Phe Ala Cys Asp Ile Tyr Ile Trp
    275                 280                 285

Ala Pro Leu Ala Gly Thr Cys Gly Val Leu Leu Leu Ser Leu Val Ile
290                 295                 300

Thr Leu Tyr Cys Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Glu Gly Gly Cys Glu Leu Arg Val
            340                 345                 350

Lys Phe Ser Arg Ser Ala Asp Ala Pro Ala Tyr Lys Gln Gly Gln Asn
    355                 360                 365

Gln Leu Tyr Asn Glu Leu Asn Leu Gly Arg Arg Glu Glu Tyr Asp Val
            370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
            435                 440                 445

Asp Thr Tyr Asp Ala Leu His Met Gln Ala Leu Pro Pro Arg
    450                 455                 460

<210> SEQ ID NO 165
<211> LENGTH: 464
<212> TYPE: PRT
<213> ORGANISM: Artificial Sequence
<220> FEATURE:
<223> OTHER INFORMATION: anti-BCMA CAR

<400> SEQUENCE: 165

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95
```

```
Ala His Gly Gly Glu Ser Asp Val Trp Gly Gln Gly Thr Thr Val Thr
                100                 105                 110
Val Ser Ser Ala Ser Gly Gly Gly Gly Ser Gly Gly Arg Ala Ser Gly
            115                 120                 125
Gly Gly Gly Ser Glu Ile Val Leu Thr Gln Ser Pro Gly Thr Leu Ser
        130                 135                 140
Leu Ser Pro Gly Glu Arg Ala Thr Leu Ser Cys Arg Ala Ser Gln Ser
145                 150                 155                 160
Ile Gly Ser Ser Ser Leu Ala Trp Tyr Gln Gln Lys Pro Gly Gln Ala
                165                 170                 175
Pro Arg Leu Leu Met Tyr Gly Ala Ser Ser Arg Ala Ser Gly Ile Pro
            180                 185                 190
Asp Arg Phe Ser Gly Ser Gly Ser Gly Thr Asp Phe Thr Leu Thr Ile
        195                 200                 205
Ser Arg Leu Glu Pro Glu Asp Phe Ala Val Tyr Tyr Cys Gln Gln Tyr
210                 215                 220
Ala Gly Ser Pro Pro Phe Thr Phe Gly Gln Gly Thr Lys Val Glu Ile
225                 230                 235                 240
Lys Thr Thr Thr Pro Ala Pro Arg Pro Pro Thr Pro Ala Pro Thr Ile
                245                 250                 255
Ala Ser Gln Pro Leu Ser Leu Arg Pro Glu Ala Cys Arg Pro Ala Ala
            260                 265                 270
Gly Gly Ala Val His Thr Arg Gly Leu Asp Phe Ala Cys Asp Ile Tyr
        275                 280                 285
Ile Trp Ala Pro Leu Ala Gly Thr Cys Gly Val Leu Leu Leu Ser Leu
290                 295                 300
Val Ile Thr Leu Tyr Cys Lys Arg Gly Arg Lys Lys Leu Leu Tyr Ile
305                 310                 315                 320
Phe Lys Gln Pro Phe Met Arg Pro Val Gln Thr Thr Gln Glu Glu Asp
                325                 330                 335
Gly Cys Ser Cys Arg Phe Pro Glu Glu Glu Glu Gly Gly Cys Glu Leu
            340                 345                 350
Arg Val Lys Phe Ser Arg Ser Ala Asp Ala Pro Ala Tyr Lys Gln Gly
        355                 360                 365
Gln Asn Gln Leu Tyr Asn Glu Leu Asn Leu Gly Arg Arg Glu Glu Tyr
370                 375                 380
Asp Val Leu Asp Lys Arg Arg Gly Arg Asp Pro Glu Met Gly Gly Lys
385                 390                 395                 400
Pro Arg Arg Lys Asn Pro Gln Glu Gly Leu Tyr Asn Glu Leu Gln Lys
                405                 410                 415
Asp Lys Met Ala Glu Ala Tyr Ser Glu Ile Gly Met Lys Gly Glu Arg
            420                 425                 430
Arg Arg Gly Lys Gly His Asp Gly Leu Tyr Gln Gly Leu Ser Thr Ala
        435                 440                 445
Thr Lys Asp Thr Tyr Asp Ala Leu His Met Gln Ala Leu Pro Pro Arg
    450                 455                 460

<210> SEQ ID NO 166
<211> LENGTH: 467
<212> TYPE: PRT
<213> ORGANISM: Artificial Sequence
<220> FEATURE:
<223> OTHER INFORMATION: anti-BCMA CAR

<400> SEQUENCE: 166
```

-continued

```
Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr Asn Phe
            20                  25                  30

Gly Met Asn Trp Val Lys Gln Ala Pro Gly Lys Gly Phe Lys Trp Met
        35                  40                  45

Ala Trp Ile Asn Thr Tyr Thr Gly Glu Ser Tyr Phe Ala Asp Asp Phe
50                  55                  60

Lys Gly Arg Phe Ala Phe Ser Val Glu Thr Ser Ala Thr Thr Ala Tyr
65                  70                  75                  80

Leu Gln Ile Asn Asn Leu Lys Thr Glu Asp Thr Ala Thr Tyr Phe Cys
                85                  90                  95

Ala Arg Gly Glu Ile Tyr Tyr Gly Tyr Asp Gly Gly Phe Ala Tyr Trp
            100                 105                 110

Gly Gln Gly Thr Leu Val Thr Val Ser Ala Gly Gly Gly Ser Gly
        115                 120                 125

Gly Gly Gly Ser Gly Gly Gly Ser Asp Val Val Met Thr Gln Ser
130                 135                 140

His Arg Phe Met Ser Thr Ser Val Gly Asp Arg Val Ser Ile Thr Cys
145                 150                 155                 160

Arg Ala Ser Gln Asp Val Asn Thr Ala Val Ser Trp Tyr Gln Gln Lys
                165                 170                 175

Pro Gly Gln Ser Pro Lys Leu Leu Ile Phe Ser Ala Ser Tyr Arg Tyr
            180                 185                 190

Thr Gly Val Pro Asp Arg Phe Thr Gly Ser Gly Ser Gly Ala Asp Phe
        195                 200                 205

Thr Leu Thr Ile Ser Ser Val Gln Ala Glu Asp Leu Ala Val Tyr Tyr
210                 215                 220

Cys Gln Gln His Tyr Ser Thr Pro Trp Thr Phe Gly Gly Gly Thr Lys
225                 230                 235                 240

Leu Asp Ile Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
290                 295                 300

Leu Ser Leu Val Ile Thr Leu Tyr Cys Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Arg Val Lys Phe Ser Arg Ser Ala Asp Ala Pro Ala Tyr
        355                 360                 365

Lys Gln Gly Gln Asn Gln Leu Tyr Asn Glu Leu Asn Leu Gly Arg Arg
370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
```

```
                420           425            430
Gly Glu Arg Arg Gly Lys Gly His Asp Gly Leu Tyr Gln Gly Leu
        435              440            445

Ser Thr Ala Thr Lys Asp Thr Tyr Asp Ala Leu His Met Gln Ala Leu
        450              455            460

Pro Pro Arg
465

<210> SEQ ID NO 167
<211> LENGTH: 472
<212> TYPE: PRT
<213> ORGANISM: Artificial Sequence
<220> FEATURE:
<223> OTHER INFORMATION: anti-BCMA CAR

<400> SEQUENCE: 167

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser Gly Gly Gly Gly Ser Gly Gly Gly Gly Ser Gly
        115                 120                 125

Gly Gly Gly Ser Gln Ile Gln Leu Val Gln Ser Gly Pro Glu Leu Lys
    130                 135                 140

Lys Pro Gly Glu Thr Val Lys Ile Ser Cys Lys Ala Ser Gly Tyr Thr
145                 150                 155                 160

Phe Thr Asp Tyr Ser Ile Asn Trp Val Lys Arg Ala Pro Gly Lys Gly
                165                 170                 175

Leu Lys Trp Met Gly Trp Ile Asn Thr Glu Thr Arg Glu Pro Ala Tyr
            180                 185                 190

Ala Tyr Asp Phe Arg Gly Arg Phe Ala Phe Ser Leu Glu Thr Ser Ala
        195                 200                 205

Ser Thr Ala Tyr Leu Gln Ile Asn Asn Leu Lys Tyr Glu Asp Thr Ala
    210                 215                 220

Thr Tyr Phe Cys Ala Leu Asp Tyr Ser Tyr Ala Met Asp Tyr Trp Gly
225                 230                 235                 240

Gln Gly Thr Ser Val Thr Val Ser Ser Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
```

```
                305                 310                 315                 320
Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
                340                 345                 350

Glu Glu Glu Gly Gly Cys Glu Leu Arg Val Lys Phe Ser Arg Ser Ala
                355                 360                 365

Asp Ala Pro Ala Tyr Lys Gln Gly Gln Asn Gln Leu Tyr Asn Glu Leu
                370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                    405                 410                 415

Gly Leu Tyr Asn Glu Leu Gln Lys Asp Lys Met Ala Glu Ala Tyr Ser
                420                 425                 430

Glu Ile Gly Met Lys Gly Glu Arg Arg Arg Gly Lys Gly His Asp Gly
                435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470

<210> SEQ ID NO 168
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 168

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
                20                  25                  30

Ser Ile Asn Trp Val Lys Arg Ala Pro Gly Lys Gly Leu Lys Trp Met
            35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
                100                 105                 110

Val Thr Val Ser Ser Gly Gly Gly Gly Ser Gly Gly Gly Gly Ser Gly
            115                 120                 125

Gly Gly Gly Ser Asp Ile Val Leu Thr Gln Ser Pro Ala Ser Leu Ala
130                 135                 140

Met Ser Leu Gly Lys Arg Ala Thr Ile Ser Cys Arg Ala Ser Glu Ser
145                 150                 155                 160

Val Ser Val Ile Gly Ala His Leu Ile His Trp Tyr Gln Gln Lys Pro
                165                 170                 175

Gly Gln Pro Pro Lys Leu Leu Ile Tyr Leu Ala Ser Asn Leu Glu Thr
                180                 185                 190

Gly Val Pro Ala Arg Phe Ser Gly Ser Gly Ser Gly Thr Asp Phe Thr
```

-continued

```
             195                 200                 205
Leu Thr Ile Asp Pro Val Glu Glu Asp Val Ala Ile Tyr Ser Cys
    210                 215                 220
Leu Gln Ser Arg Ile Phe Pro Arg Thr Phe Gly Gly Thr Lys Leu
225                 230                 235                 240
Glu Ile Lys Thr Thr Thr Pro Ala Pro Arg Pro Pro Thr Pro Ala Pro
                245                 250                 255
Thr Ile Ala Ser Gln Pro Leu Ser Leu Arg Pro Glu Ala Cys Arg Pro
            260                 265                 270
Ala Ala Gly Gly Ala Val His Thr Arg Gly Leu Asp Phe Ala Cys Asp
            275                 280                 285
Ile Tyr Ile Trp Ala Pro Leu Ala Gly Thr Cys Gly Val Leu Leu Leu
            290                 295                 300
Ser Leu Val Ile Thr Leu Tyr Cys Lys Arg Gly Arg Lys Lys Leu Leu
305                 310                 315                 320
Tyr Ile Phe Lys Gln Pro Phe Met Arg Pro Val Gln Thr Thr Gln Glu
                325                 330                 335
Glu Asp Gly Cys Ser Cys Arg Phe Pro Glu Glu Glu Glu Gly Gly Cys
            340                 345                 350
Glu Leu Arg Val Lys Phe Ser Arg Ser Ala Asp Ala Pro Ala Tyr Lys
            355                 360                 365
Gln Gly Gln Asn Gln Leu Tyr Asn Glu Leu Asn Leu Gly Arg Arg Glu
            370                 375                 380
Glu Tyr Asp Val Leu Asp Lys Arg Arg Gly Arg Asp Pro Glu Met Gly
385                 390                 395                 400
Gly Lys Pro Arg Arg Lys Asn Pro Gln Glu Gly Leu Tyr Asn Glu Leu
                405                 410                 415
Gln Lys Asp Lys Met Ala Glu Ala Tyr Ser Glu Ile Gly Met Lys Gly
            420                 425                 430
Glu Arg Arg Arg Gly Lys Gly His Asp Gly Leu Tyr Gln Gly Leu Ser
            435                 440                 445
Thr Ala Thr Lys Asp Thr Tyr Asp Ala Leu His Met Gln Ala Leu Pro
    450                 455                 460
Pro Arg
465

<210> SEQ ID NO 169
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 169

Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Arg His Tyr
                20                  25                  30
Ser Met Asn Trp Val Lys Gln Ala Pro Gly Lys Gly Leu Lys Trp Met
            35                  40                  45
Gly Arg Ile Asn Thr Glu Ser Gly Val Pro Ile Tyr Ala Asp Asp Phe
        50                  55                  60
Lys Gly Arg Phe Ala Phe Ser Val Glu Thr Ser Ala Ser Thr Ala Tyr
65                  70                  75                  80
Leu Val Ile Asn Asn Leu Lys Asp Glu Asp Thr Ala Ser Tyr Phe Cys
```

```
                    85                  90                  95
Ser Asn Asp Tyr Leu Tyr Ser Leu Asp Phe Trp Gly Gln Gly Thr Ala
                100                 105                 110

Leu Thr Val Ser Ser Gly Gly Gly Gly Ser Gly Gly Gly Gly Ser Gly
            115                 120                 125

Gly Gly Gly Ser Asp Ile Val Leu Thr Gln Ser Pro Ser Leu Ala
130                 135                 140

Met Ser Leu Gly Lys Arg Ala Thr Ile Ser Cys Arg Ala Ser Glu Ser
145                 150                 155                 160

Val Thr Ile Leu Gly Ser His Leu Ile Tyr Trp Tyr Gln Gln Lys Pro
                165                 170                 175

Gly Gln Pro Pro Thr Leu Leu Ile Gln Leu Ala Ser Asn Val Gln Thr
                180                 185                 190

Gly Val Pro Ala Arg Phe Ser Gly Ser Gly Ser Arg Thr Asp Phe Thr
                195                 200                 205

Leu Thr Ile Asp Pro Val Glu Glu Asp Asp Val Ala Val Tyr Tyr Cys
                210                 215                 220

Leu Gln Ser Arg Thr Ile Pro Arg Thr Phe Gly Gly Gly Thr Lys Leu
225                 230                 235                 240

Glu Ile Lys Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
                260                 265                 270

Ala Ala Gly Gly Ala Val His Thr Arg Gly Leu Asp Phe Ala Cys Asp
                275                 280                 285

Ile Tyr Ile Trp Ala Pro Leu Ala Gly Thr Cys Gly Val Leu Leu Leu
                290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
                340                 345                 350

Glu Leu Arg Val Lys Phe Ser Arg Ser Ala Asp Ala Pro Ala Tyr Lys
                355                 360                 365

Gln Gly Gln Asn Gln Leu Tyr Asn Glu Leu Asn Leu Gly Arg Arg Glu
                370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
                420                 425                 430

Glu Arg Arg Arg Gly Lys Gly His Asp Gly Leu Tyr Gln Gly Leu Ser
                435                 440                 445

Thr Ala Thr Lys Asp Thr Tyr Asp Ala Leu His Met Gln Ala Leu Pro
                450                 455                 460

Pro Arg
465

<210> SEQ ID NO 170
<211> LENGTH: 466
<212> TYPE: PRT
<213> ORGANISM: Artificial Sequence
```

```
<220> FEATURE:
<223> OTHER INFORMATION: anti-BCMA CAR

<400> SEQUENCE: 170

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Ser Met Asn Trp Val Lys Gln Ala Pro Gly Lys Gly Leu Lys Trp Met
        35                  40                  45

Gly Arg Ile Asn Thr Glu Thr Gly Glu Pro Leu Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Val Ile Asn Asn Leu Lys Asn Glu Asp Thr Ala Thr Phe Phe Cys
                85                  90                  95

Ser Asn Asp Tyr Leu Tyr Ser Cys Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Gly Ser Asp Ile Val Leu Thr Gln Ser Pro Pro Ser Leu Ala
    130                 135                 140

Met Ser Leu Gly Lys Arg Ala Thr Ile Ser Cys Arg Ala Ser Glu Ser
145                 150                 155                 160

Val Thr Ile Leu Gly Ser His Leu Ile Tyr Trp Tyr Gln Gln Lys Pro
                165                 170                 175

Gly Gln Pro Pro Thr Leu Leu Ile Gln Leu Ala Ser Asn Val Gln Thr
            180                 185                 190

Gly Val Pro Ala Arg Phe Ser Gly Ser Gly Ser Arg Thr Asp Phe Thr
        195                 200                 205

Leu Thr Ile Asp Pro Val Glu Glu Asp Asp Val Ala Val Tyr Tyr Cys
    210                 215                 220

Leu Gln Ser Arg Thr Ile Pro Arg Thr Phe Gly Gly Gly Thr Lys Leu
225                 230                 235                 240

Glu Ile Lys Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Ile Tyr Ile Trp Ala Pro Leu Ala Gly Thr Cys Gly Val Leu Leu Leu
    290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Lys
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400
```

```
Gly Lys Pro Arg Arg Lys Asn Pro Gln Glu Gly Leu Tyr Asn Glu Leu
            405                 410                 415

Gln Lys Asp Lys Met Ala Glu Ala Tyr Ser Glu Ile Gly Met Lys Gly
        420                 425                 430

Glu Arg Arg Arg Gly Lys Gly His Asp Gly Leu Tyr Gln Gly Leu Ser
    435                 440                 445

Thr Ala Thr Lys Asp Thr Tyr Asp Ala Leu His Met Gln Ala Leu Pro
450                 455                 460

Pro Arg
465

<210> SEQ ID NO 171
<211> LENGTH: 482
<212> TYPE: PRT
<213> ORGANISM: Artificial Sequence
<220> FEATURE:
<223> OTHER INFORMATION: anti-BCMA CAR

<400> SEQUENCE: 171

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240

Ser Val Thr Val Ser Ser Phe Val Pro Val Phe Leu Pro Ala Lys Pro
                245                 250                 255

Thr Thr Thr Pro Ala Pro Arg Pro Pro Thr Pro Ala Pro Thr Ile Ala
            260                 265                 270

Ser Gln Pro Leu Ser Leu Arg Pro Glu Ala Cys Arg Pro Ala Ala Gly
        275                 280                 285
```

```
Gly Ala Val His Thr Arg Gly Leu Asp Phe Ala Cys Asp Ile Tyr Ile
            290                 295                 300

Trp Ala Pro Leu Ala Gly Thr Cys Gly Val Leu Leu Leu Ser Leu Val
305                 310                 315                 320

Ile Thr Leu Tyr Cys Asn His Arg Asn Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
                420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 172
<211> LENGTH: 440
<212> TYPE: PRT
<213> ORGANISM: Artificial Sequence
<220> FEATURE:
<223> OTHER INFORMATION: anti-BCMA CAR

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
                20                  25                  30

Tyr Ile Asn Trp Val Arg Gln Ala Pro Gly Gln Gly Leu Glu Trp Met
            35                  40                  45

Gly Trp Ile Tyr Phe Ala Ser Gly Asn Ser Glu Tyr Asn Gln Lys Phe
50                  55                  60

Thr Gly Arg Val Thr Met Thr Arg Asp Thr Ser Ile Asn Thr Ala Tyr
65                  70                  75                  80

Met Glu Leu Ser Ser Leu Thr Ser Glu Asp Thr Ala Val Tyr Phe Cys
                85                  90                  95

Ala Ser Leu Tyr Asp Tyr Asp Trp Tyr Phe Asp Val Trp Gly Gln Gly
                100                 105                 110

Thr Met Val Thr Val Ser Ser Gly Gly Gly Ser Gly Gly Gly Gly
            115                 120                 125

Ser Gly Gly Gly Gly Ser Asp Ile Val Met Thr Gln Thr Pro Leu Ser
        130                 135                 140

Leu Ser Val Thr Pro Gly Gln Pro Ala Ser Ile Ser Cys Lys Ser Ser
145                 150                 155                 160
```

```
Gln Ser Leu Val His Ser Asn Gly Asn Thr Tyr Leu His Trp Tyr Leu
                165                 170                 175

Gln Lys Pro Gly Gln Ser Pro Gln Leu Leu Ile Tyr Lys Val Ser Asn
            180                 185                 190

Arg Phe Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Ile
    210                 215                 220

Tyr Tyr Cys Ser Gln Ser Ser Ile Tyr Pro Trp Thr Phe Gly Gln Gly
225                 230                 235                 240

Thr Lys Leu Glu Ile Lys Gly Leu Ala Val Ser Thr Ile Ser Ser Phe
                245                 250                 255

Phe Pro Pro Gly Tyr Gln Ile Tyr Ile Trp Ala Pro Leu Ala Gly Thr
            260                 265                 270

Cys Gly Val Leu Leu Leu Ser Leu Val Ile Thr Leu Tyr Cys Lys Arg
        275                 280                 285

Gly Arg Lys Lys Leu Leu Tyr Ile Phe Lys Gln Pro Phe Met Arg Pro
    290                 295                 300

Val Gln Thr Thr Gln Glu Glu Asp Gly Cys Ser Cys Arg Phe Pro Glu
305                 310                 315                 320

Glu Glu Glu Gly Gly Cys Glu Leu Arg Val Lys Phe Ser Arg Ser Ala
                325                 330                 335

Asp Ala Pro Ala Tyr Gln Gln Gly Gln Asn Gln Leu Tyr Asn Glu Leu
            340                 345                 350

Asn Leu Gly Arg Arg Glu Glu Tyr Asp Val Leu Asp Lys Arg Arg Gly
        355                 360                 365

Arg Asp Pro Glu Met Gly Gly Lys Pro Arg Arg Lys Asn Pro Gln Glu
    370                 375                 380

Gly Leu Tyr Asn Glu Leu Gln Lys Asp Lys Met Ala Glu Ala Tyr Ser
385                 390                 395                 400

Glu Ile Gly Met Lys Gly Glu Arg Arg Arg Gly Lys Gly His Asp Gly
                405                 410                 415

Leu Tyr Gln Gly Leu Ser Thr Ala Thr Lys Asp Thr Tyr Asp Ala Leu
            420                 425                 430

His Met Gln Ala Leu Pro Pro Arg
        435                 440

<210> SEQ ID NO 173
<211> LENGTH: 469
<212> TYPE: PRT
<213> ORGANISM: Artificial Sequence
<220> FEATURE:
<223> OTHER INFORMATION: anti-BCMA CAR

<400> SEQUENCE: 173

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ile Asn Thr Ala Tyr
65                  70                  75                  80
```

```
Met Glu Leu Ser Ser Leu Thr Ser Glu Asp Thr Ala Val Tyr Phe Cys
                85                  90                  95

Ala Ser Leu Tyr Asp Tyr Asp Trp Tyr Phe Asp Val Trp Gly Gln Gly
                100                 105                 110

Thr Met Val Thr Val Ser Ser Gly Gly Gly Gly Ser Gly Gly Gly Gly
            115                 120                 125

Ser Gly Gly Gly Ser Asp Ile Val Met Thr Gln Thr Pro Leu Ser
130                 135                 140

Leu Ser Val Thr Pro Gly Gln Pro Ala Ser Ile Ser Cys Lys Ser Ser
145                 150                 155                 160

Gln Ser Leu Val His Ser Asn Gly Asn Thr Tyr Leu His Trp Tyr Leu
                165                 170                 175

Gln Lys Pro Gly Gln Ser Pro Gln Leu Leu Ile Tyr Lys Val Ser Asn
                180                 185                 190

Arg Phe Ser Gly Val Pro Asp Arg Phe Ser Gly Ser Gly Ser Gly Thr
                195                 200                 205

Asp Phe Thr Leu Lys Ile Ser Arg Val Glu Ala Glu Asp Val Gly Ile
                210                 215                 220

Tyr Tyr Cys Ser Gln Ser Ser Ile Tyr Pro Trp Thr Phe Gly Gln Gly
225                 230                 235                 240

Thr Lys Leu Glu Ile Lys Thr Thr Thr Pro Ala Pro Arg Pro Pro Thr
                245                 250                 255

Pro Ala Pro Thr Ile Ala Ser Gln Pro Leu Ser Leu Arg Pro Glu Ala
                260                 265                 270

Cys Arg Pro Ala Ala Gly Gly Ala Val His Thr Arg Gly Leu Asp Phe
                275                 280                 285

Ala Cys Asp Ile Tyr Ile Trp Ala Pro Leu Ala Gly Thr Cys Gly Val
                290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
                340                 345                 350

Gly Gly Cys Glu Leu Arg Val Lys Phe Ser Arg Ser Ala Asp Ala Pro
                355                 360                 365

Ala Tyr Gln Gln Gly Gln Asn Gln Leu Tyr Asn Glu Leu Asn Leu Gly
                370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
                420                 425                 430

Met Lys Gly Glu Arg Arg Arg Gly Lys Gly His Asp Gly Leu Tyr Gln
                435                 440                 445

Gly Leu Ser Thr Ala Thr Lys Asp Thr Tyr Asp Ala Leu His Met Gln
450                 455                 460

Ala Leu Pro Pro Arg
465

<210> SEQ ID NO 174
<211> LENGTH: 655
<212> TYPE: PRT
```

<213> ORGANISM: Artificial Sequence
<220> FEATURE:
<223> OTHER INFORMATION: anti-BCMA CAR

<400> SEQUENCE: 174

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Ser | Phe | Pro | Asp | Tyr |
| | | | 20 | | | | | 25 | | | | | 30 | | |
| Tyr | Ile | Asn | Trp | Val | Arg | Gln | Ala | Pro | Gly | Gln | Gly | Leu | Glu | Trp | Met |
| | | | 35 | | | | | 40 | | | | | 45 | | |
| Gly | Trp | Ile | Tyr | Phe | Ala | Ser | Gly | Asn | Ser | Glu | Tyr | Asn | Gln | Lys | Phe |
| | 50 | | | | | 55 | | | | | 60 | | | | |
| Thr | Gly | Arg | Val | Thr | Met | Thr | Arg | Asp | Thr | Ser | Ile | Asn | Thr | Ala | Tyr |
| 65 | | | | | 70 | | | | | 75 | | | | | 80 |
| Met | Glu | Leu | Ser | Ser | Leu | Thr | Ser | Glu | Asp | Thr | Ala | Val | Tyr | Phe | Cys |
| | | | | 85 | | | | | 90 | | | | | 95 | |
| Ala | Ser | Leu | Tyr | Asp | Tyr | Asp | Trp | Tyr | Phe | Asp | Val | Trp | Gly | Gln | Gly |
| | | | 100 | | | | | 105 | | | | | 110 | | |
| Thr | Met | Val | Thr | Val | Ser | Ser | Gly | Gly | Gly | Gly | Ser | Gly | Gly | Gly | Gly |
| | | | 115 | | | | | 120 | | | | | 125 | | |
| Ser | Gly | Gly | Gly | Gly | Ser | Asp | Ile | Val | Met | Thr | Gln | Thr | Pro | Leu | Ser |
| 130 | | | | | 135 | | | | | 140 | | | | | |
| Leu | Ser | Val | Thr | Pro | Gly | Gln | Pro | Ala | Ser | Ile | Ser | Cys | Lys | Ser | Ser |
| 145 | | | | | 150 | | | | | 155 | | | | | 160 |
| Gln | Ser | Leu | Val | His | Ser | Asn | Gly | Asn | Thr | Tyr | Leu | His | Trp | Tyr | Leu |
| | | | | 165 | | | | | 170 | | | | | 175 | |
| Gln | Lys | Pro | Gly | Gln | Ser | Pro | Gln | Leu | Leu | Ile | Tyr | Lys | Val | Ser | Asn |
| | | | 180 | | | | | 185 | | | | | 190 | | |
| Arg | Phe | Ser | Gly | Val | Pro | Asp | Arg | Phe | Ser | Gly | Ser | Gly | Ser | Gly | Thr |
| | | 195 | | | | | 200 | | | | | 205 | | | |
| Asp | Phe | Thr | Leu | Lys | Ile | Ser | Arg | Val | Glu | Ala | Glu | Asp | Val | Gly | Ile |
| | 210 | | | | | 215 | | | | | 220 | | | | |
| Tyr | Tyr | Cys | Ser | Gln | Ser | Ser | Ile | Tyr | Pro | Trp | Thr | Phe | Gly | Gln | Gly |
| 225 | | | | | 230 | | | | | 235 | | | | | 240 |
| Thr | Lys | Leu | Glu | Ile | Lys | Glu | Pro | Lys | Ser | Pro | Asp | Lys | Thr | His | Thr |
| | | | | 245 | | | | | 250 | | | | | 255 | |
| Cys | Pro | Pro | Cys | Pro | Ala | Pro | Pro | Val | Ala | Gly | Pro | Ser | Val | Phe | Leu |
| | | | 260 | | | | | 265 | | | | | 270 | | |
| Phe | Pro | Pro | Lys | Pro | Lys | Asp | Thr | Leu | Met | Ile | Ala | Arg | Thr | Pro | Glu |
| | | 275 | | | | | 280 | | | | | 285 | | | |
| Val | Thr | Cys | Val | Val | Val | Asp | Val | Ser | His | Glu | Asp | Pro | Glu | Val | Lys |
| | 290 | | | | | 295 | | | | | 300 | | | | |
| Phe | Asn | Trp | Tyr | Val | Asp | Gly | Val | Glu | Val | His | Asn | Ala | Lys | Thr | Lys |
| 305 | | | | | 310 | | | | | 315 | | | | | 320 |
| Pro | Arg | Glu | Glu | Gln | Tyr | Asn | Ser | Thr | Tyr | Arg | Val | Val | Ser | Val | Leu |
| | | | | 325 | | | | | 330 | | | | | 335 | |
| Thr | Val | Leu | His | Gln | Asp | Trp | Leu | Asn | Gly | Lys | Glu | Tyr | Lys | Cys | Lys |
| | | | 340 | | | | | 345 | | | | | 350 | | |
| Val | Ser | Asn | Lys | Ala | Leu | Pro | Ala | Pro | Ile | Glu | Lys | Thr | Ile | Ser | Lys |
| | | 355 | | | | | 360 | | | | | 365 | | | |
| Ala | Lys | Gly | Gln | Pro | Arg | Glu | Pro | Gln | Val | Tyr | Thr | Leu | Pro | Pro | Ser |
| | 370 | | | | | 375 | | | | | 380 | | | | |
| Arg | Asp | Glu | Leu | Thr | Lys | Asn | Gln | Val | Ser | Leu | Thr | Cys | Leu | Val | Lys |

```
                385                 390                 395                 400
        Gly Phe Tyr Pro Ser Asp Ile Ala Val Glu Trp Glu Ser Asn Gly Gln
                        405                 410                 415
        Pro Glu Asn Asn Tyr Lys Thr Thr Pro Pro Val Leu Asp Ser Asp Gly
                        420                 425                 430
        Ser Phe Phe Leu Tyr Ser Lys Leu Thr Val Asp Lys Ser Arg Trp Gln
                        435                 440                 445
        Gln Gly Asn Val Phe Ser Cys Ser Val Met His Glu Ala Leu His Asn
                    450                 455                 460
        His Tyr Thr Gln Lys Ser Leu Ser Leu Ser Pro Gly Lys Ile Tyr Ile
        465                 470                 475                 480
        Trp Ala Pro Leu Ala Gly Thr Cys Gly Val Leu Leu Leu Ser Leu Val
                        485                 490                 495
        Ile Thr Leu Tyr Cys Lys Arg Gly Arg Lys Lys Leu Leu Tyr Ile Phe
                        500                 505                 510
        Lys Gln Pro Phe Met Arg Pro Val Gln Thr Thr Gln Glu Glu Asp Gly
                    515                 520                 525
        Cys Ser Cys Arg Phe Pro Glu Glu Glu Glu Gly Gly Cys Glu Leu Arg
            530                 535                 540
        Val Lys Phe Ser Arg Ser Ala Asp Ala Pro Ala Tyr Gln Gln Gly Gln
        545                 550                 555                 560
        Asn Gln Leu Tyr Asn Glu Leu Asn Leu Gly Arg Arg Glu Glu Tyr Asp
                        565                 570                 575
        Val Leu Asp Lys Arg Arg Gly Arg Asp Pro Glu Met Gly Gly Lys Pro
                    580                 585                 590
        Arg Arg Lys Asn Pro Gln Glu Gly Leu Tyr Asn Glu Leu Gln Lys Asp
                        595                 600                 605
        Lys Met Ala Glu Ala Tyr Ser Glu Ile Gly Met Lys Gly Glu Arg Arg
                    610                 615                 620
        Arg Gly Lys Gly His Asp Gly Leu Tyr Gln Gly Leu Ser Thr Ala Thr
        625                 630                 635                 640
        Lys Asp Thr Tyr Asp Ala Leu His Met Gln Ala Leu Pro Pro Arg
                        645                 650                 655

<210> SEQ ID NO 175
<211> LENGTH: 440
<212> TYPE: PRT
<213> ORGANISM: Artificial Sequence
<220> FEATURE:
<223> OTHER INFORMATION: anti-BCMA CAR

<400> SEQUENCE: 175

Gln Val Gln Leu Val Gln Ser Gly Ala Glu Val Lys Lys Pro Gly Ala
        1               5                   10                  15
        Ser Val Lys Val Ser Cys Lys Ala Ser Gly Tyr Ser Phe Pro Asp Tyr
                        20                  25                  30
        Tyr Ile Asn Trp Val Arg Gln Ala Pro Gly Gln Gly Leu Glu Trp Met
                    35                  40                  45
        Gly Trp Ile Tyr Phe Ala Ser Gly Asn Ser Glu Tyr Asn Gln Lys Phe
                50                  55                  60
        Thr Gly Arg Val Thr Met Thr Arg Asp Thr Ser Ser Thr Ala Tyr
        65                  70                  75                  80
        Met Glu Leu Ser Ser Leu Arg Ser Glu Asp Thr Ala Val Tyr Phe Cys
                        85                  90                  95
        Ala Ser Leu Tyr Asp Tyr Asp Trp Tyr Phe Asp Val Trp Gly Gln Gly
```

```
            100                 105                 110
Thr Met Val Thr Val Ser Ser Gly Gly Gly Ser Gly Gly Gly
        115                 120                 125
Ser Gly Gly Gly Ser Asp Ile Val Met Thr Gln Thr Pro Leu Ser
    130                 135                 140
Leu Ser Val Thr Pro Gly Glu Pro Ala Ser Ile Ser Cys Lys Ser
145                 150                 155                 160
Gln Ser Leu Val His Ser Asn Gly Asn Thr Tyr Leu His Trp Tyr Leu
                165                 170                 175
Gln Lys Pro Gly Gln Ser Pro Gln Leu Leu Ile Tyr Lys Val Ser Asn
            180                 185                 190
Arg Phe Ser Gly Val Pro Asp Arg Phe Ser Gly Ser Gly Ser Gly Ala
        195                 200                 205
Asp Phe Thr Leu Lys Ile Ser Arg Val Glu Ala Glu Asp Val Gly Val
    210                 215                 220
Tyr Tyr Cys Ala Glu Thr Ser His Val Pro Trp Thr Phe Gly Gln Gly
225                 230                 235                 240
Thr Lys Leu Glu Ile Lys Gly Leu Ala Val Ser Thr Ile Ser Ser Phe
                245                 250                 255
Phe Pro Pro Gly Tyr Gln Ile Tyr Ile Trp Ala Pro Leu Ala Gly Thr
            260                 265                 270
Cys Gly Val Leu Leu Leu Ser Leu Val Ile Thr Leu Tyr Cys Lys Arg
        275                 280                 285
Gly Arg Lys Lys Leu Leu Tyr Ile Phe Lys Gln Pro Phe Met Arg Pro
    290                 295                 300
Val Gln Thr Thr Gln Glu Glu Asp Gly Cys Ser Cys Arg Phe Pro Glu
305                 310                 315                 320
Glu Glu Glu Gly Gly Cys Glu Leu Arg Val Lys Phe Ser Arg Ser Ala
                325                 330                 335
Asp Ala Pro Ala Tyr Gln Gln Gly Gln Asn Gln Leu Tyr Asn Glu Leu
            340                 345                 350
Asn Leu Gly Arg Arg Glu Glu Tyr Asp Val Leu Asp Lys Arg Arg Gly
        355                 360                 365
Arg Asp Pro Glu Met Gly Gly Lys Pro Arg Arg Lys Asn Pro Gln Glu
    370                 375                 380
Gly Leu Tyr Asn Glu Leu Gln Lys Asp Lys Met Ala Glu Ala Tyr Ser
385                 390                 395                 400
Glu Ile Gly Met Lys Gly Glu Arg Arg Arg Gly Lys Gly His Asp Gly
                405                 410                 415
Leu Tyr Gln Gly Leu Ser Thr Ala Thr Lys Asp Thr Tyr Asp Ala Leu
            420                 425                 430
His Met Gln Ala Leu Pro Pro Arg
        435                 440

<210> SEQ ID NO 176
<211> LENGTH: 469
<212> TYPE: PRT
<213> ORGANISM: Artificial Sequence
<220> FEATURE:
<223> OTHER INFORMATION: anti-BCMA CAR

<400> SEQUENCE: 176

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
```

```
                20                  25                  30
Tyr Ile Asn Trp Val Arg Gln Ala Pro Gly Gln Gly Leu Glu Trp Met
            35                  40                  45
Gly Trp Ile Tyr Phe Ala Ser Gly Asn Ser Glu Tyr Asn Gln Lys Phe
        50                  55                  60
Thr Gly Arg Val Thr Met Thr Arg Asp Thr Ser Ser Thr Ala Tyr
65                  70                  75                  80
Met Glu Leu Ser Ser Leu Arg Ser Glu Asp Thr Ala Val Tyr Phe Cys
                85                  90                  95
Ala Ser Leu Tyr Asp Tyr Asp Trp Tyr Phe Asp Val Trp Gly Gln Gly
            100                 105                 110
Thr Met Val Thr Val Ser Ser Gly Gly Gly Ser Gly Gly Gly Gly
        115                 120                 125
Ser Gly Gly Gly Gly Ser Asp Ile Val Met Thr Gln Thr Pro Leu Ser
                130                 135                 140
Leu Ser Val Thr Pro Gly Glu Pro Ala Ser Ile Ser Cys Lys Ser Ser
145                 150                 155                 160
Gln Ser Leu Val His Ser Asn Gly Asn Thr Tyr Leu His Trp Tyr Leu
                165                 170                 175
Gln Lys Pro Gly Gln Ser Pro Gln Leu Leu Ile Tyr Lys Val Ser Asn
            180                 185                 190
Arg Phe Ser Gly Val Pro Asp Arg Phe Ser Gly Ser Gly Ser Gly Ala
        195                 200                 205
Asp Phe Thr Leu Lys Ile Ser Arg Val Glu Ala Glu Asp Val Gly Val
        210                 215                 220
Tyr Tyr Cys Ala Glu Thr Ser His Val Pro Trp Thr Phe Gly Gln Gly
225                 230                 235                 240
Thr Lys Leu Glu Ile Lys Thr Thr Thr Pro Ala Pro Arg Pro Pro Thr
            245                 250                 255
Pro Ala Pro Thr Ile Ala Ser Gln Pro Leu Ser Leu Arg Pro Glu Ala
        260                 265                 270
Cys Arg Pro Ala Ala Gly Gly Ala Val His Thr Arg Gly Leu Asp Phe
        275                 280                 285
Ala Cys Asp Ile Tyr Ile Trp Ala Pro Leu Ala Gly Thr Cys Gly Val
        290                 295                 300
Leu Leu Leu Ser Leu Val Ile Thr Leu Tyr Cys Lys Arg Gly Arg Lys
305                 310                 315                 320
Lys Leu Leu Tyr Ile Phe Lys Gln Pro Phe Met Arg Pro Val Gln Thr
            325                 330                 335
Thr Gln Glu Glu Asp Gly Cys Ser Cys Arg Phe Pro Glu Glu Glu Glu
            340                 345                 350
Gly Gly Cys Glu Leu Arg Val Lys Phe Ser Arg Ser Ala Asp Ala Pro
        355                 360                 365
Ala Tyr Gln Gln Gly Gln Asn Gln Leu Tyr Asn Glu Leu Asn Leu Gly
        370                 375                 380
Arg Arg Glu Glu Tyr Asp Val Leu Asp Lys Arg Arg Gly Arg Asp Pro
385                 390                 395                 400
Glu Met Gly Gly Lys Pro Arg Arg Lys Asn Pro Gln Glu Gly Leu Tyr
            405                 410                 415
Asn Glu Leu Gln Lys Asp Lys Met Ala Glu Ala Tyr Ser Glu Ile Gly
            420                 425                 430
Met Lys Gly Glu Arg Arg Arg Gly Lys Gly His Asp Gly Leu Tyr Gln
        435                 440                 445
```

```
Gly Leu Ser Thr Ala Thr Lys Asp Thr Tyr Asp Ala Leu His Met Gln
    450                 455                 460

Ala Leu Pro Pro Arg
465

<210> SEQ ID NO 177
<211> LENGTH: 655
<212> TYPE: PRT
<213> ORGANISM: Artificial Sequence
<220> FEATURE:
<223> OTHER INFORMATION: anti-BCMA CAR

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Asp Ile Val Met Thr Gln Thr Pro Leu Ser
    130                 135                 140

Leu Ser Val Thr Pro Gly Glu Pro Ala Ser Ile Ser Cys Lys Ser Ser
145                 150                 155                 160

Gln Ser Leu Val His Ser Asn Gly Asn Thr Tyr Leu His Trp Tyr Leu
                165                 170                 175

Gln Lys Pro Gly Gln Ser Pro Gln Leu Leu Ile Tyr Lys Val Ser Asn
            180                 185                 190

Arg Phe Ser Gly Val Pro Asp Arg Phe Ser Gly Ser Gly Ser Gly Ala
        195                 200                 205

Asp Phe Thr Leu Lys Ile Ser Arg Val Glu Ala Glu Asp Val Gly Val
    210                 215                 220

Tyr Tyr Cys Ala Glu Thr Ser His Val Pro Trp Thr Phe Gly Gln Gly
225                 230                 235                 240

Thr Lys Leu Glu Ile Lys Glu Pro Lys Ser Pro Asp Lys Thr His Thr
                245                 250                 255

Cys Pro Pro Cys Pro Ala Pro Val Ala Gly Pro Ser Val Phe Leu
            260                 265                 270

Phe Pro Pro Lys Pro Lys Asp Thr Leu Met Ile Ala Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335
```

-continued

Thr Val Leu His Gln Asp Trp Leu Asn Gly Lys Glu Tyr Lys Cys Lys
              340                 345                 350

Val Ser Asn Lys Ala Leu Pro Ala Pro Ile Glu Lys Thr Ile Ser Lys
          355                 360                 365

Ala Lys Gly Gln Pro Arg Glu Pro Gln Val Tyr Thr Leu Pro Pro Ser
     370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys Ile Tyr Ile
465                 470                 475                 480

Trp Ala Pro Leu Ala Gly Thr Cys Gly Val Leu Leu Leu Ser Leu Val
                485                 490                 495

Ile Thr Leu Tyr Cys Lys Arg Gly Arg Lys Lys Leu Leu Tyr Ile Phe
            500                 505                 510

Lys Gln Pro Phe Met Arg Pro Val Gln Thr Thr Gln Glu Glu Asp Gly
        515                 520                 525

Cys Ser Cys Arg Phe Pro Glu Glu Glu Gly Gly Cys Glu Leu Arg
    530                 535                 540

Val Lys Phe Ser Arg Ser Ala Asp Ala Pro Ala Tyr Gln Gln Gly Gln
545                 550                 555                 560

Asn Gln Leu Tyr Asn Glu Leu Asn Leu Gly Arg Arg Glu Glu Tyr Asp
                565                 570                 575

Val Leu Asp Lys Arg Arg Gly Arg Asp Pro Glu Met Gly Gly Lys Pro
            580                 585                 590

Arg Arg Lys Asn Pro Gln Glu Gly Leu Tyr Asn Glu Leu Gln Lys Asp
        595                 600                 605

Lys Met Ala Glu Ala Tyr Ser Glu Ile Gly Met Lys Gly Glu Arg Arg
    610                 615                 620

Arg Gly Lys Gly His Asp Gly Leu Tyr Gln Gly Leu Ser Thr Ala Thr
625                 630                 635                 640

Lys Asp Thr Tyr Asp Ala Leu His Met Gln Ala Leu Pro Pro Arg
                645                 650                 655

<210> SEQ ID NO 178
<211> LENGTH: 28
<212> TYPE: PRT
<213> ORGANISM: Artificial Sequence
<220> FEATURE:
<223> OTHER INFORMATION: CD8a TM

<400> SEQUENCE: 178

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25

<210> SEQ ID NO 179

```
<211> LENGTH: 21
<212> TYPE: PRT
<213> ORGANISM: Artificial Sequence
<220> FEATURE:
<223> OTHER INFORMATION: CD8a TM

<400> SEQUENCE: 179

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 180
<211> LENGTH: 4
<212> TYPE: PRT
<213> ORGANISM: Artificial Sequence
<220> FEATURE:
<223> OTHER INFORMATION: linking peptide

<400> SEQUENCE: 180

Arg Ala Ala Ala
1

<210> SEQ ID NO 181
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 181

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Asp Tyr Thr Glu Asp Tyr Trp Gly Gln Gly Thr
            100                 105                 110

Leu Val Thr Val Ser Ser
        115

<210> SEQ ID NO 182
<211> LENGTH: 110
<212> TYPE: PRT
<213> ORGANISM: Artificial Sequence
<220> FEATURE:
<223> OTHER INFORMATION: Variable light (VL) Anti-BCMA

<400> SEQUENCE: 182

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Lys Tyr
            20                  25                  30

Asn Leu Val Ser Trp Tyr Gln Gln Pro Pro Gly Lys Ala Pro Lys Leu
        35                  40                  45
```

```
Ile Ile Tyr Asp Val Asn Lys Arg Pro Ser Gly Val Ser Asn Arg Phe
        50                  55                  60

Ser Gly Ser Lys Ser Gly Asn Thr Ala Thr Leu Thr Ile Ser Gly Leu
 65                  70                  75                  80

Gln Gly Asp Asp Glu Ala Asp Tyr Tyr Cys Ser Ser Tyr Gly Gly Ser
                 85                  90                  95

Arg Ser Tyr Val Phe Gly Thr Gly Thr Lys Val Thr Val Leu
            100                 105                 110

<210> SEQ ID NO 183
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 183

Glu Val Gln Leu Val Gln Ser Gly Gly Gly Leu Val Gln Pro Gly Arg
 1               5                  10                  15

Ser Leu Arg Leu Ser Cys Thr Ala Ser Gly Phe Thr Phe Gly Asp Tyr
                20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
 50                  55                  60

Ser Val Lys Gly Arg Phe Thr Ile Ser Arg Asp Asp Ser Lys Ser Ile
 65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser
        115

<210> SEQ ID NO 184
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 184

Asp Ile Gln Met Thr Gln Ser Pro Ala Phe Leu Ser Ala Ser Val Gly
 1               5                  10                  15

Asp Arg Val Thr Val Thr Cys Arg Ala Ser Gln Gly Ile Ser Asn Tyr
                20                  25                  30

Leu Ala Trp Tyr Gln Gln Lys Pro Gly Asn Ala Pro Arg Leu Leu Ile
            35                  40                  45

Tyr Ser Ala Ser Thr Leu Gln Ser Gly Val Pro Ser Arg Phe Arg Gly
 50                  55                  60

Thr Gly Tyr Gly Thr Glu Phe Ser Leu Thr Ile Asp Ser Leu Gln Pro
 65                  70                  75                  80

Glu Asp Phe Ala Thr Tyr Tyr Cys Gln Gln Ser Tyr Thr Ser Arg Gln
                85                  90                  95

Thr Phe Gly Pro Gly Thr Arg Leu Asp Ile Lys
            100                 105
```

-continued

```
<210> SEQ ID NO 185
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 185
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser
        115

```
<210> SEQ ID NO 186
<211> LENGTH: 108
<212> TYPE: PRT
<213> ORGANISM: Artificial Sequence
<220> FEATURE:
<223> OTHER INFORMATION: Variable light (VL) Anti-BCMA

<400> SEQUENCE: 186
```

Ser Tyr Val Leu Thr Gln Pro Pro Ser Val Ser Val Ala Pro Gly Gln
1               5                   10                  15

Thr Ala Arg Ile Thr Cys Gly Ala Asn Asn Ile Gly Ser Lys Ser Val
            20                  25                  30

His Trp Tyr Gln Gln Lys Pro Gly Gln Ala Pro Met Leu Val Val Tyr
        35                  40                  45

Asp Asp Asp Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Phe Cys His Leu Trp Asp Arg Ser Arg Asp His
                85                  90                  95

Tyr Val Phe Gly Thr Gly Thr Lys Leu Thr Val Leu
            100                 105

```
<210> SEQ ID NO 187
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 187
```

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

```
Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
 50                  55                  60

Gln Gly Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Gly Tyr Ser Lys Ser Ile Val Ser Tyr Met Asp Tyr Trp
                100                 105                 110

Gly Gln Gly Thr Leu Val Thr Val Ser Ser
                115                 120

<210> SEQ ID NO 188
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 188

Leu Pro Val Leu Thr Gln Pro Pro Ser Thr Ser Gly Thr Pro Gly Gln
 1               5                  10                  15

Arg Val Thr Val Ser Cys Ser Gly Ser Ser Ser Asn Ile Gly Ser Asn
                 20                  25                  30

Val Val Phe Trp Tyr Gln Gln Leu Pro Gly Thr Ala Pro Lys Leu Val
             35                  40                  45

Ile Tyr Arg Asn Asn Gln Arg Pro Ser Gly Val Pro Asp Arg Phe Ser
 50                  55                  60

Val Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Tyr Val Phe Gly Thr Gly Thr Lys Val Thr Val Leu Gly
                100                 105                 110

<210> SEQ ID NO 189
<211> LENGTH: 17
<212> TYPE: PRT
<213> ORGANISM: Artificial Sequence
<220> FEATURE:
<223> OTHER INFORMATION: Linker

<400> SEQUENCE: 189

Ala Ser Gly Gly Gly Gly Ser Gly Gly Arg Ala Ser Gly Gly Gly Gly
 1               5                  10                  15

Ser
```

METHODS AND COMBINATIONS FOR TREATMENT AND T CELL MODULATION

CROSS-REFERENCE TO RELATED APPLICATIONS

This application is a National Stage application under 35 U.S.C. § 371 of International Application No. PCT/US2019/060367, filed on Nov. 7, 2019, which claims priority to U.S. Provisional Application No. 62/757,755, filed Nov. 8, 2018, and U.S. Provisional Application No. 62/826,928, filed Mar. 29, 2019, the contents of which are hereby incorporated by reference in their entirety for all purposes.

INCORPORATION BY REFERENCE OF SEQUENCE LISTING

The present application is being filed along with a Sequence Listing in electronic format. The Sequence Listing is provided as a file entitled 735042019400SeqList.TXT, created May 6, 2021, which is 327,952 bytes in size. The information in the electronic format of the Sequence Listing is incorporated by reference in its entirety.

FIELD

The present disclosure relates in some aspects to methods, compositions and uses involving immunotherapies, such as adoptive cell therapy, e.g., T cell therapy, and an immunomodulatory compound, such as a structural or functional analog or derivative of thalidomide and/or an inhibitor of E3-ubiquitin ligase. The provided methods, compositions and uses include those for combination therapies involving the administration or use of one or more immunomodulatory compounds in conjunction with a T cell therapy, such as a genetically engineered T cell therapy involving cells engineered with a recombinant receptor, such as chimeric antigen receptor (CAR)-expressing T cells. Also provided are compositions, methods of administration to subjects, articles of manufacture and kits for use in the methods. In some aspects, features of the methods and cells provide for increased or improved activity, efficacy, persistence, expansion and/or proliferation of T cells for adoptive cell therapy or endogenous T cells recruited by immunotherapeutic agents.

BACKGROUND

Various strategies are available for immunotherapy, for example administering engineered T cells for adoptive therapy. For example, strategies are available for engineering T cells expressing genetically engineered antigen receptors, such as CARs, and administering compositions containing such cells to subjects. Improved strategies are needed to improve efficacy of the cells, for example, improving the persistence, activity and/or proliferation of the cells upon administration to subjects. Provided are methods, compositions, kits, and systems that meet such needs.

SUMMARY

Provided herein are methods for rescuing T cell activity, involving exposing a plurality of T cells having an exhausted phenotype to an effective amount of an immunomodulatory compound selected from: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3). In some embodiments of the methods provided herein, the one or more T cells include T cells that express a recombinant receptor that specifically binds to a target antigen.

Provided herein are methods for preventing or inhibiting or reducing or delaying the onset of T cell exhaustion, the method comprising exposing a plurality of T cells to an effective amount of an immunomodulatory compound selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3), wherein at least a portion of the exposing is carried out under conditions that induce, or are capable of inducing, an exhausted phenotype in T cells of the plurality in the absence of the compound.

Provided herein are methods for reducing or delaying the onset of T cell exhaustion, the method involving exposing a plurality of T cells to an effective amount of an immunomodulatory compound selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3), wherein at least a portion of the exposing is carried out during conditions that induce, or are capable of inducing, an exhausted phenotype in T cells of the plurality in the absence of the compound.

Provided herein are methods for increasing T cell activity or potency and preventing or inhibiting, reducing or delaying the onset of T cell exhaustion, involving exposing a plurality of T cells to an effective amount of an immunomodulatory compound selected from: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3), wherein at least a portion of the exposing is carried out under conditions that induce, or are capable of inducing, an exhausted phenotype in T cells of the plurality in the absence of the compound.

In some embodiments of any of the methods provided herein, the conditions include T cell stimulatory conditions, optionally including exposure to at least one T cell stimulatory agent that is capable of stimulating a signal in T cells of the plurality, said signal optionally including a primary and/or costimulatory signal. In some embodiments, the conditions include persistent, repeat, prolonged or long term exposure to the at least one T cell stimulatory agent.

In some embodiments of any of the methods provided herein, the at least one T cell stimulatory agent includes a polyclonal agent, an antigen specifically recognized by a receptor expressed on T cells of the plurality or an agent that is bound by an antigen receptor expressed by T cells of the plurality. In some embodiments, the at least one T cell stimulatory agent is or includes PMA and ionomycin or is or includes a T cell receptor agonist or a T cell receptor complex agonist. In some embodiments, the agent specifically binds to a member of a TCR complex, optionally wherein the agent specifically binds to a CD3, optionally a CD3zeta.

In some embodiments of any of the methods provided herein, the at least one T cell stimulatory agent includes an anti-CD3 antibody. In some embodiments, the at least one T cell stimulatory agent specifically binds to a T cell costimulatory molecule, optionally wherein the T cell costimulatory molecule is CD28, CD137 (4-1-BB), OX40, CD40L or ICOS or wherein the at least one T cell stimulatory agent further includes an agent that specifically binds to a T cell costimulatory molecule, optionally wherein the T cell costimulatory molecule is CD28, CD137 (4-1-BB), OX40, CD40L or ICOS. In some embodiments, the at least one T cell stimulatory agent includes an anti-CD28 antibody. In some embodiments, the at least one T cell stimulatory agent includes or further includes an MHC-peptide complex recognized by an antigen receptor expressed by one or more T cells of the plurality, or an antigen recognized by an antigen receptor expressed by one or more T cells of the plurality. In some embodiments, the one or more of the plurality of T cells express a recombinant antigen receptor that binds a target antigen. In some embodiments, the at least one T cell stimulatory agent binds to the recombinant antigen receptor. In some embodiments, the at least one T cell stimulatory agent is or comprises an anti-idioptypic antibody specific to the recombinant antigen receptor. In some embodiments, the at least one T cell stimulatory agent is or includes the target antigen or a portion thereof recognized by or bound by the recombinant antigen receptor and/or wherein the conditions include exposure to the target antigen. In some embodiments of any of the methods provided herein, the recombinant antigen receptor is a recombinant T cell receptor (TCR). In some embodiments, the recombinant antigen receptor is a chimeric antigen receptor (CAR).

In some embodiments of any of the methods provided herein, the one or more T cells are primary human T cells, optionally from a subject. In some embodiments, the exposing of the T cells to an effective amount of an immunomodulatory compound is carried out ex vivo. In other embodiments, the exposing is carried out in vivo, and the exposing includes administration of the compound to a subject, optionally wherein, where the T cells are from the subject, wherein the administration of the compound is to said subject; and/or the exposing includes administration of said plurality of T cells to a subject, optionally wherein, where the T cells are from the subject, wherein the administration of the compound is to said subject. In some embodiments of any of the methods provided herein, the exposing of the T cells to an effective amount of an immunomodulatory compound includes said administration of said compound and, wherein, prior to the exposing, said subject has been administered a composition comprising the plurality of T cells to the subject for treating a disease or condition, optionally wherein the target antigen is associated with the disease or condition.

In some embodiments of any of the methods provided herein, the exposing of the T cells to an effective amount of an immunomodulatory compound includes said administration of said compound and, wherein, prior to the exposing, said subject has been administered a composition containing the plurality of T cells to the subject for treating a disease or condition, optionally wherein the target antigen is associated with the disease or condition; or said exposure includes administration of said T cells to said subject for treating a disease or condition, optionally wherein the target antigen is associated with the disease or condition, wherein, prior to the exposing, said subject has been administered said compound; or said exposure includes administration of said T cells to said subject for treating a disease or condition, optionally wherein the target antigen is associated with the disease or condition, and includes administration of said compound to said subject.

Provided herein are methods of treatment that involve administering, to a subject, an immunomodulatory compound, wherein said immunomodulatory compound is selected from: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3), wherein, (a) said subject, prior to the administration of the compound, has been administered a T cell therapy that includes a dose of T cells expressing a recombinant antigen receptor that binds a target antigen, or (b) prior to or at the time of administration of said compound, said subject or a blood sample from the subject contains, or has been confirmed to contain, one or more T cells expressing a recombinant antigen receptor, wherein at the time of the administration of the compound: (i) one or more of the recombinant receptor-expressing T cells in the subject has an exhausted phenotype; (ii) one or more of the recombinant receptor-expressing T cells in the subject have been determined to have an exhausted phenotype; (iii) an exhausted phenotype of one or more recombinant receptor-expressing T cells, or a marker or parameter indicative thereof, has been detected or measured in the subject or in a biological sample from the subject; (iv) at least at or about 10%, at least at or about 20%, at least at or about 30%, at least at or about 40%, or at least at or about 50% of the total recombinant receptor-expressing T cells in a biological sample from the subject has an exhausted phenotype; and/or (v) greater than at or about 10%, greater than at or about 20%, greater than at or about 30%, greater than at or about 40%, or greater than at or about 50% of the recombinant receptor-expressing T cells in a biological sample from the subject has an exhausted phenotype compared to the percentage of the recombinant receptor-expressing cells having the exhausted phenotype in a comparable biological sample at a prior time point.

Provided herein are methods of treatment that involve (a) selecting a subject as a candidate for administration of an immunomodulator compound, said selected subject having exhausted recombinant receptor-expressing T cells; and (b) administering to the subject the immunomodulatory compound, wherein the immunomodulatory compound is selected from: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3).

In some embodiments of any of the methods provided herein, a tissue, tumor, biological fluid or biological sample of or from said selected subject: (i) includes one or more T cells that express a recombinant antigen receptor that binds to a target antigen and that have an exhausted phenotype; (ii) includes a plurality of T cells that express a recombinant antigen receptor that binds to a target antigen, wherein at least at or about 10%, at least at or about 20%, at least at or about 30%, at least at or about 40%, at least at or about 50%, at least at or about 60%, at least at or about 70% or at least at or about 80%, of the T cells in said tissue, fluid, tumor or sample expressing the recombinant receptor have an exhausted phenotype; and/or (iii) includes a plurality of T cells that express a recombinant antigen receptor that binds to a target antigen, wherein greater than at or about 10% more, greater than at or about 20% more, greater than at or about 30% more, greater than at or about 40% more, or greater than at or about 50% more, or greater than 2-fold more, or greater than 3-fold more, or greater than 5-fold more, or greater than 10-fold more, of the T cells in the tissue, tumor, fluid or sample of or from the selected subject that express the recombinant antigen receptor have an exhausted phenotype, as compared to the percentage or number of T cells expressing the recombinant receptor in the, or in a comparable, fluid, tissue, tumor or sample from said subject at earlier time point had said exhausted phenotype. In some embodiments of any of the methods provided herein, prior to said administration of the compound, said subject has been administered a plurality of T cells expressing the recombinant receptor, and the earlier time point is a time just prior to the administration of the plurality of T cells that express a recombinant antigen receptor to the subject.

In some embodiments of any of the methods provided herein, said selection of said subject includes determining that, or is based on determination that, a tissue, tumor, biological fluid or biological sample of or from said selected subject: (i) one or more T cells that express a recombinant antigen receptor that binds to a target antigen and that have an exhausted phenotype; (ii) includes a plurality of T cells that express a recombinant antigen receptor that binds to a target antigen, wherein at least at or about 10%, at least at or about 20%, at least at or about 30%, at least at or about 40%, at least at or about 50%, at least at or about 60%, at least at or about 70% or at least at or about 80%, of the T cells in said tissue, fluid, tumor or sample expressing the recombinant receptor have an exhausted phenotype; and/or (iii) includes a plurality of T cells that express a recombinant antigen receptor that binds to a target antigen, wherein greater than at or about 10% more, greater than at or about 20% more, greater than at or about 30% more, greater than at or about 40% more, or greater than at or about 50% more, or greater than 2-fold more, or greater than 3-fold more, or greater than 5-fold more, or greater than 10-fold more, of the T cells in the tissue, tumor, fluid or sample of or from the selected subject that express the recombinant antigen receptor have an exhausted phenotype, as compared to the percentage or number of T cells expressing the recombinant receptor in the, or in a comparable, fluid, tissue, tumor or sample from said subject at earlier time point had said exhausted phenotype.

In some embodiments of any of the methods provided herein, prior to said administration of the compound, said subject has been administered a plurality of T cells expressing the recombinant receptor and optionally wherein said earlier time point is subsequent to the administration of the T cells and prior to said selection.

In some embodiments of any of the methods provided herein, the prior time point is a time: subsequent to the administration of T cells expressing said recombinant receptor to said selected subject and is at or before a peak or maximum level of T cells expressing recombinant receptor are detectable in the blood of the subject; within 1 day, 2 days, 3 days, 4 days, 5 days, 6 days, 7 days, 8 days, 9 days, 10 days, 11 days, 12 days, 13 days, 14 days, or more prior to said determination or selection.

In some embodiments of any of the methods provided herein, at the time of the administration of the T cell therapy the subject had a disease or condition; at the time of the administration of the T cell therapy and at the time of the administration of the compound the subject has a disease or condition; at the time of the administration of the T cell therapy the subject had a disease or condition and at the time of the administration of the compound the disease or condition has relapsed or progressed or been deemed non-responsive to said compound in the subject following the administration of the T cell therapy.

In some embodiments of any of the methods provided herein, the exhaustion phenotype, with reference to a T cell or population of T cells, includes an increase in the level or degree of surface expression on the T cell or T cells, or in the percentage of T said population of T cells exhibiting surface expression, of one or more exhaustion marker, optionally 2, 3, 4, 5 or 6 exhaustion markers, compared to a reference T cell population under the same conditions. In other embodiments, the exhaustion phenotype, with reference to a T cell or population of T cells, includes a decrease in the level or degree of an activity exhibited by said T cells or population of T cells upon exposure to an antigen or antigen receptor-specific agent, compared to a reference T cell population, under the same conditions.

In some embodiments of any of the methods provided herein, the increase in the level, degree or percentage is by greater than at or about 1.2-fold, at or about 1.5-fold, at or about 2.0-fold, at or about 3-fold, at or about 4-fold, at or about 5-fold, at or about 6-fold, at or about 7-fold, at or about 8-fold, at or about 9-fold, at or about 10-fold or more. In some embodiments, the decrease in the level, degree or percentage is by greater than at or about 1.2-fold, at or about 1.5-fold, at or about 2.0-fold, at or about 3-fold, at or about 4-fold, at or about 5-fold, at or about 6-fold, at or about 7-fold, at or about 8-fold, at or about 9-fold, at or about 10-fold or more.

In some embodiments of any of the methods provided herein, the reference T cell population is a population of T cells known to have a non-exhausted phenotype, is a population of naïve T cells, is a population of central memory T cells, or is a population of stem central memory T cells, optionally from the same subject, or of the same species as the subject, from which the T cell or T cells having the exhausted phenotype are derived. In some embodiments, the reference T cell population (a) is a subject-matched population including bulk T cells isolated from the blood of the subject from which the T cell or T cells having the exhausted phenotype is derived, optionally wherein the bulk T cells do not express the recombinant receptor and/or (b) is obtained from the subject from which the T cell or T cells having the exhausted phenotype is derived, prior to receiving administration of a dose of T cells expressing the recombinant receptor. In other embodiments, the reference T cell population is a composition including a sample of the T cell therapy, or pharmaceutical composition including T cells expressing the recombinant receptor, prior to its administration to the subject, optionally wherein the composition is a cryopreserved sample.

In some embodiments of any of the methods provided herein, one or more of the one or more exhaustion marker is an inhibitory receptor. In some embodiments, one or more of the one or more exhaustion marker is selected from among PD-1, CTLA-4, TIM-3, LAG-3, BTLA, 2B4, CD160, CD39, VISTA, and TIGIT. In some embodiments, the activity or is one or more of proliferation, cytotoxicity or production of one or a combination of inflammatory cytokines, optionally wherein the one or a combination of cytokines is selected from IL-2, IFN-gamma and TNF-alpha. In some embodiments, the exposure to said antigen or antigen receptor-specific agent includes incubation with the antigen or antigen receptor-specific agent, optionally an agent that binds the recombinant receptor, wherein said antigen is optionally the target antigen.

In some embodiments of any of the methods provided herein, the antigen or antigen receptor-specific agent includes antigen-expressing target cells, optionally cells of said disease, disorder or condition. In some embodiments, the target antigen is associated with, specific to, and/or expressed on a cell or tissue of a disease, disorder or condition. In certain embodiments, the target antigen is a tumor antigen. In some embodiments, the target antigen is selected from among αvβ6 integrin (avb6 integrin), B cell maturation antigen (BCMA), BAFF-R, B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, CS-1, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, TACI, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In some embodiments of any of the methods provided herein, the disease or condition is a B cell malignancy or a B cell-derived malignancy. In some embodiments, the target antigen is CD20, CD19, CD22, ROR1, CD45, CD21, CD5, CD33, Igkappa, Iglambda, CD79a, CD79b or CD30. In certain embodiments, the target antigen is CD19. In some embodiments of any of the methods provided herein, the disease or condition is a multiple myeloma. In some embodiments, the target antigen is BCMA, G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI or FcRH5. In certain embodiments, the target antigen is BCMA.

In some embodiments of any of the methods provided herein, the biological sample is a blood sample. In some embodiments, the biological sample is a tumor sample, optionally a tumor biopsy sample.

Provided herein are methods of treatment involving (a) administering a T cell therapy to a subject having a cancer, said T cell therapy including a dose of T cells expressing a recombinant antigen receptor that binds to a target antigen; and (b) administering to the subject an immune modulatory compound selected from: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination and/or depletion and/or degradation of Ikaros (IKZF1) and/or Aiolos (IKZF3), whereby, following said administration of said therapy and said compound, a factor indicative of expansion or activity of T cells expressing the recombinant receptor and a factor indicative of durability of response are increased as compared to a reference method, wherein: the reference method involving the administering in (a), alone, or the administration in (a) without the administration of the immune modulatory compound; the factor indicative of expansion or activity involving (i) a measure of the maximum number of T cells observed in the blood or cancer of the subject following said administration, (ii) the number of days elapsed between said administration and reaching of said maximum number of T cells in the blood or cancer of the subject, or (iii) the area under the curve (AUC) of CAR-expressing cells over time, (iv) the degree of response in the subject.

In some embodiments of any of the methods provided herein, the measure of durability of response is the time of progression free survival, survival, or duration of best response. In some embodiments, the reference method involves administration of IL-2.

Provided herein are methods of treatment involving (a) administering a T cell therapy to a subject having a cancer, said T cell therapy including a dose of T cells expressing a recombinant antigen receptor that binds to a target antigen; and (b) administering to the subject an immune modulatory compound selected from: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination and/or depletion and/or degradation of Ikaros (IKZF1) and/or Aiolos (IKZF3), at an amount, duration and/or frequency effective to: (1) effect an increase in antigen-specific or antigen receptor-driven activity of naïve or non-exhausted T cells in the subject, which optionally include T cells expressing said recombinant receptor, following exposure of the T cells to antigen or to an antigen receptor-specific agent as compared to the absence of said administration of said compound; or (2) prevent, inhibit or delay the onset of an exhaustion phenotype, in naïve or non-exhausted T cells T cells in the subject, which optionally include T cells expressing said recombinant receptor, following exposure of the T cells to antigen or to an antigen receptor-specific agent, as compared to the absence of said administration of said compound; or (3) reverse an exhaustion phenotype in exhausted T cells, optionally including T cells expressing said recombinant receptor, in the subject, as compared to the absence of said administration of said subject.

In some embodiments of any of the methods provided herein, the amount, duration and/or frequency is effective (i) to effect said increase in antigen-specific or antigen receptor-driven activity and (ii) to prevent, inhibit or delay said onset of exhaustion phenotype and/or to reverse said exhaustion phenotype. In some embodiments, the amount, duration and/or frequency is effective (i) to effect said increase in antigen-specific or antigen receptor-driven activity and (ii) to prevent, inhibit or delay said onset of exhaustion phenotype. In other embodiments, the amount, duration and/or frequency is effective (i) to effect said increase in antigen-specific or antigen receptor-driven activity and (ii) to prevent, inhibit or delay said onset of exhaustion phenotype and to reverse said exhaustion phenotype.

Provided herein are methods of treatment involving (a) administering a T cell therapy to a subject having a cancer, said T cell therapy including a dose of T cells expressing a recombinant antigen receptor that binds to a target antigen; and (b) administering to the subject an immune modulatory compound selected from: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination and/or depletion and/or degradation of Ikaros (IKZF1) and/or Aiolos (IKZF3), at an amount, duration and/or frequency effective to: (1) effect an increase in antigen-specific or antigen receptor-driven activity of naïve or non-exhausted T cells in the subject, which optionally include T cells expressing said recombinant receptor, following exposure of the T cells to antigen or to an antigen receptor-specific agent as compared to the absence of said administration of said compound; or (2) prevent, inhibit or delay the onset of an exhaustion phenotype, in naïve or non-exhausted T cells T cells in the subject, which optionally include T cells expressing said recombinant receptor, following exposure of the T cells to antigen or to an antigen receptor-specific agent, as compared to the absence of said administration of said compound; or (3) reverse an exhaustion phenotype in exhausted T cells, optionally including T cells expressing said recombinant receptor, in the subject, as compared to the absence of said administration of said subject.

In some embodiments of any of the methods provided herein, the amount, duration and/or frequency is effective (i) to effect said increase in antigen-specific or antigen receptor-driven activity and (ii) to prevent, inhibit or delay said onset of exhaustion phenotype and/or to reverse said exhaustion phenotype. In some embodiments, the amount, duration and/or frequency is effective (i) to effect said increase in antigen-specific or antigen receptor-driven activity and (ii) to prevent, inhibit or delay said onset of exhaustion phenotype. In other embodiments, the amount, duration and/or frequency is effective (i) to effect said increase in antigen-specific or antigen receptor-driven activity and (ii) to prevent, inhibit or delay said onset of exhaustion phenotype and to reverse said exhaustion phenotype.

In some embodiments of any of the methods provided herein, the immunomodulatory compound is administered in an effective amount of from or from about 1 mg to 50 mg per day it is administered, from or from about 1 mg to 25 mg per day it is administered, from or from about 1 mg to 10 mg per day it is administered, from or from about 1 mg to 5 mg per day it is administered, from or from about 5 mg to 50 mg per day it is administered, from or from about 5 mg to 25 mg per day it is administered, from or from about 5 mg to 10 mg per day it is administered. In some embodiments, the administration of the compound is carried out in a cycling regimen involving administration of an effective amount of the compound (i) daily for a period of more than one week, (ii) per day for no more than 6 days per week for a period of more than one week, (ii) per day for no more than 5 days per week for a period of more than one week; or per day for no more than 4 days per week for a period of more than one week. In certain embodiments, the administration of the compound is carried out in a cycling regimen involving administration of an effective amount of the compound per day for no more than 5 days per week for a period of more than one week.

In some embodiments of any of the methods provided herein, the compound depletes or degrades Ikaros (IKZF1).

In some embodiments of any of the methods provided herein, the compound is a compound of the following structure:

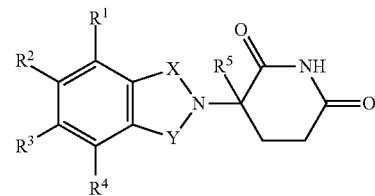

wherein
one of X and Y is —C(O)— and the other of X and Y is —C(O)— or —CH$_2$—;
(1) each of $R^1$, $R^2$, $R^3$, and $R^4$ are independently halo, alkyl of 1 to 4 carbon atoms, or alkoxy or 1 to 4 carbon atoms, or
(2) one of $R^1$, $R^3$, $R^4$, and $R^5$ is —NHR$^a$ and the remaining of $R^1$, $R^2$, $R^3$, and $R^4$ is are hydrogen, wherein $R^a$ is hydrogen or alkyl of 1 to 8 carbon atoms;
$R^5$ is hydrogen or alkyl of 1 to 8 carbon atoms, benzyl, or halo;
provided that $R^5$ is other than hydrogen if X and Y are —C(O)— and (i) each of $R^1$, $R^2$, $R^3$, and $R^4$ is fluoro; or (ii) one of $R^1$, $R^2$, $R^3$, and $R^4$ is amino;
or a pharmaceutically acceptable salt thereof.

In some embodiments of any of the methods provided herein, the compound is a compound of the following structure:

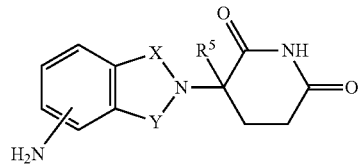

wherein one of X and Y is —C(O)— and the other of X and Y is —C(O)— or —CH₂—, and R⁵ is hydrogen or lower alkyl, or a pharmaceutically acceptable salt thereof. In some embodiments, the compound that is or includes 3-(4-amino-1-oxo-1,3-dihydro-2H-isoindol-2-yl)piperidine-2,6-dione having the following structure:

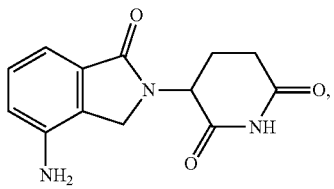

or an enantiomer or mixture of enantiomers thereof, or a pharmaceutically acceptable salt, solvate, hydrate, co-crystal, clathrate, or polymorph thereof. In some embodiments, the compound is 3-(4-amino-1-oxo-1,3-dihydro-2H-isoindol-2-yl)piperidine-2,6-dione.

In some embodiments, the compound is a compound that is or includes 3-(5-amino-2-methyl-4-oxo-4H-quinazolin-3-yl)-piperidine-2,6-dione having the following structure:

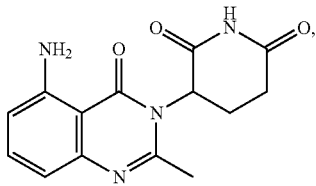 [SMILES: Cc1nc2cccc(N)c2c(=O)n1C1CCC(=O)NC1=O]

or an enantiomer or mixture of enantiomers thereof, or a pharmaceutically acceptable salt, solvate, hydrate, co-crystal, clathrate, or polymorph thereof (also referred to as Compound 1). In some embodiments, the compound is 3-(5-amino-2-methyl-4-oxo-4H-quinazolin-3-yl)-piperidine-2,6-dione.

In some embodiments of any of the methods provided herein, the immunomodulatory compound is administered in an effective amount of from or from about 1 mg to 50 mg per day, from or from about 1 mg to 25 mg per day, from or from about 1 mg to 10 mg per day, from or from about 1 mg to 5 mg per day, from or from about 5 mg to 50 mg per day, from or from about 5 mg to 25 mg per day, from or from about 5 mg to 10 mg per day, optionally wherein the administration is daily for a duration in a cycling regimen.

In some embodiments of any of the methods provided herein, the compound is a compound of the following structure:

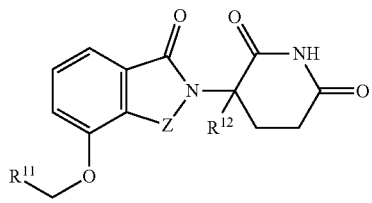

or a pharmaceutically acceptable salt, solvate or stereoisomer thereof, wherein:

Z is C=O or CH₂;
R¹¹ is —Z¹—R¹³;
R¹² is H or (C₁-C₆)alkyl;
Z¹ is 6 to 10 membered aryl, heteroaryl, or heterocycle, each of which may be optionally substituted with one or more halogen; or a bond;
R¹³ is —(CH₂)ₙ-aryl, —O—(CH₂)ₙ-aryl, or —(CH₂)ₙ—O-aryl, wherein the aryl is optionally substituted with one or more: (C₁-C₆)alkyl; itself optionally substituted with one or more halogen; (C₁-C₆)alkoxy, itself substituted with one or more halogen; oxo; amino; carboxyl; cyano; hydroxyl; halogen; deuterium; 6 to 10 membered aryl or heteroaryl, optionally substituted with one or more (C₁-C₆)alkyl, (C₁-C₆)alkoxy, or halogen; —CONH₂; or —COO—(C₁-C₆) alkyl, wherein the alkyl may be optionally substituted with one or more halogen; —(CH₂)ₙ-heterocycle, —O—(CH₂)ₙ-heterocycle or —(CH₂)ₙ—O-heterocycle, wherein the heterocycle is optionally substituted with one or more: (C₁-C₆) alkyl, itself substituted with one or more halogen; (C₁-C₆)alkoxy, itself substituted with one or more halogen; oxo; amino; carboxyl; cyano; hydroxyl; halogen; deuterium; 6 to 10 membered aryl or heteroaryl, optionally substituted with one or more (C₁-C₆)alkyl, (C₁-C₆)alkoxy or halogen; —CONH₂; or —COO—(C₁-C₆)alkyl, wherein the alkyl may be optionally substituted with one or more halogen; or —(CH₂)ₙ-heteroaryl, —O—(CH₂)ₙ-heteroaryl or —(CH₂)ₙ—O-heteroaryl, wherein the heteroaryl is optionally substituted with one or more: (C₁-C₆)alkyl, itself optionally substituted with one or more halogen; (C₁-C₆) alkoxy, itself substituted with one or more halogen; oxo; amino; carboxyl; cyano; hydroxyl; halogen; deuterium; 6 to 10 membered aryl or heteroaryl, optionally substituted with one or more (C₁-C₆)alkyl, (C₁-C₆)alkoxy or halogen; —CONH₂; or —COO—(C₁-C₆)alkyl, wherein the alkyl may be optionally substituted with one or more halogen; and n is 0, 1, 2 or 3.

In some embodiments, the compound is or a

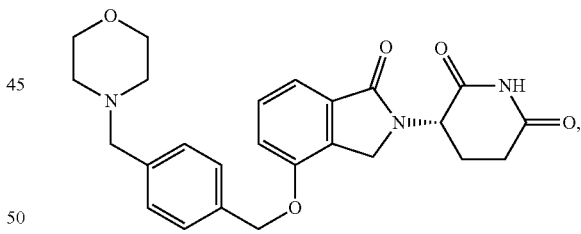

pharmaceutically acceptable salt, solvate, or stereoisomer thereof. In certain embodiments, the compound is the Form A crystal form of the hydrochloride salt of

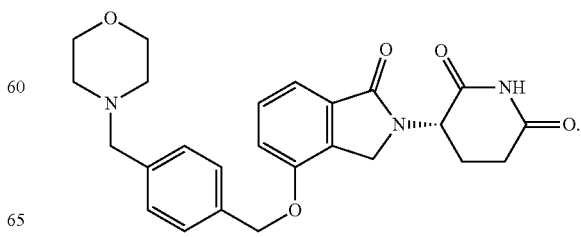

In some embodiments, the XRPD pattern of the Form A crystal form of the hydrochloride salt of

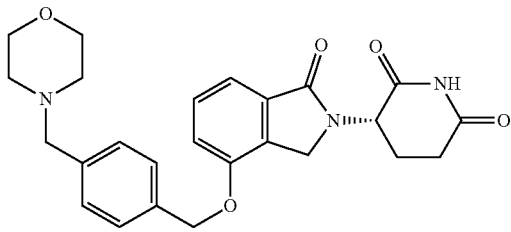 [SMILES: O=C1CC[C@H](N2Cc3c(OCc4ccc(CN5CCOCC5)cc4)cccc3C2=O)C(=O)N1]

is characterized by XRPD peaks located at 1, 2, 3, 4, 5, 6, 7, 8, 9, 10, 11, 12, 13, 14, 15, 16, 17, 18, 19, 20 or all of the following or approximately the following positions: 9.69, 12.82, 15.09, 15.94, 16.76, 17.65, 19.44, 19.80, 2230, 22.47, 22.95, 23.02, 24.29, 24.48, 24.70, 26.27, 26.77, 27.60, 29.43, 29.72, and 32.91 degrees 2Θ.

In some embodiments of any of the methods provided herein, the immunomodulatory compound is administered from or from about 0.1 mg to 1 mg per day, from or from about 0.1 mg to 0.6 mg per day, from or from about 0.1 mg to 0.3 mg, optionally wherein the administration is daily for a period of time in a cycling regimen.

Provided herein are methods of treatment involving (a) administering a T cell therapy to a subject having a cancer, said T cell therapy including a dose of T cells expressing a recombinant antigen receptor that binds to a target antigen; and (b) administering to the subject a compound that is or includes 3-(5-amino-2-methyl-4-oxo-4H-quinazolin-3-yl)-piperidine-2,6-dione having the following structure:

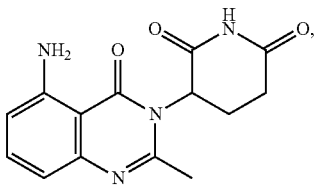 [SMILES: Cc1nc2cccc(N)c2c(=O)n1C1CCC(=O)NC1=O]

or an enantiomer or mixture of enantiomers thereof, or a pharmaceutically acceptable salt, solvate, hydrate, co-crystal, clathrate, or polymorph thereof (Compound 1), wherein the administration of the compound is carried out in a cycling regimen involving administration of an effective amount of the compound per day for no more than 5 days per week for a period of more than one week.

In some embodiments of any of the methods provided herein, the administration of the compound is initiated subsequently to initiation of administration of the T cell therapy. In some embodiments, the administration of the compound is initiated concurrently with the T cell therapy and/or is initiated within one day of, prior to or subsequently to, initiating the administration of the T cell therapy.

In some embodiments, the administration of the compound is initiated at or about or within at or about one day prior to or subsequently to initiating the administration of the T cell therapy.

Provided herein are methods of treatment involving administering to a subject having a cancer a compound that is or includes 3-(5-amino-2-methyl-4-oxo-4H-quinazolin-3-yl)-piperidine-2,6-dione having the following structure:

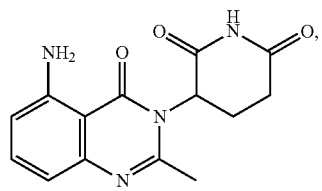 [SMILES: Cc1nc2cccc(N)c2c(=O)n1C1CCC(=O)NC1=O]

or an enantiomer or mixture of enantiomers thereof, or a pharmaceutically acceptable salt, solvate, hydrate, co-crystal, clathrate, or polymorph thereof (Compound 1), said subject having been administered, prior to the administration of the compound, a T cell therapy including a dose of genetically engineered T cells expressing a recombinant antigen receptor, wherein the administration of the compound is carried out in a cycling regimen involving administration of an effective amount of the compound per day for no more than 5 days per week for a period of more than one week. In some embodiments, the cancer is a B cell malignancy, B cell-derived malignancy, non-hematological cancer or a solid tumor.

In some embodiments of any of the methods provided herein, the target antigen is a tumor antigen, optionally wherein the target antigen is associated with, specific to, and/or expressed on a cell or tissue of the cancer. In some embodiments, the target antigen is selected from B cell maturation antigen (BCMA), αvβ6 integrin (avb6 integrin), BAFF-R, B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD5, CD19, CD20, CD21, CD22, CD23, CD24, CD30, CD38, CD44, CD44v6, CD44v7/8, CD45, CD79a, CD79b, CD123, CD133, CD138, CD171, CS-1, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), Igkappa, Iglambda, IL-22 receptor alpha (IL-22Rα), IL-13 receptor alpha 2 (IL-13Rα2), kinase insert domain receptor (kdr), L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), ROR1, survivin, TACI, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen. In certain embodiments, the B cell malignancy is a lymphoma. In some embodiments, the lymphoma is a non-Hodgkin lymphoma (NHL). In some embodiments, the NHL includes aggressive NHL, diffuse large B cell lymphoma (DLBCL), DLBCL-NOS, optionally transformed indolent; EBV-positive DLBCL-NOS; T cell/histiocyte-rich large B-cell lymphoma; primary mediastinal large B cell lymphoma (PMBCL); follicular lymphoma (FL), optionally, follicular lymphoma Grade 3B (FL3B); and/or high-grade B-cell lymphoma with MYC and BCL2 and/or BCL6 rearrangements with DLBCL histology (double/triple hit).

In some embodiments of any of the methods provided herein, the subject is or has been identified as having an Eastern Cooperative Oncology Group Performance Status (ECOG) status of less than or equal to 1.

In some embodiments of any of the methods provided herein, the target antigen is CD20, CD19, CD22, ROR1, CD45, CD21, CD5, CD33, Igkappa, Iglambda, CD79a, CD79b or CD30. In certain embodiments, the target antigen is CD19. In some embodiments, the target antigen is not CD20, CD19, CD22, ROR1, CD45, CD21, CD5, CD33, Igkappa, Iglambda, CD79a, CD79b or CD30. In some embodiments, the cancer is a multiple myeloma. In some embodiments, the target antigen is BCMA, G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI or FcRH5.

In some embodiments of any of the methods provided herein, the method further includes continuing the cycling regimen after the end of the period, if, at the end of the period, the subject exhibits a partial response (PR) or stable disease (SD). In some embodiments, the cycling regimen is continued for greater than six months if, at or about six months, the subject exhibits a partial response (PR) or stable disease (SD) after the treatment. In other embodiments, the cycling regimen is continued until the subject has achieved a complete response (CR) following the treatment or until the cancer has progressed or relapsed following remission after the treatment.

In some embodiments of any of the methods provided herein, the administration of the compound is initiated at or after peak or maximum level of the cells of the T cell therapy are detectable in the blood of the subject. In some embodiments, the administration of the compound is initiated about 14 to about 35 days after initiation of administration of the T cell therapy. In certain embodiments, the administration of the compound is initiated about 21 to about 35 days after initiation of administration of the T cell therapy. In other embodiments, the administration of the compound is initiated about 21 to about 28 days after initiation of administration of the T cell therapy. In some embodiments, the administration of the compound is initiated at or about 21 days, at or about 22 days, at or about 23 days, at or about 24 days, at or about 25 days, at or about 26 days, at or about 27 days, or at or about 28 days after initiation of administration of the T cell therapy. In certain embodiments, the administration of the compound is initiated at or about 28 days after the initiation of administration of the T cell therapy. In some embodiments of any of the methods provided herein, at the time of the initiation of the administration of the compound, the subject does not exhibit a severe toxicity following the administration of the T cell therapy.

In some embodiments of any of the methods provided herein, the severe toxicity is severe cytokine release syndrome (CRS), optionally grade 3 or higher, prolonged grade 3 or higher or grade 4 or 5 CRS; and/or the severe toxicity is severe neurotoxicity, optionally grade 3 or higher, prolonged grade 3 or higher or grade 4 or 5 neurotoxicity.

In some embodiments of any of the methods provided herein, the administration of the compound is suspended and/or the cycling regimen is modified if the subject exhibits a toxicity following the administration of the compound, optionally a hematologic toxicity. In some embodiments, the toxicity is selected from severe neutropenia, optionally febrile neutropenia, prolonged grade 3 or higher neutropenia. In some embodiments, the administration of the compound is restarted after the subject no longer exhibits the toxicity. In some embodiments, the cycling regimen is modified after the administration of the compound is restarted. In some embodiments, the modified cycling regimen involves administering a reduced amount of the compound and/or decreasing frequency of the administration of the compound. In certain embodiments, the modified cycling regimen involves administering a reduced amount of the compound. In some embodiments, the dose of the compound is reduced and the reduced amount is between at or about 1 mg and at or about 2 mg per day for no more than 5 days per week. In some embodiments, the reduced amount is at or about 1 mg or at or about 2 mg per day for no more than 5 days per week. In some embodiments, the cycling regimen is not modified after the administration of the compound is restarted. In some embodiments, the cycling regimen involves administration of no more than about 2 mg of the compound per day for no more than 5 days per week. In certain embodiments, the cycling regimen involves administration of at or about 1 mg of the compound per day for no more than 5 days a week.

In some embodiments of any of the methods provided herein, the compound is or comprises a solvate of (S)-3-[4-(4-morpholin-4-ylmethyl-benzyloxy)-1-oxo-1,3-dihydro-isoindol-2-yl]-piperidine-2,6-dione. In some embodiments, the compound is or comprises (S)-3-[4-(4-morpholin-4-ylmethyl-benzyloxy)-1-oxo-1,3-dihydro-isoindol-2-yl]-piperidine-2,6-dione.

In some embodiments of any of the methods provided herein, the compound is or includes a solvate of 3-(5-amino-2-methyl-4-oxo-4H-quinazolin-3-yl)-piperidine-2,6-dione. In some embodiments, the compound is or includes a hydrate of 3-(5-amino-2-methyl-4-oxo-4H-quinazolin-3-yl)-piperidine-2,6-dione. In some embodiments, the compound is or includes a pharmaceutically acceptable salt of 3-(5-amino-2-methyl-4-oxo-4H-quinazolin-3-yl)-piperidine-2,6-dione. In certain embodiments, the compound is or includes 3-(5-amino-2-methyl-4-oxo-4H-quinazolin-3-yl)-piperidine-2,6-dione.

In some embodiments of any of the methods provided herein, the compound is administered orally. In some embodiments, the period extends for at or about 6 months after initiation of administration of the T cell therapy if the subject has at 6 months achieved a complete response (CR). In other embodiments, the cycling regimen is continued for the duration of the period even if the subject has achieved a complete response (CR) at a time point prior to the end of the period. In some embodiments, the subject achieves a complete response (CR) during the period and prior to the end of the period.

In some embodiments of any of the methods provided herein, the method further involves continuing the cycling regimen after the end of the period, if, at the end of the period, the subject exhibits a partial response (PR) or stable disease (SD). In some embodiments any of the methods provided herein, the cycling regimen is continued for greater than six months if, at or about six months, the subject exhibits a partial response (PR) or stable disease (SD) after the treatment. In some embodiments, the cycling regimen is continued until the subject has achieved a complete response (CR) following the treatment or until the cancer has progressed or relapsed following remission after the treatment.

In some embodiments of any of the methods provided herein, the administration of the compound is initiated at or after peak or maximum level of the cells of the T cell therapy are detectable in the blood of the subject. In some embodiments of any of the methods provided herein, the administration of the compound is initiated about 14 to about 35 days after initiation of administration of the T cell therapy. In some embodiments of any of the methods provided herein, the administration of the compound is initiated about 21 to about 35 days after initiation of administration of the T cell therapy. In some embodiments of any of the methods provided herein, the administration of the compound is initiated about 21 to about 28 days after initiation of administration of the T cell therapy. In some embodiments of any of the methods provided herein, the administration of the compound is initiated at or about 21 days, at or about 22 days, at or about 23 days, at or about 24 days, at or about 25 days, at or about 26 days, at or about 27 days, or at or about 28 days after initiation of administration of the T cell therapy.

In some embodiments of any of the methods provided herein, the administration of the compound is initiated at or about 28 days after the initiation of the administration of the T cell therapy. In some embodiments of any of the methods provided herein, at the time of the initiation of the administration of the compound, the subject does not exhibit a severe toxicity following the administration of the T cell therapy. In some embodiments, the severe toxicity is severe cytokine release syndrome (CRS), optionally grade 3 or higher, prolonged grade 3 or higher or grade 4 or 5 CRS; and/or the severe toxicity is severe neurotoxicity, optionally grade 3 or higher, prolonged grade 3 or higher or grade 4 or 5 neurotoxicity.

In some embodiments of any of the methods provided herein, the administration of the compound is suspended and/or the cycling regimen is modified if the subject exhibits a toxicity following the administration of the compound, optionally a hematologic toxicity. In some embodiments, the toxicity is selected from severe neutropenia, optionally febrile neutropenia, prolonged grade 3 or higher neutropenia. In some embodiments, the administration of the compound is restarted after the subject no longer exhibits the toxicity. In some embodiments, the cycling regimen is modified after the administration of the compound is restarted. In some embodiments, the modified cycling regimen involves administering a reduced amount of the compound and/or decreasing frequency of the administration of the compound. In certain embodiments, the modified cycling regimen involves administering a reduced amount of the compound. In some embodiments, the dose of the compound is reduced and the reduced amount is between at or about 1 mg and at or about 2 mg per day for no more than 5 days per week. In certain embodiments, the reduced amount is at or about 1 mg or at or about 2 mg per day for no more than 5 days per week. In some embodiments, the cycling regimen is not modified after the administration of the compound is restarted. In some embodiments, the cycling regimen involves administration of no more than about 2 mg of the compound per day for no more than 5 days per week. In some embodiments, the cycling regimen involves administration of at or about 1 mg of the compound per day for no more than 5 days a week.

In some embodiments of any of the methods provided herein, the compound is or includes a solvate of 3-(5-amino-2-methyl-4-oxo-4H-quinazolin-3-yl)-piperidine-2,6-dione. In some embodiments of any of the methods provided herein, the compound is or includes a hydrate of 3-(5-amino-2-methyl-4-oxo-4H-quinazolin-3-yl)-piperidine-2,6-dione. In some embodiments of any of the methods provided herein, the compound is or includes a pharmaceutically acceptable salt of 3-(5-amino-2-methyl-4-oxo-4H-quinazolin-3-yl)-piperidine-2,6-dione. In some embodiments of any of the methods provided herein, the compound is or includes 3-(5-amino-2-methyl-4-oxo-4H-quinazolin-3-yl)-piperidine-2,6-dione. In some embodiments of any of the methods provided herein, the compound is administered orally.

In some embodiments of any of the methods provided herein, the administration of the compound: reverses an exhaustion phenotype in recombinant receptor-expressing T cells in the subject; prevents, inhibits or delays the onset of an exhaustion phenotype in recombinant receptor-expressing T cells in the subject; or reduces the level or degree of an exhaustion phenotype in recombinant receptor-expressing T cells in the subject; or reduces the percentage, of the total number of recombinant receptor-expressing T cells in the subject, that have an exhaustion phenotype.

In some embodiments of any of the methods provided herein, the initiation of the administration of the compound is carried out subsequently to the administration of the T cell therapy and, following administration of the compound or initiation thereof, the subject exhibits a restoration or rescue of an antigen- or tumor-specific activity or function of recombinant receptor-expressing T cells in said subject, optionally wherein said restoration, rescue, and/or initiation of administration of said compound, is at a point in time after recombinant receptor-expressing T cells in the subject or the in the blood of the subject have exhibited an exhausted phenotype.

In some embodiments of any of the methods provided herein, the administration of the compound includes administration at an amount, frequency and/or duration effective to: (a) effect an increase in antigen-specific or antigen receptor-driven activity of naïve or non-exhausted T cells in the subject, which optionally include T cells expressing said recombinant receptor, following exposure of the T cells to antigen or to an antigen receptor-specific agent as compared to the absence of said administration of said compound; or (b) prevent, inhibit or delay the onset of an exhaustion phenotype, in naïve or non-exhausted T cells T cells in the subject, which optionally include T cells expressing said recombinant receptor, following exposure of the T cells to antigen or to an antigen receptor-specific agent, as compared to the absence of said administration of said compound; or (c) reverse an exhaustion phenotype in exhausted T cells, optionally including T cells expressing said recombinant receptor, in the subject, as compared to the absence of said administration of said subject. In some embodiments, the administration of the compound includes administration at an amount, frequency and/or duration effective (i) to effect said increase in activity and (ii) to prevent, inhibit or delay said onset of said exhaustion phenotype and/or reverse said exhaustion phenotype. In some embodiments, the T cells in the subject include T cells expressing said recombinant receptor and/or said antigen is the target antigen.

In some embodiments of any of the methods provided herein, the exhaustion phenotype, with reference to a T cell or population of T cells, includes: an increase in the level or degree of surface expression on the T cell or T cells, or in the percentage of T said population of T cells exhibiting surface expression, of one or more exhaustion marker, optionally 2, 3, 4, 5 or 6 exhaustion markers, compared to a reference T cell population under the same conditions; or a decrease in the level or degree of an activity exhibited by said T cells or population of T cells upon exposure to an antigen or antigen receptor-specific agent, compared to a reference T cell population, under the same conditions. In some embodiments, the increase in the level, degree or percentage is by greater than at or about 1.2-fold, at or about 1.5-fold, at or about 2.0-fold, at or about 3-fold, at or about 4-fold, at or about 5-fold, at or about 6-fold, at or about 7-fold, at or about 8-fold, at or about 9-fold, at or about 10-fold or more. In other embodiments, the decrease in the level, degree or percentage is by greater than at or about 1.2-fold, at or about 1.5-fold, at or about 2.0-fold, at or about 3-fold, at or about 4-fold, at or about 5-fold, at or about 6-fold, at or about 7-fold, at or about 8-fold, at or about 9-fold, at or about 10-fold or more.

In some embodiments of any of the methods provided herein, the reference T cell population is a population of T cells known to have a non-exhausted phenotype, is a population of naïve T cells, is a population of central memory T cells, or is a population of stem central memory T cells, optionally from the same subject, or of the same species as the subject, from which the T cell or T cells having the exhausted phenotype are derived.

In some embodiments of any of the methods provided herein, the reference T cell population (a) is a subject-matched population including bulk T cells isolated from the blood of the subject from which the T cell or T cells having the exhaustion phenotype is derived, optionally wherein the bulk T cells do not express the recombinant receptor and/or (b) is obtained from the subject from which the T cell or T cells having the exhausted phenotype is derived, prior to receiving administration of a dose of T cells expressing the recombinant receptor. In some embodiments, the reference T cell population is a composition including a sample of the T cell therapy, or pharmaceutical composition including T cells expressing the recombinant receptor, prior to its administration to the subject, optionally wherein the composition is a cryopreserved sample.

In some embodiments of any of the methods provided herein, the one or more exhaustion marker is an inhibitory receptor. In some embodiments, the one or more exhaustion marker is selected from among PD-1, CTLA-4, TIM-3, LAG-3, BTLA, 2B4, CD160, CD39, VISTA, and TIGIT.

In some embodiments of any of the methods provided herein, the activity or is one or more of proliferation, cytotoxicity or production of one or a combination of inflammatory cytokines, optionally wherein the one or a combination of cytokines is selected from IL-2, IFN-gamma and TNF-alpha. In some embodiments, the exposure to said antigen or antigen receptor-specific agent includes incubation with the antigen or antigen receptor-specific agent, optionally an agent that binds the recombinant receptor, wherein said antigen is optionally the target antigen. In some embodiments, the antigen or antigen receptor-specific agent includes antigen-expressing target cells, optionally cells of said disease, disorder or condition. In certain embodiments, the target antigen is a human antigen.

In some embodiments of any of the methods provided herein, the subject is a human. In some embodiments of any of the methods provided herein, the recombinant antigen receptor is a chimeric antigen receptor that specifically binds the target antigen. In some embodiments, the chimeric antigen receptor (CAR) includes an extracellular antigen-recognition domain that specifically binds to a target antigen and an intracellular signaling domain including an ITAM. In some embodiments, the intracellular signaling domain includes a signaling domain of a CD3-zeta (CD3) chain, optionally a human CD3-zeta chain. In some embodiments, the chimeric antigen receptor (CAR) further includes a costimulatory signaling region. In other embodiments, the costimulatory signaling region includes a signaling domain of CD28 or 4-1BB, optionally human CD28 or human 4-1BB. In some embodiments, the costimulatory domain is or includes a signaling domain of human 4-1BB.

In some embodiments of any of the methods provided herein, the CAR includes an scFv specific for the target antigen; a transmembrane domain; a cytoplasmic signaling domain derived from a costimulatory molecule, which optionally is or includes a 4-1BB, optionally human 4-1BB; and a cytoplasmic signaling domain derived from a primary signaling ITAM-containing molecule, which optionally is or includes a CD3zeta signaling domain, optionally a human CD3zeta signaling domain; and optionally wherein the CAR further includes a spacer between the transmembrane domain and the scFv; the CAR includes, in order, an scFv specific for the target antigen; a transmembrane domain; a cytoplasmic signaling domain derived from a costimulatory molecule, which optionally is or includes a 4-1BB signaling domain, optionally a human 4-1BB signaling domain; and a cytoplasmic signaling domain derived from a primary signaling ITAM-containing molecule, which optionally is a CD3zeta signaling domain, optionally human CD3zeta signaling domain; or the CAR includes, in order, an scFv specific for the target antigen; a spacer; a transmembrane domain, a cytoplasmic signaling domain derived from a costimulatory molecule, which optionally is a 4-1BB signaling domain, and a cytoplasmic signaling domain derived from a primary signaling ITAM-containing molecule, which optionally is or includes a CD3zeta signaling domain.

In some embodiments of any of the methods provided herein, the dose of genetically engineered T cells includes from or from about $1 \times 10^5$ to $5 \times 10^8$ total CAR-expressing T cells, $1 \times 10^6$ to $2.5 \times 10^8$ total CAR-expressing T cells, $5 \times 10^6$ to $1 \times 10^8$ total CAR-expressing T cells, $1 \times 10^7$ to $2.5 \times 10^8$ total CAR-expressing T cells, $5 \times 10^7$ to $1 \times 10^8$ total CAR-expressing T cells, each inclusive. In some embodiments of any of the methods provided herein, the dose of genetically engineered T cells includes at least or at least about $1 \times 10^5$ CAR-expressing cells, at least or at least about $2.5 \times 10^5$ CAR-expressing cells, at least or at least about $5 \times 10^5$ CAR-expressing cells, at least or at least about $1 \times 10^6$ CAR-expressing cells, at least or at least about $2.5 \times 10^6$ CAR-expressing cells, at least or at least about $5 \times 10^6$ CAR-expressing cells, at least or at least about $1 \times 10^7$ CAR-expressing cells, at least or at least about $2.5 \times 10^7$ CAR-expressing cells, at least or at least about $5 \times 10^7$ CAR-expressing cells, at least or at least about $1 \times 10^8$ CAR-expressing cells, at least or at least about $2.5 \times 10^8$ CAR-expressing cells, or at least or at least about $5 \times 10^8$ CAR-expressing cells. In certain embodiments, the dose of genetically engineered T cells includes at or about $5 \times 10^7$ total CAR-expressing T cells. In other embodiments, the dose of genetically engineered T cells includes at or about 1×10⁸ CAR-expressing cells.

In some embodiments of any of the methods provided herein, the dose of cells is administered parenterally, optionally intravenously.

In some embodiments of any of the methods provided herein, the T cells are primary T cells obtained from a subject. In some embodiments, the T cells are autologous to the subject. In other embodiments, the T cells are allogeneic to the subject.

In some embodiments of any of the methods provided herein, the dose of genetically engineered T cells includes CD4+ T cells expressing the CAR and CD8+ T cells expressing the CAR and the administration of the dose includes administering a plurality of separate compositions, said plurality of separate compositions including a first composition including one of the CD4+ T cells and the CD8+ T cells and the second composition including the other of the CD4+ T cells or the CD8+ T cells.

In some embodiments of any of the methods provided herein, prior to the administration, the subject has been preconditioned with a lymphodepleting therapy including the administration of fludarabine and/or cyclophosphamide. In some embodiments of any of the methods provided herein, the method further involves, immediately prior to the administration, administering a lymphodepleting therapy to the subject including the administration of fludarabine and/or cyclophosphamide. In some embodiments, the lymphodepleting therapy includes administration of cyclophosphamide at about 200-400 mg/m², optionally at or about 300 mg/m², inclusive, and/or fludarabine at about 20-40 mg/m², optionally 30 mg/m², daily for 2-4 days, optionally for 3 days, or wherein the lymphodepleting therapy includes administration of cyclophosphamide at about 500 mg/m². In some embodiments, the lymphodepleting therapy includes administration of cyclophosphamide at or about 300 mg/m² and fludarabine at about 30 mg/m² daily for 3 days; and/or the lymphodepleting therapy includes administration of cyclophosphamide at or about 500 mg/m² and fludarabine at about 30 mg/m² daily for 3 days.

In some embodiments of any of the methods provided herein, at least 35%, at least 40% or at least 50% of subjects treated according to the method achieve a complete response (CR) that is durable, or is durable in at least 60, 70, 80, 90, or 95% of subjects achieving the CR, for at or greater than 6 months or at or greater than 9 months; and/or wherein at least 60, 70, 80, 90, or 95% of subjects achieving a CR by six months remain in response, remain in CR, and/or survive or survive without progression, for greater at or greater than 3 months and/or at or greater than 6 months and/or at greater than nine months; and/or at least 50%, at least 60% or at least 70% of the subjects treated according to the method achieve objective response (OR) optionally wherein the OR is durable, or is durable in at least 60, 70, 80, 90, or 95% of subjects achieving the OR, for at or greater than 6 months or at or greater than 9 months; and/or wherein at least 60, 70, 80, 90, or 95% of subjects achieving an OR by six months remain in response or surviving for greater at or greater than 3 months and/or at or greater than 6 months.

Also provided herein are kits that include (a) a T cell therapy including a dose of T cells expressing a recombinant antigen receptor that binds to a target antigen; and (b) an immune modulatory compound selected from: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination and/or depletion and/or degradation of Ikaros (IKZF1) and/or Aiolos (IKZF3); and (c) instructions for administering the compound and/or the T cell therapy according any of the methods provided herein.

BRIEF DESCRIPTION OF THE DRAWINGS

indicates insufficient cells for re-plating in the assay.

FIG. 12A shows the number of CD3⁺/CAR⁺ T cells in peripheral blood measured at certain time points post-infusion for subjects grouped by best overall response.

FIG. 12B shows CD3⁺/CAR⁺ T cells in peripheral blood measured at certain time points post-infusion for subjects who achieved a response, grouped by continued response at 3 months.

FIGS. 12C-2D show CD4⁺/CAR⁺ T and CD8⁺/CAR⁺ T cell levels in peripheral blood measured at certain time points post-infusion for subjects who achieved a response, grouped by continued response at 3 months.

FIG. 18A shows the cytolytic activity of the anti-CD19 CAR+ T cells from two donor cells (pt 1 and pt 2) restimulated with K562-CD19 cells (labeled with NucLight Red (NLR)) and in the presence of 1 μM lenalidomide or 50 nM or 500 nM of the alternative compound targeting a kinase.

FIG. 18B shows the percent target cell killing of the anti-CD19 CAR+ T cells from two donor cells (1 or 2) restimulated with K562-CD19 cells compared to the vehicle-only control (set at 100%).

FIG. 19B and FIG. 19C show flow cytometry histograms for CD25 in CD4+ T cells (left panel) or CD8+ T cells (right panel) present in an anti-BCMA CAR+ T cell composition after incubation with beads (200 μg/mL BCMA-conjugated bead composition) at a ratio of 1:1 T cells to beads or immobilized anti-CD3, respectively, in the presence or absence of lenalidomide.

FIG. 21G shows histogram plots of CTV staining of CD4+ T cells or CD8+ T cells in an anti-BCMA CAR+ T cell composition after incubation for 4 or 7 days with BCMA-conjugated beads in the presence of 5 μM lenalidomide or absence of lenalidomide (vehicle).

FIG. 23A and FIG. 23B show the cytolytic activity of the anti-BCMA CAR+ T cells at each of the time points for two different donors.

FIG. 26A) and chromatin accessibility (based on ATAC-seq results; FIG. 26B), in anti-BCMA CAR-expressing T cells generated from 4 different donors (Donors 1-4), stimulated with BCMA-conjugated beads, for 24 hours (24 hr+stim) or 7 days (d7+stim), or cultured without stimulation for 24 hours (24 hr), in the presence or absence of lenalidomide.

FIGS. 27A and 27B show volcano plots depicting statistical significance of expression (log 10 of adjusted p-value) with the log 2 fold-change in gene expression, including genes or peaks that show increased (right side) or decreased (left side) expression, in CAR+ T cells stimulated with BCMA-conjugated beads, for 24 hours (24 hr+stim, FIG. 27A) or 7 days (d7+stim, FIG. 27B), in the presence or absence of lenalidomide. The tables indicate the number of genes or peaks that showed statistically significant increase (up) or decrease (down) in expression.

FIG. 30 shows motif enrichment analysis, enrichment log p-value, prevalence and transcription factors predicted to bind the motifs for peaks with increased accessibility in the presence of lenalidomide in day 7 cultures.

(FIG. 39A) Percentage change in cell doublings at day 24 of serial stimulation in the presence of 10 nM, 100 nM or 500 nM Compound 1 was shown in FIG. 39B. Data represents mean+/−S.E.M of triplicated treatments from 3 donors. Each arrow represents a re-stimulation time point.

(FIG. 40A) Percentage change in cell doublings at day 24 of serial stimulation in the presence of 100 nM or 1000 nM lenalidomide was shown in FIG. 40B. Data represents mean+/−S.E.M of triplicated treatments from three donors. Each arrow represents a re-stimulation time point.

FIGS. 43A-43M show analysis of cytolytic function and gene expression analysis of anti-CD19 CAR-expressing T cells in the presence of Compound 1 or a vehicle control, following long-term stimulation. Anti-CD19 CAR-expressing T cells were subjected to chronic stimulation conditions by being incubated with plate-bound anti-idiotypic (anti-ID) antibody for a period of 5 or 6 days. After the 5 or 6-day culture period, the anti-CD19 CAR-expressing T cells were removed from culture and incubated with CD19+ tumor spheroids in the presence of Compound 1, at concentrations ranging from 0.001 μM to 10 μM, or a vehicle control, for up to 10 days. Freshly thawed anti-CD19 CAR-expressing T cells that had not been subjected to chronic stimulatory conditions were incubated with the tumor spheroids in parallel as controls. Cells were assessed at various times for cytolytic function (FIGS. 43A, 43E, and 43F), tumor volume reduction (FIGS. 43B, 43C right panel, 43D, 43F, 43G and 43 H), CAR T cell number (FIG. 43I), and cytokine production (FIG. 43C left panel and 43 J). FIG. 43K shows plots of log 2 fold change (log 2FC) of gene expression in anti-CD19 CAR-T cells after both the long-term stimulation and subsequent incubation with Compound 1 relative to chronic stimulation control (y-axis), versus gene expression in anti-CD19 CAR+ T cells that that were chronically stimulated and compared to those had not been stimulated in the long-term stimulation assay (x-axis). FIG. 43L shows plot of log$_2$ fold change with Compound 1(y-axis) versus without Compound 1 (x-axis). FIG. 43M shows KEGG pathway analysis of CAR-T RNA-seq data.

FIG. 44A shows plots of log$_2$ fold change (log 2FC) of gene expression in anti-CD19 CAR-expressing T cells after the long-term stimulation, in the presence of Compound 1 or IL-2 relative to chronic stimulation control (y-axis) versus gene expression in anti-CD19 CAR-expressing T cells that were chronically stimulated and compared to those that had not been stimulated in the long-term stimulation assay (x-axis). FIG. 44B shows a plot of log$_2$ fold change with Compound 1 (y-axis) versus without Compound 1 (x-axis). In FIGS. 44A and 44B, genes with increased or decreased expression are identified. FIG. 44C shows gene set enrichment scores for genes showing increased or decreased expression in the presence of Compound 1. FIG. 44D shows KEGG pathway analysis of CAR-T RNA-seq data. Cells were assessed at various times for cytolytic function (FIG. 44E) and cytokine production (FIG. 44F).

FIG. 48C shows the size of Granta-519 tumor spheroids at various times following co-culture with 1 µM Compound 1 (left panel) or 0.001 µM or 0.01 µM of Compound 2 (right panel). FIG. 48D shows the average tumor volume of the Granta-519 tumor spheroids after 9 days in the presence of Compound 2.

FIG. 50B shows the cytokine levels of IFNγ, IL-2 and TNFalpha measured from the supernatant of the chronically stimulated anti-CD19 CAR T cells that had been co-cultured for 5 days with CD19 tumor spheroids and treated with Compound 1 or Compound 2.

FIG. 51A shows the cytolytic activity, as measured by tumor cell number, of RL CD19+ tumor cells cocultured with anti-CD19 CAR T cells in the presence of Compound 2 (0.001 µM, 0.01 µM or 0.1 µM). FIG. 51B shows

FIG. 53A shows cytolytic activity of anti-BCMA CAR T cells from three donors during long term stimulation in the presence of lenalidomide (1000 nM) or Compound 2 (1 nM or 10 nM). FIGS. 53B-D shows the production of IFN-gamma (FIG. 53B), IL-2 (FIG. 53C), and TNF-alpha (FIG. 53D) in anti-BCMA CAR T cells from three donors during long term stimulation in the presence of lenalidomide (1000 nM) or Compound 2 (1 nM or 10 nM).

FIG. 55 shows cytolytic activity of anti-BCMA CAR T cells from three donors during chronic stimulation for 7 days with BCMA-conjugated beads in the presence of IMiD/CELMoD resistant cell line DF-15R and Compound 2 (1 nM or 10 nM). FIGS. 55B-D shows the production of IFN-gamma (FIG. 55B), IL-2 (FIG. 55C), and TNF-alpha (FIG. 55D) in anti-BCMA CAR T cells from three donors during chronic stimulation in the presence of IMiD/CELMoD resistant cell line DF-15R and Compound 2 (1 nM or 10 nM).

DETAILED DESCRIPTION

Figure 1A:
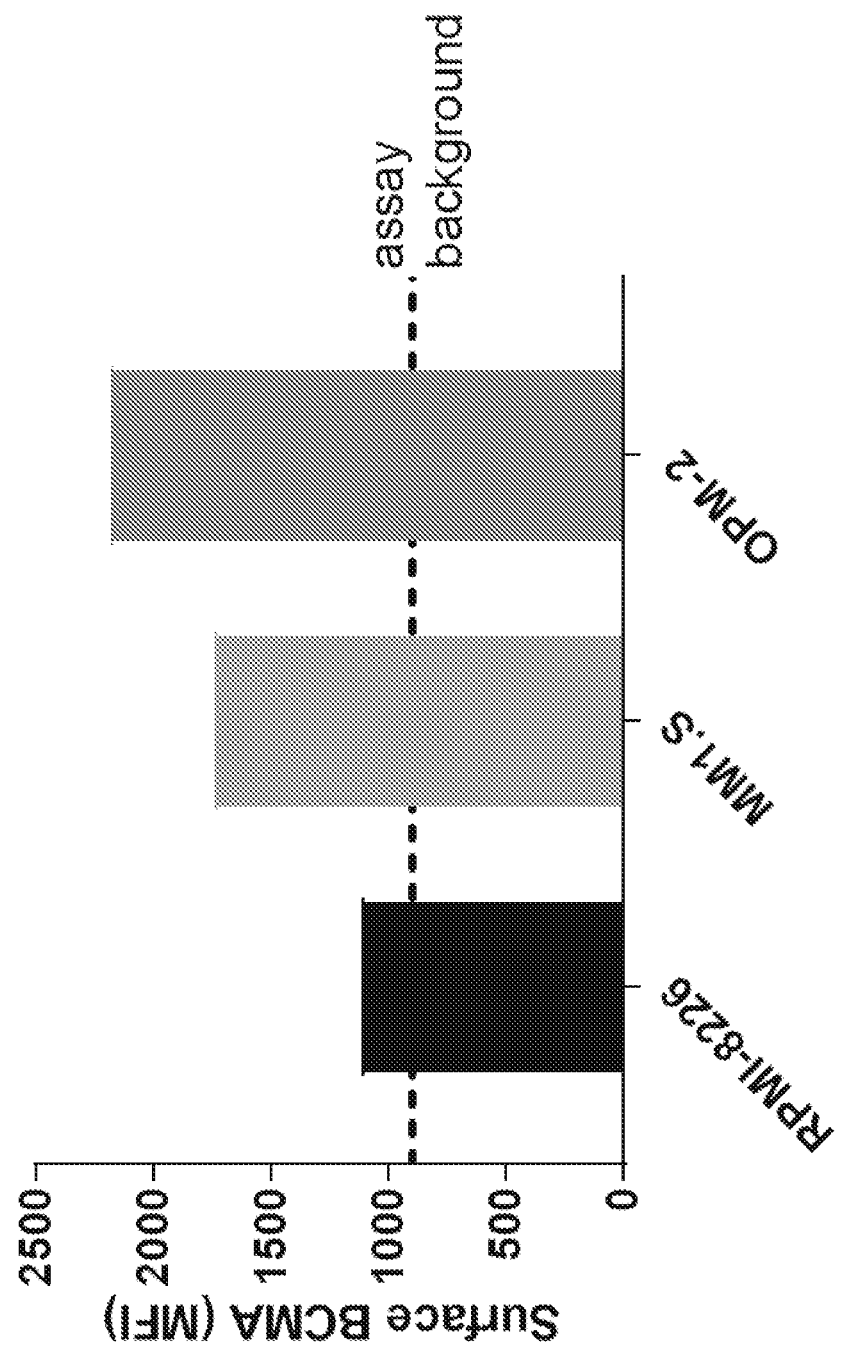
FIG. 1A shows the surface BCMA expression of multiple myeloma cells lines (RPMI-8226, MM1.S, and OPM-2). The dotted line indicates background and BCMA-negative cell lines were stained with anti-BCMA antibody. MFI, median fluorescence intensity.

Provided herein are combination therapies involving administration of an immunotherapy involving T cell function or activity, such as a T cell therapy, and an immunomodulatory compound, such as a structural or functional analog or derivative of thalidomide and/or an inhibitor of E3-ubiquitin ligase. In some aspects, the provided methods enhance or modulate proliferation and/or activity of T cell activity associated with administration of an immunotherapy or immunotherapeutic agent, such as a composition including cells for adoptive cell therapy, e.g., such as a T cell therapy (e.g. CAR-expressing T cells). In some embodiments, the combination therapy involves administration of an immunomodulatory compound, such as a structural or functional analog of thalidomide and/or an inhibitor of E3-ubiquitin ligase, and administration of the T cell therapy, such as a composition including cells for adoptive cell therapy, e.g., such as a T cell therapy (e.g. CAR-expressing T cells).

T cell-based therapies, such as adoptive T cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. The engineered expression of recombinant receptors, such as chimeric antigen receptors (CARs), on the surface of T cells enables the redirection of T-cell specificity. In clinical studies, CAR-T cells, for example anti-CD19 CAR-T cells, have produced durable, complete responses in both leukemia and lymphoma patients (Porter et al. (2015) Sci Transl Med., 7:303ra139; Kochenderfer (2015) J. Clin. Oncol., 33: 540-9; Lee et al. (2015) Lancet, 385:517-28; Maude et al. (2014) N Engl J Med, 371:1507-17).

In certain contexts, available approaches to adoptive cell therapy may not always be entirely satisfactory. For example, in certain cases, although CAR T cell persistence can be detected in many subjects with lymphoma, fewer complete responses (CRs) have been observed in subjects with NHL compared to subjects with ALL. More specifically, while higher overall response rates of up to 80% (CR rate 47% to 60%) have been reported after CAR T cell infusion, responses in some are transient and subjects have been shown to relapse in the presence of persistent CAR T cells (Neelapu, 58th Annual Meeting of the American Society of Hematology (ASH): 2016; San Diego, CA, USA. Abstract No. LBA-6.2016; Abramson, Blood. 2016 Dec. 1; 128(22):4192). Another study reported a long term CR rate of 40% (Schuster, Ann Hematol. 2016 October; 95(11): 1805-10).

In some aspects, an explanation for this is the immunological exhaustion of circulating CAR-expressing T cells and/or changes in T lymphocyte populations. In some contexts, optimal efficacy can depend on the ability of the administered cells to recognize and bind to a target, e.g., target antigen, to traffic, localize to and successfully enter appropriate sites within the subject, tumors, and environments thereof. In some contexts, optimal efficacy can depend on the ability of the administered cells to become activated, expand, to exert various effector functions, including cytotoxic killing and secretion of various factors such as cytokines, to persist, including long-term, to differentiate, transition or engage in reprogramming into certain phenotypic states (such as long-lived memory, less-differentiated, and effector states), to avoid or reduce immunosuppressive conditions in the local microenvironment of a disease, to provide effective and robust recall responses following clearance and re-exposure to target ligand or antigen, and avoid or reduce exhaustion, anergy, peripheral tolerance, terminal differentiation, and/or differentiation into a suppressive state.

In some embodiments, the exposure and persistence of engineered cells is reduced or declines after administration to the subject. Yet, observations indicate that, in some cases, increased exposure of the subject to administered cells expressing the recombinant receptors (e.g., increased number of cells or duration over time) may improve efficacy and therapeutic outcomes in adoptive cell therapy. Preliminary analysis conducted following the administration of different CD19-targeting CAR-expressing T cells to subjects with various CD19-expressing cancers in multiple clinical trials revealed a correlation between greater and/or longer degree of exposure to the CAR-expressing cells and treatment outcomes. Such outcomes included patient survival and remission, even in individuals with severe or significant tumor burden.

In some embodiments, following long-term stimulation or exposure to antigen and/or exposure under conditions in the tumor microenviroment, T cells can over time become hypofunctional and/or exhibit features associated with exhausted state. In some aspects, this reduces the persistence and efficacy of the T cells against antigen and limits their ability to be effective. There is a need for methods to improve the efficacy and function of CAR T cells, particularly to minimize, reduce, prevent or reverse hypofunctional or exhaustive states.

The provided methods involve administering T cell therapy, such as a composition including cells for adoptive cell therapy, e.g., such as a T cell therapy (e.g. CAR-expressing T cells), and an immunomodulatory compound, such as a structural or functional analog or derivative of thalidomide and/or an inhibitor of E3 ubiquitin ligase, e.g. lenalidomide, Compound 1 or Compound 2. In some embodiments, the immunomodulatory compound for use in the provided methods and uses is an E3 ligase modulatory compound that is an inhibitor of E3 ubiquitin ligase. In some embodiments, the immunomodulatory compound for use in the provided methods and uses is lenalidomide. In some embodiments, the immunomodulatory compound for use in the provided methods and uses is Compound 1 (3-(5-amino-2-methyl-4-oxo-4H-quinazolin-3-yl)-piperidine-2,6-dione). In some embodiments, the immunomodulatory compound for use in the provided methods and uses is Compound 2 ((S)-3-[4-(4-morpholin-4-ylmethyl-benzyloxy)-1-oxo-1,3-dihydro-isoindol-2-yl]-piperidine-2,6-dione).

Lenalidomide, which has the structural formula 3-(4-amino-1-oxo-1,3-dihydro-2H-isoindol-2-yl)piperidine-2,6-dione, or is an enantiomer or a mixture of enantiomers thereof, or a pharmaceutically acceptable salt, solvate, hydrate, co-crystal, clathrate, or polymorph thereof, is an immunomodulatory drug currently approved for the treatment of multiple myeloma (MM) and mantle cell lymphoma (MCL), and clinically tested in the therapy of diffuse large B-cell lymphoma of activated B cell immunophenotype. In some cases, lenalidomide increases antitumor immune responses at least partially by modulating the activity of E3 ubiquitin ligase Cereblon (CRBN), which leads to increased ubiquitinylation of Ikaros and Aiolos transcription factors, which in turn results in changed expression of various receptors on the surface of tumor cells (see e.g., Otáhal et al. (2016) *Oncoimmunology.*, April; 5(4): e1115940).

Compound 1, which has the structural formula 3-(5-amino-2-methyl-4-oxo-4H-quinazolin-3-yl)-piperidine-2,6-dione), or a pharmaceutically acceptable salt, solvate, hydrate, stereoisomer, tautomer or racemic mixtures thereof, is an immunomodulatory drug that is a pleiotropic small molecule that can directly impair primary tumor growth, modulate the immunosuppressive tumor microenvironment and facilitate a more robust anti-tumor inflammatory response. Compound 1 exerts anti-proliferative activity against B-cells, and is being evaluated as a single agent treatment for targeting tumors in B-cell lymphoid malignancies.

Compound 2, which as the structural formula (S)-3-[4-(4-morpholin-4-ylmethyl-benzyloxy)-1-oxo-1,3-dihydro-isoindol-2-yl]-piperidine-2,6-dione or a pharmaceutically acceptable salt, solvate, hydrate, stereoisomer, tautomer or racemic mixtures thereof, also is a cereblon (CRBN) E3 ligase modulatory compound that modulates CRBN, which induces ubiquitination of the transcription factors Aiolos and Ikaros. In some aspects, the ubiquitination increases their proteasome-dependent degradation. Compound 2 binds more potently to CRBN, and is more efficient at degrading Aiolos and Ikaros than lenalidomide and pomalidomide. As shown herein, Compound 2 also is 10-20 times more potent at degrading Ikaros and Aiolos relative to Compound 1. Compound 2 has direct anti-proliferative effects on lymphoma cells. As shown herein, Compound 2 also augments T cell function.

Immunomodulatory drugs, such as Compound 1, Compound 2, and lenalidomide, have been shown to directly affect malignant lymphocyte survival through the degradation of Ikaros family transcription factors. The molecular target for such compounds has been identified as the protein Cereblon (CRBN), a substrate receptor of the Cullin 4 RING E3 ubiquitin ligase complex. Binding to a hydrophobic tri-tryptophan pocket within CRBN promotes the recruitment, ubiquitination, and subsequent proteasomal degradation of several protein substrates, including Aiolos (IKZF3) and Ikaros (IKZF1). (Fischer, *Nature*. 2014 August; 512, 49-53; Chamberlain, *Nat Struct Mol Biol*. 2014 September; 21(9):803-9; Gandhi, *Br J Haematol*. 2014 March; 164(6): 811-21; Lu, *Science*. 2014 Jan. 17; 343(6168):305-9; and Krönke, Oncoimmunology, 2014; 3(7): e941742.) Ikaros is expressed in immature stages of myeloid differentiation and regulates early neutrophil differentiation (Dumortier et al. (2003) *Blood* 101:2219). Thus, in some cases, depletion of Ikaros, such as by administration of an immunomodulatory compound, e.g. Compound 1, to subjects can, in some instances, result in neutropenia. To mitigate neutropenia while maintaining anti-tumor activity against B cell lymphomas, it has been found that a dose of 4 mg of Compound 1 given for five days followed by a two day rest period (5/7 days) is the maximum tolerated dose (MTD) for treatment of subjects with DLBCL (Carpio et al. (2015) *Blood*, 126: 1594). See also, International Published Appl. No. WO2017096024.

In addition to its cell autonomous activity against malignant B cells, E3 ligase modulatory compounds, such as Compound 1, also exerts co-stimulatory effects on immune cells such T and NK-cells. This activity also has been shown to be through CRBN mediated degradation of Aiolos and Ikaros, which are negative regulators of activation molecules and cytokines such as interleukin-2 (IL-2) expression. (Gandhi, *Br J Haematol*. 2014 March; 164(6):811-21, Krönke, Oncoimmunology, 2014; 3(7): e941742.).

The provided methods are based on observations that the immunomodulatory compound, such as a structural or functional analog or derivative of thalidomide and/or an inhibitor of E3 ubiquitin ligase, e.g. lenalidomide, Compound 1 or Compound 2 as described, improves T cell function, including functions related to the ability to produce one or more cytokines, cytotoxicity, expansion, proliferation, and persistence of T cells. In some aspects, the provided methods enhance or modulate proliferation and/or activity of T cell activity associated with administration of the T cell therapy (e.g. CAR-expressing T cells). It is found that such methods and uses provide for or achieve improved or greater T cell functionality, and thereby improved anti-tumor efficacy.

It also is found herein that, in addition to potentiating T cell function, such immunomodulatory compounds, e.g. lenalidomide, Compound 1 or Compound 2, exhibit effects to reverse, delay, or prevent T cell exhaustion, including by increasing T cell signaling and/or altering one or more genes that are differentially regulated following chronic (long-term) stimulation. Thus, while in some cases agents that increase or potentiate T cell activity may drive the cells to an exhausted state, it is found herein that activity of such immunomodulatory compounds, e.g. lenalidomide, Compound 1 or Compound 2, to exert a potentiating effect on T cell activity is decoupled from T cell exhaustion. In some embodiments, the provided methods involving compound administration of such immunomodulatory compounds, e.g. lenalidomide, Compound 1 or Compound 2, is capable of potentiating activity of naïve T cells and delaying, limiting, reducing, inhibiting or preventing exhaustion.

Moreover, observations herein show that the immunomodulatory compounds, e.g. lenalidomide or Compound 1, exhibit activity to rescue T cells from T cell exhaustion, such as by restoring or partially restoring one or more T cell activities after a cell has shown features of exhaustion. Remarkably, results herein show that exposure of T cells, that have been chronically stimulated and exhibit features of exhausted T cells, to an immunomodulatory compound described herein, such as Compound 1, are able to recover activity or have their activity restored or partially restored. These results are not observed with interleukin 2 (IL-2), which, in some cases, is a downstream modulator induced by such immunomodulatory compounds. The observations herein support that the provided methods may also achieve improved or more durable responses as compared to certain alternative methods, such as in particular groups of subjects treated.

These observations were made using a chronic stimulation assay to render CAR T cells hypofunctional (e.g. reduced cytolysis and IL-2 secretion). Using this model, CAR T cells were examined to assess impact of immunoodulatory compounds that inhibit E3 ligase, e.g. lenalidomide, Compound 1 or Compound 2, on CAR T cell function when present during (concurrent) or following (rescue) exposure to conditions leading to a hypofunctional, exhaustive state. Upon rechallenge with antigen, the findings provided herein demonstrate that concurrent treatment of CAR T cells during such conditions reversed activity and phenotypes, including gene signatures, associated with CAR T cell hypofunctionality and preserved more effector function. Likewise, the results show that immunoodulatory compounds that inhibit E3 ligase, e.g. lenalidomide, Compound 1 or Compound 2, could rescue or restore T cell function, including cytokine production and cytolytic activity, of exhausted T cells. Further, the results were seen with different target antigens and different CARs.

In some embodiments, the effect on T cell exhaustion as observed by the immunomodulatory compounds, such as lenalidomide or Compound 1, is not observed by or induced by IL-2. In some embodiments, such effect, such as the ability to reduce, prevent or delay T cell exhaustion or to rescue or restore T cell activity in exhausted T cells, is not induced by a physiologically relevant amount or a therapeutically effective amount of IL-2. In some embodiments, the effect induced by the immunomodulatory compound, e.g. lenalidomide or Compound 1, such as the ability to reduce, prevent or delay T cell exhaustion or to rescue or restore T cell activity in exhausted T cells, is induced by greater than or greater than or about 1.2-fold, 2.0-fold, 3-fold, 4.0-fold, 5.0-fold, 6.0-fold, 7.0-fold, 10.0-fold, or more seen or induced by IL-2, such as a physiologically relevant amount or a therapeutically effective amount of IL-2.

Observations provided herein also demonstrate that immunoodulatory compounds that inhibit E3 ligase exhibit activity to increase effector cytokine production by CAR T cells, while at the same time slowing their proliferative rate. This results is not due to an effect of the compounds on viability of T cells. This effect on proliferation was observed at varied concentration, and was found to be due to accumulation of the T cells in G1 phase. This decoupling of effector cytokine production from proliferation rate could be clinically beneficial, such as by limiting differentiation of T cells in vivo which could limit efficacy.

The provided findings indicate that combination therapy of the immunomodulatory compound, such as a structural or functional analog or derivative of thalidomide and/or an inhibitor of E3 ubiquitin ligase, e.g. lenalidomide, Compound 1, or Compound 2, in methods involving T cells, such as involving administration of adoptive T cell therapy, achieves improved function of the T cell therapy, such as by potentiating T cell activity and reducing, preventing or delaying T cell exhaustion or rescuing cells from T cell exhaustion. In some embodiments, combination of the cell therapy (e.g., administration of engineered T cells) with the immunomodulatory compound, e.g., lenalidomide or Compound 1, improves or enhances one or more functions and/or effects of the T cell therapy, such as persistence, expansion, cytotoxicity, and/or therapeutic outcomes, e.g., ability to kill or reduce the burden of tumor or other disease or target cell.

In particular aspects, it is found herein that an immunomodulatory compound, such as a structural or functional analog or derivative of thalidomide and/or an inhibitor of E3 ubiquitin ligase, e.g. lenalidomide, Compound 1 or Compound 2, promotes continued function and/or survival of cells of a T cell therapy (e.g. CAR-T cells) after activation, including after encounter with antigen. In some aspects, lenalidomide, Compound 1 or Compound 2 increases the ability of such T cells to persist or function long-term, such as by preventing exhaustion or cell death. In particular embodiments, combination therapy with an immunomodulatory compound that is an inhibitor of an E3 ligase, e.g. lenalidomide, Compound 2 or Compound 2, may provide a useful therapeutic approach for enhancing and prolonging the activity of CAR T cells across B cell malignancies by modulating the tumor microenvironment, by improving persistent anti-tumor function of CAR T cells. In some cases, the compound may also have direct anti-tumor effects on lymphoma cells. In some embodiments, such improvements can result in a combination therapy exhibiting improved overall responses, e.g. reduction in tumor burden, and/or increased survival compared to in subjects treated with a monotherapy involving administration of the T cell therapy (e.g. CAR-T cell) or immunomodulatory compound (e.g. lenalidomide, Compound 1 or Compound 2) alone. In some aspects, the provided methods increase overall response and/or survival by or more than 1.5-fold, 2.0-fold, 3.0-fold, 4.0-fold, 5.0-fold, 10-fold or more compared to an alternative treatment, such as compared to a monotherapy involving administration of the T cell therapy (e.g. CAR-T cell) or immunomodulatory compound (e.g. lenalidomide or Compound 1) alone.

The provided methods include administering Compound 1 in an effective amount to exhibit a T cell modulatory effect. It is found herein that particular dosages of exemplary immunomodulatory compounds as described, e.g. lenalidomide or Compound 1, increase or enhance T cell function of a T cell therapy, e.g. CAR-T cell therapy. In some cases, doses that are too high may negatively impact T cell function. As shown herein, prolonged treatment of Compound 1 at physiologically-relevant concentrations (10 or 100 nM) can increase long-term proliferative potential of CAR-expressing T cells while higher concentrations, e.g. such as at or about 500 mM, may be detrimental to long term product performance. In some embodiments, the dose of Compound 1 that is administered from or from about 1 mg to about 10 mg, such as from or from about 1 mg to about 5 mg. The dose can be administered daily in a course of treatment or cycling regimen.

Similar results were seen with the immunomodulatory drug lenalidomide, although its T cell potency activity was lower than Compound 1. In CAR-expressing T cells, Ikaros expression was decreased in a concentration dependent manner in the presence of lenalidomide or Compound 1 at similar half maximal effective concentration (EC50) values, however, the magnitude of Ikaros loss was greater following Compound 1 treatment. In certain embodiments, doses of 40-150 nM Compound 1 (correlating to ~1 mg dose level) results in 50% Ikaros degradation in the T cells (e.g., CAR-expressing T cells). Further, in vitro studies assessing the effect of Compound 1 on antigen-dependent cytokine production by CD19 directed CAR-expressing T cells demonstrated increased levels of IFNγ and IL-2 compared to vehicle control or equimolar concentrations of lenalidomide. Thus, administering Compound 1 according to the provided methods could increase the activity of CAR-expressing cells for treating a cancer by potentiating and/or restoring T cell function and activity of the engineered T cells, and, in some aspects, may also exhibit its cell autonomous antineoplastic effects.

In particular embodiments, Compound 2 can be used in any of the provided methods. As described, findings indicate that Compound 2 is 10-20 times more potent than Compound 1 and thus also is more potent than Compound 2. In some embodiments, the provided methods include administering Compound 2 in an effective amount to exhibit a T cell modulatory effect. In some embodiments, the effective amount is 10-20 less than the amount of Compound 1 for the same or similar effect. In some embodiments, the dose of Compound 2 that is administered is from or from about 0.1 mg to about 1 mg, such as from or from about 0.3 mg to about 0.6 mg. The dose can be administered daily in a course of treatment or cycling regimen.

In some embodiments, the combination with the immunomodulatory compound, while improving one or more outcomes or functional attributes, does not affect one or more side effects or unwanted changes in the T cells, such as does not reduce the ability of the cells to become activated, secrete one or more desired cytokines, expand and/or persist, e.g., as measured in an in vitro assay as compared to such cells cultured under conditions otherwise the same but in the absence of the immunomodulatory compound. Thus in some embodiments, provided are methods and combinations that result in improvements in T cell function or phenotype, e.g., in intrinsic T cell functionality and/or intrinsic T cell phenotype, generally without compromising one or more other desired properties of functionality, e.g., of CAR-T cell functionality.

In some embodiments, the provided methods can potentiate T cell therapy, e.g. CAR-T cell therapy, which, in some aspects, can improve outcomes for treatment. In some embodiments, the methods are particularly advantageous in subjects in which the cells of the T cell therapy exhibit weak expansion, have become exhausted, exhibit a reduced or decreased persistence in the subject and/or in subjects that have a cancer that is resistant or refractory to other therapies, is an aggressive or high-risk cancer, and/or that is or is likely to exhibit a relatively lower response rate to a CAR-T cell therapy administered without the immunomodulatory compound compared to another type of cancer or compared to administration with a different CAR-T cell therapy.

In some embodiments, the provided methods are used at a time at which a T cell therapy (e.g. CAR T cells) may exhibit or are likely to exhibit features of exhaustion. In some embodiments, an exhaustive phenotype is evident after T cells, having reached peak expansion, begin to decline in number in the blood of the subject. In some embodiments, the methods of exposing or contacting T cells of a T cell therapy (CAR T cells) with an immunomodulatory compound that inhibits E3 ligase, e.g. lenalidomide, Compound 1 or Compound 2, are carried out at a time at which the T cells exhibit an increase in a hypofunctional or exhaustive state compared to at the time just prior to exposure of the T cells to an antigen (baseline) or to a time point at which the cells have been exposed to the antigen but are continuing to proliferate and have not yet reached peak expansion. In some embodiments, an increase in hypofunctional or exhaustive state can be determined by increased expression of an exhaustion marker compared to tge previous earlier timepoint. In some embodiments, the increase in the hypofunctional or exhaustive state, such as increase in expression of an exhaustion marker, is at a time following administration of the T cell therapy (e.g. CAR T cells) to a subject having a disease or condition associated with the antigen targeted by the T cell therapy. The T cells, such as T cells in peripheral blood after administration to a subject, can be monitored for markers of T cell activation or exhaustion such as PD-1. TIM-3 and LAG-3.

In some aspects, the provided methods can enhance, increase or potentiate T cell therapy, such as to overcome lack of persistence and/or exhaustion of T cells, e.g. in subjects in which, at or about day 12-15 days after initiation of administration of the T cell therapy, less than 10 μL, such as less than 5 μL or less than 1 μL of such cells, or a CD8+ or CD3+ subset thereof, are detectable in the blood. In some embodiments, a subject having received administration of a T cell therapy, e.g. CAR-T cell, is monitored for the presence, absence or level of T cells of the therapy in the subject, such as in a biological sample of the subject, e.g. in the blood of the subject. In some embodiments, an immunomodulatory compound, such as a structural or functional analog or derivative of thalidomide and/or an inhibitor of E3 ubiquitin ligase, e.g. lenalidomide, Compound 1 or Compound 2, is administered to a subject having received the T cell therapy (e.g. CAR-T cells) but in which such cells have weakly expanded and/or are at or below a threshold level in a sample of the subject, e.g. blood sample, at a time when strong or robust expansion of the CAR-T cells in the subject is typically observed in a plurality of subjects administered a T cell therapy (e.g. CAR-T), in some cases, this same T cell therapy (e.g. same CAR-T cells). In some aspects, an immunomodulatory compound, such as a structural or functional analog or derivative of thalidomide and/or an inhibitor of E3 ubiquitin ligase, e.g., lenalidomide, Compound 1 or Compound 2, is administered if, at or about day 12-15 after initiation of administration of the T cell therapy, less than 10 μL, such as less than 5 μL or less than 1 μL of such cells, or a CD8+ or CD3+ subset thereof, are detectable in the blood.

In certain aspects, the provided methods can enhance, increase or potentiate T cell therapy in subjects in which a peak response to the T cell therapy has been observed but in which the response, e.g. presence of T cells and/or reduction in tumor burden, has become reduced or is no longer detectable. In some aspects, an immunomodulatory compound, such as a structural or functional analog or derivative of thalidomide and/or an inhibitor of E3 ubiquitin ligase, e.g. lenalidomide, Compound 1 or Compound 2, is administered to a subject within a week, such as within 1, 2 or 3 days after: (i) peak or maximum level of the cells of the T cell therapy are detectable in the blood of the subject; (ii) the number of cells of the T cell therapy detectable in the blood, after having been detectable in the blood, is not detectable or is reduced, optionally reduced compared to a preceding time point after administration of the T cell therapy; (iii) the number of cells of the T cell therapy detectable in the blood is decreased by or more than 1.5-fold, 2.0-fold, 3.0-fold, 4.0-fold, 5.0-fold, 10-fold or more the peak or maximum number cells of the T cell therapy detectable in the blood of the subject after initiation of administration of the T cell therapy; (iv) at a time after a peak or maximum level of the cells of the T cell therapy are detectable in the blood of the subject, the number of cells of or derived from the T cells detectable in the blood from the subject is less than less than 10%, less than 5%, less than 1% or less than 0.1% of total peripheral blood mononuclear cells (PBMCs) in the blood of the subject; (v) the subject exhibits disease progression and/or has relapsed following remission after treatment with the T cell therapy; and/or (iv) the subject exhibits increased tumor burden as compared to tumor burden at a time prior to or after administration of the T cells and prior to initiation of administration of the immunomodulatory compound.

In some embodiments, the methods can be used for treating a disease or condition, e.g. a B cell malignancy or hematological malignancy, and in particular such diseases, conditions or malignancies in which responses, e.g. complete response, to treatment with the T cell therapy alone, such as a composition including cells for adoptive cell therapy, e.g., such as a T cell therapy (e.g. CAR-expressing T cells), is relatively low compared to treatment with other T cell therapies or treatment of other diseases or malignancies (e.g. a CR in a less than or less than about 60%, less than about 50% or less than about 45% of the subjects so treated) and/or in which the subject is not responsive to treatment with the immunomodulatory compound, such as a structural or functional analog or derivative of thalidomide and/or an inhibitor of E3 ubiquitin ligase, e.g. lenalidomide, Compound 1 or Compound 2, alone.

In some embodiments, the combination therapy provided herein is for use in a subject having a cancer in which after initiation of administration of the T cell therapy, such as a composition including cells for adoptive cell therapy, e.g., CAR-expressing T cells, the subject has relapsed following remission after treatment with the T cell therapy. In some embodiments, subjects that have relapsed following such remission are administered an immunomodulatory compound, such as a structural or functional analog or derivative of thalidomide and/or an inhibitor of E3 ubiquitin ligase, e.g. lenalidomide, Compound 1 or Compound 2. In some embodiments, the combination therapy provided herein is for use in a subject having a disease or condition, e.g. cancer, in which the amount of the immunomodulatory compound administered is insufficient, as a single agent and/or in the absence of administration of the T cell therapy, to ameliorate, reduce or prevent the disease or condition or a symptom or outcome thereof, such as is insufficient to ameliorate, reduce or prevent the disease or condition in the subject or a symptom or outcome thereof. In some embodiments, the method thereby reduces or ameliorates a symptom or outcome or burden of the disease or condition to a degree that is greater than the combination of (i) the degree of reduction or amelioration effected by the administration of the immunomodulatory agent alone, optionally on average in a population of subjects having the disease or condition, and (ii) the degree of reduction or amelioration by the administration of the T cell therapy alone, optionally on average in a population of subjects having the disease or condition. In some embodiment, the method reduces or ameliorates such symptoms, outcomes or burdens of the disease, e.g. compared to on average in a population of subjects having the disease or condition, by greater than or greater than about 1.5-fold, 2.0-fold, 3.0-fold, 4.0-fold, 5.0-fold, 6.0-fold, 7.0-fold, 8.0-fold, 9.0-fold, 10.0 fold, 20.0-fold, 30.0-fold, 40.0-fold, 50.0-fold or more.

In some embodiments, the provided combination therapy is used in connection with treating certain diseases or conditions, e.g., cancer, in which optimal stimulation of a recombinant antigen receptor, e.g. CAR-T cell, is difficult to achieve and/or is not consistently observed. In some embodiments, less than optimal stimulation may be a result of low or inaccessible levels of disease antigen in vivo, e.g. at or on the tumor. In some embodiments, certain cancers, such as NHL, e.g. high-risk or aggressive NHL, such as DLBCL, and/or chronic lymphocytic leukemia (CLL) can be associated with defects in or reduction in intrinsic T cell functionality, which, in some cases, is influenced by the disease itself. For example, the pathogenesis of many cancers, such as CLL and NHL, e.g. DLBCL, can be associated with immunodeficiency, leading to promotion of tumor growth and immune evasion, such as due to immunosuppression of T cells, e.g. driven by one or more factors in the tumor microenvironment. In some cases, alleviating intrinsic T cell defects obtained from cancers of such patients for use in connection with adoptive cell therapy could provide for more potent responses to adoptive T cell therapy, e.g. CAR-T cell therapy. In some cases, less than optimal stimulation can be due to differences in expression level of the CAR on engineered T cells administered to the subject. In any of such embodiments, administration of the immunomodulatory compound, such as a structural or functional analog or derivative of thalidomide and/or an inhibitor of E3 ubiquitin ligase, e.g., lenalidomide, Compound 1 or Compound 2, can enhance the stimulation or activity of such T cells in vivo in the subject.

In some embodiments of the provided methods, one or more properties of administered genetically engineered cells can be improved or increased or greater compared to administered cells of a reference composition, such as increased or longer expansion and/or persistence of such administered cells in the subject or an increased or greater recall response upon restimulation with antigen. In some embodiments, the increase can be at least a 1.2-fold, at least 1.5-fold, at least 2-fold, at last 3-fold, at least 4-fold, at least 5-fold, at least 6-fold, at least 7-fold, at least 8-fold, at least 9-fold, or at least 10-fold increase in such property or feature compared to the same property or feature upon administration of a reference cell composition. In some embodiments, the increase in one or more of such properties or features can be observed or is present within 7 days, 14 days, 21 days, within one months, two months, three months, four months, five months, six months, or 12 months after administration of the genetically engineered cells and the initiation of administration of the immunomodulatory compound, such as a structural or functional analog or derivative of thalidomide and/or an inhibitor of E3 ubiquitin ligase, e.g., lenalidomide or Compound 1.

In some embodiments, a reference cell composition can be a composition of T cells from the blood of a subject not having or not suspected of having the cancer or is a population of T cells obtained, isolated, generated, produced, incubated and/or administered under the same or substantially the conditions, except not having been incubated or administered in the presence of the immunomodulatory compound. In some embodiments, the reference cell composition contains genetically engineered cells that are substantially the same, including expression of the same recombinant receptor, e.g., CAR. In some aspects, such T cells are treated identically or substantially identically, such as manufactured similarly, formulated similarly, administered in the same or about the same dosage amount and other similar factors.

In some embodiments, the provided methods result in genetically engineered cell with increased persistence and/or better potency in a subject to which it is administered. In some embodiments, the persistence of genetically engineered cells, such as CAR-expressing T cells, in the subject is greater as compared to that which would be achieved by alternative methods, such as those involving administration of a reference cell composition, e.g. administration of the T cell therapy but in the absence of administration of the immunomodulatory compound. In some embodiments, the persistence is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more.

In some embodiments, the degree or extent of persistence of administered cells can be detected or quantified after administration to a subject. For example, in some aspects, quantitative PCR (qPCR) is used to assess the quantity of cells expressing the recombinant receptor (e.g., CAR-expressing cells) in the blood or serum or organ or tissue (e.g., disease site) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample. In some embodiments, flow cytometric assays detecting cells expressing the receptor generally using antibodies specific for the receptors also can be performed. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor. In any of such embodiments, the extent or level of expression of another marker associated with the recombinant receptor (e.g. CAR-expressing cells) can be used to distinguish the administered cells from endogenous cells in a subject.

Also provided are methods for engineering, preparing, and producing the cells, compositions containing the cells and/or immunomodulatory compound, and kits and devices containing and for using, producing and administering the cells and/or immunomodulatory compound, such as in accord with the provided combination therapy methods.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section heading used herein are for organizational purposes only and are not to be construed as limiting the subject matter described.

I. Combination Therapy

Provided herein are methods for combination therapy for treating a disease or disorder, e.g. a cancer or proliferative disease, that includes administering to a subject a combination therapy of 1) an immunomodulatory compound, such as a structural or functional analog or derivative of thalidomide and/or an inhibitor of E3 ubiquitin ligase, e.g. lenalidomide or Compound 1, and Compound 2) a T cell therapy, e.g. CAR-expressing cell, e.g. T cells. In particular embodiments, the immunomodulatory compound is an inhibitor of E3 ubiquitin ligase. In some embodiments, the T cell therapy is an adoptive immune cell therapy comprising T cells that specifically recognize and/or target an antigen associated with a disease or disorder, e.g. a cancer or proliferative disease. Also provided are combinations and articles of manufacture, such as kits, that contain a composition comprising the T cell therapy and/or a composition comprising the immunomodulatory compound, and uses of such compositions and combinations to treat or prevent diseases, conditions, and disorders, including cancers.

In some embodiments, such methods can include administration of the immunomodulatory compound, such as a structural or functional analog or derivative of thalidomide and/or an inhibitor of E3 ubiquitin ligase, e.g. lenalidomide, Compound 1 or Compound 2, prior to, simultaneously with, during, during the course of (including once and/or periodically during the course of), and/or subsequently to, the administration (e.g., initiation of administration) of the T cell therapy (e.g. CAR-expressing T cells). In some embodiments, the administrations can involve sequential or intermittent administrations of the immunomodulatory compound and T cell therapy.

In some embodiments, the cell therapy is adoptive cell therapy. In some embodiments, the cell therapy is or comprises a tumor infiltrating lymphocytic (TIL) therapy, a transgenic TCR therapy or a recombinant-receptor expressing cell therapy (optionally T cell therapy), which optionally is a chimeric antigen receptor (CAR)-expressing cell therapy. In some embodiments, the therapy is a B cell targeted therapy. In some embodiments, the therapy targets B cell maturation antigen (BCMA). In some embodiments, the therapy targets CD19. In some embodiments, the cells and dosage regimens for administering the cells can include any as described in the following subsection A under "Administration of T Cell therapy."

In some embodiments, the immunomodulatory compound potentiates T-cell functionality. In some embodiments, the immunomodulatory compound drives anti-myeloma activity. In some embodiments, the immunomodulatory compound alters the suppressive microenvironment.

In some embodiments, the immunomodulatory compound is a structural or functional analog or derivative of thalidomide. In some embodiments, the immunomodulatory compound is an inhibitor of E3 ubiquitin ligase. In some embodiments, the immunomodulatory compound is lenalidomide or a compound with the same or similar properties of lenalidomide, including analogs or derivatives, a stereoisomer of lenalidomide or a pharmaceutically acceptable salt, solvate, hydrate, co-crystal, clathrate, or polymorph thereof. In some embodiments, the immunomodulatory compound is Compound 1 as described or a compound with the same or similar properties of Compound 1, including analogs or derivatives, a stereoisomer of Compound 1 or a pharmaceutically acceptable salt, solvate, hydrate, co-crystal, clathrate, or polymorph thereof. In some embodiments, the immunomodulatory compound is Compound 1 as described or a compound with the same or similar properties of Compound 1, including analogs or derivatives, a stereoisomer of Compound 1 or a pharmaceutically acceptable salt, solvate, hydrate, co-crystal, clathrate, or polymorph thereof. In some embodiments, the dosage regimens for administering the immunomodulatory compound can include any as described in the following subsection B under "Administration of the Immunomodulatory Compound."

In some embodiments, the T cell therapy (e.g. CAR-expressing T cells) and immunomodulatory compound are provided as pharmaceutical compositions for administration to the subject. In some embodiments, the pharmaceutical compositions contain therapeutically effective amounts of one or both of the agents for combination therapy, e.g., T cells for adoptive cell therapy and an immunomodulatory compound as described. In some embodiments, the agents are formulated for administration in separate pharmaceutical compositions. In some embodiments, any of the pharmaceutical compositions provided herein can be formulated in dosage forms appropriate for each route of administration.

In some embodiments, the combination therapy, which includes administering the T cell therapy, including engineered cells, such as CAR-T cell therapy, and the immunomodulatory compound is administered to a subject or patient having a disease or condition to be treated (e.g. cancer) or at risk for having the disease or condition (e.g. cancer). In some aspects, the methods treat, e.g., ameliorate one or more symptom of, the disease or condition, such as by lessening tumor burden in a cancer expressing an antigen recognized by the immunotherapy or immunotherapeutic agent, e.g. recognized by an engineered T cell.

In some embodiments, the disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by bacterial, viral or other pathogens. Exemplary antigens, which include antigens associated with various diseases and conditions that can be treated, include any of antigens described herein. In particular embodiments, the recombinant receptor expressed on engineered cells of a combination therapy, including a chimeric antigen receptor or transgenic TCR, specifically binds to an antigen associated with the disease or condition.

In some embodiments, the disease or condition is a tumor, such as a solid tumor, lymphoma, leukemia, blood tumor, metastatic tumor, or other cancer or tumor type.

In some embodiments, the cancer or proliferative disease is a B cell malignancy or hematological malignancy. In some embodiments the cancer or proliferative disease is lymphoblastic leukemia (ALL), non-Hodgkin's lymphoma (NHL), or chronic lymphocytic leukemia (CLL). In some embodiments, the cancer is CLL. In some embodiments, the methods can be used to treat a myeloma, a lymphoma or a leukemia. In some embodiments, the methods can be used to treat a non-Hodgkin lymphoma (NHL), an acute lymphoblastic leukemia (ALL), a chronic lymphocytic leukemia (CLL), a diffuse large B-cell lymphoma (DLBCL), acute myeloid leukemia (AML), or a myeloma, e.g., a multiple myeloma (MM). In some embodiments, the methods can be used to treat a MM or a DBCBL.

In some embodiments, the antigen associated with the disease or disorder is selected from the group consisting of ROR1, B cell maturation antigen (BCMA), Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Rα2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, G Protein Coupled Receptor 5D (GPCR5D), oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, and a pathogen-specific antigen. In some embodiments, the antigen is associated with or is a universal tag.

In some embodiments the cancer or proliferative disease expresses BCMA. In some embodiments, the provided methods employ a recombinant receptor-expressing T cell (e.g. CAR-T cell) that targets BCMA.

In some embodiments the cancer or proliferative disease expresses CD19. In some embodiments, the provided methods employ a recombinant receptor-expressing T cell (e.g. CAR-T cell) that targets CD19.

In some embodiments, the methods can be used to treat a non-hematologic cancer, such as a solid tumor. In some embodiments, the methods can be used to treat a bladder, lung, brain, melanoma (e.g. small-cell lung, melanoma), breast, cervical, ovarian, colorectal, pancreatic, endometrial, esophageal, kidney, liver, prostate, skin, thyroid, or uterine cancers. In some embodiments, the cancer or proliferative disease is cancer is a pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Graves disease, Crohn's disease, multiple sclerosis, asthma, and/or a disease or condition associated with transplant.

For the prevention or treatment of disease, the appropriate dosage of immunomodulatory compound (e.g., lenalidomide, Compound 1 or Compound 2) and/or immunotherapy, such as a T cell therapy (e.g. CAR-expressing T cells), may depend on the type of disease to be treated, the particular immunomodulatory compound, cells and/or recombinant receptors expressed on the cells, the severity and course of the disease, route of administration, whether the immunomodulatory compound and/or the T cell therapy are administered for preventive or therapeutic purposes, previous therapy, frequency of administration, the subject's clinical history and response to the cells, and the discretion of the attending physician. The compositions and cells are in some embodiments suitably administered to the subject at one time or over a series of treatments. Exemplary dosage regimens and schedules for the provided combination therapy are described.

In some embodiments, the T cell therapy and the immunomodulatory compound are administered as part of a further combination treatment, which can be administered simultaneously with or sequentially to, in any order, another therapeutic intervention. In some contexts, the T cell therapy, e.g. engineered T cells, such as CAR-expressing T cells, are co-administered with another therapy sufficiently close in time such that the T cell therapy enhances the effect of one or more additional therapeutic agents, or vice versa. In some embodiments, the cells are administered prior to the one or more additional therapeutic agents. In some embodiments, the T cell therapy, e.g. engineered T cells, such as CAR-expressing T cells, are administered after the one or more additional therapeutic agents. In some embodiments, the combination therapy methods further include a lymphodepleting therapy, such as administration of a chemotherapeutic agent. In some embodiments, the combination therapy further comprises administering another therapeutic agent, such as an anti-cancer agent, a checkpoint inhibitor, or another immune modulating agent. Uses include uses of the combination therapies in such methods and treatments, and uses of such compositions in the preparation of a medicament in order to carry out such combination therapy methods. In some embodiments, the methods and uses thereby treat the disease or condition or disorder, such as a cancer or proliferative disease, in the subject.

Prior to, during or following administration of the immunotherapy (e.g. T cell therapy, such as CAR-T cell therapy) and/or an immunomodulatory compound, the biological activity of the T cell therapy, e.g. the biological activity of the engineered cell populations, in some embodiments is measured, e.g., by any of a number of known methods. Parameters to assess include the ability of the engineered cells to destroy target cells, persistence and other measures of T cell activity, such as measured using any suitable method known in the art, such as assays described further below in Section III. In some embodiments, the biological activity of the cells, e.g., T cells administered for the T cell based therapy, is measured by assaying cytotoxic cell killing, expression and/or secretion of one or more cytokines, proliferation or expansion, such as upon restimulation with antigen. In some aspects the biological activity is measured by assessing the disease burden and/or clinical outcome, such as reduction in tumor burden or load. In some embodiments, administration of one or both agents of the combination therapy and/or any repeated administration of the therapy, can be determined based on the results of the assays before, during, during the course of or after administration of one or both agents of the combination therapy.

In some embodiments, the combined effect of the immunomodulatory compound in combination with the cell therapy can be synergistic compared to treatments involving only the immunomodulatory compound or monotherapy with the cell therapy. For example, in some embodiments, the methods provided herein result in an increase or an improvement in a desired therapeutic effect, such as an increased or an improvement in the reduction or inhibition of one or more symptoms associated with cancer.

In some embodiments, the immunomodulatory compound increases the expansion or proliferation of the engineered T cells, such as CAR T-Cells. In some embodiments, the increase in expansion or proliferation is observed in vivo upon administration to a subject. In some embodiments, the increase in the number of engineered T cells, e.g. CAR-T cells, is increased by greater than or greater than about 1.2-fold, 1.5-fold, 2.0-fold, 3.0-fold, 4.0-fold, 5.0-fold, 6.0-fold, 7.0-fold, 8.0-fold, 9.0-fold, 10.0 fold or more.

A. Administration of T Cell Therapy

In some embodiments of the methods, compositions, combinations, kits and uses provided herein, the combination therapy includes administering to a subject an immune cell therapy, such as a T cell therapy (e.g. CAR-expressing T cells). Administration of such therapies can be initiated prior to, subsequent to, simultaneously with administration of one or more immunomodulatory compound as described.

In some embodiments, the cell-based therapy is or comprises administration of cells, such as immune cells, for example T cell or NK cells, that target a molecule expressed on the surface of a lesion, such as a tumor or a cancer. In some embodiments, the immune cells express a T cell receptor (TCR) or other antigen-binding receptor. In some embodiments, the immune cells express a recombinant receptor, such as a transgenic TCR or a chimeric antigen receptor (CAR). In some embodiments, the cells are autologous to the subject. In some embodiments, the cells are allogeneic to the subject.

In some aspects, the T cell therapy is or comprises a tumor infiltrating lymphocytic (TIL) therapy, a transgenic TCR therapy or a T cell therapy comprising genetically engineered cells, such as a recombinant-receptor expressing cell therapy. In some embodiments, the recombinant receptor specifically binds to a ligand, such as one associated with a disease or condition, e.g. associated with or expressed on a cell of a tumor or cancer. In some embodiments, the T cell therapy includes administering T cells engineered to express a chimeric antigen receptor (CAR).

In some embodiments, the provided cells express and/or are engineered to express receptors, such as recombinant receptors, including those containing ligand-binding domains or binding fragments thereof, and T cell receptors (TCRs) and components thereof, and/or functional non-TCR antigen receptors, such as chimeric antigen receptors (CARs). In some embodiments, the recombinant receptor contains an extracellular ligand-binding domain that specifically binds to an antigen. In some embodiments, the recombinant receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Among the engineered cells, including engineered cells containing recombinant receptors, are described in Section II below. Exemplary recombinant receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061, WO2016/0046724, WO2016/014789, WO2016/090320, WO2016/094304, WO2017/025038, WO2017/173256, U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, 8,479,118, and 9,765,342, and European patent application number EP2537416, and/or those described by Sadelain et al., *Cancer Discov.*, 3(4): 388-398 (2013); Davila et al., *PLoS ONE* 8(4): e61338 (2013); Turtle et al., *Curr. Opin. Immunol.*, 24(5): 633-39 (2012); Wu et al., *Cancer*, 18(2): 160-75 (2012). In some aspects, the genetically engineered antigen receptors include a CAR as described in U.S. Pat. No. 7,446,190, and those described in International Patent Application Publication No.: WO/2014055668 A1.

In some embodiments, the antigen is or includes $\alpha\beta6$ integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13R$\alpha$2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the combination therapy includes administration to a subject cells, e.g. T cells, expressing a recombinant receptor that specifically recognize and/or target an antigen associated with the cancer and/or present on a universal tag. In some embodiments, the antigen recognized or targeted by the T cells is ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, G Protein Coupled Receptor 5D (GPCR5D), oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, optionally a human antigen of any of the foregoing; a pathogen-specific antigen.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) *Nat Rev Clin Oncol.* 8(10):577-85). See, e.g., Themeli et al., (2013) *Nat Biotechnol.* 31(10): 928-933; Tsukahara et al., (2013) *Biochem Biophys Res Commun* 438(1): 84-9; Davila et al., (2013) *PLoS ONE* 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose includes fewer than about $1 \times 10^8$ total recombinant receptor (e.g., CAR)-expressing cells, T cells, or peripheral blood mononuclear cells (PBMCs), e.g., in the range of about $1 \times 10^6$ to $1 \times 10^8$ such cells, such as $2 \times 10^6$, $5 \times 10^6$, $1 \times 10^7$, $5 \times 10^7$, or $1 \times 10^8$ or total such cells, or the range between any two of the foregoing values.

The cells can be administered by any suitable means. The cells are administered in a dosing regimen to achieve a therapeutic effect, such as a reduction in tumor burden. Dosing and administration may depend in part on the schedule of administration of the immunomodulatory compound, which can be administered prior to, subsequent to and/or simultaneously with initiation of administration of the T cell therapy. Various dosing schedules of the T cell therapy include but are not limited to single or multiple administrations over various time-points, bolus administration, and pulse infusion.

I. Compositions and Formulations

In some embodiments, the dose of cells of the T cell therapy, such a T cell therapy comprising cells engineered with a recombinant antigen receptor, e.g. CAR or TCR, is provided as a composition or formulation, such as a pharmaceutical composition or formulation. Such compositions can be used in accord with the provided methods, such as in the prevention or treatment of diseases, conditions, and disorders.

In some embodiments, the T cell therapy, such as engineered T cells (e.g. CAR T cells), are formulated with a pharmaceutically acceptable carrier. In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition in some embodiments contains cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

In some cases, the cell therapy is administered as a single pharmaceutical composition comprising the cells. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

2. Dosage Schedule and Administration

In some embodiments, a dose of cells is administered to subjects in accord with the provided combination therapy methods. In some embodiments, the size or timing of the doses is determined as a function of the particular disease or condition in the subject. One may empirically determine the size or timing of the doses for a particular disease in view of the provided description.

In certain embodiments, the cells, or individual populations of sub-types of cells, are administered to the subject at a range of about 0.1 million to about 100 billion cells and/or that amount of cells per kilogram of body weight of the subject, such as, e.g., 0.1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight of the subject. Dosages may vary depending on attributes particular to the disease or disorder and/or patient and/or other treatments. In some embodiments, such values refer to numbers of recombinant receptor-expressing cells; in other embodiments, they refer to number of T cells or PBMCs or total cells administered.

In some embodiments, the cell therapy comprises administration of a dose comprising a number of cell from or from about $1\times10^5$ to $1\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or about at least $1\times10^5$ total recombinant receptor-expressing cells, total T cells, or total peripheral blood mononuclear cells (PBMCs), such at least or at least $1\times10^6$, at least or about at least $1\times10^7$, at least or about at least $1\times10^8$ of such cells.

In some embodiments, for example, where the subject is a human, the dose includes fewer than about $5\times10^8$ total recombinant receptor (e.g., CAR)-expressing cells, T cells, or peripheral blood mononuclear cells (PBMCs), e.g., in the range of about $1\times10^6$ to $5\times10^8$ such cells, such as $2\times10^6$, $5\times10^6$, $1\times10^7$, $5\times10^7$, $1\times10^8$, or $5\times10^8$ total such cells, or the range between any two of the foregoing values.

In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1\times10^5$ to $1\times10^8$ CD3+ or CD8+ total T cells or CD3+ or CD8+ recombinant receptor-expressing cells, from or from about $5\times10^5$ to $1\times10^7$ CD3+ or CD8+ total T cells or CD3+ or CD8+ recombinant receptor-expressing cells, or from or from about $1\times10^6$ to $1\times10^7$ CD3+ or CD8+ total T cells or CD3+ or CD8+ recombinant receptor-expressing cells, each inclusive. In some embodiments, the cell therapy comprises administration of a dose comprising a number of cell from or from about $1\times10^5$ to $1\times10^8$ total CD3+/CAR+ or CD8+/CAR+ cells, from or from about $5\times10^5$ to $1\times10^7$ total CD3+/CAR+ or CD8+/CAR+ cells, or from or from about $1\times10^6$ to $1\times10^7$ total CD3+/CAR+ or CD8+/CAR+ cells, each inclusive.

In some embodiments, the dose of genetically engineered cells comprises from or from about $1\times10^5$ to $5\times10^8$ total CAR-expressing T cells, $1\times10^5$ to $2.5\times10^8$ total CAR-expressing T cells, $1\times10^5$ to $1\times10^8$ total CAR-expressing T cells, $1\times10^5$ to $5\times10^7$ total CAR-expressing T cells, $1\times10^5$ to $2.5\times10^7$ total CAR-expressing T cells, $1\times10^5$ to $1\times10^7$ total CAR-expressing T cells, $1\times10^5$ to $5\times10^6$ total CAR-expressing T cells, $1\times10^5$ to $2.5\times10^6$ total CAR-expressing T cells, $1\times10^5$ to $1\times10^6$ total CAR-expressing T cells, $1\times10^6$ to $5\times10^8$ total CAR-expressing T cells, $1\times10^6$ to $2.5\times10^8$ total CAR-expressing T cells, $1\times10^6$ to $1\times10^8$ total CAR-expressing T cells, $1\times10^6$ to $5\times10^7$ total CAR-expressing T cells, $1\times10^6$ to $2.5\times10^7$ total CAR-expressing T cells, $1\times10^6$ to $1\times10^7$ total CAR-expressing T cells, $1\times10^6$ to $5\times10^6$ total CAR-expressing T cells, $1\times10^6$ to $2.5\times10^6$ total CAR-expressing T cells, $2.5\times10^6$ to $5\times10^8$ total CAR-expressing T cells, $2.5\times10^6$ to $2.5\times10^8$ total CAR-expressing T cells, $2.5\times10^6$ to $1\times10^8$ total CAR-expressing T cells, $2.5\times10^6$ to $5\times10^7$ total CAR-expressing T cells, $2.5\times10^6$ to $2.5\times10^7$ total CAR-expressing T cells, $2.5\times10^6$ to $1\times10^7$ total CAR-expressing T cells, $2.5\times10^6$ to $5\times10^6$ total CAR-expressing T cells, $5\times10^6$ to $5\times10^8$ total CAR-expressing T cells, $5\times10^6$ to $2.5\times10^8$ total CAR-expressing T cells, $5\times10^6$ to $1\times10^8$ total CAR-expressing T cells, $5\times10^6$ to $5\times10^7$ total CAR-expressing T cells, $5\times10^6$ to $2.5\times10^7$ total CAR-expressing T cells, $5\times10^6$ to $1\times10^7$ total CAR-expressing T cells, $1\times10^7$ to $5\times10^8$ total CAR-expressing T cells, $1\times10^7$ to $2.5\times10^8$ total CAR-expressing T cells, $1\times10^7$ to $1\times10^8$ total CAR-expressing T cells, $1\times10^7$ to $5\times10^7$ total CAR-expressing T cells, $1\times10^7$ to $2.5\times10^7$ total CAR-expressing T cells, $2.5\times10^7$ to $5\times10^8$ total CAR-expressing T cells, $2.5\times10^7$ to $2.5\times10^8$ total CAR-expressing T cells, $2.5\times10^7$ to $1\times10^8$ total CAR-expressing T cells, $2.5\times10^7$ to $5\times10^7$ total CAR-expressing T cells, $5\times10^7$ to $5\times10^8$ total CAR-expressing T cells, $5\times10^7$ to $2.5\times10^8$ total CAR-expressing T cells, $5\times10^7$ to $1\times10^8$ total CAR-expressing T cells, $1\times10^8$ to $5\times10^8$ total CAR-expressing T cells, $1\times10^8$ to $2.5\times10^8$ total CAR-expressing T cells, or $2.5\times10^8$ to $5\times10^8$ total CAR-expressing T cells.

In some embodiments, the dose of genetically engineered cells comprises at least or at least about $1\times10^5$ CAR-expressing cells, at least or at least about $2.5\times10^5$ CAR-expressing cells, at least or at least about $5\times10^5$ CAR-expressing cells, at least or at least about $1\times10^6$ CAR-expressing cells, at least or at least about $2.5\times10^6$ CAR-expressing cells, at least or at least about $5\times10^6$ CAR-expressing cells, at least or at least about $1\times10^7$ CAR-expressing cells, at least or at least about $2.5\times10^7$ CAR-expressing cells, at least or at least about $5\times10^7$ CAR-expressing cells, at least or at least about $1\times10^8$ CAR-expressing cells, at least or at least about $2.5\times10^8$ CAR-expressing cells, or at least or at least about $5\times10^8$ CAR-expressing cells.

In some embodiments, the cell therapy comprises administration of a dose comprising a number of cell from or from about $1\times10^5$ to $5\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1\times10^5$ total recombinant receptor-expressing cells, total T cells, or total peripheral blood mononuclear cells (PBMCs), such at least or at least $1\times10^6$, at least or at least about $1\times10^7$, at least or at least about $1\times10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1\times10^5$ to $5\times10^8$ CD3+ or CD8+ total T cells or CD3+ or CD8+ recombinant receptor-expressing cells, from or from about $5\times10^5$ to $1\times10^7$ CD3+ or CD8+ total T cells or CD3+ or CD8+ recombinant receptor-expressing cells, or from or from about $1\times10^6$ to $1\times10^7$ CD3+ or CD8+ total T cells or CD3+ or CD8+ recombinant receptor-expressing cells, each inclusive. In some embodiments, the cell therapy comprises administration of a dose comprising a number of cell from or from about $1\times10^5$ to $5\times10^8$ total CD3+/CAR+ or CD8+/CAR+ cells, from or from about $5\times10^5$ to $1\times10^7$ total CD3+/CAR+ or CD8+/CAR+ cells, or from or from about $1\times10^6$ to $1\times10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1\times10^6$ and $5\times10^8$ total recombinant receptor (e.g., CAR)-expressing CD8+ cells, e.g., in the range of about $5\times10^6$ to $1\times10^8$ such cells, such cells $1\times10^7$, $2.5\times10^7$, $5\times10^7$, $7.5\times10^7$, $1\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing CD8+ T cells, $1\times10^7$ to $2.5\times10^7$ total recombinant receptor-expressing CD8+ T cells, from or from about $1\times10^7$ to $0.75\times10^8$ total recombinant receptor-expressing CD8+ T cells, each inclusive. In some embodiments, the dose of cells comprises the administration of or about $1\times10^7$, $2.5\times10^7$, $5\times10^7$ $7.5\times10^7$, $1\times10^8$, or $5\times10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In some embodiments, the cell therapy comprises administration of a dose comprising a number of cells that is at least or at least about or is or is about $0.1\times10^6$ cells/kg body weight of the subject, $0.2\times10^6$ cells/kg, $0.3\times10^6$ cells/kg, $0.4\times10^6$ cells/kg, $0.5\times10^6$ cells/kg, $1\times10^6$ cell/kg, $2.0\times10^6$ cells/kg, $3\times10^6$ cells/kg or $5\times10^6$ cells/kg.

In some embodiments, the cell therapy comprises administration of a dose comprising a number of cells is between or between about $0.1\times10^6$ cells/kg body weight of the subject and $1.0\times10^7$ cells/kg, between or between about $0.5\times10^6$ cells/kg and $5\times10^6$ cells/kg, between or between about $0.5\times10^6$ cells/kg and $3\times10^6$ cells/kg, between or between about $0.5\times10^6$ cells/kg and $2\times10^6$ cells/kg, between or between about $0.5\times10^6$ cells/kg and $1\times10^6$ cell/kg, between or between about $1.0\times10^6$ cells/kg body weight of the subject and $5\times10^6$ cells/kg, between or between about $1.0\times10^6$ cells/kg and $3\times10^6$ cells/kg, between or between about $1.0\times10^6$ cells/kg and $2\times10^6$ cells/kg, between or between about $2.0\times10^6$ cells/kg body weight of the subject and $5\times10^6$ cells/kg, between or between about $2.0\times10^6$ cells/kg and $3\times10^6$ cells/kg, or between or between about $3.0\times10^6$ cells/kg body weight of the subject and $5\times10^6$ cells/kg, each inclusive.

In some embodiments, the dose of cells comprises between at or about $2\times10^5$ of the cells/kg and at or about $2\times10^6$ of the cells/kg, such as between at or about $4\times10^5$ of the cells/kg and at or about $1\times10^6$ of the cells/kg or between at or about $6\times10^5$ of the cells/kg and at or about $8\times10^5$ of the cells/kg. In some embodiments, the dose of cells comprises no more than $2\times10^5$ of the cells (e.g. antigen-expressing, such as CAR-expressing cells) per kilogram body weight of the subject (cells/kg), such as no more than at or about $3\times10^5$ cells/kg, no more than at or about $4\times10^5$ cells/kg, no more than at or about $5\times10^5$ cells/kg, no more than at or about $6\times10^5$ cells/kg, no more than at or about $7\times10^5$ cells/kg, no more than at or about $8\times10^5$ cells/kg, nor more than at or about $9\times10^5$ cells/kg, no more than at or about $1\times10^6$ cells/kg, or no more than at or about $2\times10^6$ cells/kg. In some embodiments, the dose of cells comprises at least or at least about or at or about $2\times10^5$ of the cells (e.g. antigen-expressing, such as CAR-expressing cells) per kilogram body weight of the subject (cells/kg), such as at least or at least about or at or about $3\times10^5$ cells/kg, at least or at least about or at or about $4\times10^5$ cells/kg, at least or at least about or at or about $5\times10^5$ cells/kg, at least or at least about or at or about $6\times10^5$ cells/kg, at least or at least about or at or about $7\times10^5$ cells/kg, at least or at least about or at or about $8\times10^5$ cells/kg, at least or at least about or at or about $9\times10^5$ cells/kg, at least or at least about or at or about 1×10⁶ cells/kg, or at least or at least about or at or about 2×10⁶ cells/kg.

In the context of adoptive cell therapy, administration of a given "dose" of cells encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

The term "split dose" refers to a dose that is split so that it is administered over more than one day. This type of dosing is encompassed by the present methods and is considered to be a single dose. In some embodiments, the cells of a split dose are administered in a plurality of compositions, collectively comprising the cells of the dose, over a period of no more than three days.

Thus, the dose of cells may be administered as a split dose. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8+ and CD4+ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4+ to CD8+ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4+ to CD8+ cells, and/or is based on a desired fixed or minimum dose of CD4+ and/or CD8+ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of CD4+ to CD8+ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, administration of the immunomodulatory compound in combination with the cells is able to significantly increase the expansion or proliferation of the cells, and thus a lower dose of cells can be administered to the subject. In some cases, the provided methods allow a lower dose of such cells to be administered, to achieve the same or better efficacy of treatment as the dose in a method in which the cell therapy is administered without administering the immunomodulatory compound, such as at least 1.5-fold, 2-fold, 3-fold, 4-fold, 5-fold or 10-fold less than the dose in a method in which the cell therapy is administered without administering the immunomodulatory compound, e.g., lenalidomide or Compound 1.

In some embodiments, for example, the dose contains between or between about $5.0 \times 10^6$ and $2.25 \times 10^7$, $5.0 \times 10^6$ and $2.0 \times 10^7$, $5.0 \times 10^6$ and $1.5 \times 10^7$, $5.0 \times 10^6$ and $1.0 \times 10^7$, $5.0 \times 10^6$ and $7.5 \times 10^6$, $7.5 \times 10^6$ and $2.25 \times 10^7$, $7.5 \times 10^6$ and $2.0 \times 10^7$, $7.5 \times 10^6$ and $1.5 \times 10^7$, $7.5 \times 10^6$ and $1.0 \times 10^7$, $1.0 \times 10^7$ and $2.25 \times 10^7$, $1.0 \times 10^7$ and $2.0 \times 10^7$, $1.0 \times 10^7$ and $1.5 \times 10^7$, $1.5 \times 10^7$ and $2.25 \times 10^7$, $1.5 \times 10^7$ and $2.0 \times 10^7$, $2.0 \times 10^7$ and $2.25 \times 10^7$. In some embodiments, the dose of cells contains a number of cells, that is between at least or at least about $5 \times 10^6$, $6 \times 10^6$, $7 \times 10^6$, $8 \times 10^6$, $9 \times 10^6$, $10 \times 10^6$ and about $15 \times 10^6$ recombinant-receptor expressing cells, such as recombinant-receptor expressing cells that are CD8+. In some embodiments, such dose, such as such target number of cells refers to the total recombinant-receptor expressing cells in the administered composition.

In some embodiments, for example, the lower dose contains less than about $5 \times 10^6$ cells, recombinant receptor (e.g. CAR)-expressing cells, T cells, and/or PBMCs per kilogram body weight of the subject, such as less than about $4.5 \times 10^6$, $4 \times 10^6$, $3.5 \times 10^6$, $3 \times 10^6$, $2.5 \times 10^6$, $2 \times 10^6$, $1.5 \times 10^6$, $1 \times 10^6$, $5 \times 10^5$, $2.5 \times 10^5$, or $1 \times 10^5$ such cells per kilogram body weight of the subject. In some embodiments, the lower dose contains less than about $1 \times 10^5$, $2 \times 10^5$, $5 \times 10^5$, or $1 \times 10^6$ of such cells per kilogram body weight of the subject, or a value within the range between any two of the foregoing values. In some embodiments, such values refer to numbers of recombinant receptor-expressing cells; in other embodiments, they refer to number of T cells or PBMCs or total cells administered.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses. In some embodiments, one or more subsequent dose of cells can be administered to the subject. In some embodiments, the subsequent dose of cells is administered greater than or greater than about 7 days, 14 days, 21 days, 28 days or 35 days after initiation of administration of the first dose of cells. The subsequent dose of cells can be more than, approximately the same as, or less than the first dose. In some embodiments, administration of the T cell therapy, such as administration of the first and/or second dose of cells, can be repeated.

In some embodiments, initiation of administration of the cell therapy, e.g. the dose of cells or a first dose of a split dose of cells, is administered before (prior to), concurrently with or after (subsequently or subsequent to) the administration of the immunomodulatory compound, e.g., lenalidomide, Compound 1 or Compound 2.

In some embodiments, the dose of cells, or the subsequent dose of cells, is administered concurrently with initiating administration of the immunomodulatory compound in accord with the combination therapy methods. In some embodiments, the dose of cells, or the subsequent dose of cells, is administered on the same day as initiating administration of the immunomodulatory compound in accord with the combination therapy methods. In some embodiments, the dose of cells, or the subsequent dose of cells, is administered within 1 day, within 2 days, within 3 days, within 4 days, within 5 days, within 6 days, or within 7 days of initiating administration of the immunomodulatory compound in accord with the combination therapy methods.

In some embodiments, the dose of cells, or the subsequent dose of cells, is administered prior to starting or initiating administration of the immunomodulatory compound in accord with the provided combination therapy. In some embodiments, the dose of cells is administered at least or at least about 1 hour, at least or at least about 2 hours, at least or at least about 3 hours, at least or at least about 6 hours, at least or at least about 12 hours, at least or at least about 1 day, at least or at least about 2 days, at least or at least about 3 days, at least or about at least 4 days, at least or at least about 5 days, at least or about at least 6 days, at least or at least about 7 days, at least or about at least 12 days, at least or at least about 14 days, at least or about at least 15 days, at least or at least about 21 days, at least or at least about 28 days, at least or about at least 30 days, at least or at least about 35 days, at least or at least about 42 days, at least or about at least 60 days or at least or about at least 90 days prior to administering the immunomodulatory compound in accord with the provided combination therapy.

In some embodiments, the administration of the immunomodulatory compound (e.g., lenalidomide or Compound 1) immunomodulatory compound in accord with the provided combination therapy is at a time in which the prior administration of the immunotherapy (e.g., T cell therapy, such as CAR-T cell therapy) is associated with, or is likely to be associated with, a decreased functionality of the T cells compared to the functionality of the T cells at a time just prior to initiation of the immunotherapy (e.g., T cell therapy, such as CAR-T cell therapy) or at a preceding time point after initiation of the T cell therapy. In some embodiments, the method involves, subsequent to administering the dose of cells of the T cell therapy, e.g., adoptive T cell therapy, but prior to administering the immunomodulatory compound, assessing a sample from the subject for one or more function of T cells, such as expansion or persistence of the cells, e.g. as determined by level or amount in the blood, or other phenotypes or desired outcomes as described herein, e.g., such as those described in Section III. In some embodiments, the method involves, subsequent to administering the dose of cells of the T cell therapy, e.g., adoptive T cell therapy, but prior to administering the immunomodulatory compound, assessing a sample from the subject for expression of one or more exhaustion markers. Various parameters for determining or assessing the regimen of the combination therapy are described in Section III.

B. Administration of the Immunomodulatory Compound

The provided combination therapy methods, compositions, combinations, kits and uses involve administration of an immunomodulatory compound, such as a structural or functional analog or derivative of thalidomide and/or an inhibitor of E3 ubiquitin ligase, e.g. lenalidomide, Compound 1 or Compound 2, which can be administered prior to, subsequently to, during, simultaneously or near simultaneously, sequentially and/or intermittently with administration of the T cell therapy, e.g., administration of T cells expressing a chimeric antigen receptor (CAR).

In some embodiments, the immunomodulatory compound is one of a class of immunomodulatory compounds that is a structural or functional analog or derivative of thalidomide and/or an inhibitor of E3 ubiquitin ligase. In particular embodiments, the immunomodulatory compound is an inhibitor of E3 ubiquitin ligase.

In some embodiments, the immunomodulatory compound binds to cereblon (CRBN). In some embodiments, the immunomodulatory compound binds to the CRBN E3 ubiquitin-ligase complex. In some embodiments, the immunomodulatory compound binds to CRBN and the CRBN E3 ubiquitin-ligase complex. In some embodiments, the immunomodulatory compound up-regulates the protein or gene expression of CRBN. In some aspects, CRBN is the substrate adaptor for the CRL4$^{CRBN}$ E3 ubiquitin ligase, and modulates the specificity of the enzyme. In some embodiments, binding to CRB or the CRBN E3 ubiquitin ligase complex inhibits E3 ubiquitin ligase activity. In some embodiments, the immunomodulatory compound induces the ubiqutination of KZF1 (Ikaros) and IKZF3 (Aiolos) and/or induces degradation of IKZF1 (Ikaros) and IKZF3 (Aiolos). In some embodiments, the immunomodulatory compound induces the ubiquitination of casein kinase 1A1 (CK1α) by the CRL4$^{CRBN}$ E3 ubiquitin ligase. In some embodiments, the ubiquitination of CK1α results in CK1α degradation.

In some embodiments, the immunomodulatory compound is an inhibitor of the Ikaros (IKZF1) transcription factor. In some embodiments, the immunomodulatory compound enhances ubiquitination of Ikaros. In some embodiments, the immunomodulatory compound enhances the degradation of Ikaros. In some embodiments, the immunomodulatory compound down-regulates the protein or gene expression of Ikaros. In some embodiments, administration of the immunomodulatory compound causes a decrease in Ikaros protein levels.

In some embodiments, the immunomodulatory compound is an inhibitor of the Aiolos (IKZF3) transcription factor. In some embodiments, the immunomodulatory compound enhances ubiquitination of Aiolos. In some embodiments, the immunomodulatory compound enhances the degradation of Aiolos. In some embodiments, the immunomodulatory compound down-regulates the protein or gene expression of Aiolos. In some embodiments, administration of the immunomodulatory compound causes a decrease in Aiolos protein levels.

In some embodiments, the immunomodulatory compound is an inhibitor of both the Ikaros (IKZF1) and Aiolos (IKZF3) transcription factors. In some embodiments, the immunomodulatory compound enhances ubiquitination of both Ikaros and Aiolos. In some embodiments, the immunomodulatory compound enhances the degradation of both Ikaros and Aiolos. In some embodiments, the immunomodulatory compound enhances ubiquitination and degradation of both Ikaros and Aiolos. In some embodiments, administration of the immunomodulatory compound causes both Aiolos protein levels and Ikaros protein levels to decrease.

In some embodiments, the immunomodulatory compound is a Selective cytokine inhibitory drug (SelCID). In some embodiments, the immunomodulatory compound inhibit the activity of phosphodiesterase-4 (PDE4). In some embodiments, the immunomodulatory compound suppresses the enzymatic activity of the CDC25 phosphatases. In some embodiments, the immunomodulatory compound alters the intracellular trafficking of CDC25 phosphatases.

In some embodiments, the immunomodulatory compound in the combination therapy is thalidomide (2-(2,6-dioxopiperidin-3-yl)-1H-isoindole-1,3(2H)-dione) or an analog or derivative of thalidomide. In certain embodiments, a thalidomide derivative includes structural variants of thalidomide that have a similar biological activity. Exemplary thalidomide derivatives include, but are not limited to lenalidomide (REVLIMMUNOMODULATORY COMPOUND™; Celgene Corporation), pomalidomide (also known as ACTIMMUNOMODULATORY COMPOUND™ or POMALYST™ (Celgene Corporation)), CC-1088, CDC-501, and CDC-801, and the compounds disclosed in U.S. Pat. Nos. 5,712,291; 7,320,991; and 8,716,315; U.S. Appl. No. 2016/0313300; and PCT Pub. Nos. WO 2002/068414 and WO 2008/154252.

In some embodiments, the immunomodulatory compound is 1-oxo- and 1,3 dioxo-2-(2,6-dioxopiperldin-3-yl) isoindolines substituted with amino in the benzo ring as described in U.S. Pat. No. 5,635,517 which is incorporated herein by reference.

In some embodiments, the immunomodulatory compound is a compound of the following formula:

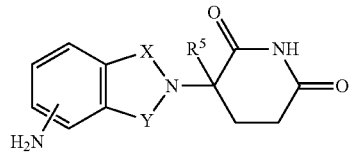

wherein one of X and Y is —C(O)— and the other of X and Y is —C(O)— or —CH$_2$—, and R$^5$ is hydrogen or lower alkyl, or a pharmaceutically acceptable salt thereof. In some embodiments, X is —C(O)— and Y is —CH$_2$—. In some embodiments, both X and Y are —C(O)—. In some embodiments, R$^5$ is hydrogen. In other embodiments, R$^5$ is methyl.

In some embodiments, the immunomodulatory compound is a compound that belongs to a class of substituted 2-(2,6-dioxopiperidin-3-yl)phthalimmunomodulatory compounds and substituted 2-(2,6-dioxopiperldin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference.

In some embodiments, the immunomodulatory compound is a compound of the following formula:

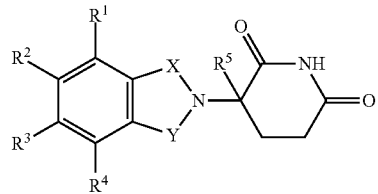

wherein
one of X and Y is —C(O)— and the other of X and Y is —C(O)— or —CH$_2$—;
(1) each of R$^1$, R$^2$, R$^3$, and R$^4$ are independently halo, alkyl of 1 to 4 carbon atoms, or alkoxy or 1 to 4 carbon atoms, or
(2) one of R$^1$, R$^3$, R$^4$, and R$^5$ is —NHR$^a$ and the remaining of R$^1$, R$^2$, R$^3$, and R$^4$ is are hydrogen, wherein R$^a$ is hydrogen or alkyl of 1 to 8 carbon atoms;

R⁵ is hydrogen or alkyl of 1 to 8 carbon atoms, benzyl, or halo; provided that R⁵ is other than hydrogen if X and Y are —C(O)— and (i) each of R¹, R², R³, and R⁴ is fluoro; or (ii) one of R¹, R², R³, and R⁴ is amino;

or a pharmaceutically acceptable salt thereof.

In some embodiments, the immunomodulatory compound is a compound that belongs to a class of isoindole-immunomodulatory compounds disclosed in U.S. Pat. No. 7,091,353, U.S. Patent Publication No. 2003/0045552, and International Application No. PCT/USOI/50401 (International Publication No. WO02/059106), each of which are incorporated herein by reference. For example, in some embodiments, the immunomodulatory compound is [2-(2,6-dioxopiperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl) methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl) methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl) methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl] methyl}(octylamino)carboxamide; or N-{[2-(2,6-dioxo(3-piperidyl))-1,3-dioxoisoindolin-4-yl]methyl}(benzylamino) carboxamide.

In some embodiments, the immunomodulatory compound is a compound that belongs to a class of isoindole-immunomodulatory compounds disclosed in U.S. Patent Application Publication Nos. 2002/0045643, International Publication No. WO 98/54170, and U.S. Pat. No. 6,395,754, each of which is incorporated herein by reference. In some embodiments, the immunomodulatory compound is a tetra substituted 2-(2,6-dioxopiperdin-3-yl)-1-oxoisoindolines described in U.S. Pat. No. 5,798,368, which is incorporated herein by reference. In some embodiments, the immunomodulatory compound is 1-oxo and 1,3-dioxo-2-(2,6-dioxopiperidin-3-yl) isoindolines disclosed in U.S. Pat. No. 6,403,613, which is incorporated herein by reference. In some embodiments the immunomodulatory compound is a 1-oxo or 1,3-dioxoisoindoline substituted in the 4- or 5-position of the indoline ring as described in U.S. Pat. Nos. 6,380,239 and 7,244,759, both of which are incorporated herein by reference.

In some embodiments, the immunomodulatory compound is 2-(4-amino-1-oxo-1,3-dihydro-isoindol-2-yl)-4-carbamoyl-butyric acid or 4-(4-amino-1-oxo-1,3-dihydro-isoindol-2-yl)-4-carbamoyl-butyric acid. In some embodiments, the immunomodulatory compound is 4-carbamoyl-4-{4-[(furan-2-yl-methyl)-amino]-1,3-dioxo-1,3-dihydro-isoindol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, or 2-{4-[(furan-2-yl-methyl)-amino]-1,3-dioxo-1,3-dihydro-isoindol-2-yl}-pentanedioic acid.

In some embodiments, the immunomodulatory compound is a isoindoline-1-one or isoindoline-1,3-dione substituted in the 2-position with 2,6-dioxo-3-hydroxypiperidin-5-yl as described in U.S. Pat. No. 6,458,810, which is incorporated herein by reference. In some embodiments, the immunomodulatory compound is 3-(5-amino-2-methyl-4-oxo-4H-quinazolin-3-yl)-piperidine-2,6-dione, or an enantiomer or a mixture of enantiomers thereof; or a pharmaceutically acceptable salt, solvate, hydrate, co-crystal, clathrate, or polymorph thereof. In some embodiments, the immunomodulatory compound is 3-[4-(4-morpholin-4-ylmethyl-benzyloxy)-1-oxo-1,3-dihydro-isoindol-2-yl]-piperidine-2,6-dione.

In some embodiments, the immunomodulatory compound is a 4'arylmethoxy isoindoline compound, as described in U.S. Pat. No. 9,828,361, which is incorporated herein by reference. In some embodiments, the immunomodulatory compound is a compound of the following formula:

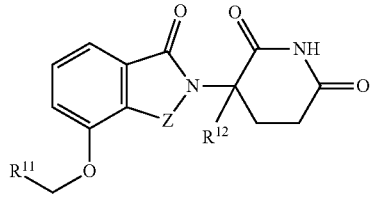

or a pharmaceutically acceptable salt, solvate or stereoisomer thereof, wherein:

Z is C=O or CH₂;

R¹¹ is —Z¹—R¹³;

R¹² is H or (C₁-C₆)alkyl;

Z¹ is 6 to 10 membered aryl, heteroaryl, or heterocycle, each of which may be optionally substituted with one or more halogen; or a bond;

R¹³ is —(CH₂)ₙ-aryl, —O—(CH₂)ₙ-aryl, or —(CH₂)ₙ—O-aryl, wherein the aryl is optionally substituted with one or more: (C₁-C₆)alkyl; itself optionally substituted with one or more halogen; (C₁-C₆)alkoxy, itself substituted with one or more halogen; oxo; amino; carboxyl; cyano; hydroxyl; halogen; deuterium; 6 to 10 membered aryl or heteroaryl, optionally substituted with one or more (C₁-C₆)alkyl, (C₁-C₆)alkoxy, or halogen; —CONH₂; or —COO—(C₁-C₆) alkyl, wherein the alkyl may be optionally substituted with one or more halogen; —(CH₂)ₙ-heterocycle, —O—(CH₂)ₙ-heterocycle or —(CH₂)ₙ—O-heterocycle, wherein the heterocycle is optionally substituted with one or more: (C₁-C₆) alkyl, itself optionally substituted with one or more halogen; (C₁-C₆)alkoxy, itself substituted with one or more halogen; oxo; amino; carboxyl; cyano; hydroxyl; halogen; deuterium; 6 to 10 membered aryl or heteroaryl, optionally substituted with one or more (C₁-C₆)alkyl, (C₁-C₆)alkoxy or halogen; —CONH₂; or —COO—(C₁-C₆)alkyl, wherein the alkyl may be optionally substituted with one or more halogen; or —(CH₂)ₙ-heteroaryl, —O—(CH₂)ₙ-heteroaryl or —(CH₂)ₙ—O-heteroaryl, wherein the heteroaryl is optionally substituted with one or more: (C₁-C₆)alkyl, itself optionally substituted with one or more halogen; (C₁-C₆) alkoxy, itself substituted with one or more halogen; oxo; amino; carboxyl; cyano; hydroxyl; halogen; deuterium; 6 to 10 membered aryl or heteroaryl, optionally substituted with one or more $(C_1-C_6)$alkyl, $(C_1-C_6)$alkoxy or halogen; —$CONH_2$; or —COO—$(C_1-C_6)$alkyl, wherein the alkyl may be optionally substituted with one or more halogen; and n is 0, 1, 2 or 3.

In some embodiments, the immunomodulatory compound is a (S)-3-[4-(4-morpholin-4-ylmethyl-benzyloxy)-1-oxo-1,3-dihydro-isoindol-2-yl]-piperidine-2,6-dione, or a pharmaceutically acceptable salt, solvate, hydrate, co-crystal, clathrate, or polymorph thereof. In some embodiments, (S)-3-[4-(4-morpholin-4-ylmethyl-benzyloxy)-1-oxo-1,3-dihydro-isoindol-2-yl]-piperidine-2,6-dione is also called (3S)-3-[7-[[4-(morpholin-4-ylmethyl)phenyl]methoxy]-3-oxo-1H-isoindol-2-yl]piperidine-2,6-dione, (S)-3-(4-((4-(morpholinomethyl)benzyl)oxy)-1-oxoisoindolin-2-yl)piperidine-2,6-dione, or iberdomide. In some embodiments, the immunomodulatory compound is iberdomide or iberdomide hydrochloride.

In some embodiments, the immunomodulatory compound is an enantiomer or a mixture of enantiomers of (S)-3-[4-(4-morpholin-4-ylmethyl-benzyloxy)-1-oxo-1,3-dihydro-isoindol-2-yl]-piperidine-2,6-dione, or a pharmaceutically acceptable salt, solvate, hydrate, co-crystal, clathrate, or polymorph thereof. In some embodiments, the immunomodulatory compound is (S)-3-[4-(4-morpholin-4-ylmethyl-benzyloxy)-1-oxo-1,3-dihydro-isoindol-2-yl]-piperidine-2,6-dione, or a pharmaceutically acceptable salt, solvate, hydrate, co-crystal, clathrate, or polymorph thereof. In some embodiments, the immunomodulatory compound is (R)-3-[4-(4-morpholin-4-ylmethyl-benzyloxy)-1-oxo-1,3-dihydro-isoindol-2-yl]-piperidine-2,6-dione, or a pharmaceutically acceptable salt, solvate, hydrate, co-crystal, clathrate, or polymorph thereof. In some embodiments, the immunomodulatory compound is a solvate of (S)-3-[4-(4-morpholin-4-ylmethyl-benzyloxy)-1-oxo-1,3-dihydro-isoindol-2-yl]-piperidine-2,6-dione. In some embodiments, the immunomodulatory compound is a hydrate of (S)-3-[4-(4-morpholin-4-ylmethyl-benzyloxy)-1-oxo-1,3-dihydro-isoindol-2-yl]-piperidine-2,6-dione. In some embodiments, the immunomodulatory compound is a salt or solid form of 3-(4-((4-(morpholinomethyl)benzyl)oxy)-1-oxoisoindolin-2-yl)piperidine-2,6-dione, or a stereoisomer thereof, as described in U.S. Pat. No. 9,629,849, which is incorporated herein by reference. In some embodiments, the immunomodulatory compound is a pharmaceutically acceptable salt of 3-[4-(4-morpholin-4-ylmethyl-benzyloxy)-1-oxo-1,3-dihydro-isoindol-2-yl]-piperidine-2,6-dione. In some embodiments, the immunomodulatory compound is a pharmaceutically acceptable salt of (S)-3-[4-(4-morpholin-4-ylmethyl-benzyloxy)-1-oxo-1,3-dihydro-isoindol-2-yl]-piperidine-2,6-dione. For example, in some embodiments, the immunomodulatory compound is a hydrochloride salt of (S)-3-[4-(4-morpholin-4-ylmethyl-benzyloxy)-1-oxo-1,3-dihydro-isoindol-2-yl]-piperidine-2,6-dione. In certain embodiments, the immunomodulatory compound is the Form A crystal form of the hydrochloride salt of (S)-3-[4-(4-morpholin-4-ylmethyl-benzyloxy)-1-oxo-1,3-dihydro-isoindol-2-yl]-piperidine-2,6-dione, as disclosed in U.S. Pat. No. 9,629,849. In some embodiments, the Form A crystal form of the hydrochloride salt of (S)-3-[4-(4-morpholin-4-ylmethyl-benzyloxy)-1-oxo-1,3-dihydro-isoindol-2-yl]-piperidine-2,6-dione is characterized by XRPD peaks located at t 1, 2, 3, 4, 5, 6, 7, 8, 9, 10, 11, 12, 13, 14, 15, 16, 17, 18, 19, 20 or all of the following or approximately the following positions: 9.69, 12.82, 15.09, 15.94, 16.76, 17.65, 19.44, 19.80, 2230, 22.47, 22.95, 23.02, 24.29, 24.48, 24.70, 26.27, 26.77, 27.60, 29.43, 29.72, and 32.91 degrees 20. In some embodiments, the immunomodulatory compound is a salt, hydrate, anhydrate, or solvate of the hydrochloride salt of 3-(4-((4-(morpholinomethyl)benzyl)oxy)-1-oxoisoindolin-2-yl)piperidine-2,6-dione. In some embodiments, the immunomodulatory compound is a polymorph of (S)-3-[4-(4-morpholin-4-ylmethyl-benzyloxy)-1-oxo-1,3-dihydro-isoindol-2-yl]-piperidine-2,6-dione. In some embodiments, the immunomodulatory compound is (S)-3-[4-(4-morpholin-4-ylmethyl-benzyloxy)-1-oxo-1,3-dihydro-isoindol-2-yl]-piperidine-2,6-dione. In some embodiments, the immunomodulatory compound, is

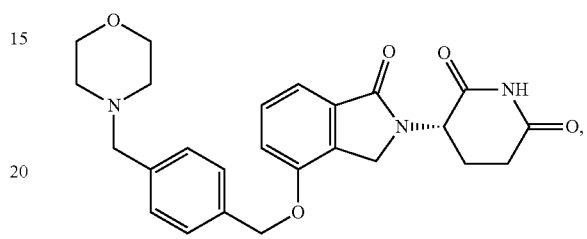

or a pharmaceutically acceptable salt, solvate, hydrate, co-crystal, clathrate, or polymorph thereof (hereinafter Compound 2).

In some embodiments, the immunomodulatory compound is as described in Oshima, K. et al., *Nihon Rinsho.*, 72(6): 1130-5 (2014); Millrine, D. et al., *Trends Mol Med.*, 23(4): 348-364 (2017); and Collins, et al., *Biochem J.*, 474(7): 1127-1147 (2017).

In some embodiments, the immunomodulatory compound is an inhibitor of E3 ubiquitin ligase. In some embodiments, the immunomodulatory compound is a derivative of thalidomide. In some embodiments, the immunomodulatory compound is a structural and/or functional analogue of thalidomide. In some embodiments, the immunomodulatory compound is lenalidomide, pomalidomide, avadomide, or a pharmaceutically acceptable salt thereof.

In some embodiments, the immunomodulatory compound is lenalidomide, pomalidomide, avadomide, a stereoisomer of lenalidomide, pomalidomide, avadomide or a pharmaceutically acceptable salt, solvate, hydrate, co-crystal, clathrate, or polymorph thereof. In some embodiments, the immunomodulatory compound is lenalidomide, a stereoisomer of lenalidomide or a pharmaceutically acceptable salt, solvate, hydrate, co-crystal, clathrate, or polymorph thereof.

In some embodiments, the immunomodulatory compound is avadomide, which also is known as 3-(5-amino-2-methyl-4-oxo-4H-quinazolin-3-yl)-piperidine-2,6-dione having the following structure

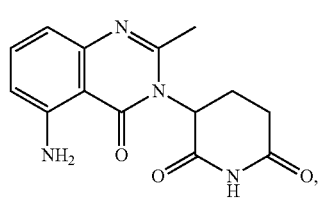

(Formula I)

or is an enantiomer or a mixture of enantiomers thereof, or a pharmaceutically acceptable salt, solvate, hydrate, co-crystal, clathrate, or polymorph thereof (hereinafter Compound 1).

In some embodiments, the immunomodulatory compound is an enantiomer or a mixture of enantiomers of 3-(5-amino-2-methyl-4-oxo-4H-quinazolin-3-yl)-piperidine-2,6-dione, or a pharmaceutically acceptable salt, solvate, hydrate, co-crystal, clathrate, or polymorph of 3-(5-amino-2-methyl-4-oxo-4H-quinazolin-3-yl)-piperidine-2,6-dione. In some embodiments, the immunomodulatory compound is a solvate of 3-(5-amino-2-methyl-4-oxo-4H-quinazolin-3-yl)-piperidine-2,6-dione. In some embodiments, the immunomodulatory compound is a hydrate of 3-(5-amino-2-methyl-4-oxo-4H-quinazolin-3-yl)-piperidine-2,6-dione. In some embodiments, the immunomodulatory compound is a pharmaceutically acceptable salt of 3-(5-amino-2-methyl-4-oxo-4H-quinazolin-3-yl)-piperidine-2,6-dione. In some embodiments, the immunomodulatory compound is a polymorph of 3-(5-amino-2-methyl-4-oxo-4H-quinazolin-3-yl)-piperidine-2,6-dione. In some embodiments, the immunomodulatory compound is 3-(5-amino-2-methyl-4-oxo-4H-quinazolin-3-yl)-piperidine-2,6-dione. In some embodiments, the immunomodulatory compound has the structure of Formula I.

In some embodiments, the immunomodulatory compound is lenalidomide, which also is known as 3-(4-amino-1-oxo-1,3-dihydro-2H-isoindol-2-yl)piperidine-2,6-dione, or is an enantiomer or a mixture of enantiomers thereof, or a pharmaceutically acceptable salt, solvate, hydrate, co-crystal, clathrate, or polymorph thereof. In some embodiments, lenalidomide is 2,6-Piperidinedione, 3-(4-amino-1,3-dihydro-1-oxo-2H-isoindol-2-yl)-, 3-(4-Amino-1-oxo-1,3-dihydro-2H-isoindol-2-yl)-2,6-piperidinedione, 3-(4-Amino-1-oxo-1,3-dihydro-2H-isoindol-2-yl)-2,6-piperidinedione, 3-(4-Amino-1-oxo-1,3-dihydro-2H-isoindol-2-yl)piperidin-2,6-dion, 3-(4-amino-1-oxo-1,3-dihydro-2H-isoindol-2-yl)piperidine-2,6-dione, 3-(4-amino-1-oxo-1,3-dihydro-2H-isoindol-2-yl)piperidine-2,6-dione, all of which can be used interchangeably, or is an enantiomer or a mixture of enantiomers thereof, or a pharmaceutically acceptable salt, solvate, hydrate, co-crystal, clathrate, or polymorph thereof.

In some embodiments, the immunomodulatory compound is (R)-3-(4-amino-1-oxo-1,3-dihydro-2H-isoindol-2-yl)piperidine-2,6-dione. In some embodiments, the immunomodulatory compound is (S)-3-(4-amino-1-oxo-1,3-dihydro-2H-isoindol-2-yl)piperidine-2,6-dione. In some embodiments, the immunomodulatory compound is a mixture of (R)-3-(4-amino-1-oxo-1,3-dihydro-2H-isoindol-2-yl)piperidine-2,6-dione and (S)-3-(4-amino-1-oxo-1,3-dihydro-2H-isoindol-2-yl)piperidine-2,6-dione.

In some embodiments, the immunomodulatory compound is

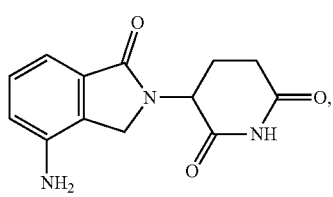

(Formula II)

or an enantiomer or a mixture of enantiomers thereof; or a pharmaceutically acceptable salt, solvate, hydrate, co-crystal, clathrate, or polymorph thereof. In some embodiments, the immunomodulatory compound is

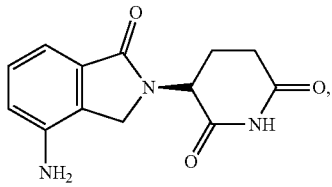

(Formula IIA)

or a pharmaceutically acceptable salt, solvate, hydrate, co-crystal, clathrate, or polymorph thereof. In other embodiments, the immunomodulatory compound is

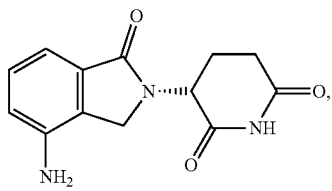

(Formula IIB)

or a pharmaceutically acceptable salt, solvate, hydrate, co-crystal, clathrate, or polymorph thereof. In certain embodiments, the immunomodulatory compound comprises a mixture of

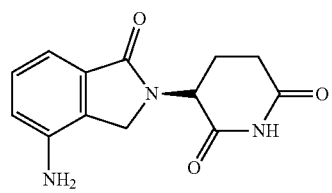

(Formula IIA)

and

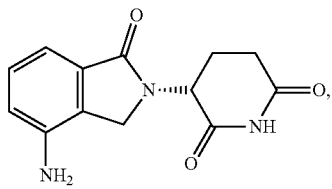

(Formula IIB)

or pharmaceutically acceptable salts, solvates, hydrates, co-crystals, clathrates, or polymorphs thereof.

In some embodiments, the immunomodulatory compound is an enantiomer or a mixture of enantiomers of 3-(4-Amino-1-oxo-1,3-dihydro-2H-isoindol-2-yl)piperidine-2,6-dione, or a pharmaceutically acceptable salt, solvate, hydrate, co-crystal, clathrate, or polymorph of 3-(4-Amino-1-oxo-1,3-dihydro-2H-isoindol-2-yl)piperidine-2,6-dione. In some embodiments, the immunomodulatory compound is a solvate of (R)-3-(4-Amino-1-oxo-1,3-dihydro-2H-isoindol-2-yl)piperidine-2,6-dione and/or (S)-3-(4-Amino-1-oxo-1,3-dihydro-2H-isoindol-2-yl)piperidine-2,6-dione. In some embodiments, the immunomodulatory compound is a hydrate of (RS)-3-(4-Amino-1-oxo-1,3-dihydro-2H-isoindol-2-yl)piperidine-2,6-dione and/or (S)-3-(4-Amino-1-oxo-1,3-dihydro-2H-isoindol-2-yl)piperidine-2,6-dione. In some embodiments, the immunomodulatory compound is a pharmaceutically acceptable salt of (R)-3-(4-Amino-1-oxo-1,3-dihydro-2H-isoindol-2-yl)piperidine-2,6-dione and/or (S)-3-(4-Amino-1-oxo-1,3-dihydro-2H-isoindol-2-yl)piperidine-2,6-dione. In some embodiments, the immunomodulatory compound is lenalidomide, or 3-(4-amino-1-oxo-1,3-dihydro-2H-isoindol-2-yl)piperidine-2,6-dione. In some embodiments, the immunomodulatory compound has the structure of Formula II. In some embodiments, the immunomodulatory compound has the structure of Formula IIA or Formula IIB or a mixture thereof.

In some embodiments, the immunomodulatory compound is pomalidomide, which is also known as 4-amino-2-(2,6-dioxopiperidin-3-yl)isoindoline-1,3-dione, or is an enantiomer or a mixture of enantiomers thereof; or a pharmaceutically acceptable salt, solvate, hydrate, co-crystal, clathrate, or polymorph thereof. In some embodiments, the immunomodulatory compound is

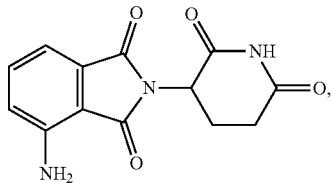

(Formula III)

or an enantiomer or a mixture of enantiomers thereof; or a pharmaceutically acceptable salt, solvate, hydrate, co-crystal, clathrate, or polymorph thereof. In some embodiments, the immunomodulatory compound is

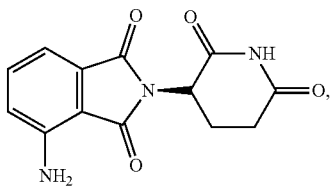

(Formula IIIA)

or a pharmaceutically acceptable salt, solvate, hydrate, co-crystal, clathrate, or polymorph thereof. In other embodiments, the immunomodulatory compound is

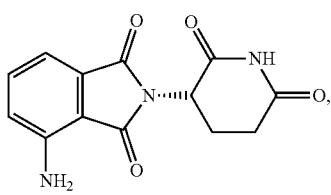

(Formula IIIB)

or a pharmaceutically acceptable salt, solvate, hydrate, co-crystal, clathrate, or polymorph thereof. In certain embodiments, the immunomodulatory compound comprises a mixture of

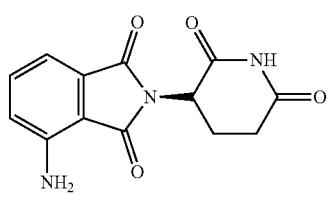

(Formula IIIA)

and

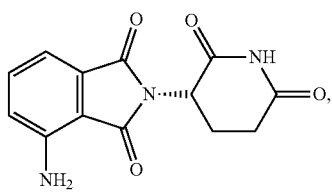

(Formula IIIB)

or pharmaceutically acceptable salts, solvates, hydrates, co-crystals, clathrates, or polymorphs thereof.

In some embodiments, the immunomodulatory compound is an enantiomer or a mixture of enantiomers of 4-amino-2-(2,6-dioxopiperidin-3-yl)isoindoline-1,3-dione, or a pharmaceutically acceptable salt, solvate, hydrate, co-crystal, clathrate, or polymorph of 4-amino-2-(2,6-dioxopiperidin-3-yl)isoindoline-1,3-dione. In some embodiments, the immunomodulatory compound is (R)-4-amino-2-(2,6-dioxopiperidin-3-yl)isoindoline-1,3-dione and/or (S)-4-amino-2-(2,6-dioxopiperidin-3-yl)isoindoline-1,3-dione, or a pharmaceutically acceptable salt, solvate, hydrate, co-crystal, clathrate, or polymorph of (R)-4-amino-2-(2,6-dioxopiperidin-3-yl)isoindoline-1,3-dione and/or (S)-4-amino-2-(2,6-dioxopiperidin-3-yl)isoindoline-1,3-dione. In some embodiments, the immunomodulatory compound is a solvate of (R)-4-amino-2-(2,6-dioxopiperidin-3-yl)isoindoline-1,3-dione and/or (S)-4-amino-2-(2,6-dioxopiperidin-3-yl)isoindoline-1,3-dione. In some embodiments, the immunomodulatory compound is a hydrate of (R)-4-amino-2-(2,6-dioxopiperidin-3-yl)isoindoline-1,3-dione and/or (S)-4-amino-2-(2,6-dioxopiperidin-3-yl)isoindoline-1,3-dione. In some embodiments, the immunomodulatory compound is a pharmaceutically acceptable salt of (R)-4-amino-2-(2,6-dioxopiperidin-3-yl)isoindoline-1,3-dione and/or (S)-4-amino-2-(2,6-dioxopiperidin-3-yl)isoindoline-1,3-dione. In some embodiments, the immunomodulatory compound is (R)-4-amino-2-(2,6-dioxopiperidin-3-yl)isoindoline-1,3-dione, (S)-4-amino-2-(2,6-dioxopiperidin-3-yl)isoindoline-1,3-dione, or a mixture thereof in any ratio. In some embodiments, the immunomodulatory compound has the structure of Formula III. In some embodiments, the immunomodulatory compound has the structure of Formula IIIA or Formula IIIB or a mixture thereof.

In some embodiments, the immunomodulatory compound is iberdomide, which also is known as (S)-3-[4-(4-morpholin-4-ylmethyl-benzyloxy)-1-oxo-1,3-dihydro-isoindol-2-yl]-piperidine-2,6-dione, having the following structure

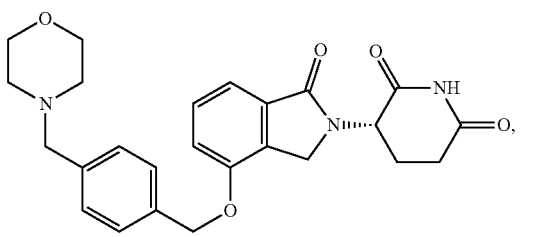 [SMILES: O=C1CC[C@H](N2Cc3c(OCc4ccc(CN5CCOCC5)cc4)cccc3C2=O)C(=O)N1]

(Formula IV)

or is an enantiomer or a mixture of enantiomers thereof, or a pharmaceutically acceptable salt, solvate, hydrate, co-crystal, clathrate, or polymorph thereof (hereinafter Compound 2). In some embodiments, the immunomodulatory compound is iberdomide hydrochloride.

In some embodiments, the immunomodulatory compound is or comprises lenalidomide. Lenalidomide is FDA approved for the treatment of multiple myeloma, myelodysplastic syndrome associated with deletion 5q, and most recently in relapsed/refractory mantle-cell lymphoma (MCL). Lenalidomide is a synthetic derivative of thalidomide, and is currently understood to have multiple immunomodulatory effects, including enforcement of immune synapse formation between T cell and antigen presenting cells (APCs). For example, in some cases, lenalidomide modulates T cell responses and results in increased interleukin (IL)-2 production in $CD4^+$ and $CD8^+$ T cells, induces the shift of T helper (Th) responses from Th2 to Th1, inhibits expansion of regulatory subset of T cells (Tregs), and improves functioning of immunological synapses in follicular lymphoma (FL) and chronic lymphocytic leukemia (CLL) (Otahal et al., Oncoimmunology (2016) 5(4): e1115940). Lenalidomide also has direct tumoricidal activity in patients with multiple myeloma (MM) and directly and indirectly modulates survival of CLL tumor cells by affecting supportive cells, such as nurse-like cells found in the microenvironment of lymphoid tissues.

I. Compositions and Formulations

In some embodiments of the combination therapy methods, compositions, combinations, kits and uses provided herein, the combination therapy can be administered in one or more compositions, e.g., a pharmaceutical composition containing an immunomodulatory compound, e.g., lenalidomide, Compound 1 or Compound 2.

In some embodiments, the composition, e.g., a pharmaceutical composition containing the immunomodulatory compound, e.g., lenalidomide or Compound 1, can include carriers such as a diluent, adjuvant, excipient, or vehicle with which the immunomodulatory compound, e.g., lenalidomide, Compound 1 or Compound 2, and/or the cells are administered. Examples of suitable pharmaceutical carriers are described in "Remington's Pharmaceutical Sciences" by E. W. Martin. Such compositions will contain a therapeutically effective amount of the immunomodulatory compound, e.g. lenalidomide, Compound 1 or Compound 2, generally in purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Saline solutions and aqueous dextrose and glycerol solutions also can be employed as liquid carriers, particularly for injectable solutions. The pharmaceutical compositions can contain any one or more of a diluents(s), adjuvant(s), antiadherent(s), binder (s), coating(s), filler(s), flavor(s), color(s), lubricant(s), glidant(s), preservative(s), detergent(s), sorbent(s), emulsifying agent(s), pharmaceutical excipient(s), pH buffering agent(s), or sweetener(s) and a combination thereof. In some embodiments, the pharmaceutical composition can be liquid, solid, a lyophilized powder, in gel form, and/or combination thereof. In some aspects, the choice of carrier is determined in part by the particular inhibitor and/or by the method of administration.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG), stabilizers and/or preservatives. The compositions containing the immunomodulatory compound, e.g., lenalidomide or Compound 1 can also be lyophilized.

In some embodiments, the pharmaceutical compositions can be formulated for administration by any known route including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. In some embodiments, other modes of administration also are contemplated. In some embodiments, the administration is by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, administration is by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration. In some embodiments, it is administered by multiple bolus administrations, for example, over a period of no more than 3 days, or by continuous infusion administration.

In some embodiments, the administration can be local, topical or systemic depending upon the locus of treatment. In some embodiments local administration to an area in need of treatment can be achieved by, for example, but not limited to, local infusion during surgery, topical application, e.g., in conjunction with a wound dressing after surgery, by injection, by means of a catheter, by means of a suppository, or by means of an implant. In some embodiments, compositions also can be administered with other biologically active agents, either sequentially, intermittently or in the same composition. In some embodiments, administration also can include controlled release systems including controlled release formulations and device controlled release, such as by means of a pump. In some embodiments, the administration is oral.

In some embodiments, pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. In some embodiments, unit dosage forms, include, but are not limited to, tablets, capsules, pills, powders, granules, sterile parenteral solutions or suspensions, and oral solutions or suspensions, and oil water emulsions containing suitable quantities of the compounds or pharmaceutically acceptable derivatives thereof. Unit dose forms can be contained ampoules and syringes or individually packaged tablets or capsules. Unit dose forms can be administered in fractions or multiples thereof. In some embodiments, a multiple dose form is a plurality of identical unit dosage forms packaged in a single container to be administered in segregated unit dose form. Examples of multiple dose forms include vials, bottles of tablets or capsules or bottles of pints or gallons.

Active ingredients may be entrapped in microcapsules, in colloidal drug delivery systems (for example, liposomes, albumin microspheres, microemulsions, nano-particles and nanocapsules) or in macroemulsions. In certain embodiments, the pharmaceutical composition containing the immunomodulatory compound, e.g., lenalidomide, Compound 1 or Compound 2, is formulated as an inclusion complex, such as cyclodextrin inclusion complex, or as a liposome. Liposomes can serve to target the host cells (e.g., T-cells or NK cells) to a particular tissue. Many methods are available for preparing liposomes, such as those described in, for example, Szoka et al., Ann. Rev. Biophys. Bioeng., 9: 467 (1980), and U.S. Pat. Nos. 4,235,871, 4,501,728, 4,837,028, and 5,019,369.

The pharmaceutical composition containing the immunomodulatory compound, e.g., lenalidomide, Compound 1 or Compound 2, in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

The compositions containing the immunomodulatory compound, e.g., lenalidomide, Compound 1 or Compound 2, can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

Sustained-release preparations may be prepared. Suitable examples of sustained-release preparations include semipermeable matrices of solid hydrophobic polymers containing the antibody, which matrices are in the form of shaped articles, e.g. films, or microcapsules.

In some embodiments, the composition containing the immunomodulatory compound, e.g., lenalidomide, Compound 1 or Compound 2, are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

2 Immunomodulatory Compound Dosage Schedule

In some embodiments, the provided combination therapy method involves administering to the subject a therapeutically effective amount of an immunomodulatory drug (immunomodulatory compound), e.g., lenalidomide, Compound 1 or Compound 2, and the cell therapy, such as a T cell therapy (e.g. CAR-expressing T cells).

In some embodiments, the administration of the immunomodulatory compound, e.g., lenalidomide, Compound 1 or Compound 2, is initiated prior to, subsequently to, during, during the course of, simultaneously, near simultaneously, sequentially and/or intermittently with the administration of the cell therapy, such as a T cell therapy (e.g. CAR-expressing T cells). In some embodiments, the method involves initiating the administration of the immunomodulatory compound, e.g., lenalidomide, Compound 1 or Compound 2 prior to administration of the T cell therapy. In other embodiments, the method involves initiating the administration of the immunomodulatory compound, e.g., lenalidomide, Compound 1 or Compound 2, after administration of the T cell therapy. In some embodiments, the dosage schedule comprises initiating the administration of the immunomodulatory compound, e.g., lenalidomide, Compound 1 or Compound 2, concurrently or simultaneously with the administration of the T cell therapy.

In some embodiments, the immunomodulatory compound, e.g., lenalidomide, Compound 1 or Compound 2, is administered in a cycle. In some embodiments, the cycle comprises an administration period in which the immunomodulatory compound, e.g., lenalidomide, Compound 1 or Compound 2, is administered followed by a rest period during which the immunomodulatory compound, e.g., lenalidomide, Compound 1 or Compound 2, is not administered. In some embodiments, the total number of days of the cycle, e.g. from the beginning of initiating administration of the immunomodulatory compound, is greater than or greater than about or is about 21 days, 28 days, 30 days, 40 days, 50 days, 60 days or more.

In some embodiments, the initiation of the administration of the immunomodulatory compound, e.g., lenalidomide, Compound 1 or Compound 2, is carried out in at least one cycle and initiation of administration of the T cell therapy are carried out on the same day, optionally concurrently. In some embodiments, the initiation of the administration of the immunomodulatory compound, e.g., lenalidomide, Compound 1 or Compound 2, in at least one cycle is prior to initiation of administration of the T cell therapy. In some embodiments, the initiation of the administration of the immunomodulatory compound, e.g., lenalidomide, Compound 1 or Compound 2, in at least one cycle is concurrent with or on the same day as initiation of administration of the T cell therapy. In some embodiments, the immunomodulatory compound, e.g., lenalidomide, Compound 1 or Compound 2, is administered from or from about 0 to 30 days, such as 0 to 15 days, 0 to 6 days, 0 to 96 hours, 0 to 24 hours, 0 to 12 hours, 0 to 6 hours, or 0 to 2 hours, 2 hours to 15 days, 2 hours to 6 days, 2 hours to 96 hours, 2 hours to 24 hours, 2 hours to 12 hours, 2 hours to 6 hours, 6 hours to 30 days, 6 hours to 15 days, 6 hours to 6 days, 6 hours to 96 hours, 6 hours to 24 hours, 6 hours to 12 hours, 12 hours to 30 days, 12 hours to 15 days, 12 hours to 6 days, 12 hours to 96 hours, 12 hours to 24 hours, 24 hours to 30 days, 24 hours to 15 days, 24 hours to 6 days, 24 hours to 96 hours, 96 hours to 30 days, 96 hours to 15 days, 96 hours to 6 days, 6 days to 30 days, 6 days to 15 days, or 15 days to 30 days prior to initiation of the T cell therapy. In some aspects, the immunomodulatory compound, e.g., lenalidomide, Compound 1 or Compound 2, is administered no more than about 96 hours, 72 hours, 48 hours, 24 hours, 12 hours, 6 hours, 2 hours or 1 hour prior to initiation of the T cell therapy.

In some of any such embodiments in which the immunomodulatory compound, e.g., lenalidomide, is given prior to the cell therapy (e.g. T cell therapy, such as CAR-T cell therapy), the administration of the immunomodulatory compound, e.g., lenalidomide, Compound 1 or Compound 2, continues at regular intervals until the initiation of the cell therapy and/or for a time after the initiation of the cell therapy.

In some embodiments, the immunomodulatory compound, e.g., lenalidomide, Compound 1 or Compound 2, is administered, or is further administered, after administration of the cell therapy (e.g. T cell therapy, such as CAR-T cell therapy). In some embodiments, the immunomodulatory compound, e.g., lenalidomide, Compound 1 or Compound 2, is administered within or within about 1 hours, 2 hours, 6 hours, 12 hours, 24 hours, 48 hours, 96 hours, 4 days, 5 days, 6 days or 7 days, 14 days, 15 days, 21 days, 24 days, 28 days, 30 days, 36 days, 42 days, 60 days, 72 days or 90 days after initiation of administration of the cell therapy (e.g. T cell therapy). In some embodiments, the provided methods involve continued administration, such as at regular intervals, of the immunomodulatory compound after initiation of administration of the cell therapy.

In some embodiments, the immunomodulatory compound, e.g., lenalidomide, Compound 1 or Compound 2, is administered up to or up to about 1 day, up to or up to about 2 days, up to or up to about 3 days, up to or up to about 4 days, up to or up to about 5 days, up to or up to about 6 days, up to or up to about 7 days, up to or up to about 12 days, up to or up to about 14 days, up to or up to about 21 days, up to or up to about 24 days, up to or up to about 28 days, up to or up to about 30 days, up to or up to about 35 days, up to or up to about 42 days, up to or up to about 60 days or up to or up to about 90 days, up to or up to about 120 days, up to or up to about 180 days, up to or up to about 240 days, up to or up about 360 days, or up to or up to about 720 days or more after the initiation of administration of the cell therapy (e.g. T cell therapy, such as CAR-T cell therapy).

In some of any such above embodiments, the immunomodulatory compound, e.g., lenalidomide, Compound 1 or Compound 2, is administered prior to and after initiation of administration of the cell therapy (e.g. T cell therapy, such as CAR-T cell therapy).

In some embodiments, the initiation of the administration of the immunomodulatory compound, e.g., lenalidomide, Compound 1 or Compound 2, is carried out at or after, optionally immediately after or within 1 to 3 days after: (i) peak or maximum level of the cells of the T cell therapy are detectable in the blood of the subject; (ii) the number of cells of the T cell therapy detectable in the blood, after having been detectable in the blood, is not detectable or is reduced, optionally reduced compared to a preceding time point after administration of the T cell therapy; (iii) the number of cells of the T cell therapy detectable in the blood is decreased by or more than 1.5-fold, 2.0-fold, 3.0-fold, 4.0-fold, 5.0-fold, 10-fold or more the peak or maximum number cells of the T cell therapy detectable in the blood of the subject after initiation of administration of the T cell therapy; (iv) at a time after a peak or maximum level of the cells of the T cell therapy are detectable in the blood of the subject, the number of cells of or derived from the T cells detectable in the blood from the subject is less than less than 10%, less than 5%, less than 1% or less than 0.1% of total peripheral blood mononuclear cells (PBMCs) in the blood of the subject; (v) the subject exhibits disease progression and/or has relapsed following remission after treatment with the T cell therapy; and/or (iv) the subject exhibits increased tumor burden as compared to tumor burden at a time prior to or after administration of the T cells and prior to initiation of administration of the immunomodulatory compound.

In some embodiments, the initiation of the administration of the immunomodulatory compound, e.g., lenalidomide, Compound 1 or Compound 2, in at least one cycle is after initiation of administration of the T cell therapy. In some embodiments, the initiation of the administration of the immunomodulatory compound, e.g., lenalidomide, Compound 1 or Compound 2, is at least or about at least 1 day, at least or about at least 2 days, at least or about at least 3 days, at least or about at least 4 days, at least or about at least 5 days, at least or about at least 6 days, at least or about at least 7 days, at least or about at least 8 days, at least or about at least 9 days, at least or about at least 10 days, at least or at least about 12 days, at least or about at least 14 days, at least or at least about 15 days, at least or about at least 21 days, at least or at least about 24 days, at least or about at least 28 days, at least or about at least 30 days, at least or about at least 35 days or at least or about at least 42 days, at least or about at least 60 days, or at least or about at least 90 days after initiation of the administration of the T cell therapy. In some embodiments, the initiation of the administration of the immunomodulatory compound, e.g., lenalidomide, Compound 1 or Compound 2, is carried out at least 2 days after, at least 1 week after, at least 2 weeks after, at least 3 weeks after, or at least 4 weeks after, the initiation of the administration of the T cell therapy. In some embodiments, the initiation of the administration of the immunomodulatory compound, e.g., lenalidomide, Compound 1 or Compound 2, is carried out 2 to 28 days or 7 to 21 days after initiation of administration of the T cell therapy. In some embodiments, the initiation of the administration of the immunomodulatory compound, e.g., lenalidomide, Compound 1 or Compound 2, is carried out at a time that is greater than or greater than about 14 days, 15 days, 16 days, 17 days, 18 days, 19, days, 20 days, 21 days, 24 days, or 28 days after initiation of the administration of the T cell therapy. In some embodiments, the immunomodulatory compound, e.g., lenalidomide, Compound 1 or Compound 2, is administered several times a day, twice a day, daily, every other day, three times a week, twice a week, or once a week after initiation of the cell therapy. In some embodiments, the immunomodulatory compound, e.g., lenalidomide, Compound 1 or Compound 2, is administered daily. In some embodiments the immunomodulatory compound, e.g., lenalidomide, Compound 1 or Compound 2, is administered twice a day. In some embodiments, the immunomodulatory compound, e.g., lenalidomide, Compound 1 or Compound 2, is administered three times a day. In other embodiments, the immunomodulatory compound, e.g., lenalidomide, Compound 1 or Compound 2, is administered every other day. In some embodiments, the immunomodulatory compound, e.g., lenalidomide, Compound 1 or Compound 2, is administered daily. In some embodiments, the immunomodulatory compound, e.g., lenalidomide, Compound 1 or Compound 2, is administered during the administration period for a plurality of consecutive days, such as for up to about 7, 8, 9, 10, 11, 12, 13, 14, 15, 16, 17, 18, 19, 20, 21, 22, 23, 24, 25, 26, 27, 28, 29, 30, or more than 30 consecutive days. In some embodiments, the immunomodulatory compound, e.g., lenalidomide, Compound 1 or Compound 2, is administered for greater than or greater than about 7 consecutive days, greater than or greater than about 14 consecutive days, greater than or greater than about 21 consecutive days, greater than or greater than about 21 consecutive days, or greater than or greater than about 28 consecutive days. In some embodiments, the immunomodulatory compound, e.g., lenalidomide, Compound 1 or Compound 2, is administered during the administration period for up to 21 consecutive days. In some embodiments, the immunomodulatory compound, e.g., lenalidomide, Compound 1 or Compound 2, is administered during the administration period for up to 21 consecutive days, wherein the cycle comprises greater than 30 days beginning upon initiation of the administration of the immunomodulatory compound.

In some embodiments, the immunomodulatory compound, e.g., lenalidomide or Compound 1, is administered during the administration period for no more than about 7, 8, 9, 10, 11, 12, 13, 14, 15, 16, 17, 18, 19, 20, 21, 22, 23, 24, 25, 26, 27, 28, 29, 30, or no more than 30 consecutive days. In certain embodiments, the immunomodulatory compound, e.g., lenalidomide, Compound 1 or Compound 2, is administered once daily for 14 days over a 21 day treatment cycle. In certain embodiments, the immunomodulatory compound, e.g., lenalidomide, Compound 1 or Compound 2, is administered once daily for 21 days over a 28 day treatment cycle. In some embodiments, the immunomodulatory compound, e.g., lenalidomide, Compound 1 or Compound 2, is administered during the administration period for no more than 14 consecutive days.

In some embodiments, the immunomodulatory compound, e.g., lenalidomide, Compound 1 or Compound 2, is administered in a cycle, wherein the cycle comprises the administration of the immunomodulatory compound, e.g., lenalidomide, Compound 1 or Compound 2 for a plurality of consecutive days followed by a rest period during which the immunomodulatory compound is not administered. In some embodiments, the rest period is greater than about 1 day, greater than about 3 consecutive days, greater than about 5 consecutive days, greater than about 7 consecutive days, greater than about 8 consecutive days, greater than about 9 consecutive days, greater than about 10 consecutive days, greater than about 11 consecutive days, greater than about 12 consecutive days, greater than about 13 consecutive days, greater than about 14 consecutive days, greater than about 15 consecutive days, greater than about 16 consecutive days, greater than about 17 consecutive days, greater than about 18 consecutive days, greater than about 19 consecutive days, greater than about 20 consecutive days, or greater than about 21 or more consecutive days. In some embodiments, the rest period is greater than 7 consecutive days, greater than 14 consecutive days, greater than 21 days, or greater than 28 days. In some embodiments, the rest period is greater than about 14 consecutive days. In some embodiments, the cycle of administration of the immunomodulatory compound does not contain a rest period.

In some embodiments, the immunomodulatory compound, e.g., lenalidomide, Compound 1 or Compound 2, is administered in a cycle, wherein the cycle is repeated at least one time. In some embodiments, the immunomodulatory compound, e.g., lenalidomide, Compound 1 or Compound 2, is administered for at least 2 cycles, at least 3 cycles, at least 4 cycles, at least 5 cycles, at least 6 cycles, at least 7 cycles, at least 8 cycles, at least 9 cycles, at least 10 cycles, at least 11 cycles, or at least 12 cycles. In some embodiments, the immunomodulatory compound, e.g., lenalidomide, Compound 1 or Compound 2, is administered for 1, 2, 3, 4, 5, 6, 7, 8, 9, 10, 11, 12, 13, 14, 15, 16, 17, 18, 19, 20, 21, 22, 23, or 24 cycles.

In some embodiments, the immunomodulatory compound, e.g., lenalidomide, Compound 1 or Compound 2, is administered six times daily, five times daily, four times daily, three times daily, twice daily, once daily, every other day, every three days, twice weekly, once weekly or only one time prior to or subsequently to initiation of administration of the T cell therapy. In some embodiments, the immunomodulatory compound, e.g., lenalidomide or Compound 1, is administered in multiple doses in regular intervals prior to, during, during the course of, and/or after the period of administration of the T cell therapy. In some embodiments, the immunomodulatory compound, e.g., lenalidomide, Compound 1 or Compound 2, is administered in one or more doses in regular intervals prior to the administration of the T cell therapy. In some embodiments, the immunomodulatory compound, e.g., lenalidomide or Compound 1, is administered in one or more doses in regular intervals after the administration of the T cell therapy. In some embodiments, one or more of the doses of the immunomodulatory compound, e.g., lenalidomide, Compound 1 or Compound 2, can occur simultaneously with the administration of a dose of the T cell therapy.

In some embodiments, the dose, frequency, duration, timing and/or order of administration of the immunomodulatory compound, e.g., lenalidomide, Compound 1 or Compound 2, is determined, based on particular thresholds or criteria of results of the screening step and/or assessment of treatment outcomes described herein, e.g., those described in Section III herein.

In some embodiments, the method involves administering the cell therapy to a subject that has been previously administered a therapeutically effective amount of the immunomodulatory compound. In some embodiments, the immunomodulatory compound is administered to a subject before administering a dose of cells expressing a recombinant receptor to the subject. In some embodiments, the treatment with the immunomodulatory compound occurs at the same time as the administration of the dose of cells. In some embodiments, the immunomodulatory compound is administered after the administration of the dose of cells.

In some embodiments, the immunomodulatory compound, e.g., lenalidomide, Compound 1 or Compound 2, is administered daily for 7, 8, 9, 10, 11, 12, 13, 14, 15, 16, 17, 18, 19, 20, 21, or more than 21 days. In some embodiments, the immunomodulatory compound, e.g., lenalidomide, Compound 1 or Compound 2, is administered twice a day for 7, 8, 9, 10, 11, 12, 13, 14, 15, 16, 17, 18, 19, 20, 21, or more than 21 days. In some embodiments, the immunomodulatory compound, e.g., lenalidomide, Compound 1 or Compound 2, is administered three times a day for 7, 8, 9, 10, 11, 12, 13, 14, 15, 16, 17, 18, 19, 20, 21, or more than 21 days. In some embodiments, the immunomodulatory compound, e.g., lenalidomide, Compound 1 or Compound 2, is administered every other day for 7, 8, 9, 10, 11, 12, 13, 14, 15, 16, 17, 18, 19, 20, 21, or more than 21 days.

In some embodiments of the methods provided herein, the immunomodulatory compound, e.g., lenalidomide, Compound 1 or Compound 2, and the T cell therapy are administered simultaneously or near simultaneously.

In some embodiments, immunomodulatory compound, e.g. lenalidomide, Compound 1 or Compound 2, is administered at a dose of from or from about 0.1 mg to about 100 mg, from or from about 0.1 mg to 50 mg, from or from about 0.1 mg to 25 mg, from or from about 0.1 mg to 10 mg, from or from about 0.1 mg to 5 mg, from or from about 0.1 mg to 1 mg, from or from about 1 mg to 100 mg, from or from about 1 mg to 50 mg, from or from about 1 mg to 25 mg, from or from about 1 mg to 10 mg, from or from about 1 mg to 5 mg, from or from about 5 mg to 100 mg, from or from about 5 mg to 50 mg, from or from about 5 mg to 25 mg, from or from about 5 mg to 10 mg, from or from about 10 mg to 100 mg, from or from about 10 mg to 50 mg, from or from 10 mg to 25 mg, from or from about 25 mg to 100 mg, from or from about 25 mg to 50 mg or from or from about 50 mg to 100 mg, each inclusive. In some embodiments, the amount is a once daily amount of the immunomodulatory compound, e.g. lenalidomide, Compound 1 or Compound 2.

In some embodiments, the immunomodulatory compound, e.g. lenalidomide, Compound 1, is administered at a dosage of from about 1 mg to about 20 mg, e.g., from about 1 mg to about 10 mg, from about 2.5 mg to about 7.5 mg, from about 5 mg to about 15 mg, such as about 5 mg, 10 mg, 15 mg or 20 mg. In some embodiments, the immunomodulatory compound, e.g. lenalidomide or Compound 1 is administered at a dose of from about 10 µg/kg to 5 mg/kg, e.g., about 100 µg/kg to about 2 mg/kg, about 200 µg/kg to about 1 mg/kg, about 400 µg/kg to about 600 µg/kg, such as about 500 µg/kg. In some embodiments, the amount is a once daily amount of the immunomodulatory compound, e.g. lenalidomide or Compound 1. In some embodiments, the immunomodulatory compound is Compound 1. In some embodiments, the immunomodulatory compound, e.g., lenalidomide, Compound 1, or Compound 2, is administered at a total daily dosage amount of at least or at least about 0.1 mg per day, 0.5 mg per day, 1.0 mg per day, 2.5 mg per day, 5 mg per day, 10 mg per day, 25 mg per day, 50 mg per day or 100 mg per day. In some embodiments, the dose of the immunomodulatory compound, e.g. lenalidomide or Compound 1 is or is about 25 mg per day. In particular embodiments, the dose of the immunomodulatory compound, e.g. lenalidomide or Compound 1 is or is about 10 mg per day. In some embodiments, the immunomodulatory compound is Compound 1.

In some embodiments, the immunomodulatory compound, e.g. lenalidomide or Compound 1, is administered in an amount greater than or greater than about 1 mg, 2.5 mg, 5 mg, 7.5 mg, 10 mg, 15 mg and less than 25 mg. In some embodiments, the immunomodulatory compound, e.g. lenalidomide or Compound 1, is administered in an amount greater than or greater than about 1 mg per day, 2.5 mg per day, 5 mg per day, 7.5 mg per day, 10 mg per day, 15 mg per day and less than 25 mg per day. In some embodiments, the immunomodulatory compound is Compound 1.

In some embodiments, the provided methods include administering an effective amount of Compound 2 per day to a subject to modulate activity and/or function of the T cell therapy. In some embodiments, Compound 2 is administered at a dosage of from or from about 0.1 mg to at or about 1 mg. In some embodiments, the amount is at or about 0.1 mg, at or about 0.2 mg, at or about 0.3 mg, at or about 0.4 mg, at or about 0.5 mg, at or about 0.6 mg, at or about 0.7 mg, at or about 0.8 mg, at or about 0.9 mg or at or about 1.0 mg, or any value between any of the foregoing. In some embodiments, the amount of Compound 2 is administered in a cycling regimen involving daily administration for three weeks in a four week period or cycle. The administration of Compound 2 is carried out for a period of time, such as generally for more than one week, such as for at or greater than one month, at or greater than two months, at or greater than three months, at or greater than four months, at or greater than five months or at or greater than six months. Exemplary dosing regimens are described herein. In some embodiments, the provided methods include administering an effective amount of Compound 1 per day to a subject to modulate activity and/or function of the T cell therapy. In some embodiments, the effective amount is no more than 3 mg per day. In some embodiments, the effective amount is from or from about 1 mg to about 3 mg per day for the extent of the period, such as is at or about 1 mg per day, 1.5 mg per day, 2.0 mg per day, 2.5 mg per day or 3 mg per day. In some embodiments, the amount of Compound 1 is administered in a cycling regimen involving daily administration for no more than 5 days per week. The administration of Compound 1 is carried out for a period of time, such as generally for more than one week, such as for at or greater than one month, at or greater than two months, at or greater than three months, at or greater than four months, at or greater than five months or at or greater than six months. Exemplary dosing regimens are described herein. In some embodiments, for each week of a cycling regimen, or for at least one week of the cycling regimen, Compound 1 is administered for consecutive days in a week (e.g. each of 3, 4 or 5 days) followed by several days of rest during which the compound is not administered. In some embodiments, Compound 1 is administered in a cycling regimen, or at least one week of the cycling regimen, in the amount (e.g. 1 mg to 3 mg per day) for 5 days followed by a rest period of two days during which the compound is not administered (5/7 day per week).

In some aspects, the provided methods minimize or avoid toxicity following administration of the T cell therapy and/or immunomodulatory compound, e.g. lenalidomide or Compound 1, to a subject. In some aspects, the methods provided herein involve administering doses that are substantially lower than doses identified to be the MTD for the compound.

For example, it has been reported that for Compound 1 a starting dose of 2 mg given 5/7 days is 2 times lower than the MTD when 3 mg Compound 1 is given 5/7 days (Carpio et al. (2015). In some aspects, the provided methods are carried out by administering an amount of the compound that is or is less than 3 mg per day given 5/7 days, such as is or is about 2.5 mg, 2.0 mg, 1.5 mg, 1.0 mg given 5/7 days per week. In some embodiments, Compound 1 is administered to the subject a sufficient time after receiving a lymphodepleting therapy, such that myelosuppressive effects of Compound 1 and the lymphodepleting therapy are minimized. In some embodiments, the administration of Compound 1 is initiated at a time after, or that is suspected or likely to be after, peak CAR-T cells are present in the blood of the subject, e.g. at or after 14 days after initiation of administration of the T cell, such as 14 to 28 days, e.g. at or about 21 days or 28 days after initiation of administration of the cell therapy. In some embodiments, Compound 1 is administered at a time when the subject does not exhibit a severe toxicity following the administration of the cell therapy.

In some of any of the embodiments, the methods and uses include administration of Compound 1. In some embodiments, the administration of Compound 1 is initiated after (subsequent to) the initiation of the cell therapy, such as a T cell therapy (e.g., CAR-expressing T cells). In some embodiments, administration of Compound 1 is initiated at or after peak or maximum level of the cells of the T cell therapy is detectable in the blood of the subject. In some cases, initiation of administration Compound 1 is carried out at or within a week, such as within 1, 2 or 3 days after (i) a time in which peak or maximum level of the cells of the T cell therapy are detectable in the blood of the subject; (ii) the number of cells of the T cell therapy detectable in the blood, after having been detectable in the blood, is not detectable or is reduced, optionally reduced compared to a preceding time point after administration of the T cell therapy; (iii) the number of cells of the T cell therapy detectable in the blood is decreased by or more than 1.5-fold, 2.0-fold, 3.0-fold, 4.0-fold, 5.0-fold, 10-fold or more the peak or maximum number cells of the T cell therapy detectable in the blood of the subject after initiation of administration of the T cell therapy; (iv) at a time after a peak or maximum level of the cells of the T cell therapy are detectable in the blood of the subject, the number of cells of or derived from the cells detectable in the blood from the subject is less than less than 10%, less than 5%, less than 1% or less than 0.1% of total peripheral blood mononuclear cells (PBMCs) in the blood of the subject; (v) the subject exhibits disease progression and/or has relapsed following remission after treatment with the T cell therapy; and/or (iv) the subject exhibits increased tumor burden as compared to tumor burden at a time prior to or after administration of the cells and prior to initiation of administration of Compound 1. In certain aspects, the provided methods are carried out to enhance, increase or potentiate T cell therapy in subjects in which a peak response to the T cell therapy has been observed but in which the response, e.g. presence of T cells and/or reduction in tumor burden, has become reduced or is no longer detectable.

In some embodiments, the administration of Compound 1 is initiated at or about 14 to about 35 days after initiation of administration of the T cell therapy. In some embodiments, the administration of Compound 1 is initiated about 21 to about 35 days after initiation of administration of the T cell therapy. In some embodiments, the administration of Compound 1 is initiated about 21 to about 28 days after initiation of administration of the T cell therapy. In some embodiments, the administration of Compound 1 is initiated at or about 14 days, at or about 15 days, at or about 16 days, at or about 17 days, at or about 18 days, at or about 19 days, at or about 20 days, at or about 21 days, at or about 22 days, at or about 23 days, at or about 24 days, at or about 25 days, at or about 26 days, at or about 27 days, at or about 28 days, at or about 29 days, at or about 30 days, at or about 31 days, at or about 32 days, at or about 33 days, at or about 34 days, or at or about 35 days after initiation of administration of the T cell therapy.

In some embodiments, at the time at which the subject is first administered Compound 1 and/or at any subsequent time after initiation of the administration, the subject does not exhibit a sign or symptom of a severe toxicity, such as severe cytokine release syndrome (CRS) or severe toxicity. In some embodiments, the administration of Compound 1 is at a time at which the subject does not exhibit a sign or symptom of severe CRS and/or does not exhibit grade 3 or higher CRS, such as prolonged grade 3 CRS or grade 4 or 5 CRS. In some embodiments, the administration of Compound 1 is at a time at which the subject does not exhibit a sign or symptom of severe neurotoxicity and/or does not exhibit grade 3 or higher neurotoxicity, such as prolonged grade 3 neurotoxicity or grade 4 or grade 5 neurotoxicity. In some aspects, between the time of the initiation of the administration of the T cell therapy and the time of the administration of Compound 1, the subject has not exhibited severe CRS and/or has not exhibited grade 3 or higher CRS, such as prolonged grade 3 CRS or grade 4 or 5 CRS. In some instances, between the time of the initiation of the administration of the T cell therapy and the time of the administration of Compound 1, the subject has not exhibited severe neurotoxicity and/or does not exhibit grade 3 or higher neurotoxicity, such as prolonged grade 3 neurotoxicity or grade 4 or 5 neurotoxicity.

In some embodiments, administration of Compound 1 per day it is administered is at an amount of from or from about 0.1 mg to 5 mg. In some embodiments, administration of Compound 1 per day it is administered is at an amount of about 0.1 mg to about 5 mg, about 0.5 mg to about 5 mg, about 1 mg to about 5 mg, about 1.5 mg to about 5 mg, about 2 mg to about 5 mg, about 2.5 mg to about 5 mg, about 3 mg to about 5 mg, about 0.1 mg to about 4 mg, about 0.1 mg to about 4 mg, about 1 mg to about 4 mg, about 1.5 mg to about 4 mg, about 2 mg to about 4 mg, about 2.5 mg to about 4 mg, about 3 mg to about 4 mg, about 0.1 mg to about 3.5 mg, about 0.5 mg to about 3.5 mg, about 1 mg to about 3.5 mg, about 1.5 mg to about 3.5 mg, about 2 mg to about 3.5 mg, about 2.5 mg to about 3.5 mg, about 3 mg to about 3.5 mg, about 0.1 mg to about 3 mg, about 0.5 mg to about 3 mg, about 1 mg to about 3 mg, about 1.5 mg to about 3 mg, about 2 mg to about 3 mg, about 2.5 mg to about 3 mg, about 0.1 mg to about 2.5 mg, about 0.5 mg to about 2.5 mg, about 1 mg to about 2.5 mg, about 1.5 mg to about 2.5 mg, about 2 mg to about 2.5 mg, about 0.1 mg to about 2 mg, about 0.5 mg to about 2 mg, about 1 mg to about 2 mg, about 1.5 mg to about 2 mg, about 0.1 mg to about 1.5 mg, about 0.5 mg to about 1.5 mg, about 1 mg to about 1.5 mg, about 0.1 mg to about 1 mg, or about 0.5 mg to about 1 mg.

In some embodiments, administration of Compound 1 per day it is administered is at an amount of about or at least about, or at or at least at 0.5 mg. In some embodiments, administration of Compound 1 per day it is administered is at an amount of about or at least about, or at or at least at 1 mg. In some embodiments, administration of Compound 1 per day it is administered is at an amount of about or at least about, or at or at least at 1.5 mg. In some embodiments, administration of Compound 1 per day it is administered is at an amount of about or at least about, or at or at least at 2 mg. In some embodiments, administration of Compound 1 per day it is administered is at an amount of about or at least about, or at or at least at 2.5 mg. In some embodiments, administration of Compound 1 per day it is administered is at an amount of about or at least about, or at or at least at 3 mg. In some of any such embodiments, administration of Compound 1 per day it is administered is at an amount of no more than about 5 mg. In some embodiments, administration of Compound 1 per day it is administered is at an amount of no more than about 4.5 mg. In some embodiments, administration of Compound 1 per day it is administered is at an amount of no more than about 4 mg. In some embodiments, administration of Compound 1 per day it is administered is at an amount of no more than about 3.5 mg. In some embodiments, administration of Compound 1 per day it is administered is at an amount of no more than about 3 mg. In some embodiments, administration of Compound 1 per day it is administered is at an amount of no more than about 2.5 mg. In some embodiments, administration of Compound 1 per day it is administered is at an amount of no more than about 2 mg. In some embodiments, administration of Compound 1 per day it is administered is at an amount of no more than about 1.5 mg. In some embodiments, administration of Compound 1 per day it is administered is at an amount of no more than about 1 mg.

In some embodiments, administration of Compound 1 per day it is administered is at an amount of at or about 3 mg. In some embodiments, administration of Compound 1 per day it is administered is at an amount of at or about 2.5 mg. In some embodiments, administration of Compound 1 per day it is administered is at an amount of at or about 2 mg. In some embodiments, administration of Compound 1 per day it is administered is at an amount of at or about 1.5 mg. In some embodiments, administration of Compound 1 per day it is administered is at an amount of at or about 1 mg per day.

In some embodiments, Compound 1 is administered in an amount that achieves a maximum concentration ($C_{max}$) of Compound 1 in the blood, such as for each week of a cycling regimen or for at least one week of a cycling regimen, in a range of about 10 nM to about 500 nM, about 40 nM to about 500 nM, about 60 nM to about 500 nM, about 80 nM to about 500 nM, about 100 nM to about 500 nM, about 150 nM to about 500 nM, about 200 nM to about 500 nM, about 250 nM to about 500 nM, about 300 nM to about 500 nM, about 350 nM to about 500 nM, about 400 nM to about 500 nM, 10 nM to about 400 nM, about 40 nM to about 400 nM, about 60 nM to about 400 nM, about 80 nM to about 400 nM, about 100 nM to about 400 nM, about 150 nM to about 400 nM, about 200 nM to about 400 nM, about 250 nM to about 400 nM, about 300 nM to about 400 nM, about 350 nM to about 400 nM, 10 nM to about 350 nM, about 40 nM to about 350 nM, about 60 nM to about 350 nM, about 80 nM to about 350 nM, about 100 nM to about 350 nM, about 150 nM to about 350 nM, about 200 nM to about 350 nM, about 250 nM to about 350 nM, about 300 nM to about 350 nM, about 10 nM to about 300 nM, about 40 nM to about 300 nM, about 60 nM to about 300 nM, about 80 nM to about 300 nM, about 100 nM to about 300 nM, about 150 nM to about 300 nM, about 200 nM to about 300 nM, about 250 nM to about 250 nM, about 10 nM to about 250 nM, about 40 nM to about 250 nM, about 60 nM to about 250 nM, about 80 nM to about 250 nM, about 100 nM to about 250 nM, about 150 nM to about 250 nM, about 200 nM to about 250 nM, about 10 nM to about 200 nM, about 40 nM to about 200 nM, about 60 nM to about 200 nM, about 80 nM to about 200 nM, about 100 nM to about 200 nM, about 150 nM to about 200 nM, about 10 nM to about 150 nM, about 40 nM to about 150 nM, about 60 nM to about 150 nM, about 80 nM to about 150 nM, about 100 nM to about 150 nM, about 10 nM to about 100 nM, about 40 nM to about 100 nM, about 60 nM to about 100 nM, or about 80 nM to about 100 nM. In some embodiments, Compound 1 is administered at an amount that maintains the $C_{max}$ in the range for at least about 30 minutes, 1 hour, 2 hours, 4 hours, 8 hours, 16 hours or 24 hours In some embodiments, Compound 1 is administered at an amount that achieves a $C_{max}$ of Compound 1 in the blood at about or at least about 40 nM. In some embodiments, Compound 1 is administered at an amount that achieves a $C_{max}$ of Compound 1 in the blood at about or at least about 60 nM. In some embodiments, Compound 1 is administered at an amount that achieves a $C_{max}$ of Compound 1 in the blood, such as for each week of a cycling regimen or for at least one week of a cycling regimen, of at about or at least about 80 nM. In some embodiments, Compound 1 is administered at an amount that achieves a $C_{max}$ of Compound 1 in the blood, such as for each week of a cycling regimen or for at least one week of a cycling regimen, of at about or at least about 90 nM. In some embodiments, Compound 1 is administered at an amount that achieves a $C_{max}$ of Compound 1 in the blood, such as for each week of a cycling regimen or for at least one week of a cycling regimen, of at about or at least about 100 nM. In some embodiments, Compound 1 is administered at an amount that maintains the $C_{max}$ for at least about 30 minutes, 1 hour, 2 hours, 4 hours, 8 hours, 16 hours or 24 hours.

In some embodiments, Compound 1 is administered at an amount that achieves a $C_{max}$ of Compound 1 in the blood, such as for each week of a cycling regimen or for at least one week of a cycling regimen, of at no more than about 500 nM. In some embodiments, Compound 1 is administered at an amount that achieves a $C_{max}$ of Compound 1 in the blood, such as for each week of a cycling regimen or for at least one week of a cycling regimen, of at no more than about 400 nM. In some embodiments, Compound 1 is administered at an amount that achieves a $C_{max}$ of Compound 1 in the blood, such as for each week of a cycling regimen or for at least one week of a cycling regimen, of at no more than about 350 nM. In some embodiments, Compound 1 is administered at an amount that achieves a $C_{max}$ of Compound 1 in the blood, such as for each week of a cycling regimen or for at least one week of a cycling regimen, of at no more than about 300 nM. In some embodiments, Compound 1 is administered at an amount that achieves a $C_{max}$ of Compound 1 in the blood, such as for each week of a cycling regimen or for at least one week of a cycling regimen, of at no more than about 250 nM. In some embodiments, Compound 1 is administered at an amount that achieves a $C_{max}$ of Compound 1 in the blood, such as for each week of a cycling regimen or for at least one week of a cycling regimen, of at no more than about 200 nM. In some embodiments, Compound 1 is administered at an amount that achieves a $C_{max}$ of Compound 1 in the blood, such as for each week of a cycling regimen or for at least one week of a cycling regimen, of at no more than about 150 nM.

In some embodiments, Compound 1 is administered in a cycling regimen that involves repeated dosing of the compound for a specified period or duration. In some embodiments, Compound 1 is administered in a cycling regimen in which, for each week of the cycling regimen or for at least one week of the cycling regimen, the compound is administered in an effective amount, such as an amount described above, on each of no more than 5 days per week for a period of more than one week. In some embodiments, the amount of Compound 1 for each administration or per day it is administered is no more than 3 mg (e.g., no more than 3 mg, 2.5 mg, 2 mg, 1.5 mg, 1 mg, 0.5 mg). In some embodiments, the amount of Compound 1 for each administration or per day it is administered is at or about 3 mg, at or about 2.5 mg, at or about 2 mg, at or about 1.5 mg, at or about 1 mg, at or about 0.5 mg. In some embodiments, the amount of Compound 1 for each administration or per day it is administered is about 1 mg to about 2 mg (e.g., at or about 1 mg, at or about 2 mg).

In some embodiments, each week of a cycling regimen comprises administering Compound 1 each of no more than 5 days per week. In some embodiments, each week of a cycling regimen comprises administering Compound 1 for each of no more than 4 days per week. In some embodiments, each week of a cycling regimen comprises administering Compound 1 for each of no more than 3 days per week.

In some embodiments, each week of a cycling regimen comprises administering Compound 1 for 3 to 5 days per week. In some embodiments, each week of a cycling regimen comprises administering Compound 1 for 4 to 5 days per week. In some embodiments, each week of a cycling regimen comprises administering Compound 1 for 3 to 4 days per week.

In some embodiments, the each week of a cycling regimen, or at least one week of a cycling regimen, comprises administering Compound 1 on each of no more than 5 consecutive days per week followed by a rest period for the remainder of the week during which the compound is not administered. In some embodiments, each week of a cycling regimen, or at least one week of a cycling regimen, comprises administering Compound 1 for 3 to 5 consecutive days per week followed by a rest period for the remainder of the week during which the compound is not administered. In some embodiments, each week of the cycling regimen, or at least one week of the cycling regimen, comprises administering Compound 1 on each of 3 consecutive days per week followed by a rest period of 4 days during which the compound is not administered. In some embodiments, each week of a cycling regimen, or at least one week of a cycling regimen, comprises administering Compound 1 on each of 4 consecutive days per week followed by a rest period of 3 days during which the compound is not administered. In some embodiments, each week of a cycling regimen, or at least one week of a cycling regimen, comprises administering Compound 1 one each of 5 consecutive days per week followed by a rest period of 2 days during which the compound is not administered.

In some embodiments, the cycling regimen for administering Compound 1 is carried out for a period of time subsequent to initiation of administration of the T cell therapy. In some embodiments, administration of Compound 1 extends for a period of more than one week after initiation of administration of the T cell therapy. In some embodiments, administration of Compound 1 extends for a period of about or at least about one month after initiation of administration of the T cell therapy. In some embodiments, administration of Compound 1 extends for a period of about or at least about two months after initiation of administration of the T cell therapy. In some embodiments, administration of Compound 1 extends for a period of about or at least about three months after initiation of administration of the T cell therapy. In some embodiments, administration of Compound 1 extends for a period of about or at least about four months after initiation of administration of the T cell therapy. In some embodiments, administration of Compound 1 extends for a period of about or at least about five months after initiation of administration of the T cell therapy.

In some embodiments, administration of Compound 1 extends for a period of at least three months. In some embodiments, administration of Compound 1 extends for a period of at or about 90 days, at or about 100 days, at or about 105 days, at or about 110 days, at or about 115 days, at or about 120 days, at or about 125 days, at or about 130 days, at or about 135 days, at or about 140 days, at or about 145 days, at or about 150 days, at or about 155 days, at or about 160 days, at or about 165 days, at or about 170 days, at or about 175 days, at or about 180 days, at or about 185 days, at or about 190 days, at or about 195 days, at or about 200 days or more after initiation of administration of the T cell therapy.

In some embodiments, administration of Compound 1 extends for a period of at or about 90 days or at or about three months after initiation of administration of the T cell therapy (e.g., CAR T cell therapy). In some embodiments, administration of Compound 1 extends for a period of at or about 120 days or four months after initiation of administration of the T cell therapy (e.g., CAR T cell therapy). In some embodiments, administration of Compound 1 extends for a period of at or about 150 days or five months after initiation of administration of the T cell therapy (e.g., CAR T cell therapy). In some embodiments, administration of Compound 1 extends for a period of at or about 180 days or six months after initiation of administration of the T cell therapy (e.g., CAR T cell therapy).

In some embodiments, administration of Compound 1 is ended or stopped at the end of the period (e.g. at or about 3, 4, 5, or 6 months) after initiation of administration of the T cell therapy (e.g., CAR T cell therapy) if the subject has, prior to or at or about 6 months, achieved a complete response (CR) following the treatment or the cancer (e.g. B cell malignancy) has progressed or relapsed following remission after the treatment. In some embodiments, the period is of a fixed duration such that the administration of Compound 1 is continued for the period even if the subject has achieved a complete response (CR) at a time point prior to the end of the period. In some embodiments the subject is has a CR with minimal residual disease (MRD). In some embodiments, the subject has a CR that is MRD−.

In some embodiments, administration of Compound 1 is continued after the end of the period, e.g. continued for longer than at or about 3, 4, 5 or 6 months after initiation of administration of the T cell therapy (e.g. CAR T cells), if the subject exhibits a partial response (PR) or stable disease (SD) after the treatment. In some embodiments, administration of Compound 1 is continued for greater than 6 months after initiation of administration of the T cell therapy (e.g., CAR T cell therapy). In some embodiments, for subjects that exhibited a PR or SD at the end of the initial period, administration of Compound 1 is continued until the subject has achieved a complete response (CR) following the treatment or until the cancer (e.g. B cell malignancy, such as an NHL, e.g. DLBCL) has progressed or relapsed following remission after the treatment.

In some embodiments, administration of Compound 1 is carried out in a cycling regimen comprising administering Compound 1 in an amount of no more than about 3 mg (e.g., 1 to 3 mg, 1 mg, 2 mg, or 3 mg) per day for no more than 5 days (e.g., 3 days, 4 day or 5 days) per week for a period of more than one week. In some embodiments, each week of the cycling regimen involves administration of the compound for each of 3 consecutive days, 4 consecutive days or 5 consecutive days followed by a rest period for the remainder of the week during which the compound is not administered. In some embodiments, the each week of the cycling regimen comprises administration of the compound for 5 days followed by a rest period of two days during which the compound is not administered. In some embodiments, the administration of Compound 1 is initiated greater than about 14 to about 35 days (e.g., about 21 to about 35 days) after initiation of the administration of the cell therapy. In some embodiments, at the time of administering Compound 1, the subject does not exhibit a severe toxicity following administration of the T cell therapy (e.g. CAR T cells). In some embodiments, the B cell malignancy is NHL, such as relapsing/refractory aggressive NHL or DLBCL. In some embodiments, the cell therapy, such as CAR-expressing T cells, comprise a chimeric antigen receptor specifically binding to a B cell antigen. In some embodiments, the B cell antigen is CD19.

In some embodiments, administration of Compound 1 is carried out in a cycling regimen comprising administering an effective amount of Compound for no more than 5 days (e.g., 3 days, 4 day or 5 days) per week for a period that extends at or about or greater than 3 months, at or about or greater than 4 months, at or about or greater than 5 months or at or about or greater than 6 months after initiation of administration of the cell therapy (e.g., T cell therapy). In some embodiments, the period extends for at or about 3 months, at or about 4 months, at or about 5 months or at or about 6 months. In some embodiments, each week of the cycling regimen involves administration of the compound for each of 3 consecutive days, 4 consecutive days or 5 consecutive days followed by a rest period for the remainder of the week during which the compound is not administered. In some embodiments, each week of cycling regimen comprises administration of the compound on each of 5 consecutive days followed by a rest period of two days during which the compound is not administered. In some embodiments, the administration of Compound 1 is initiated greater than about 14 to about 35 days (e.g., about 21 to about 35 days, such as at or about 28 days) after initiation of the administration of the cell therapy. In some embodiments, at the time of administering Compound 1, the subject does not exhibit a severe toxicity following administration of the cell therapy. In some embodiments, the administration of Compound 1 is ended or stopped, if the subject has, prior to at or about the end of the period, achieved a complete response (CR) following the treatment or the cancer, e.g. B cell malignancy, has progressed or relapsed following remission after the treatment. In some embodiments, administration of Compound 1 is continued for the period even if the subject has achieved a complete response (CR) at a time point prior to the end of the period. In some embodiments, the administration of Compound 1 is continued after the end of the initial period if, after initiation of administration of the T cell therapy, the subject exhibits a partial response (PR) or stable disease (SD) after the treatment. In some embodiments, the administration of Compound 1 is repeated until the subject has achieved a complete response (CR) following the treatment or until the cancer, e.g. B cell malignancy, has progressed or relapsed following remission after the treatment. In some embodiments, the B cell malignancy is NHL, such as relapsing/refractory aggressive NHL or DLBCL. In some embodiments, the T cell therapy, such as CAR-expressing T cells, comprise a chimeric antigen receptor specifically binding to a B cell antigen. In some embodiments, the B cell antigen is CD19.

In some embodiments, administration of Compound 1 is carried out in a cycling regimen comprising administering Compound 1 in an amount of no more than about 3 mg (e.g., 1 to 3 mg, 1 mg, 2 mg, or 3 mg) per day on each of no more than 5 days (e.g., 3 days, 4 day or 5 days) per week for a period of about or greater than three months (e.g., for a period of at or about three months, four months, five months, or six months) after initiation of administration of the T cell therapy (e.g., CAR T cell therapy). In some embodiments, each week of the cycling regimen involves administration of the compound on each of 3 consecutive days, 4 consecutive days or 5 consecutive days followed by a rest period for the remainder of the week during which the compound is not administered. In some embodiments, each week of the cycling regimen comprises administration of the compound on each of 5 days followed by a rest period of two days during which the compound is not administered. In some embodiments, the administration of Compound 1 is initiated greater than about 14 to about 35 days (e.g., about 21 to about 35 days, e.g. at or about 28 days) after initiation of the administration of the cell therapy. In some embodiments, at the time of administering Compound 1, the subject does not exhibit a severe toxicity following administration of the cell therapy. In some embodiments, the B cell malignancy is NHL, such as relapsing/refractory aggressive NHL or DLBCL. In some embodiments, administration of Compound 1 is ended or stopped at or about 6 months after initiation of administration of the T cell therapy if the subject has, prior to at or about 6 months, achieved a complete response (CR) following the treatment or the cancer, e.g. B cell malignancy, has progressed or relapsed following remission after the treatment. In some embodiments, the cycling regimen is continued for the entire period even if the subject has achieved a complete response (CR) at a time point prior to the end of the period. In some embodiments, the administration of Compound 1 is further continued after the end of the period, such as is continued for greater than 6 months after initiation of administration of the cell therapy, if, at or about six months, the subject exhibits a partial response (PR) or stable disease (SD) after the treatment. In some embodiments, the administration of Compound 1 is continued until the subject has achieved a complete response (CR) following the treatment or until the cancer, e.g. B cell malignancy, has progressed or relapsed following remission after the treatment. In some embodiments, the cell therapy, such as CAR-expressing T cells, comprise a chimeric antigen receptor specifically binding to a B cell antigen. In some embodiments, the B cell antigen is CD19.

In some embodiments, administration of Compound 1 is carried out in a cycling regimen comprising administering Compound 1 at an amount of about 1 mg to about 3 mg (e.g., 1 mg, 2 mg or 3 mg) per day on each of 5 consecutive days per week followed by a rest period of 2 days during which the compound is not administered for a period of at or about or greater than six months after initiation of the cell therapy (e.g., T cell therapy). In some embodiments, the administration of Compound 1 is initiated greater than about 14 to about 35 days (e.g., about 21 to about 35 days, e.g. at or about 28 days) after initiation of the administration of the cell therapy. In some embodiments, at the time of administering Compound 1, the subject does not exhibit a severe toxicity following administration of the cell therapy. In some embodiments, administration of Compound 1 is stopped at or about 6 months after initiation of administration of the cell therapy if the subject has, at or about 6 months, achieved a complete response (CR) following the treatment or the cancer, e.g. B cell malignancy, has progressed or relapsed following remission after the treatment. In some embodiments, administration of Compound 1 is continued for the period even if the subject has achieved a complete response (CR) at a time point prior to at or about 6 months. In some embodiments, administration of Compound 1 is further administered for greater than 6 months after initiation of administration of the T cell therapy if, at or about six months, the subject exhibits a partial response (PR) or stable disease (SD) after the treatment. In some embodiments, the administration is continued until the subject has achieved a complete response (CR) following the treatment or until the B cell malignancy has progressed or relapsed following remission after the treatment. In some embodiments, the B cell malignancy is NHL, such as relapsing/refractory aggressive NHL or DLBCL. In some embodiments, the cell therapy, such as CAR-expressing T cells, comprise a chimeric antigen receptor specifically binding to a B cell antigen. In some embodiments, the B cell antigen is CD19.

In some cases, the cycling regimen can be interrupted at any time, and/or for one or more times. In some cases, the cycling regimen is interrupted or modified if the subject develops one or more adverse event, dose-limiting toxicity (DLT), neutropenia or febrile neutropenia, thrombocytopenia, cytokine release syndrome (CRS) and/or neurotoxicity (NT), such as those as described in Section IV. In some embodiments, the amount of Compound 1 for each administration or per day in certain days of a week is altered after the subject develops one or more adverse event, dose-limiting toxicity (DLT), neutropenia or febrile neutropenia, thrombocytopenia, cytokine release syndrome (CRS) and/or neurotoxicity (NT).

In any of the aforementioned embodiments, the immunomodulatory compound, e.g. lenalidomide, Compound 1 or Compound 2, may be administered orally. In some embodiments, the immunomodulatory compound, e.g. lenalidomide, Compound 1 or Compound 2, is administered as a tablet or capsule.

In some embodiments, dosages, such as daily dosages, are administered in one or more divided doses, such as 2, 3, or 4 doses, or in a single formulation. The immunomodulatory compound, e.g., lenalidomide, Compound 1 or Compound 2 can be administered alone, in the presence of a pharmaceutically acceptable carrier, or in the presence of other therapeutic agents.

It is understood that higher or lower dosages of the immunomodulatory compound could be used, for example depending on the particular agent and the route of administration. In some embodiments, the immunomodulatory compound may be administered alone or in the form of a pharmaceutical composition wherein the compound is in admixture or mixture with one or more pharmaceutically acceptable carriers, excipients, or diluents. In some embodiments, the immunomodulatory compound may be administered either systemically or locally to the organ or tissue to be treated. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes. In some embodiments, the route of administration is oral, parenteral, rectal, nasal, topical, or ocular routes, or by inhalation. In some embodiments, the immunomodulatory compound is administered orally. In some embodiments, the immunomodulatory compound is administered orally in solid dosage forms, such as capsules, tablets and powders, or in liquid dosage forms, such as elixirs, syrups and suspensions.

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. If symptoms have been alleviated to an appropriate level, treatment may cease. Patients may, however, require intermittent treatment on a long-term basis upon any recurrence of symptoms. Patients may also require chronic treatment on a long-term basis.

C. Lymphodepleting Treatment

In some aspects, the provided methods can further include administering one or more lymphodepleting therapies, such as prior to or simultaneous with initiation of administration of the T cell therapy. In some embodiments, the lymphodepleting therapy comprises administration of a phosphamide, such as cyclophosphamide. In some embodiments, the lymphodepleting therapy can include administration of fludarabine.

In some aspects, preconditioning subjects with immunodepleting (e.g., lymphodepleting) therapies can improve the effects of adoptive cell therapy (ACT). Preconditioning with lymphodepleting agents, including combinations of cyclosporine and fludarabine, have been effective in improving the efficacy of transferred tumor infiltrating lymphocyte (TIL) cells in cell therapy, including to improve response and/or persistence of the transferred cells. See, e.g., Dudley et al., *Science,* 298, 850-54 (2002); Rosenberg et al., *Clin Cancer Res,* 17(13):4550-4557 (2011). Likewise, in the context of CAR+ T cells, several studies have incorporated lymphodepleting agents, most commonly cyclophosphamide, fludarabine, bendamustine, or combinations thereof, sometimes accompanied by low-dose irradiation. See Han et al. *Journal of Hematology & Oncology,* 6:47 (2013); Kochenderfer et al., *Blood,* 119: 2709-2720 (2012); Kalos et al., *Sci Transl Med,* 3(95):95ra73 (2011); Clinical Trial Study Record Nos.: NCT02315612; NCT01822652.

Such preconditioning can be carried out with the goal of reducing the risk of one or more of various outcomes that could dampen efficacy of the therapy. These include the phenomenon known as "cytokine sink," by which T cells, B cells, NK cells compete with TILs for homeostatic and activating cytokines, such as IL-2, IL-7, and/or IL-15; suppression of TILs by regulatory T cells, NK cells, or other cells of the immune system; impact of negative regulators in the tumor microenvironment. Muranski et al., *Nat Clin Pract Oncol.* December; 3(12): 668-681 (2006).

Thus in some embodiments, the provided method further involves administering a lymphodepleting therapy to the subject. In some embodiments, the method involves administering the lymphodepleting therapy to the subject prior to the administration of the dose of cells. In some embodiments, the lymphodepleting therapy contains a chemotherapeutic agent such as fludarabine and/or cyclophosphamide. In some embodiments, the administration of the cells and/or the lymphodepleting therapy is carried out via outpatient delivery.

In some embodiments, the methods include administering a preconditioning agent, such as a lymphodepleting or chemotherapeutic agent, such as cyclophosphamide, fludarabine, or combinations thereof, to a subject prior to the administration of the dose of cells. For example, the subject may be administered a preconditioning agent at least 2 days prior, such as at least 3, 4, 5, 6, or 7 days prior, to the first or subsequent dose. In some embodiments, the subject is administered a preconditioning agent no more than 7 days prior, such as no more than 6, 5, 4, 3, or 2 days prior, to the administration of the dose of cells.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the fludarabine can be administered in a single dose or can be administered in a plurality of doses, such as given daily, every other day or every three days. In some embodiments, the cyclophosphamide is administered once daily for one or two days.

In some embodiments, where the lymphodepleting agent comprises fludarabine, the subject is administered fludarabine at a dose between or between about 1 mg/m$^2$ and 100 mg/m$^2$, such as between or between about 10 mg/m$^2$ and 75 mg/m², 15 mg/m² and 50 mg/m², 20 mg/m² and 30 mg/m², or 24 mg/m² and 26 mg/m². In some instances, the subject is administered 25 mg/m² of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m²) of cyclophosphamide and 3 to 5 doses of 25 mg/m² fludarabine prior to the dose of cells.

In one exemplary dosage regime, prior to receiving the first dose, subjects receive an immunomodulatory compound 1 day before the administration of cells and an lymphodepleting preconditioning chemotherapy of cyclophosphamide and fludarabine (CY/FLU), which is administered at least two days before the first dose of CAR-expressing cells and generally no more than 7 days before administration of cells. In another exemplary dosage regime, subjects receive the immunomodulatory compound concurrently with the administration of cells, such as on the same day. In yet another exemplary dosage regime, subjects receive the immunomodulatory compound several days after the administration of cells, such as 7, 8, 9, 10, 11, 12, 13, 14, or more than 14 days after. In some cases, for example, cyclophosphadmide is given from 24 to 27 days after the administration of the immunomodulatory compound, e.g., lenalidomide, Compound 1 or Compound 2. After preconditioning treatment, subjects are administered the dose of CAR-expressing T cells as described above.

In some embodiments, the administration of the preconditioning agent prior to infusion of the dose of cells improves an outcome of the treatment. For example, in some aspects, preconditioning improves the efficacy of treatment with the dose or increases the persistence of the recombinant receptor-expressing cells (e.g., CAR-expressing cells, such as CAR-expressing T cells) in the subject. In some embodiments, preconditioning treatment increases disease-free survival, such as the percent of subjects that are alive and exhibit no minimal residual or molecularly detectable disease after a given period of time following the dose of cells. In some embodiments, the time to median disease-free survival is increased.

Once the cells are administered to the subject (e.g., human), the biological activity of the engineered cell populations in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells also can be measured by assaying expression and/or secretion of certain cytokines, such as CD107a, IFNγ, IL-2, and TNF. In some aspects the biological activity is measured by assessing clinical outcome, such as reduction in tumor burden or load. In some aspects, toxic outcomes, persistence and/or expansion of the cells, and/or presence or absence of a host immune response, are assessed.

In some embodiments, the administration of the preconditioning agent prior to infusion of the dose of cells improves an outcome of the treatment such as by improving the efficacy of treatment with the dose or increases the persistence of the recombinant receptor-expressing cells (e.g., CAR-expressing cells, such as CAR-expressing T cells) in the subject. Therefore, in some embodiments, the dose of preconditioning agent given in the method which is a combination therapy with the immunomodulatory compound and cell therapy is higher than the dose given in the method without the immunomodulatory compound.

II. T Cell Therapy and Engineering Cells

In some embodiments, the T cell therapy for use in accord with the provided combination therapy methods includes administering engineered cells expressing recombinant receptors designed to recognize and/or specifically bind to molecules associated with the disease or condition and result in a response, such as an immune response against such molecules upon binding to such molecules. The receptors may include chimeric receptors, e.g., chimeric antigen receptors (CARs), and other transgenic antigen receptors including transgenic T cell receptors (TCRs).

In some embodiments, the cells contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or $CD8^+$ or $CD4^+$ cells are enriched or selected. Among the compositions are pharmaceutical compositions and formulations for administration, such as for adoptive cell therapy. Also provided are therapeutic methods for administering the cells and compositions to subjects, e.g., patients.

Thus, in some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

A. Recombinant Receptors

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

I. Chimeric Antigen Receptors (CARs)

In some embodiments, engineered cells, such as T cells, employed in the provided embodiments express a CAR with specificity for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as chimeric receptor, contains an intracellular signaling region, which includes a cytoplasmic signaling domain or region (also interchangeably called an intracellular signaling domain or region), such as a cytoplasmic (intracellular) region capable of inducing a primary activation signal in a T cell, for example, a cytoplasmic signaling domain or region of a T cell receptor (TCR) component (e.g. a cytoplasmic signaling domain or region of a zeta chain of a CD3-zeta (CD3) chain or a functional variant or signaling portion thereof) and/or that comprises an immunoreceptor tyrosine-based activation motif (ITAM).

In some embodiments, the chimeric receptor further contains an extracellular ligand-binding domain that specifically binds to a ligand (e.g. antigen) antigen. In some embodiments, the chimeric receptor is a CAR that contains an extracellular antigen-recognition domain that specifically binds to an antigen. In some embodiments, the ligand, such as an antigen, is a protein expressed on the surface of cells.

In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule. Generally, a CAR containing an antibody or antigen-binding fragment that exhibits TCR-like specificity directed against peptide-MHC complexes also may be referred to as a TCR-like CAR. In some embodiments, the extracellular antigen binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061, WO2016/0046724, WO2016/014789, WO2016/090320, WO2016/094304, WO2017/025038, WO2017/173256, U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, 8,479,118, and 9,765,342, and European patent application number EP2537416, and/or those described by Sadelain et al., Cancer Discov., 3(4): 388-398 (2013); Davila et al., PLoS ONE 8(4): e61338 (2013); Turtle et al., Curr. Opin. Immunol., 24(5): 633-39 (2012); Wu et al., Cancer, 18(2): 160-75 (2012). In some aspects, the antigen receptors include a CAR as described in U.S. Pat. No. 7,446,190, and those described in International Patent Application Publication No. WO/2014055668 A1. Examples of the CARs include CARs as disclosed in any of the aforementioned publications, such as WO2014031687, U.S. Pat. Nos. 8,339, 645, 7,446,179, US 2013/0149337, U.S. Pat. Nos. 7,446, 190, 8,389,282, Kochenderfer et al., Nature Reviews Clinical Oncology, 10, 267-276 (2013); Wang et al., J. Immunother. 35(9): 689-701 (2012); and Brentjens et al., Sci Transl Med. 5(177) (2013). See also WO2014031687, U.S. Pat. Nos. 8,339,645, 7,446,179, US 2013/0149337, U.S. Pat. Nos. 7,446,190, and 8,389,282. The chimeric receptors, such as CARs, generally include an extracellular antigen binding domain, such as a portion of an antibody molecule, generally a variable heavy (VH) chain region and/or variable light (VL) chain region of the antibody, e.g., an scFv antibody fragment.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy ($V_H$) and variable light ($V_L$) chains of a monoclonal antibody (mAb), or a single domain antibody (sdAb), such as sdFv, nanobody, $V_H$H and $V_{NAR}$. In some embodiments, an antigen-binding fragment comprises antibody variable regions joined by a flexible linker.

Among the antigen binding domains included in the CARs are antibody fragments. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; heavy chain variable ($V_H$) regions, single-chain antibody molecules such as scFvs and single-domain antibodies comprising only the $V_H$ region; and multispecific antibodies formed from antibody fragments. In particular embodiments, the antibodies are single-chain antibody fragments comprising a heavy chain variable ($V_H$) region and/or a light chain variable ($V_L$) region, such as scFvs.

In certain embodiments, multispecific binding molecules, e.g., multispecific chimeric receptors, such as multispecific CARs, can contain any of the multispecific antibodies, including, e.g. bispecific antibodies, multispecific single-chain antibodies, e.g., diabodies, triabodies, and tetrabodies, tandem di-scFvs, and tandem tri-scFvs.

Single-domain antibodies (sdAbs) are antibody fragments comprising all or a portion of the heavy chain variable region or all or a portion of the light chain variable region of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

In some embodiments, the antibody or antigen-binding fragment thereof is a single-chain antibody fragment, such as a single chain variable fragment (scFv) or a diabody or a single domain antibody (sdAb). In some embodiments, the antibody or antigen-binding fragment is a single domain antibody comprising only the $V_H$ region. In some embodiments, the antibody or antigen binding fragment is an scFv comprising a heavy chain variable ($V_H$) region and a light chain variable ($V_L$) region.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In certain embodiments, the antigen or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the CAR is an anti-BCMA CAR that is specific for BCMA, e.g. human BCMA. Chimeric antigen receptors containing anti-BCMA antibodies, including mouse anti-human BCMA antibodies and human anti-human BCMA antibodies, and cells expressing such chimeric receptors have been previously described. See Carpenter et al., Clin Cancer Res., 2013, 19(8):2048-2060, U.S. Pat. No. 9,765,342, WO 2016/090320, WO2016090327, WO2010104949A2, WO2016/0046724, WO2016/014789, WO2016/094304, WO2017/025038, and WO2017173256. In some embodiments, the anti-BCMA CAR contains an antigen-binding domain, such as an scFv, containing a variable heavy ($V_H$) and/or a variable light ($V_L$) region derived from an antibody described in WO 2016/090320 or WO2016090327. In some embodiments, the antigen-binding domain is an antibody fragment containing a variable heavy chain ($V_H$) and a variable light chain ($V_L$) region. In some aspects, the $V_H$ region is or includes an amino acid sequence having at least 90%, 91%, 92%, 93%, 94%, 95%, 96%, 97%, 98% or 99% sequence identity to the $V_H$ region amino acid sequence set forth in any of SEQ ID NOs: 30, 32, 34, 36, 38, 40, 42, 77, 79, 81, 83, 85, 87, 89, 91, 93, 95, 97, 99, 101, 103, 105, 107, 109, 111, 181, 183, 185 and 188; and/or the $V_L$ region is or includes an amino acid sequence having at least 90%, 91%, 92%, 93%, 94%, 95%, 96%, 97%, 98%, or 99% sequence identity to the $V_L$ region amino acid sequence set forth in any of SEQ ID NOs: 31, 33, 35, 37, 39, 41, 43, 78, 80, 82, 84, 86, 88, 90, 92, 94, 96, 98, 100, 102, 104, 106, 108, 110, 112, 182, 184, 186 and 189.

In some embodiments, the antigen-binding domain, such as an scFv, contains a $V_H$ set forth in SEQ ID NO: 30 and a $V_L$ set forth in SEQ ID NO:31. In some embodiments, the antigen-binding domain, such as an scFv, contains a $V_H$ set forth in SEQ ID NO: 32 and a $V_L$ set forth in SEQ ID NO:33. In some embodiments, the antigen-binding domain, such as an scFv, contains a $V_H$ set forth in SEQ ID NO: 34 and a $V_L$ set forth in SEQ ID NO: 35. In some embodiments, the antigen-binding domain, such as an scFv, contains a $V_H$ set forth in SEQ ID NO: 36 and a $V_L$ set forth in SEQ ID NO:37. In some embodiment the antigen-binding domain, such as an scFv, contains a $V_H$ set forth in SEQ ID NO: 38 and a $V_L$ set forth in SEQ ID NO: 39. In some embodiments, the antigen-binding domain, such as an scFv, contains a $V_H$ set forth in SEQ ID NO: 40 and a $V_L$ set forth in SEQ ID NO: 41. In some embodiments, the antigen-binding domain, such as an scFv, contains a $V_H$ set forth in SEQ ID NO: 42 and a $V_L$ set forth in SEQ ID NO: 43. In some embodiments, the antigen-binding domain, such as an scFv, contains a $V_H$ set forth in SEQ ID NO: 77 and a $V_L$ set forth in SEQ ID NO: 78. In some embodiments, the antigen-binding domain, such as an scFv, contains a $V_H$ set forth in SEQ ID NO: 79 and a $V_L$ set forth in SEQ ID NO: 80. In some embodiments, the antigen-binding domain, such as an scFv, contains a $V_H$ set forth in SEQ ID NO: 81 and a $V_L$ set forth in SEQ ID NO: 82. In some embodiments, the antigen-binding domain, such as an scFv, contains a $V_H$ set forth in SEQ ID NO: 83 and a $V_L$ set forth in SEQ ID NO: 84. In some embodiments, the antigen-binding domain, such as an scFv, contains a $V_H$ set forth in SEQ ID NO: 85 and a $V_L$ set forth in SEQ ID NO: 86. In some embodiments, the antigen-binding domain, such as an scFv, contains a $V_H$ set forth in SEQ ID NO: 87 and a $V_L$ set forth in SEQ ID NO: 88. In some embodiments, the antigen-binding domain, such as an scFv, contains a $V_H$ set forth in SEQ ID NO: 89 and a $V_L$ set forth in SEQ ID NO: 90. In some embodiments, the antigen-binding domain, such as an scFv, contains a $V_H$ set forth in SEQ ID NO: 91 and a $V_L$ set forth in SEQ ID NO: 92. In some embodiments, the antigen-binding domain, such as an scFv, contains a $V_H$ set forth in SEQ ID NO: 93 and a $V_L$ set forth in SEQ ID NO: 94. In some embodiments, the antigen-binding domain, such as an scFv, contains a $V_H$ set forth in SEQ ID NO: 95 and a $V_L$ set forth in SEQ ID NO: 96. In some embodiments, the antigen-binding domain, such as an scFv, contains a $V_H$ set forth in SEQ ID NO: 97 and a $V_L$ set forth in SEQ ID NO: 98. In some embodiments, the antigen-binding domain, such as an scFv, contains a $V_H$ set forth in SEQ ID NO: 99 and a $V_L$ set forth in SEQ ID NO: 100. In some embodiments, the antigen-binding domain, such as an scFv, contains a $V_H$ set forth in SEQ ID NO: 101 and a $V_L$ set forth in SEQ ID NO: 102. In some embodiments, the antigen-binding domain, such as an scFv, contains a $V_H$ set forth in SEQ ID NO: 103 and a $V_L$ set forth in SEQ ID NO: 104. In some embodiments, the antigen-binding domain, such as an scFv, contains a $V_H$ set forth in SEQ ID NO: 105 and a $V_L$ set forth in SEQ ID NO: 106. In some embodiments, the antigen-binding domain, such as an scFv, contains a $V_H$ set forth in SEQ ID NO: 107 and a $V_L$ set forth in SEQ ID NO: 106. In some embodiments, the antigen-binding domain, such as an scFv, contains a $V_H$ set forth in SEQ ID NO: 30 and a $V_L$ set forth in SEQ ID NO: 108. In some embodiments, the antigen-binding domain, such as an scFv, contains a $V_H$ set forth in SEQ ID NO: 109 and a $V_L$ set forth in SEQ ID NO: 110. In some embodiments, the antigen-binding domain, such as an scFv, contains a $V_H$ set forth in SEQ ID NO: 111 and a $V_L$ set forth in SEQ ID NO: 112. In some embodiments, the antigen-binding domain, such as an scFv, contains a $V_H$ set forth in SEQ ID NO: 181 and a $V_L$ set forth in SEQ ID NO: 182. In some embodiments, the antigen-binding domain, such as an scFv, contains a $V_H$ set forth in SEQ ID NO: 183 and a $V_L$ set forth in SEQ ID NO: 184. In some embodiments, the antigen-binding domain, such as an scFv, contains a $V_H$ set forth in SEQ ID NO: 185 and a $V_L$ set forth in SEQ ID NO: 186. In some embodiments, the antigen-binding domain, such as an scFv, contains a $V_H$ set forth in SEQ ID NO: 187 and a $V_L$ set forth in SEQ ID NO: 188. In some embodiments, the $V_H$ or $V_L$ has a sequence of amino acids that exhibits at least 85%, 86%, 87%, 88%, 89%, 90%, 91%, 92%, 93%, 94%, 95%, 96%, 97%, 98%, 99% or more sequence identity to any of the foregoing $V_H$ or $V_L$ sequences, and retains binding to BCMA. In some embodiments, the $V_H$ region is amino-terminal to the $V_L$ region. In some embodiments, the $V_H$ region is carboxy-terminal to the $V_L$ region. In some embodiments, the variable heavy and variable light chains are connected by a linker. In some embodiments, the linker is set forth in SEQ ID NO: 70, 72, 73, 74 or 189.

In some embodiments, the CAR is an anti-CD19 CAR that is specific for CD19, e.g. human CD19. In some embodiments the antigen-binding domain includes a $V_H$ and/or $V_L$ derived from FMC63, which, in some aspects, can be an scFv. In some embodiments the scFv and/or $V_H$ domains is derived from FMC63. FMC63 generally refers to a mouse monoclonal IgG1 antibody raised against Nalm-1 and -16 cells expressing CD19 of human origin (Ling, N. R., et al. (1987). *Leucocyte typing III*. 302). The FMC63 antibody comprises CDRH1 and H2 set forth in SEQ ID NOS: 44, 45 respectively, and CDRH3 set forth in SEQ ID NOS: 46 or 47 and CDRL1 set forth in SEQ ID NOS: 48 and CDR L2 set forth in SEQ ID NO: 49 or 50 and CDR L3 sequences set forth in SEQ ID NO: 51 or 52. The FMC63 antibody comprises the heavy chain variable region ($V_H$) comprising the amino acid sequence of SEQ ID NO: 53 and the light chain variable region ($V_L$) comprising the amino acid sequence of SEQ ID NO: 54. In some embodiments, the svFv comprises a variable light chain containing the CDRL1 sequence of SEQ ID NO:48, a CDRL2 sequence of SEQ ID NO:49, and a CDRL3 sequence of SEQ ID NO:51 and/or a variable heavy chain containing a CDRH1 sequence of SEQ ID NO:44, a CDRH2 sequence of SEQ ID NO:45, and a CDRH3 sequence of SEQ ID NO:46. In some embodiments, the scFv comprises a variable heavy chain region of FMC63 set forth in SEQ ID NO:53 and a variable light chain region of FMC63 set forth in SEQ ID NO:54. In some embodiments, the variable heavy and variable light chains are connected by a linker. In some embodiments, the linker is set forth in SEQ ID NO: 70, 72, 73, 74 or 189. In some embodiments, the scFv comprises, in order, a $V_H$, a linker, and a $V_L$. In some embodiments, the scFv comprises, in order, a $V_L$, a linker, and a $V_H$. In some embodiments, the svFv is encoded by a sequence of nucleotides set forth in SEQ ID NO:69 or a sequence that exhibits at least 85%, 86%, 87%, 88%, 89%, 90%, 91%, 92%, 93%, 94%, 95%, 96%, 97%, 98%, or 99% sequence identity to SEQ ID NO:69. In some embodiments, the scFv comprises the sequence of amino acids set forth in SEQ ID NO:55 or a sequence that exhibits at least 85%, 86%, 87%, 88%, 89%, 90%, 91%, 92%, 93%, 94%, 95%, 96%, 97%, 98%, or 99% sequence identity to SEQ ID NO:55.

In some embodiments the antigen-binding domain includes a $V_H$ and/or $V_L$ derived from SJ25C1, which, in some aspects, can be an scFv. SJ25C1 is a mouse monoclonal IgG1 antibody raised against Nalm-1 and -16 cells expressing CD19 of human origin (Ling, N. R., et al. (1987). *Leucocyte typing III*. 302). The SJ25C1 antibody comprises CDRH1, H2 and H3 set forth in SEQ ID NOS: 59-61, respectively, and CDRL1, L2 and L3 sequences set forth in SEQ ID NOS: 56-58, respectively. The SJ25C1 antibody comprises the heavy chain variable region ($V_H$) comprising the amino acid sequence of SEQ ID NO: 62 and the light chain variable region ($V_L$) comprising the amino acid sequence of SEQ ID NO: 63. In some embodiments, the svFv comprises a variable light chain containing the CDRL1 sequence of SEQ ID NO:56, a CDRL2 sequence of SEQ ID NO: 57, and a CDRL3 sequence of SEQ ID NO:58 and/or a variable heavy chain containing a CDRH1 sequence of SEQ ID NO:59, a CDRH2 sequence of SEQ ID NO:60, and a CDRH3 sequence of SEQ ID NO:61. In some embodiments, the scFv comprises a variable heavy chain region of SJ25C1 set forth in SEQ ID NO:62 and a variable light chain region of SJ25C1 set forth in SEQ ID NO:63. In some embodiments, the variable heavy and variable light chain are connected by a linker. In some embodiments, the linker is set forth in SEQ ID NO:64. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:65 or a sequence that exhibits at least 85%, 86%, 87%, 88%, 89%, 90%, 91%, 92%, 93%, 94%, 95%, 96%, 97%, 98%, or 99% sequence identity to SEQ ID NO:65.

In some embodiments, the antibody is an antigen-binding fragment, such as an scFv, that includes one or more linkers joining two antibody domains or regions, such as a heavy chain variable ($V_H$) region and a light chain variable ($V_L$) region. Accordingly, the antibodies include single-chain antibody fragments, such as scFvs and diabodies, particularly human single-chain antibody fragments, typically comprising linker(s) joining two antibody domains or regions, such $V_H$ and $V_L$ regions. The linker typically is a peptide linker, e.g., a flexible and/or soluble peptide linker, such as one rich in glycine and serine. Among the linkers are those rich in glycine and serine and/or in some cases threonine. In some embodiments, the linkers further include charged residues such as lysine and/or glutamate, which can improve solubility. In some embodiments, the linkers further include one or more proline.

In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO:19) or GGGS (3GS; SEQ ID NO:71), such as between 2, 3, 4, and 5 repeats of such a sequence. Exemplary linkers include those having or consisting of an sequence set forth in SEQ ID NO:72 (GGGGSGGGGSGGGGS), SEQ ID NO:189 (ASGGGGSGGRASGGGGS), SEQ ID NO:73 (GSTSGSGKPGSGEGSTKG) or SEQ ID NO: 74 (SRGGGGSGGGGSGGGGSLEMA).

In some embodiments, the recombinant receptor such as the CAR, such as the antibody portion of the recombinant receptor, e.g., CAR, further includes a spacer, which may be or include at least a portion of an immunoglobulin constant region or variant or modified version thereof, such as a hinge region, e.g., an IgG4 hinge region, an IgG1 hinge region, a $CH_1/CL$, and/or Fc region. In some embodiments, the recombinant receptor further comprises a spacer and/or a hinge region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer.

Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. In some embodiments, the spacer is a spacer having at least a particular length, such as having a length that is at least 100 amino acids, such as at least 110, 125, 130, 135, 140, 145, 150, 160, 170, 180, 190, 200, 210, 220, 230, 240, or 250 amino acids in length. Exemplary spacers include IgG4 hinge alone, IgG4 hinge linked to $C_H2$ and $C_H3$ domains, or IgG4 hinge linked to the $C_H3$ domain. Exemplary spacers include IgG4 hinge alone, IgG4 hinge linked to $C_H2$ and $C_H3$ domains, or IgG4 hinge linked to the $C_H3$ domain. Exemplary spacers include, but are not limited to, those described in Hudecek et al., Clin. Cancer Res., 19:3153 (2013), Hudecek et al. (2015) Cancer Immunol Res. 3(2): 125-135, international patent application publication number WO2014031687, U.S. Pat. No. 8,822,647 or published app. No. US2014/0271635. In some embodiments, the spacer includes a sequence of an immunoglobulin hinge region, a $C_H2$ and $C_H3$ region. In some embodiments, one of more of the hinge, $C_H2$ and $C_H3$ is derived all or in part from IgG4 or IgG2. In some cases, the hinge, $C_H2$ and $C_H3$ is derived from IgG4. In some aspects, one or more of the hinge, $C_H2$ and $C_H3$ is chimeric and contains sequence derived from IgG4 and IgG2. In some examples, the spacer contains an IgG4/2 chimeric hinge, an IgG2/4 $C_H2$, and an IgG4 $C_H3$ region.

In some embodiments, the spacer, which can be a constant region or portion thereof of an immunoglobulin, is of a human IgG, such as IgG4 or IgG1. In some embodiments, the spacer has the sequence ESKYGPPCPPCP (set forth in SEQ ID NO: 1). In some embodiments, the spacer has the sequence set forth in SEQ ID NO: 3. In some embodiments, the spacer has the sequence set forth in SEQ ID NO: 4. In some embodiments, the encoded spacer is or contains the sequence set forth in SEQ ID NO: 29. In some embodiments, the constant region or portion is of IgD. In some embodiments, the spacer has the sequence set forth in SEQ ID NO: 5. In some embodiments, the spacer has the sequence set forth in SEQ ID NO: 125.

In some embodiments, the spacer can be derived all or in part from IgG4 and/or IgG2 and can contain mutations, such as one or more single amino acid mutations in one or more domains. In some examples, the amino acid modification is a substitution of a proline (P) for a serine (S) in the hinge region of an IgG4. In some embodiments, the amino acid modification is a substitution of a glutamine (Q) for an asparagine (N) to reduce glycosylation heterogeneity, such as an N177Q mutation at position 177, in the $C_H2$ region, of the full-length IgG4 Fc sequence or an N176Q. at position 176, in the CH2 region, of the full-length IgG4 Fc sequence.

Other exemplary spacer regions include hinge regions derived from CD8a, CD28, CTLA4, PD-1, or FcγRIIIa. In some embodiments, the spacer contains a truncated extracellular domain or hinge region of a CD8a, CD28, CTLA4, PD-1, or FcγRIIIa. In some embodiments, the spacer is a truncated CD28 hinge region. In some embodiments, a short oligo- or polypeptide linker, for example, a linker of between 2 and 10 amino acids in length, such as one containing alanines or alanine and arginine, e.g., alanine triplet (AAA) or RAAA (SEQ ID NO: 180), is present and forms a linkage between the scFv and the spacer region of the CAR. In some embodiments, the spacer has the sequence set forth in SEQ ID NO: 114. In some embodiments, the spacer has the sequence set forth in SEQ ID NO: 116. In some embodiments, the spacer has the sequence set forth in any of SEQ ID NOs: 117-119, In some embodiments, the spacer has the sequence set forth in SEQ ID NO: 120. In some embodiments, the spacer has the sequence set forth in SEQ ID NO: 122. In some embodiments, the spacer has the sequence set forth in SEQ ID NO: 124.

In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4, 5 or 29, 114, 116, 117, 118, 119, 120, 122, 124, or 125.

This antigen recognition domain generally is linked to one or more intracellular signaling components, such as signaling components that mimic stimulation and/or activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD8a, CD9, CD16, CD22, CD33, CD37, CD64, CD80, CD86, CD 134, CD137 (4-1BB), CD154, CTLA-4, or PD-1. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). Exemplary sequences of transmembrane domains are or comprise the sequences set forth in SEQ ID NOs: 8, 115, 121, 123, 178, or 179.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell stimulation and/or activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25 or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor stimulates and/or activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell stimulation and/or activation is in some aspects described as being mediated by two classes of cytoplasmic signaling sequences: those that initiate antigen-dependent primary stimulation and/or activation through the TCR (primary cytoplasmic signaling regions, domains or sequences), and those that act in an antigen-independent manner to provide a secondary or co-stimulatory signal (secondary cytoplasmic signaling regions, domains or sequences). In some aspects, the CAR includes one or both of such signaling components.

In some aspects, the CAR includes a primary cytoplasmic signaling regions, domains or sequence that regulates primary activation of the TCR complex. Primary cytoplasmic signaling regions, domains or sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b and CD66d. In some embodiments, cytoplasmic signaling molecule(s) in the CAR contain(s) a cytoplasmic signaling domain, portion thereof, or sequence derived from CD3 zeta. In some embodiments, the CAR includes a signaling region and/or transmembrane portion of a costimulatory receptor, such as CD28, 4-1BB, OX40 (CD134), CD27, DAP10, DAP12, ICOS and/or other costimulatory receptors. In some aspects, the same CAR includes both the primary cytoplasmic signaling region and costimulatory signaling components.

In some embodiments, one or more different recombinant receptors can contain one or more different intracellular signaling region(s) or domain(s). In some embodiments, the primary cytoplasmic signaling region is included within one CAR, whereas the costimulatory component is provided by another receptor, e.g., another CAR recognizing another antigen. In some embodiments, the CARs include activating or stimulatory CARs, and costimulatory CARs, both expressed on the same cell (see WO2014/055668).

In some aspects, the cells include one or more stimulatory or activating CAR and/or a costimulatory CAR. In some embodiments, the cells further include inhibitory CARs (iCARs, see Fedorov et al., *Sci. Transl. Medicine*, 5(215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and primary cytoplasmic signaling region, in the cytoplasmic portion. Exemplary CARs include intracellular components, such as intracellular signaling region(s) or domain(s), of CD3-zeta, CD28, CD137 (4-1BB), OX40 (CD134), CD27, DAP10, DAP12, NKG2D and/or ICOS. In some embodiments, the chimeric antigen receptor contains an intracellular signaling region or domain of a T cell costimulatory molecule, e.g., from CD28, CD137 (4-1BB), OX40 (CD134), CD27, DAP10, DAP12, NKG2D and/or ICOS, in some cases, between the transmembrane domain and intracellular signaling region or domain. In some aspects, the T cell costimulatory molecule is one or more of CD28, CD137 (4-1BB), OX40 (CD134), CD27, DAP10, DAP12, NKG2D and/or ICOS.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 4-1BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P10747.1) or CD8a (Accession No. P01732.1) or variant thereof, such as a transmembrane domain that comprises the sequence of amino acids set forth in SEQ ID NO: 8, 115, 178, or 179 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8, 115, 178, or 179; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3 (Accession No. P20963.2) or a CD3 zeta signaling domain as described in U.S. Pat. Nos. 7,446,190 or 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1 or SEQ ID NO: 125. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers. In some embodiments, the spacer is a CD8a hinge, such as set forth in any of SEQ ID NOs: 117-119, an FcγRIIIa hinge, such as set forth in SEQ ID NO: 124, a CTLA4 hinge, such as set forth in SEQ ID NO: 120, or a PD-1 hinge, such as set forth in SEQ ID NO: 122.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer, such as any of the Ig-hinge containing spacers, a CD28-derived transmembrane domain, a 4-1BB-derived intracellular signaling domain, and a CD3 zeta-derived signaling domain.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition. Non-limiting exemplary CAR sequences are set forth in SEQ ID NOs: 126-177.

In some embodiments, the encoded CAR can sequence can further include a signal sequence or signal peptide that directs or delivers the CAR to the surface of the cell in which the CAR is expressed. In some embodiments, the signal peptide is derived from a transmembrane protein. In some examples the signal peptide is derived from CD8a, CD33, or an IgG. Exemplary signal peptides include the sequences set forth in SEQ ID NOs: 21, 75 and 76 or variant thereof.

In some embodiments, the CAR includes an anti-CD19 antibody such as an antibody fragment, including scFvs, a spacer, such as a spacer containing a portion of an immunoglobulin molecule, such as a hinge region and/or one or more constant regions of a heavy chain molecule, such as any of the Ig-hinge containing spacers or other spacers described herein, a transmembrane domain containing all or a portion of a CD28-derived transmembrane domain, a CD28-derived intracellular signaling domain, and a CD3 zeta signaling domain. In some embodiments, the CAR includes an anti-CD19 antibody or fragment, such as scFv, a spacer such as any of the Ig-hinge containing spacers or other spacers described herein, a CD28-derived transmembrane domain, a 4-1BB-derived intracellular signaling domain, and a CD3 zeta-derived signaling domain. In some embodiments, such CAR constructs further includes a T2A ribosomal skip element and/or a tEGFR sequence, e.g., downstream of the CAR.

In some embodiments, the CAR includes an anti-BCMA antibody or fragment, such as any of the anti-human BCMA antibodies, including sdAbs and scFvs, described herein, a spacer such as any of the Ig-hinge containing spacers or other spacers described herein, a CD28 transmembrane domain, a CD28 intracellular signaling domain, and a CD3 zeta signaling domain. In some embodiments, the CAR includes an anti-BCMA antibody or fragment, such as any of the anti-human BCMA antibodies, including sdAbs and scFvs described herein, a spacer such as any of the Ig-hinge containing spacers or other spacers described herein, a CD28 transmembrane domain, a 4-1BB intracellular signaling domain, and a CD3 zeta signaling domain. In some embodiments, such CAR constructs further includes a T2A ribosomal skip element and/or a tEGFR sequence, e.g., downstream of the CAR.

2. Chimeric Auto-Antibody Receptor (CAAR)

In some embodiments, the recombinant receptor is a chimeric autoantibody receptor (CAAR). In some embodiments, the CAAR binds, e.g., specifically binds, or recognizes, an autoantibody. In some embodiments, a cell expressing the CAAR, such as a T cell engineered to express a CAAR, can be used to bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and one or more intracellular signaling region or domain (also interchangeably called a cytoplasmic signaling domain or region). In some embodiments, the intracellular signaling region comprises an intracellular signaling domain. In some embodiments, the intracellular signaling domain is or comprises a primary signaling region, a signaling domain that is capable of stimulating and/or inducing a primary activation signal in a T cell, a signaling domain of a T cell receptor (TCR) component (e.g. an intracellular signaling domain or region of a zeta chain of a CD3-zeta (CD3) chain or a functional variant or signaling portion thereof), and/or a signaling domain comprising an immunoreceptor tyrosine-based activation motif (ITAM).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

3. TCRs

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein. In some aspects, the TCR is or includes a recombinant TCR.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., *Immunobiology: The Immune System in Health and Disease*, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the recombinant receptors include recombinant TCRs and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4$^+$ or CD8$^+$ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al., (2003) Nat Immunol, 4, 55-62; Holler et al., (2000) Proc Natl Acad Sci USA, 97, 5387-92), phage display (Li et al., (2005) Nat Biotechnol, 23, 349-54), or T cell display (Chervin et al., (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified as a matter of routine. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using computer prediction models as a matter of routine. In some embodiments, for predicting MHC class I binding sites, such models include, but are not limited to, ProPred1 (Singh and Raghava (2001) *Bioinformatics* 17(12):1236-1237, and SYFPEITHI (see Schuler et al., (2007) *Immunoinformatics Methods in Molecular Biology,* 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPred1 (described in more detail in Singh and Raghava, ProPred: prediction of HLA-DR binding sites. *BIOINFORMATICS* 17(12):1236-1237 2001), and SYFPEITHI (see Schuler et al., SYFPEITHI, Database for Searching and T-Cell Epitope Prediction. in *Immunoinformatics Methods in Molecular Biology,* vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using suitable known methods, See e.g., Soo Hoo, W. F. et al., *PNAS* (USA) 89, 4759 (1992); Wülfing, C. and Plückthun, A., *J. Mol. Biol.* 242, 655 (1994); Kurucz, I. et al., *PNAS* (USA) 90 3830 (1993); International published PCT Nos. WO 96/13593, WO 96/18105, WO99/60120, WO99/18129, WO 03/020763, WO2011/044186; and Schlueter, C. J. et al., *J. Mol. Biol.* 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an a chain variable region sequence fused to the N terminus of an a chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an a chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)5-P- wherein P is proline, G is glycine and S is serine (SEQ ID NO: 16). In some embodiments, the linker has the sequence GSADDAKKDAAKKDGKS (SEQ ID NO: 17)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about $10^{-5}$ and $10^{-12}$ M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, La Jolla, CA), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAMneo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

4. Multi-Targeting

In some embodiments, the cells and methods include multi-targeting strategies, such as expression of two or more genetically engineered receptors on the cell, each recognizing the same of a different antigen and typically each including a different intracellular signaling component. Such multi-targeting strategies are described, for example, in PCT Pub. No. WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5(215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1 BB), OX40, and/or ICOS. In some embodiments, the first and second receptors include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the cells expressing the recombinant receptor further include inhibitory CARs (iCARs, see Fedorov et al., *Sci. Transl. Medicine,* 5(215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

B. Cells and Preparation of Cells for Genetic Engineering

Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of $CD4^+$ and/or of $CD8^+$ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using anti-CD3/anti-CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ cells are further enriched for or depleted of naive, central memory, effector memory, and/or central memory stem cells, such as by positive or negative selection based on surface antigens associated with the respective subpopulation. In some embodiments, enrichment for central memory T (T$_{CM}$) cells is carried out to increase efficacy, such as to improve long-term survival, expansion, and/or engraftment following administration, which in some aspects is particularly robust in such subpopulations. See Terakura et al., *Blood.* 1:72-82 (2012); Wang et al., *J Immunother.* 35(9):689-701 (2012). In some embodiments, combining TCM-enriched CD8$^+$ T cells and CD4$^+$ T cells further enhances efficacy.

In embodiments, memory T cells are present in both CD62L$^+$ and CD62L$^-$ subsets of CD8$^+$ peripheral blood lymphocytes. PBMC can be enriched for or depleted of CD62L-CD8$^+$ and/or CD62L+CD8$^+$ fractions, such as using anti-CD8 and anti-CD62L antibodies.

In some embodiments, the enrichment for central memory T (T$_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8$^+$ population enriched for T$_{CM}$ cells is carried out by depletion of cells expressing CD4, CD14, CD45RA, and positive selection or enrichment for cells expressing CD62L. In one aspect, enrichment for central memory T (T$_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4$^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4$^+$ T helper cells are sorted into naïve, central memory, and effector cells by identifying cell populations that have cell surface antigens. CD4$^+$ lymphocytes can be obtained by standard methods. In some embodiments, naive CD4$^+$ T lymphocytes are CD45RO-, CD45RA$^+$, CD62L+, CD4$^+$ T cells. In some embodiments, central memory CD4$^+$ cells are CD62L$^+$ and CD45RO$^+$. In some embodiments, effector CD4$^+$ cells are CD62L- and CD45RO-.

In one example, to enrich for CD4$^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher © Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in PCT Pub. Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al., J Immunother. 35(9): 651-660 (2012), Terakura et al., *Blood.* 1:72-82 (2012), and Wang et al., *J Immunother.* 35(9):689-701 (2012).

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al., *Lab Chip* 10, 1567-1573 (2010); and Godin et al., *J Biophoton.* 1(5):355-376 (2008). In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al., J Immunother. 35(9): 651-660 (2012), Terakura et al., Blood. 1:72-82 (2012), and/or Wang et al., J Immunother. 35(9):689-701 (2012).

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific $CD4^+$ and/or CD8+ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

C. Nucleic Acids, Vectors and Methods for Genetic Engineering

In some embodiments, the cells, e.g., T cells, are genetically engineered to express a recombinant receptor. In some embodiments, the engineering is carried out by introducing nucleic acid molecules that encode the recombinant receptor. Also provided are nucleic acid molecules encoding a recombinant receptor, and vectors or constructs containing such nucleic acids and/or nucleic acid molecules.

In some cases, the nucleic acid sequence encoding the recombinant receptor, e.g., chimeric antigen receptor (CAR), contains a signal sequence that encodes a signal peptide. In some aspects, the signal sequence may encode a signal peptide derived from a native polypeptide. In other aspects, the signal sequence may encode a heterologous or non-native signal peptide. In some embodiments, the signal peptide is derived from a transmembrane protein. In some examples the signal peptide is derived from CD8a, CD33, or an IgG. Non-limiting exemplary examples of signal peptides include, for example, the CD33 signal peptide set forth in SEQ ID NO:21, CD8a signal peptide set forth in SEQ ID NO:75, or the signal peptide set forth in SEQ ID NO:76 or modified variant thereof.

In some embodiments, the nucleic acid molecule encoding the recombinant receptor contains at least one promoter that is operatively linked to control expression of the recombinant receptor. In some examples, the nucleic acid molecule contains two, three, or more promoters operatively linked to control expression of the recombinant receptor. In some embodiments, nucleic acid molecule can contain regulatory sequences, such as transcription and translation initiation and termination codons, which are specific to the type of host (e.g., bacterium, fungus, plant, or animal) into which the nucleic acid molecule is to be introduced, as appropriate and taking into consideration whether the nucleic acid molecule is DNA- or RNA-based. In some embodiments, the nucleic acid molecule can contain regulatory/control elements, such as a promoter, an enhancer, an intron, a polyadenylation signal, a Kozak consensus sequence, and splice acceptor or donor. In some embodiments, the nucleic acid molecule can contain a nonnative promoter operably linked to the nucleotide sequence encoding the recombinant receptor and/or one or more additional polypeptide(s). In some embodiments, the promoter is selected from among an RNA pol I, pol II or pol III promoter. In some embodiments, the promoter is recognized by RNA polymerase II (e.g., a CMV, SV40 early region or adenovirus major late promoter). In another embodiment, the promoter is recognized by RNA polymerase III (e.g., a U6 or H1 promoter). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, the promoter is or comprises a constitutive promoter. Exemplary constitutive promoters include, e.g., simian virus 40 early promoter (SV40), cytomegalovirus immediate-early promoter (CMV), human Ubiquitin C promoter (UBC), human elongation factor 1a promoter (EF1α), mouse phosphoglycerate kinase 1 promoter (PGK), and chicken β-Actin promoter coupled with CMV early enhancer (CAGG). In some embodiments, the constitutive promoter is a synthetic or modified promoter. In some embodiments, the promoter is or comprises an MND promoter, a synthetic promoter that contains the U3 region of a modified MoMuLV LTR with myeloproliferative sarcoma virus enhancer (see Challita et al. (1995) J. Virol. 69(2):748-755). In some embodiments, the promoter is a tissue-specific promoter. In another embodiment, the promoter is a viral promoter. In another embodiment, the promoter is a non-viral promoter.

In another embodiment, the promoter is a regulated promoter (e.g., inducible promoter). In some embodiments, the promoter is an inducible promoter or a repressible promoter. In some embodiments, the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof. In some embodiments, the nucleic acid molecule does not include a regulatory element, e.g. promoter.

In some embodiments, the nucleic acid molecule encoding the recombinant receptor, e.g., CAR or other antigen receptor, further includes nucleic acid sequences encoding a marker and/or cells expressing the CAR or other antigen receptor further includes a marker, e.g., a surrogate marker, such as a cell surface marker, which may be used to confirm transduction or engineering of the cell to express the receptor, such as a truncated version of a cell surface receptor, such as truncated EGFR (tEGFR). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the nucleic acid molecule, e.g., a nucleic acid molecule encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same nucleic acid molecule that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A, a P2A, an E2A or an F2A. Extrinsic marker genes may in some cases be utilized in connection with engineered cell to permit detection or selection of cells and, in some cases, also to promote cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO:11 or 76) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some aspects, the marker, e.g. surrogate marker, includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 28, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 28. An exemplary T2A linker sequence comprises the sequence of amino acids set forth in SEQ ID NO: 6 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802, 374). In some embodiments, the sequence encodes an tEGFR sequence set forth in SEQ ID NO: 7 or 28, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 28.

In some embodiments, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known in the art. Examples of 2A sequences that can be used in the methods and nucleic acids disclosed herein, without limitation, 2A sequences from the foot-and-mouth disease virus (F2A, e.g., SEQ ID NO: 27), equine rhinitis A virus (E2A, e.g., SEQ ID NO: 26), Thosea asigna virus (T2A, e.g., SEQ ID NO: 6 or 23), and porcine teschovirus-1 (P2A, e.g., SEQ ID NO: 24 or 25) as described in U.S. Patent Publication No. 20070116690.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

Introduction of the nucleic acid molecules encoding the recombinant receptor in the cell may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some embodiments, prior to or during gene transfer, the cells are incubated or cultured in the presence of an immunomodulatory compound, e.g., lenalidomide, Compound 1 or Compound 2, including any as described herein. In some embodiments, the immunomodulatory compound, e.g., lenalidomide, Compound 1 or Compound 2 is added during the cell manufacturing process, for example, during the process of engineering CAR-T cells. In some aspects, the presence of the immunomodulatory compound can improve the quality of the population of cells produced. In some aspects, the immunomodulatory compound, e.g., lenalidomide, Compound 1 or Compound 2 may increase the proliferation or expansion of cells or may alter one or more signaling pathways thereby resulting in cells with a less-differentiated or less activated surface phenotype, despite exhibiting substantial expansion and/or effector function.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell 2:223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 November 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) *Blood.* 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) *Hum Gene Ther* 21(4): 427-437; Sharma et al. (2013) *Molec Ther Nucl* Acids 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

In some aspects, the cells further are engineered to promote expression of cytokines or other factors. Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

III. Exemplary Treatment Outcomes and Methods for Assessing Same

In some embodiments of the methods, compositions, combinations, kits and uses provided herein, the provided combination therapy results in one or more treatment outcomes, such as a feature associated with any one or more of the parameters associated with the therapy or treatment, as described below. In some embodiments, the method includes assessment of the exposure, persistence and proliferation of the T cells, e.g., T cells administered for the T cell based therapy. In some embodiments, the exposure, or prolonged expansion and/or persistence of the cells, and/or changes in cell phenotypes or functional activity of the cells, e.g., cells administered for immunotherapy, e.g. T cell therapy, in the methods provided herein, can be measured by assessing the characteristics of the T cells in vitro or ex vivo. In some embodiments, such assays can be used to determine or confirm the function of the T cells, e.g. T cell therapy, before or after administering the combination therapy provided herein.

In some embodiments, the combination therapy can further include one or more screening steps to identify subjects for treatment with the combination therapy and/or continuing the combination therapy, and/or a step for assessment of treatment outcomes and/or monitoring treatment outcomes. In some embodiments, the step for assessment of treatment outcomes can include steps to evaluate and/or to monitor treatment and/or to identify subjects for administration of further or remaining steps of the therapy and/or for repeat therapy. In some embodiments, the screening step and/or assessment of treatment outcomes can be used to determine the dose, frequency, duration, timing and/or order of the combination therapy provided herein.

In some embodiments, any of the screening steps and/or assessment of treatment of outcomes described herein can be used prior to, during, during the course of, or subsequent to administration of one or more steps of the provided combination therapy, e.g., administration of the T cell therapy (e.g. CAR-expressing T cells), and/or an immunomodulatory compound, e.g., lenalidomide or Compound 1. In some embodiments, assessment is made prior to, during, during the course of, or after performing any of the methods provided herein. In some embodiments, the assessment is made prior to performing the methods provided herein. In some embodiments, assessment is made after performing one or more steps of the methods provided herein. In some embodiments, the assessment is performed prior to administration of administration of one or more steps of the provided combination therapy, for example, to screen and identify patients suitable and/or susceptible to receive the combination therapy. In some embodiments, the assessment is performed during, during the course of, or subsequent to administration of one or more steps of the provided combination therapy, for example, to assess the intermediate or final treatment outcome, e.g., to determine the efficacy of the treatment and/or to determine whether to continue or repeat the treatments and/or to determine whether to administer the remaining steps of the combination therapy.

In some embodiments, treatment of outcomes includes improved immune function, e.g., immune function of the T cells administered for cell based therapy and/or of the endogenous T cells in the body. In some embodiments, exemplary treatment outcomes include, but are not limited to, enhanced T cell proliferation, enhanced T cell functional activity, changes in immune cell phenotypic marker expression, such as such features being associated with the engineered T cells, e.g. CAR-T cells, administered to the subject. In some embodiments, exemplary treatment outcomes include decreased disease burden, e.g., tumor burden, improved clinical outcomes and/or enhanced efficacy of therapy.

In some embodiments, the screening step and/or assessment of treatment of outcomes includes assessing the survival and/or function of the T cells administered for cell based therapy. In some embodiments, the screening step and/or assessment of treatment of outcomes includes assessing the levels of cytokines or growth factors. In some embodiments, the screening step and/or assessment of treatment of outcomes includes assessing disease burden and/or improvements, e.g., assessing tumor burden and/or clinical outcomes. In some embodiments, either of the screening step and/or assessment of treatment of outcomes can include any of the assessment methods and/or assays described herein and/or known in the art, and can be performed one or more times, e.g., prior to, during, during the course of, or subsequently to administration of one or more steps of the combination therapy. Exemplary sets of parameters associated with a treatment outcome, which can be assessed in some embodiments of the methods provided herein, include peripheral blood immune cell population profile and/or tumor burden.

In some embodiments, the methods affect efficacy of the cell therapy in the subject. In some embodiments, the persistence, expansion, and/or presence of recombinant receptor-expressing, e.g., CAR-expressing, cells in the subject following administration of the dose of cells in the method with the immunomodulatory compound is greater as compared to that achieved via a method without the administration of the immunomodulatory compound. In some embodiments of the immunotherapy methods provided herein, such as a T cell therapy (e.g. CAR-expressing T cells), assessment of the parameter includes assessing the expansion and/or persistence in the subject of the administered T cells for the immunotherapy, e.g., T cell therapy, as compared to a method in which the immunotherapy is administered to the subject in the absence of the immunomodulatory compound. In some embodiments, the methods result in the administered T cells exhibiting increased or prolonged expansion and/or persistence in the subject as compared to a method in which the T cell therapy is administered to the subject in the absence of the immunomodulatory compound.

In some embodiments, the administration of the immunomodulatory compound, e.g., lenalidomide, Compound 1 or Compound 2 decreases disease burden, e.g., tumor burden, in the subject as compared to a method in which the dose of cells expressing the recombinant receptor is administered to the subject in the absence of the immunomodulatory compound. In some embodiments, the administration of the immunomodulatory compound, e.g., lenalidomide, Compound 1 or Compound 2 decreases blast marrow in the subject as compared to a method in which the dose of cells expressing the recombinant receptor is administered to the subject in the absence of the immunomodulatory compound. In some embodiments, the administration of the immunomodulatory compound, e.g., lenalidomide, Compound 1 or Compound 2 results in improved clinical outcomes, e.g., objective response rate (ORR), progression-free survival (PFS) and overall survival (OS), compared to a method in which the dose of cells expressing the recombinant receptor is administered to the subject in the absence of the immunomodulatory compound.

In some embodiments, the subject can be screened prior to the administration of one or more steps of the combination therapy. For example, the subject can be screened for characteristics of the disease and/or disease burden, e.g., tumor burden, prior to administration of the combination therapy, to determine suitability, responsiveness and/or susceptibility to administering the combination therapy. In some embodiments, the screening step and/or assessment of treatment outcomes can be used to determine the dose, frequency, duration, timing and/or order of the combination therapy provided herein.

In some embodiments, the subject can be screened after administration of one of the steps of the combination therapy, to determine and identify subjects to receive the remaining steps of the combination therapy and/or to monitor efficacy of the therapy. In some embodiments, the number, level or amount of administered T cells and/or proliferation and/or activity of the administered T cells is assessed prior to administration and/or after administration of the immunomodulatory compound, e.g., lenalidomide, Compound 1 or Compound 2.

In some embodiments, the immunomodulatory compound, e.g., lenalidomide, Compound 1 or Compound 2 is administered until the concentration or number of engineered cells in the blood of the subject is (i) at least at or about 10 engineered cells per microliter, (ii) at least 20%, 30%, 40% or 50% of the total number of peripheral blood mononuclear cells (PBMCs), (iii) at least or at least about $1 \times 10^5$ engineered cells; or (iv) at least 5,000 copies of recombinant receptor-encoding DNA per micrograms DNA; and/or at day 90 following the initiation of the administration in (a), CAR-expressing cells are detectable in the blood or serum of the subject; and/or at day 90 following the initiation of the administration in (a), the blood of the subject contains at least 20% CAR-expressing cells, at least 10 CAR-expressing cells per microliter or at least $1 \times 10^4$ CAR-expressing cells.

In some embodiments, the immunomodulatory compound, e.g., lenalidomide, Compound 1 or Compound 2 is administered until there is a clinical benefit to the treatment, such as at least or greater than a 50% decrease in the total tumor volume or a complete response (CR) in which detectable tumor has disappeared, progression free survival or disease free survival for greater than 6 months or greater than 1 year or more.

In some embodiments, a change and/or an alteration, e.g., an increase, an elevation, a decrease or a reduction, in levels, values or measurements of a parameter or outcome compared to the levels, values or measurements of the same parameter or outcome in a different time point of assessment, a different condition, a reference point and/or a different subject is determined or assessed. For example, in some embodiments, a fold change, e.g., an increase or decrease, in particular parameters, e.g., number of engineered T cells in a sample, compared to the same parameter in a different condition, e.g., before or after administration of the immunomodulatory compound, e.g., lenalidomide, Compound 1 or Compound 2 can be determined. In some embodiments, the levels, values or measurements of two or more parameters are determined, and relative levels are compared. In some embodiments, the determined levels, values or measurements of parameters are compared to the levels, values or measurements from a control sample or an untreated sample. In some embodiments, the determined levels, values or measurements of parameters are compared to the levels from a sample from the same subject but at a different time point. The values obtained in the quantification of individual parameter can be combined for the purpose of disease assessment, e.g., by forming an arithmetical or logical operation on the levels, values or measurements of parameters by using multi-parametric analysis. In some embodiments, a ratio of two or more specific parameters can be calculated.

A. T Cell Exposure, Persistence and Proliferation

In some embodiments, the parameter associated with therapy or a treatment outcome, which include parameters that can be assessed for the screening steps and/or assessment of treatment of outcomes and/or monitoring treatment outcomes, is or includes assessment of the exposure, persistence and proliferation of the T cells, e.g., T cells administered for the T cell based therapy. In some embodiments, the increased exposure, or prolonged expansion and/or persistence of the cells, and/or changes in cell phenotypes or functional activity of the cells, e.g., cells administered for immunotherapy, e.g. T cell therapy, in the methods provided herein, can be measured by assessing the characteristics of the T cells in vitro or ex vivo. In some embodiments, such assays can be used to determine or confirm the function of the T cells used for the immunotherapy, e.g. T cell therapy, before or after administering one or more steps of the combination therapy provided herein.

In some embodiments, the administration of the immunomodulatory compound, e.g., lenalidomide, Compound 1 or Compound 2 are designed to promote exposure of the subject to the cells, e.g., T cells administered for T cell based therapy, such as by promoting their expansion and/or persistence over time. In some embodiments, the T cell therapy exhibits increased or prolonged expansion and/or persistence in the subject as compared to a method in which the T cell therapy is administered to the subject in the absence of the immunomodulatory compound, e.g., lenalidomide, Compound 1 or Compound 2.

In some embodiments, the provided methods increase exposure of the subject to the administered cells (e.g., increased number of cells or duration over time) and/or improve efficacy and therapeutic outcomes of the immunotherapy, e.g. T cell therapy. In some aspects, the methods are advantageous in that a greater and/or longer degree of exposure to the cells expressing the recombinant receptors, e.g., CAR-expressing cells, improves treatment outcomes as compared with other methods. Such outcomes may include patient survival and remission, even in individuals with severe tumor burden.

In some embodiments, the administration of the immunomodulatory compound, e.g., lenalidomide, Compound 1 or Compound 2 can increase the maximum, total, and/or duration of exposure to the cells, e.g. T cells administered for the T cell based therapy, in the subject as compared to administration of the T cells alone in the absence of the immunomodulatory compound. In some aspects, administration of the immunomodulatory compound, e.g., lenalidomide, Compound 1 or Compound 2, in the context of high disease burden (and thus higher amounts of antigen) and/or a more aggressive or resistant cancer enhances efficacy as compared with administration of the T cells alone in the absence of the immunomodulatory compound in the same context, which may result in immunosuppression, anergy and/or exhaustion which may prevent expansion and/or persistence of the cells.

In some embodiments, the presence and/or amount of cells expressing the recombinant receptor (e.g., CAR-expressing cells administered for T cell based therapy) in the subject following the administration of the T cells and before, during and/or after the administration of the immunomodulatory compound, e.g., lenalidomide, Compound 1 or Compound 2 is detected. In some aspects, quantitative PCR (qPCR) is used to assess the quantity of cells expressing the recombinant receptor (e.g., CAR-expressing cells administered for T cell based therapy) in the blood or serum or organ or tissue sample (e.g., disease site, e.g., tumor sample) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample.

In some embodiments, the cells are detected in the subject at or at least at 4, 14, 15, 27, or 28 days following the administration of the T cells, e.g., CAR-expressing T cells. In some aspects, the cells are detected at or at least at 2, 4, or 6 weeks following, or 3, 6, or 12, 18, or 24, or 30 or 36 months, or 1, 2, 3, 4, 5, or more years, following the administration of the T cells, e.g., CAR-expressing T cells and/or the immunomodulatory compound, e.g., lenalidomide or Compound 1.

In some embodiments, the persistence of receptor-expressing cells (e.g. CAR-expressing cells) in the subject by the methods, following the administration of the T cells, e.g., CAR-expressing T cells and/or the immunomodulatory compound, e.g., lenalidomide, Compound 1 or Compound 2, is greater as compared to that which would be achieved by alternative methods such as those involving the administration of the immunotherapy alone, e.g., administration the T cells, e.g., CAR-expressing T cells, in the absence of the immunomodulatory compound.

The exposure, e.g., number of cells, e.g. T cells administered for T cell therapy, indicative of expansion and/or persistence, may be stated in terms of maximum numbers of the cells to which the subject is exposed, duration of detectable cells or cells above a certain number or percentage, area under the curve for number of cells over time, and/or combinations thereof and indicators thereof. Such outcomes may be assessed using known methods, such as qPCR to detect copy number of nucleic acid encoding the recombinant receptor compared to total amount of nucleic acid or DNA in the particular sample, e.g., blood, serum, plasma or tissue, such as a tumor sample, and/or flow cytometric assays detecting cells expressing the receptor generally using antibodies specific for the receptors. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor.

In some aspects, increased exposure of the subject to the cells includes increased expansion of the cells. In some embodiments, the receptor expressing cells, e.g. CAR-expressing cells, expand in the subject following administration of the T cells, e.g., CAR-expressing T cells, and/or following administration of immunomodulatory compound, e.g., lenalidomide, Compound 1 or Compound 2. In some aspects, the methods result in greater expansion of the cells compared with other methods, such as those involving the administration of the T cells, e.g., CAR-expressing T cells, in the absence of administering the immunomodulatory compound, e.g., lenalidomide, Compound 1 or Compound 2.

In some aspects, the method results in high in vivo proliferation of the administered cells, for example, as measured by flow cytometry. In some aspects, high peak proportions of the cells are detected. For example, in some embodiments, at a peak or maximum level following the administration of the T cells, e.g., CAR-expressing T cells and/or the immunomodulatory compound, e.g., lenalidomide, Compound 1 or Compound 2, in the blood or disease-site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

In some embodiments, the method results in a maximum concentration, in the blood or serum or other bodily fluid or organ or tissue of the subject, of at least 100, 500, 1000, 1500, 2000, 5000, 10,000 or 15,000 copies of or nucleic acid encoding the receptor, e.g., the CAR, per microgram of DNA, or at least 0.1, 0.2, 0.3, 0.4, 0.5, 0.6, 0.7, 0.8, or 0.9 receptor-expressing, e.g., CAR,-expressing cells per total number of peripheral blood mononuclear cells (PBMCs), total number of mononuclear cells, total number of T cells, or total number of microliters. In some embodiments, the cells expressing the receptor are detected as at least 10, 20, 30, 40, 50, or 60% of total PBMCs in the blood of the subject, and/or at such a level for at least 1, 2, 3, 4, 5, 6, 7, 8, 9, 10, 11, 12, 24, 36, 48, or 52 weeks following the T cells, e.g., CAR-expressing T cells and/or the immunomodulatory compound, e.g., lenalidomide, Compound 1 or Compound 2, or for 1, 2, 3, 4, or 5, or more years following such administration.

In some aspects, the method results in at least a 2-fold, at least a 4-fold, at least a 10-fold, or at least a 20-fold increase in copies of nucleic acid encoding the recombinant receptor, e.g., CAR, per microgram of DNA, e.g., in the serum, plasma, blood or tissue, e.g., tumor sample, of the subject.

In some embodiments, cells expressing the receptor are detectable in the serum, plasma, blood or tissue, e.g., tumor sample, of the subject, by a specified method, e.g., by qPCR or flow cytometry-based detection method, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more days following administration of the T cells, e.g., CAR-expressing T cells, or after administration of the immunomodulatory compound, e.g., lenalidomide, Compound 1 or Compound 2, for at least at or about 2, 3, 4, 5, 6, 7, 8, 9, 10, 11, 12, 13, 14, 15, 16, 17, 18, 19, 20, 21, 22, 23, or 24 or more weeks following the administration of the T cells, e.g., CAR-expressing T cells, and/or the immunomodulatory compound, e.g., lenalidomide, Compound 1 or Compound 2.

In some aspects, at least about $1 \times 10^2$, at least about $1 \times 10^3$, at least about $1 \times 10^4$, at least about $1 \times 10^5$, or at least about $1 \times 10^6$ or at least about $5 \times 10^6$ or at least about $1 \times 10^7$ or at least about $5 \times 10^7$ or at least about $1 \times 10^8$ recombinant receptor-expressing, e.g., CAR-expressing cells, and/or at least 10, 25, 50, 100, 200, 300, 400, or 500, or 1000 receptor-expressing cells per microliter, e.g., at least 10 per microliter, are detectable or are present in the subject or fluid, plasma, serum, tissue, or compartment thereof, such as in the blood, e.g., peripheral blood, or disease site, e.g., tumor, thereof. In some embodiments, such a number or concentration of cells is detectable in the subject for at least about 20 days, at least about 40 days, or at least about 60 days, or at least about 3, 4, 5, 6, 7, 8, 9, 10, 11, or 12 months, or at least 2 or 3 years, following administration of the T cells, e.g., CAR-expressing T cells, and/or following the administration of the immunomodulatory compound, e.g., lenalidomide or Compound 1. Such cell numbers may be as detected by flow cytometry-based or quantitative PCR-based methods and extrapolation to total cell numbers using known methods. See, e.g., Brentjens et al., *Sci Transl Med*. 2013 5(177), Park et al, *Molecular Therapy* 15(4):825-833 (2007), Savoldo et al., *JCI* 121(5):1822-1826 (2011), Davila et al., (2013) *PLoS ONE* 8(4):e61338, Davila et al., *Oncoimmunology* 1(9):1577-1583 (2012), Lamers, *Blood* 2011 117:72-82, Jensen et al., *Biol Blood Marrow Transplant* 2010 September; 16(9): 1245-1256, Brentjens et al., *Blood* 2011 118(18):4817-4828.

In some aspects, the copy number of nucleic acid encoding the recombinant receptor, e.g., vector copy number, per 100 cells, for example in the peripheral blood or bone marrow or other compartment, as measured by immunohistochemistry, PCR, and/or flow cytometry, is at least 0.01, at least 0.1, at least 1, or at least 10, at about 1 week, about 2 weeks, about 3 weeks, about 4 weeks, about 5 weeks, or at least about 6 weeks, or at least about 2, 3, 4, 5, 6, 7, 8. 9, 10, 11, or 12 months or at least 2 or 3 years following administration of the cells, e.g., CAR-expressing T cells, and/or the immunomodulatory compound, e.g., lenalidomide, Compound 1 or Compound 2. In some embodiments, the copy number of the vector expressing the receptor, e.g. CAR, per microgram of genomic DNA is at least 100, at least 1000, at least 5000, or at least 10,000, or at least 15,000 or at least 20,000 at a time about 1 week, about 2 weeks, about 3 weeks, or at least about 4 weeks following administration of the T cells, e.g., CAR-expressing T cells, or immunomodulatory compound, e.g., lenalidomide, Compound 1 or Compound 2, or at least 2, 3, 4, 5, 6, 7, 8, 9, 10, 11, or 12 months or at least 2 or 3 years following such administration.

In some aspects, the receptor, e.g. CAR, expressed by the cells, is detectable by quantitative PCR (qPCR) or by flow cytometry in the subject, plasma, serum, blood, tissue and/or disease site thereof, e.g., tumor site, at a time that is at least about 3 months, at least about 6 months, at least about 12 months, at least about 1 year, at least about 2 years, at least about 3 years, or more than 3 years, following the administration of the cells, e.g., following the initiation of the administration of the T cells, e.g., CAR-expressing T cells, and/or the immunomodulatory compound, e.g., lenalidomide, Compound 1 or Compound 2.

In some embodiments, the area under the curve (AUC) for concentration of receptor- (e.g., CAR-) expressing cells in a fluid, plasma, serum, blood, tissue, organ and/or disease site, e.g. tumor site, of the subject over time following the administration of the T cells, e.g., CAR-expressing T cells and/or immunomodulatory compound, e.g., 1 lenalidomide, Compound 1 or Compound 2, is greater as compared to that achieved via an alternative dosing regimen where the subject is administered the T cells, e.g., CAR-expressing T cells, in the absence of administering the immunomodulatory compound.

In some aspects, the method results in high in vivo proliferation of the administered cells, for example, as measured by flow cytometry. In some aspects, high peak proportions of the cells are detected. For example, in some embodiments, at a peak or maximum level following the T cells, e.g., CAR-expressing T cells and/or immunomodulatory compound, e.g., lenalidomide, Compound 1 or Compound 2, in the blood, plasma, serum, tissue or disease site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

In some aspects, the increased or prolonged expansion and/or persistence of the dose of cells in the subject administered with the immunomodulatory compound, e.g., lenalidomide, Compound 1 or Compound 2 is associated with a benefit in tumor related outcomes in the subject. In some embodiments, the tumor related outcome includes a decrease in tumor burden or a decrease in blast marrow in the subject. In some embodiments, the tumor burden is decreased by or by at least at or about 10, 20, 30, 40, 50, 60, 70, 80, 90, or 100 percent after administration of the method. In some embodiments, disease burden, tumor size, tumor volume, tumor mass, and/or tumor load or bulk is reduced following the dose of cells by at least at or about 50%, 60%, 70%, 80%, 90% or more compared a subject that has been treated with a method that does not involve the administration of an immunomodulatory compound, e.g., lenalidomide, Compound 1 or Compound 2.

B. T Cell Functional Activity

In some embodiments, parameters associated with therapy or a treatment outcome, which include parameters that can be assessed for the screening steps and/or assessment of treatment of outcomes and/or monitoring treatment outcomes, includes one or more of activity, phenotype, proliferation or function of T cells. In some embodiments, any of the known assays in the art for assessing the activity, phenotypes, proliferation and/or function of the T cells, e.g., T cells administered for T cell therapy, can be used. Prior to and/or subsequent to administration of the cells and/or immunomodulatory compound, e.g., lenalidomide, Compound 1 or Compound 2, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., *J. Immunotherapy*, 32(7): 689-702 (2009), and Herman et al., *J. Immunological Methods*, 285(1): 25-40 (2004).

In some embodiments, T cells, such as recombinant-expressing (e.g. CAR) T cells, can be assessed prior to and/or subsequent to administration of the cells and/or immunomodulatory compound, e.g., lenalidomide, Compound 1 or Compound 2, to assess or determine if the T cells exhibit features of exhaustion. In some cases, exhaustion can be assessed by monitoring loss of T cell function, such as reduced or decreased antigen-specific or antigen receptor-driven activity, such as a reduced or decreased ability to produce cytokines or to drive cytolytic activity against target antigen. In some cases, exhaustion also can be assessed by monitoring expression of surface markers on T cells (e.g. CD4 and/or CD4 T cells) that are associated with an exhaustion phenotype. Among exhaustion markers are inhibitory receptors such as PD-1, CTLA-4, LAG-3 and TIM-3.

In some embodiments, such a reduced or decreased activity is observed over time following administration to the subject and/or following long-term exposure to antigen.

In particular embodiments, the provided methods (i) to effect said increase in antigen-specific or antigen receptor-driven activity and (ii) to prevent, inhibit or delay said onset of exhaustion phenotype and/or to reverse said exhaustion phenotype. In some embodiments, the amount, duration and/or frequency is effective (i) to effect said increase in antigen-specific or antigen receptor-driven activity and (ii) to prevent, inhibit or delay said onset of exhaustion phenotype. In other embodiments, the amount, duration and/or frequency is effective (i) to effect said increase in antigen-specific or antigen receptor-driven activity and (ii) to prevent, inhibit or delay said onset of exhaustion phenotype and to reverse said exhaustion phenotype.

wherein the exhaustion phenotype, with reference to a T cell or population of T cells, comprises: an increase in the level or degree of surface expression on the T cell or T cells, or in the percentage of T said population of T cells exhibiting surface expression, of one or more exhaustion marker, optionally 2, 3, 4, 5 or 6 exhaustion markers, compared to a reference T cell population under the same conditions; or a decrease in the level or degree of an activity exhibited by said T cells or population of T cells upon exposure to an antigen or antigen receptor-specific agent, compared to a reference T cell population, under the same conditions. an increase in the level or degree of surface expression on the T cell or T cells, or in the percentage of T said population of T cells exhibiting surface expression, of one or more exhaustion marker, optionally 2, 3, 4, 5 or 6 exhaustion markers, compared to a reference T cell population under the same conditions; or a decrease in the level or degree of an activity exhibited by said T cells or population of T cells upon exposure to an antigen or antigen receptor-specific agent, compared to a reference T cell population, under the same conditions.

In certain embodiments, the biological activity of the cells is measured by assaying expression and/or secretion of one or more cytokines, such as CD107a, IFNγ, IL-2, GM-CSF and TNFα, and/or by assessing cytolytic activity.

In some embodiments, assays for the activity, phenotypes, proliferation and/or function of the T cells, e.g., T cells administered for T cell therapy include, but are not limited to, ELISPOT, ELISA, cellular proliferation, cytotoxic lymphocyte (CTL) assay, binding to the T cell epitope, antigen or ligand, or intracellular cytokine staining, proliferation assays, lymphokine secretion assays, direct cytotoxicity assays, and limiting dilution assays. In some embodiments, proliferative responses of the T cells can be measured, e.g. by incorporation of $^3$H-thymidine, BrdU (5-Bromo-2'-Deoxyuridine) or 2'-deoxy-5-ethynyluridine (EdU) into their DNA or dye dilution assays, using dyes such as carboxyfluorescein diacetate succinimmunomodulatory compoundyl ester (CFSE), CellTrace Violet, or membrane dye PKH26.

In some embodiments, assessing the activity, phenotypes, proliferation and/or function of the T cells, e.g., T cells administered for T cell therapy, include measuring cytokine production from T cells, and/or measuring cytokine production in a biological sample from the subject, e.g., plasma, serum, blood, and/or tissue samples, e.g., tumor samples. In some cases, such measured cytokines can include, without limitation, interlekukin-2 (IL-2), interferon-gamma (IFNγ), interleukin-4 (IL-4), TNF-alpha (TNFα), interleukin-6 (IL-6), interleukin-10 (IL-10), interleukin-12 (IL-12), granulocyte-macrophage colony-stimulating factor (GM-CSF), CD107a, and/or TGF-beta (TGFβ). Assays to measure cytokines are well known in the art, and include but are not limited to, ELISA, intracellular cytokine staining, cytometric bead array, RT-PCR, ELISPOT, flow cytometry and bio-assays in which cells responsive to the relevant cytokine are tested for responsiveness (e.g. proliferation) in the presence of a test sample.

In some embodiments, assessing the activity, phenotypes, proliferation and/or function of the T cells, e.g., T cells administered for T cell therapy, include assessing cell phenotypes, e.g., expression of particular cell surface markers. In some embodiments, the T cells, e.g., T cells administered for T cell therapy, are assessed for expression of T cell activation markers, T cell exhaustion markers, and/or T cell differentiation markers. In some embodiments, the cell phenotype is assessed before administration. In some embodiments, the cell phenotype is assessed after administration. T cell activation markers, T cell exhaustion markers, and/or T cell differentiation markers for assessment include any markers known in the art for particular subsets of T cells, e.g., CD25, CD38, human leukocyte antigen-DR (HLA-DR), CD69, CD44, CD137, KLRG1, CD62L$^{low}$, CCR7$^{low}$, CD71, CD2, CD54, CD58, CD244, CD160, programmed cell death protein 1 (PD-1), lymphocyte activation gene 3 protein (LAG-3), T-cell immunoglobulin domain and mucin domain protein 3 (TIM-3), cytotoxic T lymphocyte antigen-4 (CTLA-4), band T lymphocyte attenuator (BTLA) and/or T-cell immunoglobulin and immunoreceptor tyrosine-based inhibitory motif domain (TIGIT) (see, e.g., Liu et al., Cell Death and Disease (2015) 6, e1792). In some embodiments, the exhaustion marker is any one or more of PD-1, CTLA-4, TIM-3, LAG-3, BTLA, 2B4, CD160, CD39, VISTA, and TIGIT. In some embodiments, the assessed cell surface marker is CD25, PD-1 and/or TIM-3. In some embodiments, the assessed cell surface marker is CD25.

In some aspects, detecting the expression levels includes performing an in vitro assay. In some embodiments, the in vitro assay is an immunoassay, an aptamer-based assay, a histological or cytological assay, or an mRNA expression level assay. In some embodiments, the parameter or parameters for one or more of each of the one or more factors, effectors, enzymes and/or surface markers are detected by an enzyme linked immunosorbent assay (ELISA), immunoblotting, immunoprecipitation, radioimmunoassay (RIA), immuno staining, flow cytometry assay, surface plasmon resonance (SPR), chemiluminescence assay, lateral flow immunoassay, inhibition assay or avidity assay. In some embodiments, detection of cytokines and/or surface markers is determined using a binding reagent that specifically binds to at least one biomarker. In some cases, the binding reagent is an antibody or antigen-binding fragment thereof, an aptamer or a nucleic acid probe.

In some embodiments, the administration of the immunomodulatory compound, e.g., lenalidomide, Compound 1 or Compound 2 increases the level of circulating CAR T cells.

C. Disease Burden

In some embodiments, parameters associated with therapy or a treatment outcome, which include parameters that can be assessed for the screening steps and/or assessment of treatment of outcomes and/or monitoring treatment outcomes, includes tumor or disease burden. The administration of the immunotherapy, such as a T cell therapy (e.g. CAR-expressing T cells) and/or the immunomodulatory compound, e.g., lenalidomide, Compound 1 or Compound 2, can reduce or prevent the expansion or burden of the disease or condition in the subject. For example, where the disease or condition is a tumor, the methods generally reduce tumor size, bulk, metastasis, percentage of blasts in the bone marrow or molecularly detectable cancer and/or improve prognosis or survival or other symptom associated with tumor burden.

In some embodiments, the provided methods result in a decreased tumor burden in treated subjects compared to alternative methods in which the immunotherapy, such as a T cell therapy (e.g. CAR-expressing T cells) is given without administration of the immunomodulatory compound, e.g., lenalidomide, Compound 1 or Compound 2. It is not necessary that the tumor burden actually be reduced in all subjects receiving the combination therapy, but that tumor burden is reduced on average in subjects treated, such as based on clinical data, in which a majority of subjects treated with such a combination therapy exhibit a reduced tumor burden, such as at least 50%, 60%, 70%, 80%, 90%, 95% or more of subjects treated with the combination therapy, exhibit a reduced tumor burden.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood, lymph or bone marrow in the context of certain hematological malignancies. Disease burden can include, in some embodiments, the mass of a tumor, the number or extent of metastases and/or the percentage of blast cells present in the bone marrow.

In some embodiments, the subject has a myeloma, a lymphoma or a leukemia. In some embodiments, the subject has a non-Hodgkin lymphoma (NHL), an acute lymphoblastic leukemia (ALL), a chronic lymphocytic leukemia (CLL), a diffuse large B-cell lymphoma (DLBCL) or a myeloma, e.g., a multiple myeloma (MM). In some embodiments, the subject has a MM or a DBCBL. In some embodiments, the subject has a follicular lymphoma (FL).

In some embodiments, the subject has a solid tumor.

In the case of MM, exemplary parameters to assess the extent of disease burden include such parameters as number of clonal plasma cells (e.g., >10% on bone marrow biopsy or in any quantity in a biopsy from other tissues; plasmacytoma), presence of monoclonal protein (paraprotein) in either serum or urine, evidence of end-organ damage felt related to the plasma cell disorder (e.g., hypercalcemia (corrected calcium >2.75 mmol/1); renal insufficiency attributable to myeloma; anemia (hemoglobin <10 g/dl); and/or bone lesions (lytic lesions or osteoporosis with compression fractures)).

In the case of DLBCL, exemplary parameters to assess the extent of disease burden include such parameters as cellular morphology (e.g., centroblastic, immunoblastic, and anaplastic cells), gene expression, miRNA expression and protein expression (e.g., expression of BCL2, BCL6, MUM1, LMO2, MYC, and p21).

In the case of leukemia, the extent of disease burden can be determined by assessment of residual leukemia in blood or bone marrow. In some embodiments, a subject exhibits morphologic disease if there are greater than or equal to 5% blasts in the bone marrow, for example, as detected by light microscopy. In some embodiments, a subject exhibits complete or clinical remission if there are less than 5% blasts in the bone marrow.

In some embodiments, for leukemia, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia cell in 100,000 normal cells. In some embodiments, a subject exhibits MRD that is molecularly detectable if at least or greater than 1 leukemia cell in 100,000 cells is detected, such as by PCR or flow cytometry. In some embodiments, the disease burden of a subject is molecularly undetectable or MRD⁻, such that, in some cases, no leukemia cells are able to be detected in the subject using PCR or flow cytometry techniques.

In some embodiments, the methods and/or administration of an immunotherapy, such as a T cell therapy (e.g. CAR-expressing T cells) and/or immunomodulatory compound, e.g., lenalidomide, Compound 1 or Compound 2 decrease(s) disease burden as compared with disease burden at a time immediately prior to the administration of the immunotherapy, e.g., T cell therapy and/or immunomodulatory compound.

In some aspects, administration of the immunotherapy, e.g. T cell therapy and/or immunomodulatory compound, e.g., lenalidomide, Compound 1 or Compound 2, may prevent an increase in disease burden, and this may be evidenced by no change in disease burden.

In some embodiments, the method reduces the burden of the disease or condition, e.g., number of tumor cells, size of tumor, duration of patient survival or event-free survival, to a greater degree and/or for a greater period of time as compared to the reduction that would be observed with a comparable method using an alternative therapy, such as one in which the subject receives immunotherapy, e.g. T cell therapy alone, in the absence of administration of the immunomodulatory compound, e.g., lenalidomide, Compound 1 or Compound 2. In some embodiments, disease burden is reduced to a greater extent or for a greater duration following the combination therapy of administration of the immunotherapy, e.g., T cell therapy, and the immunomodulatory compound, e.g., lenalidomide, Compound 1 or Compound 2, compared to the reduction that would be effected by administering each of the agent alone, e.g., administering the immunomodulatory compound to a subject having not received the immunotherapy, e.g. T cell therapy; or administering the immunotherapy, e.g. T cell therapy, to a subject having not received the immunomodulatory compound.

In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some embodiments, disease burden, e.g. tumor burden, is assessed by measuring the mass of a solid tumor and/or the number or extent of metastases. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified. In some embodiments, exemplary parameters for determination include particular clinical outcomes indicative of amelioration or improvement in the disease or condition, e.g., tumor. Such parameters include: duration of disease control, including complete response (CR), partial response (PR) or stable disease (SD) (see, e.g., Response Evaluation Criteria In Solid Tumors (RECIST) guidelines), objective response rate (ORR), progression-free survival (PFS) and overall survival (OS). Specific thresholds for the parameters can be set to determine the efficacy of the method of combination therapy provided herein.

In some embodiments, the subjects treated according to the method achieve a more durable response. In some cases, a measure of duration of response (DOR) includes the time from documentation of tumor response to disease progression. In some embodiments, the parameter for assessing response can include durable response, e.g., response that persists after a period of time from initiation of therapy. In some embodiments, durable response is indicated by the response rate at approximately 1, 2, 3, 4, 5, 6, 7, 8, 9, 10, 11, 12, 18 or 24 months after initiation of therapy. In some embodiments, the response is durable for greater than 3 months, greater than 6 months, or great than 12 months. In some particular embodiments, the subjects treated according to the method achieve a more durable response after the subject previously relapsed following remission in response to the administration of the genetically engineered cells.

In some aspects, disease burden is measured or detected prior to administration of the immunotherapy, e.g. T cell therapy, following the administration of the immunotherapy, e.g. T cell therapy but prior to administration of the immunomodulatory compound, e.g., lenalidomide, Compound 1 or Compound 2, following administration of the immunomodulatory compound but prior to the administration of the immunotherapy, e.g., T cell therapy, and/or following the administration of both the immunotherapy, e.g. T cell therapy and the immunomodulatory compound. In the context of multiple administration of one or more steps of the combination therapy, disease burden in some embodiments may be measured prior to or following administration of any of the steps, doses and/or cycles of administration, or at a time between administration of any of the steps, doses and/or cycles of administration.

In some embodiments, the burden is decreased by or by at least at or about 10, 20, 30, 40, 50, 60, 70, 80, 90, or 100 percent by the provided methods compared to immediately prior to the administration of the immunomodulatory compound, e.g., lenalidomide, Compound 1 or Compound 2 and the immunotherapy, e.g. T cell therapy. In some embodiments, disease burden, tumor size, tumor volume, tumor mass, and/or tumor load or bulk is reduced following administration of the immunotherapy, e.g. T cell therapy and the immunomodulatory compound, by at least at or about 10, 20, 30, 40, 50, 60, 70, 80, 90% or more compared to that immediately prior to the administration of the immunotherapy, e.g. T cell therapy and/or the immunomodulatory compound.

In some embodiments, reduction of disease burden by the method comprises an induction in morphologic complete remission, for example, as assessed at 1 month, 2 months, 3 months, or more than 3 months, after administration of, e.g., initiation of, the combination therapy.

In some aspects, an assay for minimal residual disease, for example, as measured by multiparametric flow cytometry, is negative, or the level of minimal residual disease is less than about 0.3%, less than about 0.2%, less than about 0.1%, or less than about 0.05%.

In some embodiments, the event-free survival rate or overall survival rate of the subject is improved by the methods, as compared with other methods. For example, in some embodiments, event-free survival rate or probability for subjects treated by the methods at 6 months following the method of combination therapy provided herein, is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods. For example, in some embodiments, the probability of relapse at 6 months following the method of combination therapy, is less than about 80%, less than about 70%, less than about 60%, less than about 50%, less than about 40%, less than about 30%, less than about 20%, or less than about 10%.

IV. Toxicity and Adverse Outcomes

In embodiments of the provided methods, the subject is monitored for toxicity or other adverse outcome, including treatment related outcomes, e.g., development of neutropenia, cytokine release syndrome (CRS) or neurotoxicity (NT), in subjects administered the provided combination therapy comprising a cell therapy (e.g., a T cell therapy) and an immunomodulatory compound, e.g. lenalidomide, Compound 1 or Compound 2. In some embodiments, the provided methods are carried out to reduce the risk of a toxic outcome or symptom, toxicity-promoting profile, factor, or property, such as a symptom or outcome associated with or indicative of severe neutropenia, severe cytokine release syndrome (CRS) or severe neurotoxicity.

In some embodiments, the methods do not result in, or do not increase the risk of, certain hematological toxicities, such as neutropenia or thrombocytopenia. In some embodiments, no more than 50% of subjects exhibit a neutropenia higher than grade 3, such as a prolonged grade 3 neutropenia or a grade 4 neutropenia, and/or a thrombocytopenia higher than grade 3, such as a grade 3 or grade 4 thrombocytopenia. In some embodiments, at least 50% of subjects treated according to the method (e.g. at least 60%, at least 70%, at least 80%, at least 90% or more of the subjects treated) do not exhibit a severe neutropenia or a severe thrombocytopenia of grade 3 or higher than grade 3

In some embodiments, the provided methods do not result in a high rate or likelihood of toxicity or toxic outcomes, or reduces the rate or likelihood of toxicity or toxic outcomes, such as severe neurotoxicity (NT) or severe cytokine release syndrome (CRS), such as compared to certain other cell therapies. In some embodiments, the methods do not result in, or do not increase the risk of, severe NT (sNT), severe CRS (sCRS), macrophage activation syndrome, tumor lysis syndrome, fever of at least at or about 38 degrees Celsius for three or more days and a plasma level of CRP of at least at or about 20 mg/dL. In some embodiments, greater than or greater than about 30%, 35%, 40%, 50%, 55%, 60% or more of the subjects treated according to the provided methods do not exhibit any grade of CRS or any grade of neurotoxcity. In some embodiments, no more than 50% of subjects treated (e.g. at least 60%, at least 70%, at least 80%, at least 90% or more of the subjects treated) a cytokine release syndrome (CRS) higher than grade 2 and/or a neurotoxicity higher than grade 2. In some embodiments, at least 50% of subjects treated according to the method (e.g. at least 60%, at least 70%, at least 80%, at least 90% or more of the subjects treated) do not exhibit a severe toxic outcome (e.g. severe CRS or severe neurotoxicity), such as do not exhibit grade 3 or higher neurotoxicity and/or does not exhibit severe CRS, or does not do so within a certain period of time following the treatment, such as within a week, two weeks, or one month of the administration of the cells.

A. Cytokine Release Syndrome (Crs) and Neurotoxicity

In some aspects, the subject is monitored for and/or the methods reduce the risk for a toxic outcome that is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure. CRS may be treated using anti-inflammatory therapy such as an anti-IL-6 therapy, e.g., anti-IL-6 antibody, e.g., tocilizumab, or antibiotics or other agents as described.

Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS typically occurs 6-20 days after infusion of cells that express a CAR. See Xu et al., *Cancer Letters* 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1β, IL-6, IL-8, and IL-10.

Exemplary outcomes associated with CRS include fever, rigors, chills, hypotension, dyspnea, acute respiratory distress syndrome (ARDS), encephalopathy, ALT/AST elevation, renal failure, cardiac disorders, hypoxia, neurologic disturbances, and death. Neurological complications include delirium, seizure-like activity, confusion, word-finding difficulty, aphasia, and/or becoming obtunded. Other CRS-related outcomes include fatigue, nausea, headache, seizure, tachycardia, myalgias, rash, acute vascular leak syndrome, liver function impairment, and renal failure. In some aspects, CRS is associated with an increase in one or more factors such as serum-ferritin, d-dimer, aminotransferases, lactate dehydrogenase and triglycerides, or with hypofibrinogenemia or hepatosplenomegaly.

In some embodiments, outcomes associated with CRS include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen (P02) levels of less than at or about 90%); and/or one or more neurologic disorders (including mental status changes, obtundation, and seizures).

Exemplary CRS-related outcomes include increased or high serum levels of one or more factors, including cytokines and chemokines and other factors associated with CRS. Exemplary outcomes further include increases in synthesis or secretion of one or more of such factors. Such synthesis or secretion can be by the T cell or a cell that interacts with the T cell, such as an innate immune cell or B cell.

In some embodiments, the CRS-associated serum factors or CRS-related outcomes include inflammatory cytokines and/or chemokines, including interferon gamma (IFN-γ), TNF-a, IL-1β, IL-2, IL-6, IL-7, IL-8, IL-10, IL-12, sIL-2Ra, granulocyte macrophage colony stimulating factor (GM-CSF), macrophage inflammatory protein (MIP)-1, tumor necrosis factor alpha (TNFα), IL-6, and IL-10, IL-1β, IL-8, IL-2, MIP-1, Flt-3L, fracktalkine, and/or IL-5. In some embodiments, the factor or outcome includes C reactive protein (CRP). In addition to being an early and easily measurable risk factor for CRS, CRP also is a marker for cell expansion. In some embodiments, subjects that are measured to have high levels of CRP, such as ≥15 mg/dL, have CRS. In some embodiments, subjects that are measured to have high levels of CRP do not have CRS. In some embodiments, a measure of CRS includes a measure of CRP and another factor indicative of CRS.

In some embodiments, one or more inflammatory cytokines or chemokines are monitored before, during, or after CAR treatment and/or Compound 1 treatment. In some aspects, the one or more cytokines or chemokines include IFN-γ, TNF-α, IL-2, IL-1β, IL-6, IL-7, IL-8, IL-10, IL-12, sIL-2Rα, granulocyte macrophage colony stimulating factor (GM-CSF), or macrophage inflammatory protein (MIP). In some embodiments, IFN-γ, TNF-α, and IL-6 are monitored.

CRS criteria that appear to correlate with the onset of CRS to predict which patients are more likely to be at risk for developing sCRS have been developed (see Davilla et al. *Science translational medicine*. 2014; 6(224):224ra25). Factors include fevers, hypoxia, hypotension, neurologic changes, elevated serum levels of inflammatory cytokines, such as a set of seven cytokines (IFNγ, IL-5, IL-6, IL-10, Flt-3L, fractalkine, and GM-CSF) whose treatment-induced elevation can correlate well with both pretreatment tumor burden and sCRS symptoms. Other guidelines on the diagnosis and management of CRS are known (see e.g., Lee et al, *Blood*. 2014; 124(2):188-95). In some embodiments, the criteria reflective of CRS grade are those detailed in Table 2 below.

TABLE 2

Exemplary Grading Criteria for CRS

| Grade | Description of Symptoms |
|---|---|
| 1 Mild | Not life-threatening, require only symptomatic treatment such as antipyretics and anti-emetics (e.g., fever, nausea, fatigue, headache, myalgias, malaise) |
| 2 Moderate | Require and respond to moderate intervention: Oxygen requirement <40%, or Hypotension responsive to fluids or low dose of a single vasopressor, or Grade 2 organ toxicity (by CTCAE v4.0) |
| 3 Severe | Require and respond to aggressive intervention: Oxygen requirement ≥40%, or Hypotension requiring high dose of a single vasopressor (e.g., norepinephrine ≥20 µg/kg/min, dopamine ≥10 µg/kg/min, phenylephrine ≥200 µg/kg/min, or epinephrine ≥10 µg/kg/min), or Hypotension requiring multiple vasopressors (e.g., vasopressin + one of the above agents, or combination vasopressors equivalent to ≥20 µg/kg/min norepinephrine), or Grade 3 organ toxicity or Grade 4 transaminitis (by CTCAE v4.0) |

TABLE 2-continued

Exemplary Grading Criteria for CRS

| Grade | Description of Symptoms |
|---|---|
| 4 Life-threatening | Life-threatening:<br>Requirement for ventilator support, or<br>Grade 4 organ toxicity (excluding transaminitis) |
| 5 Fatal | Death |

In some embodiments, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia ($PO_2$<90%) or one or more neurologic disorder(s) (including mental status changes, obtundation, and/or seizures). In some embodiments, severe CRS includes CRS with a grade of 3 or greater, such as set forth in Table 2.

In some embodiments, outcomes associated with severe CRS or grade 3 CRS or greater, such as grade 4 or greater, include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen (PO2) levels of less than at or about 90%); and/or one or more neurologic disorders (including mental status changes, obtundation, and seizures). In some embodiments, severe CRS includes CRS that requires management or care in the intensive care unit (ICU).

In some embodiments, the CRS, such as severe CRS, encompasses a combination of (1) persistent fever (fever of at least 38 degrees Celsius for at least three days) and (2) a serum level of CRP of at least at or about 20 mg/dL. In some embodiments, the CRS encompasses hypotension requiring the use of two or more vasopressors or respiratory failure requiring mechanical ventilation. In some embodiments, the dosage of vasopressors is increased in a second or subsequent administration.

In some embodiments, severe CRS or grade 3 CRS encompasses an increase in alanine aminotransferase, an increase in aspartate aminotransferase, chills, febrile neutropenia, headache, left ventricular dysfunction, encephalopathy, hydrocephalus, and/or tremor.

The method of measuring or detecting the various outcomes may be specified.

In some aspects, the toxic outcome of a therapy, such as a cell therapy, is or is associated with or indicative of neurotoxicity or severe neurotoxicity. In some embodiments, symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli *Nature Reviews Neurology* 6, 657-666 (December 2010); National Cancer Institute—Common Toxicity Criteria version 4.03 (NCI-CTCAE v4.03).

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

In some embodiments, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 3. In some embodiments, a severe neurotoxicity is deemed to be a prolonged grade 3 if symptoms or grade 3 neurotoxicity last for 10 days or longer.

TABLE 3

Exemplary Grading Criteria for neurotoxicity

| Grade | Description of Symptoms |
|---|---|
| 1 Asymptomatic or Mild | Mild or asymptomatic symptoms |
| 2 Moderate | Presence of symptoms that limit instrumental activities of daily living (ADL), such as preparing meals, shopping for groceries or clothes, using the telephone, managing money |
| 3 Severe | Presence of symptoms that limit self-care ADL, such as bathing, dressing and undressing, feeding self, using the toilet, taking medications |
| 4 Life-threatening | Symptoms that are life-threatening, requiring urgent intervention |
| 5 Fatal | Death |

In some embodiments, the methods reduce symptoms associated with CRS or neurotoxicity compared to other methods. In some aspects, the provided methods reduce symptoms, outcomes or factors associated with CRS, including symptoms, outcomes or factors associated with severe CRS or grade 3 or higher CRS, compared to other methods. For example, subjects treated according to the present methods may lack detectable and/or have reduced symptoms, outcomes or factors of CRS, e.g. severe CRS or grade 3 or higher CRS, such as any described, e.g. set forth in Table 2. In some embodiments, subjects treated according to the present methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods. In some embodiments, subjects treated according to the present methods may have reduced symptoms associated with peripheral motor neuropathy, peripheral sensory neuropathy, dysethesia, neuralgia or paresthesia.

In some embodiments, the methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

In some embodiments, the toxicity outcome is a dose-limiting toxicity (DLT). In some embodiments, the toxic outcome is the absence of a dose-limiting toxicity. In some embodiments, a dose-limiting toxicity (DLT) is defined as any grade 3 or higher toxicity as described or assessed by any known or published guidelines for assessing the particular toxicity, such as any described above and including the National Cancer Institute (NCI) Common Terminology Criteria for Adverse Events (CTCAE) version 4.0. In some embodiments, a dose-limiting toxicity (DLT) is defined when any of the events discussed below occurs following administration of the cell therapy (e.g., T cell therapy) and/or Compound 1, the events including a) febrile neutropenia; b) Grade 4 neutropenia lasting about or more than about 7 days; c) Grade 3 or 4 thrombocytopenia with clinically significant bleeding; and d) Grade 4 thrombocytopenia lasting more than 24 hours.

In some embodiments, the provided embodiments result in a low rate or risk of developing a toxicity, e.g. CRS or neurotoxicity or severe CRS or neurotoxicity, e.g. grade 3 or higher CRS or neurotoxicity, such as observed with administering a dose of T cells in accord with the provided combination therapy, and/or with the provided articles of manufacture or compositions. In some casesm this permits administration of the cell therapy on an outpatient basis. In some embodiments, the administration of the cell therapy, e.g. dose of T cells (e.g. CAR+ T cells) in accord with the provided methods, and/or with the provided articles of manufacture or compositions, is performed on an outpatient basis or does not require admission to the subject to the hospital, such as admission to the hospital requiring an overnight stay.

In some aspects, subjects administered the cell therapy, e.g. dose of T cells (e.g. CAR+ T cells) in accord with the provided methods, and/or with the provided articles of manufacture or compositions, including subjects treated on an outpatient basis, are not administered an intervention for treating any toxicity prior to or with administration of the cell dose, unless or until the subject exhibits a sign or symptom of a toxicity, such as of a neurotoxicity or CRS.

In some embodiments, if a subject administered the cell therapy, e.g. dose of T cells (e.g. CAR+ T cells), including subjects treated on an outpatient basis, exhibits a fever the subject is given or is instructed to receive or administer a treatment to reduce the fever. In some embodiments, the fever in the subject is characterized as a body temperature of the subject that is (or is measured at) at or above a certain threshold temperature or level. In some aspects, the threshold temperature is that associated with at least a low-grade fever, with at least a moderate fever, and/or with at least a high-grade fever. In some embodiments, the threshold temperature is a particular temperature or range. For example, the threshold temperature may be at or about or at least at or about 38, 39, 40, 41, or 42 degrees Celsius, and/or may be a range of at or about 38 degrees Celsius to at or about 39 degrees Celsius, a range of at or about 39 degrees Celsius to at or about 40 degrees Celsius, a range of at or about 40 degrees Celsius to at or about 41 degrees, or a range of at or about 41 degrees Celsius to at or about 42 degrees Celsius.

In some embodiments, the treatment designed to reduce fever includes treatment with an antipyretic. An antipyretic may include any agent, composition, or ingredient, that reduces fever, such as one of any number of agents known to have antipyretic effects, such as NSAIDs (such as ibuprofen, naproxen, ketoprofen, and nimesulide), salicylates, such as aspirin, choline salicylate, magnesium salicylate, and sodium salicylate, paracetamol, acetaminophen, Metamizole, Nabumetone, Phenaxone, antipyrine, febrifuges. In some embodiments, the antipyretic is acetaminophen. In some embodiments, acetaminophen can be administered at a dose of 12.5 mg/kg orally or intravenously up to every four hours. In some embodiments, it is or comprises ibuprofen or aspirin.

In some embodiments, if the fever is a sustained fever, the subject is administered an alternative treatment for treating the toxicity. For subjects treated on an outpatient basis, the subject is instructed to return to the hospital if the subject has and/or is determined to or to have a sustained fever. In some embodiments, the subject has, and/or is determined to or considered to have, a sustained fever if he or she exhibits a fever at or above the relevant threshold temperature, and where the fever or body temperature of the subject is not reduced, or is not reduced by or by more than a specified amount (e.g., by more than 1° C., and generally does not fluctuate by about, or by more than about, 0.5° C., 0.4° C., 0.3° C., or 0.2° C.), following a specified treatment, such as a treatment designed to reduce fever such as treatment with an antipyreticm, e.g. NSAID or salicylates, e.g. ibuprofen, acetaminophen or aspirin. For example, a subject is considered to have a sustained fever if he or she exhibits or is determined to exhibit a fever of at least at or about 38 or 39 degrees Celsius, which is not reduced by or is not reduced by more than at or about 0.5° C., 0.4° C., 0.3° C., or 0.2° C., or by at or about 1%, 2%, 3%, 4%, or 5%, over a period of 6 hours, over a period of 8 hours, or over a period of 12 hours, or over a period of 24 hours, even following treatment with the antipyretic such as acetaminophen. In some embodiments, the dosage of the antipyretic is a dosage ordinarily effective in such as subject to reduce fever or fever of a particular type such as fever associated with a bacterial or viral infection, e.g., a localized or systemic infection.

In some embodiments, the subject has, and/or is determined to or considered to have, a sustained fever if he or she exhibits a fever at or above the relevant threshold temperature, and where the fever or body temperature of the subject does not fluctuate by about, or by more than about, 1° C., and generally does not fluctuate by about, or by more than about, 0.5° C., 0.4° C., 0.3° C., or 0.2° C. Such absence of fluctuation above or at a certain amount generally is measured over a given period of time (such as over a 24-hour, 12-hour, 8-hour, 6-hour, 3-hour, or 1-hour period of time, which may be measured from the first sign of fever or the first temperature above the indicated threshold). For example, in some embodiments, a subject is considered to or is determined to exhibit sustained fever if he or she exhibits a fever of at least at or about or at least at or about 38 or 39 degrees Celsius, which does not fluctuate in temperature by more than at or about 0.5° C., 0.4° C., 0.3° C., or 0.2° C., over a period of 6 hours, over a period of 8 hours, or over a period of 12 hours, or over a period of 24 hours.

In some embodiments, the fever is a sustained fever; in some aspects, the subject is treated at a time at which a subject has been determined to have a sustained fever, such as within one, two, three, four, five six, or fewer hours of such determination or of the first such determination following the initial therapy having the potential to induce the toxicity, such as the cell therapy, such as dose of T cells, e.g. CAR+ T cells.

In some embodiments, one or more interventions or agents for treating the toxicity, such as a toxicity-targeting therapies, is administered at a time at which or immediately after which the subject is determined to or confirmed to (such as is first determined or confirmed to) exhibit sustained fever, for example, as measured according to any of the aforementioned embodiments. In some embodiments, the one or more toxicity-targeting therapies is administered within a certain period of time of such confirmation or determination, such as within 30 minutes, 1 hour, 2 hours, 3 hours, 4 hours, 6 hours, or 8 hours thereof.

B. Hematologic Toxicity

In some aspects, the subject is monitored for and/or the methods reduce the risk for a toxic outcome that is or is associated with or indicative of a hematologic toxicity, such as thrombocytopenia and/or neutropenia. In some cases, hematological toxicies, including thrombocytopenia and neutropenia, are graded according to Common Terminology Criteria for Adverse Events (Version 4.03; US National Cancer Institute, Bethesda, MD, USA). In some cases, a hematological toxicity, such as thrombocytopenia and/or neutropenia, is monitored before, during, and after the administration(s) of the immunomodulatory compound, e.g. lenalidomide, Compound 1 or Compound 2. In some cases, a hematologoical toxicity, such as thrombocytopenia and/or neutropenia, is monitored prior to each administration of the immunomodulatory compound, e.g. lenalidomide, Compound 1 or Compound 2. In some cases, a hematological toxicity, such as thrombocytopenia and/or neutropenia, is monitored at least every 1, 2, 3, 4, 5, 6, or 7 days after administration of the immunomodulatory compound, e.g. lenalidomide, Compound 1 or Compound 2.

In some embodiments, a complete blood count is carried out to monitor levels of leukocytes (white blood cells) in the subject, including neutrophils and platelets. A variety of methods can be used carry out a complete blood cell (CBC) count and/or a leukocyte differential count. In some embodiments, a hematology analyzer is used.

Neutropenia is characterized by a reduction in the blood neutrophil count, often leading to increased susceptibility to bacterial and fungal infections. Common symptoms of neutropenia in patients include, for example, fever, mouth sores, and ear infections. Patients with profound neutropenia often suffer from pyogenic infections such as septicemia, cutaneous cellulitis, liver abscesses, furunculosis, pneumonia, stomatitis, gingivitis, perirectal inflammation, colitis, sinusitis, and otitis media.

In some embodiments, the Absolute Neutrophil Count (ANC) is used to define levels of neutropenia. The ANC can be calculated from components of the complete blood count. In some embodiments, severity of neutropenia is classified based on the absolute neutrophil count (ANC) measured in cells per microliter of blood: a) mild neutropenia (1000 to 1500 cells/mL); b) moderate neutropenia (grade 3; 500 to 1000 cells/mL); c) severe neutropenia (grade 4; <500 cells/mL). In some embodiments, neutropenia can be graded according to criteria set forth in Table 4. Subjects with severe neutropenia often have severe risk of infection.

TABLE 4

Neutropenia grading

| Grade | ANC |
|---|---|
| Grade 1 | <2.0 × $10^9$/L (<2000/mm$^3$) and >1.5 × $10^9$/L (>1500/mm$^3$) |
| Grade 2 | <1.5 × $10^9$/L (<1500/mm$^3$) and >1.0 × $10^9$/L (>1000/mm$^3$) |
| Grade 3 | <1.0 × $10^9$/L (<1000/mm$^3$) and >0.5 × $10^9$/L (>500/mm$^3$) |
| Grade 4 | <0.5 × $10^9$/L (<500/mm$^3$) |

In some cases, neutropenia is a febrile neutropenia (also called neutropenic fever or neutropenic sepsis). Febrile neutropenia occurs when a patient has a temperature greater than 38° C. and low levels of neutrophils or neutropenia. In some embodiments, febrile neutropenia can be graded according to criteria set forth in Table 5.

TABLE 5

Exemplary Grading Criteria for Febrile Neutropenia

| Grade | Description of symptoms |
| --- | --- |
| Grade 3 | ANC <1000/mm$^3$ and a single temperature of >38.3 degrees C. (101 degrees F.) or a sustained temperature of >=38 degrees C. (100.4 degrees F.) for more than one hour |
| Grade 4 | life-threatening consequences and indicated urgent intervention |
| Grade 5 | death |

In some embodiments, a subject is monitored for thrombocytopenia. Thrombocytopenia is characterized by a platelet count of less than 150,000 cells per microliter (μL). Presentation of thrombocytopenia, particularly among patients with more severe grades, may include bleeding, ecchymoses, petechiae, purpura, and hypersplenism. Thrombocytopenia may be characterized as grade 1 thrombocytopenia (i.e., platelet count of 75,000 to 150,000/μL), grade 2 (i.e., platelet count of 50,000 to <75,000/μL), grade 3 (platelet count of 25,000 to <50,000/μL), or grade 4 (i.e., platelet count of below 25,000/μL).

In some embodiments of the provided methods, if a subject is determined to exhibit a hematological toxicity, such as thrombocytopenia and/or neutropenia or a particular grade thereof, the cycling therapy with the immunomodulatory compound, e.g. lenalidomide, Compound 1 or Compound 2 can be altered. In some aspects, the cycling therapy is altered if, after administration of the immunomodulatory compound, e.g. lenalidomide, Compound 1 or Compound 2, the subject has a grade 3 or higher thrombocytopenia; a grade 3 neutropenia; a grade 3 neutropenia that is sustained (such as at least more than 3, 5, or 7 days); a grade 4 neutropenia; a Grade 3 or higher febrile neutropenia. In some embodiments, administration of the immunomodulatory compound, e.g. lenalidomide, Compound 1 or Compound 2 is halted permanently or suspended until signs or symptoms of the toxicity is resolved, lessened or reduced. Continued monitoring of the subject can be carried out to assess one or more signs or symptoms of the toxicity, such as by CBC or differential leukocyte analysis. In some cases, if the toxicity resolves or is reduced, administration of lenalidomide, Compound 1 or Compound 2 can be restarted at the same dose or dosing regimen prior to suspending the cycling therapy, at a lower or reduced dose, and/or in a dosing regimen involving less frequent dosing. In some embodiments, in instances of restarting the cycling therapy, the dose is lowered or reduced at least or at least about or about 10%, 15%, 20%, 25%, 30%, 40%, 50%, or 60%. In some embodiments, if the dose prior to suspending the cell therapy is 2 mg (e.g. given 5/7 days), the dose is reduced to 1 mg (given 5/7 days). In some aspects, if a hematological toxicity is of such severity that suspension of the cycling therapy is for greater than 4 weeks, the cycling therapy can be permanently discontinued.

In some embodiments, one or more agents can be administered to the subject to treat, ameliorate or lessen one or more symptoms associated with the hematological toxicity. In some cases, a myeloid growth factors, such as G-CSF or GM-CSF, is administered to the subject until the hematological toxicity improves. Examples of such therapies include filgrastim or pegfilgrastim. In some aspects, such agents are administered to subjects experiencing severe neutropenia or febrile neutropenia, including any grade 3 or greater neutropenia of any duration.

C. Non-Hematologic Toxicity

In some aspects, the toxic outcome is or is associated with or indicative of one or more non-hematologic toxicity following administration of the immunomodulatory compound, e.g. lenalidomide, Compound 1 or Compound 2. Examples of non-hematologic toxicities include, but are not limited to, tumor flare reaction, infections, tumor lysis syndrome, cardiac laboratory abnormalities, thromboembolic event(s) (such as deep vein thrombosis and pulmonary embolism), and/or pneumonitis.

In some aspects, the non-hematologic toxicity is tumor flare reaction (TFR) (sometimes also referred to pseudoprogression). TFR is a sudden increase in the size of the disease-bearing sites, including the lymph nodes, spleen and/or the liver often accompanied by a low-grade fever, tenderness and swelling, diffuse rash and in some cases, an increase in the peripheral blood lymphocyte counts. In some embodiments, TFR is graded according to Common Terminology Criteria for Adverse Events (Version 3.0; US National Cancer Institute, Bethesda, MD, USA). In some embodiments, TFR is graded as follows: grade 1, mild pain not interfering with function; grade 2, moderate pain, pain or analgesics interfering with function but not interfering with activities of daily living (ADL); grade 3, severe pain, pain or analgestics interfering with function and interfering with ADL; grade 4, disabling; grade 5, death. In some embodiments, one or more agents can be administered to the subject to treat, ameliorate or lessen one or more symptoms associated with TFR, such as corticosteroids, NSAIDs and/or narcotic analgesic.

In some aspects, the non-hematologic toxicity is tumor lysis syndrome (TLS). In some embodiments, TLS can be graded according to criteria specified by the Cairo-Bishop grading system (Cairo and Bishop (2004) Br J Haematol, 127:3-11). In some embodiments, subjects can be given intravenous hydration to reduce hyperuricemia.

In some embodiments, subjects can be monitored for cardiac toxicity, such as by monitoring ECGS, LVEF and monitoring levels of troponin-T and BNP. In some embodiments, a cardiac toxicity that potentially may necessitate holding or suspending Compound 1 may occur if elevated levels of troponin-T and/or BNP with one or more cardiac symptoms is observed.

In some embodiments of the provided methods, if a subject is determined to exhibit a non-hematological toxicity, such as TFR or other non-hematological toxicity or a particular grade thereof, the cycling therapy with the immunomodulatory compound, e.g. Compound 1 can be altered. In some aspects, the cycling therapy is altered if, after administration of the immunomodulatory compound, e.g. lenalidomide, Compound 1 or Compound 2, the subject has a grade 3 or higher non-hematological toxicity, such as grade 3 or higher TFR. In some embodiments, administration of the immunomodulatory compound, e.g. lenalidomide, Compound 1 or Compound 2 is halted permanently or suspended until signs or symptoms of the toxicity is resolved, lessened or reduced. Continued monitoring of the subject can be carried out to assess one or more signs or symptoms of the toxicity. In some cases, if the toxicity resolves or is reduced, administration of the immunomodulatory compound, e.g. lenalidomide, Compound 1 or Compound 2 can be restarted at the same dose or dosing regimen prior to suspending the cycling therapy, at a lower or reduced dose, and/or in a dosing regimen involving less frequent dosing. In some embodiments, in instances of restarting the cycling therapy, the dose is lowered or reduced at least or at least about or about 10%, 15%, 20%, 25%, 30%, 40%, 50%, or 60%. In some embodiments, for Compound 1, if the dose prior to suspending the cell therapy is 2 mg (e.g. given 5/7 days), the dose is reduced to 1 mg (given 5/7 days). In some embodiments, if a grade 3 toxicity recurs even after a dose reduction, the dose can be further reduced. In some embodiments, if a grade 4 toxicity recurs even after a dose reduction, the cycling therapy can be permanently discontinued. In some aspects, if a hematological toxicity is of such severity that suspension of the cycling therapy is for greater than 4 weeks, the cycling therapy can be permanently discontinued.

V. Articles of Manufacture and Kits

Also provided are articles of manufacture containing an immunomodulatory drug (immunomodulatory compound), such as lenalidomide, Compound 1 or Compound 2, and components for the immunotherapy, e.g., antibody or antigen binding fragment thereof or T cell therapy, e.g. engineered cells, and/or compositions thereof. The articles of manufacture may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition.

The article of manufacture may include (a) a first container with a composition contained therein, wherein the composition includes the antibody or engineered cells used for the immunotherapy, e.g. T cell therapy; and (b) a second container with a composition contained therein, wherein the composition includes the second agent, such as an immunomodulatory compound, e.g., lenalidomide, Compound 1 or Compound 2. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

VI. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, a "subject" is a mammal, such as a human or other animal, and typically is human. In some embodiments, the subject, e.g., patient, to whom the immunomodulatory polypeptides, engineered cells, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or engineered cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the immunomodulatory polypeptides or engineered cells administered. In some embodiments, the provided methods involve administering the immunomodulatory polypeptides, engineered cells, or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, one can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New. Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways, for instance, using publicly available computer software such as BLAST, BLAST-2, ALIGN or Megalign (DNASTAR) software. Appropriate parameters for aligning sequences, including any algorithms needed to achieve maximal alignment over the full length of the sequences being compared, can be determined.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

VII. Exemplary Embodiments

Among the provided embodiments are:

1. A method for or rescuing T cell activity, the method comprising exposing a plurality of T cells having an exhausted phenotype to an effective amount of an immunomodulatory compound selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3).

2. The method of embodiment 1, wherein the one or more T cells comprise T cells that express a recombinant receptor that specifically binds to a target antigen.

3. A method for increasing T cell activity or potency and preventing or inhibiting, reducing or delaying the onset of T cell exhaustion, the method comprising exposing a plurality of T cells to an effective amount of an immunomodulatory compound selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3), wherein at least a portion of the exposing is carried out under conditions that induce, or are capable of inducing, an exhausted phenotype in T cells of the plurality in the absence of the compound.

4. The method of embodiment 3, wherein the conditions comprise T cell stimulatory conditions, optionally comprising exposure to at least one T cell stimulatory agent that is capable of stimulating a signal in T cells of the plurality, said signal optionally including a primary and/or costimulatory signal.

5. The method of embodiment 4, wherein the conditions comprise persistent, repeat, prolonged or long term exposure to the at least one T cell stimulatory agent.

6. The method of embodiment 4 or embodiment 5, wherein the at least one T cell stimulatory agent comprises a polyclonal agent, an antigen specifically recognized by a receptor expressed on T cells of the plurality or an agent that is bound by an antigen receptor expressed by T cells of the plurality.

7. The method of embodiment 4-6, wherein the at least one T cell stimulatory agent is or comprises PMA and ionomycin or is or comprises a T cell receptor agonist or a T cell receptor complex agonist.

8. The method of embodiment 7, wherein the agent specifically binds to a member of a TCR complex, optionally wherein the agent specifically binds to a CD3, optionally a CD3zeta.

9. The method of embodiment 8, wherein the at least one T cell stimulatory agent comprises an anti-CD3 antibody.

10. The method of any one of embodiments 4 to 9, wherein the at least one T cell stimulatory agent specifically binds to a T cell costimulatory molecule, optionally wherein the T cell costimulatory molecule is CD28, CD137 (4-1-BB), OX40, CD40L or ICOS or wherein the at least one T cell stimulatory agent further comprises an agent that specifically binds to a T cell costimulatory molecule, optionally wherein the T cell costimulatory molecule is CD28, CD137 (4-1-BB), OX40, CD40L or ICOS.

11. The method of embodiment 10, wherein the at least one T cell stimulatory agent comprises an anti-CD28 antibody.

12. The method of any one of embodiments 4 to 11, wherein the at least one T cell stimulatory agent comprises or further comprises an MHC-peptide complex recognized by an antigen receptor expressed by one or more T cells of the plurality, or an antigen recognized by an antigen receptor expressed by one or more T cells of the plurality.

13. The method of any of embodiments 3-12, wherein the one or more of the plurality of T cells express a recombinant antigen receptor that binds a target antigen.

14. The method of embodiment 13, wherein the at least one T cell stimulatory agent binds to the recombinant antigen receptor.

15. The method of embodiment 14, wherein the at least one T cell stimulatory agent is or comprises the target antigen or a portion thereof recognized by or bound by the recombinant antigen receptor and/or wherein the conditions comprise exposure to the target antigen.

16. The method of any of embodiments 13-15, wherein the recombinant antigen receptor is a recombinant T cell receptor (TCR).

17. The method of any of embodiments 13-16, wherein the recombinant antigen receptor is a chimeric antigen receptor (CAR).

18. The method of any of embodiments 1-17, wherein the one or more T cells are primary human T cells, optionally from a subject.

19. The method of any of embodiments 1-18, wherein the exposing is carried out ex vivo.

20. The method of any of embodiments 1-18, wherein the exposing is carried out in vivo and:
said exposing comprises administration of the compound to a subject, optionally wherein the T cells are from the subject, wherein the administration of the compound is to said subject; and/or said exposing comprises administration of said plurality of T cells to a subject, optionally wherein, where the T cells are from the subject, wherein the administration of the compound is to said subject.

21. The method of embodiment 20, wherein,
said exposure comprises said administration of said compound and, wherein, prior to the exposing, said subject has been administered a composition comprising the plurality of T cells to the subject for treating a disease or condition, optionally wherein the target antigen is associated with the disease or condition; or said exposure comprises administration of said T cells to said subject for treating a disease or condition, optionally wherein the target antigen is associated with the disease or condition, wherein, prior to the exposing, said subject has been administered said compound; or said exposure comprises administration of said T cells to said subject for treating a disease or condition, optionally wherein the target antigen is associated with the disease or condition, and comprises administration of said compound to said subject.

22. A method of treatment, the method comprising administering, to a subject, an immunomodulatory compound, wherein said immunomodulatory compound is selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3), wherein, (a) said subject, prior to the administration of the compound, has been administered a T cell therapy comprising a dose of T cells expressing a recombinant antigen receptor that binds a target antigen, or (b) prior to or at the time of administration of said compound, said subject or a blood sample from the subject contains, or has been confirmed to contain, one or more T cells expressing a recombinant antigen receptor, wherein at the time of the administration of the compound:

(i) one or more of the recombinant receptor-expressing T cells in the subject has an exhausted phenotype;

(ii) one or more of the recombinant receptor-expressing T cells in the subject have been determined to have an exhausted phenotype;

(iii) an exhausted phenotype of one or more recombinant receptor-expressing T cells, or a marker or parameter indicative thereof, has been detected or measured in the subject or in a biological sample from the subject;

(iv) at least at or about 10%, at least at or about 20%, at least at or about 30%, at least at or about 40%, or at least at or about 50% of the total recombinant receptor-expressing T cells in a biological sample from the subject has an exhausted phenotype; and/or (v) greater than at or about 10%, greater than at or about 20%, greater than at or about 30%, greater than at or about 40%, or greater than at or about 50% of the recombinant receptor-expressing T cells in a biological sample from the subject has an exhausted phenotype compared to the percentage of the recombinant receptor-expressing cells having the exhausted phenotype in a comparable biological sample at a prior time point.

23. A method of treatment, the method comprising:

(a) selecting a subject as a candidate for administration of an immunomodulator compound, said selected subject having exhausted recombinant receptor-expressing T cells; and (b) administering to the subject the immunomodulatory compound, wherein the immunomodulatory compound is selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion and/or degradation of Ikaros (IKZF1) and/or Aiolos (IKZF3).

24. The method of embodiment 23, wherein a tissue, tumor, biological fluid or biological sample of or from said selected subject:

(i) comprises one or more T cells that express a recombinant antigen receptor that binds to a target antigen and that have an exhausted phenotype;

(ii) comprises a plurality of T cells that express a recombinant antigen receptor that binds to a target antigen, wherein at least at or about 10%, at least at or about 20%, at least at or about 30%, at least at or about 40%, at least at or about 50%, at least at or about 60%, at least at or about 70% or at least at or about 80%, of the T cells in said tissue, fluid, tumor or sample expressing the recombinant receptor have an exhausted phenotype; and/or (iii) comprises a plurality of T cells that express a recombinant antigen receptor that binds to a target antigen, wherein greater than at or about 10% more, greater than at or about 20% more, greater than at or about 30% more, greater than at or about 40% more, or greater than at or about 50% more, or greater than 2-fold more, or greater than 3-fold more, or greater than 5-fold more, or greater than 10-fold more, of the T cells in the tissue, tumor, fluid or sample of or from the selected subject that express the recombinant antigen receptor have an exhausted phenotype, as compared to the percentage or number of T cells expressing the recombinant receptor in the, or in a comparable, fluid, tissue, tumor or sample from said subject at earlier time point had said exhausted phenotype.

25. The method of embodiment 23, wherein said selection of said subject comprises determining that, or is based on determination that, a tissue, tumor, biological fluid or biological sample of or from said selected subject:

(i) comprises one or more T cells that express a recombinant antigen receptor that binds to a target antigen and that have an exhausted phenotype;

(ii) comprises a plurality of T cells that express a recombinant antigen receptor that binds to a target antigen, wherein at least at or about 10%, at least at or about 20%, at least at or about 30%, at least at or about 40%, at least at or about 50%, at least at or about 60%, at least at or about 70% or at least at or about 80%, of the T cells in said tissue, fluid, tumor or sample expressing the recombinant receptor have an exhausted phenotype; and/or (iii) comprises a plurality of T cells that express a recombinant antigen receptor that binds to a target antigen, wherein greater than at or about 10% more, greater than at or about 20% more, greater than at or about 30% more, greater than at or about 40% more, or greater than at or about 50% more, or greater than 2-fold more, or greater than 3-fold more, or greater than 5-fold more, or greater than 10-fold more, of the T cells in the tissue, tumor, fluid or sample of or from the selected subject that express the recombinant antigen receptor have an exhausted phenotype, as compared to the percentage or number of T cells expressing the recombinant receptor in the, or in a comparable, fluid, tissue, tumor or sample from said subject at earlier time point had said exhausted phenotype.

26. The method of embodiment 24 or embodiment 25, wherein, prior to said administration of the compound, said subject has been administered a plurality of T cells expressing the recombinant receptor and optionally wherein said earlier time point is subsequent to the administration of the T cells and prior to said selection.

27. The method of embodiment 24 or embodiment 25 or embodiment 26, wherein the prior time point is a time:

subsequent to the administration of T cells expressing said recombinant receptor to said selected subject and is at or before a peak or maximum level of T cells expressing recombinant receptor are detectable in the blood of the subject;

within 1 day, 2 days, 3 days, 4 days, 5 days, 6 days, 7 days, 8 days, 9 days, 10 days, 11 days, 12 days, 13 days, 14 days, or more prior to said determination or selection.

28. The method of any of embodiments 23-27, wherein:

at the time of the administration of the T cell therapy the subject had a disease or condition;

at the time of the administration of the T cell therapy and at the time of the administration of the compound the subject has a disease or condition;

at the time of the administration of the T cell therapy the subject had a disease or condition and at the time of the administration of the compound the disease or condition has relapsed or progressed or been deemed non-responsive to said compound in the subject following the administration of the T cell therapy.

29. The method of any of embodiments 1-28, wherein the exhaustion phenotype, with reference to a T cell or population of T cells, comprises:

an increase in the level or degree of surface expression on the T cell or T cells, or in the percentage of T said population of T cells exhibiting surface expression, of one or more exhaustion marker, optionally 2, 3, 4, 5 or 6 exhaustion markers, compared to a reference T cell population under the same conditions; or a decrease in the level or degree of an activity exhibited by said T cells or population of T cells upon exposure to an antigen or antigen receptor-specific agent, compared to a reference T cell population, under the same conditions.

30. The method of embodiment 29, wherein the increase in the level, degree or percentage is by greater than at or about 1.2-fold, at or about 1.5-fold, at or about 2.0-fold, at or about 3-fold, at or about 4-fold, at or about 5-fold, at or about 6-fold, at or about 7-fold, at or about 8-fold, at or about 9-fold, at or about 10-fold or more.

31. The method of embodiment 29, wherein the decrease in the level, degree or percentage is by greater than at or about 1.2-fold, at or about 1.5-fold, at or about 2.0-fold, at or about 3-fold, at or about 4-fold, at or about 5-fold, at or about 6-fold, at or about 7-fold, at or about 8-fold, at or about 9-fold, at or about 10-fold or more.

32. The method of any of embodiments 29-31, wherein the reference T cell population is a population of T cells known to have a non-exhausted phenotype, is a population of naïve T cells, is a population of central memory T cells, or is a population of stem central memory T cells, optionally from the same subject, or of the same species as the subject, from which the T cell or T cells having the exhausted phenotype are derived.

33. The method of any of embodiments 29-32, wherein the reference T cell population (a) is a subject-matched population comprising bulk T cells isolated from the blood of the subject from which the T cell or T cells having the exhausted phenotype is derived, optionally wherein the bulk T cells do not express the recombinant receptor and/or (b) is obtained from the subject from which the T cell or T cells having the exhausted phenotype is derived, prior to receiving administration of a dose of T cells expressing the recombinant receptor.

34. The method of any of embodiments 29-32, wherein the reference T cell population is a composition comprising a sample of the T cell therapy, or pharmaceutical composition comprising T cells expressing the recombinant receptor, prior to its administration to the subject, optionally wherein the composition is a cryopreserved sample.

35. The method of any of embodiments 29-34, wherein one or more of the one or more exhaustion marker is an inhibitory receptor.

36. The method of any of embodiments 29-35, wherein one or more of the one or more exhaustion marker is selected from among PD-1, CTLA-4, TIM-3, LAG-3, BTLA, 2B4, CD160, CD39, VISTA, and TIGIT.

37. The method of any of embodiments 29-36, wherein the activity or is one or more of proliferation, cytotoxicity or production of one or a combination of inflammatory cytokines, optionally wherein the one or a combination of cytokines is selected from the group consisting of IL-2, IFN-gamma and TNF-alpha.

38. The method of any of embodiments 29-37, wherein the exposure to said antigen or antigen receptor-specific agent comprises incubation with the antigen or antigen receptor-specific agent, optionally an agent that binds the recombinant receptor, wherein said antigen is optionally the target antigen.

39. The method of embodiment 38, wherein the antigen or antigen receptor-specific agent comprises antigen-expressing target cells, optionally cells of said disease, disorder or condition.

40. The method of any of embodiments 2 and 13-36, wherein the target antigen is associated with, specific to, and/or expressed on a cell or tissue of a disease, disorder or condition.

41. The method of any of embodiments 2 and 13-40, wherein the target antigen is a tumor antigen.

42. The method of any of embodiments 2 and 13-41, wherein the target antigen is selected from among αvβ6 integrin (avb6 integrin), B cell maturation antigen (BCMA), BAFF-R, B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, CS-1, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE- A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, TACI, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

43. The method of any of embodiments 1-42, wherein the disease or condition is a B cell malignancy or a B cell-derived malignancy.

44. The method of any of embodiments 1-43, wherein the target antigen is CD20, CD19, CD22, ROR1, CD45, CD21, CD5, CD33, Igkappa, Iglambda, CD79a, CD79b or CD30.

45. The method of any of embodiments 1-44, wherein the target antigen is CD19. 46. The method of any of embodiments 1-43, wherein the disease or condition is a multiple myeloma.

47. The method of any of embodiments 1-43 and 46, wherein the target antigen is BCMA, G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI or FcRH5.

48. The method of any of embodiments 1-43, 46 and 47, wherein the target antigen is BCMA.

49. The method of any of embodiments 22-48, wherein the biological sample is a blood sample.

50. The method of any of embodiments 22-49, wherein the biological sample is a tumor sample, optionally a tumor biopsy sample.

51. A method of treatment, the method comprising (a) administering a T cell therapy to a subject having a cancer, said T cell therapy comprising a dose of T cells expressing a recombinant antigen receptor that binds to a target antigen; and (b) administering to the subject an immune modulatory compound selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination and/or depletion and/or degradation of Ikaros (IKZF1) and/or Aiolos (IKZF3), whereby, following said administration of said therapy and said compound, a factor indicative of expansion or activity of T cells expressing the recombinant receptor and a factor indicative of durability of response are increased as compared to a reference method, wherein:

the reference method comprises the administering in (a), alone, or the administration in (a) without the administration of the immune modulatory compound;

the factor indicative of expansion or activity comprises (i) a measure of the maximum number of T cells observed in the blood or cancer of the subject following said administration, (ii) the number of days elapsed between said administration and reaching of said maximum number of T cells in the blood or cancer of the subject, or (iii) the area under the curve (AUC) of CAR-expressing cells over time, (iv) the degree of response in the subject.

52. The method of embodiment 51, wherein the measure of durability of response is the time of progression free survival, survival, or duration of best response.

53. The method of embodiment 51 or embodiment 52, wherein the reference method comprises administration of IL-2.

54. A method of treatment, the method comprising:
(a) administering a T cell therapy to a subject having a cancer, said T cell therapy comprising a dose of T cells expressing a recombinant antigen receptor that binds to a target antigen; and
(b) administering to the subject an immune modulatory compound selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination and/or depletion and/or degradation of Ikaros (IKZF1) and/or Aiolos (IKZF3), at an amount, duration and/or frequency effective to:
(1) effect an increase in antigen-specific or antigen receptor-driven activity of naïve or non-exhausted T cells in the subject, which optionally comprise T cells expressing said recombinant receptor, following exposure of the T cells to antigen or to an antigen receptor-specific agent as compared to the absence of said administration of said compound; or
(2) prevent, inhibit or delay the onset of an exhaustion phenotype, in naïve or non-exhausted T cells T cells in the subject, which optionally comprise T cells expressing said recombinant receptor, following exposure of the T cells to antigen or to an antigen receptor-specific agent, as compared to the absence of said administration of said compound; or
(3) reverse an exhaustion phenotype in exhausted T cells, optionally comprising T cells expressing said recombinant receptor, in the subject, as compared to the absence of said administration of said subject.

55. The method of embodiment 54, wherein the amount, duration and/or frequency is effective (i) to effect said increase in antigen-specific or antigen receptor-driven activity and (ii) to prevent, inhibit or delay said onset of exhaustion phenotype and/or to reverse said exhaustion phenotype.

56. The method of embodiment 55, wherein the amount, duration and/or frequency is effective (i) to effect said increase in antigen-specific or antigen receptor-driven activity and (ii) to prevent, inhibit or delay said onset of exhaustion phenotype.

57. The method of embodiment 54, wherein the amount, duration and/or frequency is effective (i) to effect said increase in antigen-specific or antigen receptor-driven activity and (ii) to prevent, inhibit or delay said onset of exhaustion phenotype and to reverse said exhaustion phenotype.

58. A method of treatment, the method comprising:
(a) administering a T cell therapy to a subject having a cancer, said T cell therapy comprising a dose of T cells expressing a recombinant antigen receptor that binds to a target antigen; and
(b) administering to the subject an immune modulatory compound selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3);

and compounds that enhance or promote ubiquitination and/or depletion and/or degradation of Ikaros (IKZF1) and/or Aiolos (IKZF3), at an amount, duration and/or frequency effective to:

(1) effect an increase in antigen-specific or antigen receptor-driven activity of naïve or non-exhausted T cells in the subject, which optionally comprise T cells expressing said recombinant receptor, following exposure of the T cells to antigen or to an antigen receptor-specific agent as compared to the absence of said administration of said compound; or (2) prevent, inhibit or delay the onset of an exhaustion phenotype, in naïve or non-exhausted T cells T cells in the subject, which optionally comprise T cells expressing said recombinant receptor, following exposure of the T cells to antigen or to an antigen receptor-specific agent, as compared to the absence of said administration of said compound; or (3) reverse an exhaustion phenotype in exhausted T cells, optionally comprising T cells expressing said recombinant receptor, in the subject, as compared to the absence of said administration of said subject.

59. The method of embodiment 58, wherein the amount, duration and/or frequency is effective (i) to effect said increase in antigen-specific or antigen receptor-driven activity and (ii) to prevent, inhibit or delay said onset of exhaustion phenotype and/or to reverse said exhaustion phenotype.

60. The method of embodiment 59, wherein the amount, duration and/or frequency is effective (i) to effect said increase in antigen-specific or antigen receptor-driven activity and (ii) to prevent, inhibit or delay said onset of exhaustion phenotype.

61. The method of embodiment 58, wherein the amount, duration and/or frequency is effective (i) to effect said increase in antigen-specific or antigen receptor-driven activity and (ii) to prevent, inhibit or delay said onset of exhaustion phenotype and to reverse said exhaustion phenotype.

62. The method of any of embodiments 20-61, wherein the immunomodulatory compound is administered in an effective amount of from or from about 1 mg to 50 mg per day it is administered, from or from about 1 mg to 25 mg per day it is administered, from or from about 1 mg to 10 mg per day it is administered, from or from about 1 mg to 5 mg per day it is administered, from or from about 5 mg to 50 mg per day it is administered, from or from about 5 mg to 25 mg per day it is administered, from or from about 5 mg to 10 mg per day it is administered.

63. The method of any of embodiment 20-62, wherein the administration of the compound is carried out in a cycling regimen comprising administration of an effective amount of the compound (i) daily for a period of more than one week, (ii) per day for no more than 6 days per week for a period of more than one week, (ii) per day for no more than 5 days per week for a period of more than one week; or per day for no more than 4 days per week for a period of more than one week.

64. The method of any of embodiments 20-63, wherein the administration of the compound is carried out in a cycling regimen comprising administration of an effective amount of the compound per day for no more than 5 days per week for a period of more than one week.

65. The method of any of embodiments 1-64, wherein the compound depletes or degrade Ikaros (IKZF1).

66. The method of any of embodiments 1-65, wherein the compound is a compound of the following structure:

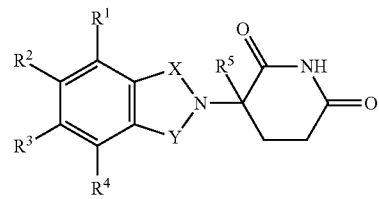

wherein one of X and Y is —C(O)— and the other of X and Y is —C(O)— or —CH$_2$—;

(1) each of $R^1$, $R^2$, $R^3$, and $R^4$ are independently halo, alkyl of 1 to 4 carbon atoms, or alkoxy or 1 to 4 carbon atoms, or (2) one of $R^1$, $R^3$, $R^4$, and $R^5$ is —NHR$^a$ and the remaining of $R^1$, $R^2$, $R^3$, and $R^4$ is are hydrogen, wherein $R^a$ is hydrogen or alkyl of 1 to 8 carbon atoms;

$R^5$ is hydrogen or alkyl of 1 to 8 carbon atoms, benzyl, or halo;

provided that $R^5$ is other than hydrogen if X and Y are —C(O)— and (i) each of $R^1$, $R^2$, $R^3$, and $R^4$ is fluoro; or (ii) one of $R^1$, $R^2$, $R^3$, and $R^4$ is amino; or a pharmaceutically acceptable salt thereof.

67. The method of any of embodiments 1-66, wherein the compound is a compound of the following structure:

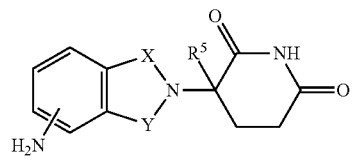

wherein one of X and Y is —C(O)— and the other of X and Y is —C(O)— or —CH$_2$—, and $R^5$ is hydrogen or lower alkyl, or a pharmaceutically acceptable salt thereof.

68. The method of any of embodiments 1-67, wherein the compound that is or comprises 3-(4-amino-1-oxo-1,3-dihydro-2H-isoindol-2-yl)piperidine-2,6-dione having the following structure:

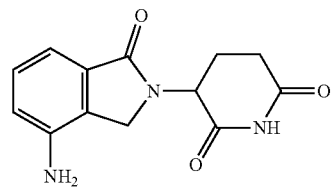 [SMILES: Nc1cccc2c1CN(C1CCC(=O)NC1=O)C2=O]

or an enantiomer or mixture of enantiomers thereof, or a pharmaceutically acceptable salt, solvate, hydrate, co-crystal, clathrate, or polymorph thereof.

69. The method of any of embodiments 1-68, wherein the compound is 3-(4-amino-1-oxo-1,3-dihydro-2H-isoindol-2-yl)piperidine-2,6-dione.

70. The method of any of embodiments 1-65, wherein the compound is a compound that is or comprises 3-(5-amino-2-methyl-4-oxo-4H-quinazolin-3-yl)-piperidine-2,6-dione having the following structure:

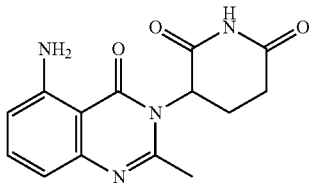 [SMILES: Cc1nc2cccc(N)c2c(=O)n1C1CCC(=O)NC1=O]

or an enantiomer or mixture of enantiomers thereof, or a pharmaceutically acceptable salt, solvate, hydrate, co-crystal, clathrate, or polymorph thereof.

71. The method of any of embodiments 1-65 and 70, wherein the compound is 3-(5-amino-2-methyl-4-oxo-4H-quinazolin-3-yl)-piperidine-2,6-dione.

72. The method of any of embodiments 1-65, wherein the compound is a compound of the following structure:

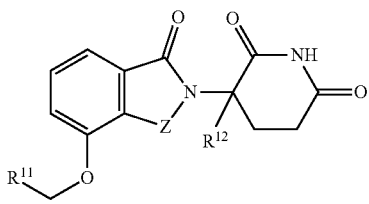

or a pharmaceutically acceptable salt, solvate or stereoisomer thereof, wherein:
Z is C=O or CH$_2$;
R$^{11}$ is —Z$^1$—R$^{13}$;
R$^{12}$ is H or (C$_1$-C$_6$)alkyl;
Z$^1$ is 6 to 10 membered aryl, heteroaryl, or heterocycle, each of which may be optionally substituted with one or more halogen; or a bond;
R$^{13}$ is —(CH$_2$)$_n$-aryl, —O—(CH$_2$)$_n$-aryl, or —(CH$_2$)$_n$—O-aryl, wherein the aryl is optionally substituted with one or more: (C$_1$-C$_6$)alkyl; itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy, or halogen; —CONH$_2$; or —COO—(C$_1$-C$_6$) alkyl, wherein the alkyl may be optionally substituted with one or more halogen; —(CH$_2$)$_n$-heterocycle, —O—(CH$_2$)$_n$-heterocycle or —(CH$_2$)$_n$—O-heterocycle, wherein the heterocycle is optionally substituted with one or more: (C$_1$-C$_6$) alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; or —(CH$_2$)$_n$-heteroaryl, —O—(CH$_2$)$_n$-heteroaryl or —(CH$_2$)$_n$—O-heteroaryl, wherein the heteroaryl is optionally substituted with one or more: (C$_1$-C$_6$)alkyl, itself optionally substituted with one or more halogen; (C$_1$-C$_6$) alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; and
n is 0, 1, 2 or 3.

73. The method of any of embodiments 1-65 and 72, wherein the compound is

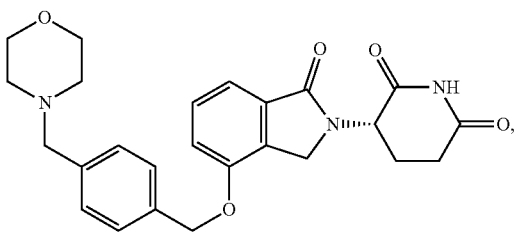 [SMILES: O=C1CC[C@H](N2Cc3c(OCc4ccc(CN5CCOCC5)cc4)cccc3C2=O)C(=O)N1]

or a pharmaceutically acceptable salt, solvate, or stereoisomer thereof.

74. The method of any of embodiments 1-65, 72 and 73, wherein the compound is the Form A crystal form of the hydrochloride salt of

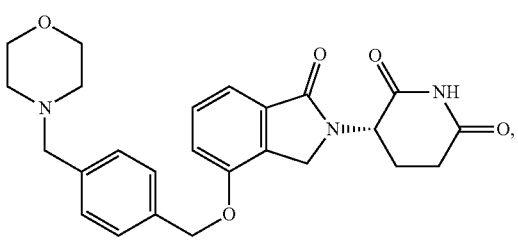 [SMILES: O=C1CC[C@H](N2Cc3c(OCc4ccc(CN5CCOCC5)cc4)cccc3C2=O)C(=O)N1]

75. The method of embodiment 74, wherein the XRPD pattern of the Form A crystal form of the hydrochloride salt of

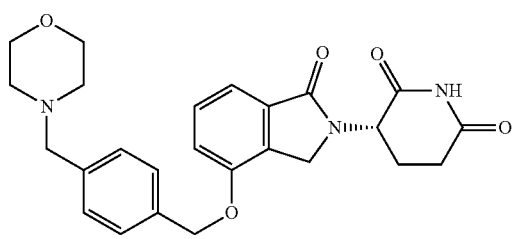 [SMILES: O=C1CC[C@H](N2Cc3c(OCc4ccc(CN5CCOCC5)cc4)cccc3C2=O)C(=O)N1]

is characterized by XRPD peaks located at 1, 2, 3, 4, 5, 6, 7, 8, 9, 10, 11, 12, 13, 14, 15, 16, 17, 18, 19, 20 or all of the following or approximately the following positions: 9.69, 12.82, 15.09, 15.94, 16.76, 17.65, 19.44, 19.80, 2230, 22.47, 22.95, 23.02, 24.29, 24.48, 24.70, 26.27, 26.77, 27.60, 29.43, 29.72, and 32.91 degrees 2θ.

76. A method of treatment, the method comprising:
(a) administering a T cell therapy to a subject having a cancer, said T cell therapy comprising a dose of T cells expressing a recombinant antigen receptor that binds to a target antigen; and
(b) administering to the subject a compound that is or comprises 3-(5-amino-2-methyl-4-oxo-4H-quinazolin-3-yl)-piperidine-2,6-dione having the following structure:

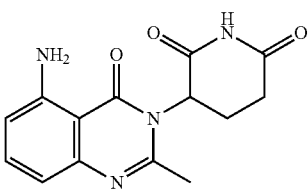 [SMILES: Cc1nc2cccc(N)c2c(=O)n1C1CCC(=O)NC1=O]

or an enantiomer or mixture of enantiomers thereof, or a pharmaceutically acceptable salt, solvate, hydrate, co-crystal, clathrate, or polymorph thereof, wherein the administration of the compound is carried out in a cycling regimen comprising administration of an effective amount of the compound per day for no more than 5 days per week for a period of more than one week, 77. The method of any of embodiments 20-76, wherein the administration of the compound is initiated subsequently to initiation of administration of the T cell therapy.

78. The method of any of embodiments 51-76, wherein the administration of the compound is initiated concurrently with the T cell therapy and/or is initiated within one day of, prior to or subsequently to, initiating the administration of the T cell therapy.

79. The method of any of embodiments 51-78, wherein the administration of the compound is initiated at or about or within at or about one day prior to or subsequently to initiating the administration of the T cell therapy.

80. A method of treatment, the method comprising administering to a subject having a cancer a compound that is or comprises 3-(5-amino-2-methyl-4-oxo-4H-quinazolin-3-yl)-piperidine-2,6-dione having the following structure:

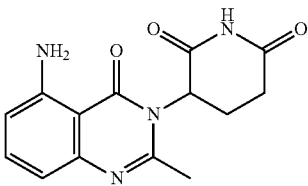 [SMILES: Cc1nc2cccc(N)c2c(=O)n1C1CCC(=O)NC1=O]

or an enantiomer or mixture of enantiomers thereof, or a pharmaceutically acceptable salt, solvate, hydrate, co-crystal, clathrate, or polymorph thereof, said subject having been administered, prior to the administration of the compound, a T cell therapy comprising a dose of genetically engineered T cells expressing a recombinant antigen receptor, wherein the administration of the compound is carried out in a cycling regimen comprising administration of an effective amount of the compound per day for no more than 5 days per week for a period of more than one week.

81. The method of any of embodiments 51-80, wherein the cancer is a B cell malignancy, B cell-derived malignancy, non-hematological cancer or a solid tumor.

82. The method of any of embodiments 51-81, wherein the target antigen is a tumor antigen, optionally wherein the target antigen is associated with, specific to, and/or expressed on a cell or tissue of the cancer, 83. The method of any of embodiments 51-82, wherein the target antigen is selected from B cell maturation antigen (BCMA), αvβ6 integrin (avb6 integrin), BAFF-R, B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD5, CD19, CD20, CD21, CD22, CD23, CD24, CD30, CD38, CD44, CD44v6, CD44v7/8, CD45, CD79a, CD79b, CD123, CD133, CD138, CD171, CS-1, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), Igkappa, Iglambda, IL-22 receptor alpha (IL-22Rα), IL-13 receptor alpha 2 (IL-13Rα2), kinase insert domain receptor (kdr), L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), ROR1, survivin, TACI, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen.

84. The method of embodiment 43, embodiment 82 or embodiment 83, wherein the B cell malignancy is a lymphoma.

85. The method of embodiment 84, wherein the lymphoma is a non-Hodgkin lymphoma (NHL).

86. The method of embodiment 85, wherein the NHL comprises aggressive NHL, diffuse large B cell lymphoma (DLBCL), DLBCL-NOS, optionally transformed indolent; EBV-positive DLBCL-NOS; T cell/histiocyte-rich large B-cell lymphoma; primary mediastinal large B cell lymphoma (PMBCL); follicular lymphoma (FL), optionally, follicular lymphoma Grade 3B (FL3B); and/or high-grade B-cell lymphoma with MYC and BCL2 and/or BCL6 rearrangements with DLBCL histology (double/triple hit).

87. The method of any one of embodiments 1-86, wherein the subject is or has been identified as having an Eastern Cooperative Oncology Group Performance Status (ECOG) status of less than or equal to 1.

88. The method of any 51-87, wherein the target antigen is CD20, CD19, CD22, ROR1, CD45, CD21, CD5, CD33, Igkappa, Iglambda, CD79a, CD79b or CD30.

89. The method of any of embodiments 43-88, wherein the target antigen is CD19.

90. The method of any of embodiments 51-87, wherein the target antigen is not CD20, CD19, CD22, ROR1, CD45, CD21, CD5, CD33, Igkappa, Iglambda, CD79a, CD79b or CD30.

91. The method of any of embodiments 51-81, wherein the cancer is a multiple myeloma.

92. The method of any of embodiments 51-91, wherein the target antigen is BCMA, G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI or FcRH5.

93. The method of any of embodiments 51-92, wherein the target antigen is BCMA. 94. The method of any of embodiments 63-93, wherein the period extends for at or about or greater than three months after the initiation of the administration of the T cell therapy.

95. The method of any of embodiments 63-94, wherein the effective amount is no more than at or about 4 mg per day.

96. The method of any of embodiments 63-95, wherein the effective amount is between at or about 1.0 mg and at or about 4 mg per day.

97. The method of any of embodiments 63-94, wherein the effective amount is no more than at or about 3 mg per day.

98. The method of any of embodiments 63-94 and 97, wherein the effective amount is between at or about 1.0 mg and at or about 3 mg.

99. The method of any of embodiments 63-94, wherein the effective amount is no more than at or about 2.5 mg per day.

100. The method of any of embodiments 63-99, wherein, for each week of the cycling regimen, or for at least one week of the cycling regimen, the administration of the compound comprises administering the compound on each of no more than 5 consecutive days of the week followed by a rest period for the remainder of the week, during which the compound is not administered.

101. The method of embodiment 100, wherein the no more than 5 consecutive days is 3 consecutive days per week followed by a rest period of 4 days, during which the compound is not administered.

102. The method of embodiment 100, wherein the no more than 5 consecutive days is 4 consecutive days per week followed by a rest period of 3 days, during which the compound is not administered.

103. The method of embodiment 100, wherein the no more than 5 consecutive days is 5 consecutive days per week followed by a rest period of 2 days, during which the compound is not administered.

104. The method of any one of embodiments 63-103, wherein the period extends for at or about or greater than four months after the initiation of the administration of the T cell therapy.

105. The method of any of embodiments 63-104, wherein the period extends for at or about or greater than five months after the initiation of the administration of the T cell therapy.

106. The method of any of embodiments 63-105, wherein the period extends for at or about or greater than six months after the initiation of the administration of the T cell therapy.

107. The method of any one of embodiments 63-106, wherein the administration of the compound per day is at an amount of at or about 3 mg.

108. The method of any one of embodiments 63-106, wherein the administration of the compound per day is at an amount of at or about 2.5 mg.

109. The method of any one of embodiments 63-106, wherein the administration of the compound per day is at an amount of at or about 2 mg.

110. The method of any one of embodiments 63-106, wherein the administration of the compound per day is at an amount of at or about 1.5 mg.

111. The method of any one of embodiments 63-106, wherein the administration of the compound per day is at an amount of at or about 1 mg per day.

112. The method of any of embodiments 63-111, wherein the cycling regimen is stopped at the end of the period, if, at the end of the period, the subject exhibits a complete response (CR) following the treatment.

113. The method of any of embodiments 63-112, wherein the cycling regimen is stopped at the end of the period if, at the end of the period, the cancer has progressed or relapsed following remission after the treatment.

114. The method of any of embodiments 63-113, wherein the period extends for from or from at or about three months to at or six months.

115. The method of any of embodiments 63-114, wherein the period extends for at or about three months after initiation of administration of the T cell therapy.

116. The method of any of embodiments 63-114, wherein the period extends for at or about 3 months after initiation of administration of the T cell therapy if the subject has, prior to at or about 3 months, achieved a complete response (CR) following the treatment or the cancer has progressed or relapsed following remission after the treatment.

117. The method of embodiment 116, wherein the period extends for at or about 3 months after initiation of administration of the T cell therapy if the subject has at 3 months achieved a complete response (CR).

118. The method of any of embodiments 63-114, wherein the period extends for at or about six months after initiation of administration of the T cell therapy.

119. The method of any of embodiments 63-118, wherein the period extends for at or about 6 months after initiation of administration of the T cell therapy if the subject has, prior to at or about 6 months, achieved a complete response (CR) following the treatment or the cancer has progressed or relapsed following remission after the treatment.

120. The method of embodiment 119, wherein the period extends for at or about 6 months after initiation of administration of the T cell therapy if the subject has at 6 months achieved a complete response (CR).

121. The method of any of embodiments 63-120, wherein the cycling regimen is continued for the duration of the period even if the subject has achieved a complete response (CR) at a time point prior to the end of the period.

122. The method of any of embodiments 63-121, wherein the subject achieves a complete response (CR) during the period and prior to the end of the period.

123. The method of any of embodiments 63-111, 114, 115, 119, 121 and 122, further comprising continuing the cycling regimen after the end of the period, if, at the end of the period, the subject exhibits a partial response (PR) or stable disease (SD).

124. The method of any of embodiments 63-123, wherein the cycling regimen is continued for greater than six months if, at or about six months, the subject exhibits a partial response (PR) or stable disease (SD) after the treatment.

125. The method of embodiment 123 or embodiment 124, wherein the cycling regimen is continued until the subject has achieved a complete response (CR) following the treatment or until the cancer has progressed or relapsed following remission after the treatment.

126. The method of any of embodiments 63-125, wherein the administration of the compound is initiated at or after peak or maximum level of the cells of the T cell therapy are detectable in the blood of the subject.

127. The method of any of embodiments 20-126, wherein the administration of the compound is initiated about 14 to about 35 days after initiation of administration of the T cell therapy.

128. The method of any of embodiments 20-127, wherein the administration of the compound is initiated about 21 to about 35 days after initiation of administration of the T cell therapy.

129. The method of any of embodiments 20-128, wherein the administration of the compound is initiated about 21 to about 28 days after initiation of administration of the T cell therapy.

130. The method of any of embodiments 20-129, wherein the administration of the compound is initiated at or about 21 days, at or about 22 days, at or about 23 days, at or about 24 days, at or about 25 days, at or about 26 days, at or about 27 days, or at or about 28 days after initiation of administration of the T cell therapy.

131. The method of any of embodiments 20-130, wherein the administration of the compound is initiated at or about 28 days after the initiation of the administration of the T cell therapy.

132. The method of any of embodiments 20-131, wherein at the time of the initiation of the administration of the compound, the subject does not exhibit a severe toxicity following the administration of the T cell therapy.

133. The method of embodiment 132, wherein:
the severe toxicity is severe cytokine release syndrome (CRS), optionally grade 3 or higher, prolonged grade 3 or higher or grade 4 or 5 CRS; and/or
the severe toxicity is severe neurotoxicity, optionally grade 3 or higher, prolonged grade 3 or higher or grade 4 or 5 neurotoxicity.

134. The method of any one of embodiments 20-133, wherein the administration of the compound is suspended and/or the cycling regimen is modified if the subject exhibits a toxicity following the administration of the compound, optionally a hematologic toxicity.

135. The method of embodiment 134, wherein the toxicity is selected from severe neutropenia, optionally febrile neutropenia, prolonged grade 3 or higher neutropenia.

136. The method of embodiment 134 or 135, wherein the administration of the compound is restarted after the subject no longer exhibits the toxicity.

137. The method of embodiment 136, wherein the cycling regimen is modified after the administration of the compound is restarted.

138. The method of any one of embodiments 134-137, wherein the modified cycling regimen comprises administering a reduced amount of the compound and/or decreasing frequency of the administration of the compound.

139. The method of any one of embodiments 134-138, wherein the modified cycling regimen comprises administering a reduced amount of the compound.

140. The method of embodiment 139, wherein the dose of the compound is reduced and the reduced amount is between at or about 1 mg and at or about 2 mg per day for no more than 5 days per week.

141. The method of embodiment 140, wherein the reduced amount is at or about 1 mg or at or about 2 mg per day for no more than 5 days per week.

142. The method of embodiment 136, wherein the cycling regimen is not modified after the administration of the compound is restarted.

143. The method of embodiment 142, wherein the cycling regimen comprises administration of no more than about 2 mg of the compound per day for no more than 5 days per week.

144. The method of embodiment 143, wherein the cycling regimen comprises administration of at or about 1 mg of the compound per day for no more than 5 days a week.

145. The method of any of embodiments 1-144, wherein the compound is or comprises a solvate of 3-(5-amino-2-methyl-4-oxo-4H-quinazolin-3-yl)-piperidine-2,6-dione.

146. The method of any of embodiments 1-144, wherein the compound is or comprises a hydrate of 3-(5-amino-2-methyl-4-oxo-4H-quinazolin-3-yl)-piperidine-2,6-dione.

147. The method of any of embodiments 1-144, wherein the compound is or comprises a pharmaceutically acceptable salt of 3-(5-amino-2-methyl-4-oxo-4H-quinazolin-3-yl)-piperidine-2,6-dione.

148. The method of any of embodiments 1-144, wherein the compound is or comprises 3-(5-amino-2-methyl-4-oxo-4H-quinazolin-3-yl)-piperidine-2,6-dione.

149. The method of any of embodiments 20-148, wherein the compound is administered orally.

150. The method of any of embodiments 51-149, wherein the administration of the compound:
reverses an exhaustion phenotype in recombinant receptor-expressing T cells in the subject;
prevents, inhibits or delays the onset of an exhaustion phenotype in recombinant receptor-expressing T cells in the subject;
or reduces the level or degree of an exhaustion phenotype in recombinant receptor-expressing T cells in the subject; or
reduces the percentage, of the total number of recombinant receptor-expressing T cells in the subject, that have an exhaustion phenotype.

151. The method of any of embodiments 22-149, wherein the initiation of the administration of the compound is carried out subsequently to the administration of the T cell therapy and, following administration of the compound or initiation thereof, the subject exhibits a restoration or rescue of an antigen- or tumor-specific activity or function of recombinant receptor-expressing T cells in said subject, optionally wherein said restoration, rescue, and/or initiation of administration of said compound, is at a point in time after recombinant receptor-expressing T cells in the subject or the in the blood of the subject have exhibited an exhausted phenotype.

152. The method of any of embodiments 22-149, wherein the administration of the compound comprises administration at an amount, frequency and/or duration effective to:
(a) effect an increase in antigen-specific or antigen receptor-driven activity of naïve or non-exhausted T cells in the subject, which optionally comprise T cells expressing said recombinant receptor, following exposure of the T cells to antigen or to an antigen receptor-specific agent as compared to the absence of said administration of said compound; or
(b) prevent, inhibit or delay the onset of an exhaustion phenotype, in naïve or non-exhausted T cells T cells in the subject, which optionally comprise T cells expressing said recombinant receptor, following exposure of the T cells to antigen or to an antigen receptor-specific agent, as compared to the absence of said administration of said compound; or
(c) reverse an exhaustion phenotype in exhausted T cells, optionally comprising T cells expressing said recombinant receptor, in the subject, as compared to the absence of said administration of said subject.

153. The method of embodiment 152, wherein the administration of the compound comprises administration at an amount, frequency and/or duration effective (i) to effect said increase in activity and (ii) to prevent, inhibit or delay said onset of said exhaustion phenotype and/or reverse said exhaustion phenotype.

154. The method of embodiments 152 or 153, wherein the T cells in the subject comprise T cells expressing said recombinant receptor and/or said antigen is the target antigen.

155. The method of any of embodiments 150-154, wherein the exhaustion phenotype, with reference to a T cell or population of T cells, comprises:
an increase in the level or degree of surface expression on the T cell or T cells, or in the percentage of T said population of T cells exhibiting surface expression, of one or more exhaustion marker, optionally 2, 3, 4, 5 or 6 exhaustion markers, compared to a reference T cell population under the same conditions; or
a decrease in the level or degree of an activity exhibited by said T cells or population of T cells upon exposure to an antigen or antigen receptor-specific agent, compared to a reference T cell population, under the same conditions.

156. The method of embodiment 155, wherein the increase in the level, degree or percentage is by greater than at or about 1.2-fold, at or about 1.5-fold, at or about 2.0-fold, at or about 3-fold, at or about 4-fold, at or about 5-fold, at or about 6-fold, at or about 7-fold, at or about 8-fold, at or about 9-fold, at or about 10-fold or more.

157. The method of embodiment 155, wherein the decrease in the level, degree or percentage is by greater than at or about 1.2-fold, at or about 1.5-fold, at or about 2.0-fold, at or about 3-fold, at or about 4-fold, at or about 5-fold, at or about 6-fold, at or about 7-fold, at or about 8-fold, at or about 9-fold, at or about 10-fold or more.

158. The method of any of embodiments 155-157, wherein the reference T cell population is a population of T cells known to have a non-exhausted phenotype, is a population of naïve T cells, is a population of central memory T cells, or is a population of stem central memory T cells, optionally from the same subject, or of the same species as the subject, from which the T cell or T cells having the exhausted phenotype are derived.

159. The method of any of embodiments 155-158, wherein the reference T cell population (a) is a subject-matched population comprising bulk T cells isolated from the blood of the subject from which the T cell or T cells having the exhausted phenotype is derived, optionally wherein the bulk T cells do not express the recombinant receptor and/or (b) is obtained from the subject from which the T cell or T cells having the exhausted phenotype is derived, prior to receiving administration of a dose of T cells expressing the recombinant receptor.

160. The method of any of embodiments 155-158, wherein the reference T cell population is a composition comprising a sample of the T cell therapy, or pharmaceutical composition comprising T cells expressing the recombinant receptor, prior to its administration to the subject, optionally wherein the composition is a cryopreserved sample.

161. The method of any of embodiments 155-160, wherein the one or more exhaustion marker is an inhibitory receptor.

162. The method of any of embodiments 155-161, wherein the one or more exhaustion marker is selected from among PD-1, CTLA-4, TIM-3, LAG-3, BTLA, 2B4, CD160, CD39, VISTA, and TIGIT.

163. The method of any of embodiments 155-162, wherein the activity or is one or more of proliferation, cytotoxicity or production of one or a combination of inflammatory cytokines, optionally wherein the one or a combination of cytokines is selected from the group consisting of IL-2, IFN-gamma and TNF-alpha.

164. The method of any of embodiments 155-163, wherein the exposure to said antigen or antigen receptor-specific agent comprises incubation with the antigen or antigen receptor-specific agent, optionally an agent that binds the recombinant receptor, wherein said antigen is optionally the target antigen.

165. The method of embodiment 164, wherein the antigen or antigen receptor-specific agent comprises antigen-expressing target cells, optionally cells of said disease, disorder or condition.

166. The method of any of embodiments 2 and 13-165, wherein the target antigen is a human antigen.

167. The method of any of embodiments 1-166, wherein the subject is a human.

168. The method of any of embodiments 1-167, wherein the recombinant antigen receptor is a chimeric antigen receptor that specifically binds the target antigen.

169. The method of embodiment 17 or embodiment 168, wherein the chimeric antigen receptor (CAR) comprises an extracellular antigen-recognition domain that specifically binds to a target antigen and an intracellular signaling domain comprising an ITAM.

170. The method of embodiment 169, wherein the intracellular signaling domain comprises a signaling domain of a CD3-zeta (CD3) chain, optionally a human CD3-zeta chain.

171. The method of embodiment 169 or embodiment 170, wherein the chimeric antigen receptor (CAR) further comprises a costimulatory signaling region.

172. The method of embodiment 171, wherein the costimulatory signaling region comprises a signaling domain of CD28 or 4-1BB, optionally human CD28 or human 4-1BB.

173. The method of embodiment 171 or embodiment 172, wherein the costimulatory domain is or comprises a signaling domain of human 4-1BB.

174. The method of any of embodiments 17 and 168-173, wherein:
the CAR comprises an scFv specific for the target antigen; a transmembrane domain; a cytoplasmic signaling domain derived from a costimulatory molecule, which optionally is or comprises a 4-1BB, optionally human 4-1BB; and a cytoplasmic signaling domain derived from a primary signaling ITAM-containing molecule, which optionally is or comprises a CD3zeta signaling domain, optionally a human CD3zeta signaling domain; and optionally wherein the CAR further comprises a spacer between the transmembrane domain and the scFv;
the CAR comprises, in order, an scFv specific for the target antigen; a transmembrane domain; a cytoplasmic signaling domain derived from a costimulatory molecule, which optionally is or comprises a 4-1BB signaling domain, optionally a human 4-1BB signaling domain; and a cytoplasmic signaling domain derived from a primary signaling ITAM-containing molecule, which optionally is a CD3zeta signaling domain, optionally human CD3zeta signaling domain; or
the CAR comprises, in order, an scFv specific for the target antigen; a spacer; a transmembrane domain, a cytoplasmic signaling domain derived from a costimulatory molecule, which optionally is a 4-1BB signaling domain, and a cytoplasmic signaling domain derived from a primary signaling ITAM-containing molecule, which optionally is or comprises a CD3zeta signaling domain.

175. The method of any of embodiments 21-174, wherein the dose of genetically engineered T cells comprises from or from about $1\times10^5$ to $5\times10^8$ total CAR-expressing T cells, $1\times10^6$ to $2.5\times10^8$ total CAR-expressing T cells, $5\times10^6$ to $1\times10^8$ total CAR-expressing T cells, $1\times10^7$ to $2.5\times10^8$ total CAR-expressing T cells, $5\times10^7$ to $1\times10^8$ total CAR-expressing T cells, each inclusive.

176. The method of any of embodiments 21-175, wherein the dose of genetically engineered T cells comprises at least or at least about $1\times10^5$ CAR-expressing cells, at least or at least about $2.5\times10^5$ CAR-expressing cells, at least or at least about $5\times10^5$ CAR-expressing cells, at least or at least about $1\times10^6$ CAR-expressing cells, at least or at least about $2.5\times10^6$ CAR-expressing cells, at least or at least about $5\times10^6$ CAR-expressing cells, at least or at least about $1\times10^7$ CAR-expressing cells, at least or at least about $2.5\times10^7$ CAR-expressing cells, at least or at least about $5\times10^7$ CAR-expressing cells, at least or at least about $1\times10^8$ CAR-expressing cells, at least or at least about $2.5\times10^8$ CAR-expressing cells, or at least or at least about $5\times10^8$ CAR-expressing cells.

177. The method of any of embodiments 21-176, wherein the dose of genetically engineered T cells comprises at or about $5\times10^7$ total CAR-expressing T cells.

178. The method of any of embodiments 21-177, wherein the dose of genetically engineered T cells comprises at or about $1\times10^8$ CAR-expressing cells.

179. The method of any of embodiments 21-178, wherein the dose of cells is administered parenterally, optionally intravenously.

180. The method of any of embodiments 21-179, wherein the T cells are primary T cells obtained from a subject.

181. The method of any of embodiments 21-180, wherein the T cells are autologous to the subject.

182. The method of any of embodiments 21-180, wherein the T cells are allogeneic to the subject.

183. The method of any of embodiments 21-182, wherein the dose of genetically engineered T cells comprises CD4+ T cells expressing the CAR and CD8+ T cells expressing the CAR and the administration of the dose comprises administering a plurality of separate compositions, said plurality of separate compositions comprising a first composition comprising one of the CD4+ T cells and the CD8+ T cells and the second composition comprising the other of the CD4+ T cells or the CD8+ T cells.

184. The method of any one of embodiments 21-183, wherein, prior to the administration, the subject has been preconditioned with a lymphodepleting therapy comprising the administration of fludarabine and/or cyclophosphamide.

185. The method of any one of embodiments 21-184, further comprising, immediately prior to the administration, administering a lymphodepleting therapy to the subject comprising the administration of fludarabine and/or cyclophosphamide.

186. The method of embodiment 184 or embodiment 185, wherein the lymphodepleting therapy comprises administration of cyclophosphamide at about 200-400 mg/m$^2$, optionally at or about 300 mg/m$^2$, inclusive, and/or fludarabine at about 20-40 mg/m$^2$, optionally 30 mg/m$^2$, daily for 2-4 days, optionally for 3 days, or wherein the lymphodepleting therapy comprises administration of cyclophosphamide at about 500 mg/m$^2$.

187. The method of any one of embodiments 184-186, wherein:
the lymphodepleting therapy comprises administration of cyclophosphamide at or about 300 mg/m$^2$ and fludarabine at about 30 mg/m$^2$ daily for 3 days; and/or
the lymphodepleting therapy comprises administration of cyclophosphamide at or about 500 mg/m$^2$ and fludarabine at about 30 mg/m$^2$ daily for 3 days.

188. The method of any of embodiments 20-187, wherein:
at least 35%, at least 40% or at least 50% of subjects treated according to the method achieve a complete response (CR) that is durable, or is durable in at least 60, 70, 80, 90, or 95% of subjects achieving the CR, for at or greater than 6 months or at or greater than 9 months; and/or
wherein at least 60, 70, 80, 90, or 95% of subjects achieving a CR by six months remain in response, remain in CR, and/or survive or survive without progression, for greater at or greater than 3 months and/or at or greater than 6 months and/or at greater than nine months; and/or
at least 50%, at least 60% or at least 70% of the subjects treated according to the method achieve objective response (OR) optionally wherein the OR is durable, or is durable in at least 60, 70, 80, 90, or 95% of subjects achieving the OR, for at or greater than 6 months or at or greater than 9 months; and/or
wherein at least 60, 70, 80, 90, or 95% of subjects achieving an OR by six months remain in response or surviving for greater at or greater than 3 months and/or at or greater than 6 months.

189. A kit comprising:
(a) a T cell therapy comprising a dose of T cells expressing a recombinant antigen receptor that binds to a target antigen; and
(b) an immune modulatory compound selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination and/or depletion and/or degradation of Ikaros (IKZF1) and/or Aiolos (IKZF3); and
(c) instructions for administering the compound and/or the T cell therapy according to the methods of any of embodiments 1-187.

VIII. EXAMPLES

The following examples are included for illustrative purposes only and are not intended to limit the scope of the invention

Example 1 Anti-BCMA CAR-T Cell Cytolytic Activity and Cytokine Production Following Incubation with BCMA Expressing Target Cell Lines in the Presence or Absence of Lenalidomide T cells were isolated by immunoaffinity-based enrichment from leukapheresis samples from healthy donors. Isolated cells were transduced with a viral vector encoding one of various exemplary anti-BCMA CARs. Each anti-BCMA CAR contained a human anti-BCMA scFv, a spacer region, a CD28 transmembrane domain, a 4-1BB-derived intracellular co-signaling sequence, and a CD3-zeta derived intracellular signaling domain. The viral vector construct further encoded a truncated EGFR (EGFRt), which served as a surrogate marker for CAR expression; the EGFRt-coding region was separated from the CAR sequence by a T2A skip sequence. After transduction, cells were expanded and the resulting compositions were frozen by cryopreservation.

Cryofrozen anti-BCMA CAR T cells were thawed and were assessed for various responses following co-culture with BCMA-expressing target cells in the presence or absence of lenalidomide. In vitro assays to evaluate target cell killing and cytokine production were conducted using two different BCMA-expressing target multiple myeloma cell lines RPMI-8226 or OPM-2. FIG. 1A shows the surface BCMA expression, as assessed by flow cytometry after staining with an anti-BCMA antibody, of exemplary multiple myeloma cells lines, including RPMI-8226 and OPM-2. The dotted line indicates background of a BCMA-negative cell line stained with anti-BCMA antibody. MFI, median fluorescence intensity. Expression of BCMA was relatively low for both cell lines (see Lee et al. (2016) Br J Haematol. 174:911-922). RPMI-8226 has been shown to be more sensitive to lenalidomide compared with OPM-2 (6.43 and 37.4 µM, respectively) (Wellcome Sanger Institute. Genomics of drug sensitivity in cancer. www.cancerrxgene-.org/translation/Drug/1020. Accessed Feb. 7, 2018).

A. RPMI-8226

1. Cytolytic Activity

Cells of the BCMA-expressing target cell line (RPMI-8226) were incubated with exemplary anti-BCMA CAR T cells expressing a CAR with a human anti-BCMA scFv at an effector to target cell (E:T) ratio of 0.3:1 in the presence of 1 µM or 10 µM lenalidomide or in the absence of lenalidomide (vehicle). Co-cultures with T cells not expressing the CAR (mock) or cultures with target cells only (no CAR T) were used as controls, each in the presence or absence (vehicle) of 10 µM or 1 µM lenalidomide. Cells from each condition were plated in triplicate.

The target RPMI-8226 cells were labeled with NucLight Red (NLR) to permit their tracking by microscopy. Cytolytic activity was assessed by measuring the loss of viable target cells over a period of six days, as determined by red fluorescent signal (using the IncuCyte® Live Cell Analysis System, Essen Bioscience). Normalized target cell numbers were generated by dividing target cell counts to cell counts at the start of each culture. The percentage of target killing was assessed by measuring the area under the curve (AUC) for normalized target cell count over time and normalizing the inverse AUC (1/AUC) values by defining a 0% value (target cells alone) and a 100% value (CAR+ T cells co-cultured with target cells in vehicle control).

Figure 1C:
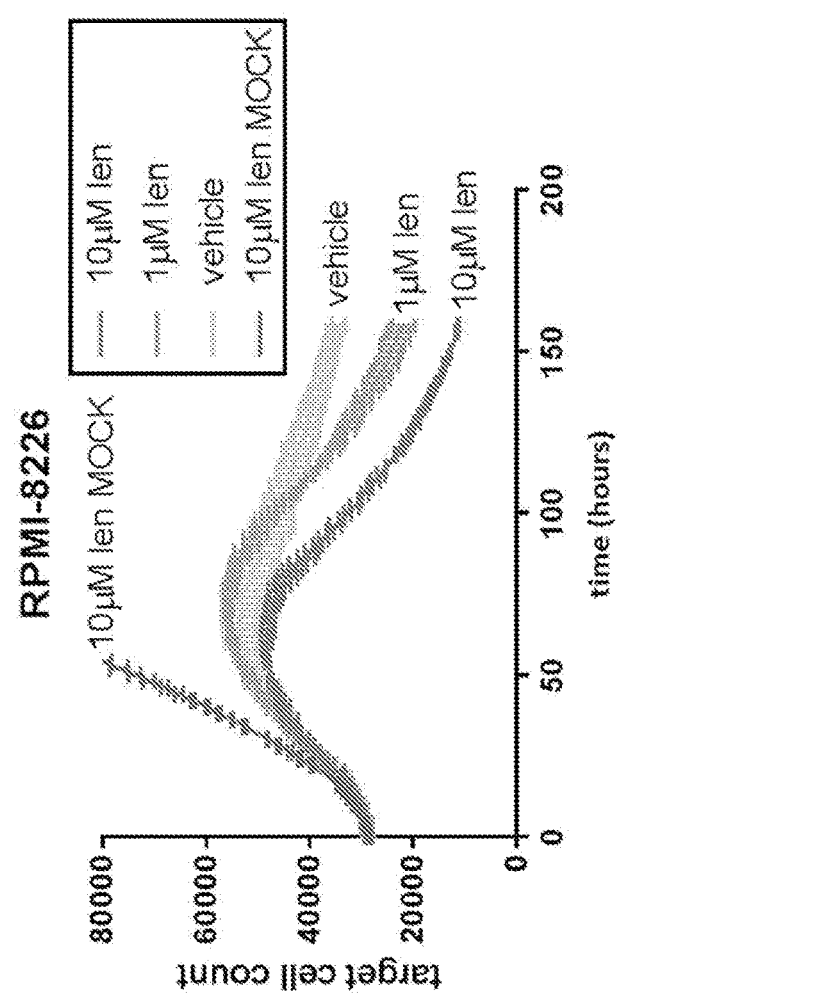
FIG. 1C shows the effect of lenalidomide on the cytolytic activity of anti-BCMA CAR+ T cells against RPMI-8226 target cells.
Figure 1B:
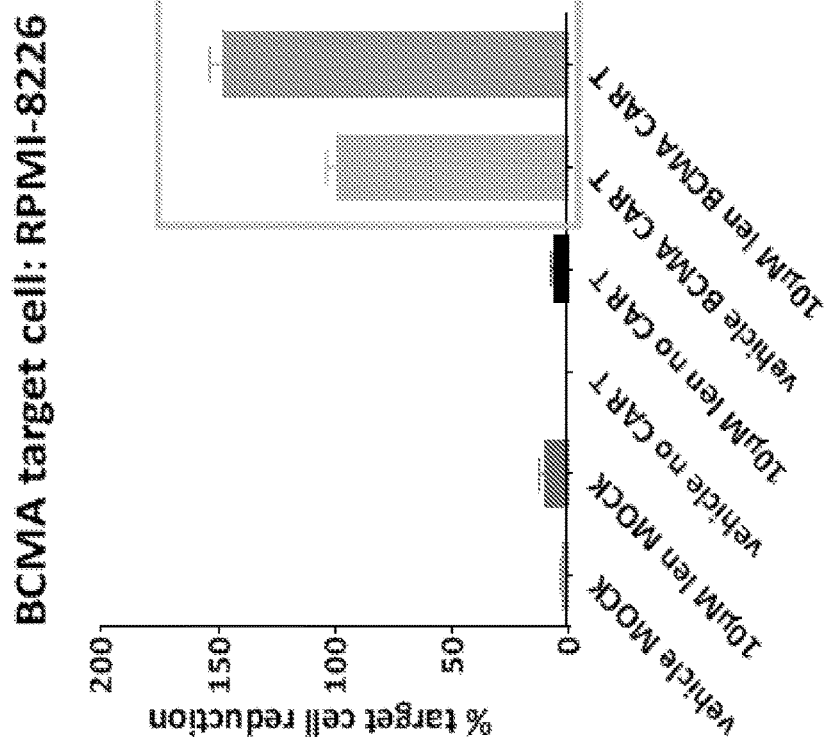
FIG. 1B shows the percent of reduction of BCMA-expressing target cells (RPMI-8226) by anti-BCMA CAR+ T cells in the presence and absence of lenalidomide (10 μM) after 6 days of co-culture.

As shown, co-culture in the presence of 1 µM (FIG. 1C) or 10 µM (FIG. 1B, 1C) lenalidomide resulted in a greater degree of target cell killing by anti-BCMA CAR+ T cells by day 6 of the co-culture, compared to incubation of target cells with anti-BCMA CAR+ T cells in the absence of lenalidomide (set at 100% in FIG. 1B). As shown in FIG. 1C, the observed effect of lenalidomide on cytolytic activity was dose-responsive and delayed, not emerging until after approximately 50 hours in culture. The results were consistent with a role of lenalidomide in promoting continued function and/or survival (such as by preventing exhaustion or cell death) of CAR-T cells after initial activation. Similar results were observed for cells engineered to expressing a number of other anti-BCMA CARs, each having different scFv binding domains.

2 Cytokine Production/Accumulation

Figure 2A:
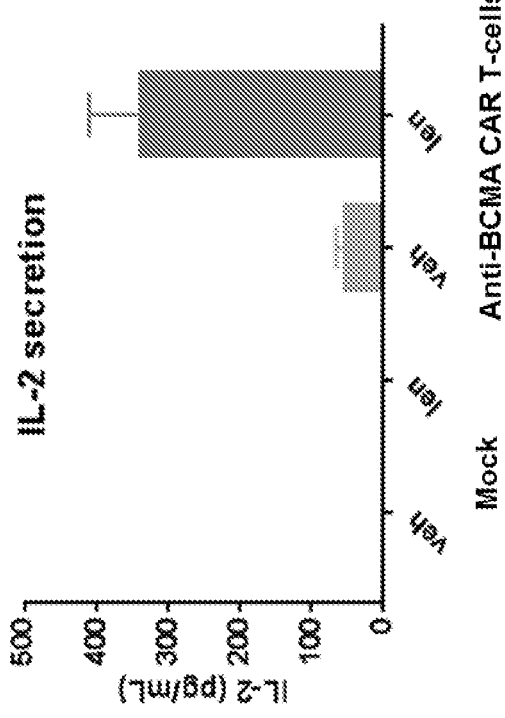
FIGS. 2A-2C show the amount of IL-2 (FIG. 2A), IFNγ (FIG. 2B), and TNF-α (FIG. 2C) observed in supernatants after incubation of RPMI-8226 target cells with anti-BCMA CAR T cells in the presence and absence of lenalidomide.
Figure 2C:
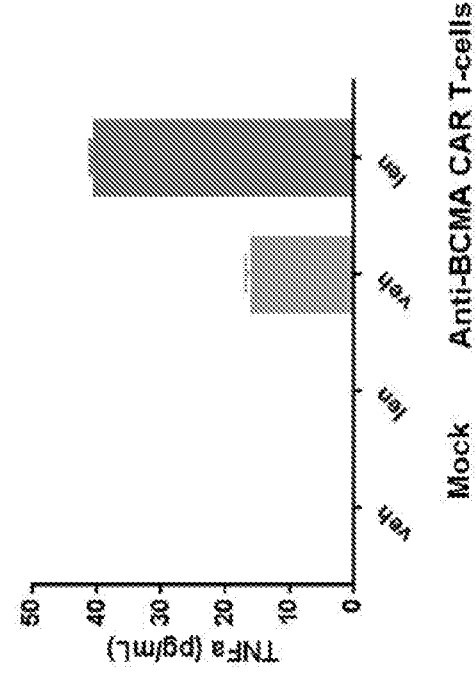
Figure 2B:
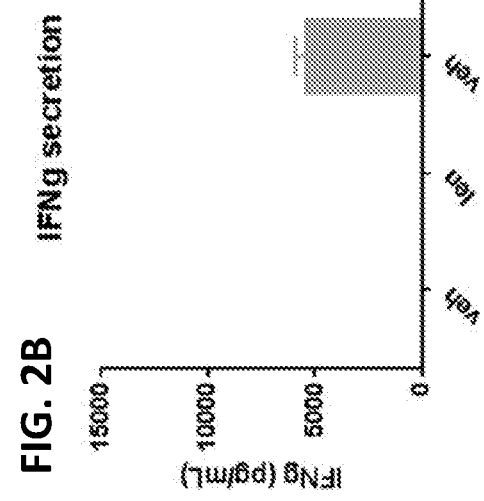

Levels of various cytokines were assessed in culture supernatants after incubating anti-BCMA CAR T cells with cells of the BCMA-expressing target cell line RPMI-8226 at a 0.3:1 effector to target cell (E:T) ratio in the presence or absence of 10 µM lenalidomide. Culture of T cells not expressing the anti-BCMA CAR (mock) was used as a control. Amounts of IL-2 (FIG. 2A), IFNγ (FIG. 2B), and TNF-α (FIG. 2C) in culture supernatants was assessed at 48 hours after culture initiation. As shown in FIGS. 2A-2C, the presence of lenalidomide was associated with an increase in CAR-dependent cytokine production and/or accumulation following co-culture of anti-BCMA CAR T cells target cells with antigen-specific target cells. These results were consistent with a role for lenalidomide in promoting CAR-mediated effector functions. Similar results were observed with cells expressing various other anti-BCMA CARs, each having different scFv binding domains.

B. OPM-2

3. Cytolytic Activity

Figure 3B:
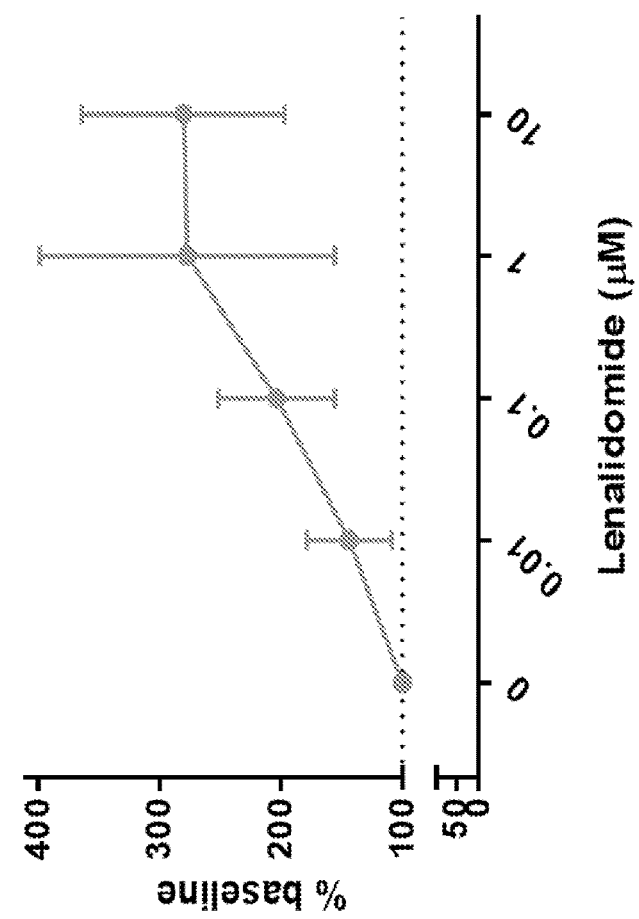
FIGS. 3B-D show the amount of IFNγ (FIG. 3B), IL-2 (FIG. 3C), and TNF-α (FIG. 3D) observed in supernatants after incubation of OPM2 target cells with anti-BCMA CAR T cells in the presence of increasing concentrations of lenalidomide, or in the absence of lenalidomide.
Figure 3A:
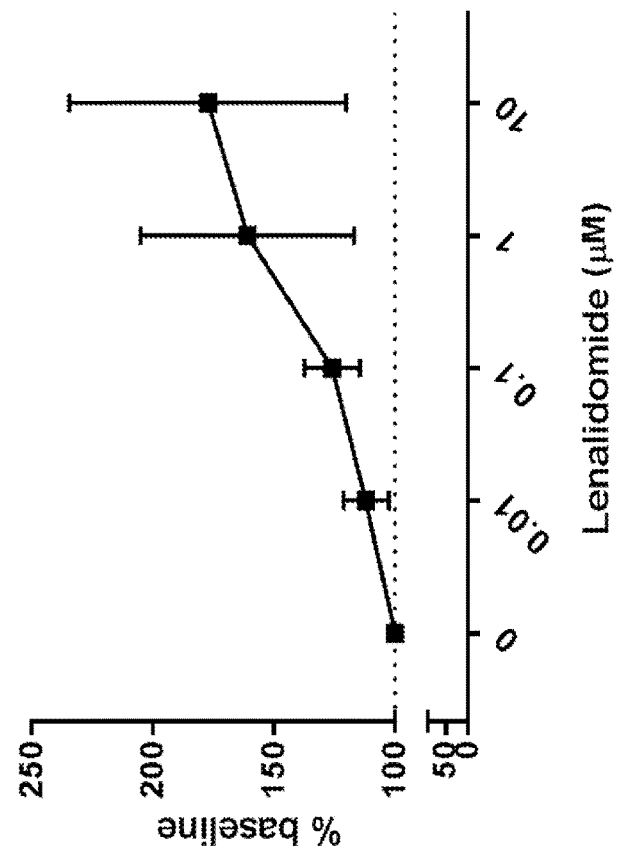
FIG. 3A shows the effect of increasing concentrations of lenalidomide on the cytolytic activity of anti-BCMA CAR+ T cells against OPM2 target cells.

Target OPM-2 multiple myeloma cells were incubated with human T cells (isolated from four different independent donors) expressing an exemplary anti-BCMA CAR) at an effector to target cell (E:T) ratio of 1:1 in the presence of 0.01 µM, 0.1 µM, 1.0 µM or 10 µM lenalidomide or in the absence of lenalidomide for a period of 7 days. The OPM-2 cells were labeled with NucLight Red (NLR) to permit tracking of target cells by microscopy substantially as described above. Cytolytic activity was assessed by measuring the loss of viable target cells at the end of the incubation. Degree of cytolytic activity observed for cultures incubated in the absence of lenalidomide was set as baseline, 100%. The results are shown in FIG. 3A. The addition of lenalidomide was observed to enhance cytolytic activity of the anti-BCMA CAR+ T cells against OPM-2 target cells, in a dose-dependent manner. Similar results were observed in other anti-BCMA CAR-expressing T cells, including those expressing different anti-BCMA CARs each having different scFv binding domains and/or engineered using cells from different donors.

4. Cytokine

Figure 3D:
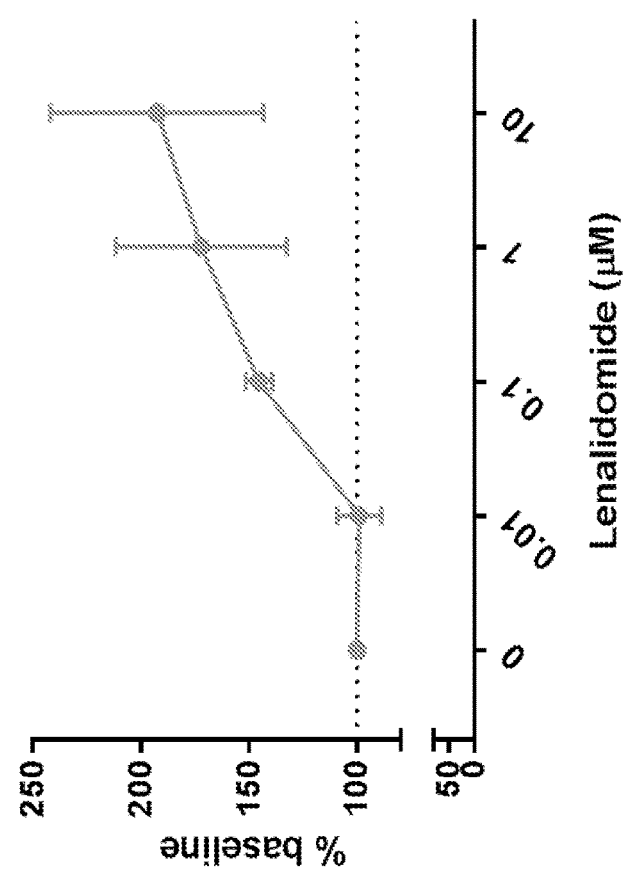
Figure 3C:
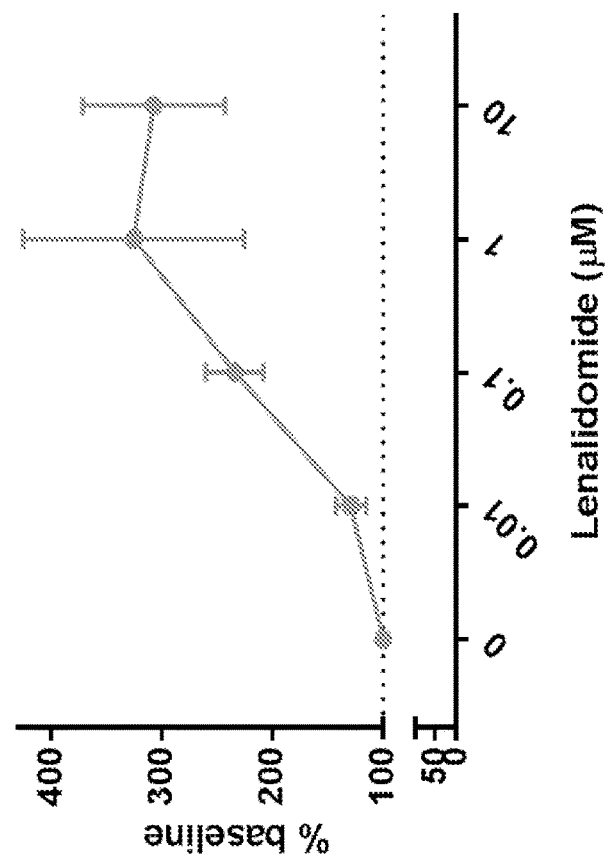

Anti-BCMA CAR T cells, produced from four independent donors, were incubated with BCMA-expressing target cell line OPM-2 at an effector to target cell (E:T) ratio of 1:1 in the presence of 0.01 µM, 0.1 µM, 1.0 µM or 10 µM lenalidomide or in the absence of lenalidomide (baseline, set at 100%). After 24 hours of culture, the presence of IFNγ (FIG. 3B), IL-2 (FIG. 3C), and TNF-α (FIG. 3D) in culture supernatants was assessed. As shown in FIGS. 3B-3D, lenalidomide was observed to enhance cytokine production and/or accumulation by antigen-stimulated anti-BCMA CAR+ T cells in a dose-dependent manner.

C. Comparison of Activity from Multiple Donor-Derived Anti-BCMA CAR+ T Cells

Figure 3E:
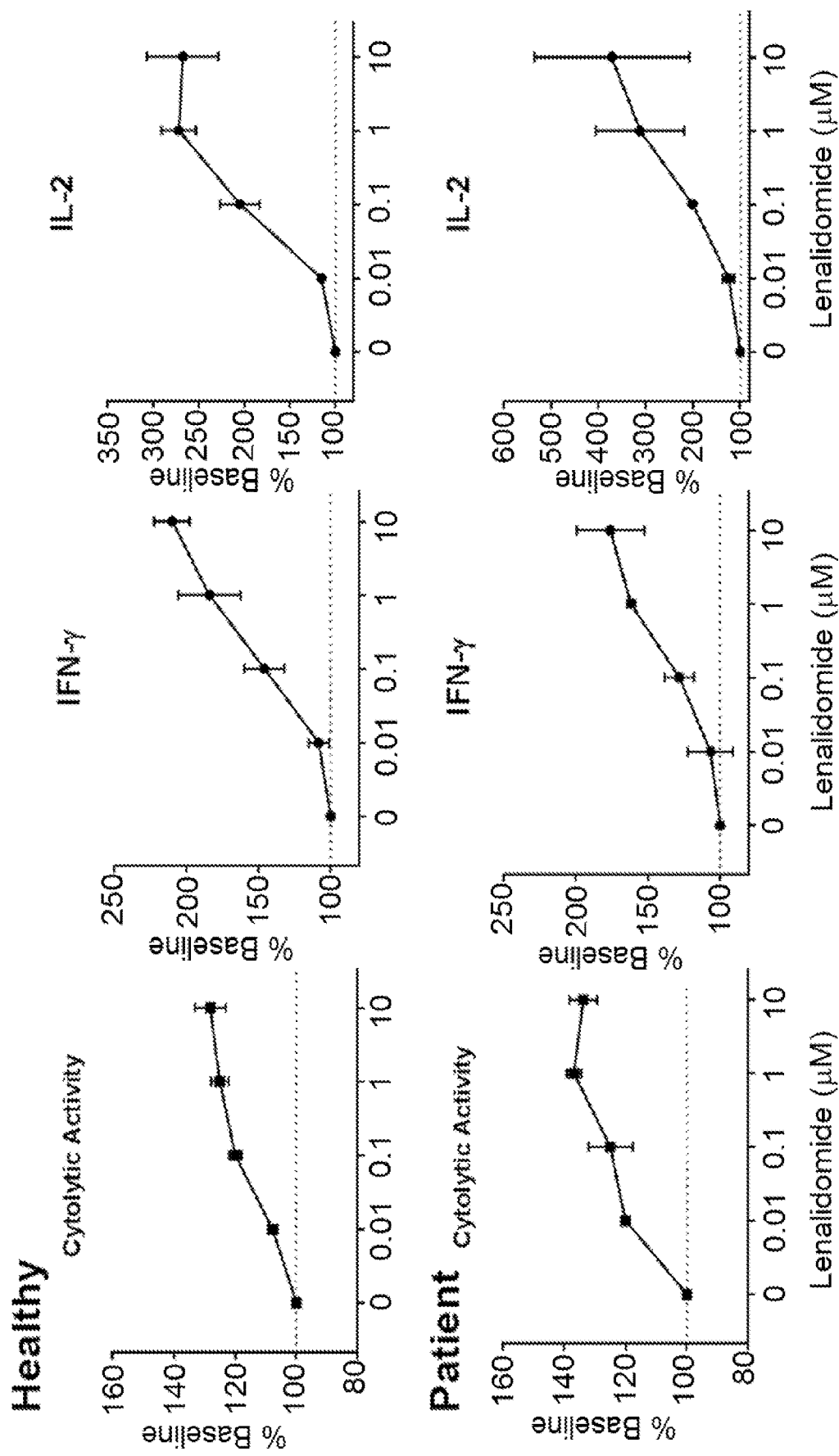
FIG. 3E shows the antigen-specific anti-BCMA CAR-T cytolytic activity and cytokine production of anti-BCMA CAR+ T cells derived from representative healthy donors and multiple myeloma patients against OPM-2 target cells in the presence of varying concentrations of lenalidomide (0.01 μM, 0.1 μM, 1.0 μM or 10 μM lenalidomide) or in the absence of lenalidomide.

In another study, anti-BCMA CAR T cells from a representative healthy donor and a multiple myeloma patient (patient was refractory to pomalidomide) were incubated with fluorescently labeled OPM-2 target cells at an effector to target cell (E:T) ratio of 0.3:1 in the presence of varying concentrations of lenalidomide (0.01 µM, 0.1 µM, 1.0 µM or 10 µM lenalidomide) or in the absence of lenalidomide for 6 to 7 days. Cytolytic activity was measured by loss of red fluorescent cells. To assess cytokine production, healthy donor and multiple myeloma patient-derived anti-BCMA CAR-T cells were cocultured with fluorescently labeled OPM-2 target cells at an effector to target cell (E:T) ratio of 1:1 in the presence of varying concentrations of lenalidomide (0.01 µM, 0.1 µM, 1.0 µM or 10 µM lenalidomide) or in the absence of lenalidomide. After 24 hours, the media was sampled to assess the presence of IFNγ and IL-2. The results as shown in FIG. 3E, which are an average of two experiments; antigen-specific anti-BCMA CAR-T cytolytic activity and cytokine production were observed to be increased by lenalidomide in a concentration-dependent manner.

The studies above were extended on anti-BCMA CAR+ T cells generated from cells from two additional healthy donors. Activity of anti-BCMA CAR+ T cells from three healthy donors and one IMiD-refractory patient (patient donor was refractory to pomalidomide) was compared against both OPM-2 and RPMI-8226 BCMA-expressing multiple myeloma cell lines. Cytolytic activity and cytokine production (IFNγ, IL-2 and TNF-α) were assayed substantially as described above. Absolute changes in cytokine levels relative to the vehicle control were calculated. Experiments were performed 2 to 3 times in each donor.

Figure 3F:
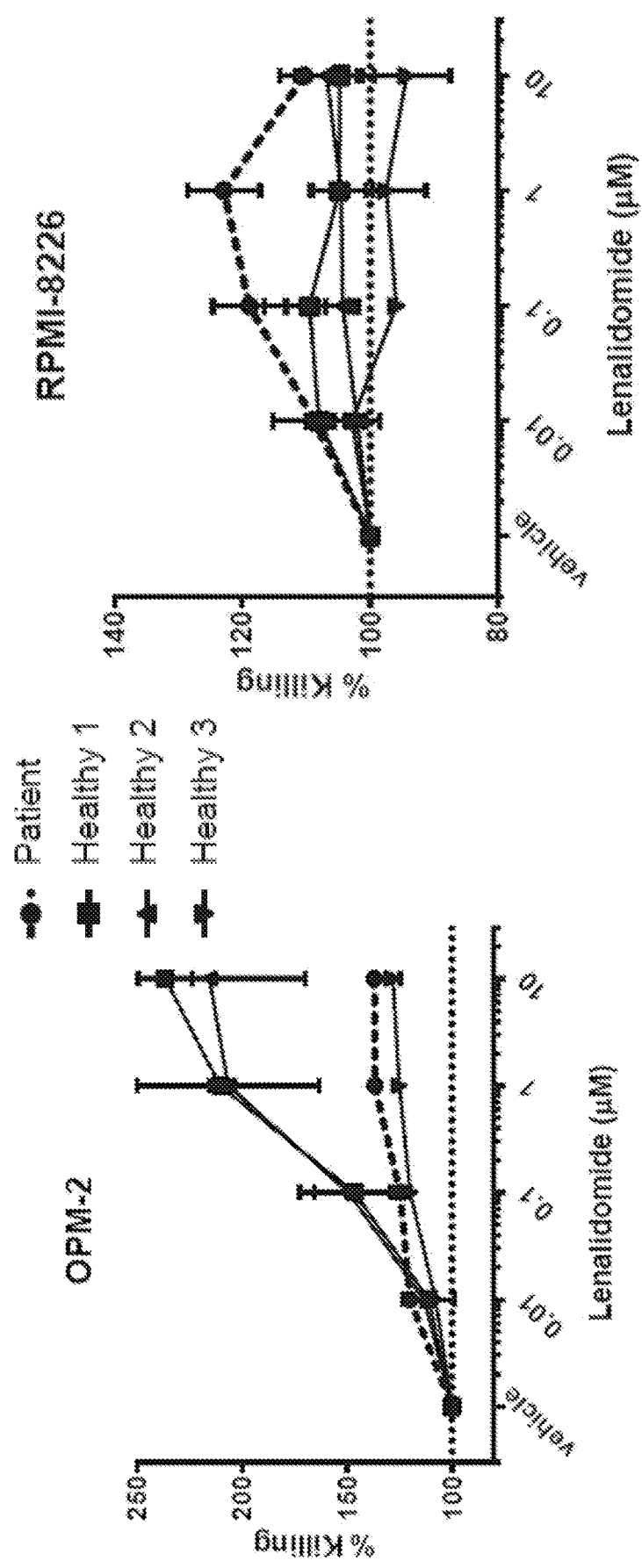
FIG. 3F shows the antigen-specific anti-BCMA CAR-T cytolytic activity of anti-BCMA CAR+ T cells derived from three healthy donors and one multiple myeloma patient against OPM-2 and RPMI-8226 target cells in the presence of varying concentrations of lenalidomide (0.01 μM, 0.1 μM, 1.0 μM or 10 μM lenalidomide) or in the absence of lenalidomide.
Figure 3G:
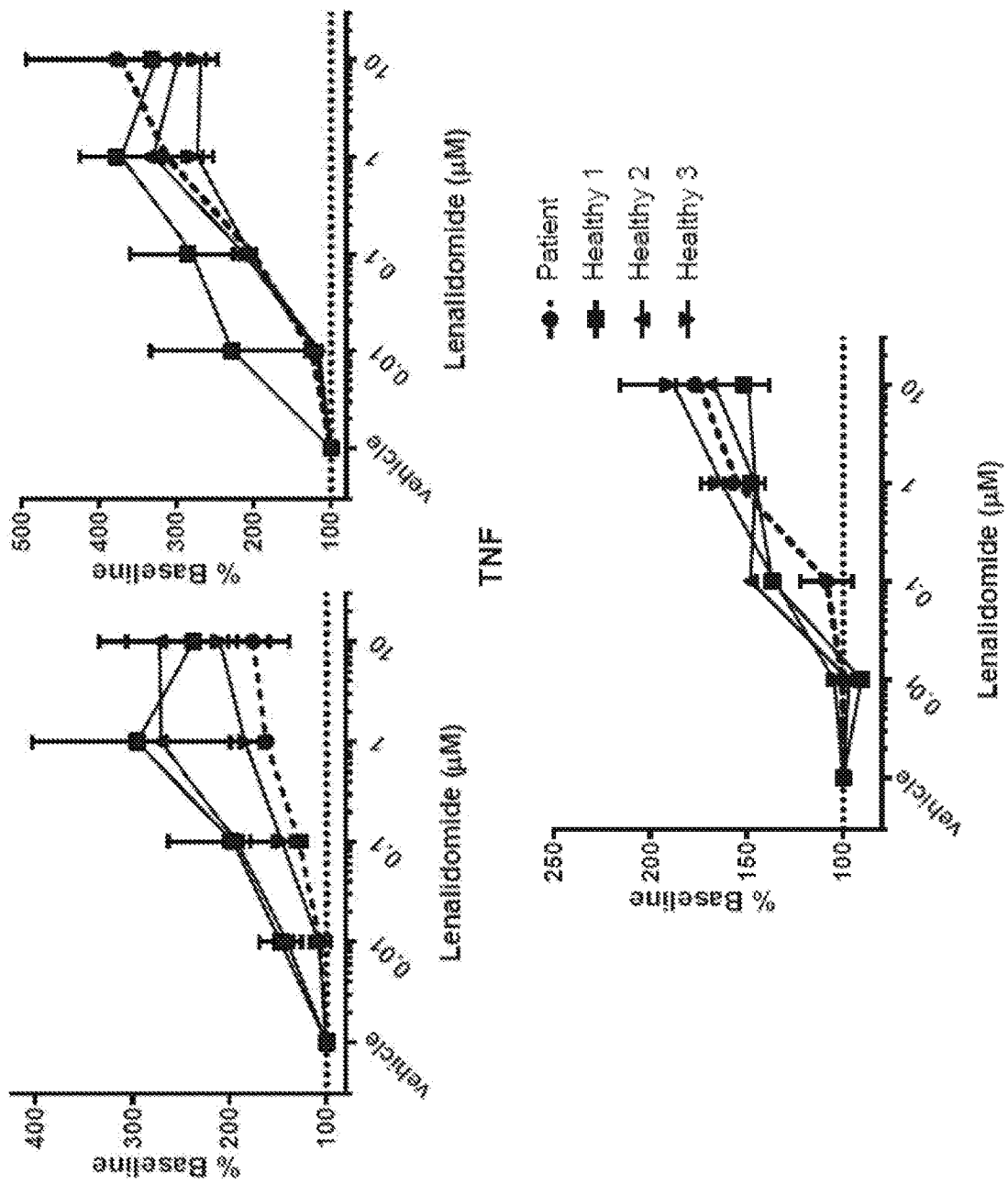
FIG. 3G shows cytokine production of anti-BCMA CAR+ T cells derived from three healthy donors and one multiple myeloma patient against OPM-2 target cells in the presence of varying concentrations of lenalidomide (0.01 μM, 0.1 μM, 1.0 μM or 10 μM lenalidomide) or in the absence of lenalidomide.
Figure 3H:
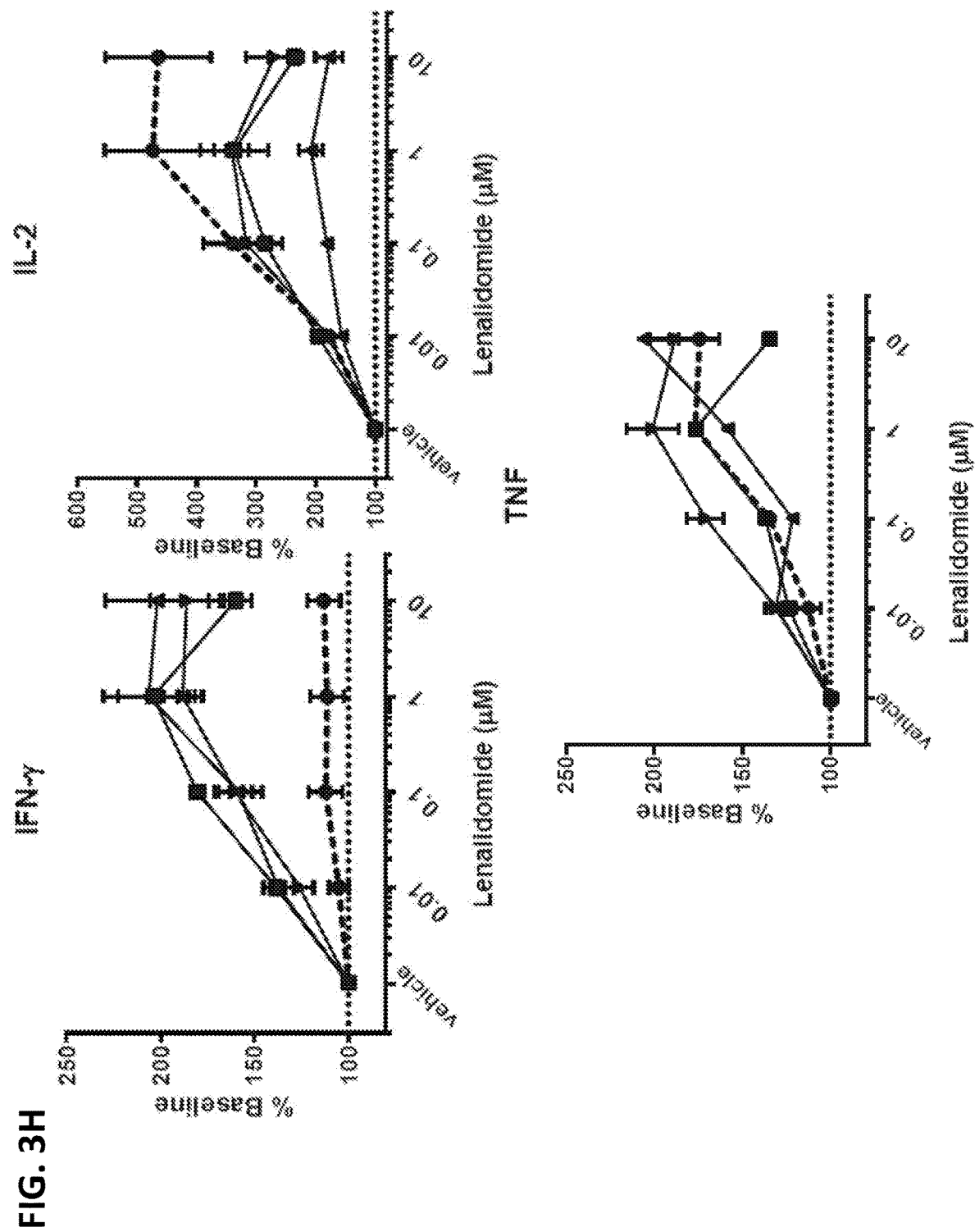
FIG. 3H shows cytokine production of anti-BCMA CAR+ T cells derived from three healthy donors and one multiple myeloma patient against RPMI-8226 target cells in the presence of varying concentrations of lenalidomide (0.01 μM, 0.1 μM, 1.0 μM or 10 μM lenalidomide) or in the absence of lenalidomide.

Increased anti-BCMA CAR T cytolytic activity against OPM-2 target cells titrated with increased concentrations of lenalidomide was observed across all donors ($P=6.2\times10^{-5}$) (FIG. 3F). As shown in FIG. 3F, the treatment effect of lenalidomide on CAR T cytolytic activity appeared to be donor-dependent in co-culture with RPMI-8226, with the patient donor showing a significant increase in cytolytic activity ($P=1.9\times10^{-8}$). In addition, all CAR T donors had significantly increased IFN-γ, IL-2, and TNF-α production in a lenalidomide concentration-dependent manner on co-culture with OPM-2 cells ($P<0.002$, FIG. 3G). Cytokine production by CAR-expressing T cells in RPMI-8226 co-culture was also significantly increased across all donors and cytokines upon treatment with lenalidomide ($P<0.003$, FIG. 3H).

Example 2 Effect of Lenalidomide on CAR-T Cell Expansion and Antigen-Specific Function with Serial Restimulation A. CAR-T Cell Expansion The ability of CAR T cells to expand and exhibit antigen-specific function ex vivo following repeated rounds of antigen stimulation can correlate with in vivo function and/or capacity of the cells to persist in vivo (e.g. following administration and initial activation in response to encounter with antigen) (Zhao et al. (2015) Cancer Cell, 28:415-28). Anti-BCMA CAR+ T cells generated as described above were plated in triplicate at $1\times10^5$ cells/well on 96-well plates. Irradiated BCMA-expressing target cells (MM1.S cells) were added at an effector-to-target (E:T) ratio of 1:2 in the presence or absence of various concentrations (0.01 μM, 0.1 μM, 1.0 μM or 10 μM) of lenalidomide.

Every 3-4 days (start of each new round), CAR T cells were counted. Cells then were harvested and re-plated at the initial seeding density with fresh media, newly-added lenalidomide at the same concentration, where applicable, and newly-thawed, newly-irradiated target cells. 8 rounds of stimulation were carried out during a 31 day culture period. For some rounds, at re-plating, cells were assessed for phenotypic markers via flow cytometry.

Figure 4A:
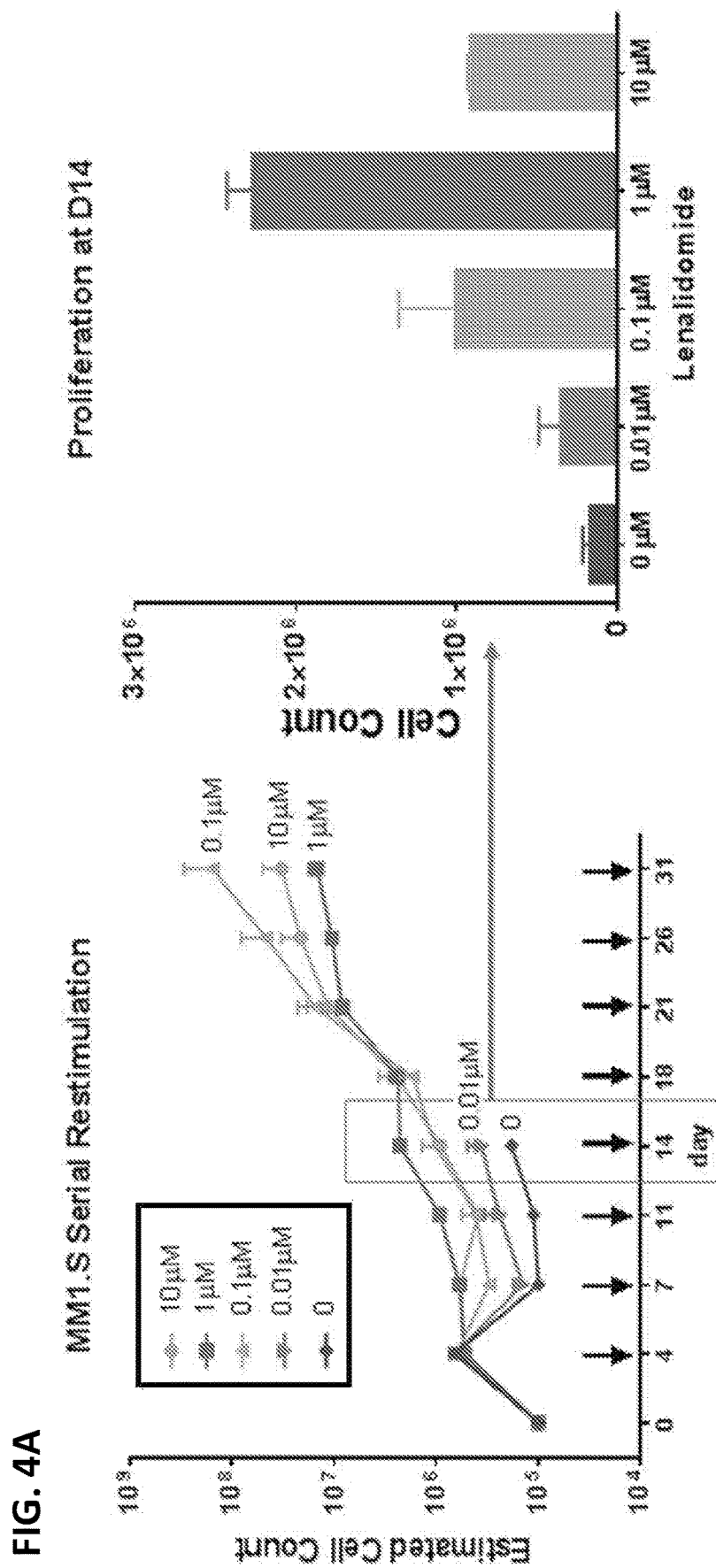
FIG. 4A depicts the expansion of anti-BCMA CAR T cells after restimulation in the presence of varying concentrations of lenalidomide.
Figure 4B:
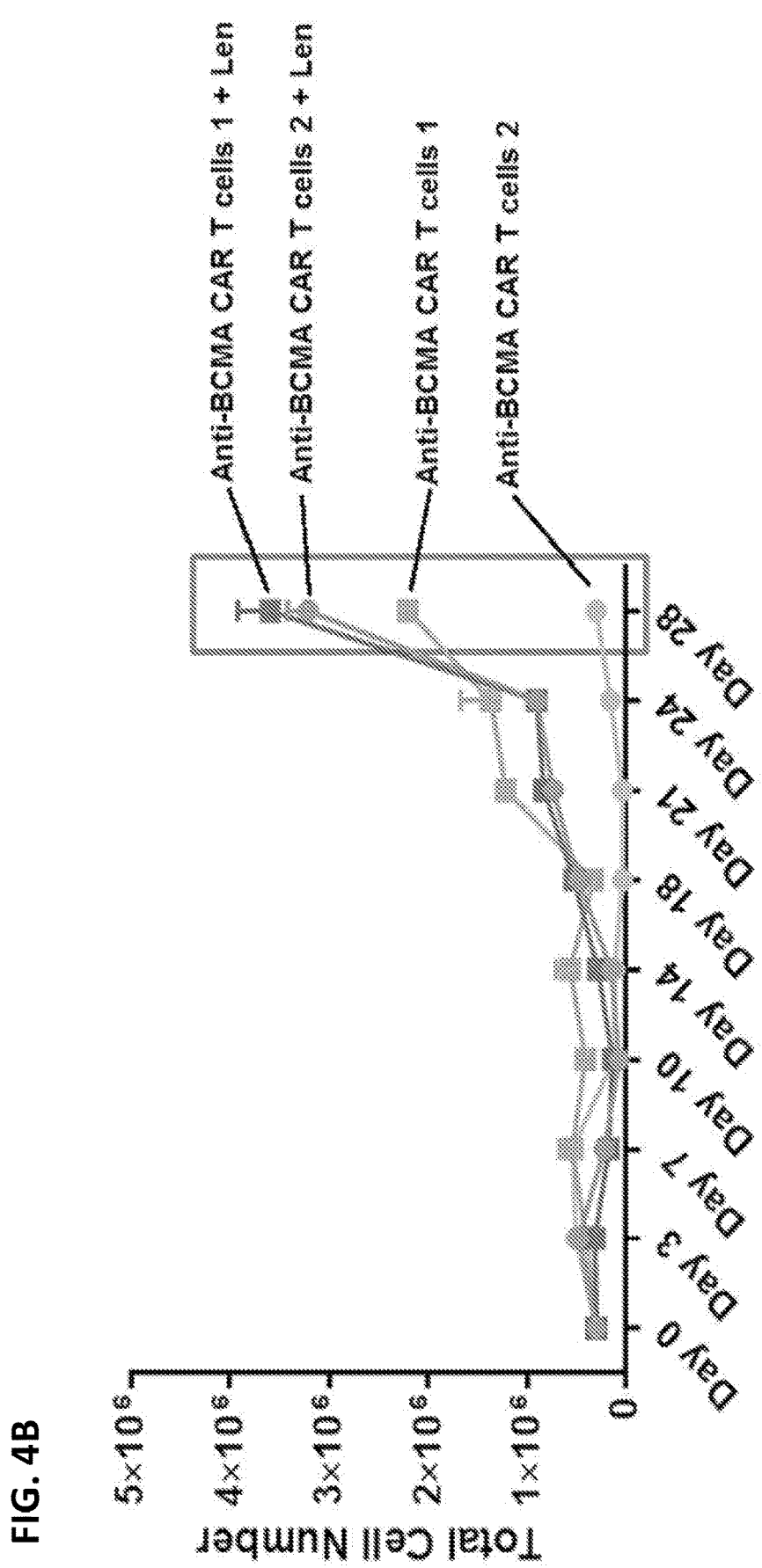
FIG. 4B depicts the expansion of anti-BCMA CAR T cells after restimulation both in the presence and absence of lenalidomide.

Exemplary results are shown in FIG. 4A. As shown, increased expansion of anti-BCMA CAR T cells was observed by day 14 for all concentrations of lenalidomide, compared to wells with no lenalidomide. The assay was performed on various compositions of anti-BCMA CAR+ T cells, each generated by introducing the CAR into T cells derived from one of six different donors. The assay was performed across cells from six different independent donors engineered to express the CAR. For each donor, there was observed an increase or no change in CAR-T expansion at the 0.1 μM concentration of lenalidomide. FIG. 4B shows results of a similar assay, in which cells engineered to express two different human anti-BCMA CARs were subjected to multiple rounds of target cell stimulation in the presence or absence of lenalidomide. As shown, the presence of lenalidomide in the cultures was observed was observed to increase expansion in both cell populations, beginning between day 21 and day 28 The results were consistent with a conclusion that lenalidomide can promote continued CAR+ T cell expansion and/or survival following repeated encounter with cognate antigen.

B. CAR-T Cell Count, Cytokine Production, and Activation

Anti-BCMA CAR+ T cells from 3 donors generated as described above were plated in triplicate on 96-well plates with irradiated BCMA-expressing target cells (MM1S cells) at an effector-to-target (E:T) ratio of 1:2, in the presence of 0.1 μM lenalidomide or vehicle control. Culture conditions were reset every 3-4 days. Replating was maintained for 28 days or until the cell count was <50,000 cells. Experiments were performed in triplicate in 3 donors. Cytokine levels (IFNγ, IL-2, and TNF-α) were assessed 24 hours after re-plating at days 5, 8, and 15 Activation of CAR-T cells was measured on cells collected at days 4, 7, and 14 by flow cytometry for CD25.

Figure 5A:
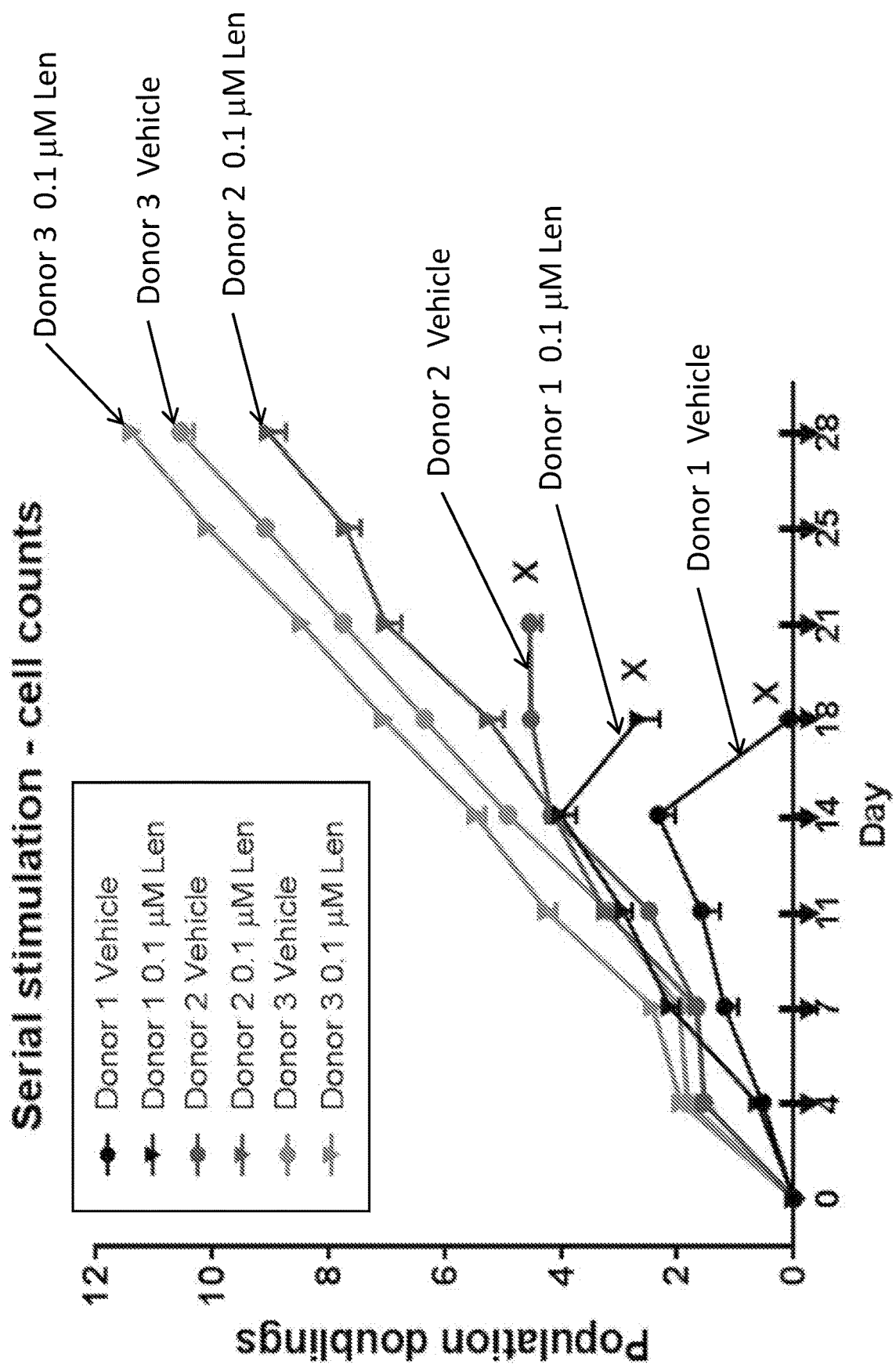
FIG. 5A shows the cell counts (projected population doublings) of the anti-BCMA CAR+ T cells from three donors for each time point in the restimulation assay, in the presence of a vehicle or 0.1 μM lenalidomide. The "x"
Figure 5B:
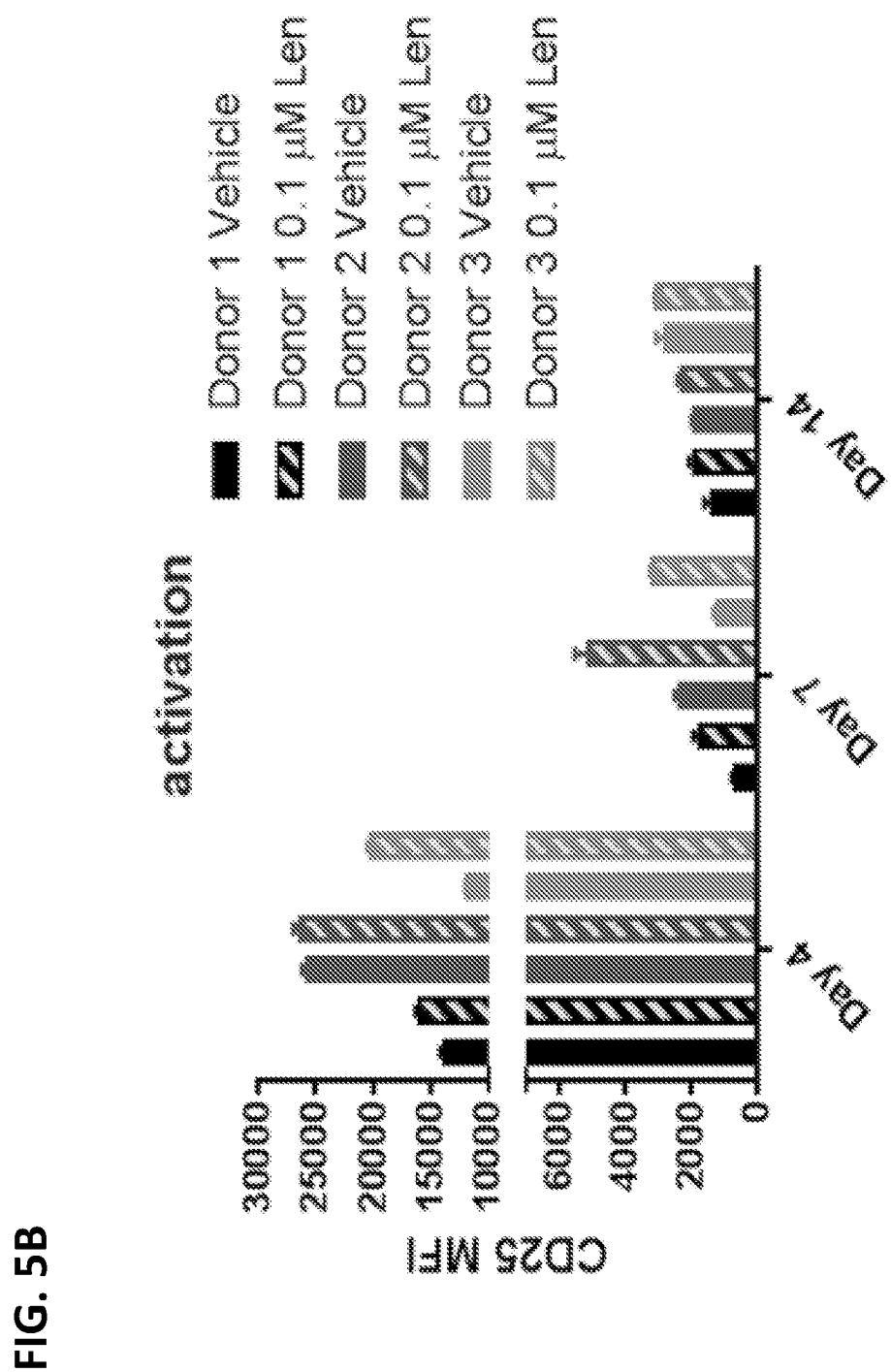
FIG. 5B shows CD25 median fluorescent intensity (MFI) (gated on live CD3⁺ CAR⁺).
Figure 5C:
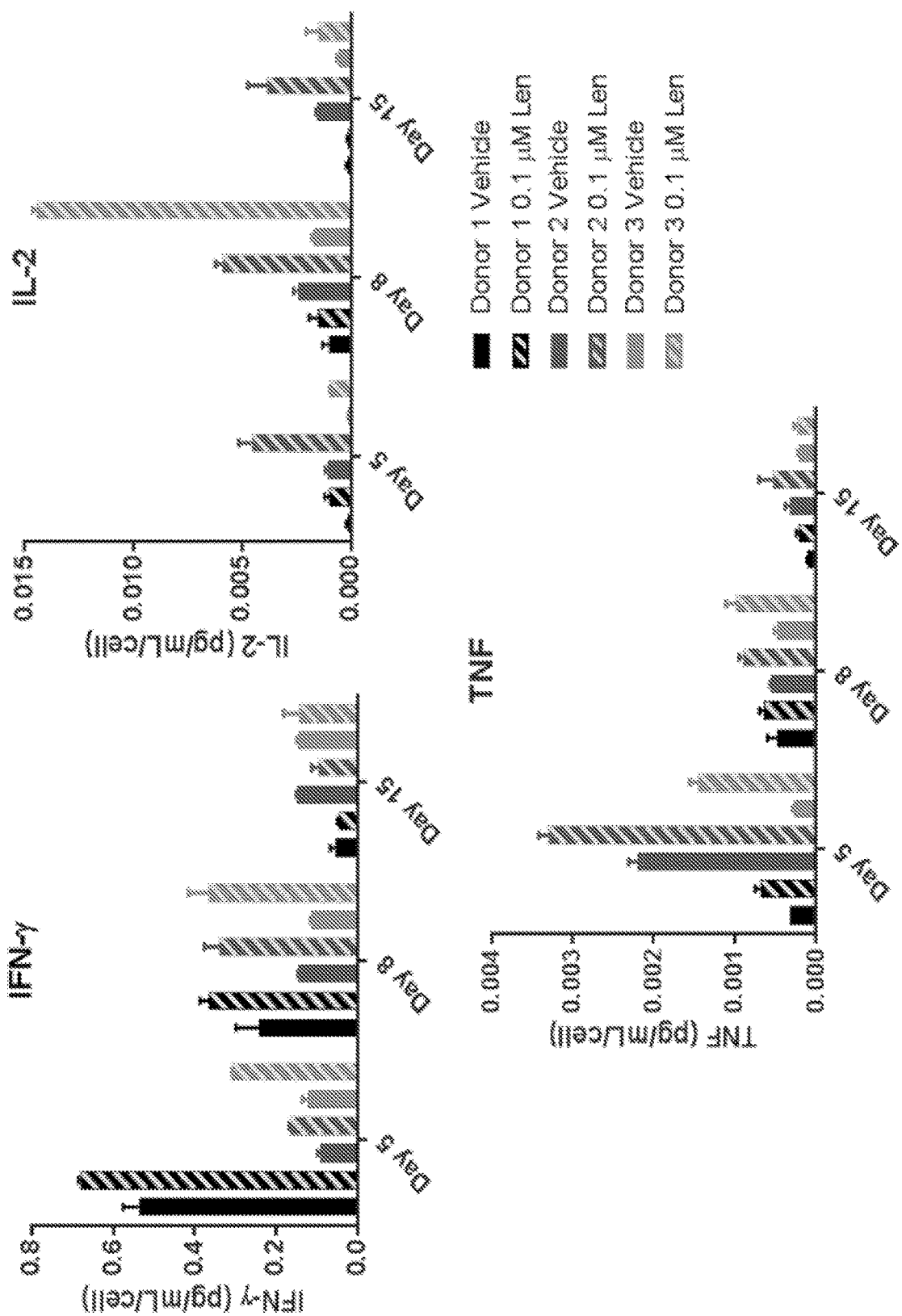
FIG. 5C shows cytokine production normalized for cell number plated (top and left bottom panels) and CD25 median fluorescent intensity (MFI) (gated on live CD3⁺ CAR⁺) (right bottom panel).

FIG. 5A shows the cell counts (projected population doublings) of the anti-BCMA CAR+ T cells for each restimulation time point. The "x" indicates insufficient cells for re-plating in the assay. The results showed that after repeated stimulation with target cells, all 3 CAR T donors treated with lenalidomide had increased projected cell counts over 28 days relative to controls ($P<0.003$). FIG. 5B shows CD25 median fluorescent intensity (MFI) (gated on live $CD3^+$ $CAR^+$) and FIG. 5C shows cytokine production normalized for cell number plated. Increased cell counts were associated with a significant increase in CAR T CD25 expression ($P<3.4\times10^{-4}$; FIG. 5B) and IL-2, IFN-γ, and TNF-α production in the media ($P<0.5$; FIG. 5C). The results showed that anti-BCMA CAR-T cell count, cytokine production, and activation were increased by lenalidomide after repeated stimulations in vitro.

Example 3 Effects of Lenalidomide on BCMA CAR-T Proliferation and Activation in 3D Myeloma Model To assess cell function in the context of a three-dimensional (3-D) human BCMA-expressing tissue microenvironment, a reconstructed bone marrow (rBone™) (zPREDICTA, San Jose, CA) was embedded with BCMA-expressing RPMI-8226. 20,000 T cells expressing another exemplary human anti-BCMA CAR (or mock T cells not expressing the CAR) were incubated in the 3-D model in the presence or absence of 1.0 μM lenalidomide.

Figure 6A:
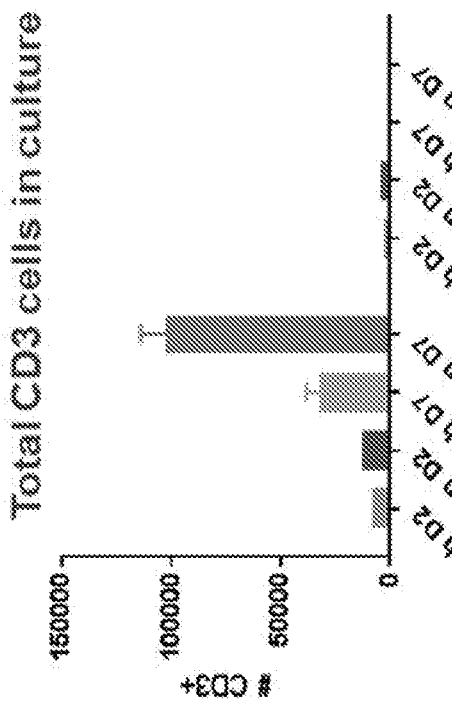
FIG. 6A shows the total number of CD3+ cells in culture on days 2 and 7 after incubating anti-BCMA CAR T-Cells or T cells that did not express a CAR (mock) in the presence or absence of lenalidomide.
Figure 6C:
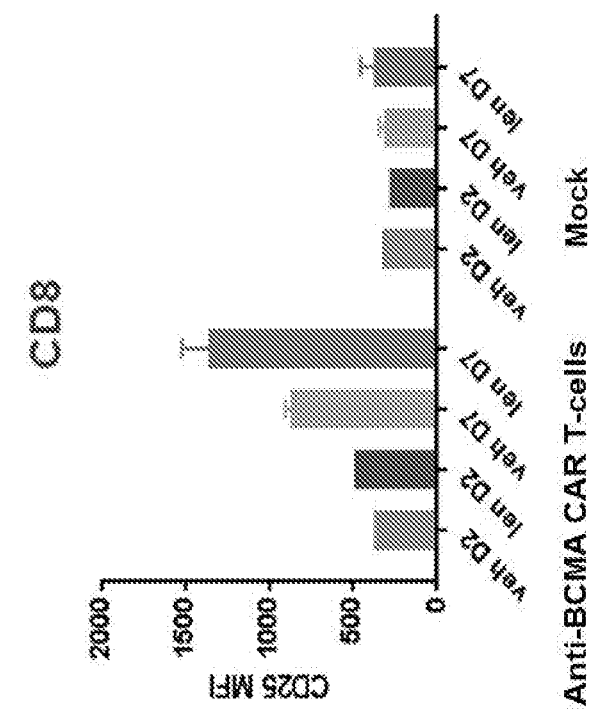
FIGS. 6B and 6C show the CD25+ expression in CD4+(FIG. 6B) and CD8+(FIG. 6C) T cells in culture on days 2 and 7 after incubating anti-BCMA CAR T-Cells or T cells that did not express a CAR (mock) in the presence or absence of lenalidomide.
Figure 6B:
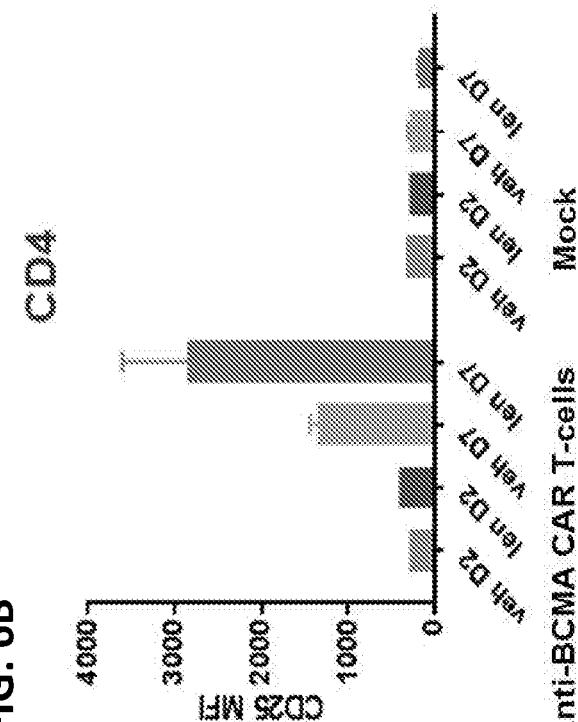

After 2 or 7 days, cells were isolated and assessed by flow cytometry for surface expression of CD3, CD25, CD4, and CD8. As shown in FIG. 6A, the presence of lenalidomide was observed to result in an increase in total number of CD3+ cells in cultures with anti-BCMA CAR+ T cells at day 7. An increase in CD25+ expression in CD4+(FIG. 6B) and CD8+(FIG. 6C) T cell populations also was observed in the presence of lenalidomide. The results were consistent with a conclusion that lenalidomide can promote increased expansion, survival and/or function of anti-BCMA CAR+ T cells in an antigen-expressing tumor microenvironment.

Example 4 Effect of Lenalidomide on CAR T-Cell Function In Vivo

Anti-tumor effects of anti-BCMA CAR T cells, alone and in combination with lenalidomide, were assessed in two different BCMA-expressing mouse tumor models—an RPMI 8226 human multiple myeloma xenograft mouse model (subcutaneous implant model) and an OPM-2 human multiple myeloma xenograft mouse model (orthotopic bone marrow model).

A. RPMI-8226 Model

Mice were injected subcutaneously (s.c.) with $5 \times 10^6$ RPMI-8226 cells, and tumor volume was allowed to grow to approximately 150 mm$^3$. At day 0, a composition containing a sub-optimal (low) dose of anti-BCMA CAR+ T cells (generated by transducing cells derived from samples of human donor subjects essentially as described above) was administered intravenously to mice (with a similar composition of T cells not expressing a CAR (mock) used as a control). Specifically, the composition contained approximately $5 \times 10^5$ CAR+(or mock) CD4+ T cells and $5 \times 10^5$ CAR+(or mock) CD8+ T cells. T cells were adoptively transferred to mice, alone or in combination with lenalidomide, administered daily, at 25 mg/kg, intraperitoneally (i.p.), beginning at d=0 (with T cell administration), continuing through day 21. In another control group, mice were administered lenalidomide alone, without administration of T cells. Tumor volume and survival of animals were monitored throughout the study. A retro-orbital (RO) bleed was taken weekly for plasma BCMA and IFN-gamma levels and for pharmacokinetic (PK) assessment of CAR+ T cells.

Figure 7A:
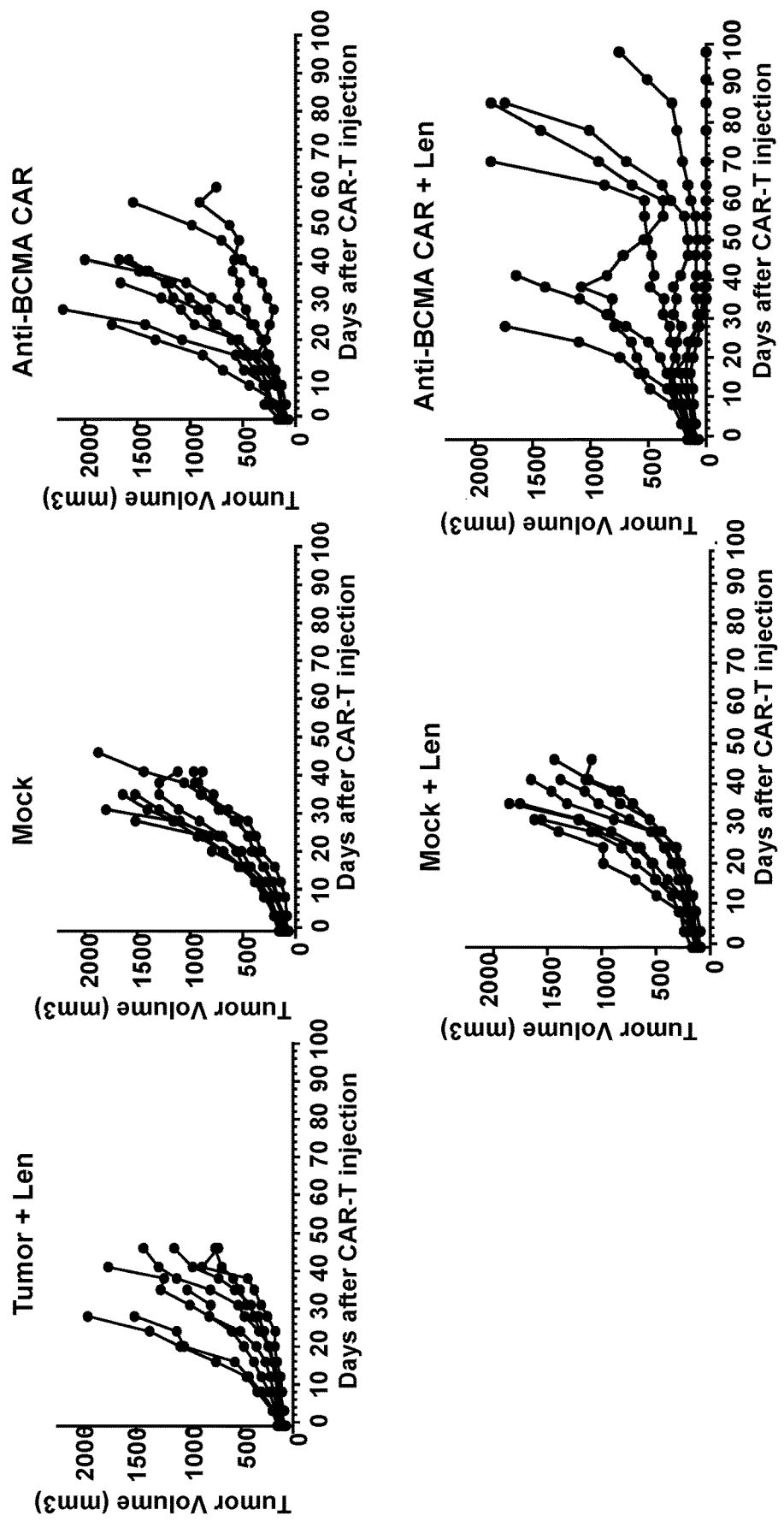
FIG. 7A shows the tumor volume of mice over time after administration of a low dose of anti-BCMA CAR+ T cells in the presence and absence of lenalidomide.

Tumor volume measurements are shown for individual animals in FIG. 7A, administration of lenalidomide and the low dose of anti-BCMA CAR+ T cells in combination was observed to result in slower tumor growth compared to mice treated with lenalidomide or anti-BCMA CAR+ T cells alone. The observed effect was most evident at later timepoints, including those subsequent to the last daily lenalidomide administration (i.e., after day 21). The results are consistent with the ability of lenalidomide to increase the ability of T cells to persist and/or function long-term.

Figure 7B:
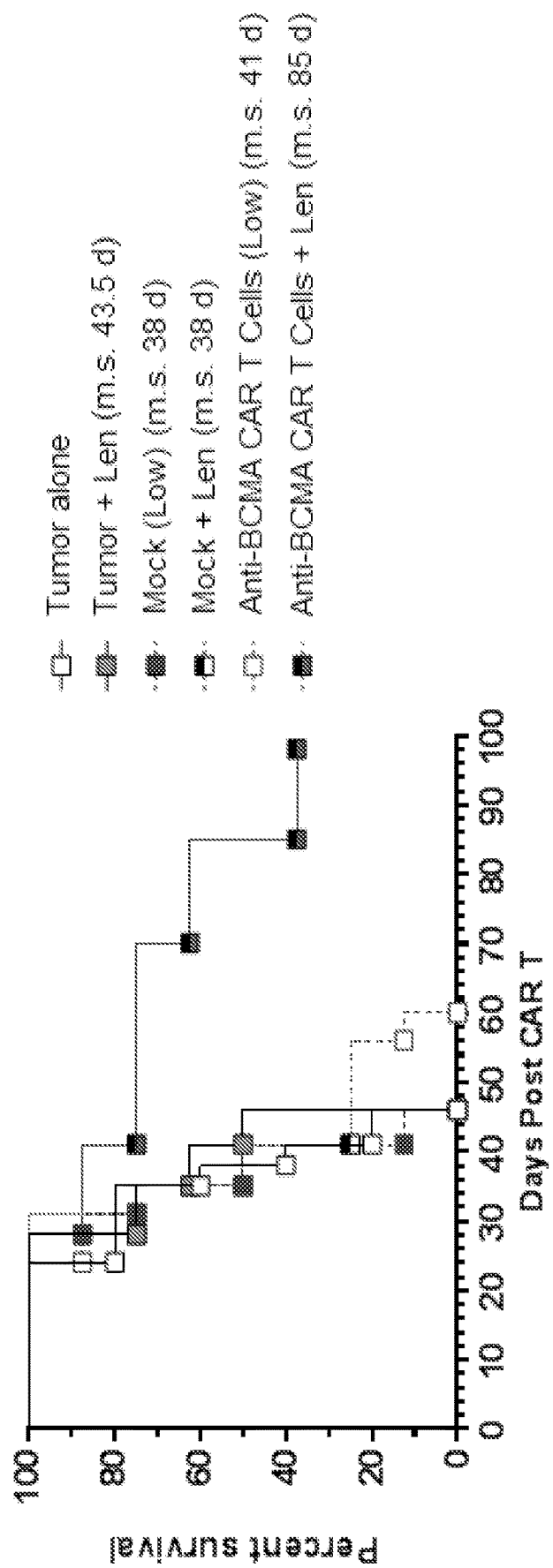
FIG. 7B shows the percent survival of mice that were administered a low dose of anti-BCMA CAR+ T cells in the presence and absence of lenalidomide. For the control groups, T cells that did not express a CAR (mock) were administered in the presence and absence of lenalidomide, and lenalidomide without T cells was also administered.

As shown in FIG. 7B, mice that had lenalidomide and anti-BCMA CAR+ T cells exhibited increased survival compared to the other treatment groups. The mean survival (ms) of mice administered anti-BCMA CAR+ T cells and lenalidomide was 85 days (double, compared to the other treatment groups, which exhibited mean survival of 38-43.5 days).

Figure 8A:
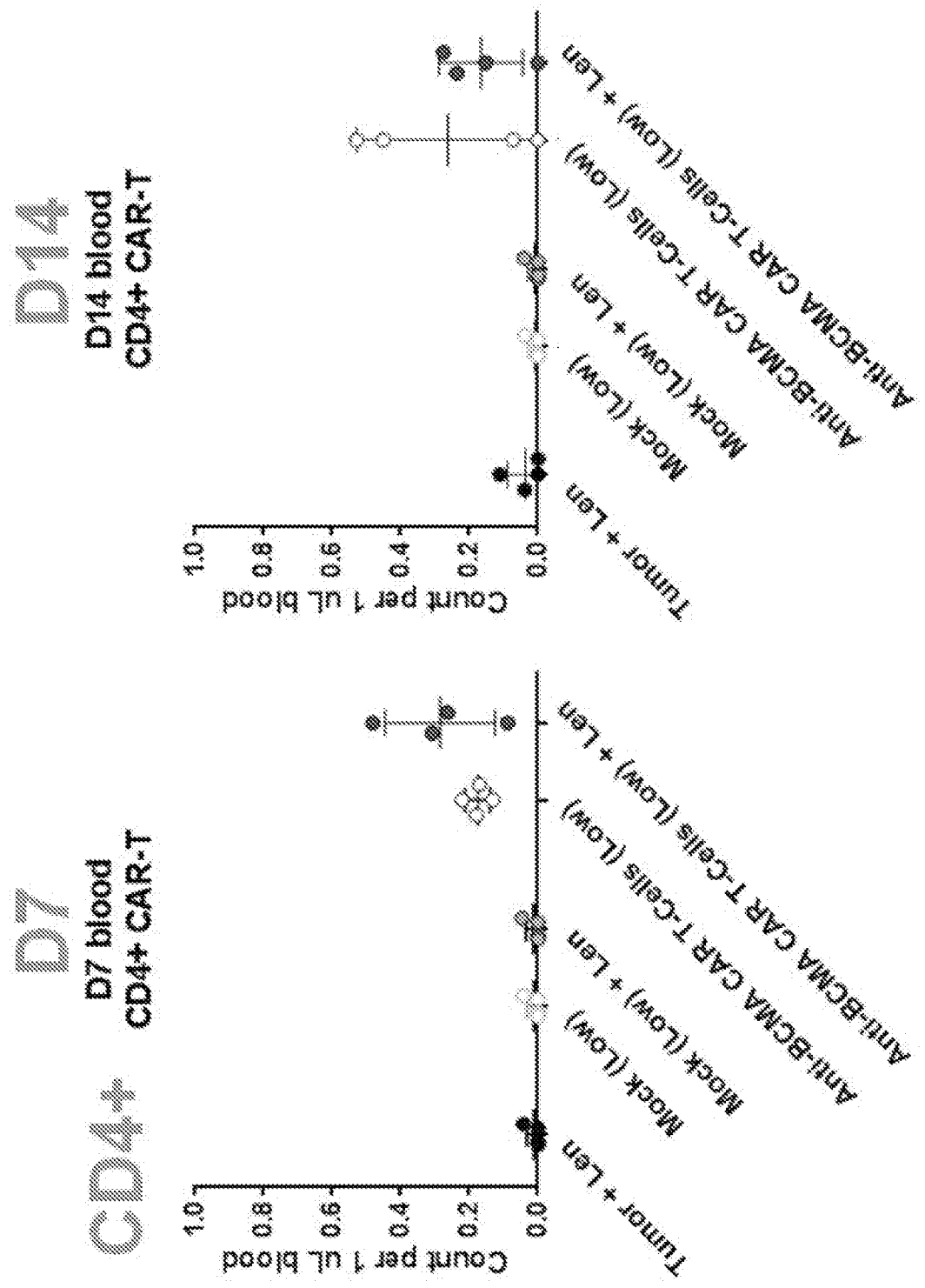
FIG. 8A shows the levels of CD4+ CAR+ T cells in the blood from mice treated with anti-BCMA CAR+ T cells and lenalidomide compared to the other treatment groups at days 7, and 14.
Figure 8B:
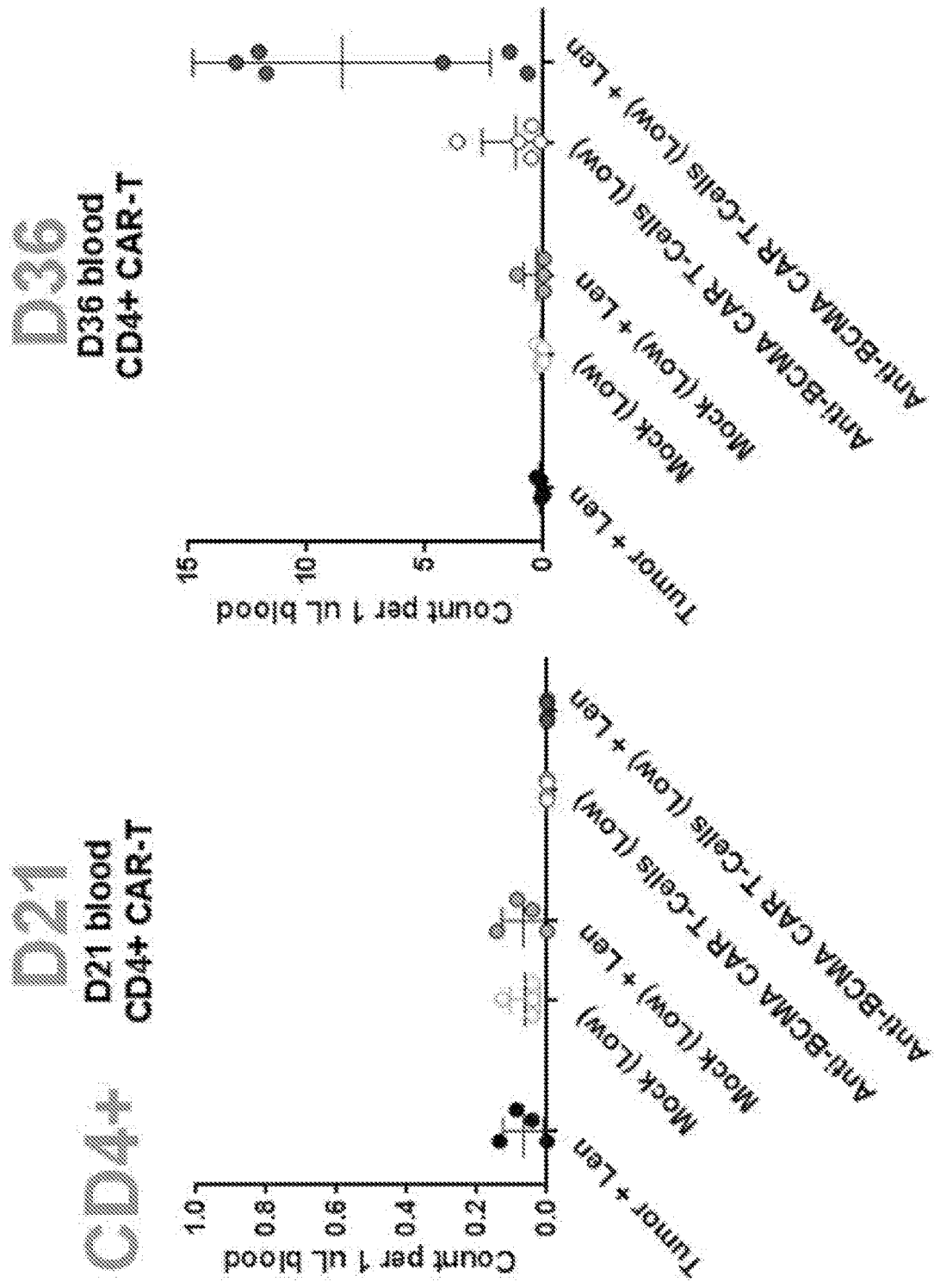
FIG. 8B shows the levels of CD4+ CAR+ T cells in the blood from mice treated with anti-BCMA CAR+ T cells and lenalidomide compared to the other treatment groups at days 21 and 36.
Figure 8C:
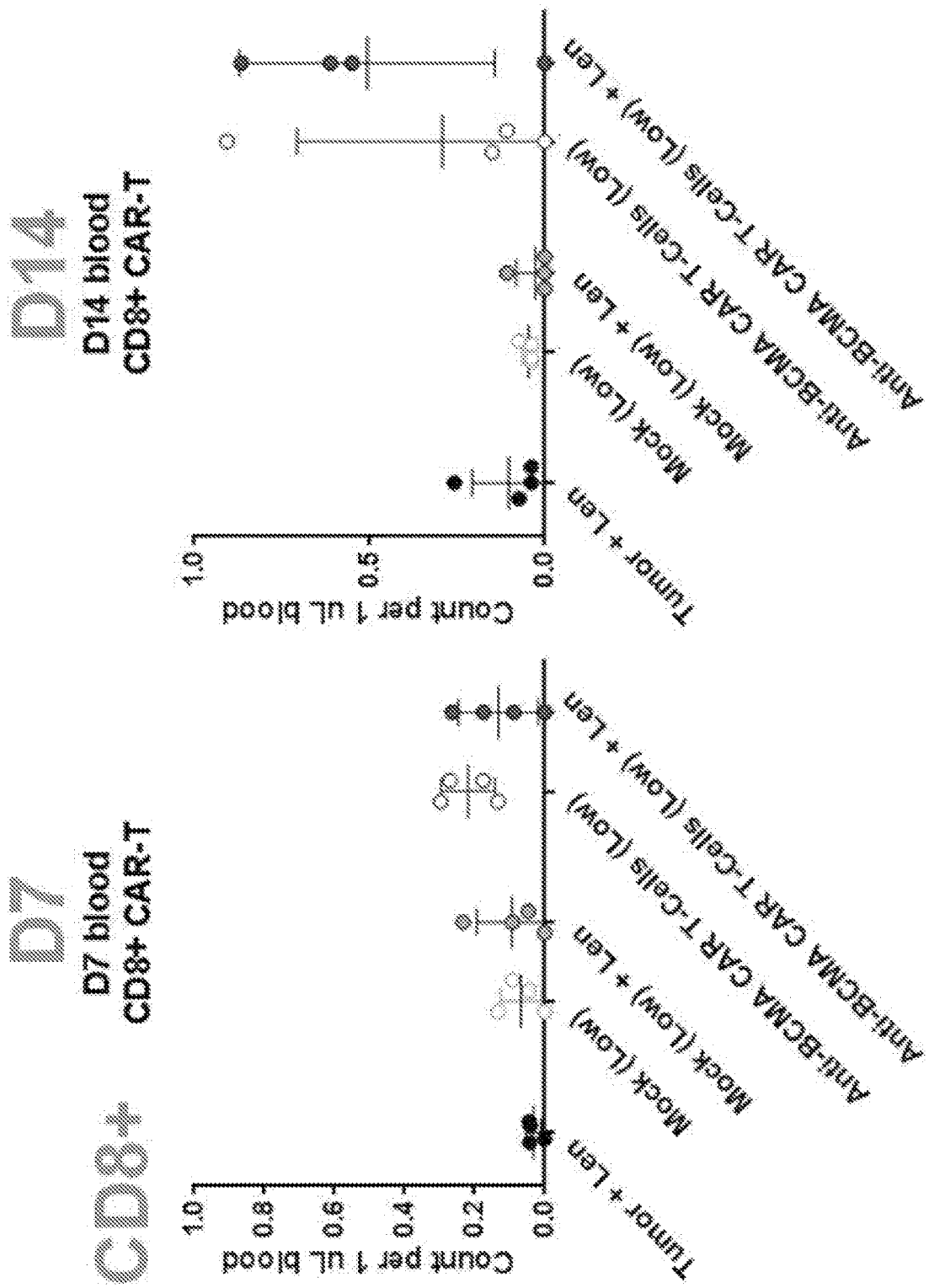
FIG. 8C shows the levels of CD8+ CAR+ T cells in the blood from mice treated with anti-BCMA CAR+ T cells and lenalidomide compared to the other treatment groups at days 7 and 14.
Figure 8D:
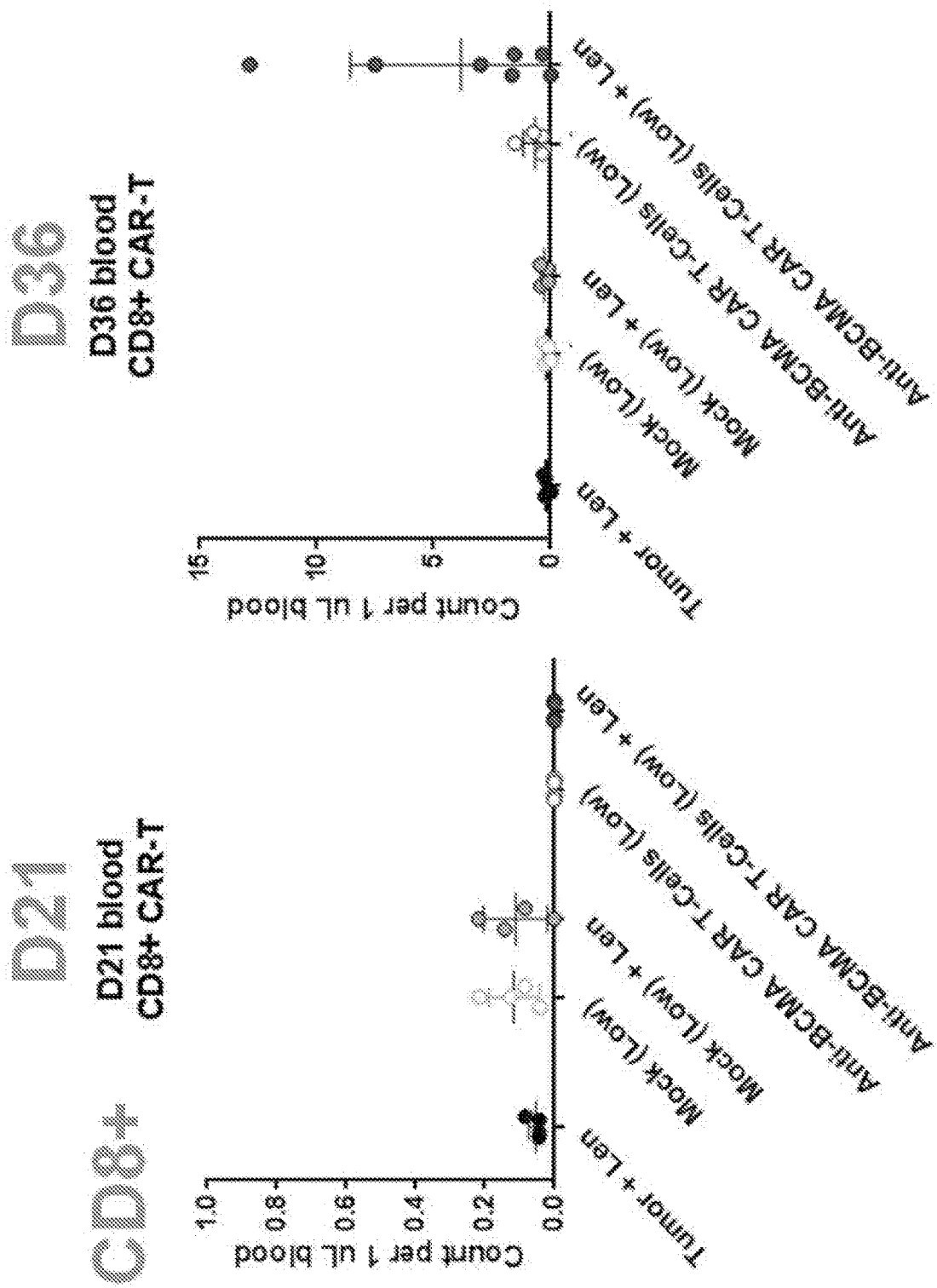
FIG. 8D shows the levels of CD8+ CAR+ T cells in the blood from mice treated with anti-BCMA CAR+ T cells and lenalidomide compared to the other treatment groups at days 21 and 36.
Figure 8E:
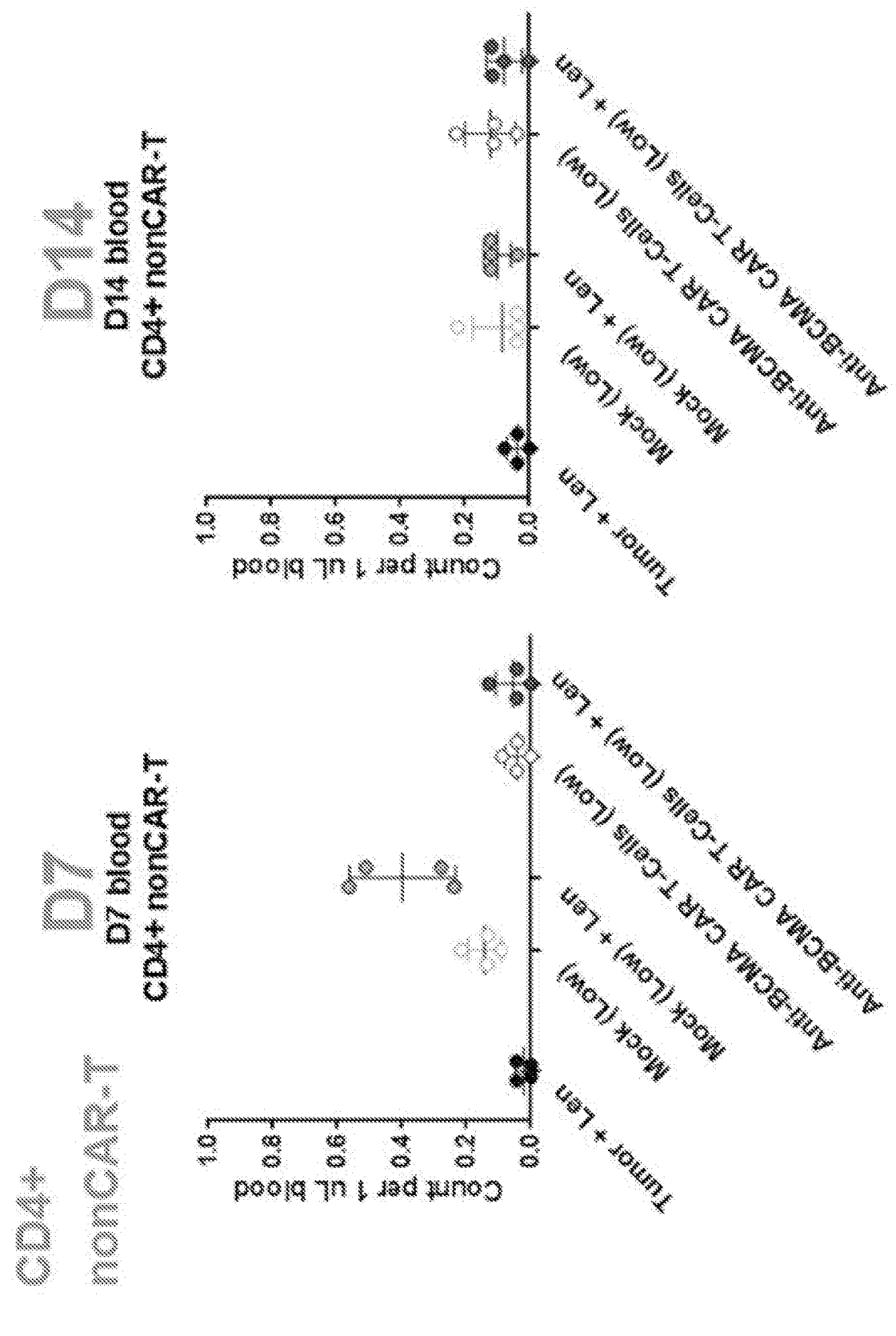
FIG. 8E shows the levels of CD4+ CAR+ T cells in the blood from mice treated with non-CAR+ T cells and lenalidomide compared to the other treatment groups at days 7, and 14.
Figure 8F:
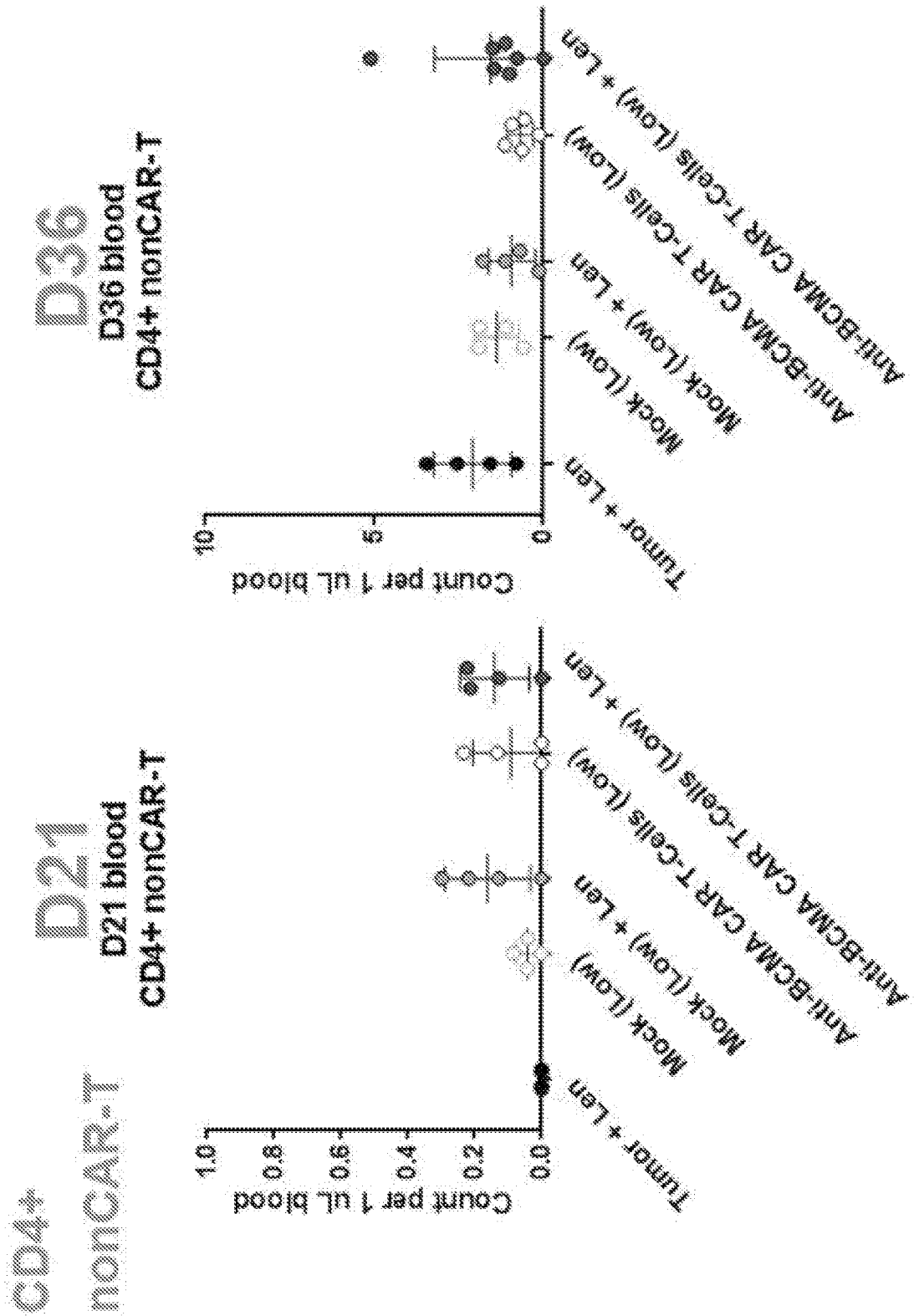
FIG. 8F shows the levels of CD4+ CAR+ T cells in the blood from mice treated with non-CAR+ T cells and lenalidomide compared to the other treatment groups at days 21 and 36.
Figure 8G:
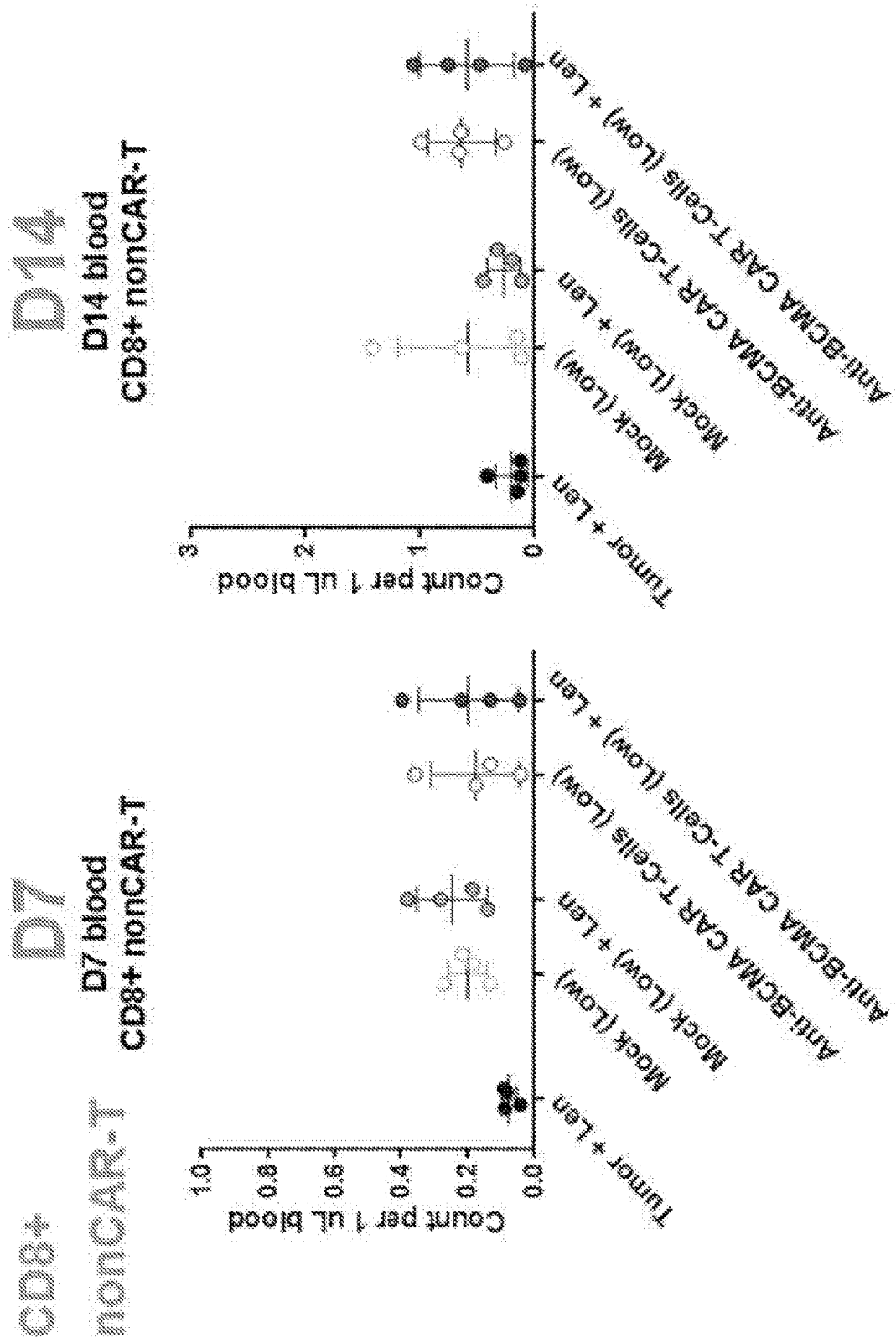
FIG. 8G shows the levels of CD8+ CAR+ T cells in the blood from mice treated with non-CAR+ T cells and lenalidomide compared to the other treatment groups at days 7 and 14.
Figure 8H:
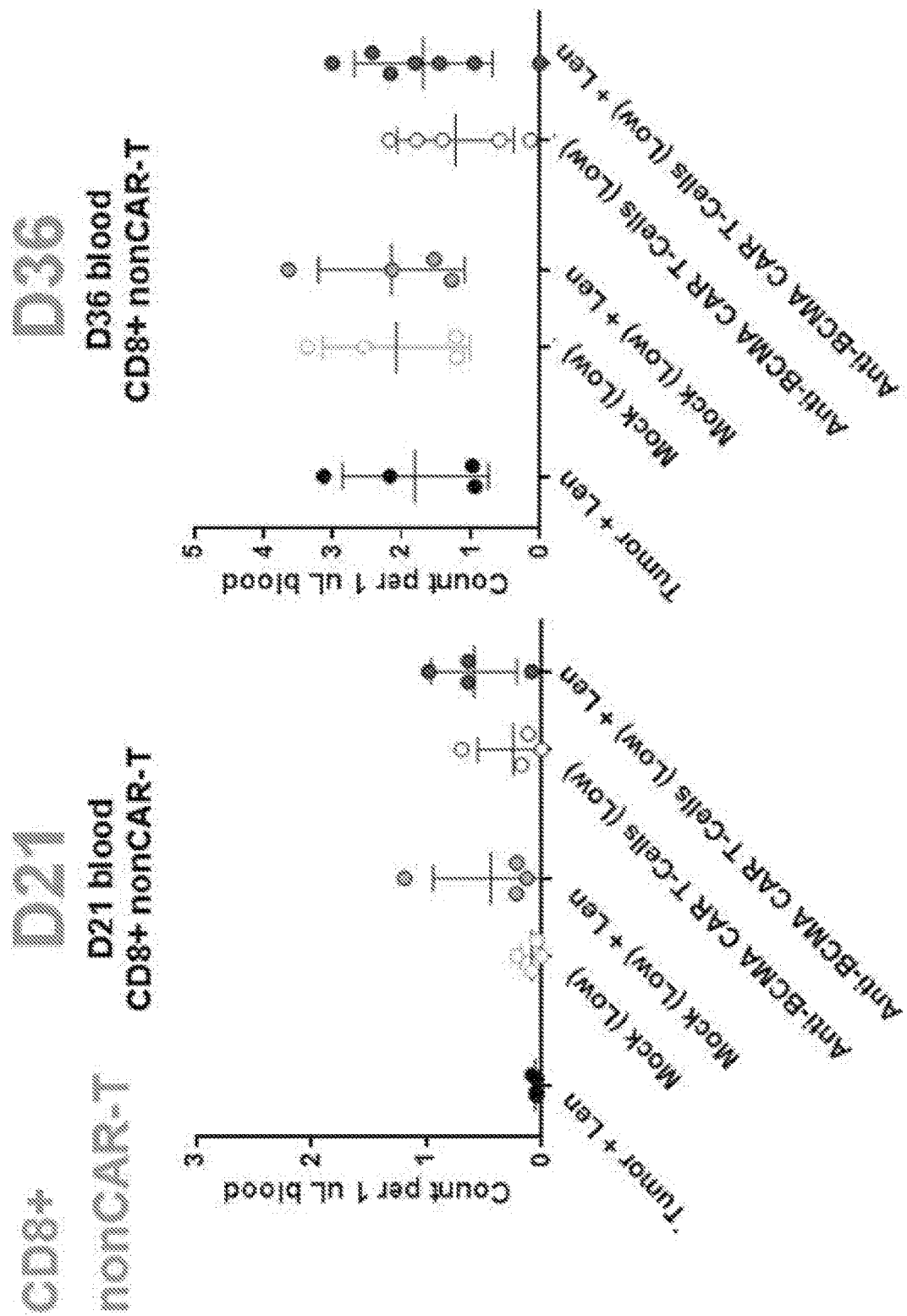
FIG. 8H shows the levels of CD8+ CAR+ T cells in the blood from mice treated with non-CAR+ T cells and lenalidomide compared to the other treatment groups at days 21 and 36.

Additionally, the number of CD4+ and CD8+ CAR+ T cells and non-CAR T cells in peripheral blood of each animal was determined at days 7, 14, 21 and 34. The numbers of CD4+ CAR T cells and non-CAR T cells are shown in FIGS. 8A and 8E (days 7 and 14), respectively, and FIGS. 8B and 8F (days 21 and 34), respectively. The numbers of CD8+ CAR T cells non-CAR T cells are shown in FIGS. 8C and 8G (days 7 and 14), respectively, and FIGS. 8D and 8H (days 21 and 34), respectively. As shown, an increase in numbers of CD4+ and CD8+ CAR+ T cells (but not non-CAR+ T cells) in blood was observed at day 36 in mice having received the combination of anti-BCMA CAR+ T cells and lenalidomide, compared to the other treatment groups.

B. OPM-2 Model i. Study 1

The effect of lenalidomide in combination with anti-BCMA CAR T was also assessed in a murine orthotopic tumor model using OPM-2 cells. Mice (NOD.Cg-Prkdc$^{scid}$IL-2rg$^{tm/Wjl}$/SzJ mice (NSG; Jackson Labs)) were injected intravenously (i.v.) with $2 \times 10^6$ OPM2 (multiple myeloma) cells transfected with firefly luciferase (OPM2-ffluc). Tumor engraftment was allowed to occur for 13 days prior to staging (14 days before CAR-T cell administration) and verified using bioluminescence imaging. Mice were administered one or more compositions in various treatment groups, as follows and summarized in Table E1.

Some groups received 10 mg/kg lenalidomide in phosphate-buffered saline via intraperitoneal injection, either (A) beginning at day −1 (one day prior to administration of CAR+ T cells) (lenalidomide (A)); or (B) at day 14 (day 14 post-initiation of CAR+ T cell administration) (lenalidomide (B)), in each case, daily, for the duration of the study. In groups receiving CAR+ T cells, anti-BCMA CAR (generated by transducing cells derived from samples of human donor subjects essentially as described above) were administered at day 0 (day 14 after tumor cell injection), at a dose of either $5 \times 10^5$ (low) or $1 \times 10^6$ (high) CAR-expressing T cells. Table E1 summarizes the dosing regimens.

TABLE E1

Study Design

| Group No. | Group Description | CAR-T cells administered (or mock-transduced T cells) |
| --- | --- | --- |
| 1 | Tumor only | 0 |
| 2 | Mock (high) | $(1 \times 10^6)$ |
| 3 | lenalidomide (A) | n/a |
| 4 | lenalidomide (B) | n/a |
| 5 | Mock + lenalidomide (A) | $(1 \times 10^6)$ |
| 6 | Mock + lenalidomide (B) | $(1 \times 10^6)$ |
| 7 | Anti-BCMA CAR+ T cells (high) | $1 \times 10^6$ |
| 8 | Anti-BCMA CAR+ T cells (low) | $5 \times 10^5$ |
| 9 | Anti-BCMA CAR+ T cells (high) + lenalidomide (A) | $1 \times 10^6$ |
| 10 | Anti-BCMA CAR+ T cells (low) + lenalidomide (A) | $5 \times 10^5$ |
| 11 | Anti-BCMA CAR+ T cells (high) + lenalidomide (B) | $1 \times 10^6$ |
| 12 | Anti-BCMA CAR+ T cells (low) + lenalidomide (B) | $5 \times 10^5$ |

Tumor burden in animals among the various groups was monitored by bioluminescence imaging up to day 39 post-CAR+ T cell dosing. For bioluminescence imaging, mice received intraperitoneal (i.p.) injections of luciferin substrate (CaliperLife Sciences, Hopkinton, MA) resuspended in PBS (15 µg/g body weight). The total flux (photon/s) was determined at each time point.

Figure 9A:
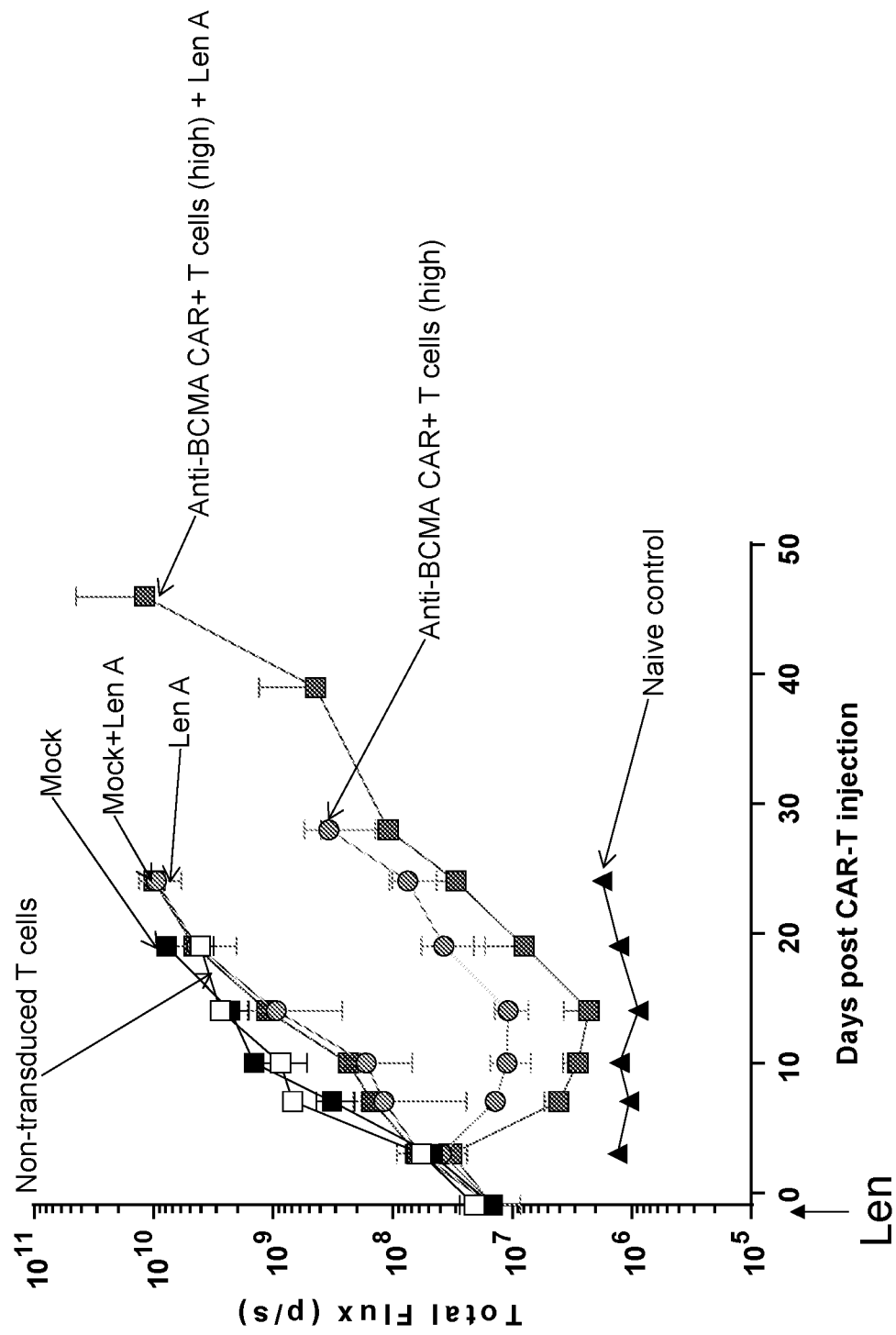
FIGS. 9A and 9B depict tumor burden results of mice treated under Regimen A (LenA), in which mice were administered lenalidomide one day prior to receiving CAR+ T cells.
Figure 9B:
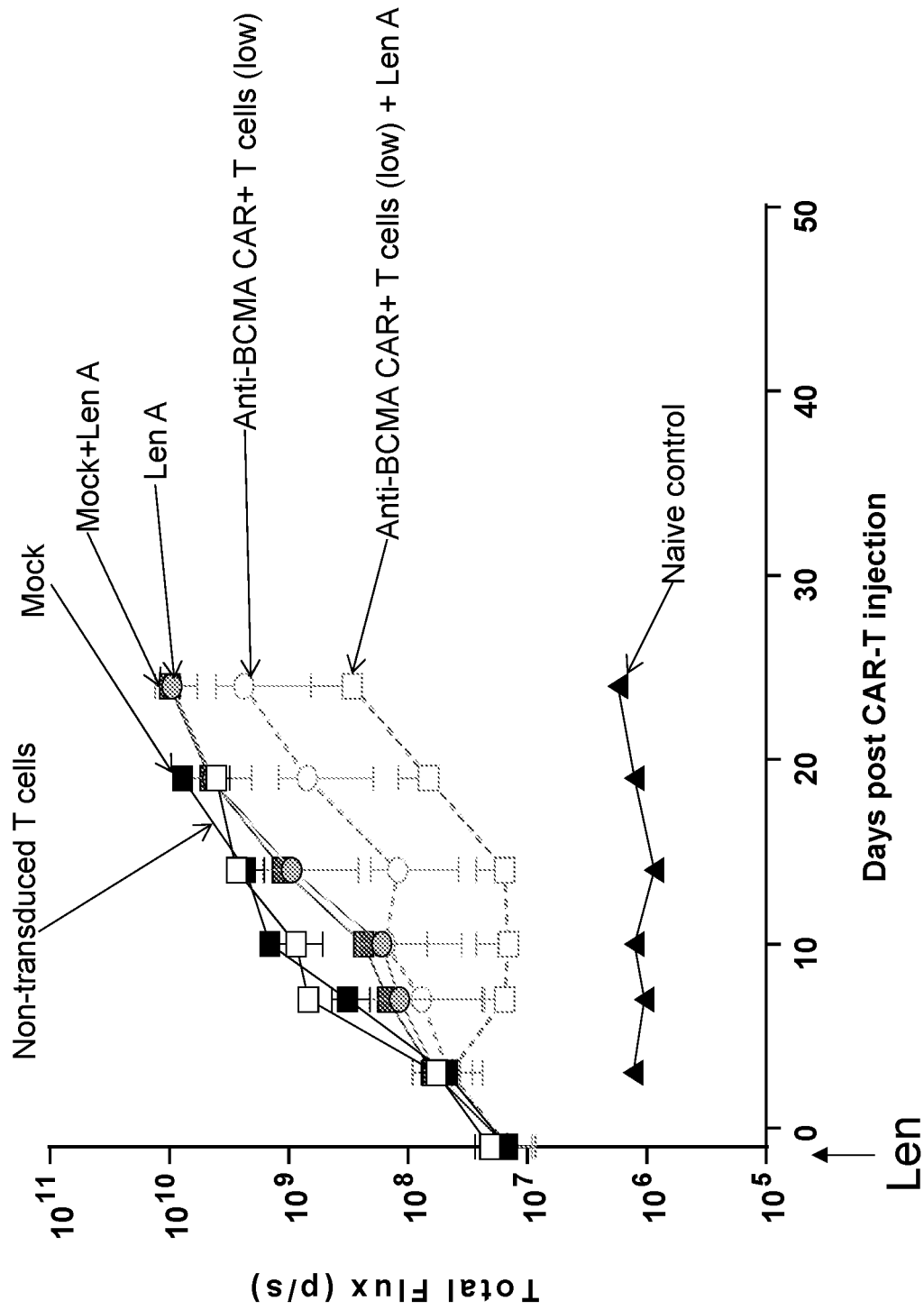
Figure 9C:
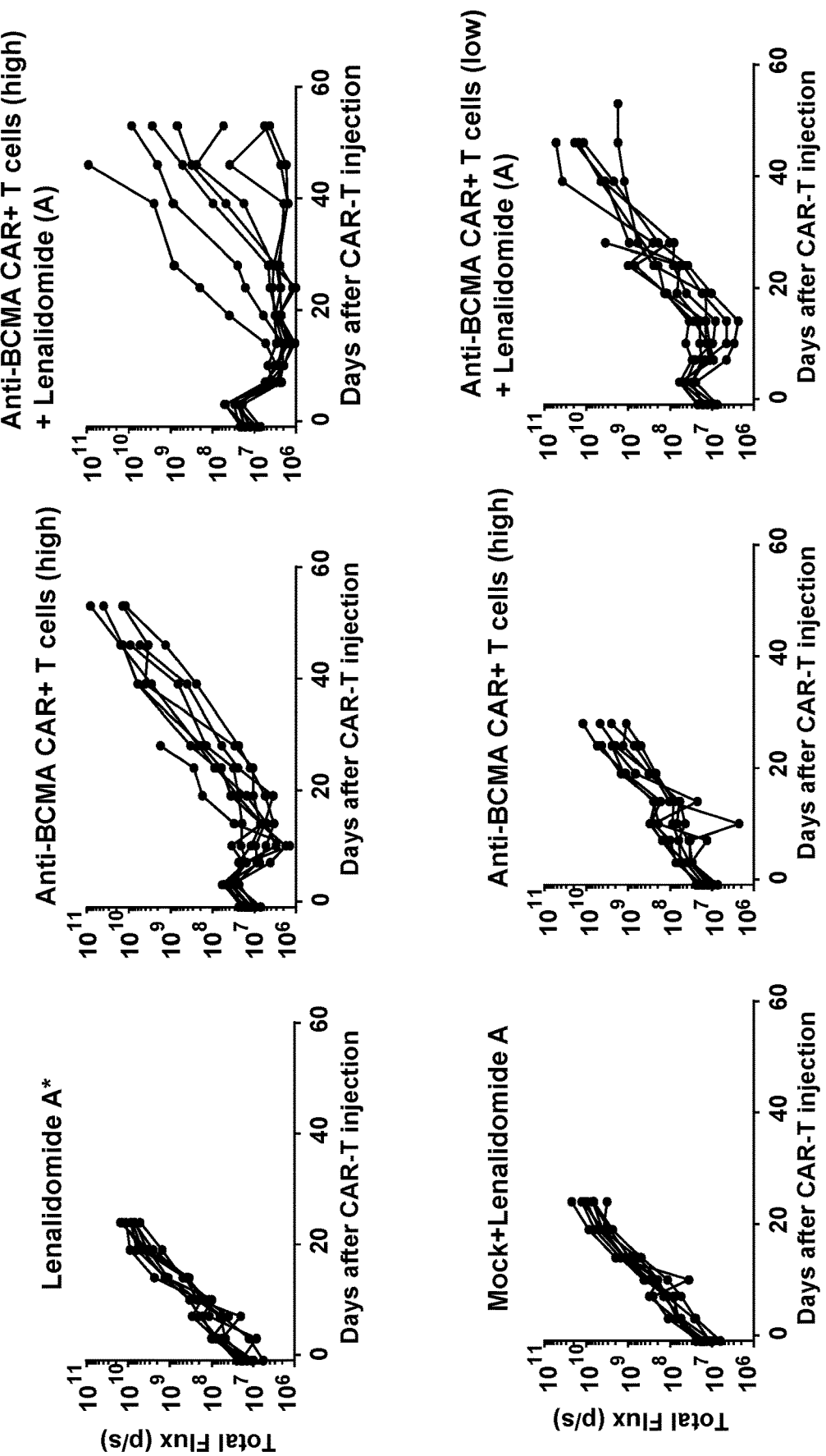
FIG. 9C shows the tumor burden of individual mice through up to day 53.
Figure 9D:
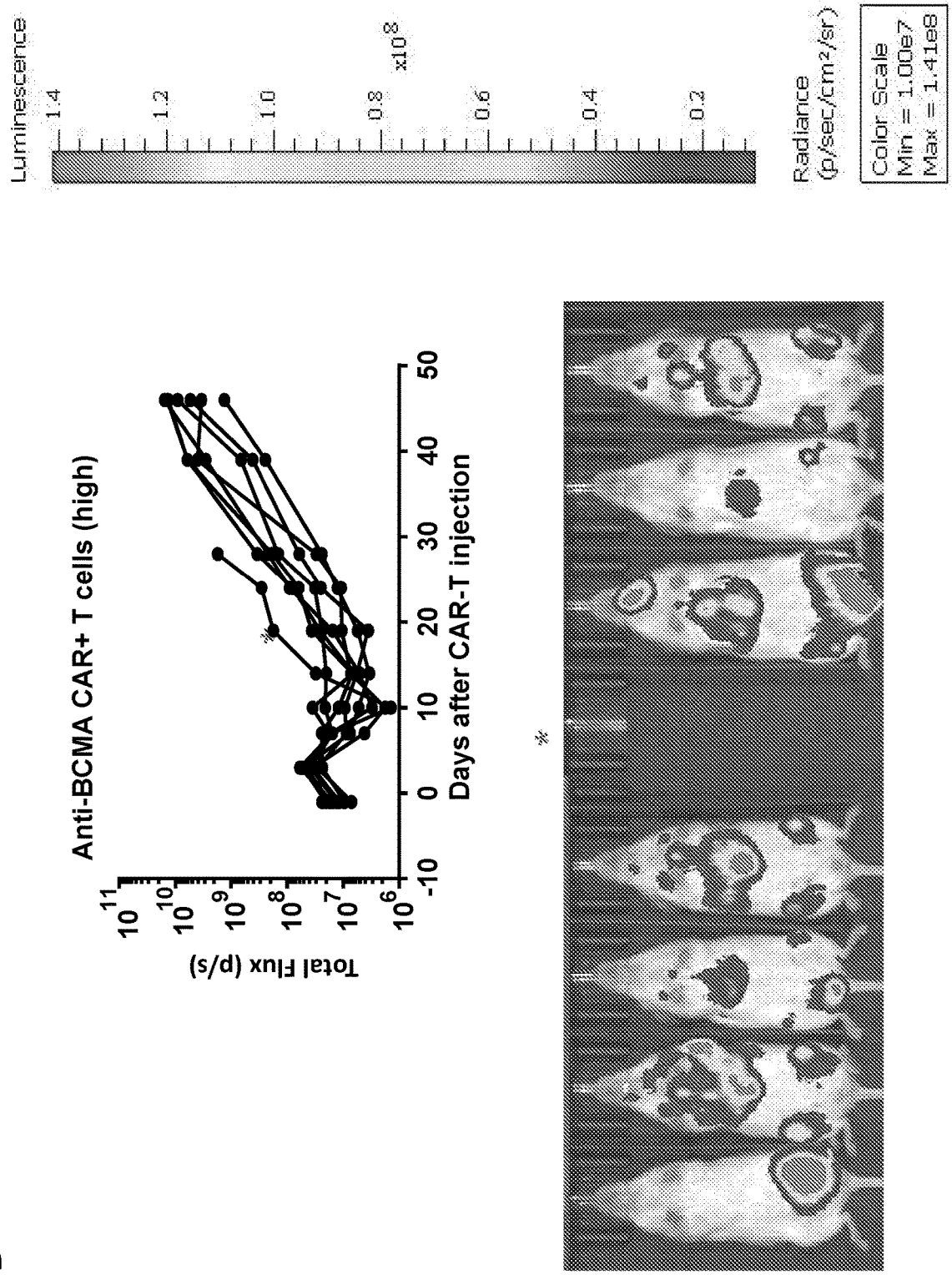
FIG. 9D shows tumor imaging results at day 46 post CAR+ cell administration for individual mice having received the higher CAR+ dose ($1\times10^6$), with lenalidomide at day −1 (Len A).
Figure 9E:
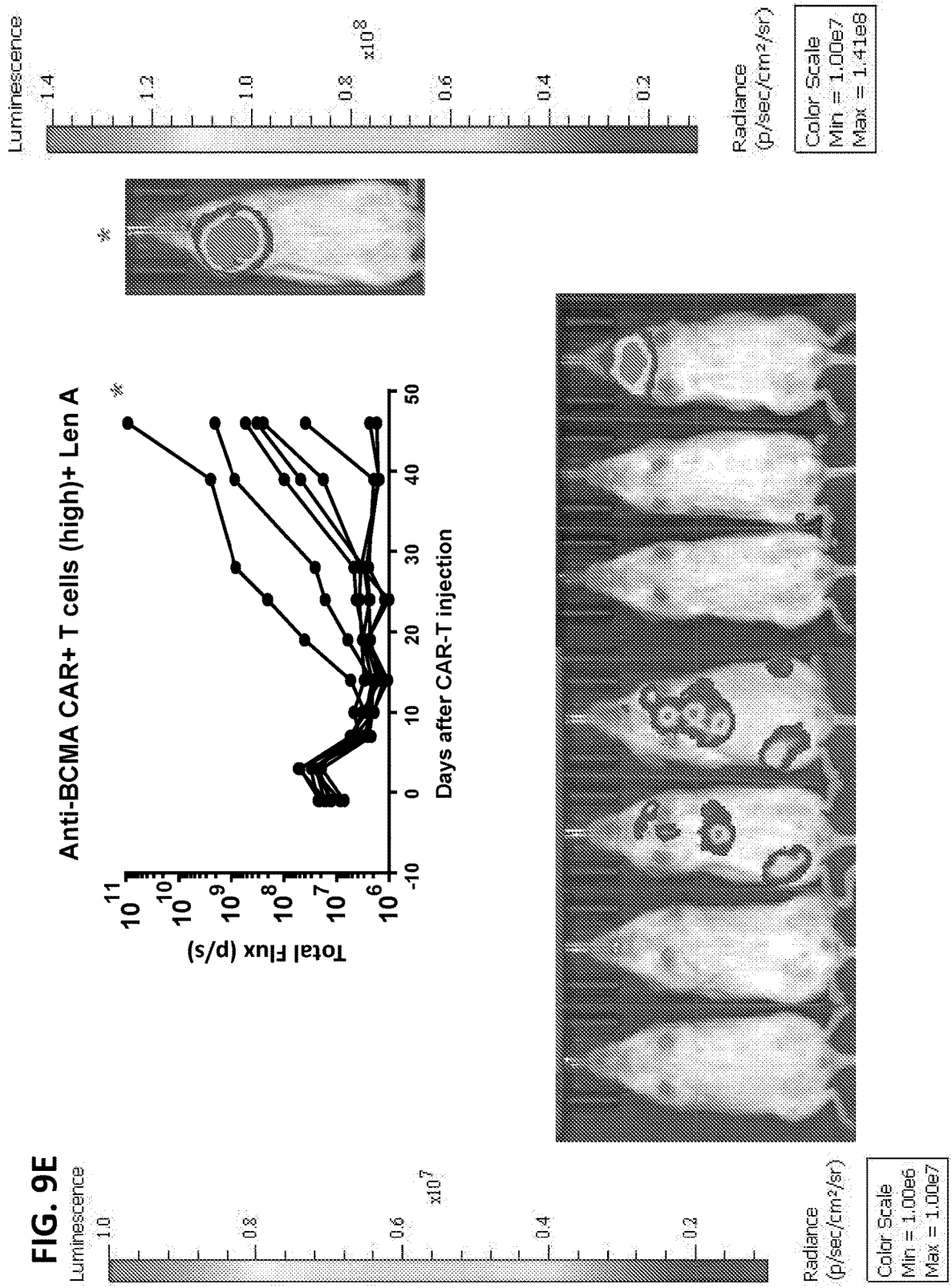
FIG. 9E shows tumor imaging results at day 46 post CAR+ cell administration for individual mice having received the higher CAR+ dose ($1\times10^6$) without lenalidomide at day −1 (Len A).

FIG. 9A and FIG. 9B depict results of tumor burden through up to day 46, in mice treated with lenalidomide daily beginning at day −1 (lenalidomide A) in the presence or absence of the high ($1 \times 10^6$; FIG. 9A) or low ($5 \times 10^5$; FIG. 9B) CAR+ T cell dose. FIG. 9C shows plots for tumor burden of individual animals through up to day 53. FIG. 9D shows plots and tumor imaging results (day 46 post-CAR+ cell administration) for individual animals having received the higher CAR+ dose, with lenalidomide at day −1 (lenalidomide A). FIG. 9E shows plots and tumor imaging results (day 46 post-CAR+ cell administration) for individual animals having received the higher CAR+ dose, without lenalidomide at day −1 (lenalidomide A). Asterisks indicate death or sacrifice of an individual animal at the time-point indicated in plot. As shown, the addition of lenalidomide was observed to result in slower tumor growth and reduced tumor burden in mice administered CAR+ T cells at both CAR+ T cell doses.

Figure 9F:
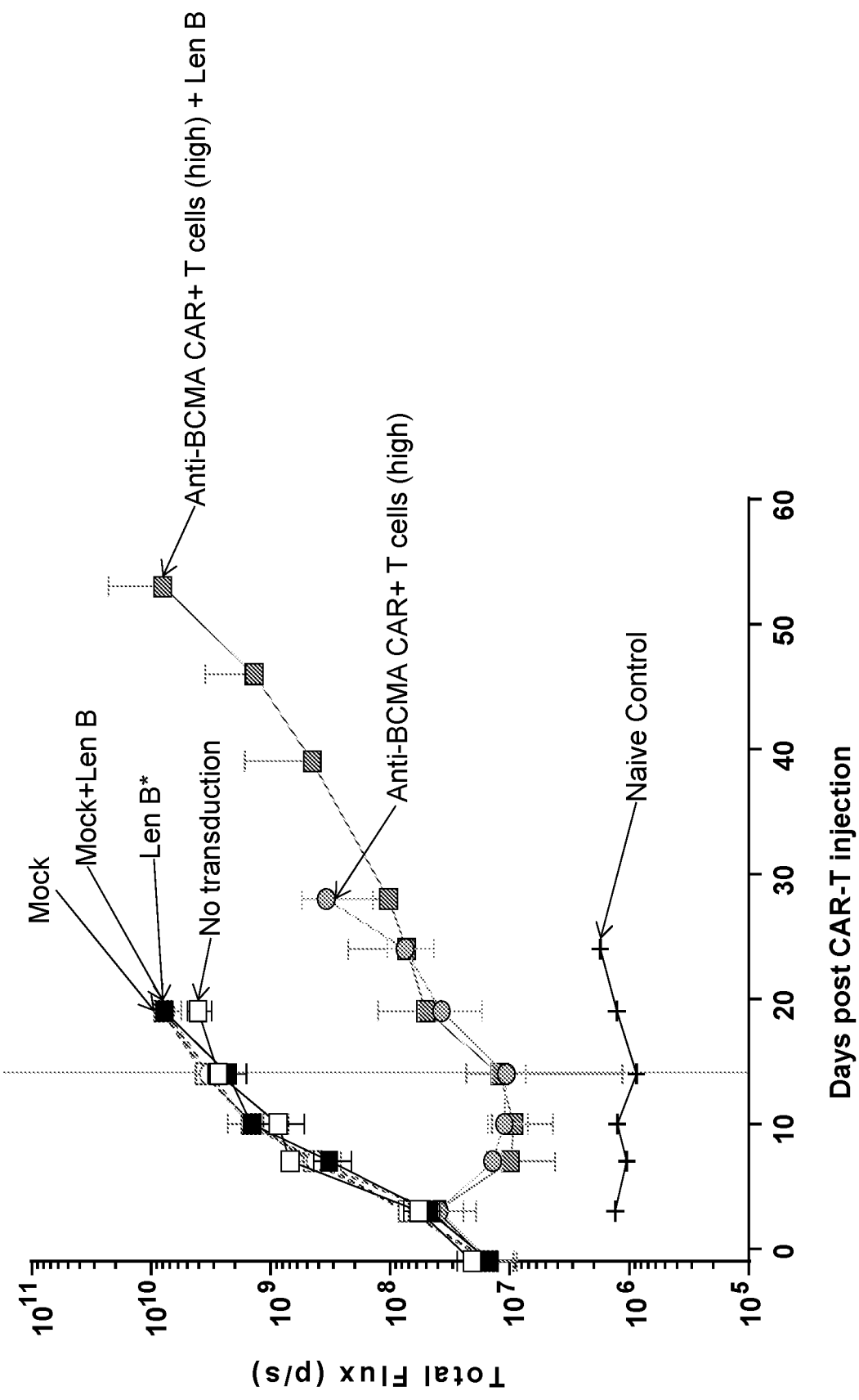
FIGS. 9F and 9G depict tumor burden results of mice treated under Regimen B (LenB), in which administration of lenalidomide was initiated at day 14 post CAR+T administration.
Figure 9G:
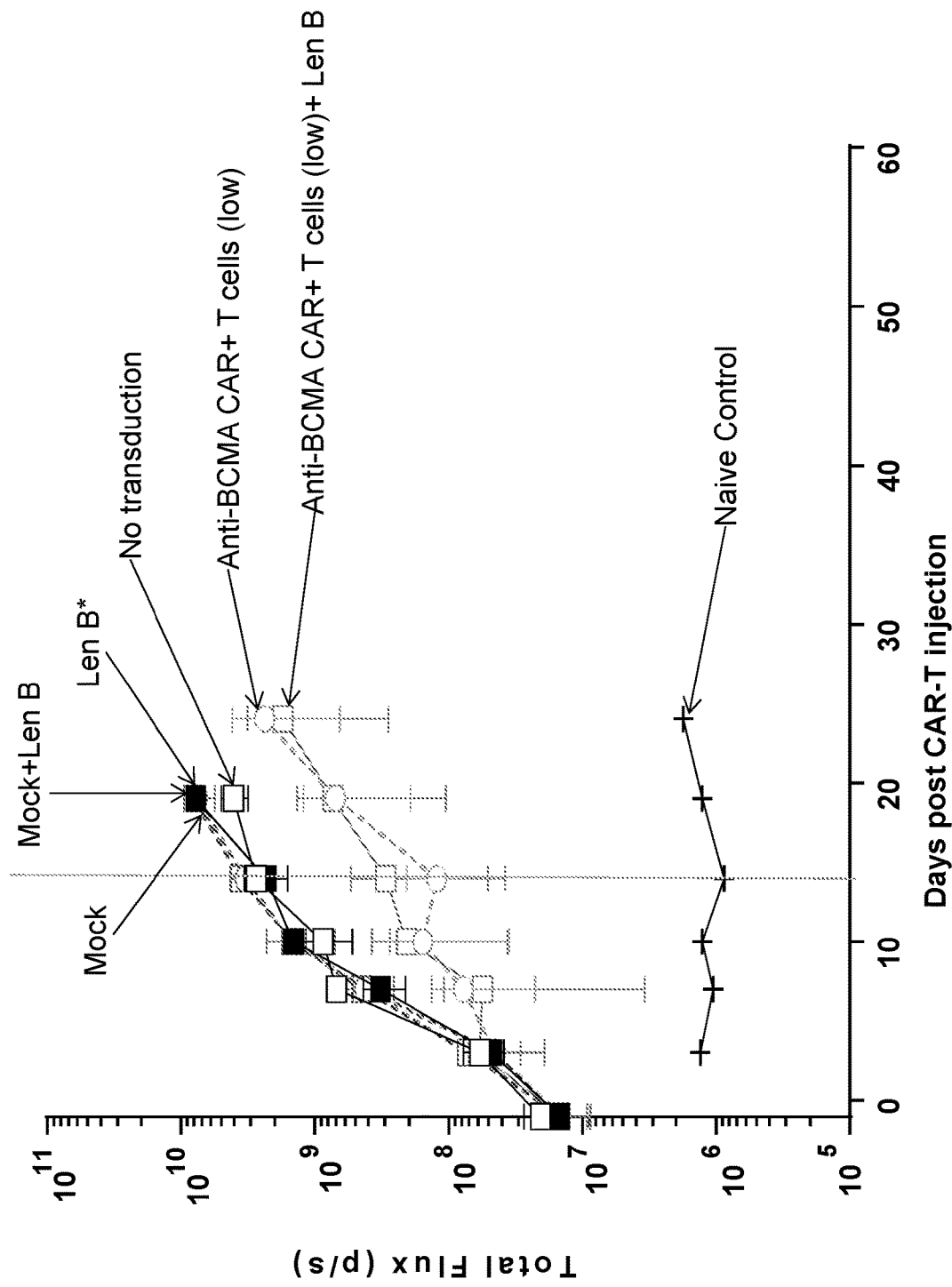
Figure 9H:
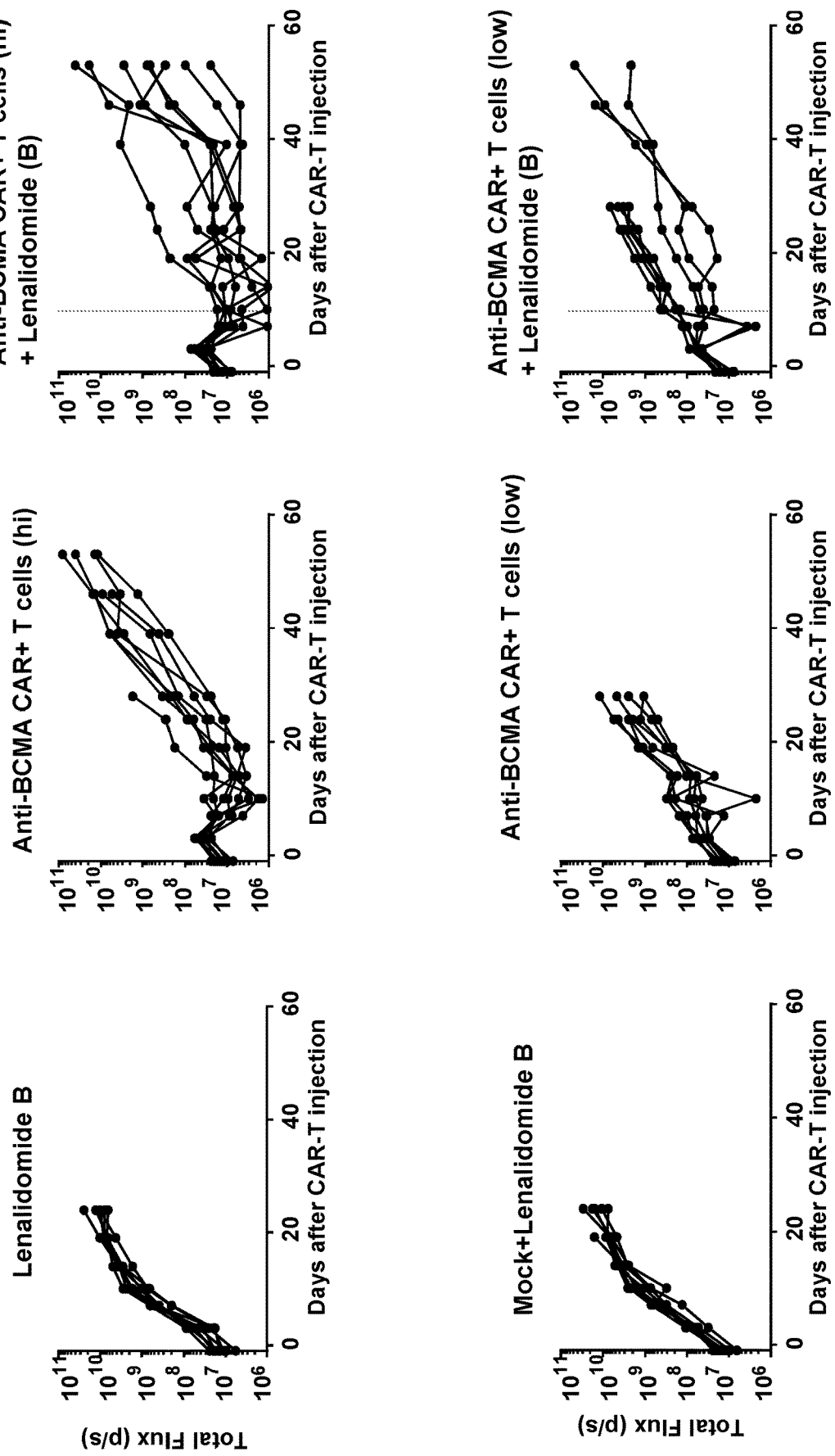
FIG. 9H shows the tumor burden of individual mice through up to day 53.
Figure 9I:
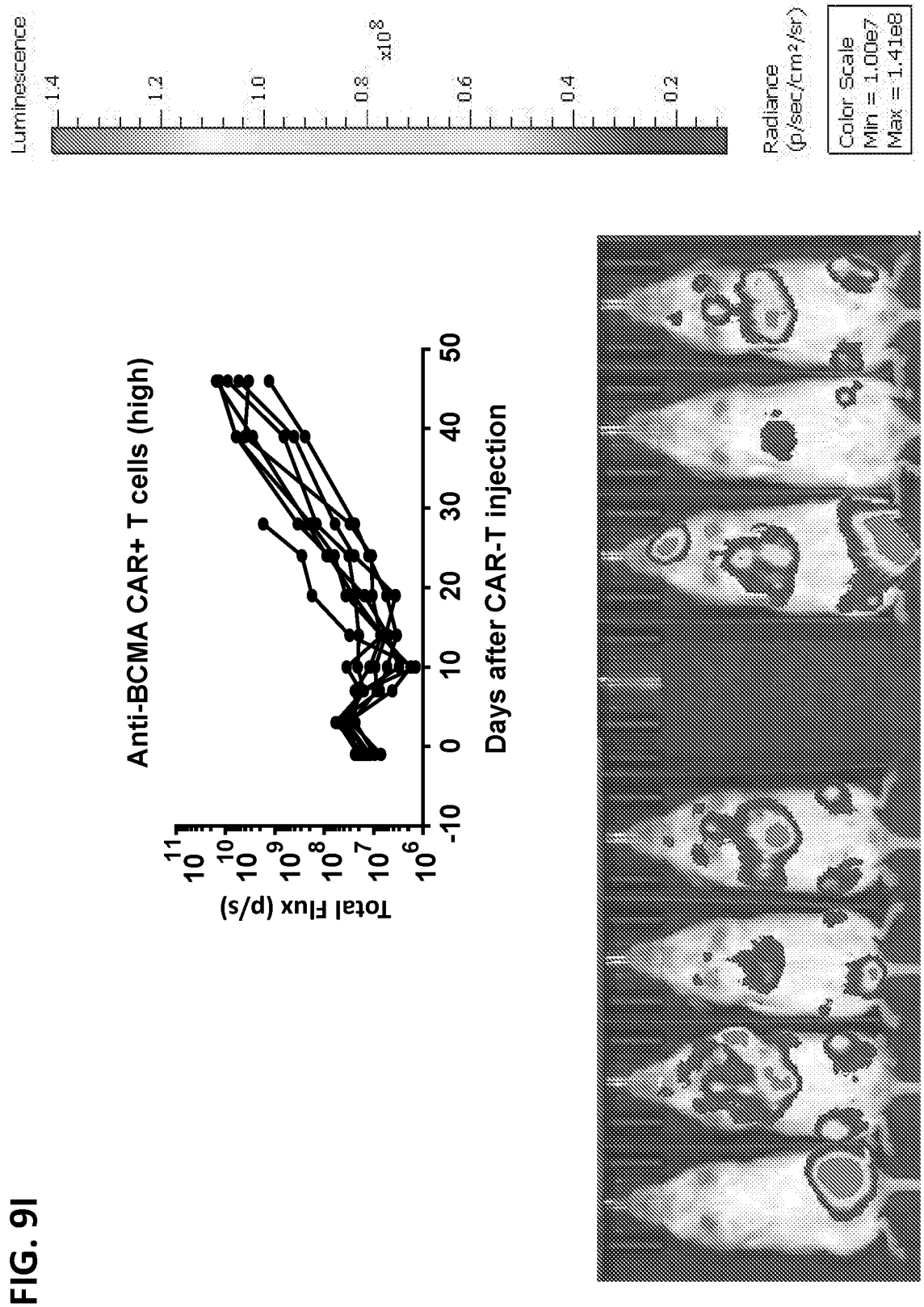
FIG. 9I shows tumor imaging results (day 46 post-CAR+ cell administration) for individual mice having received the higher CAR+ dose ($1\times10^6$), with lenalidomide at day −1 (Len A).
Figure 9J:
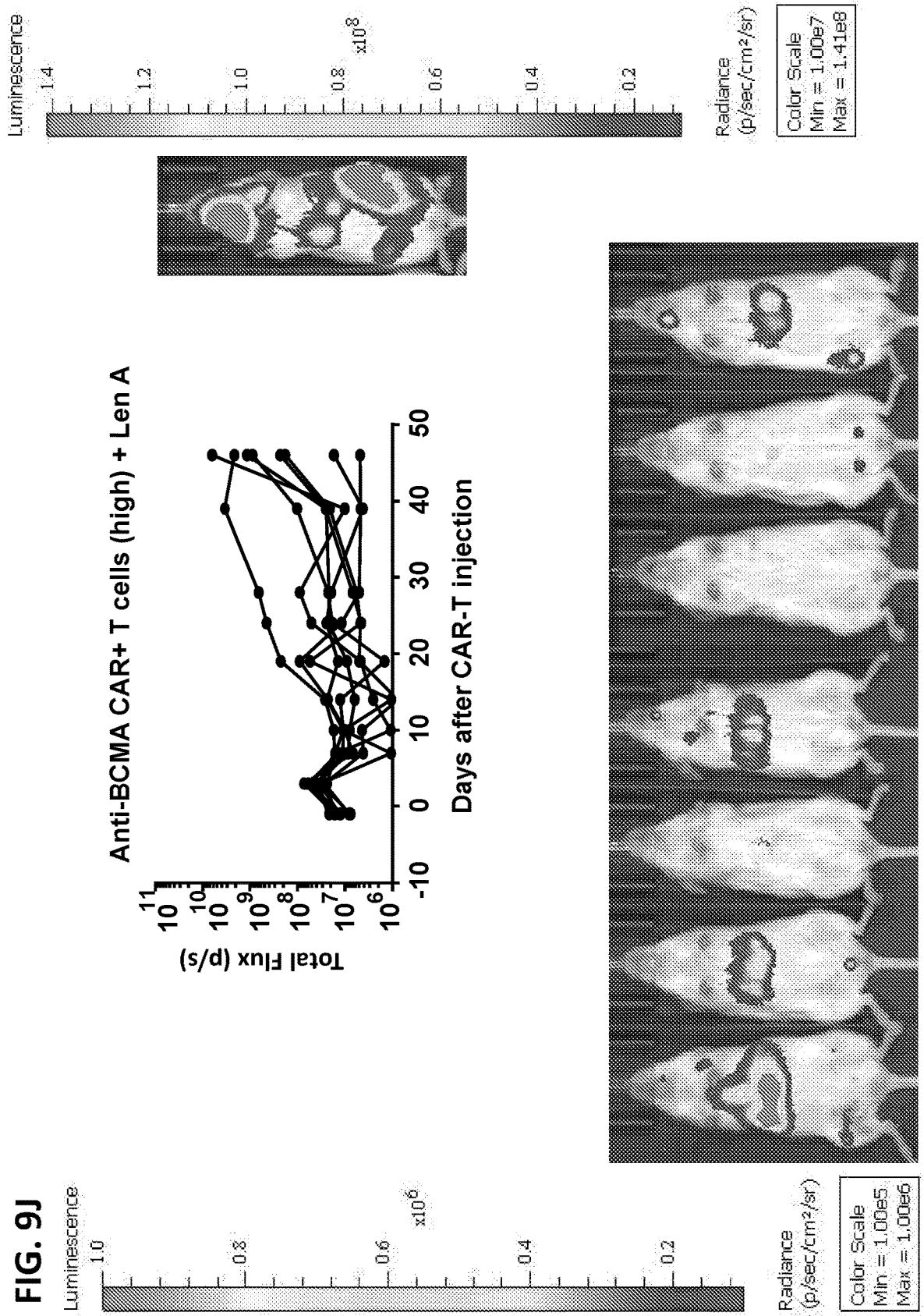
FIG. 9J shows tumor imaging results (day 46 post-CAR+ cell administration) for individual mice having received the higher CAR+ dose ($1\times10^6$), without lenalidomide at day −1 (Len A).

FIG. 9F and FIG. 9G depict tumor burden results at a time-point in a study for mice administered lenalidomide beginning at day 14 post-CAR+T administration (lenalidomide B) (vertical lines in FIGS. 9F and 9G) in the presence or absence of the high (1×10^6, FIG. 9F) or low (5×10^5, FIG. 9G) CAR+ T cell dose. FIG. 9H shows plots for tumor burden of individual animals through up to day 53. FIG. 9I shows plots and tumor imaging results (day 46 post-CAR+ cell administration) for individual animals having received the higher CAR+ dose, with lenalidomide at day −1 (lenalidomide A). FIG. 9J shows plots and tumor imaging results (day 46 post-CAR+ cell administration) for individual animals having received the higher CAR+ dose, without lenalidomide at day −1 (lenalidomide A). As shown, whereas lenalidomide alone was not observed to reduce tumor growth or tumor burden, the addition of lenalidomide was observed to result in a trend towards slower tumor growth and reduced tumor burden in mice administered both doses of CAR-T cells, with clear differences observed beginning at day 30-40 post-CAR-T cell injection for the higher (1×10^6) dose of CAR+ T cells. With this dose, combination with lenalidomide was observed to slow tumor growth whether given at day −1 or via delayed dosing.

Figure 10A:
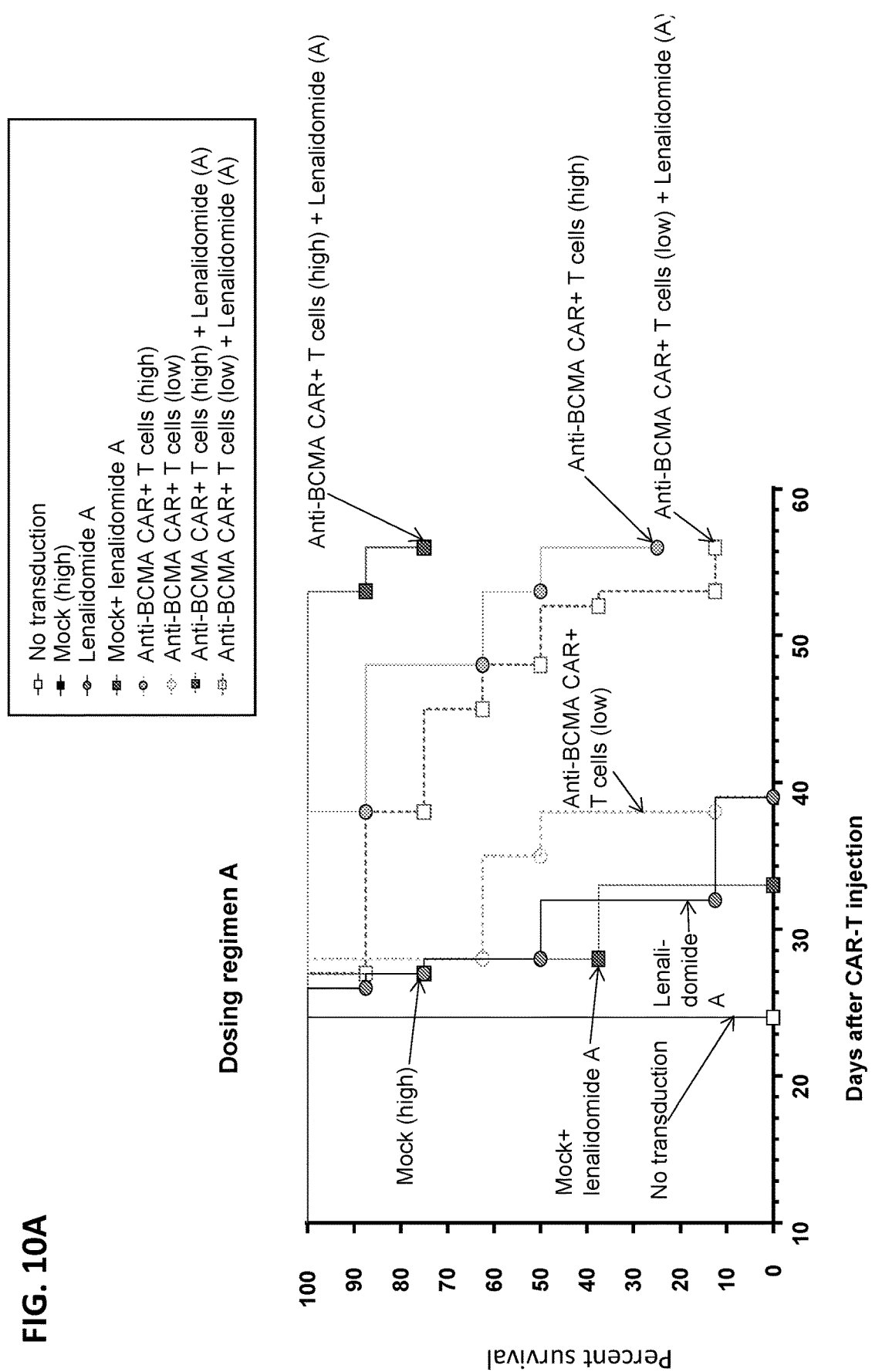
FIGS. 10A-10D show the survival of mice in the presence or absence of lenalidomide. Lenalidomide was administered via Regimen A (Len A; administration of lenalidomide initiated at day −1) or Regimen B (Len B; administration of lenalidomide initiated at day 14) in combination with low ($5\times10^5$ or 5e⁵) or high ($1\times10^6$ or 1e⁶) doses of CAR+ T cells. For the control groups, T cells that did not express a CAR (mock) were administered in the presence and absence of lenalidomide via both Regimen A and Regimen B, and lenalidomide without T cells was also administered via both Regimen A and Regimen B.
Figure 10B:
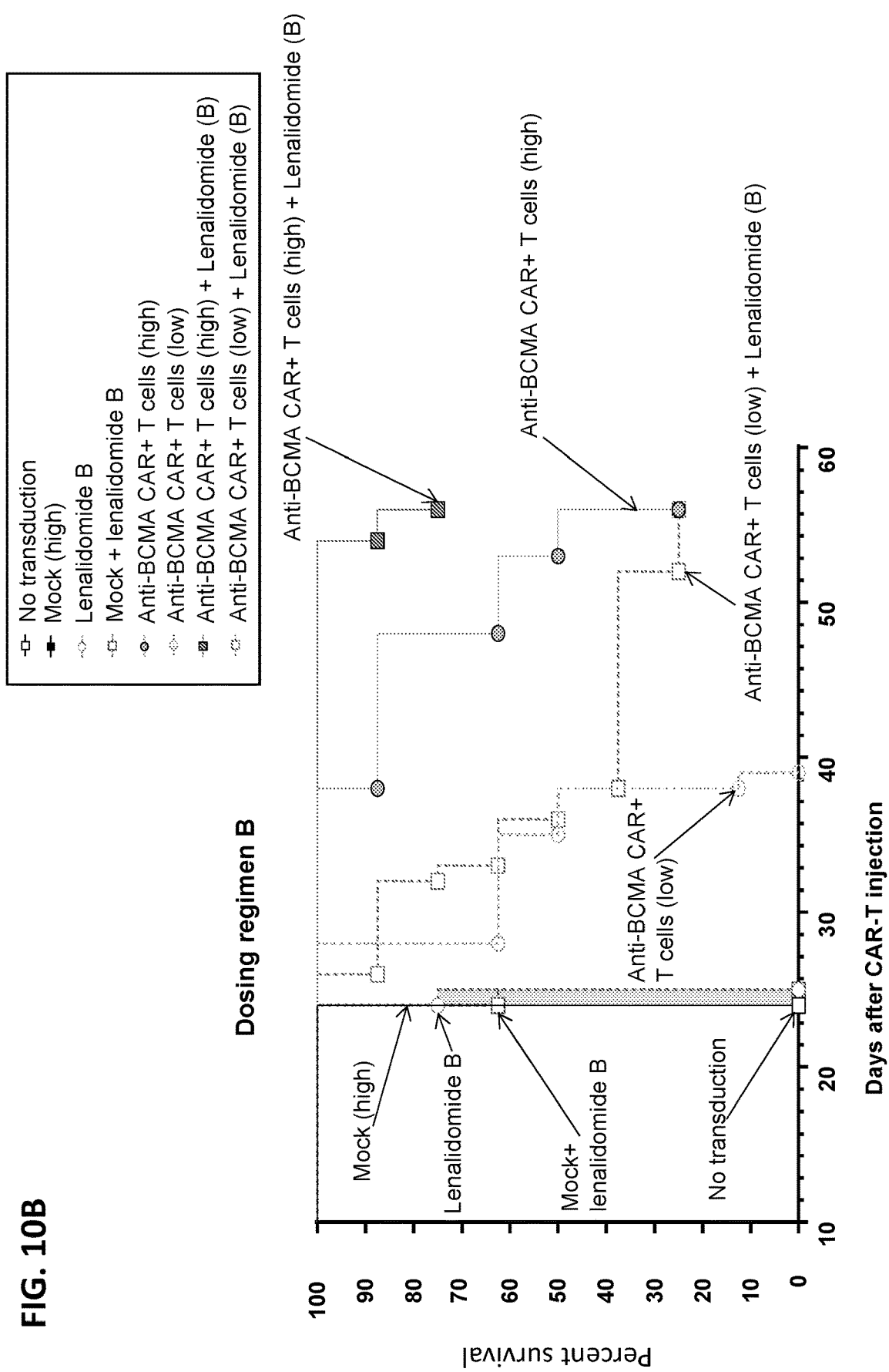
Figure 10C:
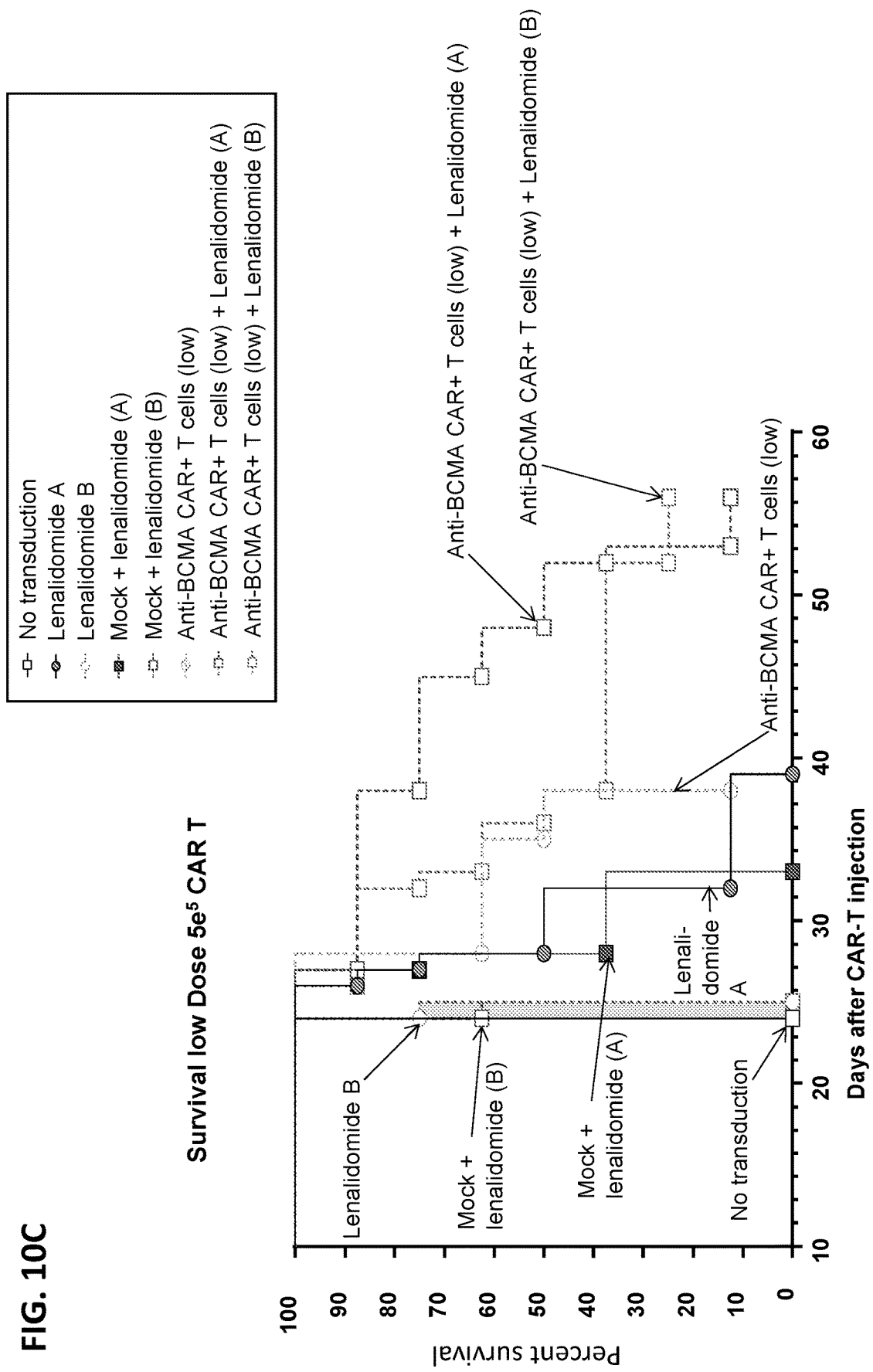
Figure 10D:
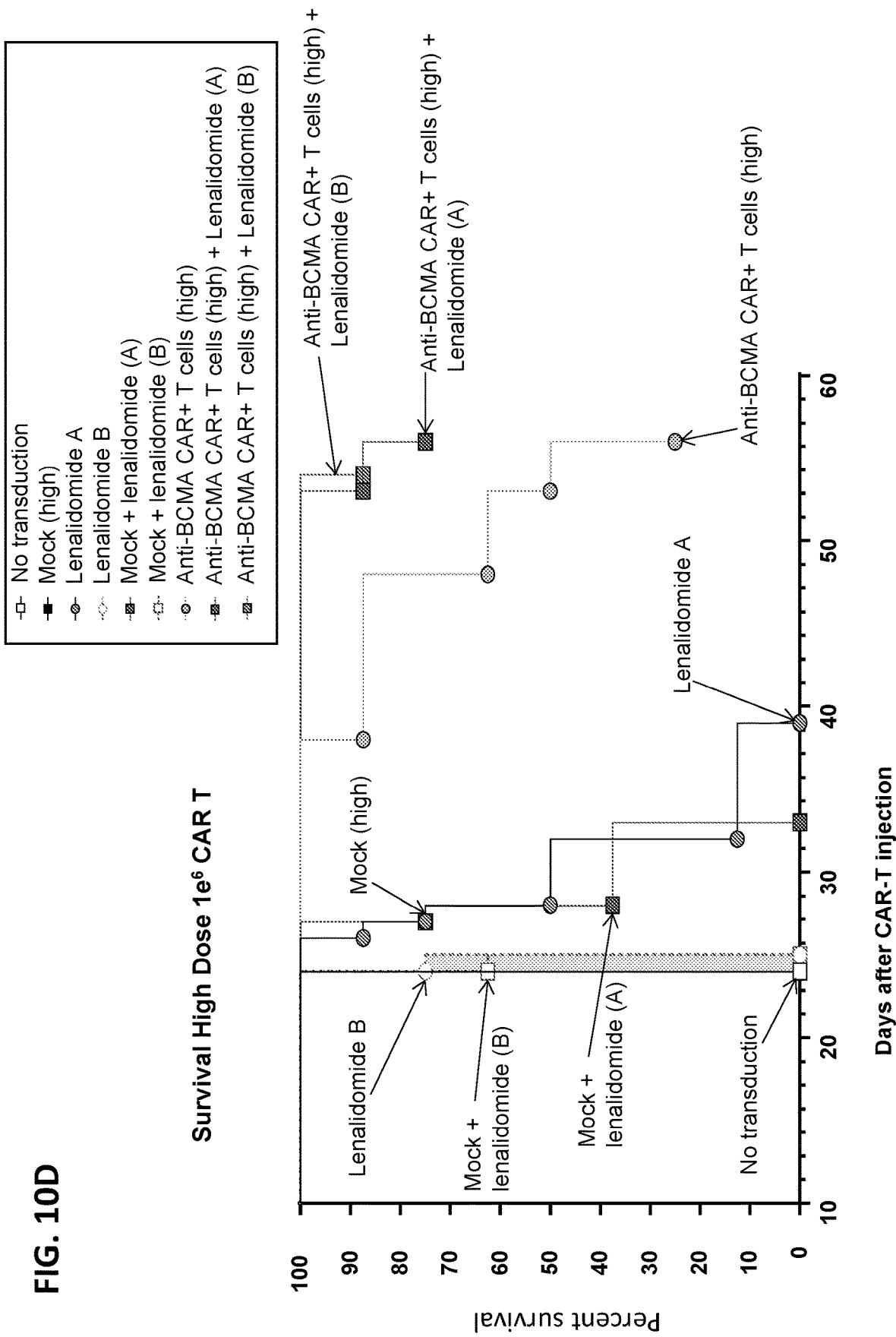

Survival results at a time-point in the study are shown in FIGS. 10A and 10B (for groups receiving lenalidomide via regimens (d-1) and B (d.14 post-CAR (delayed), respectively), and FIGS. 10C and 10D (for groups receiving high and low CAR doses, respectively). As shown, the addition of lenalidomide improved survival effects observed in mice treated with the anti-BCMA CAR+ T cells (at both the high and low doses assessed), when administered either at day −1 (A) or via delayed (d.14) dosing (B).

Table E2 lists median survival (ms) (as assessed at day 56 post-CAR+ T cell administration) and number of mice in group surviving until day 56-post-CAR+ T cell administration, for each animal group assessed in this study.

TABLE E2

Survival

| Group | Cell Dose | Median Survival (assessed at day 6) | # animals surviving day 56 post-CART |
|---|---|---|---|
| Mock hi | 1.00E+06 | 24 | 0/8 |
| lenalidomide (A) | N/A | 28 | 0/8 |
| lenalidomide (B) | N/A | 25 | 0/8 |
| Mock + lenalidomide (A) | 1.00E+06 | 28 | 0/8 |
| Mock + lenalidomide (B) | 1.00E+06 | 25 | 0/8 |
| CAR+ T cells (hi) | 1.00E+06 | 56 | 2/8 |
| CAR+ T cells (low) | 5.00E+05 | 35 | 0/8 |
| CAR+ T cells (hi) + lenalidomide (A) | 1.00E+06 | N/A | 6/8 |
| CAR+ T cells (low) + lenalidomide (A) | 5.00E+05 | 52 | 1/8 |
| CAR+ T cells (hi) + lenalidomide (B) | 1.00E+06 | N/A | 6/8 |
| CAR+ T cells (low) + lenalidomide (B) | 5.00E+05 | 36 | 2/8 |

(ii.) Study 2

In a further study, NOD/Scid/gc$^{-/-}$ (NSG) mice were injected (i.v.) with OPM-2-luciferase cells as described in Study 1 above and allowed to engraft for 14 days prior to CAR-T (or mock) cell; infusion (i.v.). In some groups, daily intraperitoneal administration of 10 mg/kg lenalidomide or vehicle control was initiated either at day −1 (one day prior to CAR-T administration) (concurrent lenalidomide (lenalidomide (C) or vehicle (vehicle (C)) or at day 14 post-CAR-T (or mock) cell administration (delayed lenalidomide (D)).

At 14 days after tumor cell injection (day 0), a subtherapeutic dose of CAR+ T cells (1×10^6 CAR-T cells (generated from two different donors)) or mock control cells was injected intravenously. Results are shown in FIGS. 10E, 10F, 10G, and 10H. Data are presented as mean±SEM. For in vivo survival, a Gehan-Breslow-Wilcoxon test was used to compare groups.

Figure 10E:
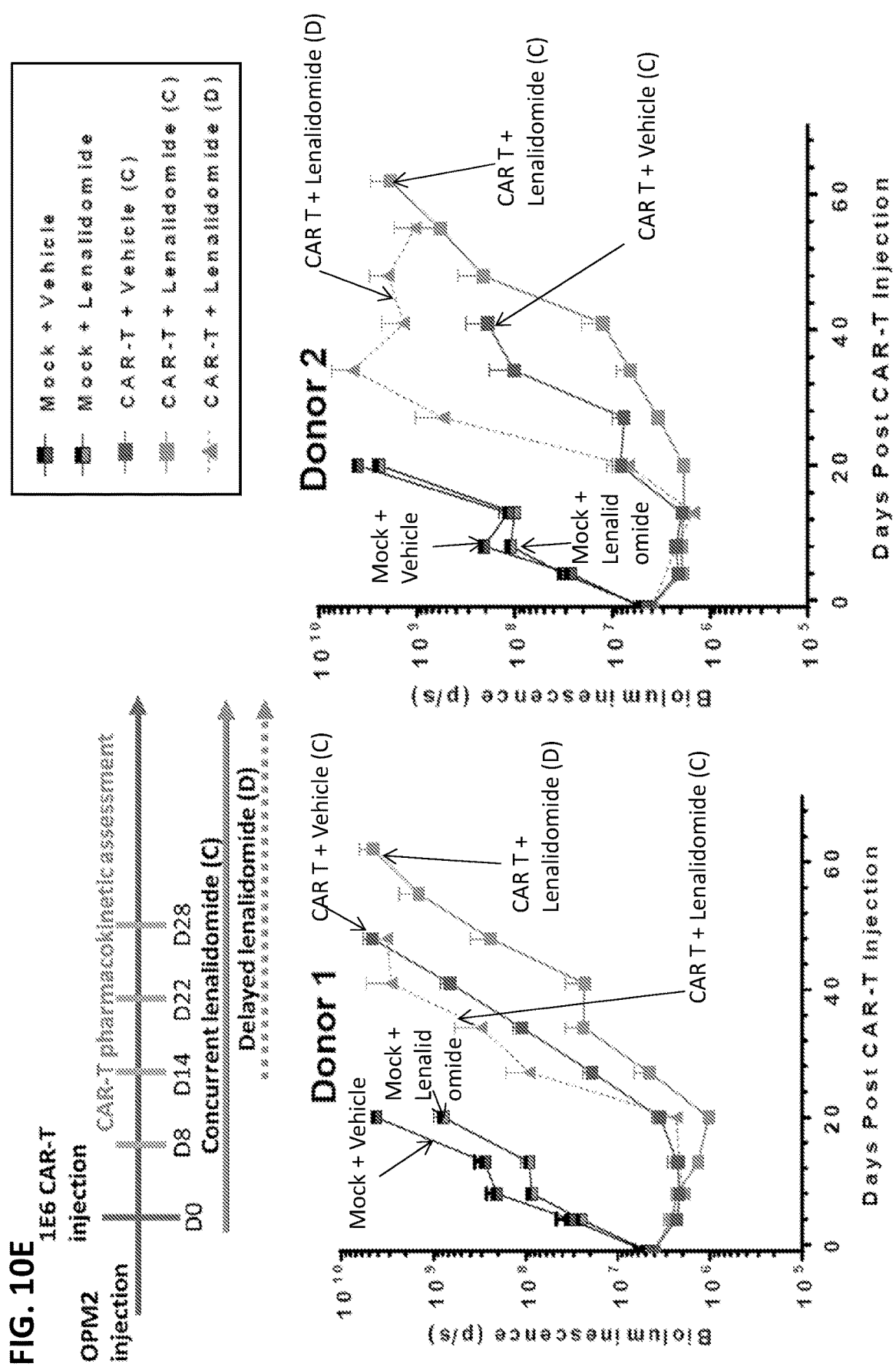
FIG. 10E shows the results of tumor burden assessment for mice having received the higher CAR+ dose ($1\times10^6$) and given a daily intraperitoneal administration of 10 mg/kg lenalidomide or vehicle control initiated at either day −1 (one day prior to CAR-T administration) (concurrent lenalidomide (lenalidomide (C) or vehicle (vehicle (C)) or at day 14 post-CAR-T (or mock) cell administration (delayed lenalidomide (D)). Results are shown through day 60, as analyzed by the bioluminescence measured by flow cytometry.
Figure 10F:
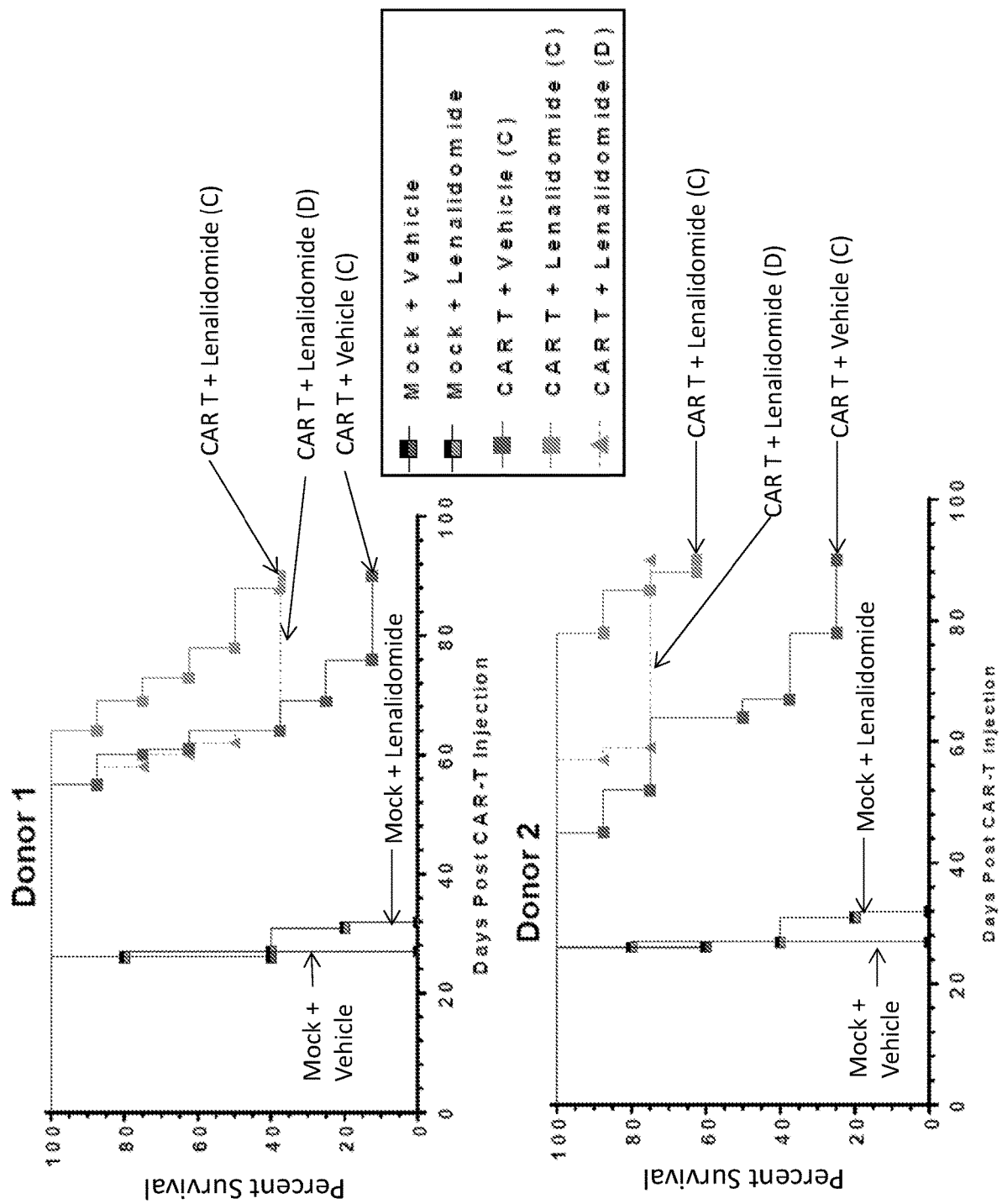
FIG. 10F shows the percent survival of mice in the presence or absence of lenalidomide.

FIG. 10E depicts the results of tumor burden assessment through day 60, as analyzed by the bioluminescence measured by flow cytometry. The addition of lenalidomide was observed to result in slower tumor growth and reduced tumor burden in mice administered CAR+ T cells generated from both donor cells. As shown in FIG. 10F, the addition of lenalidomide was observed to improve survival effects in mice treated with the anti-BCMA CAR+ T cells, particularly following concurrent administration of lenalidomide. Linear fixed-effect or mixed-effect models were used to assess the significance of lenalidomide treatments on cytolytic activity, with treatment, donor, and time treated as fixed effects and animal treated as a random effect, nested with time when repeated measurements were derived from the same animal. P values were obtained by likelihood ratio tests comparing the full model with the effect of interest against the model without the effect of interest. The addition of concurrent lenalidomide led to a significant decrease in tumor burden for donor 1 ($P=0.02$) and increased survival for donor 1 ($P=0.057$) and donor 2 ($P=0.04$) compared with vehicle-treated animals injected with anti-BCMA CAR T alone. Animals on the concurrent lenalidomide dosing regimen also showed increased CAR T counts in the peripheral blood after 7 days ($P=7.3\times10^{-6}$), but not at later time points. Lenalidomide had a small, but significant mock CAR T effect on tumor burden for donor 1 ($P=0.003$) alone. In this study, the addition of delayed dosing of lenalidomide did not improve tumor clearance and survival for both CAR T donors. The results showed that survival and tumor clearance by a subtherapeutic dose of anti-BCMA CAR-T were enhanced by lenalidomide in the in vivo OPM-2 tumor model.

Figure 10G:
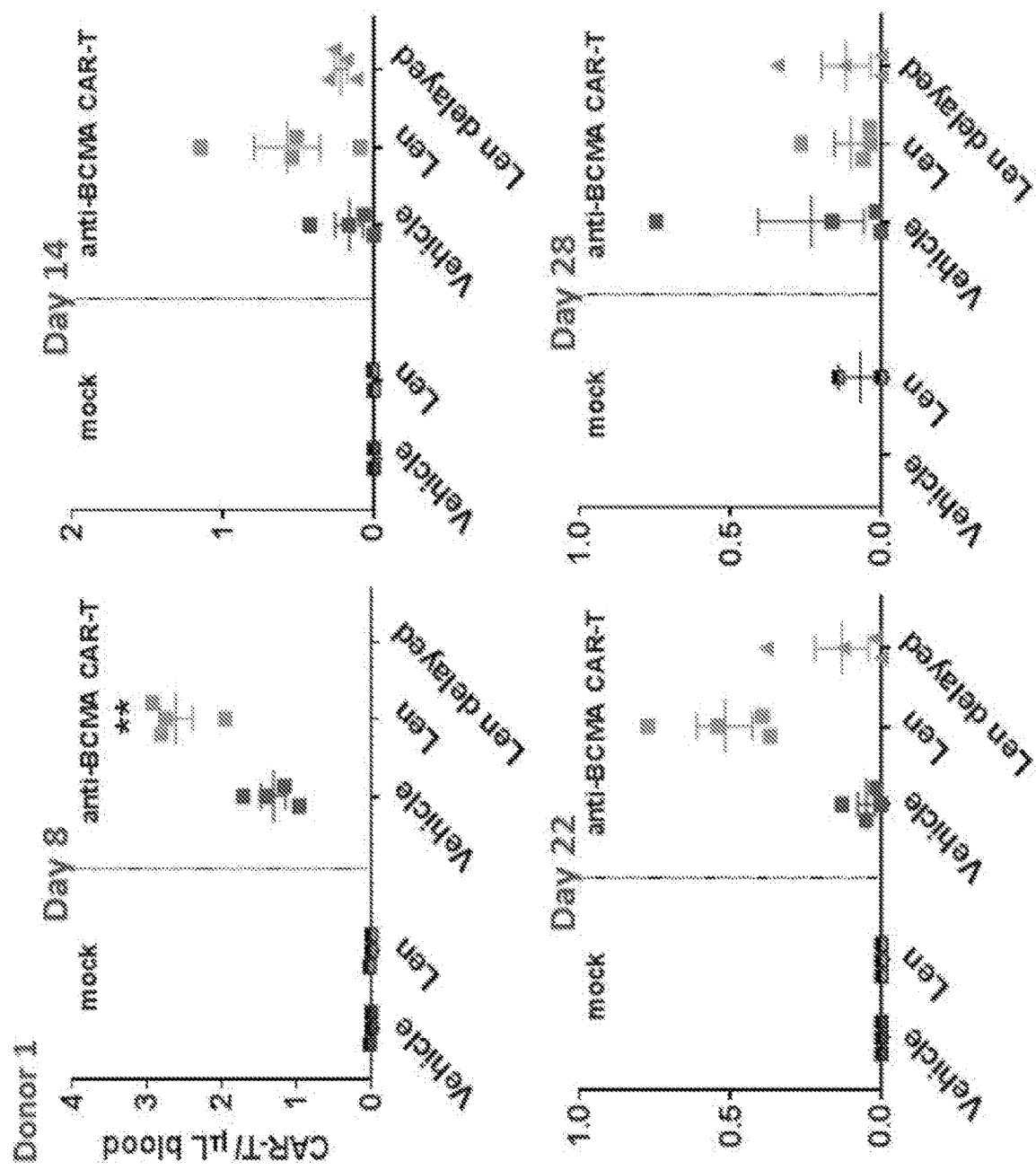
FIGS. 10G and 10H show the flow cytometric analysis of mock control cells and CAR-T cells in the blood of the mice at days 8, 14, 22, and 28 following injection of the CAR-T cells from two donors.
Figure 10H:
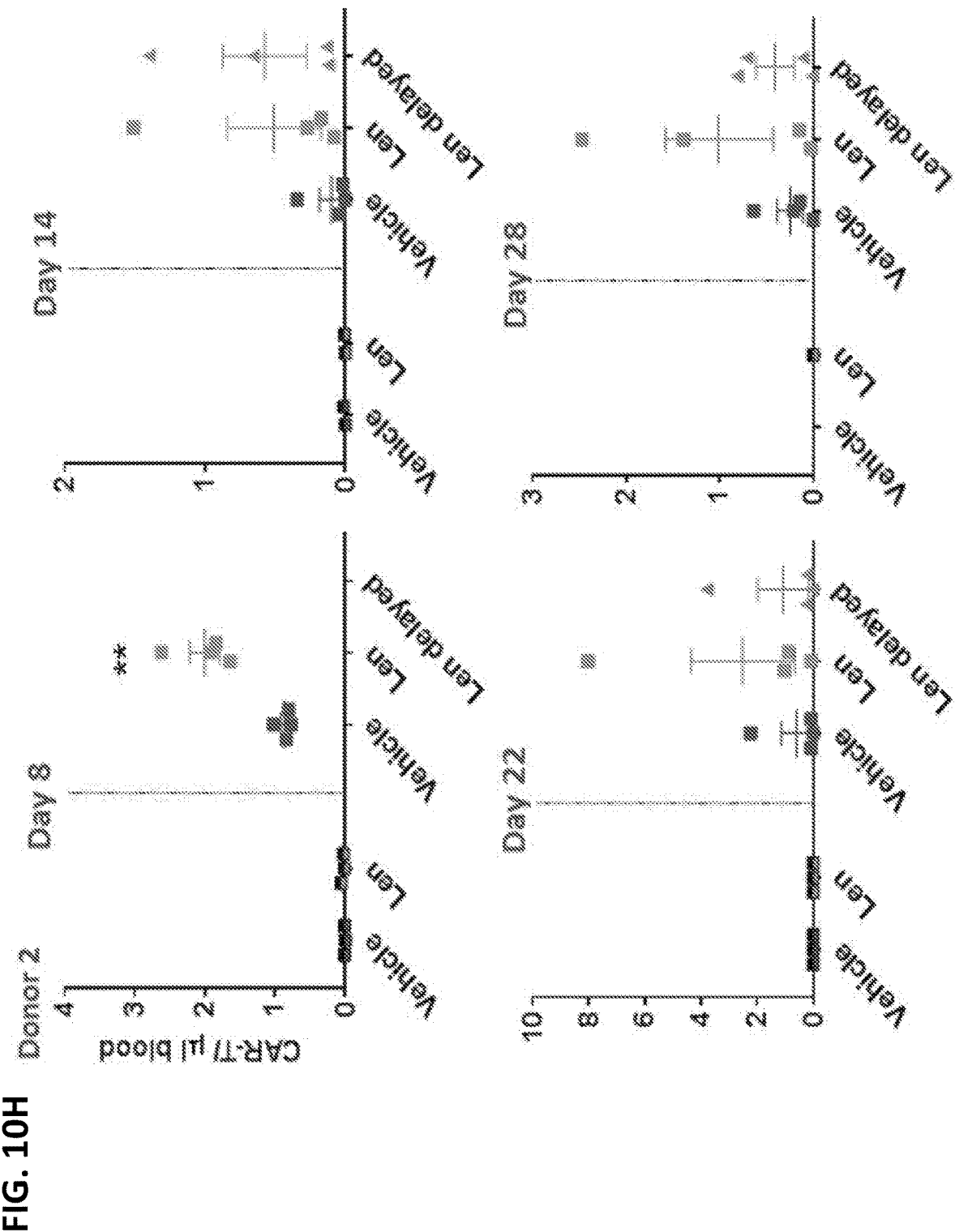

Blood from the treated mice was collected for CAR-T pharmacokinetic analysis, and cells were stained with antibodies to exclude mouse-specific cells (H2-kd, TER119, and muCD45) and analyzed by flow cytometry. Cells were gated on CD45+CD3+ CAR+ and the cells per microliter of blood was determined. For pharmacokinetic measurements, each time point was analyzed by one-way ANOVA and Tukey post-hoc test. FIGS. 10G and 10H show the flow cytometric analysis of mock control cells and CAR-T cells in the blood of the mice at days 8, 14, 22, and 28 following injection of the CAR-T cells from two donors. The results showed that increased CAR-T cell counts were observed in peripheral blood at early time points, particularly following concurrent administration of lenalidomide (** $P<0.01$).

Example 5 Effects of Lenalidomide on Anti-CD19 CAR Proliferation in Sub-Optimal Stimulation Anti-CD19 CAR-expressing T cells were generated by engineering CD4+ and CD8+ T cells (which had been isolated by immunoaffinity-based enrichment from healthy human donor subjects) with viral vector encoding the anti-CD19 CAR. The CAR contained an anti-CD19 scFv, an Ig-derived spacer, a human CD28-derived transmembrane domain, a human 4-1BB-derived intracellular signaling domain and a human CD3 zeta-derived signaling domain. The nucleic acid construct encoding the CAR also included a truncated EGFR (tEGFR) sequence for use as a transduction marker, separated from the CAR sequence by a self-cleaving T2A sequence.

Figure 11:
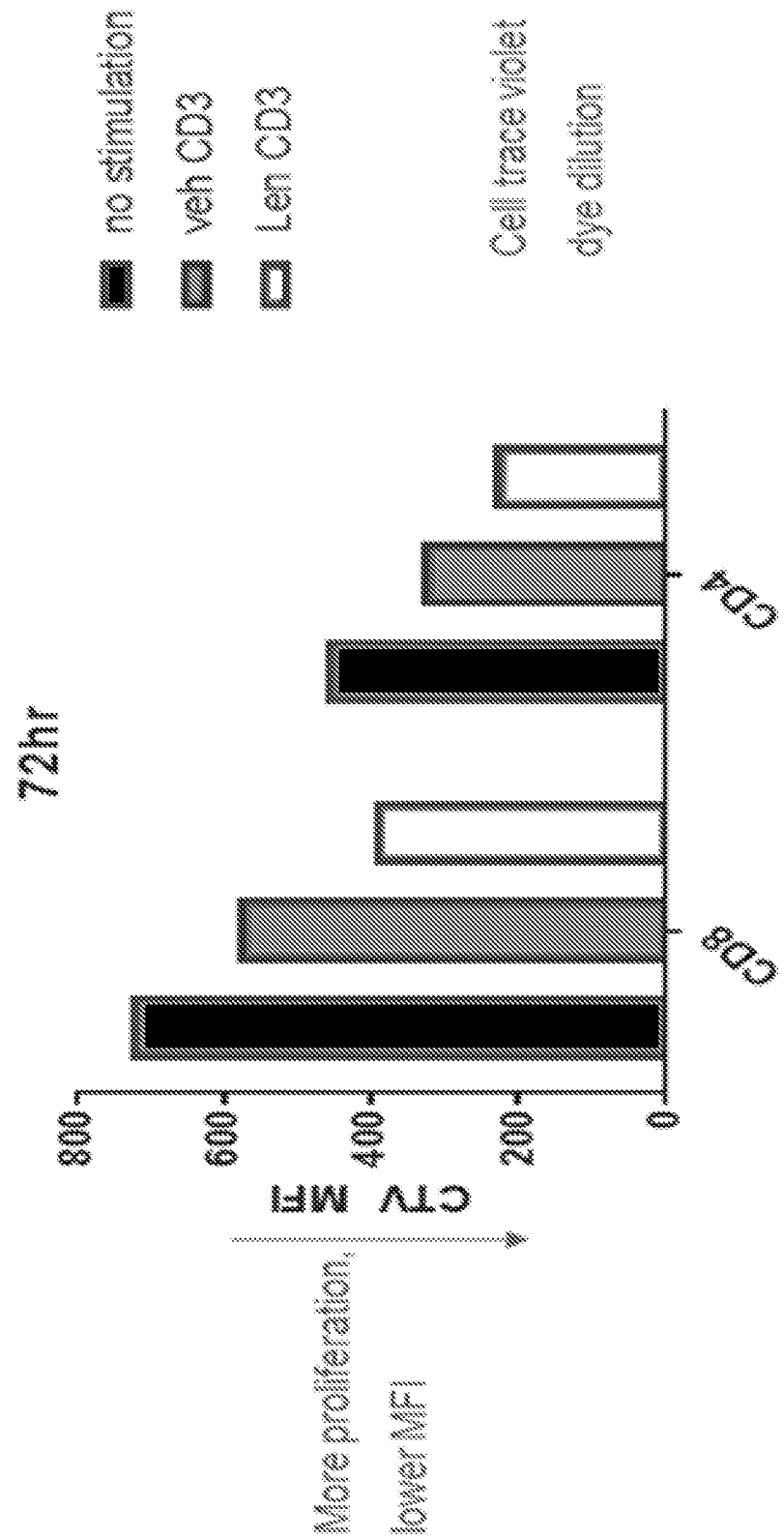
FIG. 11 shows the number of CD4+ and CD8+ T cells in cultures of anti-CD19 CAR T cells stimulated with a suboptimal concentration of anti-CD3 in the presence and absence of lenalidomide.

Anti-CD19 CAR T cells were subjected to sub-optimal stimulation via incubation with anti-CD3 (without a second reagent such as anti-CD28, designed to provide a costimulatory signal), in the presence of 5 µM lenalidomide or vehicle control. The anti-CD19 CAR-expressing T cells were labeled with CELLTRACE VIOLET dye (CTV; ThermoFisher Scientific, Waltham MA) prior to the incubation; proliferation was assessed by assessing dilution of the dye via flow cytometry. As shown in FIG. 11, in the context of the sub-optimal stimulatory conditions over a period of 72 hours, lenalidomide was observed to have enhanced proliferation of the CAR+ T cells.

Example 6 Observed Relationship Between Treatment Outcomes and Levels of Peripheral Blood CAR+ T Cells in Cohort of Human Subjects Administered Anti-CD19 CAR-Expressing Cells Treatment outcomes and numbers of CAR+ T cells in the blood, were evaluated in twenty eight adult subjects with relapsed or refractory (R/R) non-Hodgkin lymphoma (NHL) who had been administered autologous T cells expressing a CD19-targeting chimeric antigen receptor (CAR) including an anti-CD19 scFv antibody and a 4-1BB intracellular signaling domain (administered at approximately 1:1 ratio of CD4+ to CD8+ CAR+ T cells).

Prior to administration of the CAR-expressing T cells, subjects had been treated with 30 mg/m2 fludarabine daily for 3 days and 300 mg/m2 cyclophosphamide daily for 3 days. At d=0, subjects had been treated with 5×10[7] (DL-1) or 1×10[8] (DL-2) CAR-expressing T cells by intravenous infusion.

Response rates observed at a particular time-point in an ongoing study, are shown in Table E3 for a cohort of 20 Diffuse Large B-Cell Lymphoma (DLBCL) subjects treated with a single-dose of DL-1. As shown, an overall response rate (ORR) of 80% (16/20) was observed and 60% (12/20) of subjects were observed to have achieved complete remission (CR). 20% (4/20) of subjects exhibited partial response (PR) and 20% (4/20) exhibited progressive disease (PD). Of the subjects having been chemorefractory (having exhibited stable or progressive disease following last chemo-containing regimen or relapse less than 12 months after autologous SCT) prior to CAR+ T cell administration, the overall response rate was 83% (10 ORR, 7 CR, 3 PR, 2 PD, n=12). Among the subjects having been refractory (having exhibited less than complete remission following last treatment but not deemed chemorefractory), the overall response rate was 77% (13 ORR, 9 CR, 4 PR, 4PD, n=17).

TABLE E3

Overall Response

| | DLBCL Cohort, DL1 single-dose schedule | | |
|---|---|---|---|
| | All (n = 20) | Refractory* (n = 17) | Chemorefractory[†] (n = 12) |
| ORR, n (%) [95% CI] | 16 (80) [56, 94] | 13 (77) [50, 93] | 10 (83) [52, 98] |
| CR, n (%) [95% CI] | 12 (60) [36, 81] | 9 (53) [28, 77] | 7 (58) [28, 85] |
| PR | 4 (20) | 4 (24) | 3 (25) |
| PD | 4 (20) | 4 (24) | 2 (17) |

*<CR to last therapy
[†]SD or PD to last chemo-containing regimen or relapse <12 months after autologous SCT Of three DLBCL subjects that at the time of assessment had been treated with two doses of DL-1, two exhibited partial response (PR) and 1 exhibited progressive disease (PD). Among 2 subjects having at the time of assessment been treated with a single-dose of DL-2, both subjects were observed to achieve CR. Among a MCL cohort with a total of two subjected treated at the time of assessment with single-dose of DL-1 1 PR and 1 PD were observed. Two subjects with double-hit, three subjects with triple-hit, and four subjects with double-expressor DLBCL were observed to achieve responses (7 CR, 2 PR).

The number of CARP T cells in peripheral blood was determined at certain time points post-treatment using a transgene-specific reagent. The number of CD3+/CAR+ T cells in peripheral blood measured at certain time points post-infusion is shown for subjects grouped by best overall response in FIG. 12A. Higher peak CD3+/CAR+ T cells were observed in responders (CR/PR) than in subjects with progressive disease (PD). FIGS. 12B-D show levels of CD3+/CAR+ T cells, CD4+/CAR+ T cells, and CD8+/CAR+ T cells (cells/µL blood; mean±SEM) in subjects who achieved a response to treatment, grouped by durability of response (continued response (CR/PR) or PD at 3 months). The $C_{max}$ (CAR+ cells/µL blood) and area under the curve (AUC) for responders (CR/PR) and PD are shown in Table E4. The results were consistent with a conclusion that durable responses correlated with higher CD3+/CAR+ T cell levels in the blood. over time and at peak expansion.

TABLE E4

$C_{max}$ and $AUC_{0-28}$ Higher in Patients with CR/PR vs PD

| | CD3 | | CD4 | | CD8 | |
|---|---|---|---|---|---|---|
| | CR/PR (n = 16) | PD (n = 4) | CR/PR (n = 16) | PD (n = 4) | CR/PR (n = 16) | PD (n = 4) |
| $C_{max}$ (CAR+ cells/µL blood) | | | | | | |
| Mean (SD) | 612 (1919) | 2 (1) | 220 (754) | 1 (0.6) | 426 (1314) | 0.5 (0.5) |
| Median (Min, Max) | 33 (1, 7726) | 1 (1, 3) | 8 (1, 3040) | 1 (0, 2) | 4 (0, 5238) | 0.3 (0, 1) |

TABLE E4-continued $C_{max}$ and $AUC_{0-28}$ Higher in Patients with CR/PR vs PD

| | CD3 | | CD4 | | CD8 | |
|---|---|---|---|---|---|---|
| | CR/PR (n = 16) | PD (n = 4) | CR/PR (n = 16) | PD (n = 4) | CR/PR (n = 16) | PD (n = 4) |
| Q1, Q3 | 7, 123 | 0.7, 2 | 2, 46 | 0.6, 2 | 0.8, 104 | 0.1, 0.9 |
| | | | $AUC_{0-28}$ | | | |
| Mean (SD) | 5883 (18821) | 16 (13) | 2369 (8388) | 10 (7) | 3873 (11963) | 6 (6) |
| Median (Min, Max) | 196 (11, 75773) | 14 (4, 31) | 47 (7, 33740) | 9 (3, 17) | 23 (1, 47834) | 4 (1, 14) |
| Q1, Q3 | 52, 781 | 5, 26 | 16, 261 | 4, 16 | 4, 761 | 1, 10 |

Figure 13A:
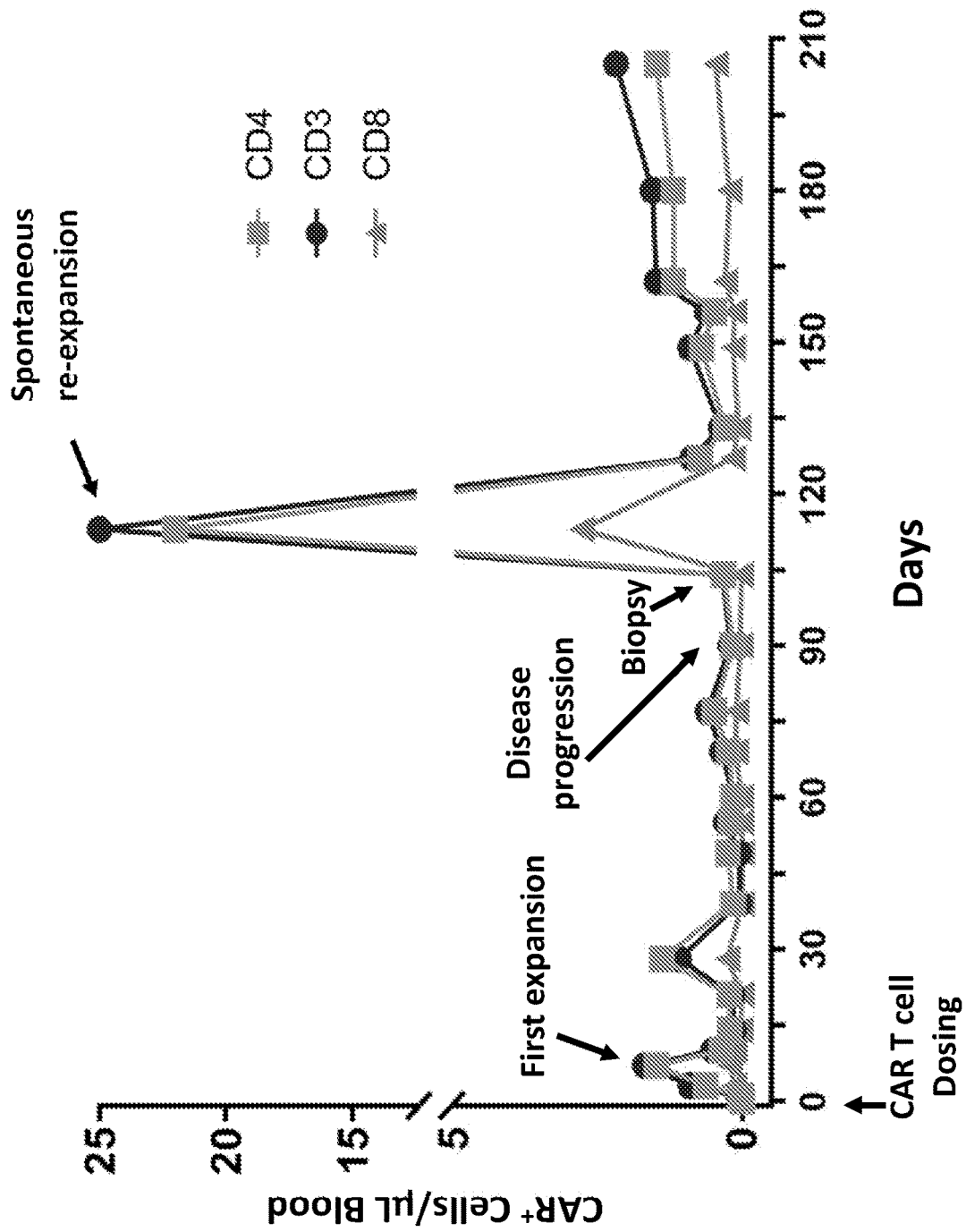
FIG. 13A shows the number of CD3+/CAR+, CD4+/CAR+, CD8+/CAR+ T cells in peripheral blood of a subject with chemorefractory transformed DLBCL measured at certain time points.
Figure 13D:
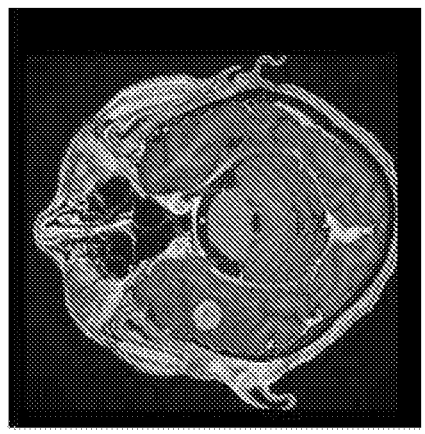
FIG. 13D is a pretreatment brain MRI (high-resolution $T_1$-weighted image with the use of contrast material; axial view) showing a homogeneously enhancing mass in the right middle cranial fossa.
Figure 13G:
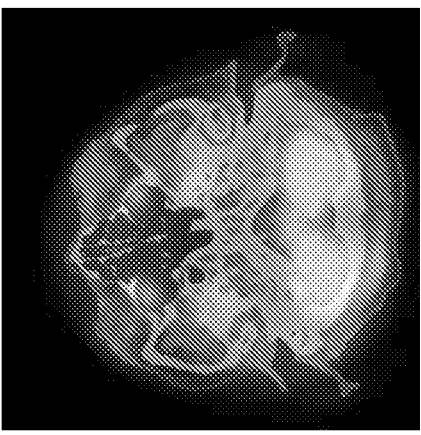
FIG. 13G is a PET-CT imaging showing resolution of the posterior auricular tumor after incisional biopsy and re-expansion of CAR+ T cells.
Figure 13C:
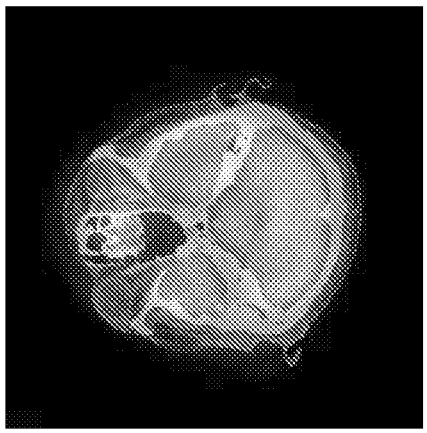
FIG. 13C is a post-treatment PET-CT image depicting resolution of the abnormality in FIG. 13B after treatment with anti-CD19 CAR+ T cells.
Figure 13F:
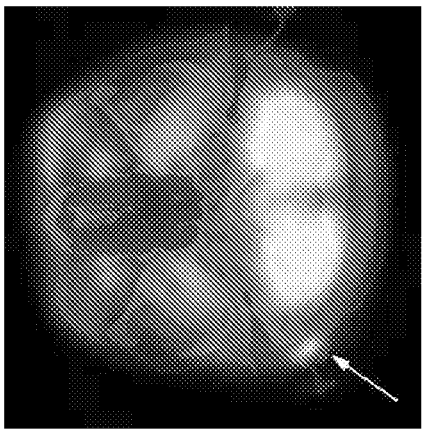
FIG. 13F is an axial PET-CT image at relapse showing right posteriour auricular tumor recurrence associated with intense uptake of $^{18}$F-flurodeoxyglycose (arrow).
Figure 13B:
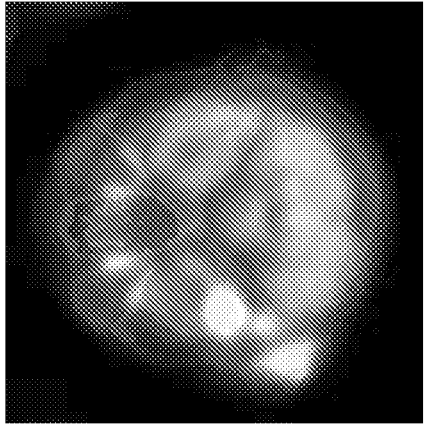
FIG. 13B depicts a pretreatment axial PET-CT image showing an intracranial abnormality in the right middle cranial foss and extensive abnormality in subcutaneous tissues in the right posterior auricular region.

For one subject with chemorefractory transformed DLBCL (germinal center subtype with a BCL2 rearrangement and multiple copies of MYC and BCL6) who had been administered the CAR+ T cells at DL-1, numbers of CD3+/CAR+, CD4+/CAR+, CD8+/CAR+ T cells in peripheral blood, measured at certain time points, are shown in FIG. 13A. The subject had previously been treated with, and was refractory to, five prior lines of therapy including dose-adjusted etoposide, doxorubicin, and cyclophosphamide with vincristine and prednisone plus rituximab (DA-EP-OCH-R) and intermediate-intensity allogenic stem-cell transplantation from an 8/8 HLA-matched unrelated donor. Following allogeneic stem cell transplantation and prior to receiving CAR+ T cells, the subject showed 100% donor chimerism in all blood lineages, had ceased taking immunosuppressive therapy, and did not have graft versus host disease (GVHD). Prior to administration of CAR+ T cells, the subject had a periauricular mass and temporal lobe lesion observed by positron-emission tomography and computed tomography (PET-CT) (FIG. 13B) and confirmed by magnetic resonance imaging (MRI) (FIG. 13D).

Figure 13E:
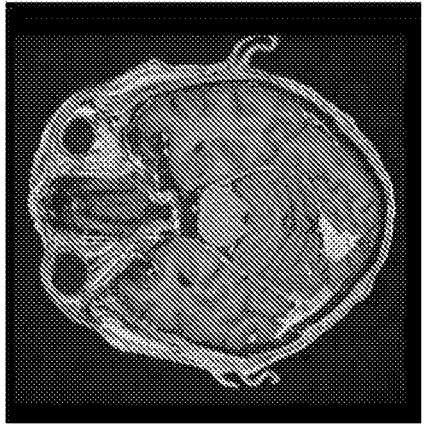
FIG. 13E is a post-treatment MRI image showing near-complete resolution of the enhancing mass.

After receiving anti-CD19 CAR-T cell treatment, the subject achieved CR 28 days post-infusion, as shown by PET-CT (FIG. 13C) and brain MRI (FIG. 13E), with no observed signs of neurotoxicity or CRS. Three months post-infusion of the CAR-T cells, relapse of the periauricular mass was noted in this subject (FIG. 13F), and an incisional biopsy was performed. As shown in FIG. 13A, following biopsy, the visible tumor receded with no further therapy. Pharmacokinetic analysis showed a marked re-expansion of the CAR+ T cells in peripheral blood (to a level higher than initial expansion observed, with peak levels observed at about 113 days post-infusion) i, which coincided with tumor regression. The subject then went on to achieve a second CR, as confirmed by restaging PET-CT one month following the biopsy (FIG. 13G), and remained in CR at 6 months post CAR-T cell infusion. Further assessment of the subject showed that the CNS response was durable and the subject remained in CR at 12 months.

The results are consistent with a conclusion that re-expansion and activation of CAR+ T cells can be initiated in vivo following reduction or loss of functional or active CAR+ T cells and/or relapse following anti-tumor response to CAR-T cell therapy. Further, following re-expansion in vivo late after initial CAR+ T cell infusion, the CAR+ T cells are able to re-exert anti-tumor activity. This result supports that CAR+ T cell re-expansion and activation can be triggered in vivo and that methods of reactivating CAR+ T cells, may further augment their efficacy.

Figure 14:
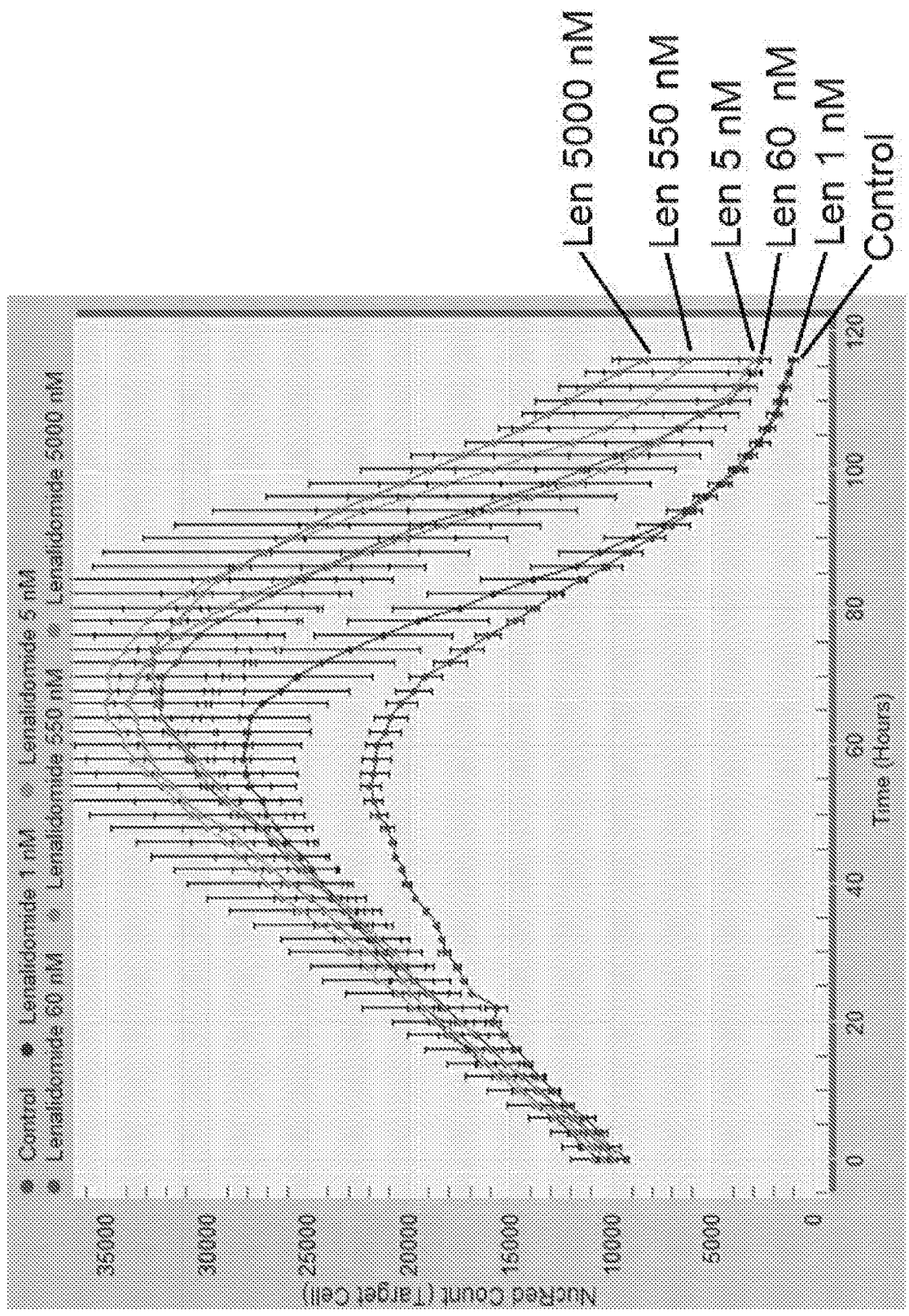
FIG. 14 shows the level of viable target cells over a period of approximately 120 hours when anti-CD19 CAR+ T cells are incubated with K562-CD19 effector cells at an effector to target cell (E:T) ratio of 5:1 in the presence or absence of 1 nM, 5 nM, 60 nM, 550 nM or 5000 nM lenalidomide or in the absence of lenalidomide (control).

Example 7 Effects of Lenalidomide on Anti-CD19 CAR T Cell Activity Following Serial Restimulation Anti-CD19 CAR+ T cells, generated substantially as described in Example 5, were thawed and were incubated with CD19-expressing cells (K562 cells transduced to express CD19) at an effector to target cell (E:T) ratio of 2.5:1 in the presence or absence of 1 nM, 5 nM, 60 nM, 550 nM or 5000 nM lenalidomide or in the absence of lenalidomide (control). The target K562-CD19 cells were labeled with NucLight Red (NLR) as described in Example 1 to permit tracking of target cells by microscopy. Cytolytic activity was assessed by measuring the loss of viable target cells over a period of about 120 hours, as determined by red fluorescent signal (using the IncuCyte® Live Cell Analysis System, Essen Bioscience). Cells from each condition were plated in triplicate. As shown in FIG. 14, the results were consistent with a conclusion that the presence of lenalidomide reduced CAR-mediated cytolytic activity in this assay. In similar assays, results varied depending on E:T ratios and with different anti-CD19 CAR+ T cell compositions (e.g., generated at different times and/or from cells from different donors).

Figure 15A:
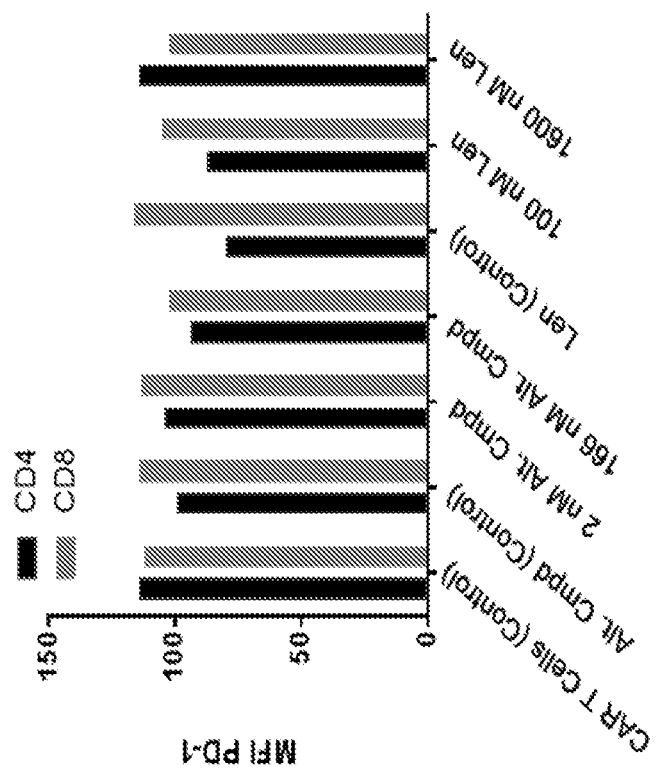
FIG. 15A shows the levels of CD25+ expression in both CD4+ and CD8+ T cells when anti-CD19 CAR+ T cells are incubated with K562-CD19 effector cells in the presence of lenalidomide or an alternative compound targeting a kinase.
Figure 15B:
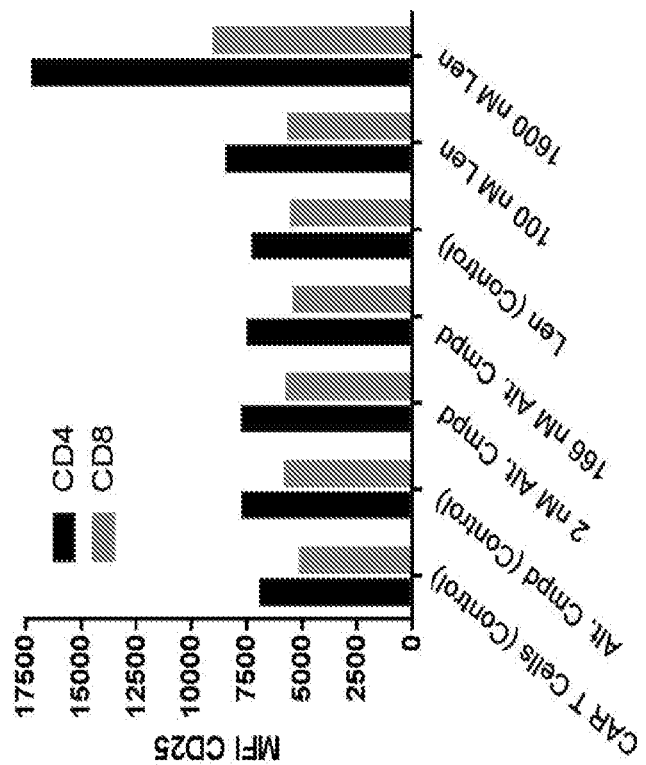
FIG. 15B shows the levels of CD25+ expression in both CD4+ and CD8+ T cells when anti-CD19 CAR+ T cells are incubated with PD-1 effector cells in the presence of lenalidomide or an alternative compound targeting a kinase.

In another study, anti-CD19 CAR+ T cells were incubated with K562-CD19 effector cells at a 2.5:1 E:T ratio in the presence of 100 nM or 1600 nM lenalidomide, 2 nM or 166 nM of an alternative compound targeting a kinase, vehicle control or in the absence of added compound (CAR-T control). After 120 hours of culture, cells were isolated and assessed by flow cytometry for surface expression of CD25 or PD-1 in CD4+ or CD8+ T cell subsets. As shown in FIG. 15A, incubation of anti-CD19 CAR+ T cells with K562-CD19 effector cells in the presence of the highest concentration of lenalidomide (e.g., 1600 nM) resulted in higher levels of CD25 expression in both CD4+ and CD8+ T cells as compared to other conditions. No difference in surface expression of PD-1 was observed in CD4+ or CD8+ T cells in the presence of lenalidomide, even at the highest concentration of 1600 nM (FIG. 15B).

Figure 16:
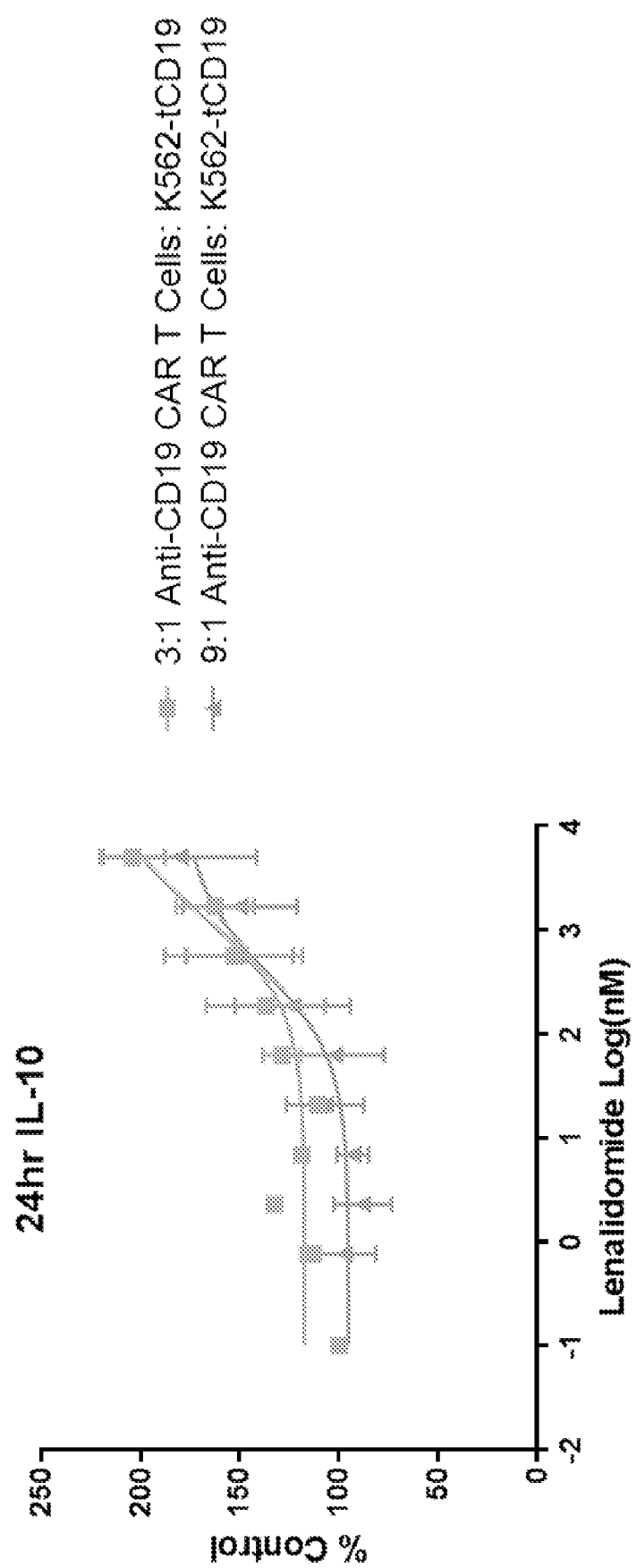
FIG. 16 shows the amount of IL-10 in culture supernatants after incubating anti-CD19 CAR+ T cells with K562-CD19 effector cells at an effector to target cell (E:T) ratio of 3:1 or 9:1, in the presence or absence of various concentrations of lenalidomide.

In a further study, the amount of IL-10 was assessed in culture supernatants after incubating, for 24 hours, anti-CD19 CAR+ T cells with K562-CD19 effector cells at an effector to target cell (E:T) ratio of 3:1 or 9:1, in the presence or absence of various concentrations of lenalidomide. As shown in FIG. 16, lenalidomide dose-dependently increased secretion and/or accumulation of IL-10 in supernatants of T cell cultures.

Figure 17A:
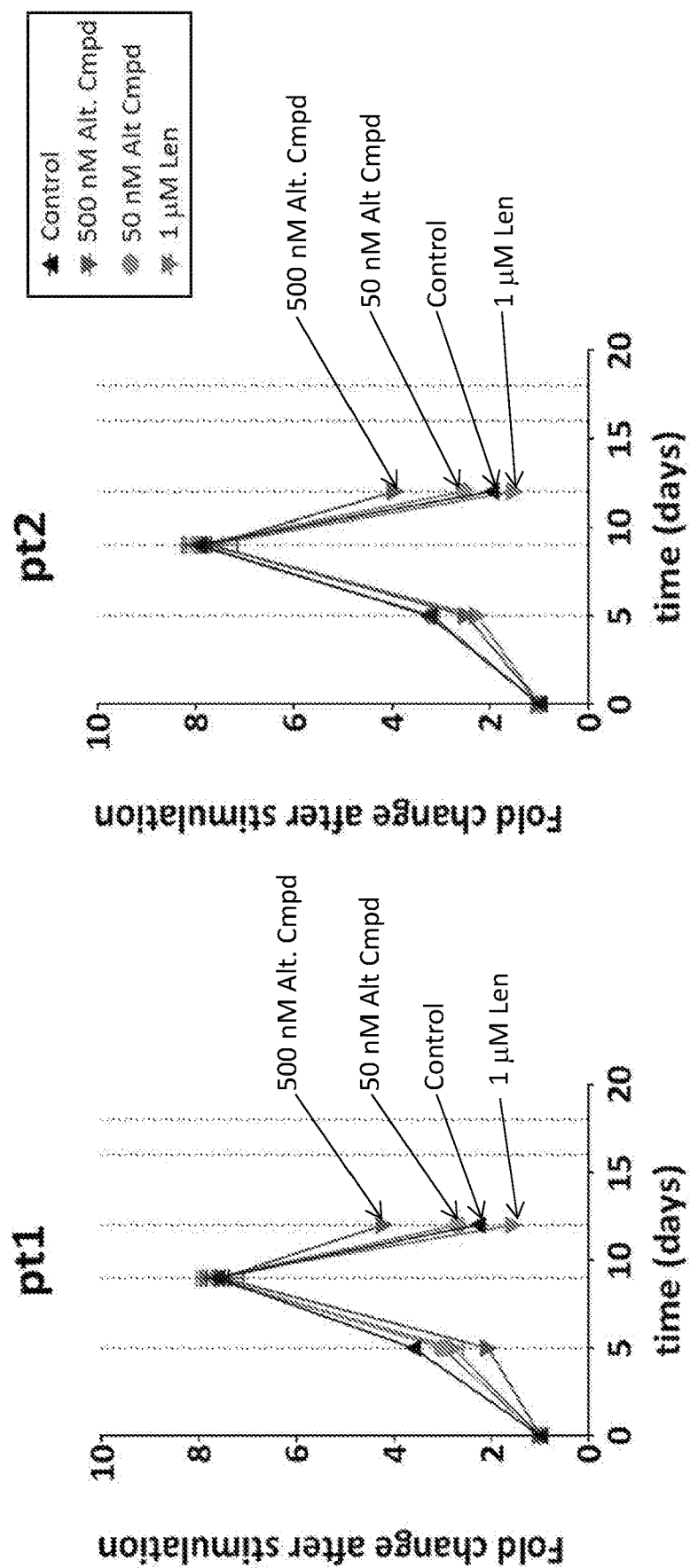
FIG. 17A shows the fold-change of cell number after stimulation of anti-CD19 CAR+ T cells from two donors (pt 1 and pt 2) with K562-CD19 effector cells in the presence or absence of 1 μM lenalidomide or 50 nM or 500 nM of an alternative compound targeting a kinase.
Figure 17B:
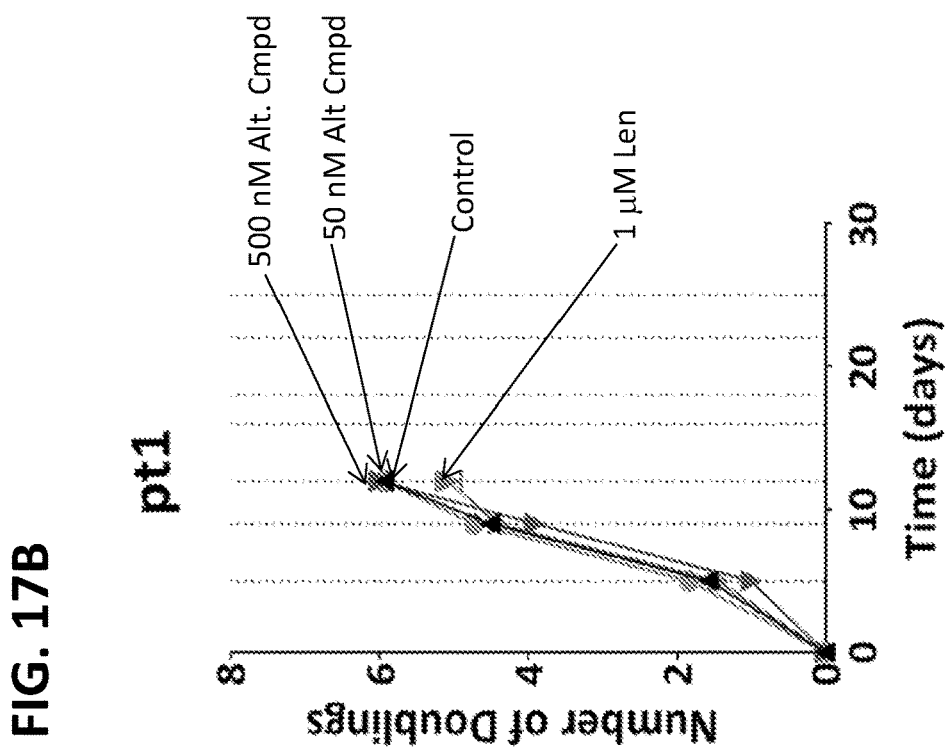
FIG. 17B shows the number of cell doublings compared to the initial number after the $2^{nd}$ and $4^{th}$ stimulations.

Example 8 Effects of Lenalidomide on Anti-CD19 CAR T Cell Expansion Following Serial Restimulation The ability of anti-CD19 CAR+ T cells to expand ex vivo following repeated stimulations was assessed using methods substantially as described in Example 2. Anti-CD19 CAR+ T cells, generated from two donors (pt1 and pt2) substantially as described in Example 5, were cultured with irradiated K562 cells transduced to express CD19 (K562-CD19 cells) at an effector target ratio of 2.5:1 in the presence or absence of 1 µM lenalidomide or 50 nM or 500 nM of an alternative compound targeting a kinase. For each donor, cells were harvested every 3-5 days from each experimental condition in the wells and counted, and restimulated with new target cells using the same culture conditions after resetting cell number to initial seeding density for each round. A total of 4 rounds of stimulation during a 12 day culture period were carried out. For each round of stimulation, the total number of cells was determined, and the results were depicted as the fold-change of cell number after stimulation (FIG. 17A) or number of doublings compared to initial number (FIG. 17B). As shown in FIGS. 17A and 17B, no change or only a minor effect in cell expansion of anti-CD19 CAR+ T cells was observed in this restimulation assay when cells were cultured in the presence of lenalidomide versus in the absence of lenalidomide.

At each reset after the pretreatment, cytolytic activity was assessed by incubation of the retimulated cells with the K562-CD19 cells (labeled with NucLight Red (NLR)) at an effector to target cell (E:T) ratio of 1 µM lenalidomide or 50 nM or 500 nM of the alternative compound. Cytolytic activity was assessed by measuring the loss of viable target cells over a period of up to 40-60 hours, as determined by red fluorescent signal (using the IncuCyte® Live Cell Analysis System, Essen Bioscience). Cells from each condition were plated in triplicate. Representative cell killing observed at the 2nd and 4th restimulation for both donors is shown in FIG. 18A (as normalized to K562-CD19-Nuc-labeled cells at t=0) or in FIG. 18B (% cell killing compared to vehicle only control (set at 100%)). As shown in FIGS. 18A and 18B, incubation with lenalidomide was observed to result in a decrease in anti-CD19 CAR+ T cell cytolytic activity in this assay, under the tested stimulation conditions.

Example 9 Generation of BCMA Conjugated Beads

B cell maturation antigen (BCMA) was conjugated to beads by covalently coupling a BCMA-Fc fusion polypeptide, containing soluble human BCMA fused at its C-terminus to an Fc region of IgG, to the surface of commercially available tosyl-activated magnetic beads (ThermoFisher, Waltham MA). The beads are superparamagnetic, non-porous, monodisperse, tosylactivated beads that covalently bind primary amino and sulfhydryl groups. Conjugation was performed using beads having a diameter of approximately 2.8 µm (designated M-280) or 4.5 µm (designated M-450).

The BCMA-Fc (SEQ ID NO: 22) contained the extracellular domain of human BCMA (GenBank No. NP_001183.2) and a human IgG1 Fc connected with a linker as follows:

```
    (extracellular domain of BCMA; SEQ ID NO: 18)
MLQMAGQCSQNEYFDSLLHACIPCQLRCSSNTPPLTCQRYCNASVTNSVKG TNA
                        (linker; SEQ ID NO: 19)
GGGGS
                        (Hum IgG1 Fc; SEQ ID NO: 20)
PKSSDKTHTCPPCPAPEAEGAPSVFLFPPKPKDTLMISRTPEVTCVVVDVS

HEDPEVKFNWYVDGVEVHNAKTKPREEQYNSTYRVVSVLTVLHQDWLNGKE

YKCKVSNKALPSSIEKTISKAKGQPREPQVYTLPPSRDELTKNQVSLTCLV

KGFYPSDIAVEWESNGQPENNYKTTPPVLDSDGSFFLYSKLTVDKSRWQQG

NVFSCSVMHEALHNHYTQKSLSLSPGK.
```

The clone encoding the human BCMA-Fc fusion construct with the N-terminal CD33 leader sequence (SEQ ID NO: 21) was inserted into an expression vector and expressed in HEK 293 cells. The resulting BCMA-Fc fusion protein was determined to have a purity of greater than 95% as assessed by gel permeation chromatography. To test binding, the BCMA-Fc fusion protein was incubated with T cells expressing anti-BCMA CARs and T cells expressing CARs that do not bind to BCMA. Results from flow cytometry indicated that the BCMA-Fc fusion protein specifically bound to anti-BCMA CAR expressing T cells.

Various concentrations of the BCMA-Fc fusion protein ranging from 5 µg to 200 µg were added to approximately 1 mL of tocylactivated beads (e.g. containing about $4 \times 10^9$ tocylactivated beads having a diameter of 2.8 µm or about $4 \times 10^8$ tocylactivated beads having a diameter of 4.5 µm). Covalent coupling was performed by overnight incubation at 37° C. in phosphate buffered solution (PBS) containing 0.1% human serum albumin (HSA). Beads were washed and resuspended in 1 mL PBS with 0.1% HSA. After conjugation, the bead concentration was determined using a Cellometer. In the examples below, the BCMA-conjugated beads used in various studies are referred to with reference either to the amount of BCMA-Fc antigen added per mL or the antigen concentration (µg/mL) during the conjugation, e.g. 5 µg or 5 µg/mL; 50 µg or 50 µg/mL; 200 µg or 200 µg/mL and so on.

Example 10 Assessment of T Cell Markers on Anti-BCMA CAR+ T Cell Stimulated with BCMA-Conjugated Beads in the Presence or Absence of Lenalidomide BCMA-conjugated beads (diameter of 4.5 µm) conjugated with various amounts of BCMA antigen as described in Example 9 were incubated with anti-BCMA CAR+ T cells in the presence or absence of lenalidomide, and the expression of T cell markers were assessed.

Approximately $1.5 \times 10^6$ CAR+ T cells were added to wells of a 12-well plate and were incubated with beads from a 200 µg/ml BCMA-conjugated bead composition at a ratio of CAR+ T cell to BCMA-conjugated bead of 1:0.3, 1:1 or 1:3 (approximately $0.5 \times 10^6$, $1.5 \times 10^6$, and $4.5 \times 10^6$ beads per well, respectively). As controls, 5 µg/mL anti-CD3 antibody was coated to wells (sub-optimal concentration for stimulation) or cells were seeded in the absence of any agent (no stimulation control). Each condition was incubated in the presence or absence of 5 µM lenalidomide. The cells were incubated for four days and then analyzed by flow cytometry for surface expression of CD4, CD8, Tim3, PD-1, CD25 and CD69.

Figure 19A:
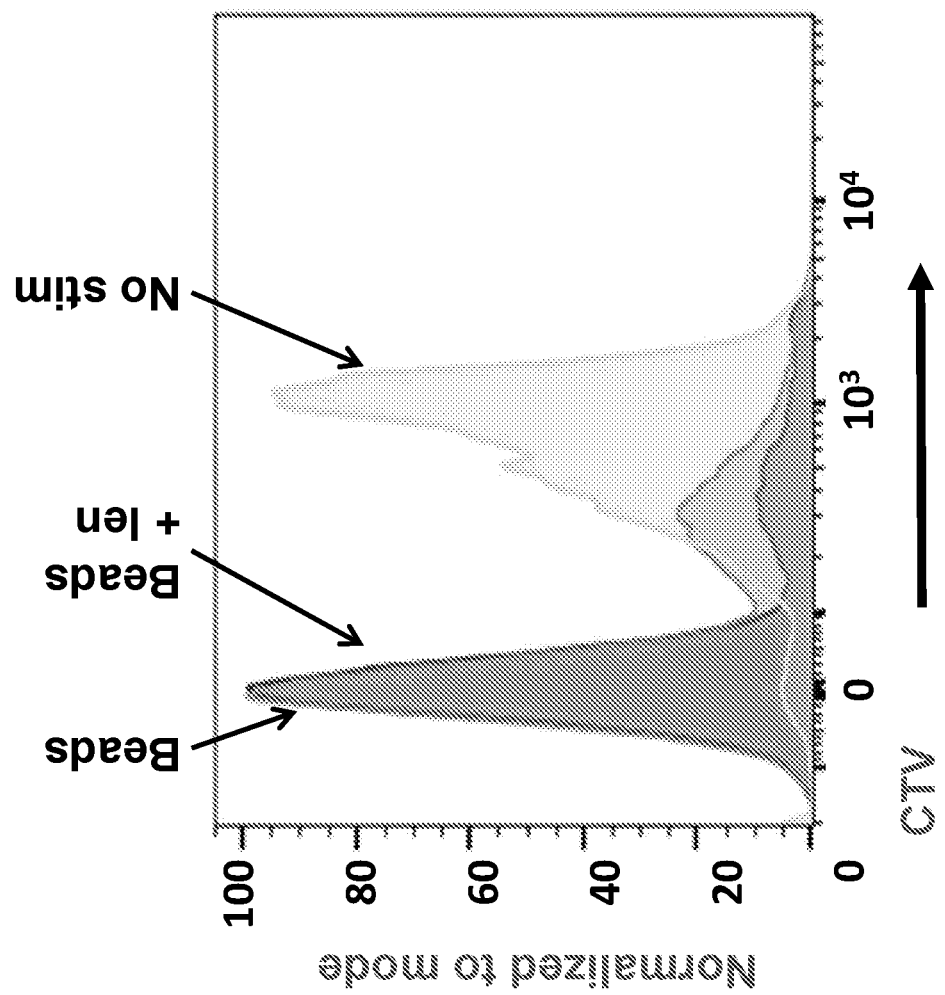
FIG. 19A shows a histogram plot of CTV staining of total cells in an anti-BCMA CAR+ T cell composition after incubation with beads (200 μg/mL BCMA-conjugated bead composition) at a ratio of 1:1 T cells to beads and in the presence or absence of 5 μM lenalidomide.
Figure 19C:
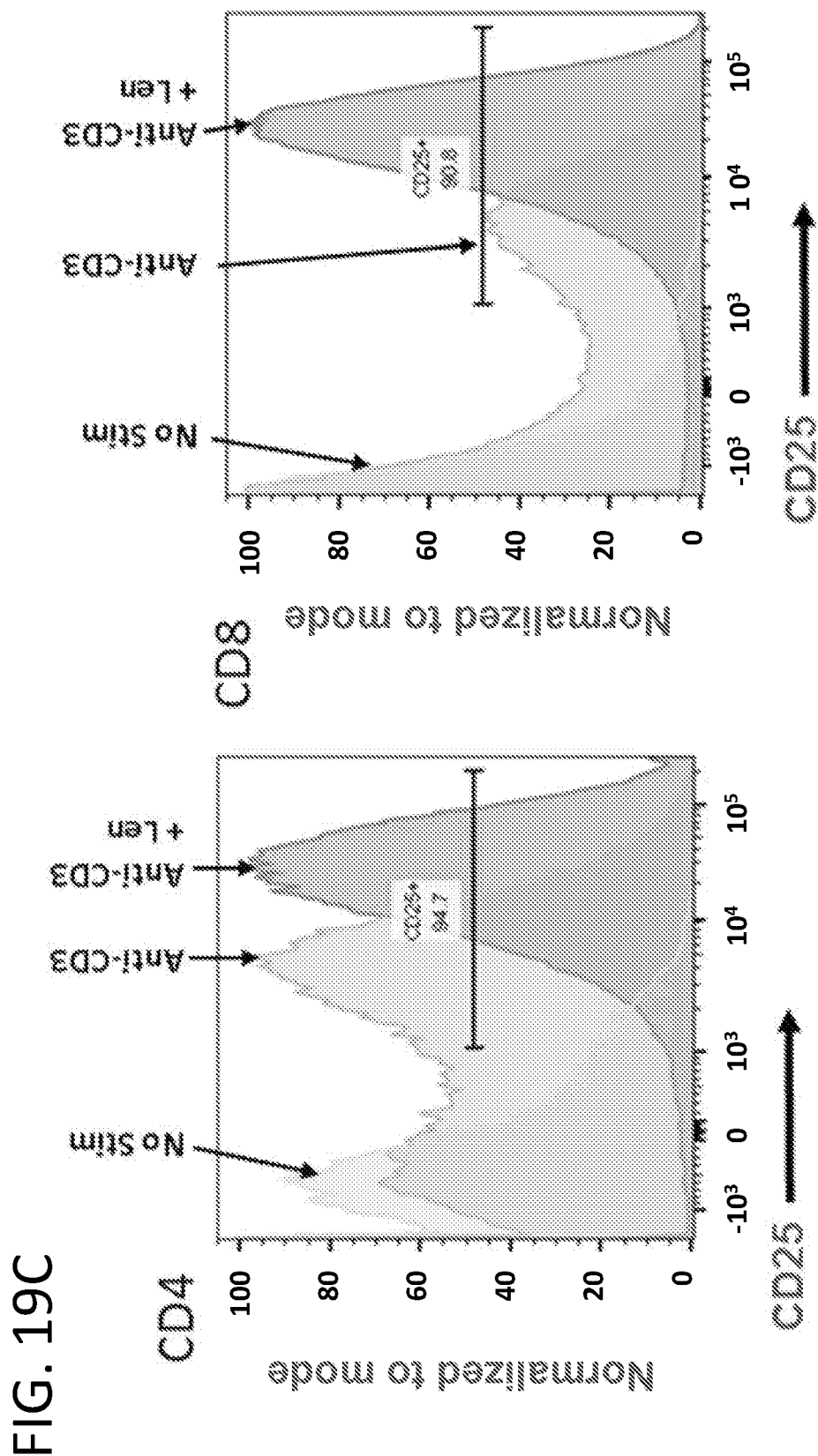

As shown in FIG. 19A, the presence of 5 µM lenalidomide increased the proliferative capacity of T cells (observed by decrease in intensity of CTV dye) following incubation for three days with beads conjugated with 200 µg BCMA antigen at a ratio of 1:1 T cells to beads compared to incubation with the beads in the absence lenalidomide (vehicle control). As shown in FIGS. 19B and 19C, the presence of lenalidomide during the incubation further increased the extent of surface expression of CD25 in CD4$^+$ and CD8$^+$ T cells induced after incubation of anti-BCMA CAR+ T cells with BCMA-conjugated beads (FIG. 19B) or anti-CD3 stimulation (FIG. 19C).

In a further experiment, anti-BCMA CAR-T cell compositions produced substantially as described in Example 1 were plated in 96-well plates at a density of 5×10$^5$ cells per well. The tested CAR-T cell compositions contained, on average, approximately 45% anti-BCMA CAR+ cells at plating. Cells from each composition were incubated for 18 hours in the presence of beads from a 5 µg/ml, 50 µg/ml, or 200 µg/ml BCMA-conjugated bead composition at a ratio of 1:1 T cells to beads. As a control, cells were incubated with anti-CD3/anti-CD28 antibody-conjugated beads (positive control) or no added agent (negative control). The incubations were carried out in the absence of lenalidomide or in the presence of 0.5 µM or 5 µM lenalidomide. Following the incubation, the cells were treated with reagents that allowed for extracellular and intracellular antibody staining by flow cytometry for the transcription factors Blimp1, EOMES, GATA-3, ikaros, helios, and Tbet and markers CD25, CD31, and PD-1.

Figure 20A:
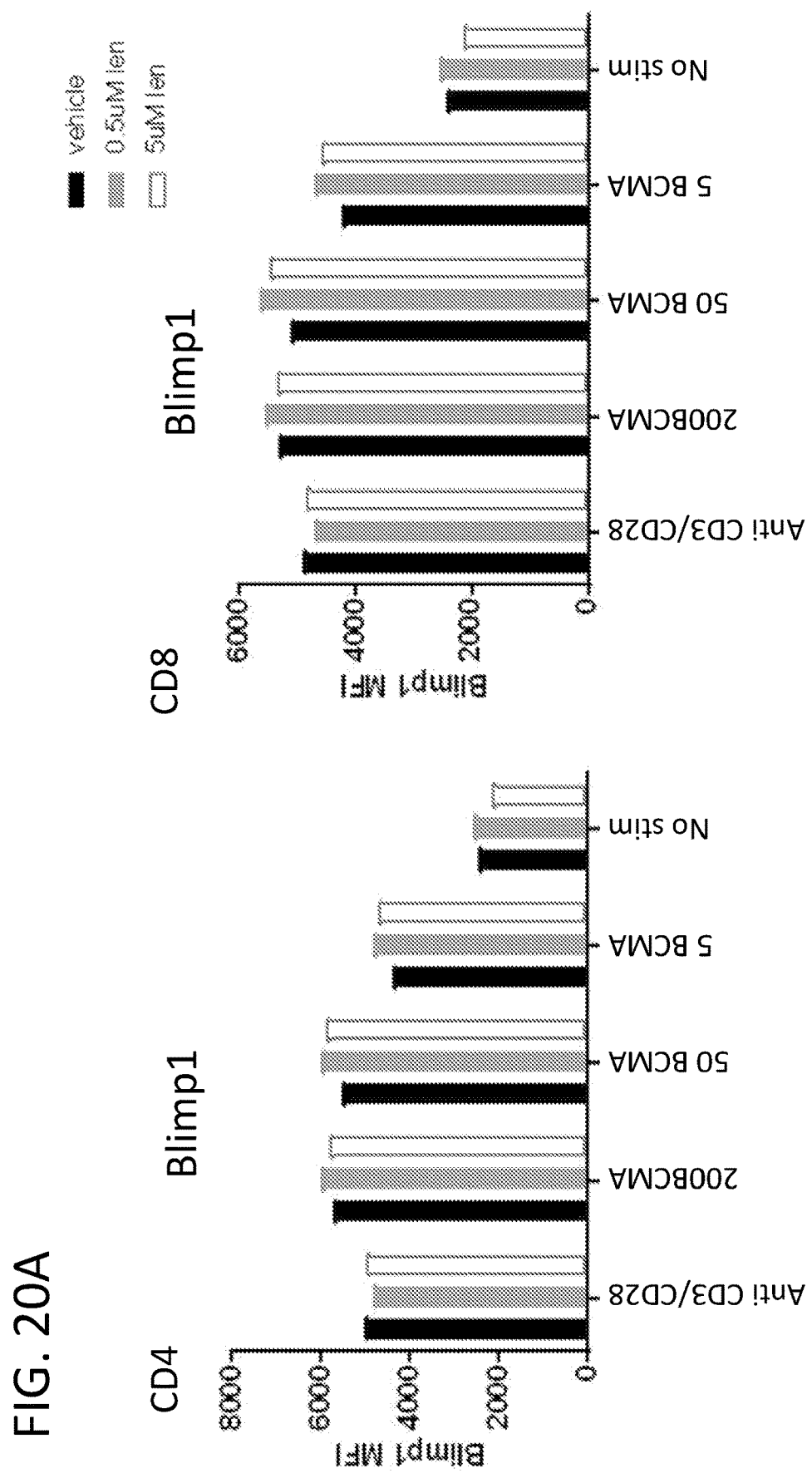
FIGS. 20A-20I show graphs displaying the levels of transcription factors and activation markers in or on CD4+ T cells (left panels) or CD8+ T cells (right panels) present in an anti-BCMA CAR+ T cell composition after incubation without stimulation or with different amounts of BCMA-conjugated bead or anti-CD3 and anti-CD28 conjugated beads and in the presence of 0 μM, 0.5 μM, or 50 μM lenalidomide. Levels of Blimp1 (FIG. 20A), CD25 (FIG. 20B), CD31 (FIG. 20C), PD-1 (FIG. 20D), Tbet (FIG. 20E), EOMES (FIG. 20F), GATA3 (FIG. 20G), Helios (FIG. 20H), and Ikaros (FIG. 20I) are shown. 200 BCMA, 50 BCMA, and 5 BCMA indicate BCMA-conjugated beads generated by incubating BCMA with the beads in an amount of 200, 50, and 5 μg of BCMA per approximately $4\times10^8$ beads, respectively.
Figure 20B:
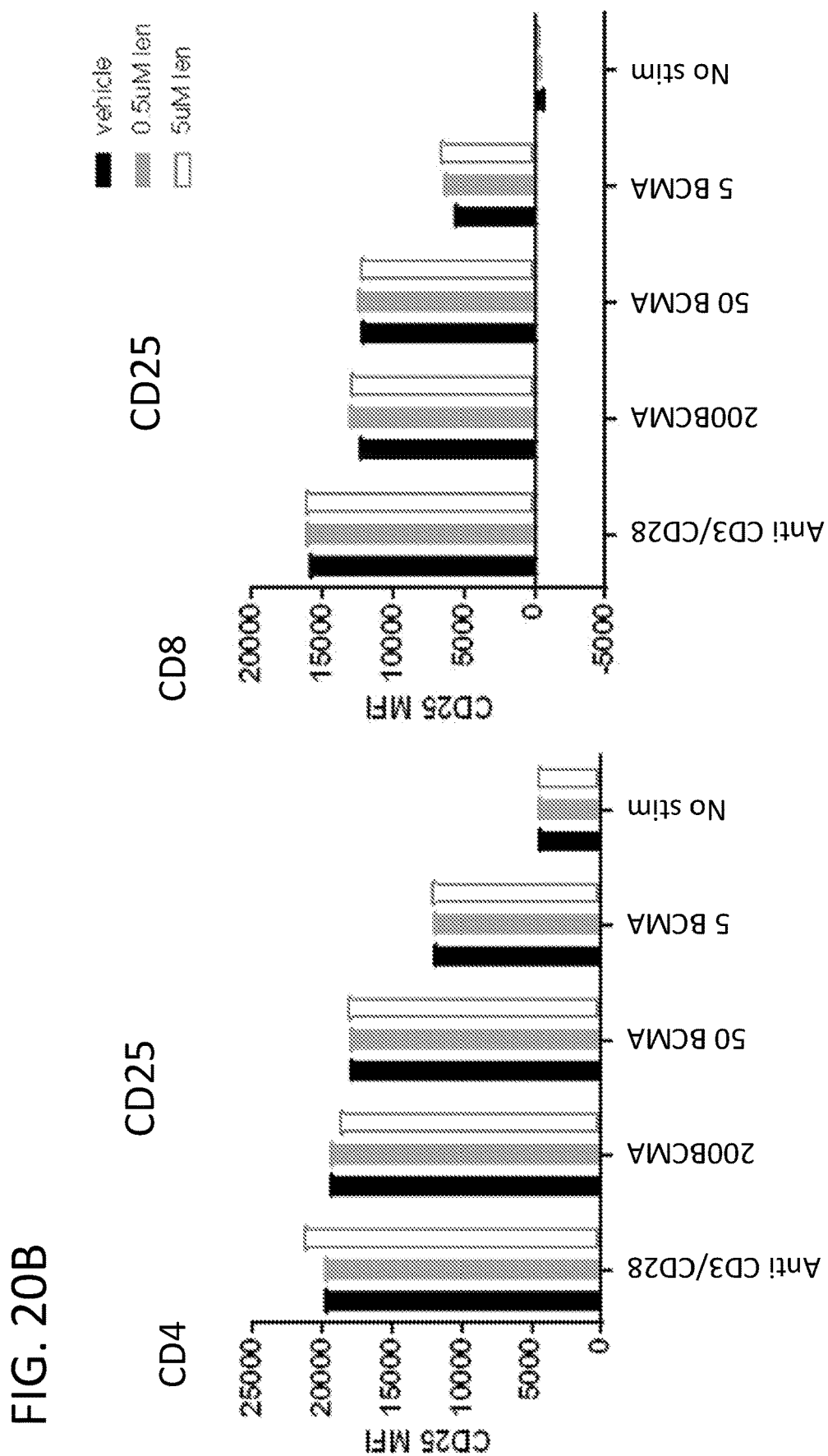
Figure 20C:
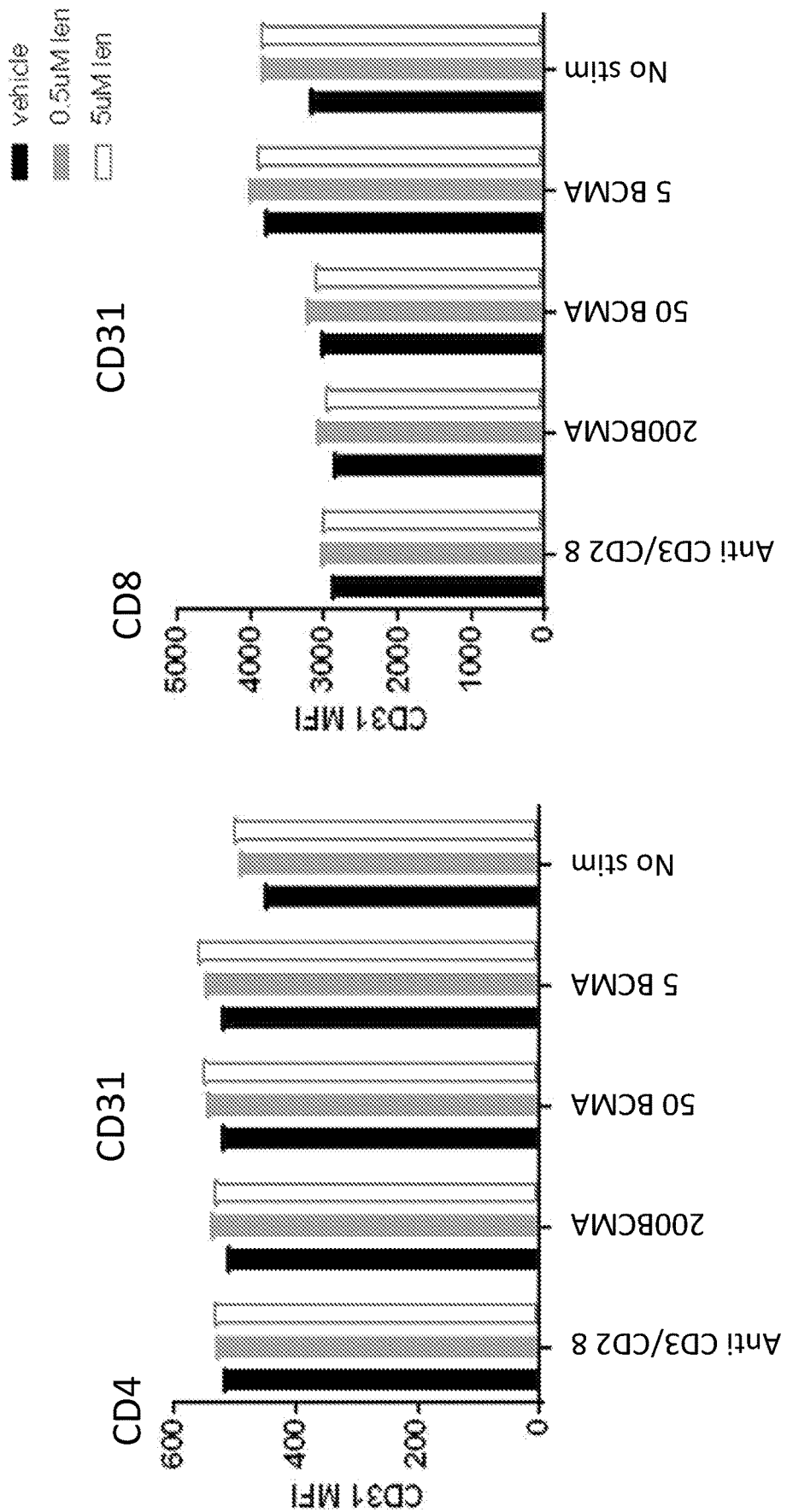
Figure 20D:
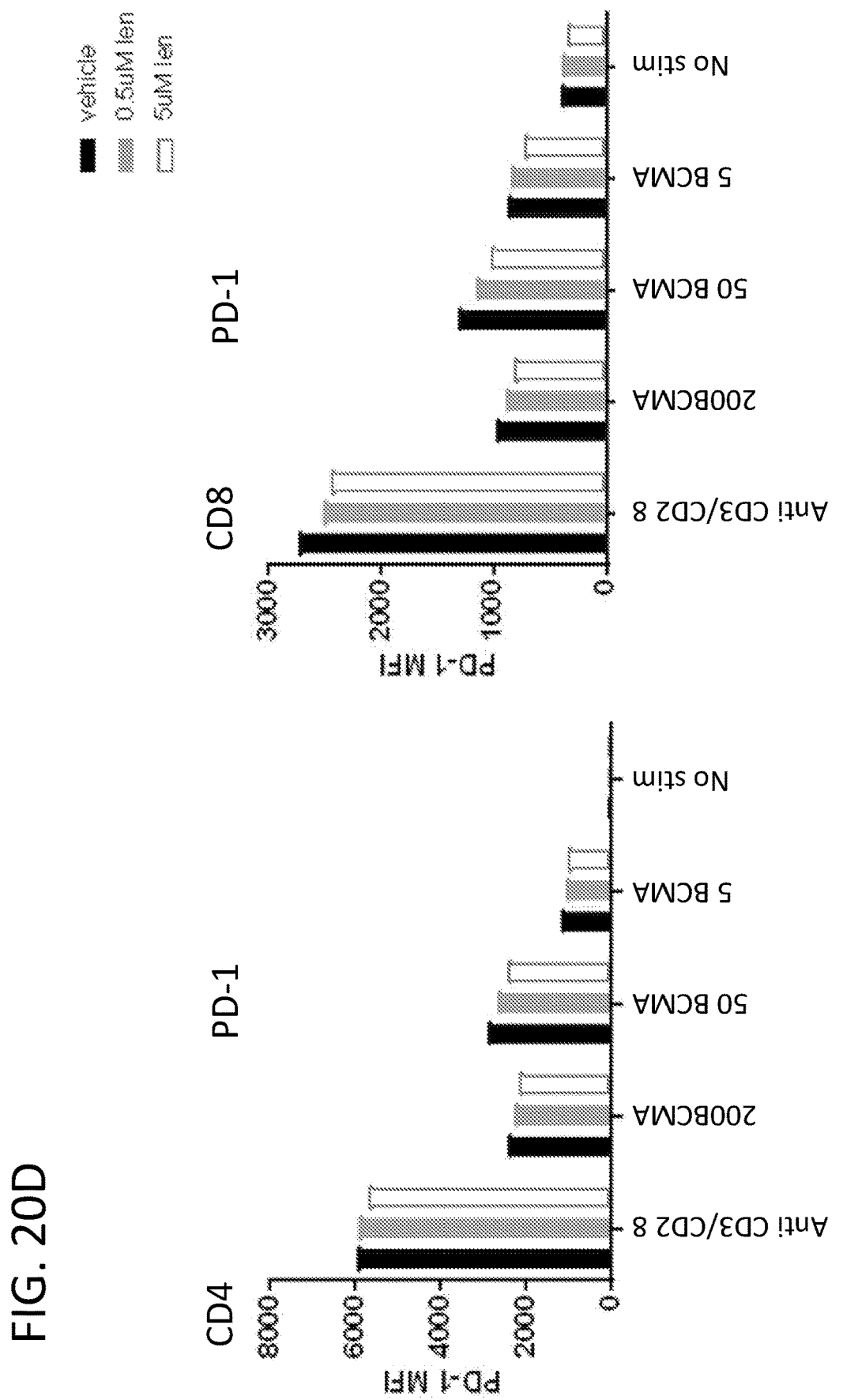
Figure 20E:
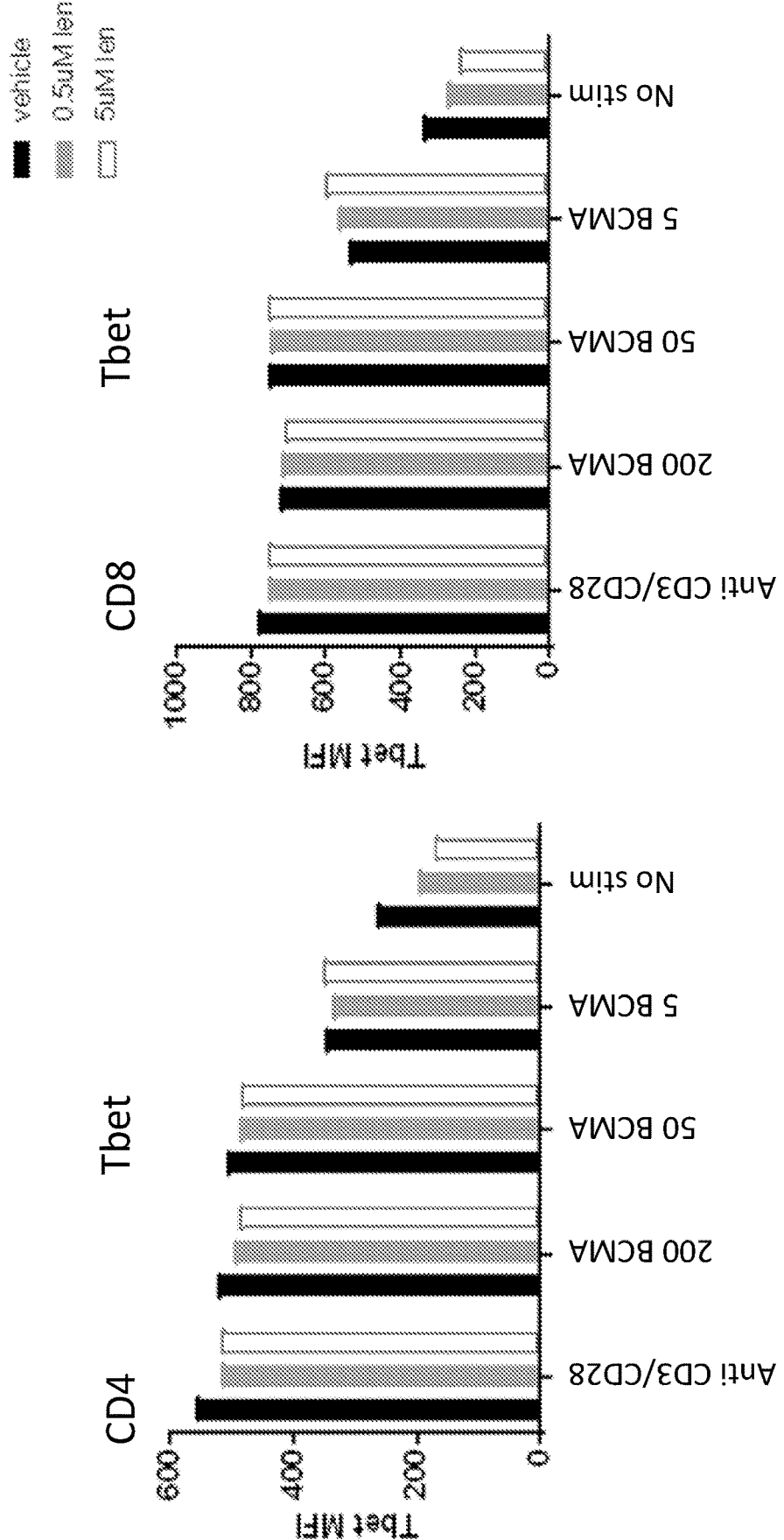
Figure 20F:
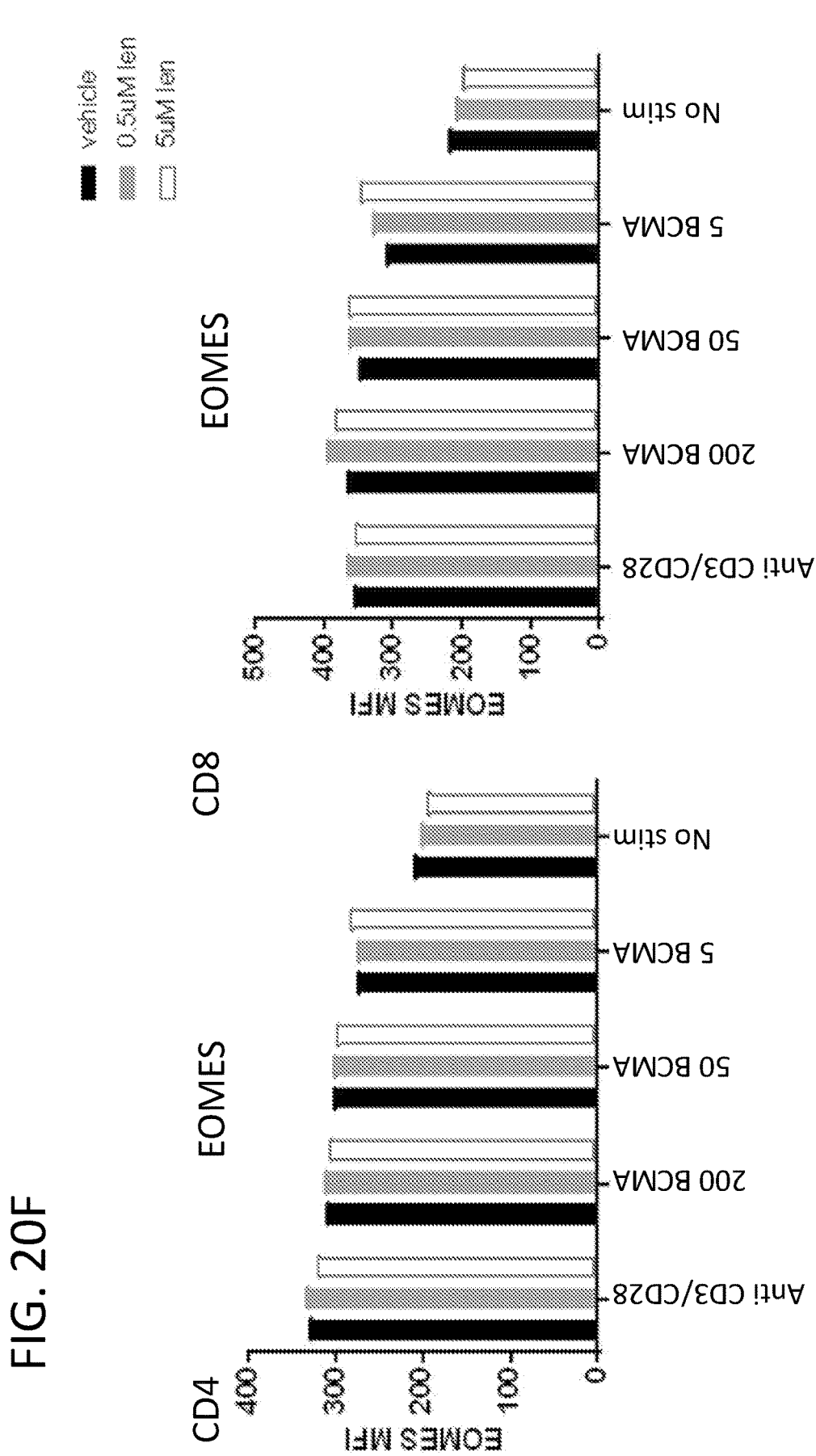
Figure 20G:
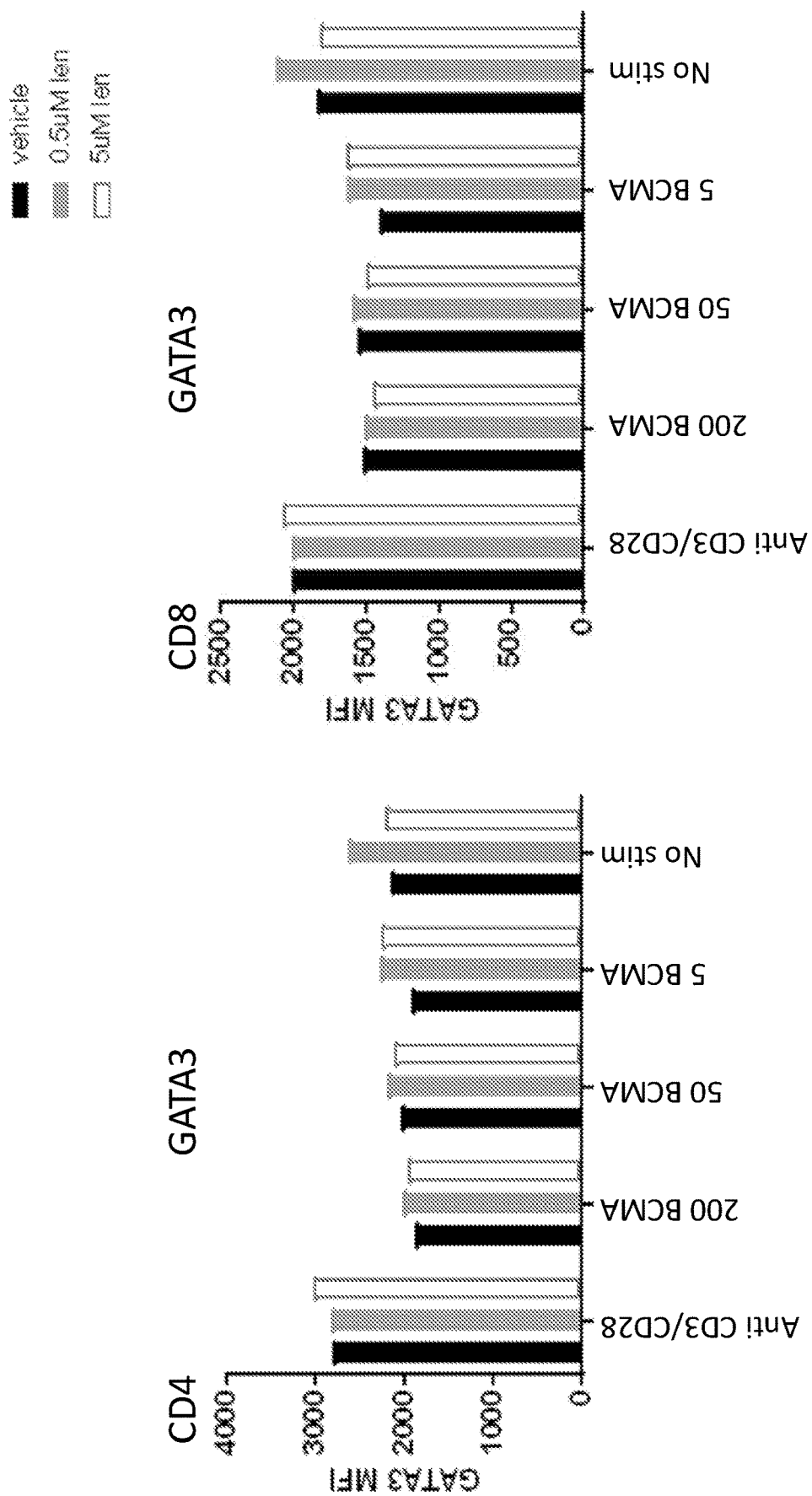
Figure 20H:
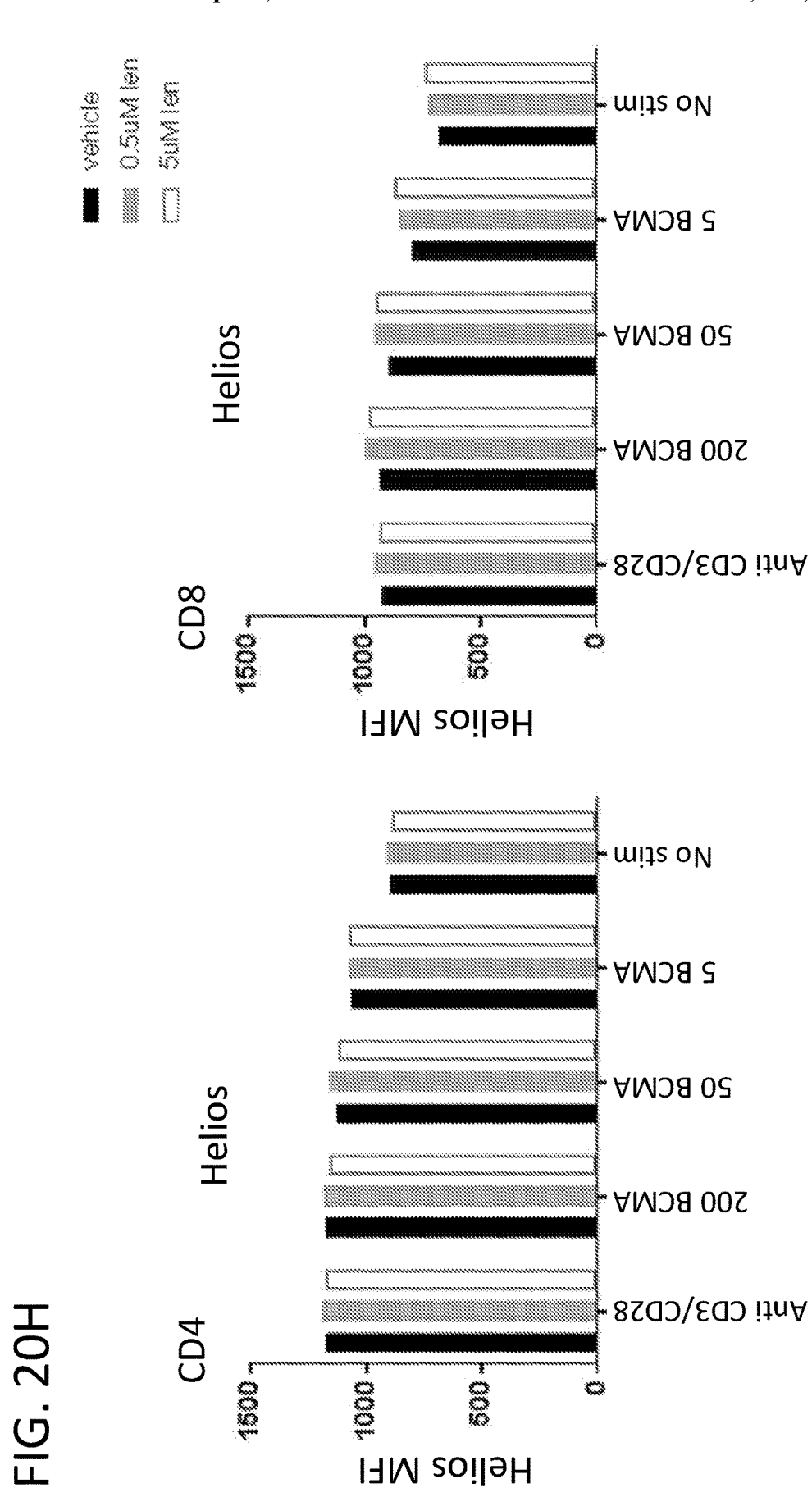
Figure 20I:
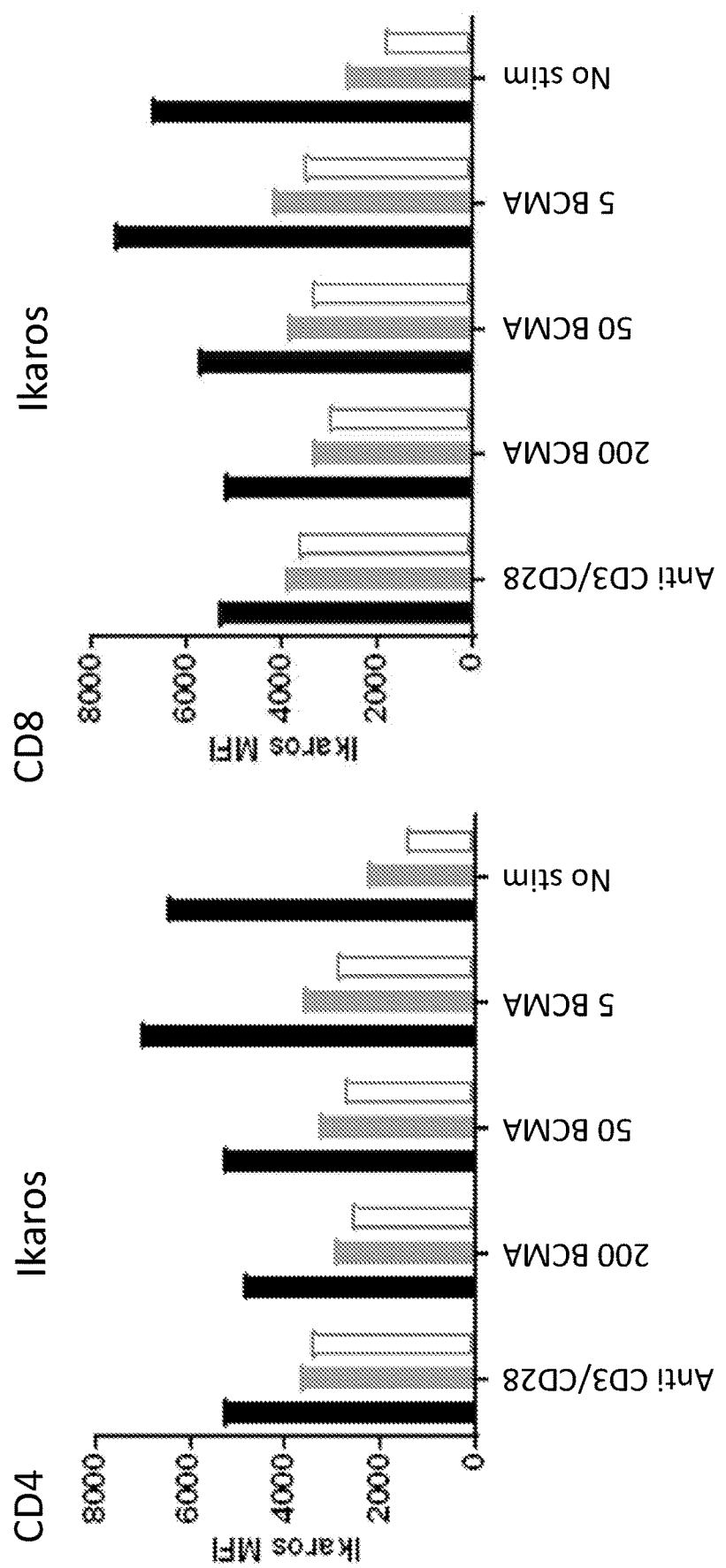

Levels of markers after the incubation of a CAR+ T cell composition from one exemplary donor are shown for BLIMP-1 (FIG. 20A), CD25 (FIG. 20B), CD31 (FIG. 20C), PD-1 (FIG. 20D), Tbet (FIG. 20E), and EOMES (FIG. 20F), GATA-3 (FIG. 20G) Helios (FIG. 20H), and Ikaros (FIG. 20I). As shown, expression of a number of the assessed T effector cell-associated transcription factors and activation markers were increased following stimulation with the BCMA-conjugated beads. For many of the assessed markers, the extent of increased expression was similar to the expression induced by stimulation with anti-CD3/anti-CD28 beads. In some cases, the degree of stimulation with BCMA-conjugated beads was greatest in the presence of 5 µg beads. As shown in FIG. 20I, the expression level of Ikaros was decreased in the presence of lenalidomide in all conditions. Similar results were observed from a CAR+ T cell composition generated from a second donor, except that no change in Helios expression was observed from cells from this donor when stimulated under the tested conditions.

Example 11 Assessment of Activity of Anti-BCMA CAR T Cells Stimulated with BCMA-Conjugated Beads in the Presence or Absence of Lenalidomide A. Effector Responses Cryofrozen anti-BCMA CAR T cells, produced substantially as described in Example 1 and formulated at a 1:1 ratio of CD4$^+$ and CD8$^+$ T cells, were thawed. Unless otherwise indicated, beads (diameter about 4.5 µm from a 5 µg/ml or 50 µg/ml BCMA-conjugated bead composition, generated as described in Example 9, were added to the wells at a ratio of T cells to beads of 1:1 in the presence or absence of 5 µM lenalidomide. Cells were incubated up to 14 days and analyzed at various time points for cytokine secretion, cell expansion by flow cytometry for the EGFRt surrogate marker, and for cytolytic activity.

a. Cytokine Expression (i) Presence of Cytokines in Supernatant

Figure 21A:
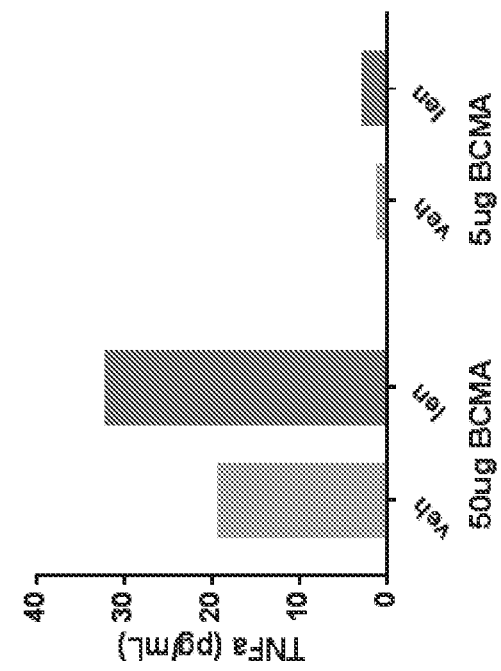
FIG. 21A-C shows graphs displaying the levels of extracellular IFN-gamma (FIG. 21A), IL-2 (FIG. 21B), and TNF alpha (FIG. 21C) from cultures following incubation of an anti-BCMA CAR+ T cell composition with two different amounts of BCMA-conjugated beads in the presence or absence of 5 μM lenalidomide. 50 μg BCMA and 5 μg BCMA indicate BCMA-conjugated beads generated by incubating BCMA with the beads in an amount of 50 and 5 μg of BCMA per approximately $4\times10^8$ beads, respectively.
Figure 21B:
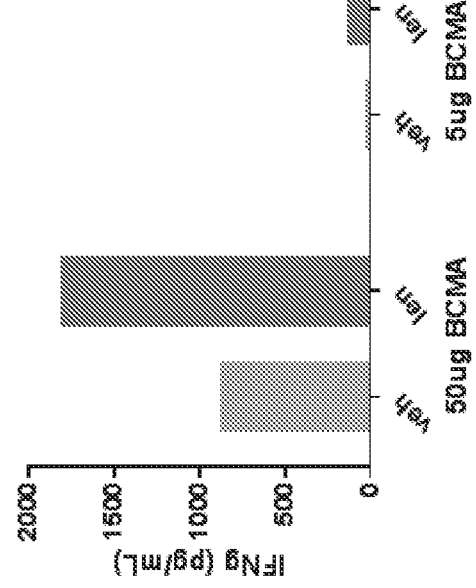
Figure 21C:
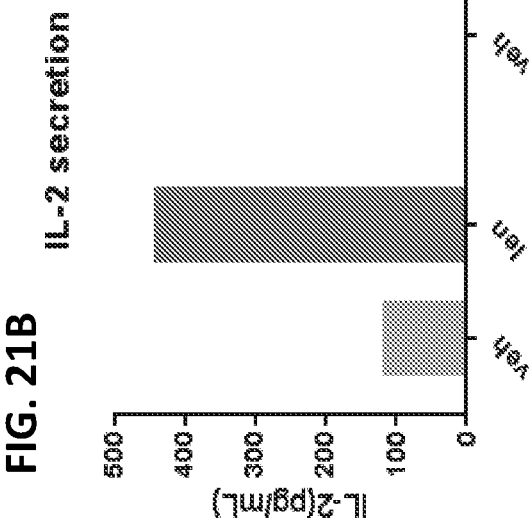

Twenty four hours after addition of BCMA-conjugated beads, the presence of TNF-α, IFNγ, and IL-2 in culture supernatants was assessed. As shown in FIGS. 21A-21C, incubation with BCMA-conjugated beads induced the secretion of IFNγ (FIG. 21A), IL-2 (FIG. 21B), and TNF-α (FIG. 21C) into culture supernatants. The degree of cytokine production was greater when the cells were incubated with beads from the 50 µg/mL BCMA-conjugated bead composition compared to the 5 µg/mL BCMA-conjugated bead composition, demonstrating that CAR stimulation via BCMA beads was dose-dependent. As shown, lenalidomide increased BCMA-induced CAR+ T cell cytokine production following stimulation with the BCMA-conjugated beads.

Figure 21D:
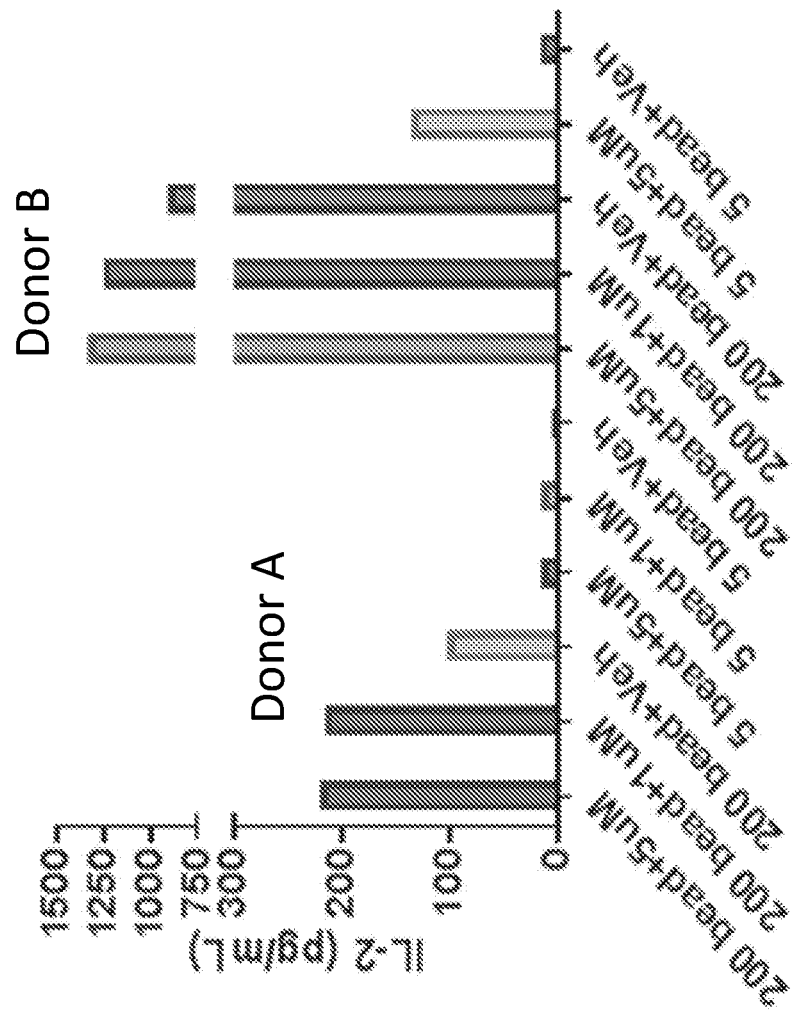
FIG. 21D shows a graph displaying the levels of extracellular IL-2 from cultures following incubation of an anti-BCMA CAR+ T cell composition from two different donors with different amounts of BCMA-conjugated beads in the presence of 0 μM, 1 μM, or 5 μM lenalidomide. 200 BCMA and 5 BCMA indicate BCMA-conjugated beads generated by incubating BCMA with the beads in an amount of 200 μg and 5 μg of BCMA per approximately $4\times10^8$ beads, respectively.

In a further exemplary study, two different anti-BCMA CAR T cell compositions were generated from different donors, each containing T cells expressing the same anti-BCMA CAR. The cells were thawed and incubated with beads (diameter about 4.5 µm) from a 5 µg/mL or 200 µg/mL BCMA-conjugated bead composition generated as described in Example 1. The incubation was carried out at a ratio of T cells to beads of 1:1 in the presence or absence of 1 µM or 5 µM lenalidomide. Twenty four hours after addition of BCMA-conjugated beads, IL-2 production by the anti-BCMA CAR+ T cells was assessed in culture supernatants. As shown in FIG. 21D, higher production of IL-2 was observed in the presence of high antigen stimulation (200 µg/mL BCMA-conjugated beads) compared to lower antigen stimulation (5 µg/mL BCMA-conjugated beads). Lenalidomide, at either 1 µM or 5 µM, increased cytokine production in the presence of both the high and low antigen stimulation.

(ii) Intracellular Cytokine Levels

Anti-BCMA CAR+ T cells were incubated in the presence of 1 µM lenalidomide or a vehicle and 50 µg/mL BCMA-Fc conjugated beads for 2 hours, and cells were assessed by flow cytometry for phosphorylated STAT 5. To assess IFNγ and TNFα cytokine levels, anti-BCMA CAR+ T cells were incubated in the presence of 0.1 µM or 1 µM lenalidomide or a vehicle and 5 µg/mL, 50 µg/mL or 200 µg/mL BCMA-Fc conjugated beads for 24 hours. The cells were gated on transduced, live CD3+ cells, and assessed by flow cytometry for intracellular cytokine accumulation of IFNγ and TNFα in CD4+ and CD8+ cells.

Figure 22A:
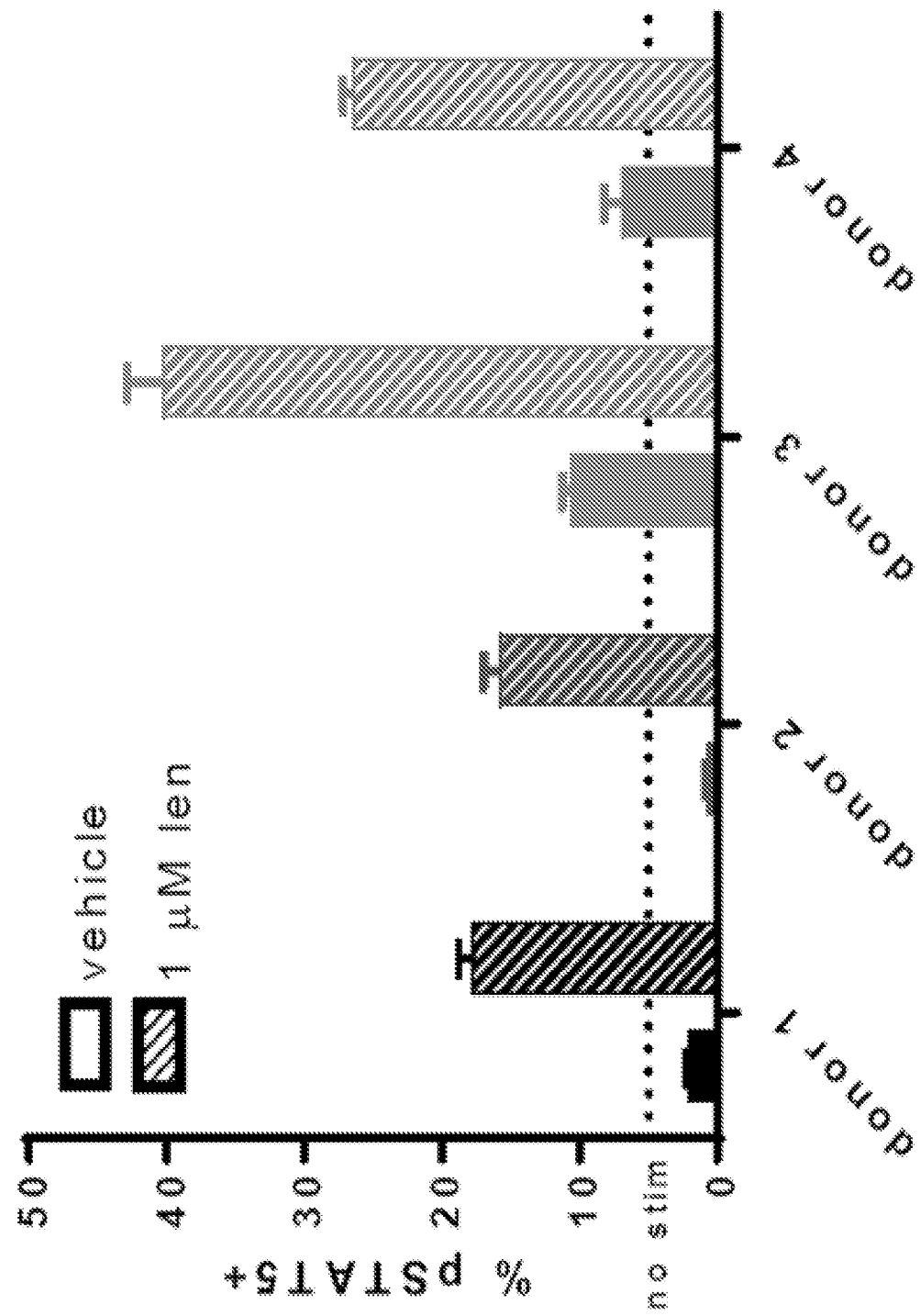
FIG. 22A shows the flow cytometric analysis of phosphorylated STAT5 after 2 hours of CAR stimulation (stim) with 50 μg BCMA beads. No stimulation control shown with dotted line.
Figure 22B:
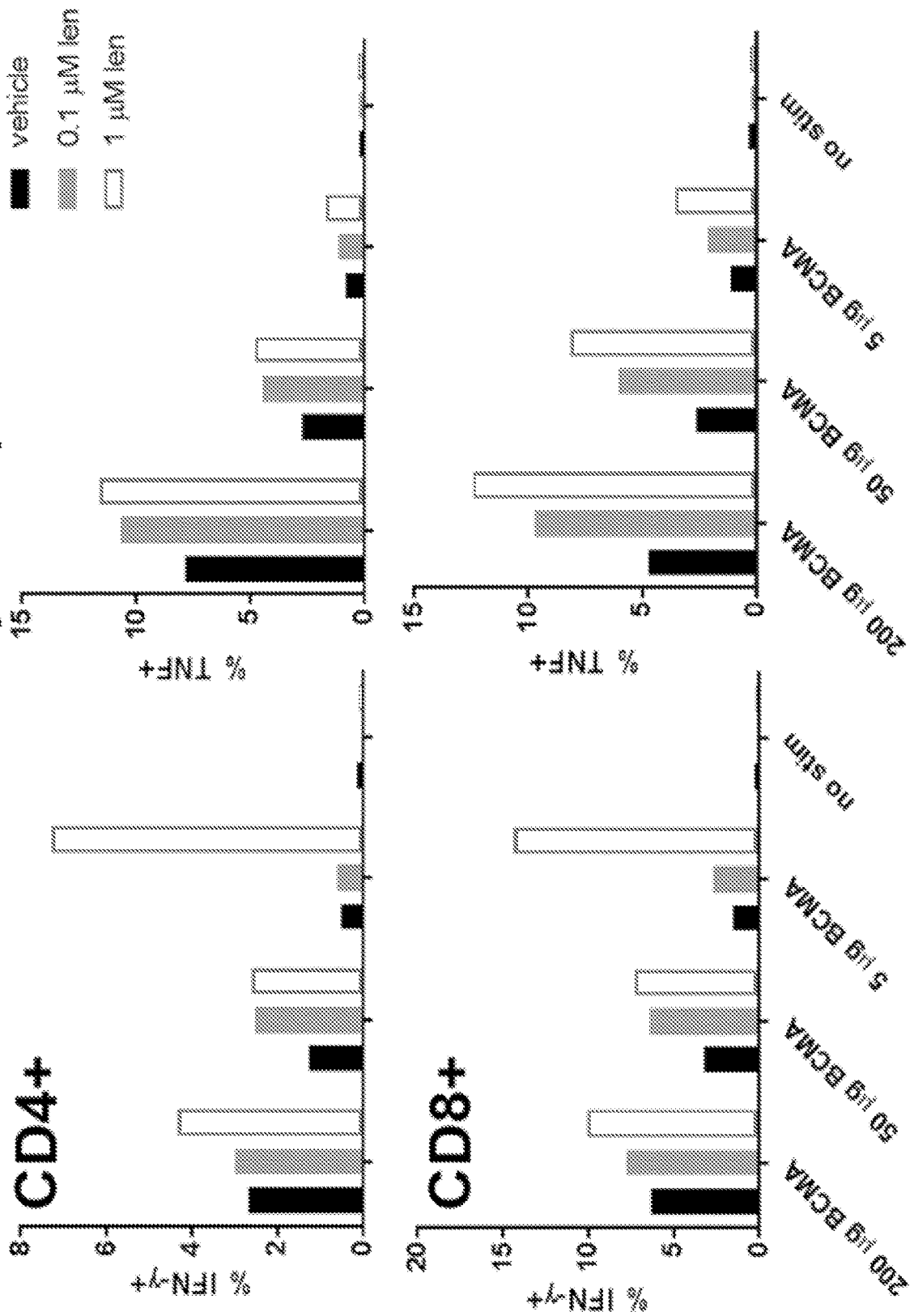
FIG. 22B shows the flow cytometric analysis of intracellular cytokine levels on a representative normal CAR T donor after 24 hours of BCMA bead stimulation (gated on transduced, live CD3+).

As shown in FIG. 22A, a 2-hour stimulation with antigen increased the percent of cells positive for phosphorylated-STAT5 compared to the no stimulation control (shown with the dotted line). Results for intracellular cytokine levels of IFNγ and TNFα from anti-BCMA CAR T cells generated from a representative normal CAR-T cell donor are shown in FIG. 22B. In this study, anti-BCMA CAR-T cell cytokine production was increased by lenalidomide across a wide range of antigen levels and concentrations.

b. Cell Proliferation

Figure 21E:
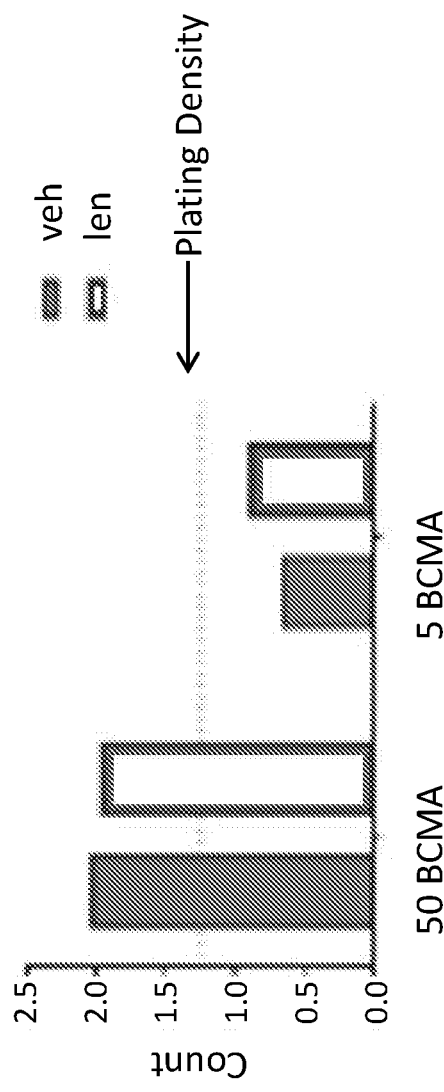
FIG. 21E and FIG. 21F shows total cell count following culture of an anti-BCMA CAR+ T cell composition after incubation for 4 days (FIG. 21E) or 7 days (FIG. 21F) with different amounts of BCMA-conjugated beads in the presence of 5 μM lenalidomide. 50 BCMA and 5 BCMA indicate BCMA-conjugated beads generated by incubating BCMA antigen with the beads in an amount of 50 μg and 5 μg of BCMA per approximately $4\times10^8$ beads, respectively.
Figure 21F:
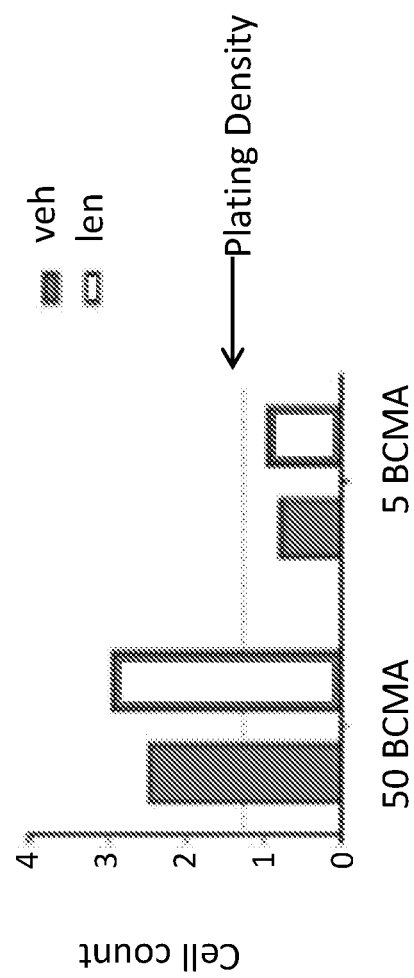

Total cell count, monitored at day 4 (FIG. 21E) and day 7 (FIG. 21F), was increased following stimulation of anti-BCMA CAR+ T cells with beads from a 50 µg/mL BCMA-conjugated bead composition, but not 5 µg/mL BCMA-conjugated bead composition, compared to the cells present at the time of initiation of the incubation (dashed line). A small increase in proliferation was observed in cells incubated with 50 μg beads in the presence of lenalidomide at day 7.

To further assess proliferation, the cells containing anti-BCMA CAR-expressing T cells were labeled with the proliferation marker dye CELLTRACE VIOLET (CTV; ThermoFisher Scientific, Waltham MA) in accordance with the manufacturer's protocol prior to incubation with the BCMA-conjugated beads. Proliferation was assessed by dye dilution using flow cytometry on cells that were stimulated with beads from the 50 μg/mL BCMA-conjugated bead composition. Compared to proliferation in the absence of lenalidomide, there was a slight delay in proliferation as assessed by CTV dilution in the presence of lenalidomide at day 4 but not day 7 (FIG. 21G).

c. Expansion

Figure 21H:
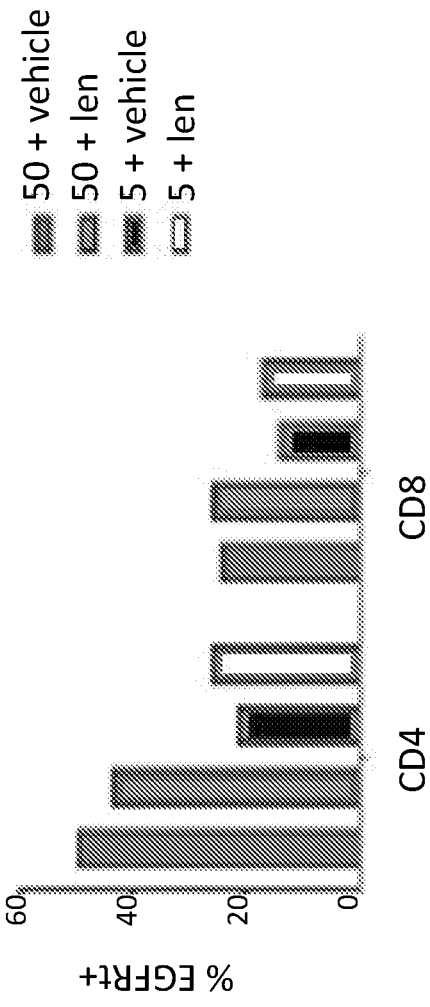
FIGS. 21H and 21I show graphs displaying the percentage of cells positive for the surrogate marker EGFRt as determined with an anti-EGFR antibody following incubation of an anti-BCMA CAR+ T cell composition for 4 days (FIG. 21H) or 7 days (FIG. 21I) with different amounts of BCMA-conjugated beads in the presence of 5 μM lenalidomide or absence of lenalidomide (vehicle). "50" and "5" indicate beads generated by incubating BCMA with the beads in an amount of 50 μg and 5 μg of BCMA per approximately $4\times10^8$ beads, respectively.
Figure 21I:
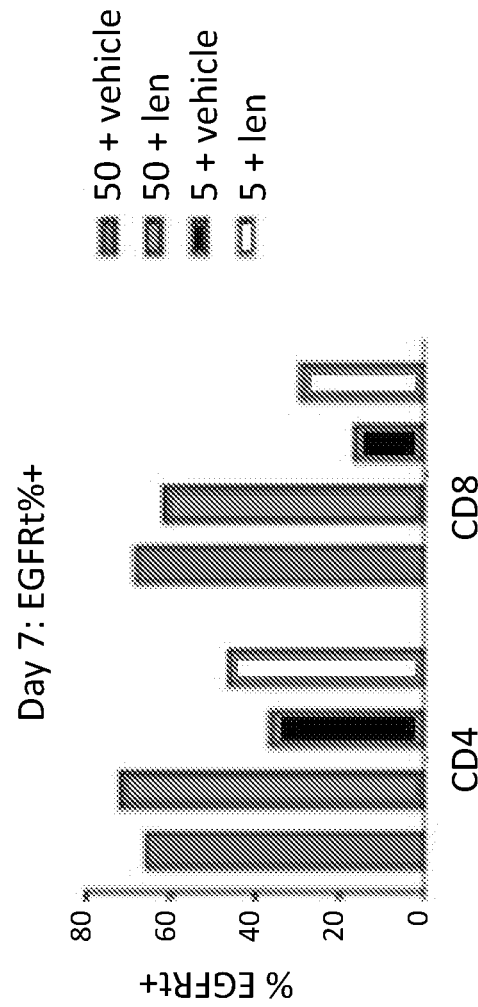

Four days and seven days after addition of BCMA-conjugated beads, the incubated cells were stained with CD4 or CD8 and with an anti-EGFR antibody to determine the percentage of cells positive for EGFRt as a surrogate for CAR+ T cells. At the time of plating, 26% of the CD4+ cells expressed anti-BCMA CAR and 39% of the CD8+ cells expressed anti-BCMA CAR as determined by staining with BCMA-Fc. The percent of EGFRt+CD4+ T cells increased from about 26% at the initiation of the incubation to greater than 40% by day 4 (FIG. 21H) and greater than 60% by day 7 (FIG. 21I) when the cells were incubated in the presence of beads from a 50 μg/mL BCMA-conjugated bead composition. As shown in FIG. 21I, the percent of EGFRt+CD8+ T cells increased by day 7 from about 38% at the initiation of the incubation to greater than 60% when the cells were incubated in the presence of beads from the 50 μg/mL BCMA-conjugated bead composition. The extent of cell expansion was greatest when cells were incubated in the presence of beads from a 50 μg/mL BCMA-conjugated bead composition compared to beads from the 5 μg/mL BCMA-conjugated bead composition. The presence of lenalidomide did not substantially impact the extent of CAR+ T cell expansion in this study.

d. Cytolytic Activity

Cytolytic activity of CAR+ T cells after incubation with BCMA-conjugated beads was assessed by incubation with the BCMA-expressing target cell line RPMI-8226, which is a BCMA+ multiple myeloma cell line. After seven days of incubation of anti-BCMA CAR+ T cells with BCMA-conjugated beads (5 μg/ml or 50 μg/ml) in the presence or absence of lenalidomide, the beads were removed from the cultures and the cells were plated with the RPMI-8226 target cells at a ratio of effector cells to target cells of 3:1 or 1:1 in the further presence or absence of 5 μM lenalidomide. To perform the cytolytic assay, the target RPMI-8226 cells were labeled with NucLight Red (NLR) to permit tracking of target cells by microscopy. Cytolytic activity was assessed by measuring the loss of viable target cells over a period of four days, as determined by red fluorescent signal (using the INCUCYTE® Live Cell Analysis System, Essen Bioscience). The number of viable cells was normalized to cells at day 0 prior to incubation with the RPMI-8226 target cells.

Figure 21J:
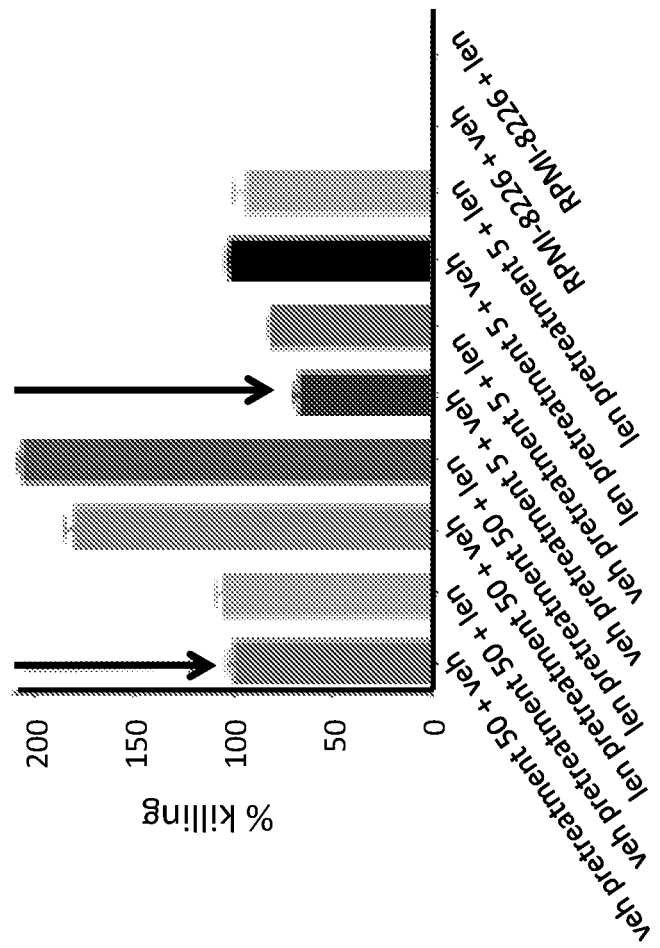
FIG. 21J shows the percent cell killing of RPMI-8226 target cells by anti-BCMA CAR+ T cells effector cells that had been incubated with different amounts of BCMA-conjugated beads in the presence of 5 μM lenalidomide or absence of lenalidomide (vehicle). Cytolytic activity of compositions containing a ratio of effector cells to target cells of 3:1 or 1:1 and in the further presence or absence of lenalidomide are shown. "50" and "5" indicate BCMA conjugated beads generated by incubating BCMA with the beads in an amount of 50 and 5 μg of BCMA per approximately $4\times10^8$ beads, respectively.

Exemplary results at the 1:1 effector to target cell ratio are shown in FIG. 21J. As shown, the anti-BCMA CAR+ T cells demonstrated effective killing in the assay. Anti-BCMA CAR+ T cells that were stimulated with beads from the 5 μg/ml BCMA-conjugated bead composition were slightly less efficient at cell killing than anti-BCMA CAR+ T cells that were stimulated with beads from the 5 μg/ml BCMA-conjugated bead composition. For all conditions, preincubation with lenalidomide during the seven day incubation prior to the killing assay increased cytolytic activity of the CAR+ T cells. The presence of lenalidomide during the cell killing assay did not substantially affect killing activity. No cell killing was observed when RPMI 8226 cells were cultured alone or in the presence of lenalidomide, demonstrating that lenalidomide did not directly influence target cell viability in this assay.

B. Serial Restimulation

Anti-BCMA CAR T cell compositions were generated from three different donors, each containing T cells expressing the same anti-BCMA CAR, thawed, and were incubated for seven days with beads (diameter about 4.5 μm) at a 1:1 ratio of beads to cells from a 50 μg/mL BCMA-conjugated bead composition generated as described in Example 9. The incubation was carried out in the presence of 5 μM lenalidomide or in the absence of lenalidomide (vehicle control). Cells were harvested after 7 days and replated for three further rounds up to 28 days, each round involving resetting to initial seeding density and incubating for an additional 7 days in the presence of the same concentration of lenalidomide.

At each reset after the pretreatment, cytolytic activity was assessed by incubation with the BCMA-expressing target cell line RPMI-8226 (labeled with NucLight Red (NLR)) at an effector to target cell (E:T) ratio of 1:1 in the further presence of or absence of lenalidomide. Cytolytic activity was assessed by measuring the loss of viable target cells over a period of up to 80-150 hours, as determined by red fluorescent signal (using the IncuCyte® Live Cell Analysis System, Essen Bioscience). Cells from each condition were plated in triplicate. The % cell killing compared to vehicle only control (set at 100%) was determined.

Figure 23A:
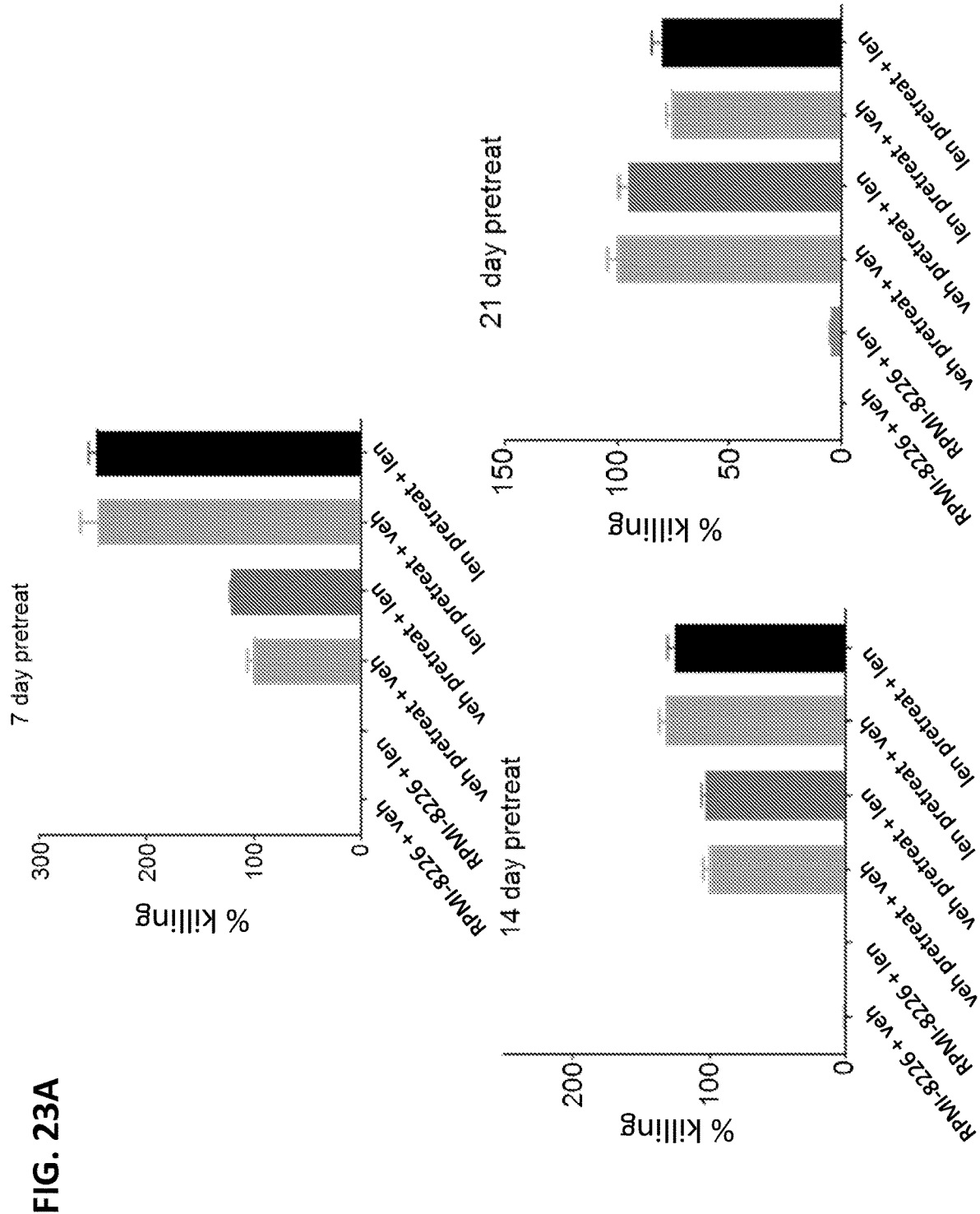
FIG. 23A-23B depicts results of a serial restimulation assay of anti-BCMA CAR T cell compositions that had been incubated for seven days with BCMA-conjugated beads (50 μg/mL). Results from three different donor compositions are shown.
Figure 23B:
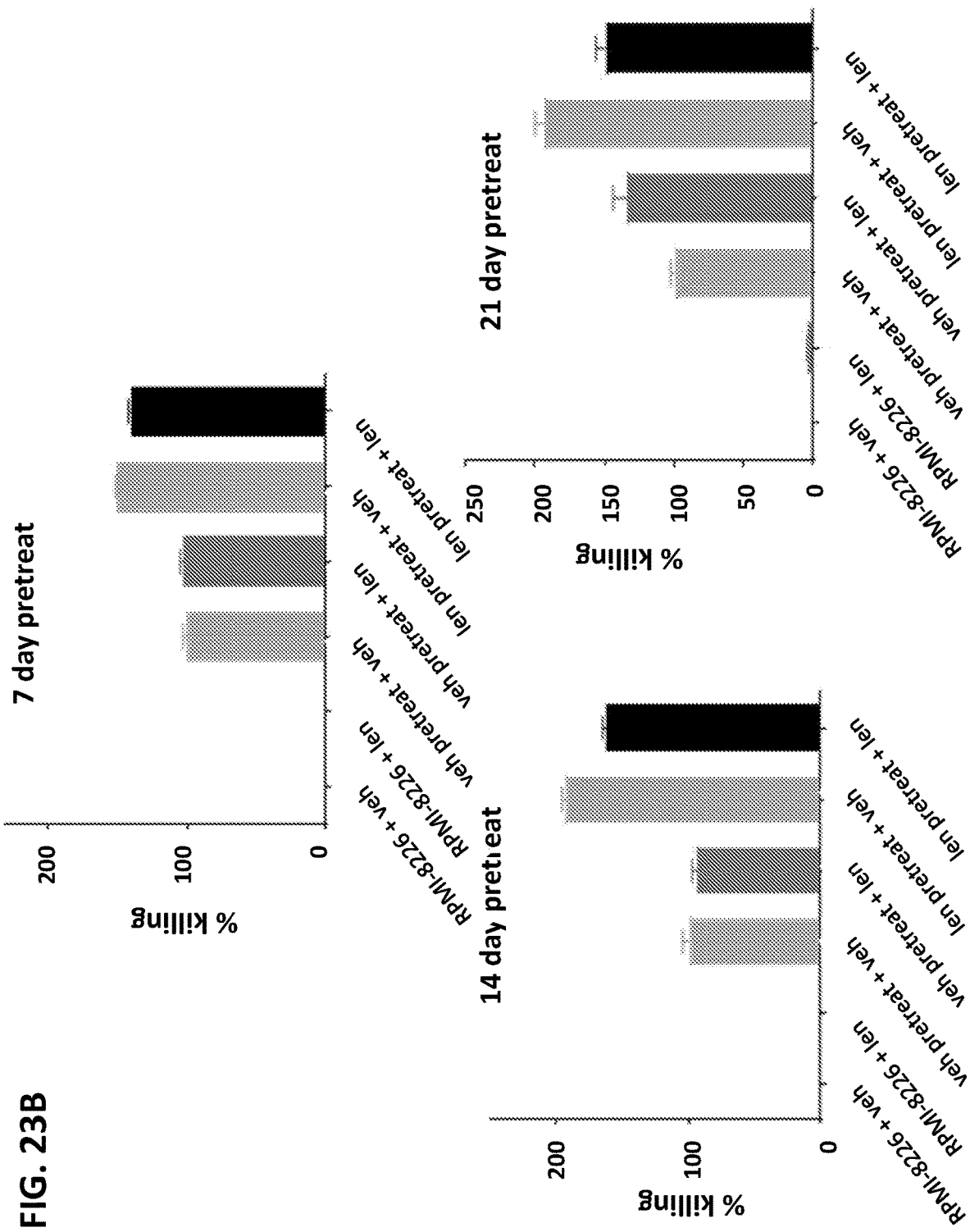

FIG. 23A shows results for cytolytic activity of anti-BCMA CAR+ T cells from an exemplary donor after pretreatment for 7 days, 14 days or 21 days. As shown, anti-BCMA CAR+ T cells that were preincubated with lenalidomide for 7 days or 14 days exhibited greater cytolytic activity compared to cells that were not preincubated in the presence of lenalidomide. In this donor, an overall decrease in killing efficacy was observed by anti-BCMA CAR+ T cells that were preincubated with lenalidomide for 14 or 21 days compared to day 7. Similar effects on cytolytic activity of anti-BCMA CAR+ T cells after pretreatment with lenalidomide for 7 or 14 days were observed in the donor; cytolytic activity after 21 days lenalidomide pretreatment was not assessed in this donor. As shown in FIG. 23B, increased killing efficacy of anti-BCMA CAR+ T cells was observed in this donor in cells that were preincubated with lenalidomide at all time points.

Example 12 Effects of Lenalidomide on PD-1 Expression and PD-L1 Signaling

Anti-BCMA CAR-T cells, generated from samples from representative healthy donors or multiple myeloma patient derived material, and cultured with 50 μg/mL BCMA-Fc conjugated beads (generated as described in Example 9) at a ratio of 1:1 bead:CAR+ T cell for 7 days, in the presence of 1 of 1 μM lenalidomide or a vehicle control. Expression of CD25, PD-1, Tim3 and Lag3 on CAR T cells (using an antibody for surrogate CAR marker) cultured under the different conditions then was assessed by flow cytometry.

Such anti-BCMA CAR- T cells prestimulated with beads in the presence or absence of lenalidomide, or freshly thawed anti-BCMA CAR-T cells generated from comparable donor samples, were then debeaded, washed, and cultured with RPMI-8226 target cells (labeled with NucLight Red (NLR) to permit their tracking by microscopy), in the presence of 1 µM lenalidomide or a vehicle control. Specifically, for pretreated cells in which pretreatment had been conducted in the presence of lenalidomide, the cells were cultured with the target cells in the presence of lenalidomide; likewise, for pretreated cells in which pretreatment had been conducted in the presence of vehicle, cells were cultured with the target cells in the presence of vehicle. Following the co-culture, cytolytic activity was assessed by measuring the loss of viable target cells over a period of seven days, as determined by red fluorescent signal. Percentage killing was normalized to anti-BCMA CAR T cells prestimulated on beads in the presence of vehicle. Cytokine production was assessed by ELISA from supernatant following culture with target cells for 24 hours. Experiments were performed twice in 3 donors. Linear fixed-effect or mixed-effect models were used to assess the significance of lenalidomide treatments on cytolytic activity and cytokine production, with treatment, donor, and time treated as fixed effects and animal treated as a random effect, nested with time when repeated measurements were derived from the same animal. P values were obtained by likelihood ratio tests comparing the full model with the effect of interest against the model without the effect of interest.

Figure 24A:
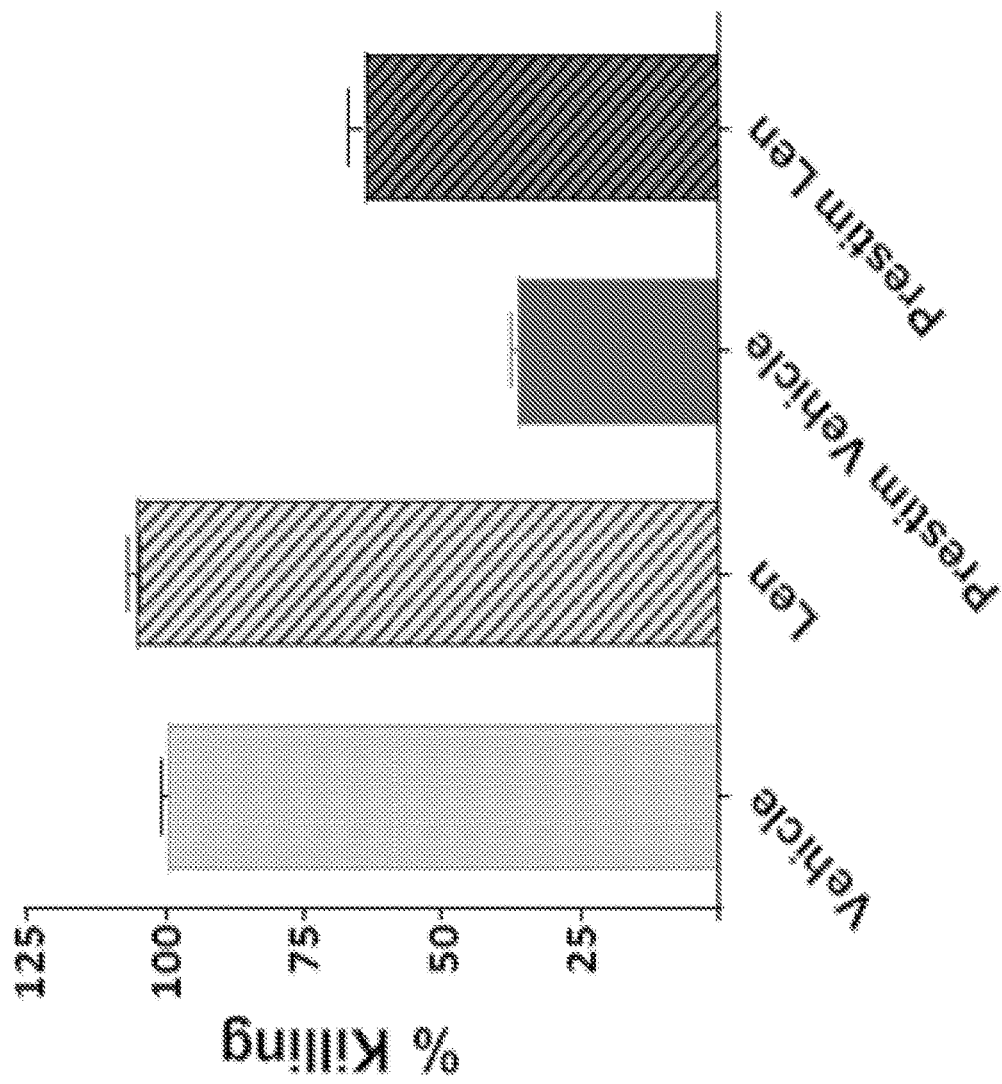
FIG. 24A shows results for CAR antigen-specific cytolytic activity and FIG. 24B shows results for cytokine production for anti-BCMA CAR-T cells that had been prestimulated with BCMA beads (compared to freshly-thawed (non-prestimulated) anti-BCMA CAR-T cells) in the co-cultures, comparing cells cultured in the presence versus absence of lenalidomide.
Figure 24B:
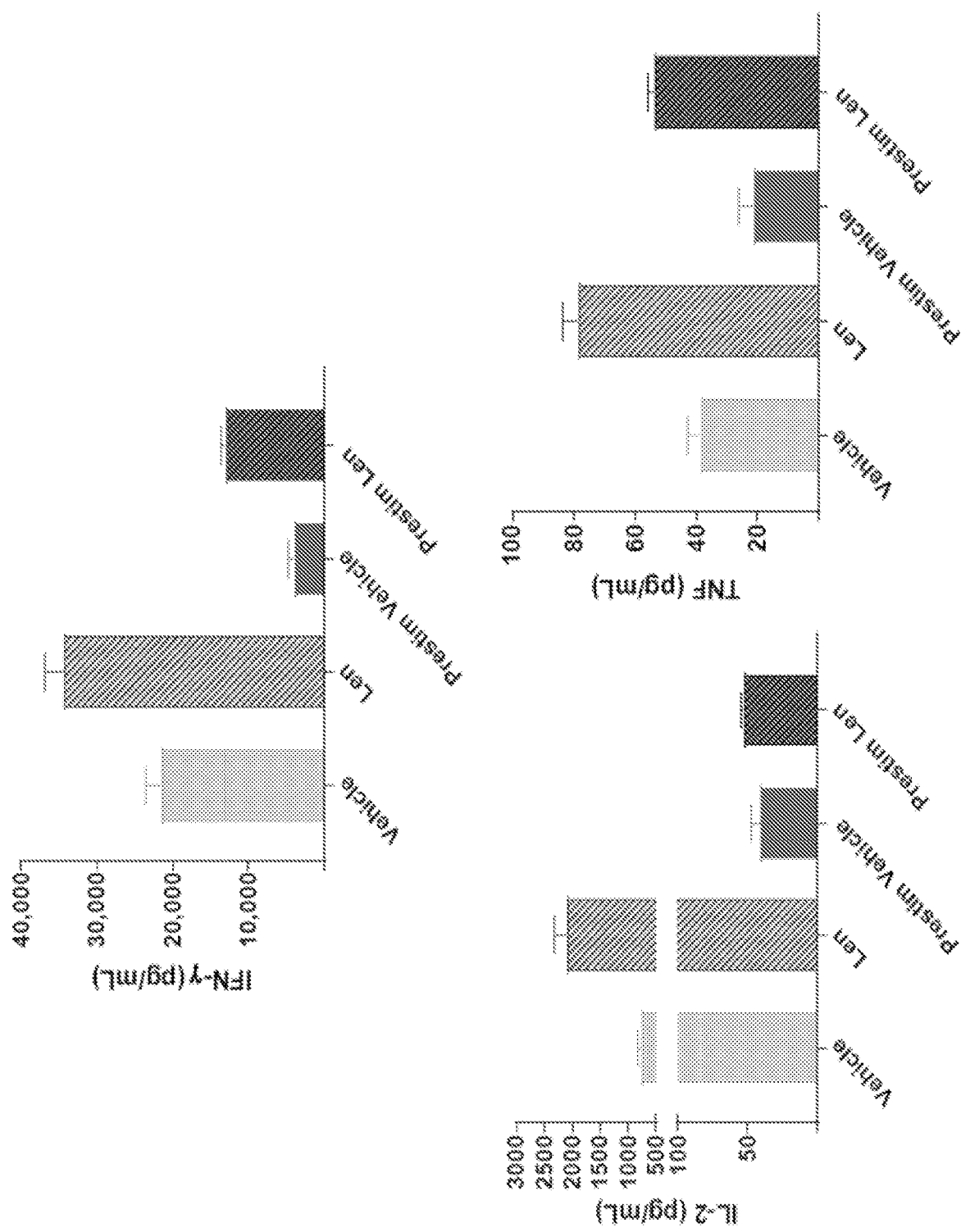

FIG. 24A shows results for CAR antigen-specific cytolytic activity and FIG. 24B shows results for cytokine production for anti-BCMA CAR-T cells that had been prestimulated with BCMA beads (compared to freshly-thawed (non-prestimulated) anti-BCMA CAR-T cells) in the co-cultures, comparing cells cultured in the presence versus absence of lenalidomide. Prestimulated CAR T cells showed decreased cytolytic activity (P=$2.1 \times 10^{-4}$) and cytokine production (P=0.03 for IFN-$\gamma$) compared with freshly thawed anti-BCMA CAR T cells. In the absence of lenalidomide in pretreatment and subsequent co-culture, the prestimulated CAR-T cells exhibited reduced cell killing and cytokine production compared to fresh CAR-T cells, indicating that chronic prestimulation leads to functional impairment. These results are consistent with an exhaustion-like phenotype having been induced by prestimulation on the BCMA-conjugated beads. The presence of lenalidomide during the prestimulation period preserved cytolytic function (P=0.04), and there was a trend toward increased cytokine production compared with cells exposed to vehicle during the prestimulation period (FIG. 24B). The presence of lenalidomide in this assay was consistent with an observation that lenalidomide may reduce the effects indicative of functional exhaustion-like phenotype in the prestimulated CAR-T cells.

Figure 24C:
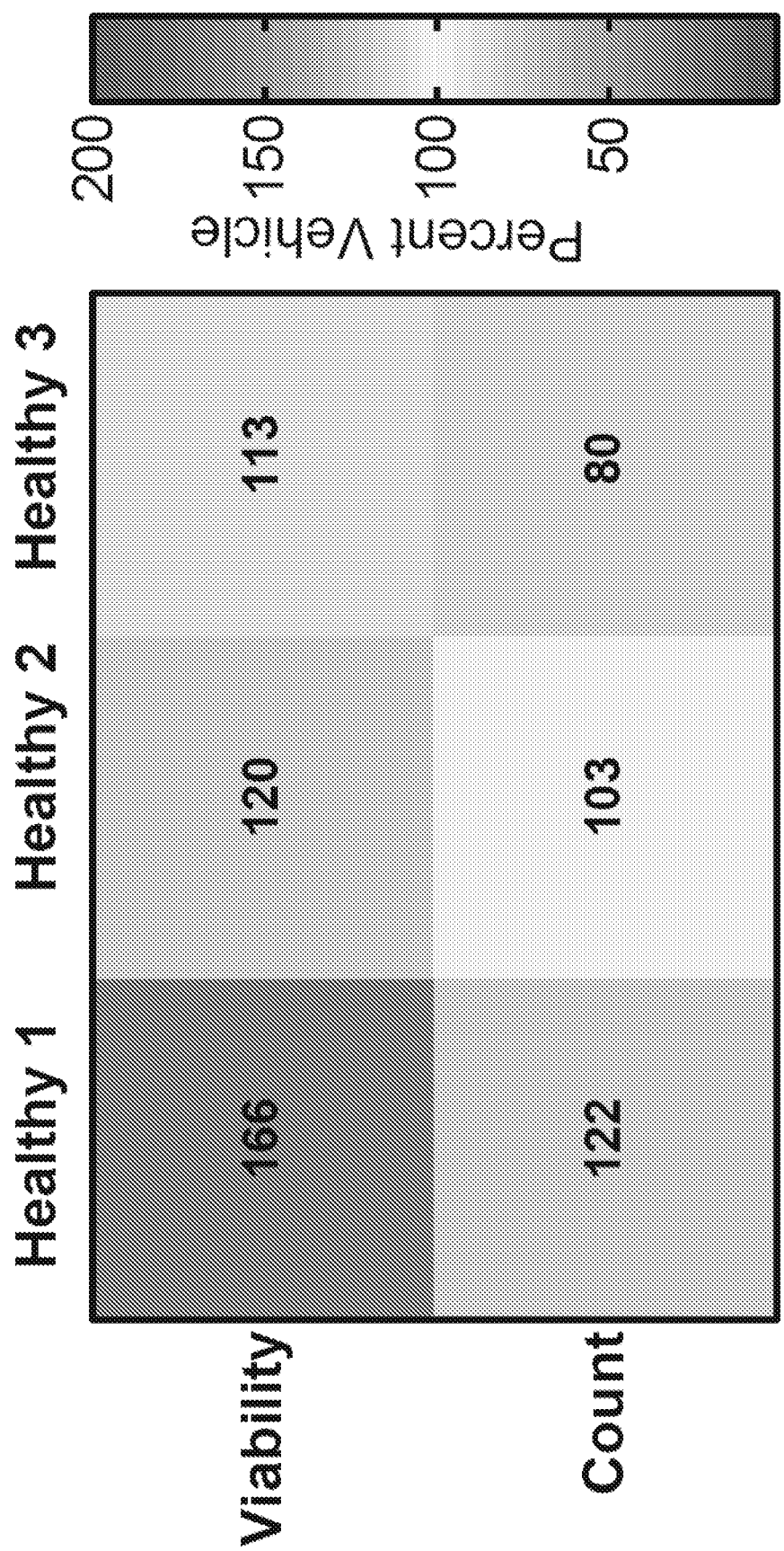
FIG. 24C shows the overall viability and cell count assessed for three anti-BCMA CAR T donors.
Figure 24D:
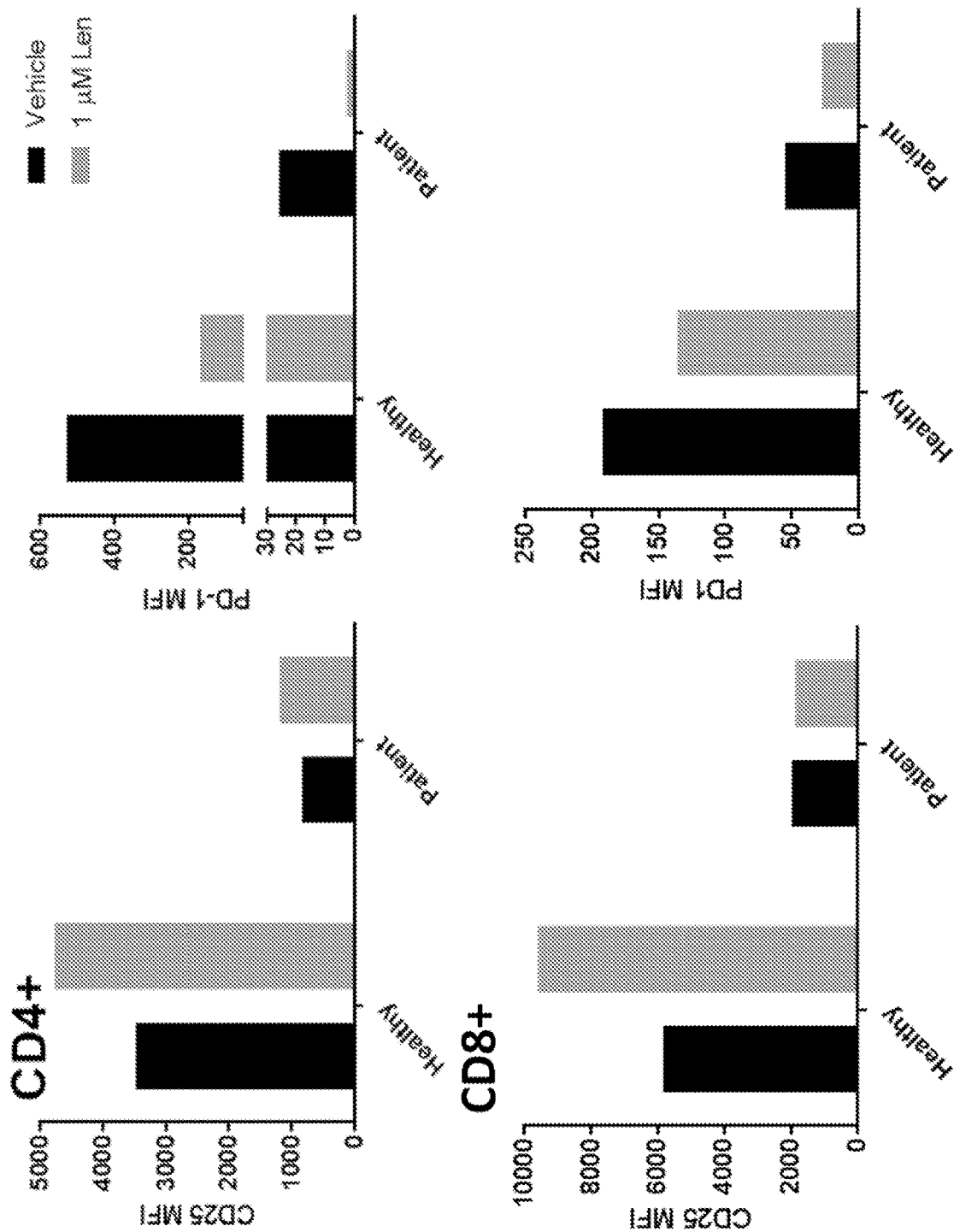
FIG. 24D shows results of flow cytometric analysis of surface CD25 and PD-1 expression (mean fluorescent intensity (MFI), for CD4+ or CD8+ anti-BCMA CAR T-cells after stimulation (pretreatment) with BCMA beads for 7 days, in the presence or absence of 1 µM lenalidomide.
Figure 24E:
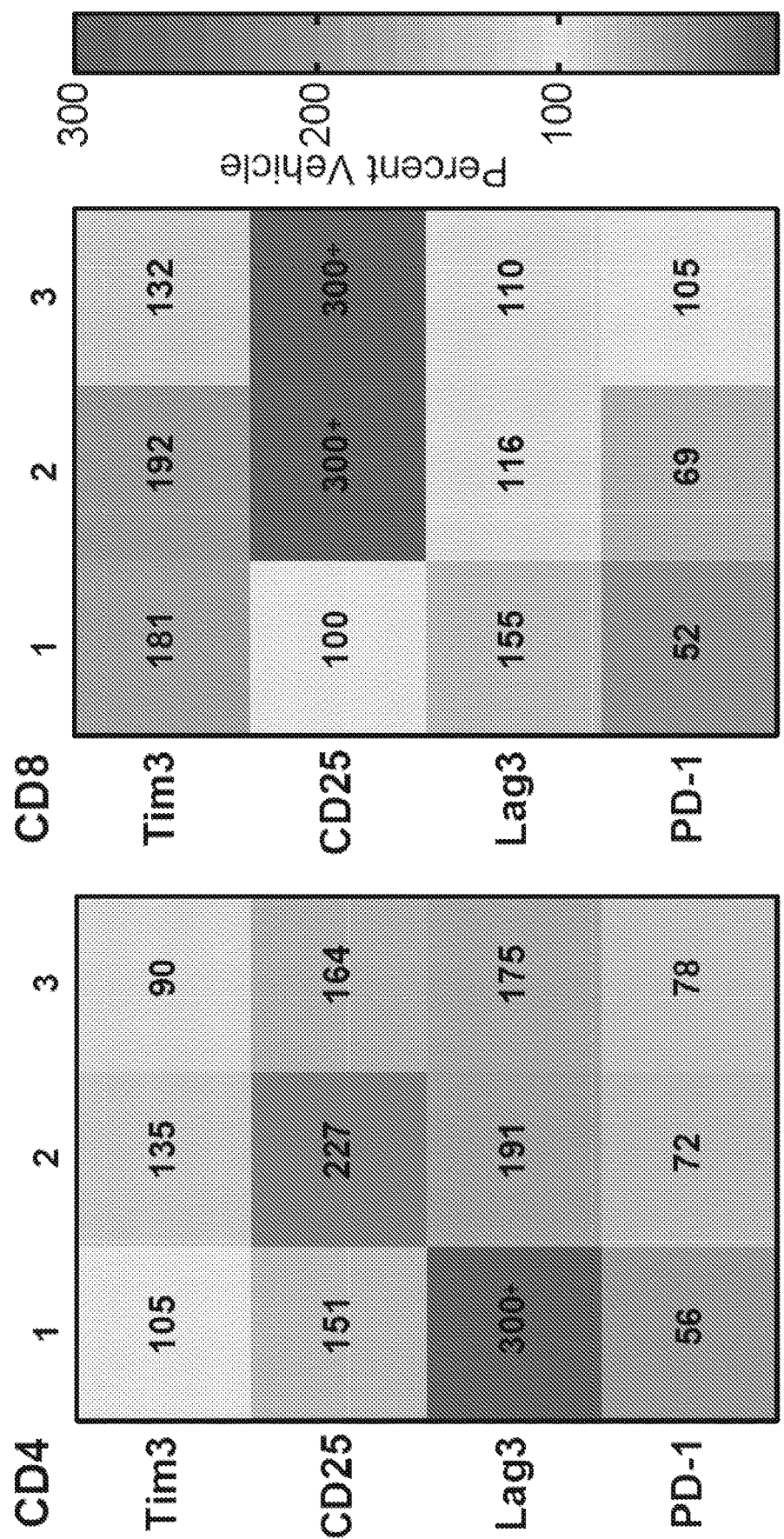
FIG. 24E shows the flow cytometric analysis across CAR T donors for median fluorescence intensity (MFI; CD25 and Tim3) or percentage positive PD-1 and Lag3 on the surface of T-cell markers in CD4+ CAR+ and CD8+ CAR+ subsets (gated on live CD3+ cells). Values shown are percentage baseline (Veh) MFI, viability, or count.

As shown in FIG. 24C, the phenotype of anti-BCMA CAR T cells stimulated for 7 days on BCMA beads was assessed, and the addition of lenalidomide significantly increased CAR+ viability of anti-BCMA CAR T material across 3 healthy donors (P=0.04). The addition of lenalidomide did not alter the total cell count across all donors in this 7-day period, and no significant differences were observed in percentage CAR+ between vehicle- and lenalidomide-treated CAR T cells. FIG. 24D shows representative results of flow cytometric analysis of surface CD25 and PD-1 expression (mean fluorescent intensity (MFI), for CD4+ or CD8+ anti-BCMA CAR T-cells after stimulation (pretreatment) with BCMA beads for 7 days, in the presence or absence of 1 µM lenalidomide. As shown, the results indicated that lenalidomide reduced PD-1 expression of BCMA-CAR-T cells, while increasing CD25 expression after prolonged stimulation. As shown in FIG. 24E, flow cytometric analysis across the three CAR T donors indicated that the addition of lenalidomide increased the surface expression of Tim3 in the CD8+ population (P=$4.0 \times 10^{-4}$), with mixed effects on the CD4+ CAR+ population. Across all donors and in both the CD4+ and CD8+ CAR+ populations, lenalidomide increased CD25 (CD4+ and CD8+; P=$2.2 \times 10^{-16}$) and the percentage positive for Lag3 expression (CD8+ P<0.03; CD4+P=0.002). Notably, a decrease in the percentage of PD-1+ cells was also observed in the CD4+ population (P=0.04), with 2 of 3 donors showing a decrease in the CD8+ population as well.

Figure 25A:
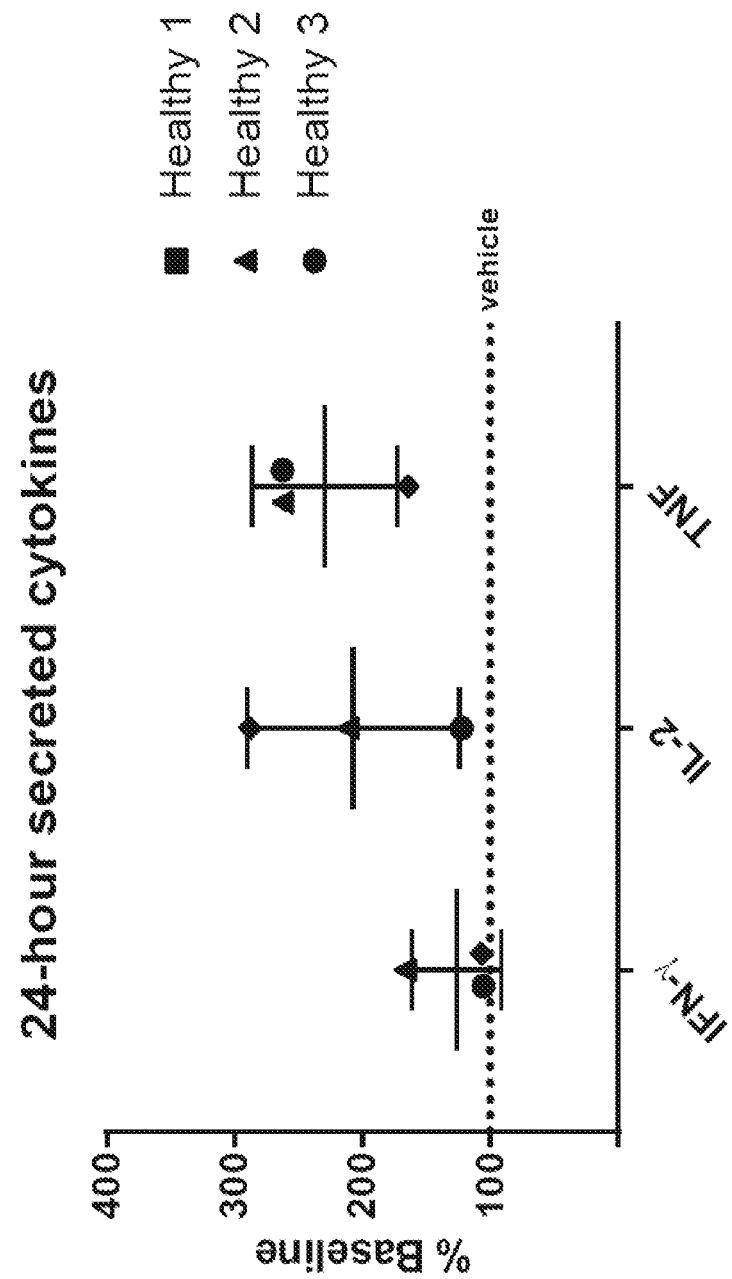
FIG. 25A shows the analysis of effector cytokine production following CAR-specific stimulation on 50 µg BCMA beads for 24 hours in the presence of 1 µM lenalidomide compared with baseline (vehicle) response for each of three donors.

In another study, recombinant human BCMA-conjugated beads were used to stimulate CAR T cells at various concentrations to titrate the magnitude of stimulation, either low (5 µg/mL), medium (50 µg/mL), and high (200 µg/mL) stimulation. At a medium stimulation condition, the secreted cytokine production 24 hours after stimulation was measured, and a 200% increase in IL-2 and TNF-$\alpha$ concentrations were observed compared with vehicle control, with donor-dependent increases in IFN-$\gamma$ (FIG. 25A). Cells were stimulated with BCMA conjugated beads for 24 hours in the presence of 0.1 µM or 1.0 µM lenalidomide, or vehicle control. A protein transport inhibitor was added in the final hours of incubation, and cells were stained for intracellular IL-2, IFN-$\gamma$, and TNF-$\alpha$.

Figure 25B:
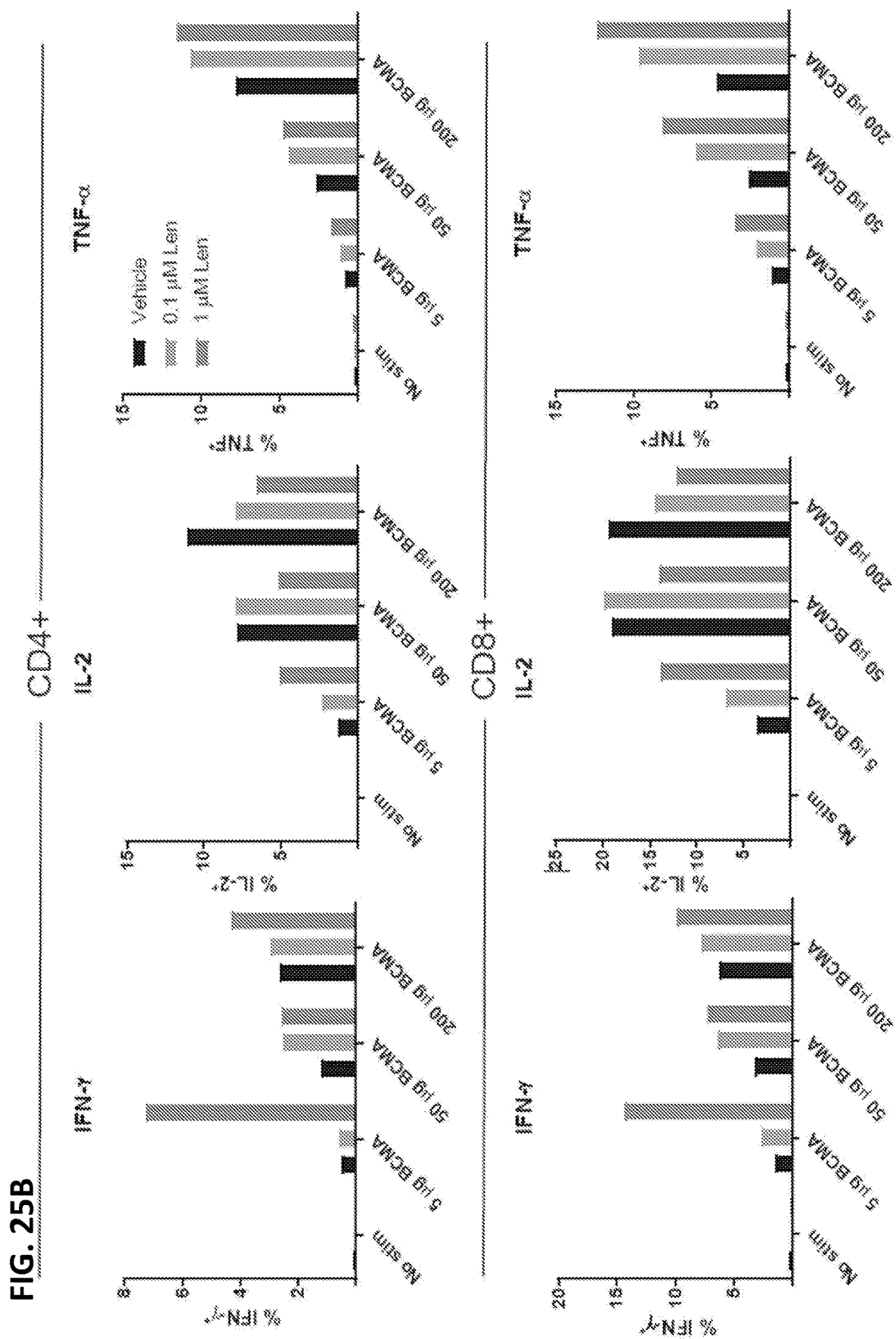
FIG. 25B shows the effects of anti-BCMA CAR T cells activated on different concentrations of BCMA beads (i.e., 5 µg, 50 µg, and 200 µg) in the presence or absence of lenalidomide (0.1 µM or 1 µM) on CAR T effector cytokine production.

Anti-BCMA CAR T cells activated on BCMA beads showed stimulation level-dependent effects on cytokine production, with 5 µg BCMA beads causing limited CAR T effector cytokine production compared with 50-µg and 200 µg BCMA beads (FIG. 25B). Lenalidomide increased the percentage of IFN-$\gamma^+$ and TNF-$\alpha^+$ intracellular staining at all stimulation levels for both CD4$^+$ and CD8$^+$ CAR T cells. The magnitude of stimulation either increased or decreased IL-2 in response to lenalidomide, with the lenalidomide decreasing the percentage of IL-2$^+$ CAR$^+$ T cells at 50-µg and 200-µg stimulation but increasing the percentage of IL-2$^+$ CAR$^+$ T cells at the 5 µg stimulation condition. In the absence of stimulation, lenalidomide had no effect on CAR T cytokine production, indicating that cytokine enhancement provided by lenalidomide requires stimulation.

Figure 25C:
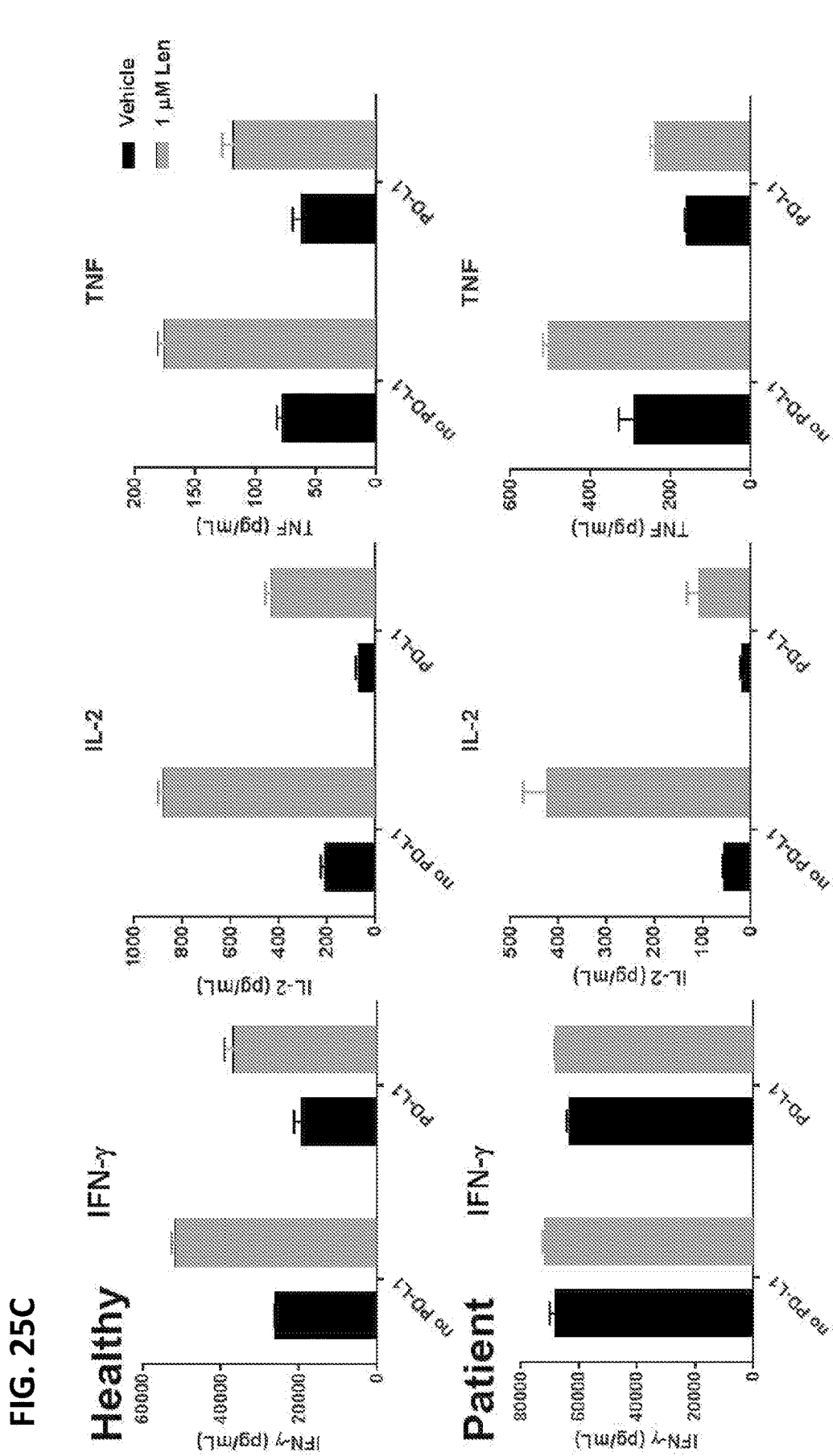
FIG. 25C shows the cytokine production of anti-BCMA CAR T cells derived from representative healthy donors and multiple myeloma patients stimulated on BCMA beads with or without addition of PD-L1 on the beads, in the presence of 1 µM lenalidomide) or in the absence of lenalidomide.

In another study, to explore whether the lenalidomide-induced potentiation of CAR T activation and cytokine production could override PD-L1-mediated inhibition, cells were cultured in the presence of BCMA beads generated as described in Example 9, with or without additional conjugation of human recombinant PD-L1-Fc. Healthy donor- or patient-derived CAR T cells were stimulated in the presence of BCMA-conjugated beads or BCMA/PD-L1 conjugated beads for 24 hours in the presence of 1 µM lenalidomide. Cytokine production was measured in the supernatant. Results are shown in FIG. 25C. As shown in FIG. 25C, evaluation of both healthy and patient donor CAR T cells demonstrated that addition of recombinant PD-L1 to recombinant BCMA beads reduced IFN-$\gamma$, IL-2, and TNF-$\alpha$. It was shown that lenalidomide treatment potentiated secreted cytokine levels beyond those from CAR T cells treated with vehicle in the presence of PD-L1. The results were consistent with a conclusion that anti-BCMA CAR-T cytokine production following incubation with BCMA-conjugated beads was increased by lenalidomide in the presence of PD-L1-mediated inhibition.

Example 13 Gene Expression and Chromatin Accessibility Analysis in CAR T Cells in the Presence or Absence of Lenalidomide Gene expression and chromatin accessibility was assessed in CAR T cells upon stimulation, in the presence or absence of lenalidomide. Anti-BCMA CAR-expressing T cells, generated from four (4) different independent donors, were stimulated with 50 µg/mL BCMA-conjugated beads for 24 hours (24 hr+stim) or 7 days (d7+stim), or cultured without stimulation for 24 hours (24 hr), in the presence or absence of lenalidomide (1 µM). Experiments were performed twice in 3 to 4 donors. The CAR-expressing cells were assessed by RNA sequencing (RNA-seq) for gene expression and assayed for transposase-accessible chromatin using sequencing (ATAC-seq) for chromatin accessibility analysis. Assays were performed on 50,000 cells at each time point.

RNA-seq was performed on the complementary DNA (cDNA) samples prepared from the RNA isolated from the cultured anti-BCMA CAR-expressing cells. ATAC-seq was performed generally as described in Buenrostro et al., Nat Methods. (2013) 10(12): 1213-1218. Paired-end ATAC reads were trimmed, aligned with Bowtie2, and filtered for quality, fragment length, duplication, and mitochondrial contribution. ATAC-seq accessibility peaks were called using MACS2 (q<0.01) and a consensus set was generated from overlapping peaks present in 2 or more samples, using DiffBind. Principal component analysis (PCA) was performed for the RNA-seq and ATAC-seq data sets, generated from DESeq2-normalized counts. Differential expression (DE, for RNA-seq) or consensus peak accessibility (DA, for ATAC-seq) were calculated, modeling donor effects (Donors 1-4) and treatment effects (lenalidomide vs. vehicle) at 24 hours and day 7. Differential locus selection cut off was q≤0.05 and log 2 fold change ≥0.5 for RNA-seq or q≤0.1 for ATAC-seq. Gene ontology (GO) enrichment analysis was performed and activation z-score was determined on the subset of genes differentially expressed at q<0.1 using Ingenuity Pathway Analysis software (Qiagen, Inc.), accounting for donor effects within each treatment condition. A motif enrichment analysis was performed for peaks that were shown to be more accessible in the presence of lenalidomide, with HOMER software, using the consensus peakset as background, for the day 7 stimulation (d7+stim) ATAC-seq data.

RNA-seq heatmaps were generated on normalized (transcripts per million) expression data, averaged across donors per condition, and row-normalized using z-scores. Motif enrichment in DA peaks at day 7 was performed with HOMER, using the consensus peak set as background.

Figure 26A:
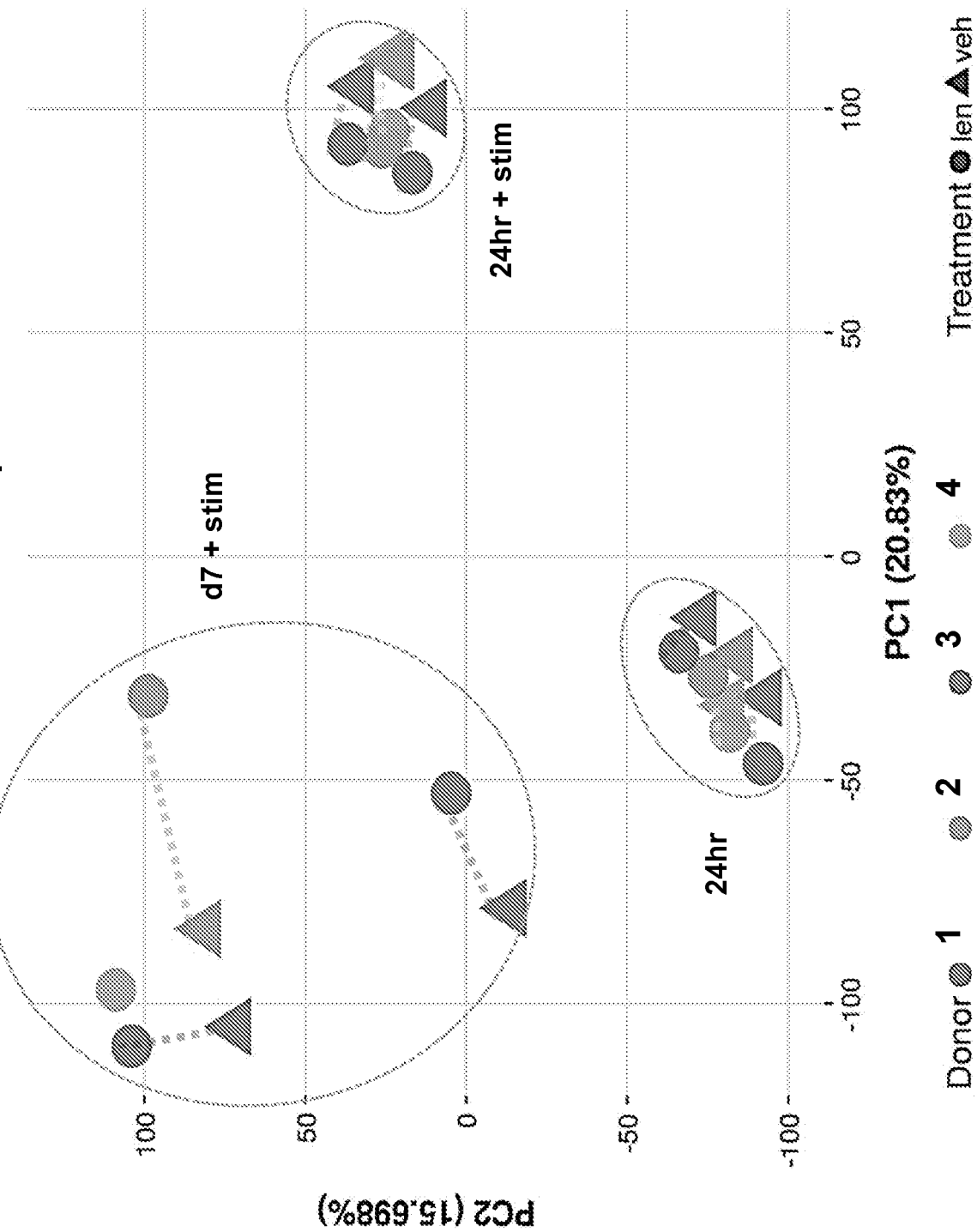
FIGS. 26A and 26B show results of principal component analysis (PCA) for gene expression (based on RNA-seq results.
Figure 26B:
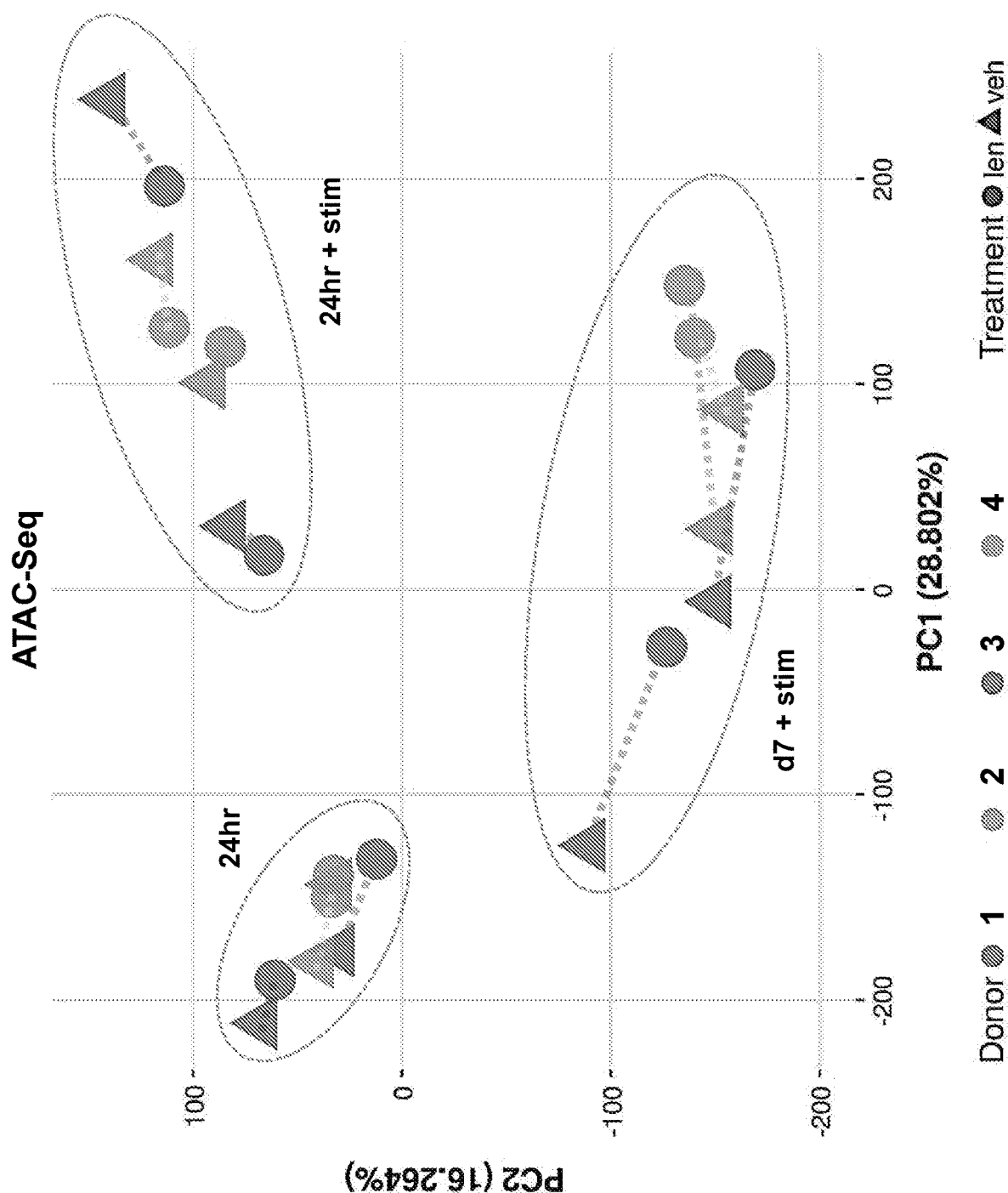

Results of PCA, representing the overall diversity across gene expression or chromatin accessibility on the genome, are shown in FIG. 26A (gene expression; based on RNA-seq results) and FIG. 26B (chromatin accessibility; based on ATAC-seq results). Ellipses were drawn to indicate the groups as it was observed that the major factors that contributed to the variation in gene expression or chromatin accessibility were culture time and presence of stimulation. Cells cultured in the presence of lenalidomide (circles) exhibited different overall gene expression and chromatin accessibility compared to cells cultured in the absence of lenalidomide (triangles, vehicle), showing a lenalidomide treatment effect in each donor and culture condition. For lenalidomide treatment, the general direction of change (shown by dotted line between triangle and circle) was similar in each donor, and the degree of change was generally greater in cells cultured for 7 days with stimulation, compared to the change in cells cultured for 24 hours, with or without stimulation. Thus, the PCA demonstrated clustering based on stimulation (stim or no stim) and time (24 hour or 7 days) for both the RNA-seq (FIG. 26A) and ATAC-seq (FIG. 26B) data sets.

Figure 27D:
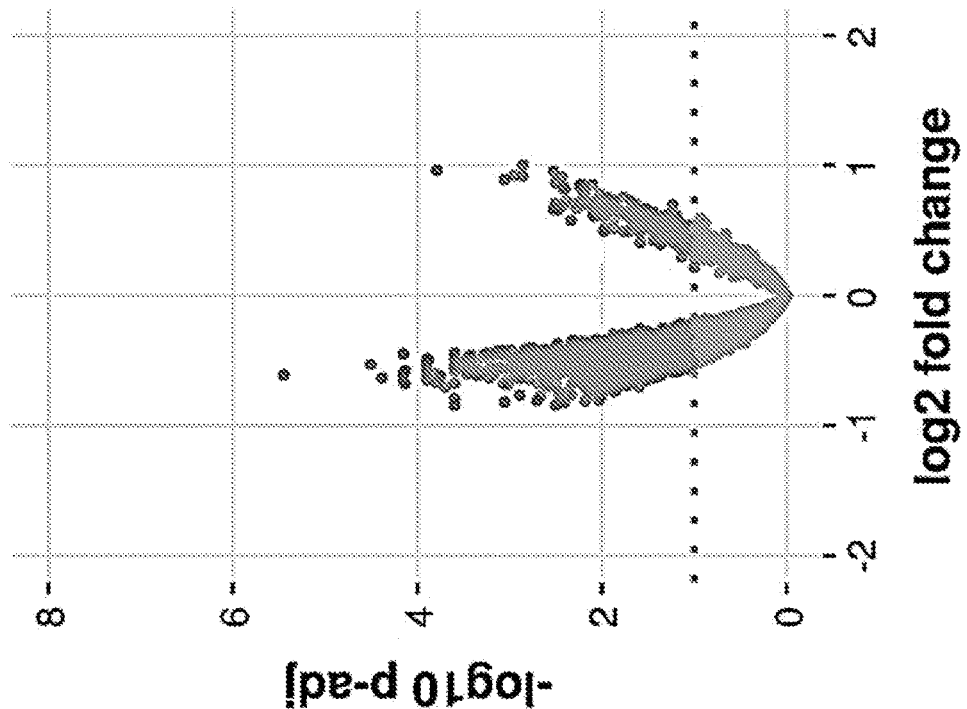
FIGS. 27C and 27D show volcano plots depicting statistical significance of expression (log 10 of adjusted p-value) with the log 2 fold-change in g chromatin accessibility, including genes or peaks that show increased (right side) or decreased (left side) accessibility, in CAR+ T cells stimulated with BCMA-conjugated beads, for 24 hours (24 hr+stim, FIG. 27C) or 7 days (d7+stim, FIG. 27D). The tables indicate the number of genes or peaks that showed statistically significant increase (up) or decrease (down) in accessibility.
Figure 27C:
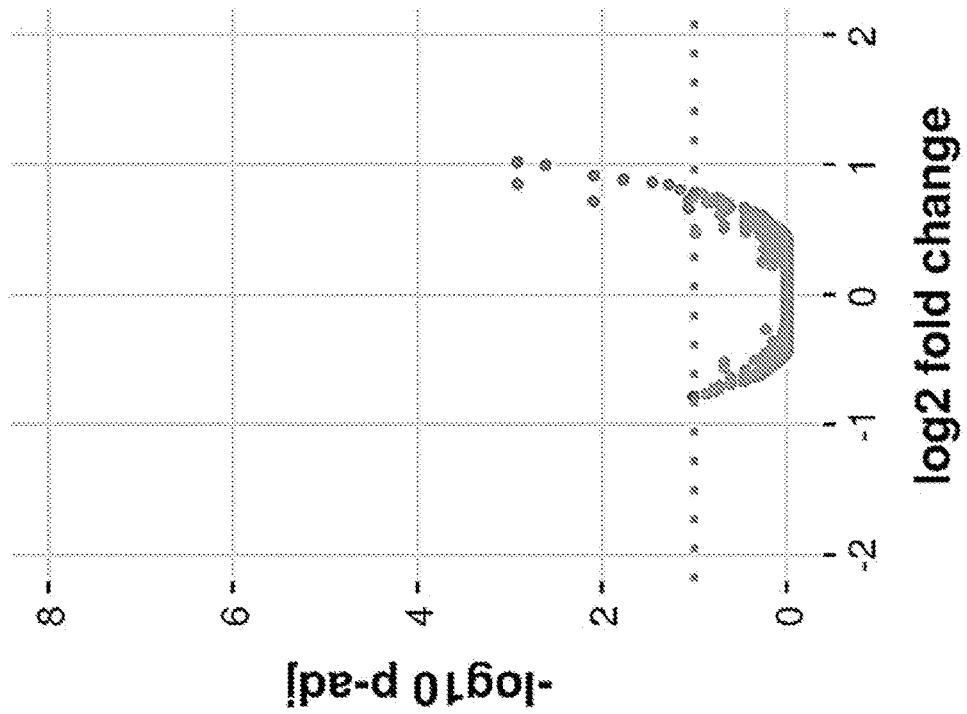

The role of lenalidomide after 24 hours or 7 days of stimulation after accounting for donor-to-donor variability was then examined. FIGS. 27A-27D show changes in gene expression (FIGS. 27A and 27B, following 24 hour and 7 day cultures with stimulation, respectively) or chromatin accessibility (FIGS. 27C and 27D, following 24 hour and 7 day cultures with stimulation, respectively) in the presence of lenalidomide. RNA-seq analysis showed upregulation of a small set of genes (214) at 24 hours, and a larger number of genes (583) changed after 7 days of stimulation in the presence of lenalidomide (FIGS. 27A and 27B). ATAC-seq analysis revealed a limited set of chromatin accessibility changes associated with lenalidomide treatment after 24 hours of stimulation, with a dramatic change in profile and an increase in the number of sites with changes in chromatin accessibility (change in chromatin accessibility at 2804 peaks) after 7 days of stimulation in the presence of lenalidomide (FIGS. 27C and 27D). These results indicated that lenalidomide treatment altered both the transcriptional and epigenetic profile of CAR-T cells.

Figure 28A:
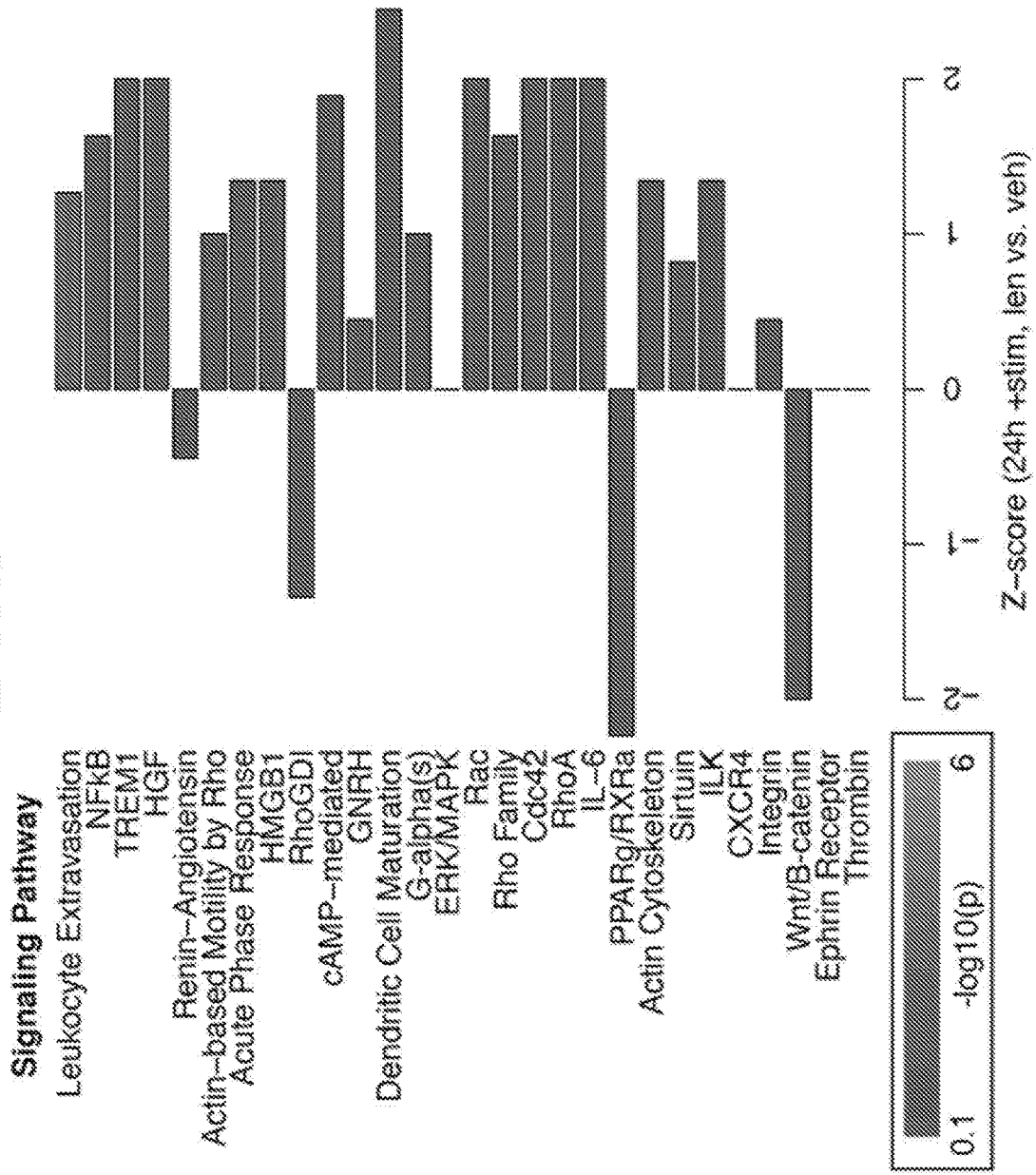
FIGS. 28A and 28B depict directionality and significance of expression for the genes in biological signaling pathways that were enriched in the sets of genes whose expression was statistically significantly increased or decreased, in CAR+ T cells stimulated with BCMA-conjugated beads, for 24 hours (24 hr+stim, FIG. 28A) or 7 days (d7+stim, FIG. 28B).
Figure 28B:
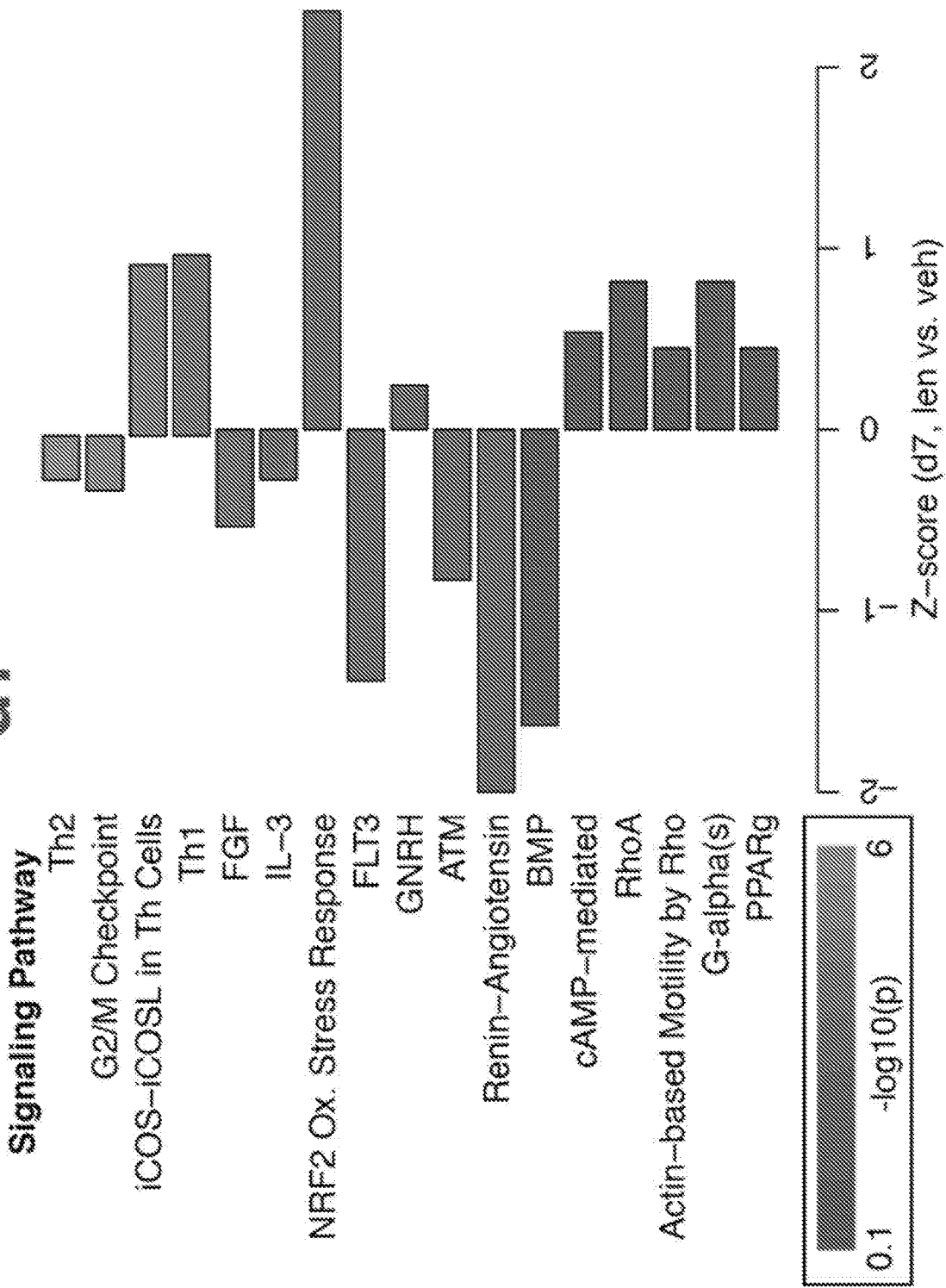

To further identify specific transcriptional changes associated with lenalidomide treatment, gene ontology analysis was applied to the RNA-seq data set, and biological signaling pathways that were enriched in differentially expressed genes (FIGS. 28A and 28B) were identified. Directionality and significance of the effects on biological pathways are shown at 24 hours (FIG. 28A) or 7 days (FIG. 28B). The results showed that the presence of lenalidomide resulted in increased expression of genes involved in T cell activation and signaling. Results showed that pathways differentially regulated in the presence and absence of lenalidomide showed an enrichment of immune synapse-associated genes, genes involved in cytokine signaling and genes involved in T cell activation pathways. Specifically, pathways associated with T-cell chemotaxis (leukocyte extravasation, integrin, ILK, and CXCR4-associated gene sets), intracellular signaling, and cytoskeleton (Rac/Rho/Cdc42) were upregulated in the presence of lenalidomide within 24 hours of stimulation compared with vehicle controls. In addition, these data support an increase in ICOS-related signaling pathways—a finding that is in line with previous publications demonstrating an increase in ICOS and ICOSL in the CD3$^+$ population of peripheral blood mononuclear cells treated with lenalidomide ex vivo (Gorgun et al. (2010) Blood, 116:3227-3237). After 7 days of stimulation, lenalidomide upregulated pathways associated with Th1 T-cell response and co-stimulation, while decreasing Th2-associated gene signatures.

Figure 29:
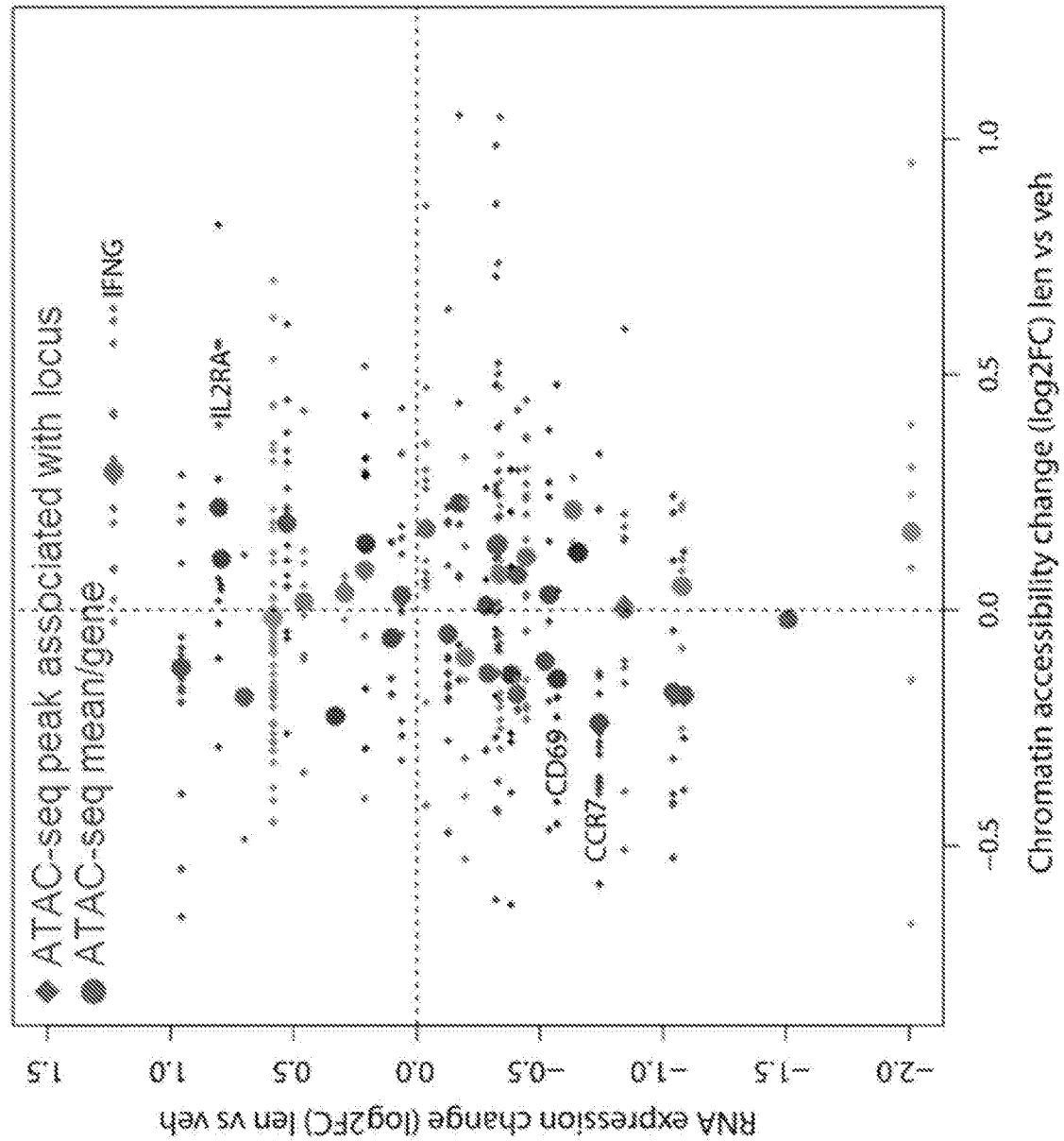
FIG. 29 shows a plot comparing individual chromatin accessibility peaks (diamond) and the mean chromatin accessibility changes for each gene (circle), with the gene expression changes, for selected genes involved in T cell activation and signaling.

For a selected subset of genes, including genes involved in T cell activation and signaling, the gene expression and chromatin accessibility changes in the presence of lenalidomide were compared for the cells cultured for 7 days with stimulation to determine whether chromatin accessibility correlated with transcription. FIG. 29 shows individual chromatin accessibility peaks (diamond) and the mean chromatin accessibility change for each gene (circle) plotted against the corresponding gene expression changes measured by RNA-seq showing concordance of signal between the two methods. Across donors, a significant increase in chromatin accessibility was observed across multiple loci associated with IFN-γ and IL-2RA (CD25), and these changes were correlated with a significant increase in transcription. Importantly, the upregulation of IFN-γ and CD25 supported previous findings from chronic stimulation experiments. Additionally, a decrease in CD69 and CCR7 chromatin accessibility and gene transcription on lenalidomide treatment was also observed.

The ATAC-seq data set for motif enrichment was analyzed, and results of the motif enrichment analysis for peaks with increased accessibility in the presence of lenalidomide in day 7 cultures are shown in FIG. 30. Motifs predicted to bind various transcription factors, understood to be involved in T cell activation and signaling, including AP-1/Jun and nuclear factor κB, were enriched in peaks with increased accessibility in the presence of lenalidomide. The results were consistent with an increase in functional activity in the CAR-expressing T cells in the presence of lenalidomide.

Without wishing to be bound by theory, the RNA- and ATAC-seq studies resulted in a number of insights into possible mechanisms for lenalidomide-induced increases in CAR T function. First, the number of transcriptional and chromatin accessibility changes associated with stimulation and time were predominant compared with the effects of lenalidomide, indicating a relatively subtle effect of lenalidomide on transcriptional networks. Second, the changes associated with lenalidomide were broad, including early changes in transcripts associated with cytoskeletal remodeling and chemotaxis. After chronic stimulation, a distinct transcriptional signature emerged that included a decrease in transcripts associated with the Th2 response, G2/M checkpoint, and ATM along with an increase in Th1, peroxisome proliferator-activated receptor γ, and actin cytoskeleton-associated genes. These effects may support a role for lenalidomide treatment and cell-cycle control and T-cell activation. Previous studies have also demonstrated the effects of IMiDs on Th1- and Th2-associated signatures as well as changes in elements associated with cytoskeletal remodeling and T-cell migration. The demonstrated early alterations in cytokine production by lenalidomide may contribute to an altered T-cell state that is able to enhance aspects of both memory and effector function simultaneously. Overall, these results suggest that additional factors beyond those previously reported are involved in the lenalidomide-induced prolongation of CAR T function, including possible changes in cell-cycle control.

The application of ATAC-seq provided further insights into potential mechanisms of action of lenalidomide. Although both stimulation and time were the predominant drivers of chromatin accessibility changes, lenalidomide treatment was associated with increases in chromatin accessibility in loci enriched in motifs associated with T-cell activation and function after chronic stimulation. These epigenetic changes were coincident with the marked functional changes in CAR T cells incubated with lenalidomide. Alterations in chromatin accessibility signatures have been associated with T-cell exhaustion and may be a more robust indicator of exhaustion compared with T-cell surface ligand expression. These data demonstrated that chronic stimulation with lenalidomide resulted in increased chromatin accessibility and gene expression of IL-2 and CD25 and decreased gene expression and chromatin accessibility of CCR7 and CD69. Previous studies suggested that CCR7-expressing cells produced higher levels of IL-2; however, the current studies indicated that the IL-2 pathway could be altered independently by lenalidomide, resulting in an alternative T-cell state. CD69, a marker of T-cell activation, has a nuclear factor κB-responsive element that is required for the CD69 response to TNF-α. The closing of CD69-associated chromatin and decrease in transcripts may be a reaction to sustained increases in TNF-α production by CAR T cells cultured with lenalidomide, or it may be a T-cell response to increased activation in the presence of lenalidomide. Lenalidomide treated cells demonstrated increased transcription factor motif enrichment of T cell activation associated factors, supporting the idea that these cells are exposed to sustained activation signaling. Overall, the lenalidomide-induced CAR T-cell state has elements of both effector T-cell function, including increased IFN-γ and TNF-α production, and memory T-cell function, including increased IL-2 and long-term proliferation.

Example 14 Assessment of Pharmacodynamic Response of Ikaros Transcription Factor in CAR-Expressing T Cells in the Presence of Compound 1 or Lenalidomide T cell compositions containing anti-CD19 CAR-expressing T cells were generated from leukapheresis samples from three healthy human adult donors by a process including immunoaffinity-based selection of T cells (including CD4+ and CD8+ cells) from the samples, resulting in two compositions, enriched for CD8+ and CD4+ cells, respectively. The cells were incubated in the presence of 3-(5-amino-2-methyl-4-oxo-4H-quinazolin-3-yl)-piperidine-2,6-dione (Compound 1) or lenalidomide, and expression of the transcription factor Ikaros was assessed.

Cells of the enriched CD4+ and CD8+ compositions were separately activated with anti-CD3/anti-CD28 beads and subjected to lentiviral transduction with a vector encoding an anti-CD19 CAR. The anti-CD19 CAR contained an anti-CD19 scFv derived from a murine antibody (variable region derived from FMC63), an immunoglobulin-derived spacer, a transmembrane domain derived from CD28, a costimulatory region derived from 4-1BB, and a CD3-zeta intracellular signaling domain. The expression construct in the viral vector further contained sequences encoding a truncated receptor, which served as a surrogate marker for CAR expression, which was separated from the CAR sequence by a T2A ribosome skip sequence. Transduced populations then were separately incubated in the presence of stimulating reagents for cell expansion. Expanded CD8+ and CD4+ cells were formulated and cryopreserved separately and stored. The cyropreserved CD4+ and CD8+ anti-CD19 CAR-expressing cells from each donor were thawed, and combined at approximately a 1:1 CAR+CD4+:CD8+ ratio prior to use.

Approximately $2.5 \times 10^5$ cells (CD4+ and CD8+ T cells combined at a 1:1 ratio) of the generated CAR+ T cell composition were stimulated overnight with a reagent specific to the CAR, and then the cells were incubated with lenalidomide (100 nM-10,000 nM), Compound 1 (10 nM-3000 nM) or a vehicle control overnight at 37° C., 5% $CO_2$. The evaluated concentrations of Compound 1 and lenalidomide encompassed the reported clinical $C_{max}$ and $C_{min}$. After incubation, anti-CD19 CAR-expressing T cells were stained with antibodies and analyzed by flow cytometry to assess surface expression of CD4, CD8 and the surrogate marker for CAR expression, and intracellular levels of Ikaros in CD4+ CAR+ or CD8+ CAR+ cells. Median fluorescence intensity (MFI) values for Ikaros were normalized and calculated as a percentage relative to vehicle control.

Figure 31A:
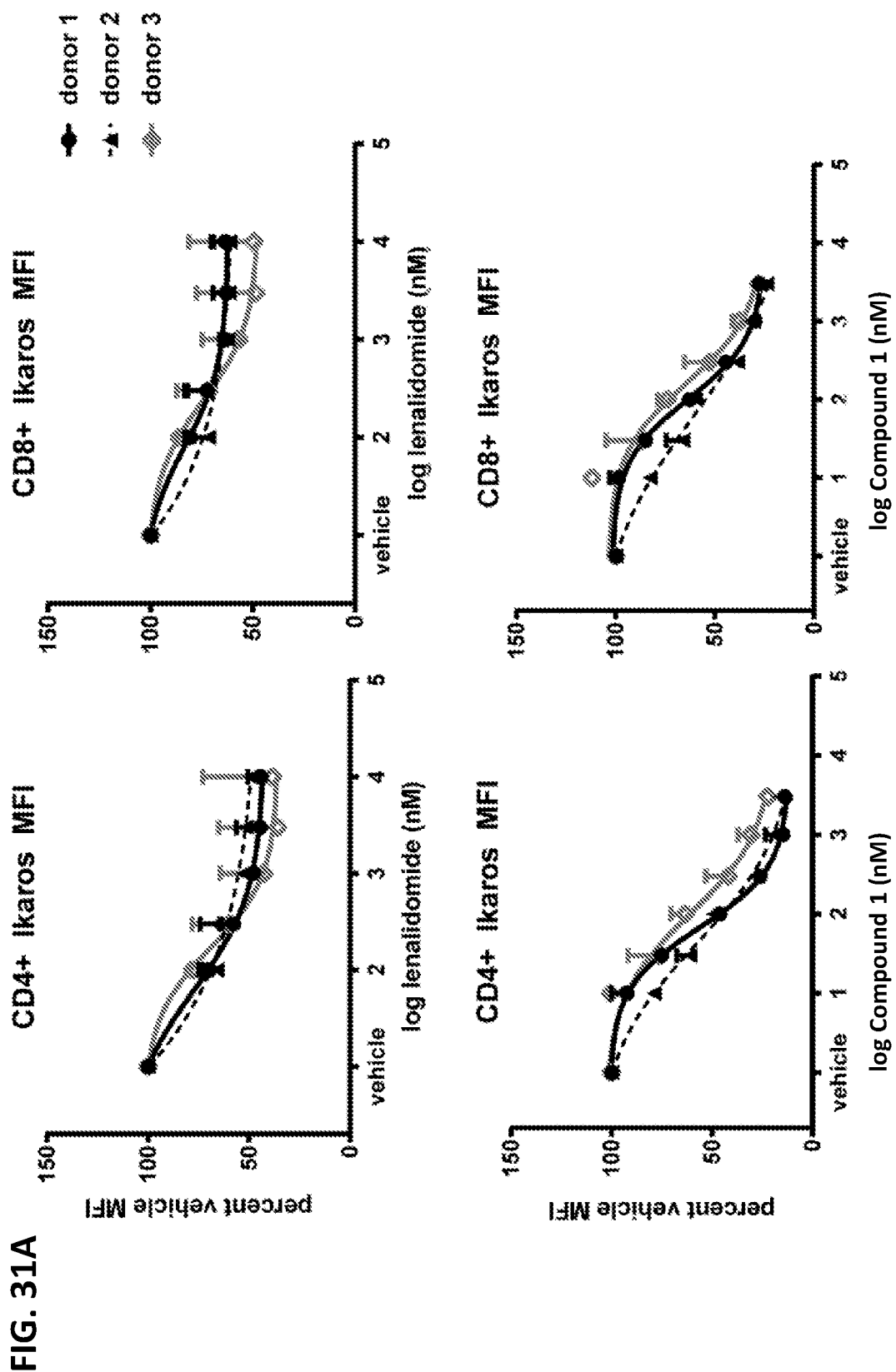
FIGS. 31A-31C show flow cytometry analysis of intracellular Ikaros or Aiolos expression on both CD4+ anti-CD19 CAR-expressing T cells and CD8+ anti-CD19 CAR-expressing T cells. CAR-expressing T cells were stimulated with CAR-T anti-idiotypic antibody at 5 µg/mL (FIG. 31A-B) or 1 µg/mL (FIG. 31C) treated across a concentration range of lenalidomide or Compound 1. Median fluorescence intensity (MFI) values for Ikaros and Aiolos were normalized and calculated as a percentage relative to as a percentage relative to vehicle control.

As shown in FIG. 31A, a concentration-dependent decrease in intracellular Ikaros expression was observed in both CD4+ anti-CD19 CAR-expressing T cells and CD8+ anti-CD19 CAR-expressing T cells after incubation with Compound 1 or lenalidomide. A greater reduction in Ikaros expression was observed in cells in the presence of Compound 1 compared to lenalidomide. The EC50 for reducing Ikaros expression was calculated as determined from the concentration of the inhibitor that reduced Ikaros MFI to 50% of its maximal MFI in the absence of the inhibitor. EC50 values for Compound 1 and lenalidomide are shown in Table E5.

TABLE E5

Ikaros EC50 (nM) in CD4+ CAR+ T cells and CD8+ CAR+ T cells.

|  | CD4+ | | CD8+ | |
| --- | --- | --- | --- | --- |
|  | Lenalidomide | Compound 1 | Lenalidomide | Compound 1 |
| Donor 1 | 61.2 | 67 | 80.9 | 100.9 |
| Donor 2 | ND | 41.5 | ND | 60.8 |
| Donor 3 | 169.8 | 99.8 | 235.5 | 161.1 |

ND = not determined

Figure 31B:
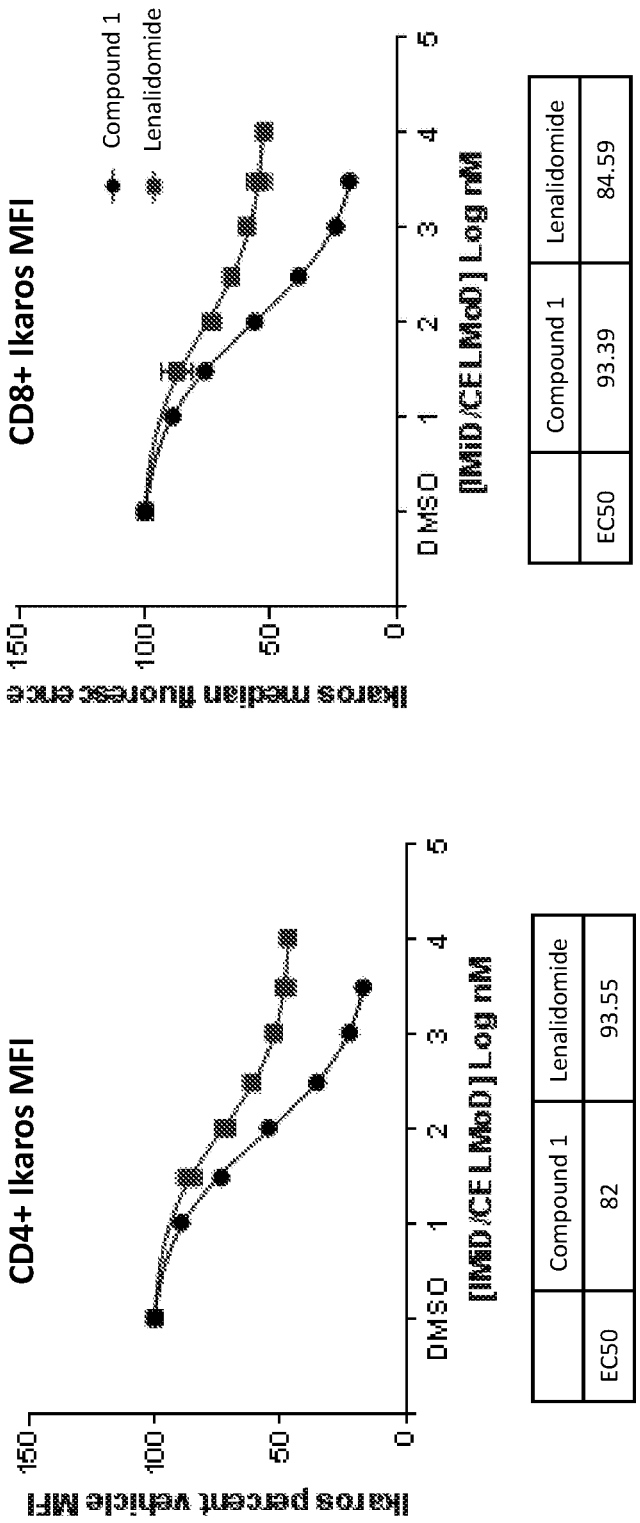

Similar results were observed with an additional CD4+ and CD8+ anti-CD19 CAR-expressing cell composition, following overnight stimulation with a reagent specific to the CAR in the presence of the indicated concentrations of lenalidomide, Compound 1 or vehicle control (FIG. 31B).

Figure 31C:
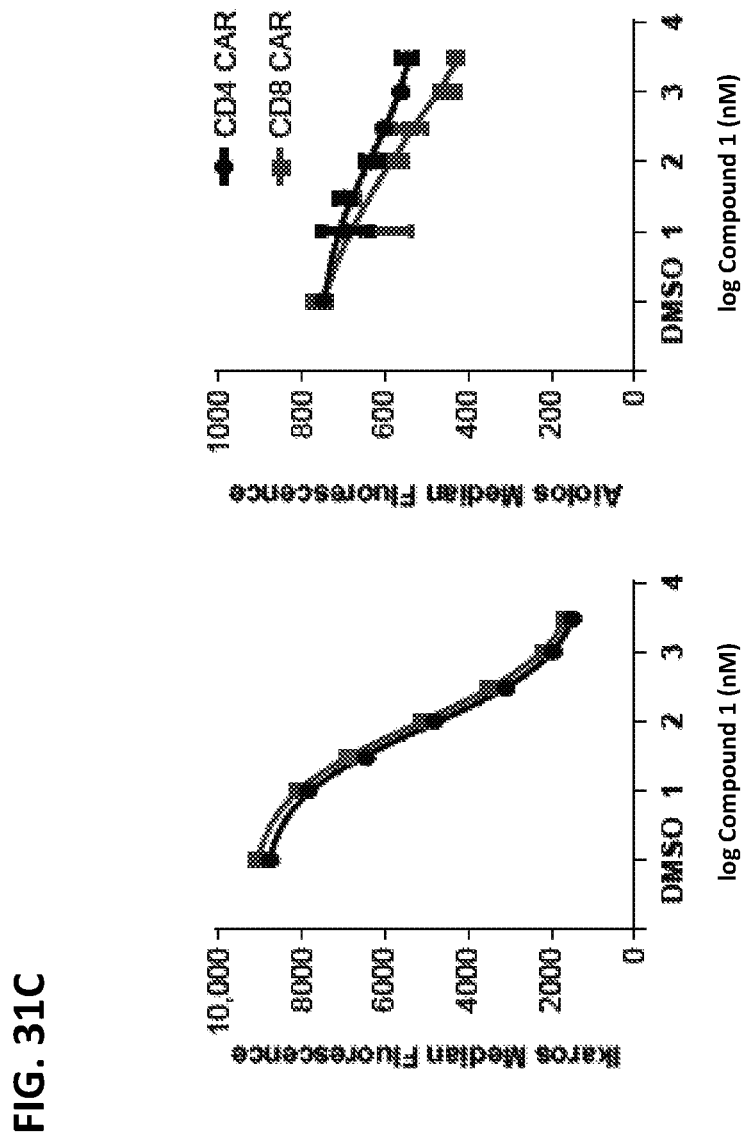

Compound 1 is known to bind Ikaros and Aiolos to cereblon (CRBN), driving ubiquitination and degradation by the proteasome. To assess expression of Ikaros and Aiolos in anti-CD19 stimulated CAR+ T cells, CD4+ and CD8+ CAR-T cells were stimulated with 1 μg/ml of a CAR-specific anti-idiotypic antibody in the presence of Compound 1 at concentrations ranging from 10 to 10000 nM. Following overnight incubation, anti-CD19 CAR-expressing T cells were stained with antibodies and analyzed by flow cytometry to assess intracellular levels of Ikaros and Aiolos in the CD4+ CAR+ or CD8+ CAR+ cells, as measured by median fluorescence intensity (MFI). As shown in FIG. 31C, a concentration dependent decrease in intracellular Ikaros and Aiolos expression was observed in both CD4+ anti-CD19 CAR-expressing T cells and CD8+ anti-CD19 CAR-expressing T cells after incubation with Compound 1.

Example 15 Evaluation of Functional Effects on CAR-Expressing T Cells Following Incubation with Target Cells in the Presence of Compound 1 or Lenalidomide Anti-CD19 CAR-expressing T cell compositions (containing CD4+ and CD8+ cells combined at a 1:1 ratio) were generated substantially as described in Example 14, and were incubated with target K562 cells transduced with human CD19 (K562.CD19) in the presence of 3-(5-amino-2-methyl-4-oxo-4H-quinazolin-3-yl)-piperidine-2,6-dione (Compound 1) (at concentrations of 10 nM, 100 nM, 500 nM, and 1000 nM), lenalidomide (at concentrations of 100 nM, 1000 nM, and 10,000 nM), or a vehicle control at 37° C., 5% $CO_2$ Cytokine expression, target cell cytolysis and expression of surface markers of anti-CD19 CAR-expressing T cells were assessed.

A. Cytokine Production

To assess cytokine production, $1 \times 10^5$ anti-CD19 CAR+ cells (CD4+ and CD8+ T cells combined at a 1:1 ratio) were incubated with K562.CD19 target cells at an E:T ratio of 5:1 or 2.5:1 in the presence or absence of lenalidomide or Compound 1 as described above. After 24 hours, supernatants were harvested and analyzed for IFN-γ, IL-2 and TNF-α cytokine production.

Figure 32A:
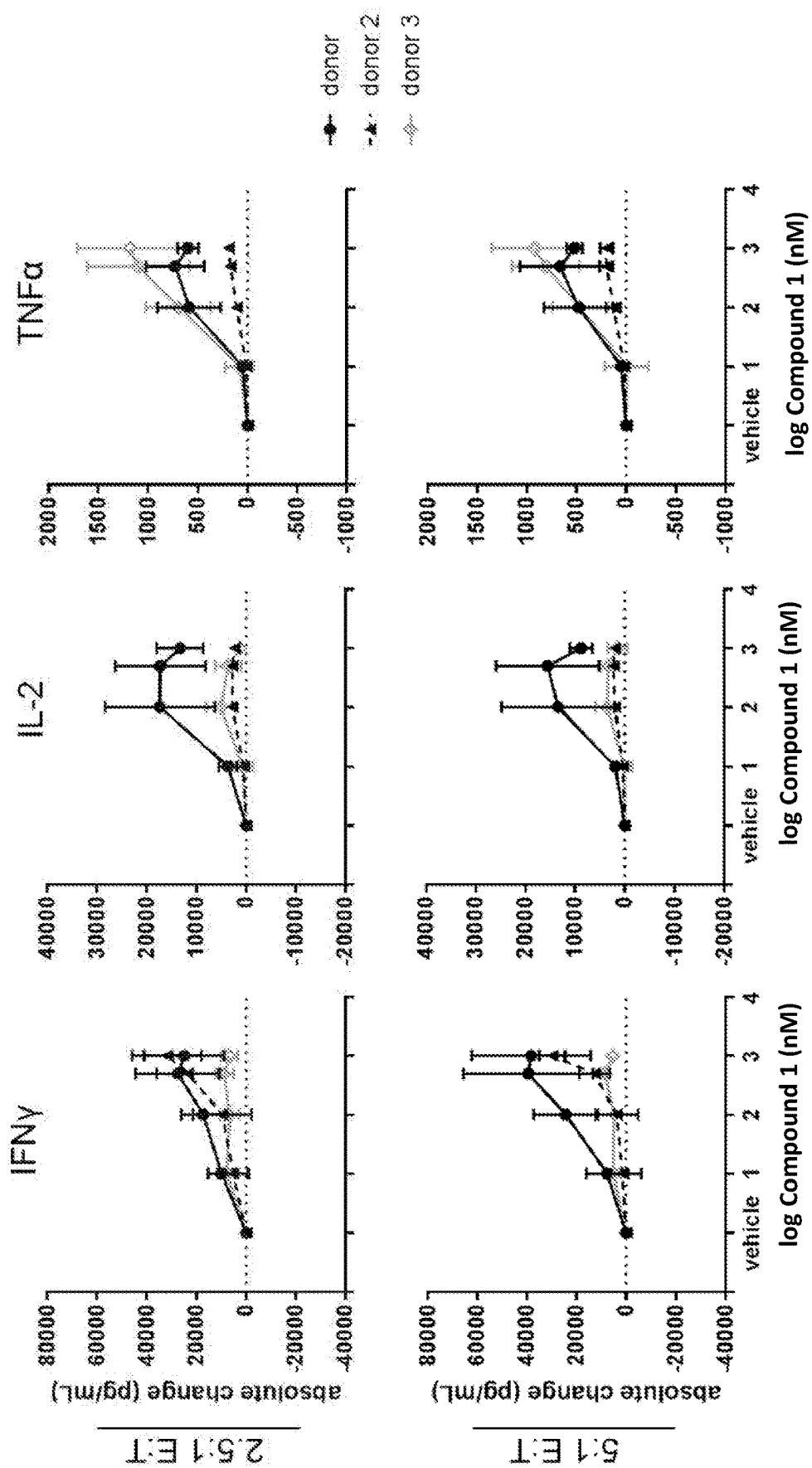
FIGS. 32A and 32B show analysis of cytokine production of anti-CD19 CAR-expressing T cells in the presence of Compound 1 (FIG. 32A) or lenalidomide (FIG. 32B) following incubation with target cells. Multiplex cytokine assay of supernatants taken at 24 hours from triplicate wells of anti-CD19 CAR-expressing T cells co-cultured with K562.CD19 target cells in the presence of several concentrations of Compound 1 or lenalidomide. IFN-γ, IL-2, and TNF-α concentrations were determined for CAR-expressing T cell from three different donors over two E:T ratios. Data represents the mean+/−S.D. across 3 experiments.
Figure 32B:
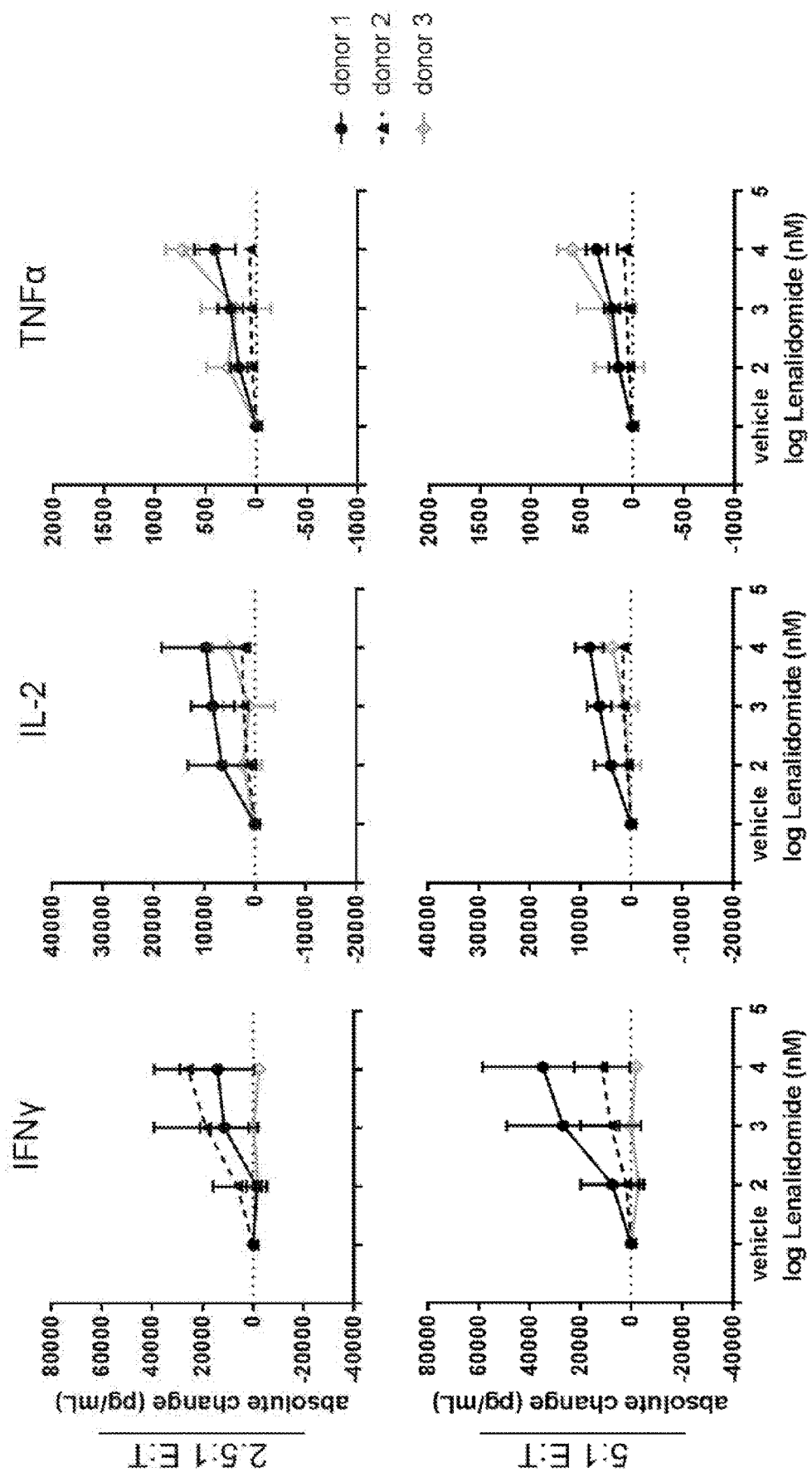

As shown in FIGS. 32A (Compound 1) and 32B (lenalidomide), cytokine production was increased in the presence of Compound 1 or lenalidomide, respectively, in a concentration-dependent manner as compared to vehicle control, at both E:T ratios of 5:1 and 2.5:1. There were differences in cytokine levels among the different donors. Compound 1 treatment resulted in greater cytokine production across multiple conditions compared to lenalidomide treatment at equivalent concentrations. The increase was statistically significant as determined from the increase in cytokine production in the presence of 100 nM and 1000 nM Compound 1 compared to the equivalent concentration of lenalidomide at the 2.5:1 and 5:1 E:T ratio as determined using an unpaired parametric t-test with Welch's correction run, see Table E6 (P-Values at 2.5:1 E:T/P-Values at 5:1 E:T).

TABLE E6

Cytokine production of anti-CD19 CAR-expressing T cells treated with Compound 1 or lenalidomide.

|  | Donor 1 | | Donor 2 | | Donor 3 | |
| --- | --- | --- | --- | --- | --- | --- |
| Concentration (nM): | 100 | 1000 | 100 | 1000 | 100 | 1000 |
| IFN-γ | ***/* | */ns | ns/ns | ns/* | */* | */*** |
| IL-2 | **/* | */* | **/ | ns/ns | ns/* | ns/ns |
| TNF-α | ***/* | */* | / | */* | /* | / |

$p \leq 0.05$: *;
$p \leq 0.01$: **;
$p \leq 0.001$: ***;
ns: not significant

B. Cytolytic Function

To assess cytolytic function, $1 \times 10^5$ or $5 \times 10^4$ anti-CD19 CAR+ cells (CD4+ and CD8+ T cells combined at a 1:1 ratio) were incubated with $2 \times 10^4$ K562.CD19 target cells at an E:T ratio of 5:1 or 2.5:1 in the presence or absence of lenalidomide or Compound 1 or vehicle control as described above. K562.CD19 target cells were transduced with NucLight Red to permit their tracking by microscopy. Cytolytic activity was assessed by measuring the loss of viable target cells over a period of five days, as determined by red fluorescent signal (using the IncuCyte® Live Cell Analysis System, Essen Bioscience). A killing index was determined using the formula: 1/AUC, and the killing index was normalized to CAR+ cells co-cultured with target cells that had been incubated with a vehicle control (set at 100% killing).

Figure 33A:
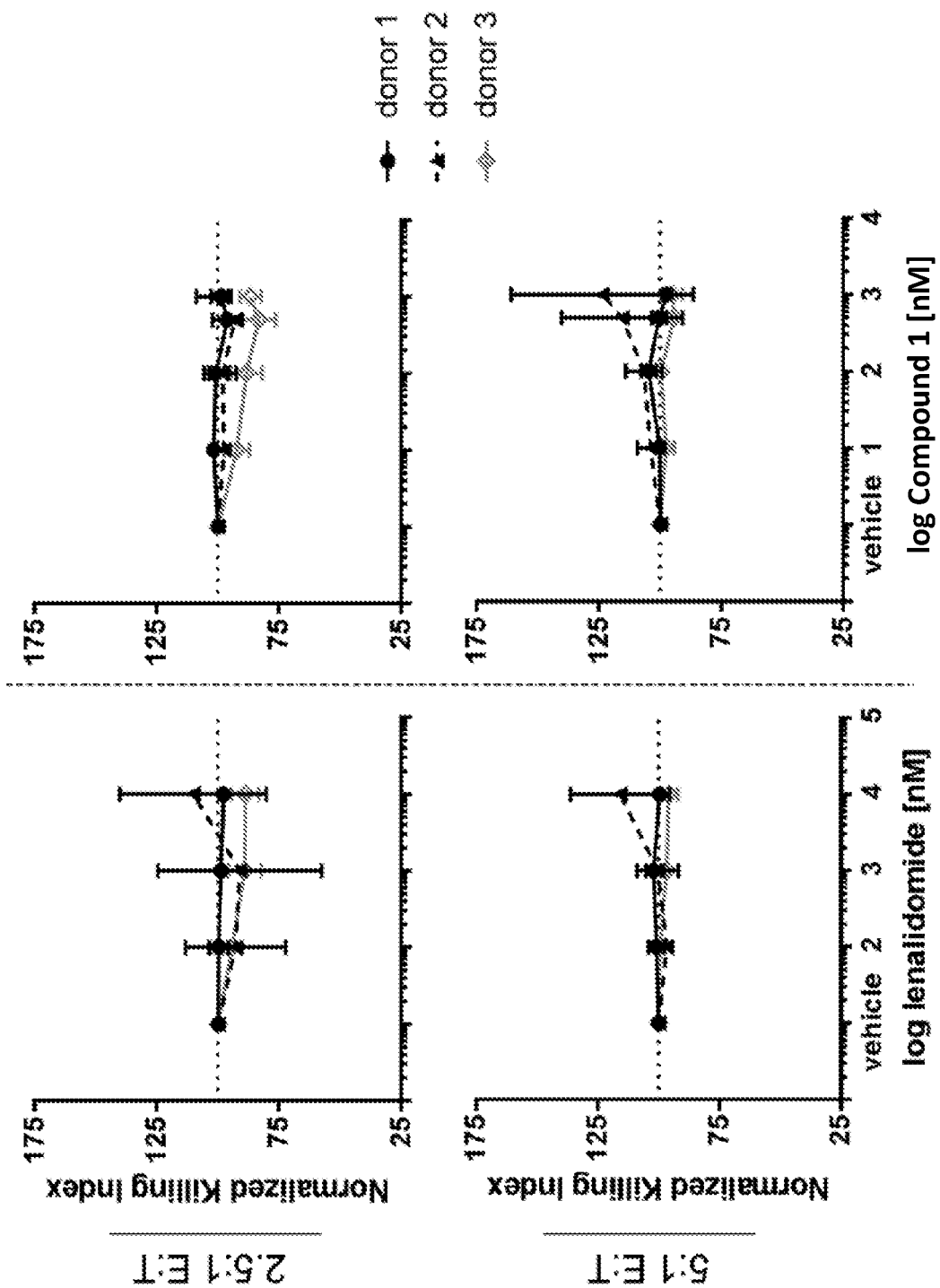
FIGS. 33A-33D show analysis of cytolytic function or cytokine production of anti-CD19 CAR-expressing T cells in the presence of Compound 1 or lenalidomide following incubation with target cells. Anti-CD19 CAR-expressing T cells from three different donors were co-cultured with K562.CD19 (FIG. 33A), or Granta-519 or Raji cells (FIGS. 33B-33D) target cells in triplicate at two E:T ratios in the presence of Compound 1 or lenalidomide over 5 days. Results were calculated as a normalized killing index. Data represents the mean+/−S.D. across 3 experiments.

As shown in FIG. 33A, Compound 1 and lenalidomide generally had a limited effect on cytolytic function of anti-CD19 CAR-expressing T cells. When the CAR was stimulated in the presence of higher antigen, as present in co-cultures containing a 2.5:1 E:T ratio, Compound 1 and lenalidomide slightly reduced cytolytic activity of anti-CD19 CAR-expressing cells for some donors. When the CAR was stimulated in the presence of lesser antigen, as present in co-cultures containing a 5:1 E:T ratio, a slight but consistent increase in cytolytic activity of anti-CD19 CAR-expressing T cells against target cells was observed from cells that had been incubated in the presence of high concentrations of Compound 1 or lenalidomide for Donor 2 while no effects were observed with Donors 1 and 3.

C. Expression of T Cell Surface Markers

To assess surface expression of various T cell markers, $1\times10^5$ K562.CD19 target cells were incubated with anti-CD19 CAR+ cells (CD4+ and CD8+ T cells combined at a 1:1 ratio) at an E:T ratio of 5:1 or 2.5:1 in the presence or absence of lenalidomide or Compound 1 or vehicle control as described above. After 24 hours, CAR-expressing T cells were stained for CD3, CD4, CD8 and the surrogate marker for CAR expression, and also for the following surface markers: CD69, CD107a, PD-1, CD25, CD62L, CCR7, CD45RO, CD27, and LAG3.

Expression levels of select markers on CD4+ CAR-expressing T cells and CD8+ CAR-expressing T cells were altered, generally less than two-fold, relative to vehicle control co-cultures. Changes in marker expression in the presence of lenalidomide or Compound 1 were donor-dependent, although for assessed memory markers expression of CD45RO was increased and CD27 was decreased across all donors and E:T ratios. Expression of CD27 was downregulated in a concentration-dependent manner in response to Compound 1 or lenalidomide. The expression of CD69 and LAG3 were increased in a concentration-dependent manner for cells derived from donor 3 after incubation with Compound 1 but not following incubation of the same donor-derived CAR+ cells with lenalidomide. Expression of the other assessed activation markers remained unchanged in donors treated with lenalidomide or Compound 1. The results are consistent with an observation that Compound 1 and lenalidomide have the potential to intrinsically modulate early activation phenotypes of CAR-expressing T cells.

D. CD19-Dependent Cytokine Production and Cytolytic Activity in

Figure 33B:
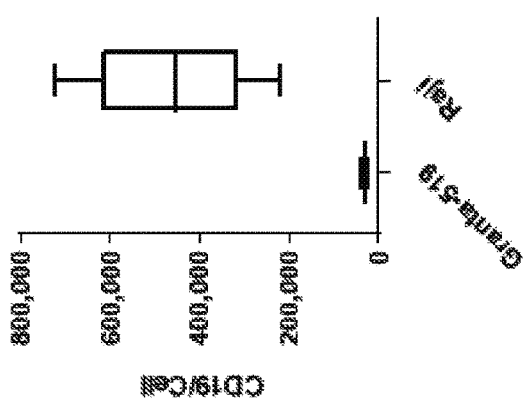

Similar studies as above were conducted using Granta-519 or Raji target cells to assess cytokine production and cytolytic activity of anti-CD19 CAR-expressing T cells upon co-culture with the target cells. As shown in FIG. 33B Raji cells were selected due to high expression of cell surface molecule CD19 when compared to Granta-519, as quantified by flow cytometry. Enumeration of CD19 was inferred by a standard curve generated using molecules of equivalent soluble fluorophore beads.

Figure 33C:
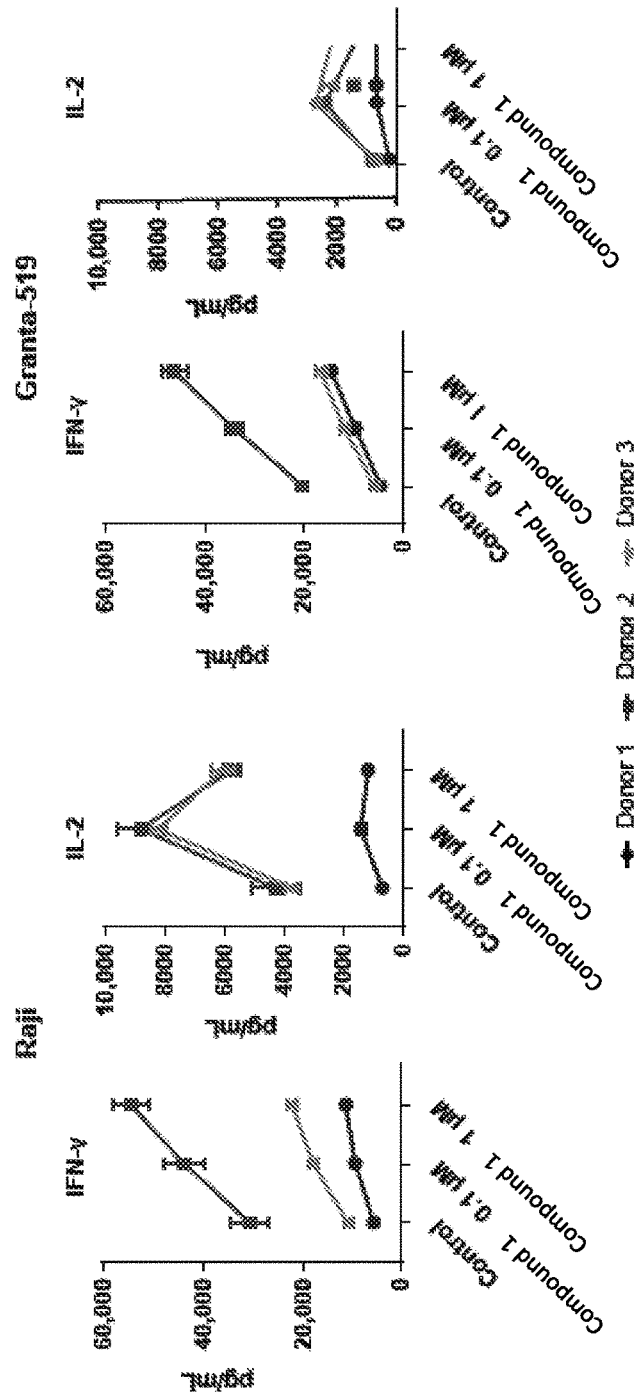
Figure 33D:
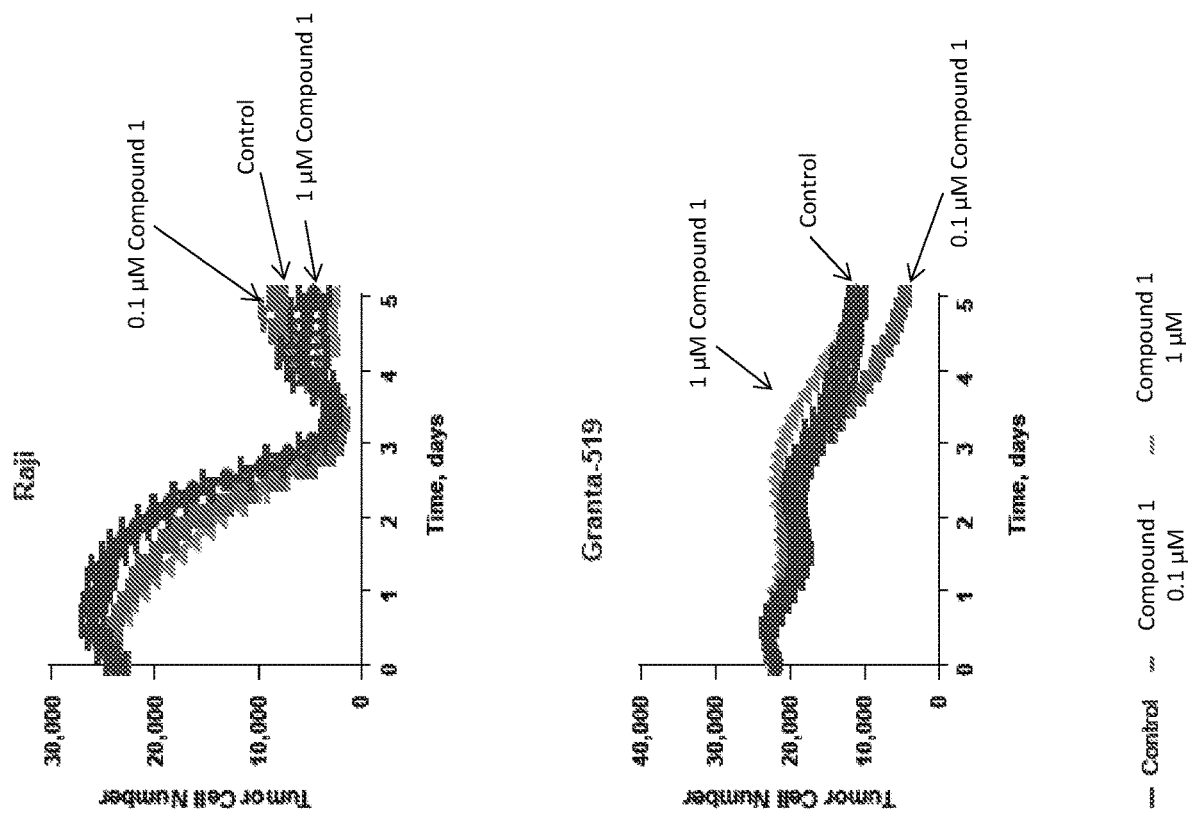

Anti-CD19 CAR+ cells T cells (CD4+ and CD8+ T cells combined at a 1:1 ratio) were incubated with Granta-519 or Raji target cells at a 2.5:1 E:T ratio in the presence of 100 or 1000 nM (0.1 and 1 µM, respectively) of Compound 1. After 24 hours of culture cytokine production was monitored in the supernatant. As shown in FIG. 33C, IFN-γ showed a concentration dependent increase in the presence of Compound 1 for CD8+ CAR-expressing T cells among the different donors, and IL-2 demonstrated a slightly more elevated increase in the presence of 100 nM (0.1 µM) Compound 1 than 1000 nM (1 µM), with both showing an increase compared to control. Cytolytic activity also was measured for pooled donors over time of the co-culture. As shown in FIG. 33D, Compound 1 had a limited effect on cytolytic activity over time for CD8+ CAR-expressing T cells.

Example 16 Evaluation of Cytokine Production and Surface Marker Expression of CAR-Expressing T Cells Following Anti-Idiotypic Antibody Stimulation in the Presence of Compound 1 or Lenalidomide Similar studies as described in Example 15 were carried out to assess cytokine production and surface marker expression following CAR-dependent stimulation of CAR-expressing T cells in the presence of 3-(5-amino-2-methyl-4-oxo-4H-quinazolin-3-yl)-piperidine-2,6-dione (Compound 1) or lenalidomide, except that CAR-expressing cells were stimulated with an anti-idiotypic antibody. The anti-idiotypic antibody was used to simulate variable stimulation levels in co-cultures, which is not generally possible with K562.CD19 target cells because the expression of antigen is uniformly high on K562.CD19 cells.

Anti-CD19 CAR-expressing T cells compositions (containing $CD4^+$ and $CD8^+$ T cells combined at a 1:1 ratio) were generated substantially as described in Example 14. Approximately $1\times10^5$ CAR-expressing cells were added to wells of a 96-well plate that had been pre-coated with an anti-idiotypic antibody specific to the scFv of the anti-CD19 CAR-expressing T cells at concentrations of 0, 0.3, 3 and 30 µg/ml. The cells were cultured in the presence of Compound 1 (at concentrations of 100 nM and 1000 nM), lenalidomide (at concentrations of 500 nM and 5000 nM), or a vehicle control at 37° C., 5% $CO_2$. Cytokine expression and expression of surface markers of anti-CD19 CAR-expressing T cells were assessed.

A. Cytokine Production

Figure 34A:
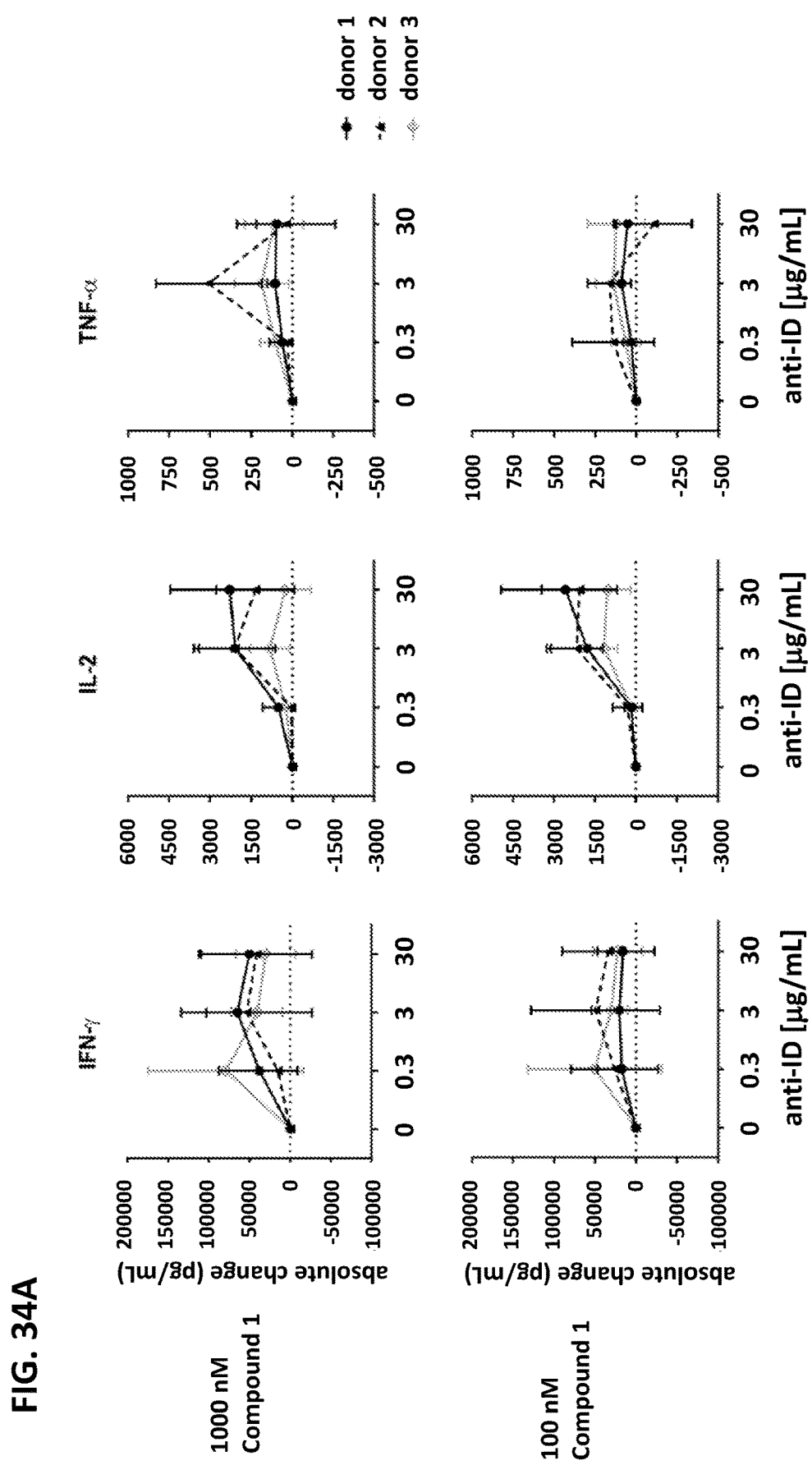
FIGS. 34A-34D show analysis of cytokine production of anti-CD19 CAR-expressing T cells or STAT5 phosphorylation in the presence of Compound 1 (FIG. 34A and FIG. 34C) or lenalidomide (FIG. 34B) following anti-idiotypic antibody stimulation. Multiplex cytokine assay of supernatants taken at 24 hours from triplicate wells of anti-CD19 CAR-expressing T cells co-cultured with agonist anti-idiotypic antibody in the presence of 100 or 1000 nM Compound 1 (FIG. 34A and FIG. 34C-34D), or 500 or 5000 nM lenalidomide (FIG. 34B). IFN-γ, IL-2, and TNF-α concentrations (FIGS. 34A-34C) and median fluorescence intensity of phosphorylated STAT5 (pSTAT5) (FIG. 34D) were determined for CAR-expressing T cells from three different donors. Data represents the mean+/−S.D. across 3 experiments.
Figure 34B:
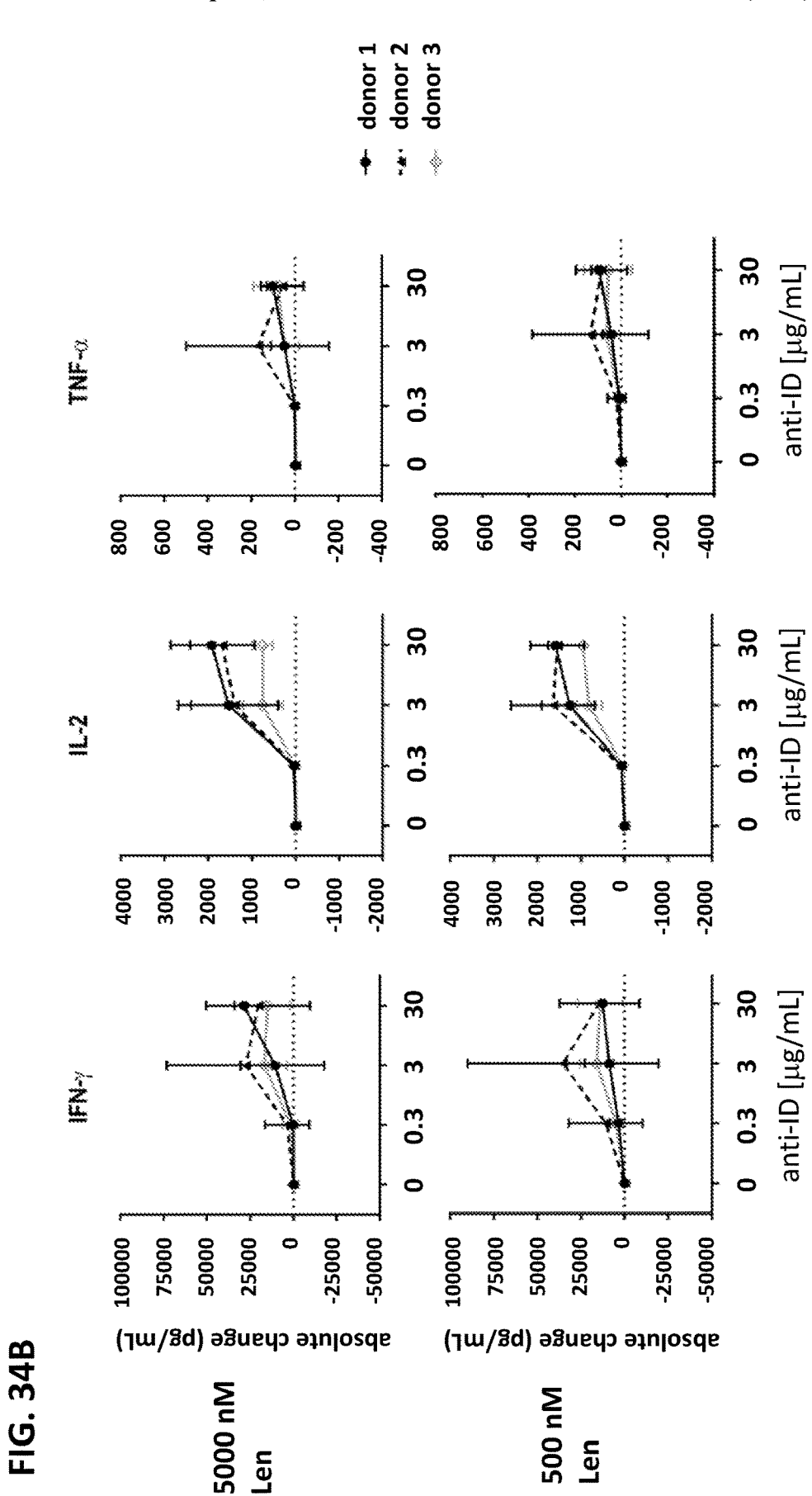
Figure 34C:
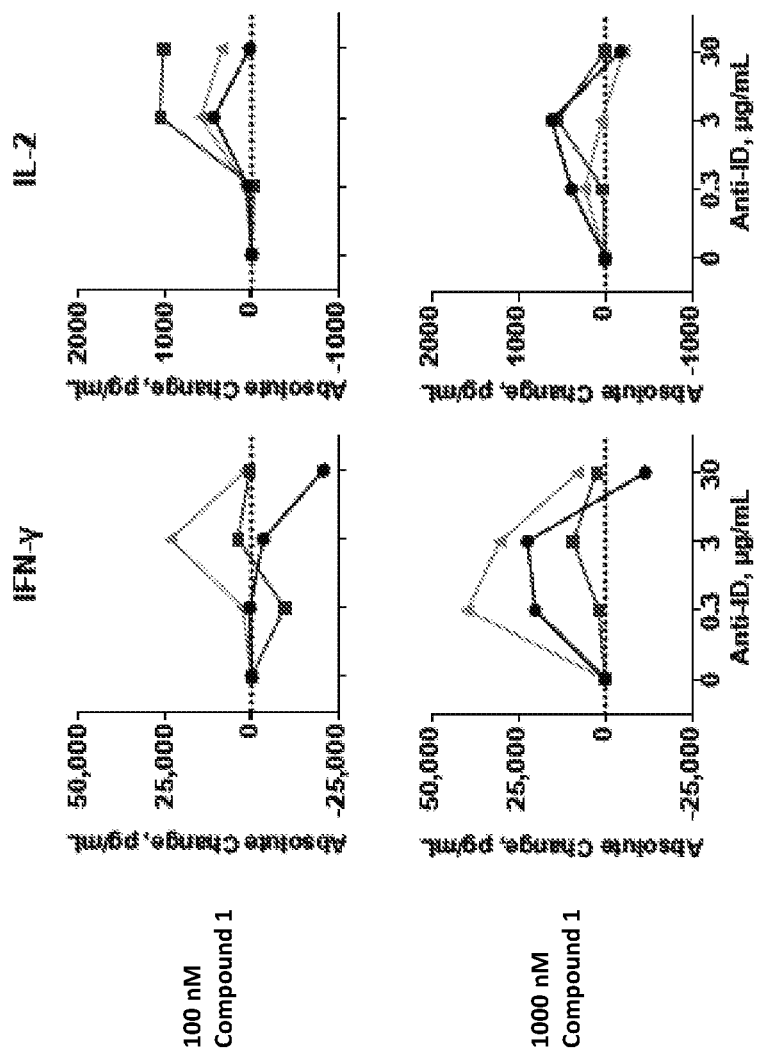

Supernatants from the stimulated cultures were harvested after 24 hours and analyzed for cytokine production. In FIGS. 34A-34C, the level of cytokine production in the absence of Compound 1 or lenalidomide (vehicle control) is indicated by a dashed line. As shown in FIGS. 34A and 34B, IFN-γ, IL-2 and TNF-α production were increased relative to the vehicle control following treatment with Compound 1 or lenalidomide, respectively. The increase was particularly evident at an intermediate level of stimulation with 3 µg/mL anti-idiotypic antibody. FIG. 34C depicts results from a similar experiment assessing cytokine production in supernatants from cell cultures harvested after 24 hours following stimulation in the presence of increasing concentrations of anti-ID agonistic antibody and compound 1 (100 nM and 1000 nM).

Figure 34D:
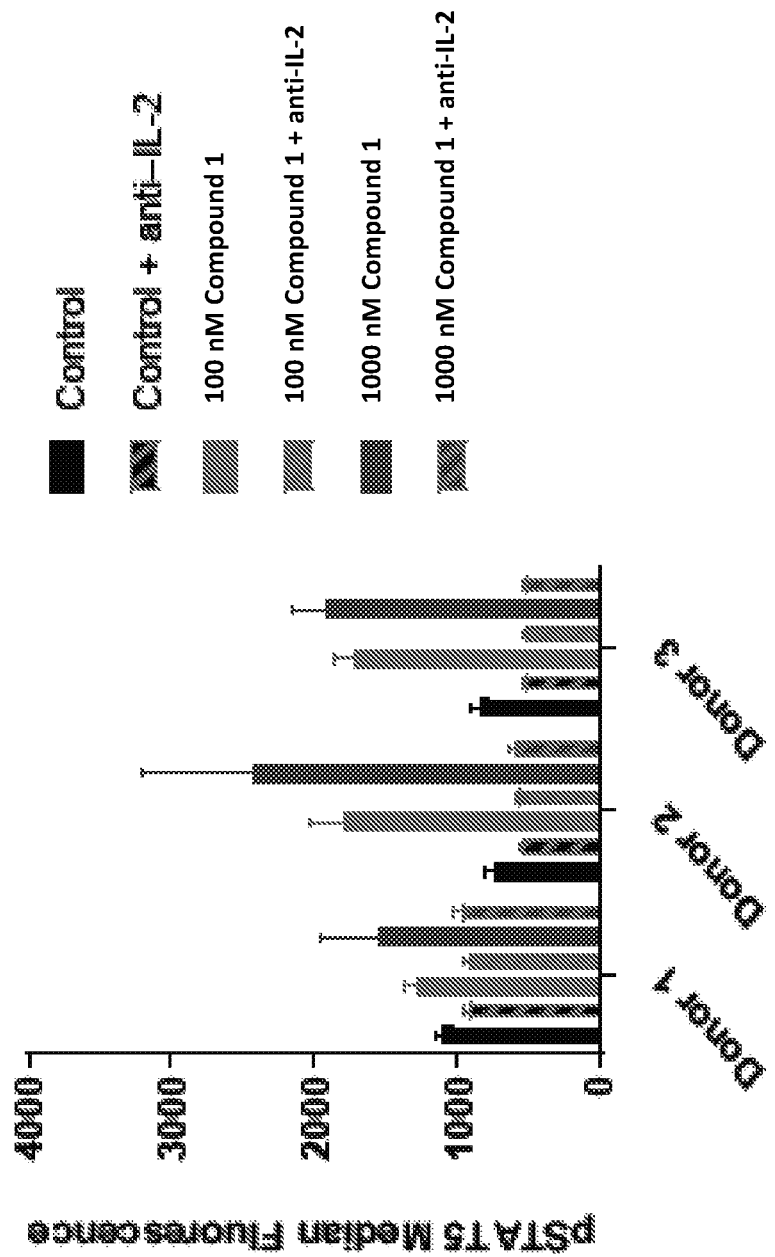

Conditioned supernatants from stimulated CAR T cultures were harvested after overnight treatment and incubated with freshly thawed CAR T cells from three donors alone or in the presence of a blocking IL-2 antibody. After short term stimulation, CAR T cells were then assessed by flow cytometry for phosphorylated STATS. As shown in FIG. 34D, median fluorescence intensity of phosphorylated STATS (pSTAT5) increased following treatment with Compound 1 for both concentrations used.

B. Expression of T Cell Surface Markers

Surface marker expression on anti-CD19 CAR-expressing T cells was assessed after 4 days in culture with various concentration of the anti-idiotypic antibody in the presence of Compound 1 or lenalidomide. CAR-expressing T cells were stained for CD3, CD4, CD8 and the surrogate marker for CAR expression, and also for the following markers: CD25, PD-1, and CD69.

Figure 35A:
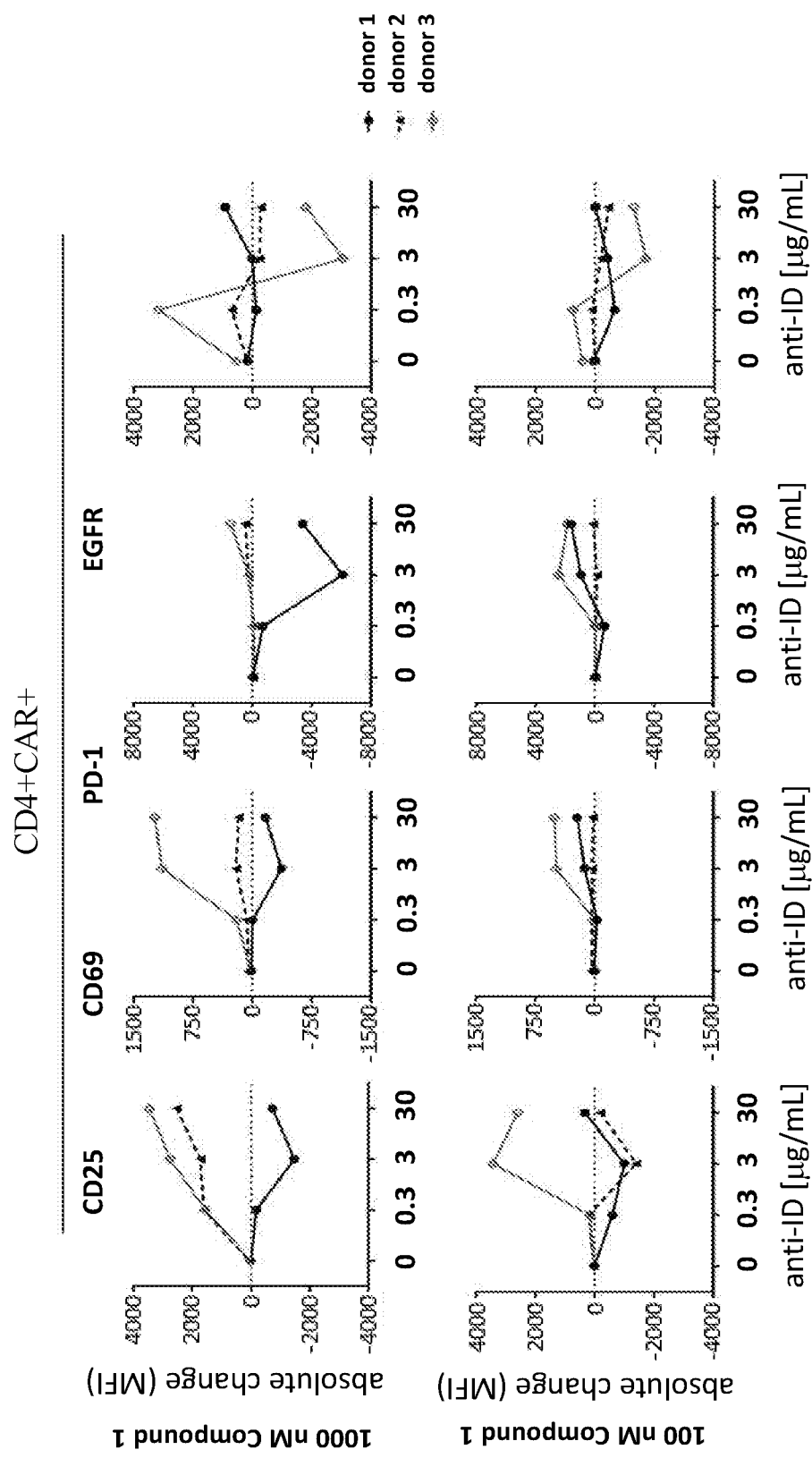
FIGS. 35A and 35B show analysis of surface marker expressions on CD4+ anti-CD19 CAR-expressing T cells (FIG. 35A) and CD8+ anti-CD19 CAR-expressing T cells (FIG. 35B) in the presence of Compound 1 following anti-idiotypic antibody stimulation. Anti-CD19 CAR-expressing T cells from three different donors were stimulated with anti-idiotypic antibody at 0, 0.3, 3, or 30 μg/mL in the presence of 100 or 1000 nM of Compound 1. Cells were analyzed by flow cytometry at day 4. The absolute change in median fluorescence intensity relative to vehicle control for each concentration of anti-idiotypic antibody was calculated. Data are representative of 3 experiments.
Figure 35B:
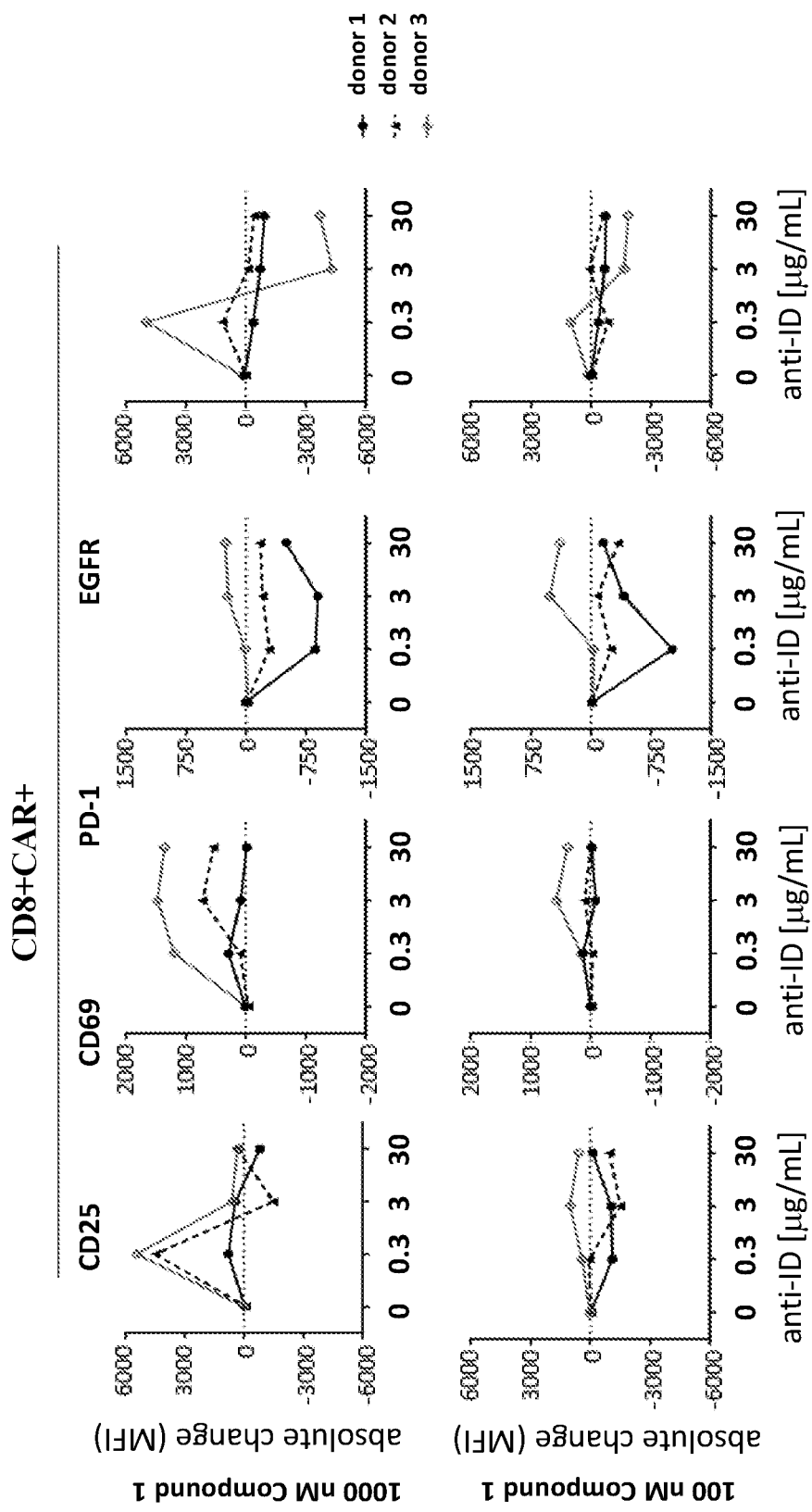
Figure 36A:
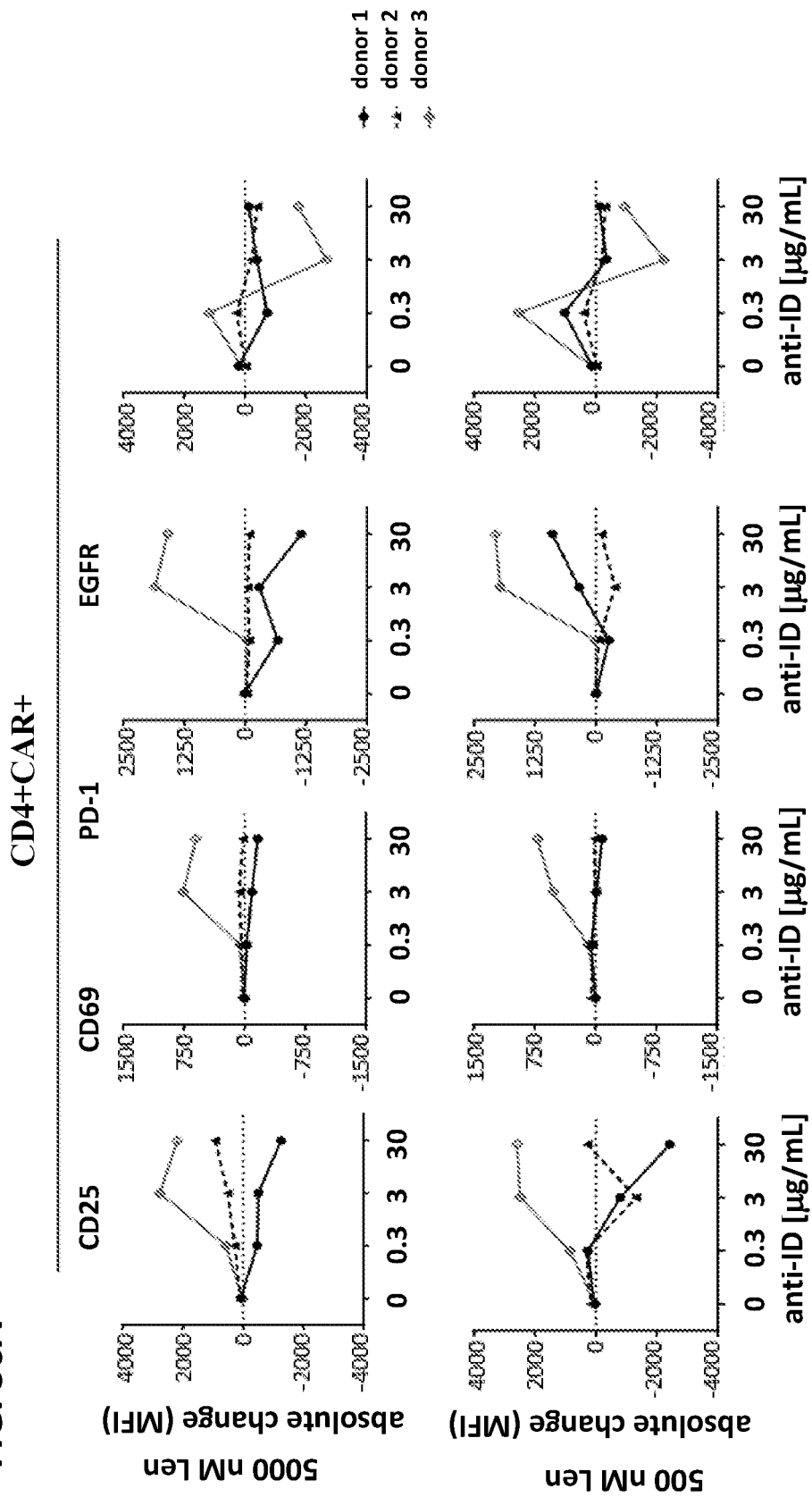
FIGS. 36A and 36B show analysis of surface marker expressions on CD4+ anti-CD19 CAR-expressing T cells (FIG. 36A) and CD8+ anti-CD19 CAR-expressing T cells (FIG. 36B) in the presence of lenalidomide following anti-idiotypic antibody stimulation. Anti-CD19 CAR-expressing T cells from three different donors were stimulated with anti-idiotypic antibody at 0, 0.3, 3, or 30 μg/mL in the presence of 500 or 5000 nM of lenalidomide. Cells were analyzed by flow cytometry at day 4. The absolute change in median fluorescence intensity relative to vehicle control for each concentration of anti-idiotypic antibody was calculated. Data are representative of 3 experiments.
Figure 36B:
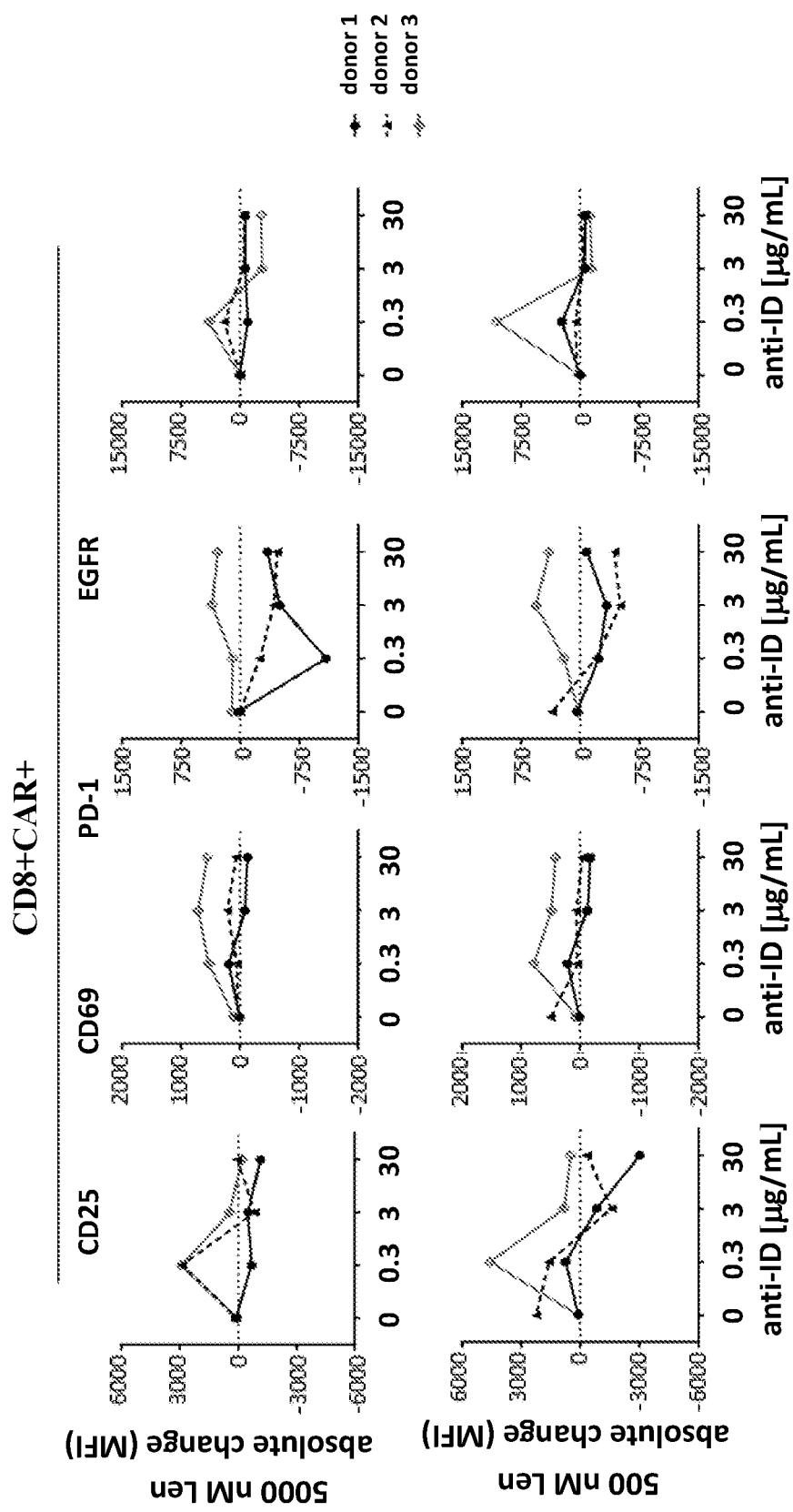

FIGS. 35A and 35B show cell surface marker expression on CD4+ and CD8+ CAR-expressing cells, respectively, on cells stimulated in the presence of Compound 1, and FIGS. 36A and 36B show cell surface marker expression on CD4+ and CD8+ CAR-expressing cells, respectively, on cells stimulated in the presence of lenalidomide. In the figures, the level of surface marker expression in the absence of Compound 1 or lenalidomide (vehicle control) is indicated by the dashed line. As shown, an increase in surface markers CD25 and CD69 was observed in CD4+ and CD8+ CAR-expressing T cells in the presence of Compound 1 or lenalidomide in some donor-derived CAR-expressing cells and depending on the amount of stimulation through the CAR. Expression of PD-1 also was increased in the presence of Compound 1 or lenalidomide in cells generated from at least one donor, although, PD-1 levels were unchanged or decreased in cells generated from the other donors. Increased expression of the surrogate marker for CAR expression was observed following addition of Compound 1 or lenalidomide at a suboptimal dose of the anti-idiotypic antibody of 0.3 μg/ml, but at higher concentrations of the anti-idiotypic antibody expression of the surrogate marker was unchanged or decreased.

Example 17 Evaluation of Surface Marker Expression and Expansion Potential of CAR-Expressing T Cells Following Serial Stimulation in the Presence of Compound 1 or Lenalidomide Serial stimulation of anti-CD19 CAR-expressing T cells was carried out to assess short-term and long-term effects of 3-(5-amino-2-methyl-4-oxo-4H-quinazolin-3-yl)-piperidine-2,6-dione (Compound 1) and lenalidomide. Anti-CD19 CAR-expressing T cell compositions (containing CD4+ and CD8+ T cells combined at a 1:1 ratio) were generated substantially as described in Example 14. The generated CAR+ T cell combinations were added at $1\times10^5$ cells per well to a 96-well plate and incubated with irradiated red fluorescent positive target K562.CD19 cells in the presence of Compound 1, lenalidomide, or a vehicle control at 37° C., 5% $CO_2$ at two different effector to target (E:T) ratio of 10:1 of 2.5:1. The incubation was carried out in the presence of Compound 1 (10, 100 or 500 nM), lenalidomide (100 or 1000 nM) or vehicle control. Every 3-4 days (start of each new round), the cells were counted. Cells then were harvested and re-plated at $1\times10^5$ anti-CD19 CAR-expressing cells with fresh media, newly added Compound 1 or lenalidomide at the same concentration, and newly-irradiated K562.CD19 target cells. This was repeated for 7 rounds of serial stimulation, and cells were assessed at various times for surface marker expression, cytolytic activity and expansion potential.

A. Expression of Surface Markers

Expression of select surface markers was assessed on cells at day 4 (i.e., 4 days after the first stimulation) and day 28 (i.e., 4 days after the seventh stimulation). Specifically, harvested cells were analyzed by flow cytometry for CD3, CD4, CD8 and the surrogate marker for CAR expression, and also for the following surface markers: CD69, CD107a, PD-1, CD25, CD62L, CCR7, CD45RO, CD27, and LAG3.

Figures 37A, 37B:
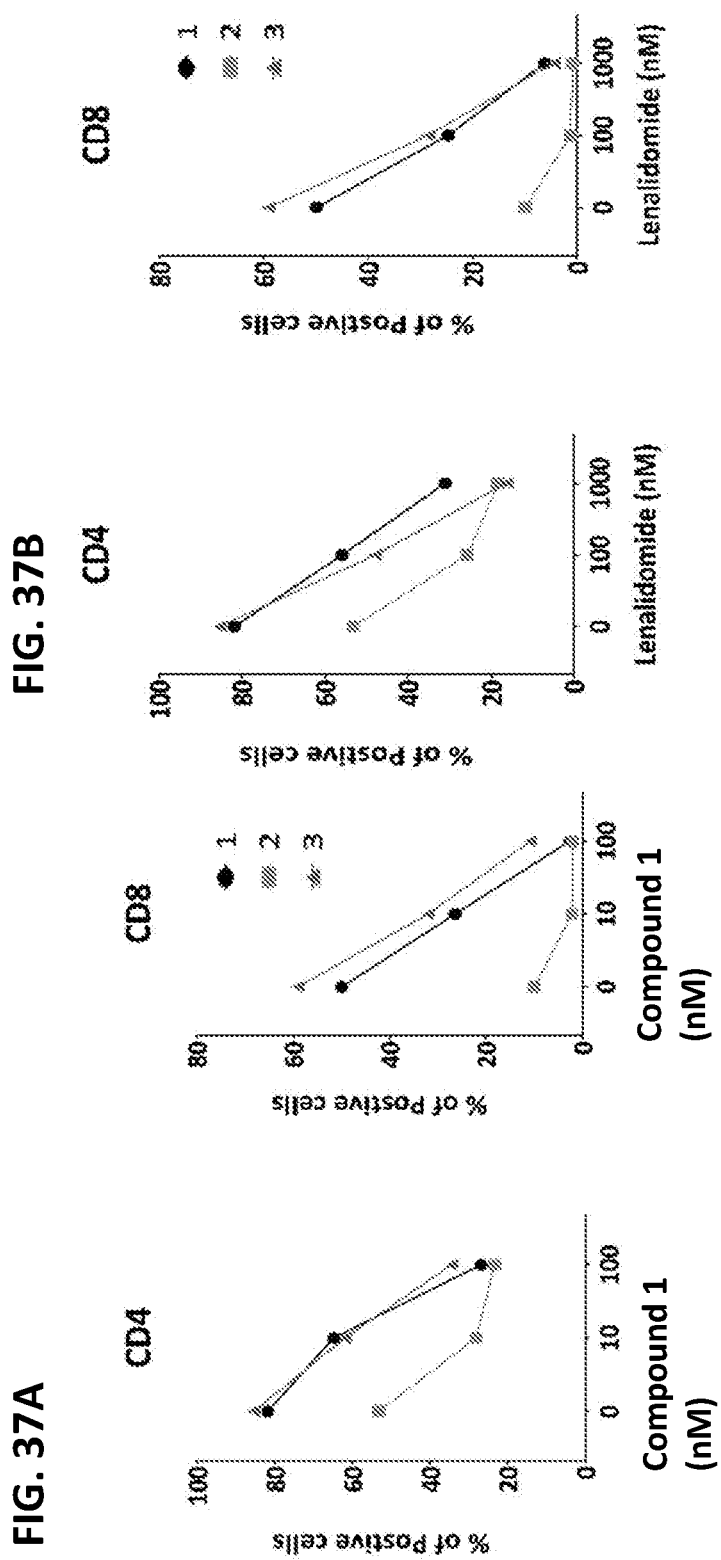
FIGS. 37A and 37B show analysis of CD28 surface expression on CD4+ and CD8+ anti-CD19 CAR-expressing T cells in the presence of Compound 1 (FIG. 37A) or lenalidomide (FIG. 37B) after serial stimulation. Anti-CD19 CAR-expressing T cells from three different donors were stimulated with K562.CD19 at an E:T ratio of 2.5:1 every 3-4 days in the presence of Compound 1 (FIG. 37A) or lenalidomide (FIG. 37B). The percentage of cells positive for CD28 was measured by flow cytometry at day 28.

Changes in assessed surface markers on CD4+ and CD8+ CAR-expressing cells following incubation with Compound 1 and lenalidomide were variously observed across all donors and E:T ratios, although the expression changes were more pronounced at day 28 compared to day 4. At day 4, CD25 and LAG3 were upregulated across all three donors in response to Compound 1 or lenalidomide treatment, with a greater decrease observed on cells from day 28 compared to day 4. CCR7 was generally decreased at day 28 across treated groups, which is consistent with the possibility that incubation with target cells in the presence of Compound 1 or lenalidomide may have driven the T cell product towards a phenotype associated with a terminally differentiated effector stat. PD-1 was downregulated to some degree in all donors and at both E:T ratios on cells at day 4 and day 28 after treatment with Compound 1 or lenalidomide, with a greater downregulation occurring on cells at day 28. As shown in FIGS. 37A and 37B, expression of CD28 was decreased in a dose-dependent manner in the presence of increasing concentrations of Compound 1 and lenalidomide, respectively, on both CD4+ and CD8+ CAR-expressing T cells from all three donors. Together, the changes in surface markers at day 28 compared to day 4 are consistent with the ability of Compound 1 and lenalidomide to impact CAR+ T cells following long-term treatment.

B. Cytolytic Function

Figure 38:
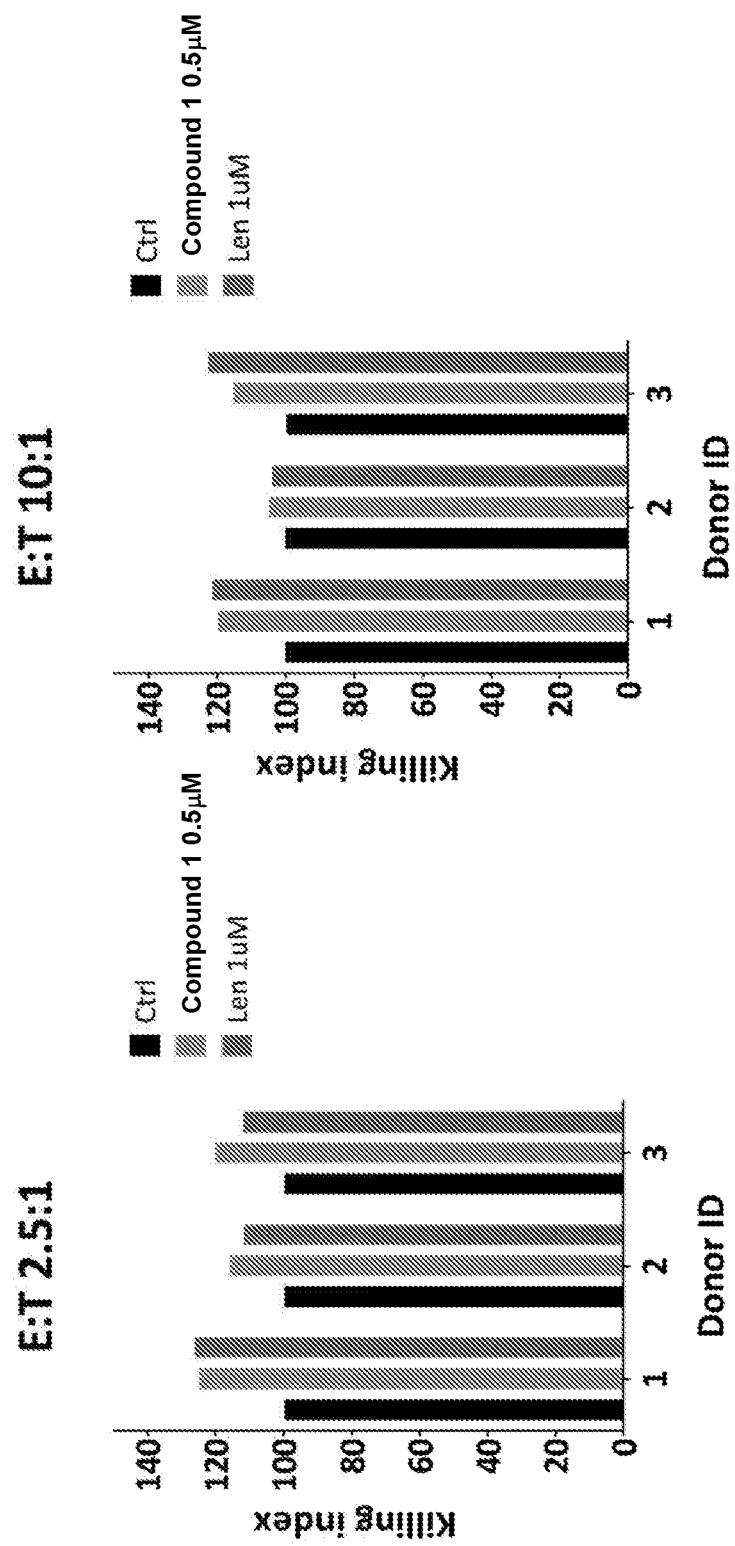
FIG. 38 shows analysis of cytolytic function of anti-CD19 CAR-expressing T cells in the presence of Compound 1 or lenalidomide following serial stimulation. Anti-CD19 CAR-expressing T cells from three different donors after 24 days of serial stimulation were co-cultured with irradiated K562.CD19 target cells in triplicate at two E:T ratios in the presence of Compound 1 or lenalidomide. Results were calculated as a normalized killing index.

At day 24 after serial stimulation, cytolytic activity of anti-CD19 CAR-expressing T cells was assessed generally as described in Example 15B. As shown in FIG. 38, long-term treatment with Compound 1 and lenalidomide were both able to increase the cytolytic activity of anti-CD19 CAR-expressing T cells.

C. Expansion

To evaluate the effect of Compound 1 and lenalidomide on expansion potential of CAR+ T cells, the cell numbers of the anti-CD19 CAR-expressing T cells were counted after each round of stimulation and cell doublings were calculated.

Figure 39A:
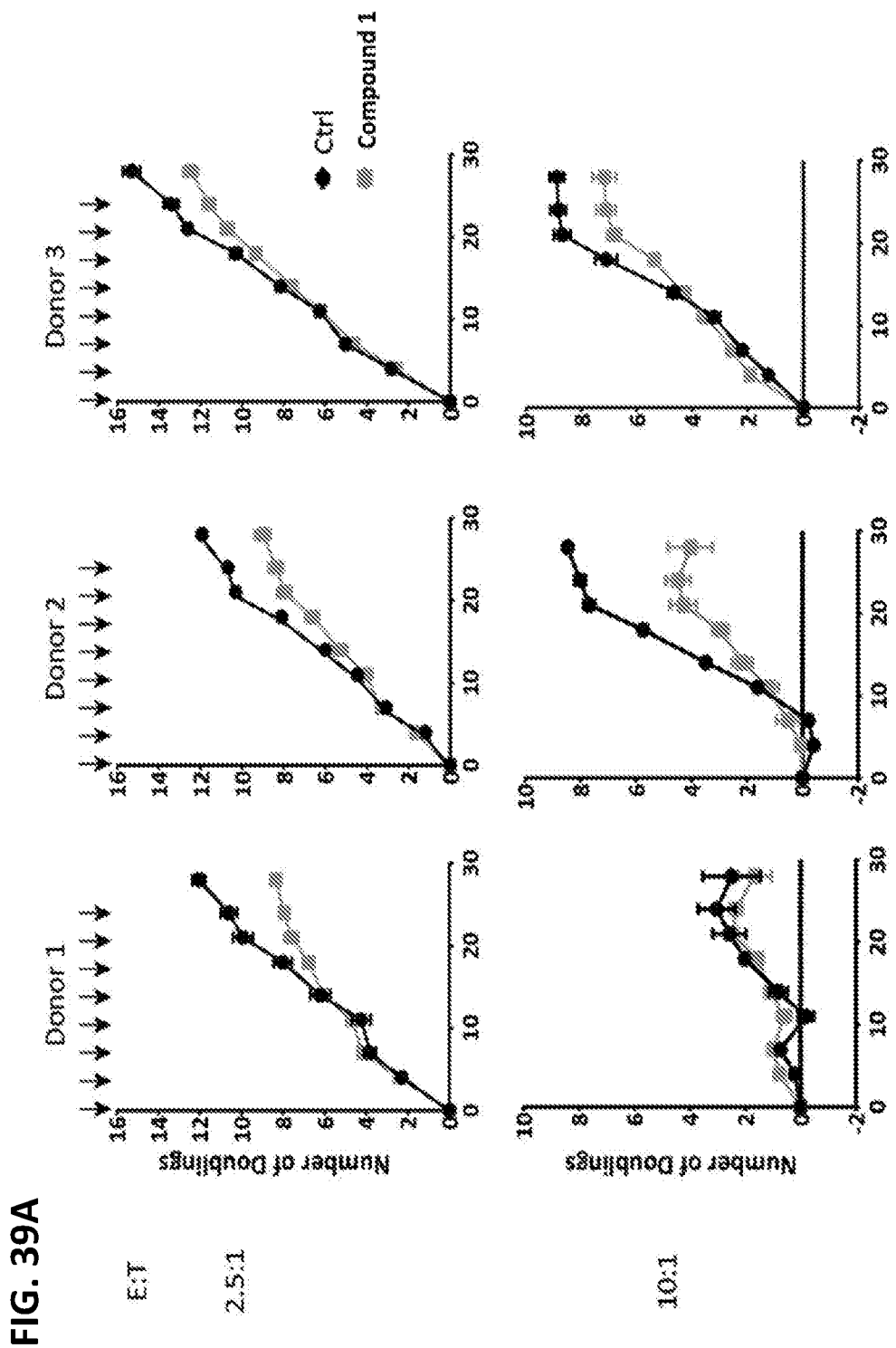
FIGS. 39A and 39B show analysis of population doublings of anti-CD19 CAR-expressing T cells during a 28-day serial stimulation period in the presence of absence of Compound 1. Anti-CD19 CAR-expressing T cells from three different donors were stimulated with with K562.CD19 target cells at an E:T ratio of 2.5:1 or 10:1 every 3-4 days in the presence of 500 nM Compound 1 for 28 days (represented by x-axis). Cells were counted after each stimulation and cell doublings were calculated.
Figure 39B:
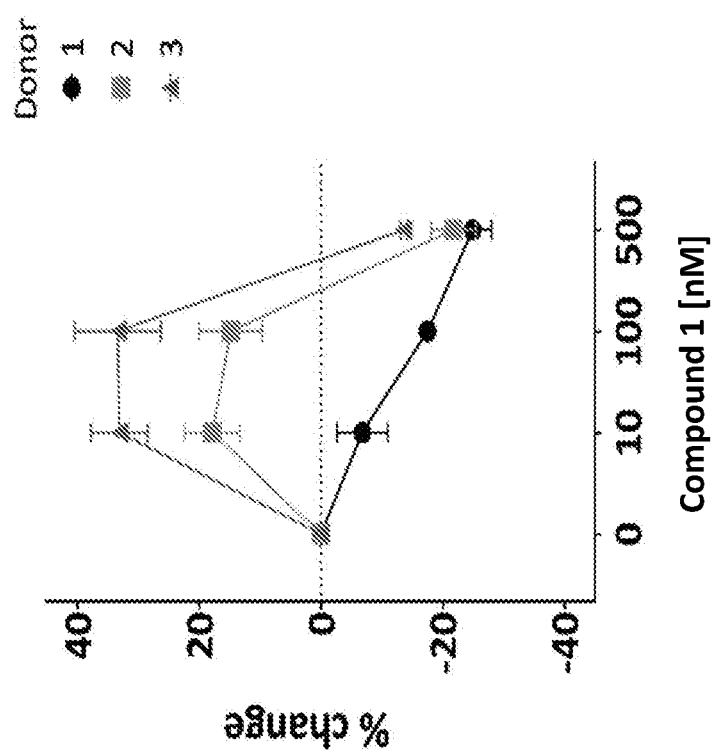

As shown in FIG. 39A, at the 2.5:1 E:T ratio, anti-CD19 CAR-expressing T cells treated with Compound 1 at concentrations of 500 nM had a comparable cell count as the treated control group until 3-4 rounds of stimulation for all donors. Similar results were observed at the 10:1 E:T ratio for two donors. At the 500 nM higher concentration of Compound 1, the number of doublings of CAR+ cells in subsequent rounds was lower than the untreated control groups. In contrast, after 24 days of treatment with Compound 1 at lower concentrations of 10 nM and 100 nM, the cell counts of anti-CD19 CAR-expressing T cells were higher than the untreated controls for two out of three donors (FIG. 39B).

Figure 40A:
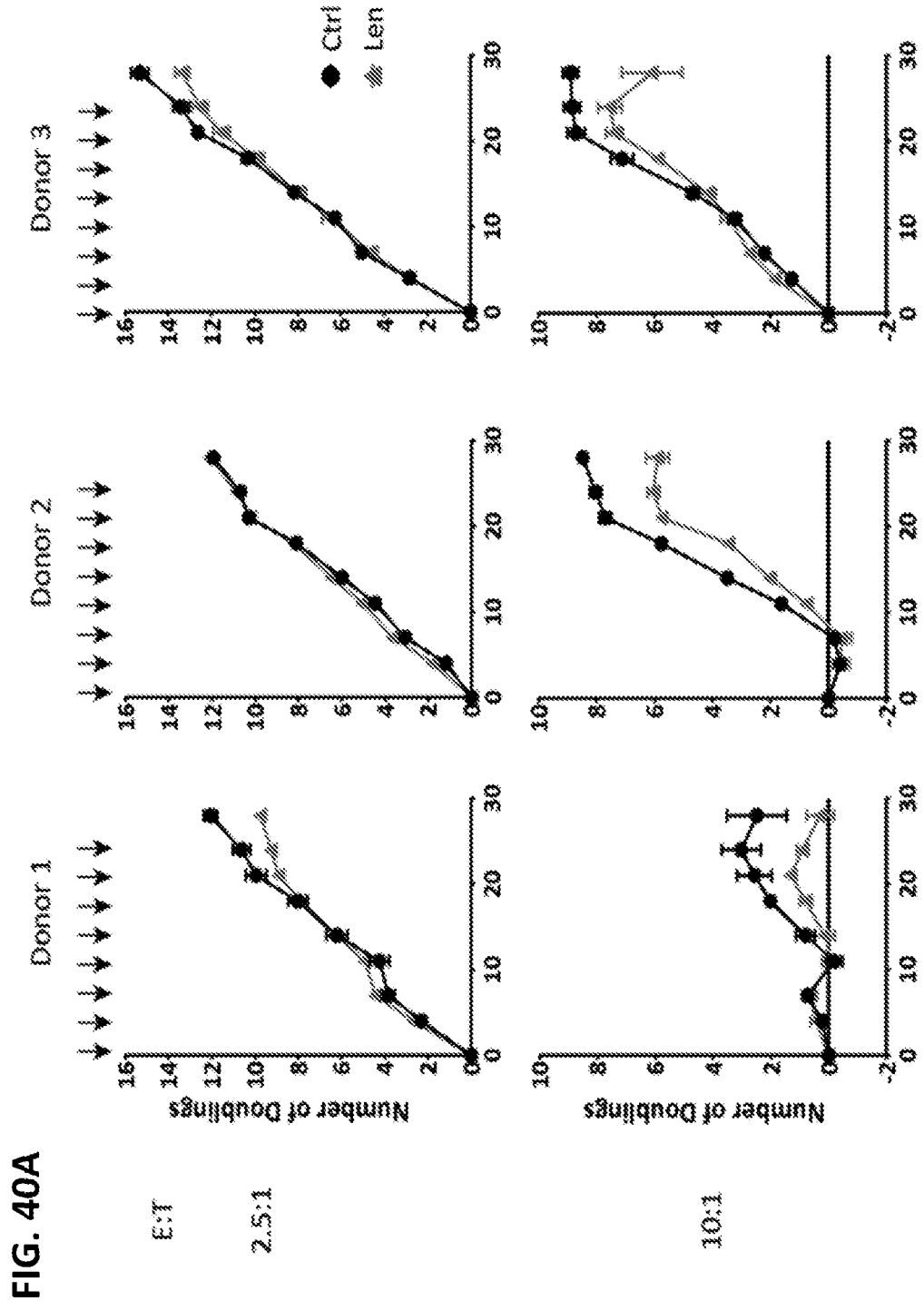
FIGS. 40A and 40B show analysis of population doublings of anti-CD19 CAR-expressing T cells during a 28-day serial stimulation period in the presence of absence of lenalidomide. Anti-CD19 CAR-expressing T cells from three different donors were stimulated with with K562.CD19 target cells at an E:T ratio of 2.5:1 or 10:1 every 3-4 days in the presence of 1000 nM lenalidomide for 28 days (represented by x-axis). Cells were counted after each stimulation and cell doublings were calculated.
Figure 40B:
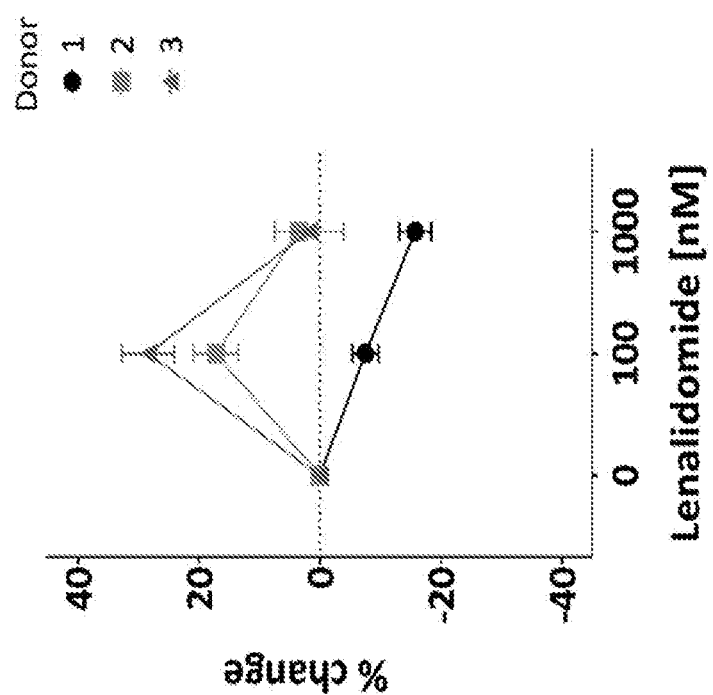

As shown in FIG. 40A, at the 2.5:1 E:T ratio in cells treated with 1000 nM lenalidomide lower cell doublings were only observed in two of the donors and not until later rounds of stimulation. This result indicates some differences in the activity of Compound 1 and lenalidomide, since 500 nM Compound 1 decreased cell counts across all donors at this E:T ratio. At the 10:1 E:T ratio, decreased cell doublings were observed after 3-4 rounds of stimulation in the presence of 1000 nM lenalidomide by cells generated from all donors (FIG. 40A). As shown in FIG. 40B, treatment with lenalidomide at a lower concentration of 100 nM increased CAR+ T cell counts for two out of three donors.

The result are consistent with an observation that prolonged treatment of CAR-expressing T cells with Compound 1 or lenalidomide at physiologically-relevant concentrations can increase long-term proliferation potential of CAR-expressing T cells, while higher concentrations may be detrimental to long term performance.

Example 18 Evaluation of Anti-Tumor Efficacy of CAR-Expressing T Cells in Combination with Compound 1 In Vivo The anti-tumor efficacy of CAR-expressing T cells in combination with 3-(5-amino-2-methyl-4-oxo-4H-quinazolin-3-yl)-piperidine-2,6-dione (Compound 1) was assessed by monitoring tumors in a tumor xenograft model. Anti-CD19 CAR-expressing T cell compositions, containing CD4+ and CD8+ T cells combined at a 1:1 ratio, were generated substantially as described in Example 14. T cell compositions were generated from three different donors.

NOD.Cg.Prkdc$^{scid}$IL2rg$^{tm1Wjl}$/SzJ (NSG) mice were injected intravenously (i.v.) with $0.5\times10^6$ Raji lymphoma tumor cells (an immortalized human B lymphocyte tumor cell line that expresses CD19) that were transfected with firefly luciferase (Raji-ffluc). Tumor engraftment was allowed to occur for 6 days and verified using bioluminescence imaging. On Day 7, mice either received no treatment, or a single intravenous (i.v.) injection of anti-CD19 CAR-expressing cells at a low dose ($0.5 \times 10^6$ cells) or a high dose ($1.0 \times 10^6$ cells). In one study group (designated "Concurrent"), mice were administered Compound 1 at a dose of 0.3 mg/kg or vehicle control via intraperitoneal injection one day prior to administration of the CAR-expressing cells (day 6), which was continued once a day for the study duration. In a second group (designated "Delayed"), mice were administered either a vehicle control or Compound 1 at a dose of 0.3 mg/kg via intraperitoneal injection starting from day 14, which was after the peak of CAR-expressing T cell expansion, and administration was continued once a day for the study duration. Tumor burden was assessed by bioluminescence every 10 days. For bioluminescence imaging, mice received intraperitoneal (i.p.) injections of luciferin substrate (CaliperLife Sciences, Hopkinton, MA) resuspended in PBS (15 µg/g body weight). The average radiance (p/s/cm$^2$/sr) was determined. Survival of mice treated as described above were assessed and compared until day 100 post-infusion of CAR-expressing T cells.

Figure 41:
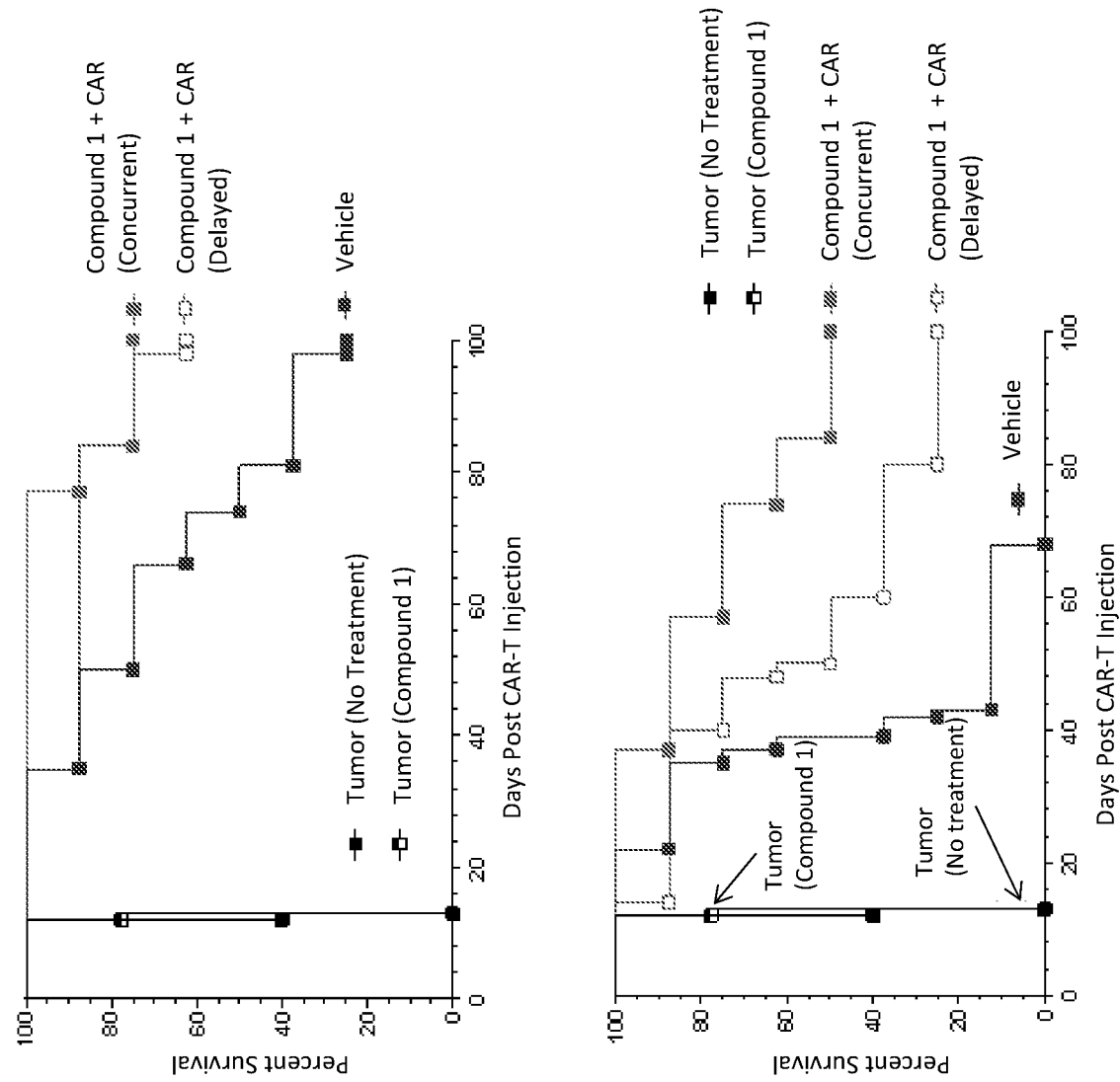
FIG. 41 shows analysis of anti-tumor efficacy of CAR-expressing T cells in combination with Compound 1, as shown by percent survival. NOD.Cg.Prkdc$^{scid}$IL2rg$^{tm/Wjl}$/SzJ (NSG) mice were injected intravenously (i.v.) with 0.5×10$^6$ Raji lymphoma tumor cells and tumor engraftment was allowed to occur for 6 days. On day 7, mice either received no treatment, or a single i.v. injection of anti-CD19 CAR-expressing cells. In one study group (designated "Concurrent"), mice were administered Compound 1 or vehicle control one day prior to administration of the CAR-expressing cells (day 6), which was continued once a day for the study duration. In a second group (designated "Delayed"), mice were administered either a vehicle control or Compound 1 starting from day 14, which was after the peak of CAR-expressing T cell expansion, and administration was continued once a day for the study duration. Survival of mice were assessed and compared until day 100 post-infusion of CAR-expressing T cells.

In this study, the combination with Compound 1 was observed to reduce tumor burden and improve survival data in both the "Concurrent" group and the "Delayed" group, as compared to administration of the CAR-expressing cells alone. Representative survival curves, Kaplan-Meier method (GraphPad Prism 7.0, GraphPad Software, La Jolla), from one donor are shown in FIG. 41. As shown, Compound 1, either administered delayed or concurrent with anti-CD19 CAR-T cells at the low and high dose, resulted in greater percent survival of mice compared to mice receiving only administration of anti-CD19 CAR-T cells. Table E7 summarizes the median survival of mice in this study.

protein inserted by knock-in into the endogenous Nr4a1 (Nur77) gene. This resulted in the expression of the reporter being controlled by the endogenous transcriptional regulatory elements of the Nur77 gene.

Figure 42:
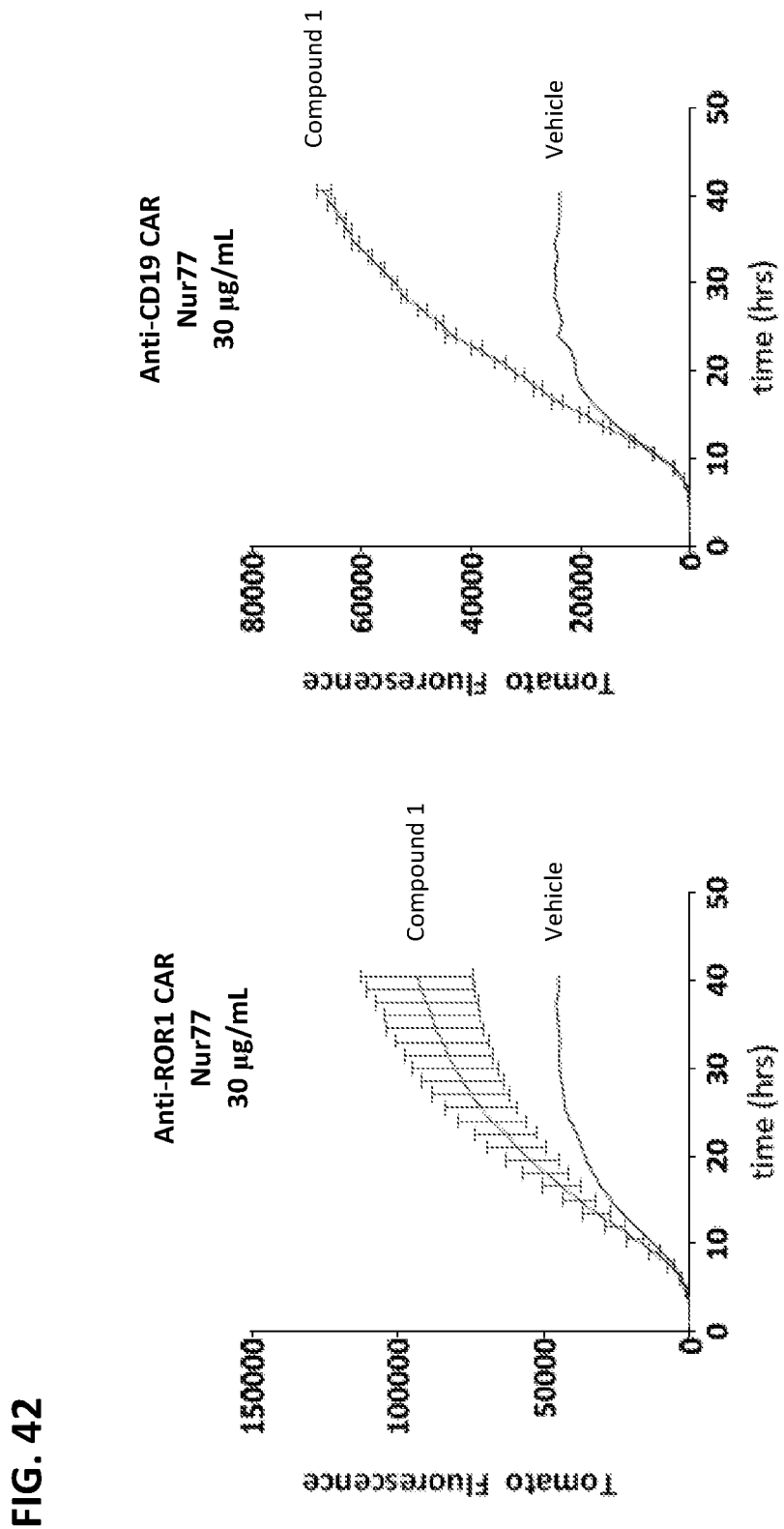
FIG. 42 shows analysis of CAR signaling in the presence of Compound 1. The expression level of dTomato in Jurkat Nur77-dTomato reporter cells expressing either an anti-CD19 CAR or an anti-ROR1 CAR, as detected by flow cytometry, was measured following incubation in the presence of Compound 1 or a vehicle control for up to 6 hours.

Anti-CD19 CAR-expressing reporter cells or anti-ROR1 CAR-expressing reporter cells were incubated, in the presence of 3-(5-amino-2-methyl-4-oxo-4H-quinazolin-3-yl)-piperidine-2,6-dione (Compound 1) or vehicle control, for up to 6 hours in of the presence of plate-bound anti-idiotypic (ID) antibody specific to the respective CAR. As shown in FIG. 42, an increase in reporter signal was observed following CAR-specific stimulation of the anti-CD19 CAR or the anti-ROR1 CAR, which in each case was increased in the presence of Compound 1. The results were consistent with a conclusion that compound 1 can be used to increase CAR signaling following recognition of the CAR antigen.

Example 20 Long-Term Stimulation on CAR T Cell Function and Effect of Compound 1 on CAR T Function Following Long-Term Stimulation Anti-CD19 CAR-expressing T cell compositions (containing CD4+ and CD8+ T cells combined at a 1:1 ratio) were generated from three different healthy donors substantially as described in Example 14. To subject cells to chronic stimulation conditions, the CAR+ T cells were incubated with plate-bound anti-idiotypic (anti-ID) antibody (see e.g. WO2018/023100), and incubated at 37° C. for a period of 6 days.

After the 6-day culture period, the anti-CD19 CAR-expressing T cells were removed from culture and incubated with A549 CD19+ tumor spheroids (to rechallenge the CAR-T cells) at an effector to target ratio of 0.5:1 unless otherwise indicated, in the presence of 3-(5-amino-2-methyl-4-oxo-4H-quinazolin-3-yl)-piperidine-2,6-dione (Compound 1), at concentrations ranging from 0.001 µM to

TABLE E7

| | Survival | | | |
|---|---|---|---|---|
| | High Dose | | Low Dose | |
| | Median Survival (Days post CAR-T) | P value* | Median Survival (Days post CAR-T) | P value* |
| Anti-CD19 CAR-T | 77.5 | | 39 | |
| Anti-CD19 CAR-T + Compound 1 (concurrent) | Undefined | 0.0301 | 92 | 0.0013 |
| Anti-CD19 CAR-T + Compound 1 (delayed) | Undefined | 0.1209 | 55 | 0.0521 |

*Gehan-Breslow-Wilcoxon test

Example 19 CAR Signaling in the Presence of Compound 1

Cells of a reporter cell line were transduced using lentiviral vectors encoding the anti-CD19 CAR described in Example 14 or an anti-ROR1 CAR were introduced into cells of a Jurkat reporter cell line to assess CAR signaling in the presence of CAR stimulation. The anti-ROR1 CAR contained an anti-ROR1 scFv derived from a murine antibody, an immunoglobulin-derived spacer, a transmembrane domain derived from CD28, a costimulatory region derived from 4-1BB, and a CD3-zeta intracellular signaling domain. The Jurkat reporter cell lines contained a red fluorescent 10 µM, or vehicle control for up to 10 days. The A549 CD19+ tumor spheroids were labeled with a dye to permit monitoring of tumor cell lysis by microscopy during the assay. Freshly thawed anti-CD19 CAR-expressing T cells that had not been subjected to the chronic stimulatory conditions were incubated with the spheroids in parallel as controls. Cells were assessed at various times for cytolytic function, CAR T cell number and cytokine production.

1. Effect of Chronic Stimulation on T Cells

Figure 43B:
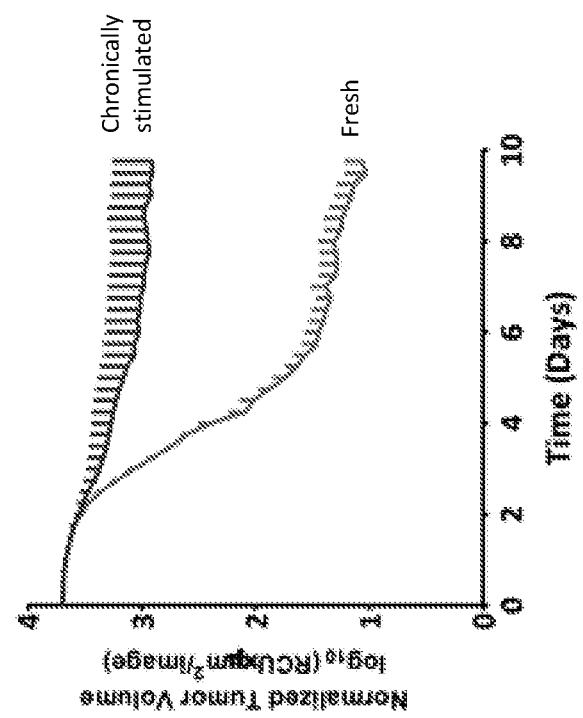
Figure 43A:
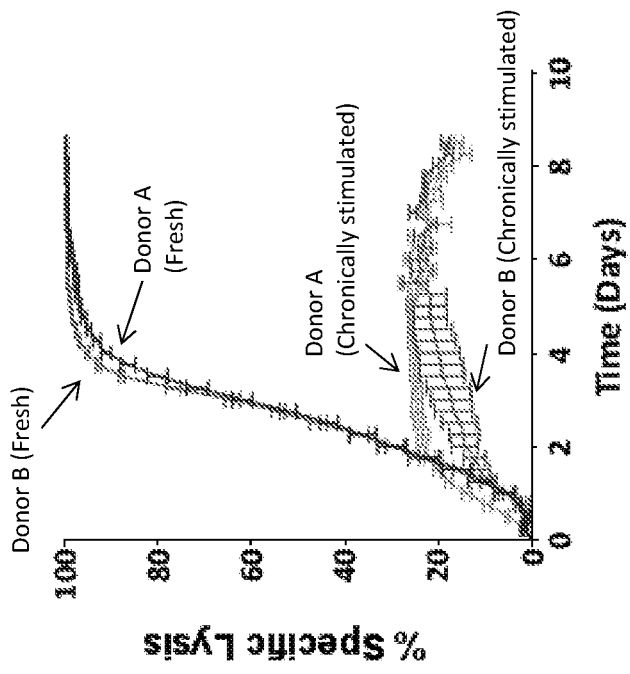

The antigen-specific cytolytic activity of the various CAR-expressing T cells was assessed by monitoring fluorescence (indicative of tumor cell lysis) over time. The cytolytic activity of anti-CD19 CAR-expressing T cells that had been stimulated over the 6 day period using chronic stimulatory conditions was reduced, as compared to freshly thawed anti-CD19 CAR-expressing T cells from the same donor, is shown in FIG. 43A (representative results from two donors are shown). Tumor (spheroid) volume also was assessed over time, as shown in FIG. 43B. A decrease in the reduction of tumor volume in the presence of chronically stimulated versus fresh CAR-T cells was observed.

Figure 43C:
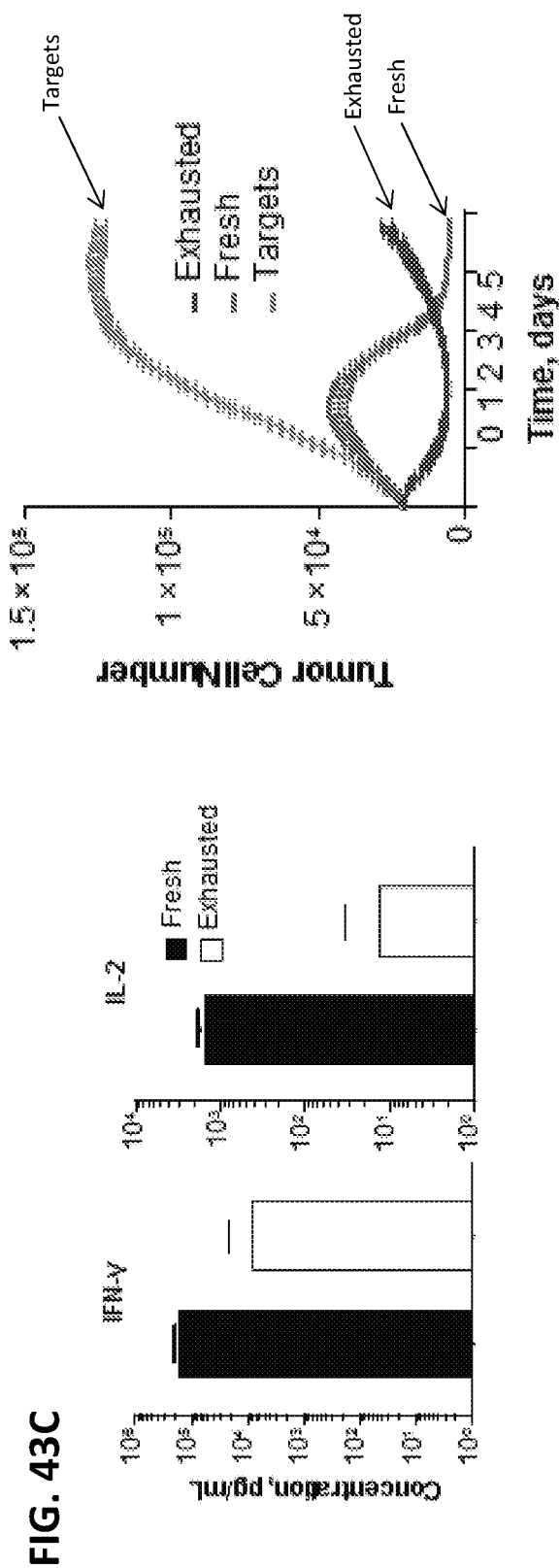

To further assess activity of chronically stimulated cells, anti-CD19 CAR-expressing T cells that had been stimulated over the 6 day period, or freshly thawed anti-CD19 CAR-expressing cells from the same donor that had not been chronically stimulated, were co-cultured with K562.CD19 target cells for 5 days and cytolytic activity and ability to produce cytokines was assessed. As shown in FIG. 43C (left panel), the levels of IFN-γ and IL-2 secretion was reduced, as compared to cytokine production by freshly thawed anti-CD19 CAR-expressing T cells from the same donor. Cytolytic activity by chronically stimulated anti-CD19 CAR-expressing cells also was reduced, compared to freshly thawed cells, as evidenced by reduced tumor cell number (FIG. 43C right panel), The results were consistent with the conclusion that the 6-day culture had subjected CAR-T cells to chronic stimulatory conditions resulting in an exhausted state of the T cells.

2. Rescue Effect of Treatment with Compound 1 after Long-Term Stimulation

Figure 43D:
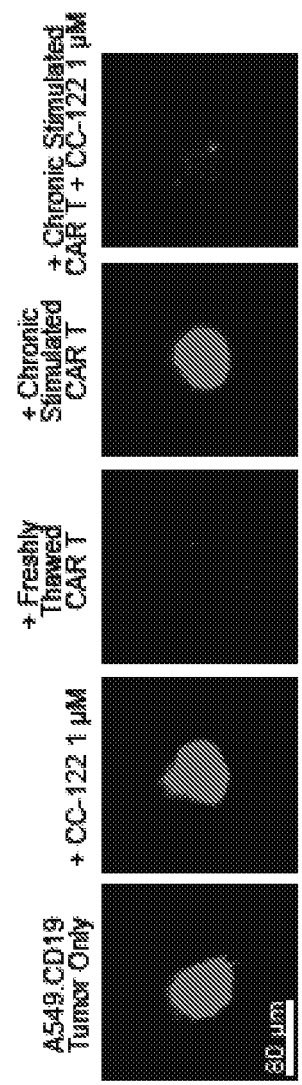
Figure 43E:
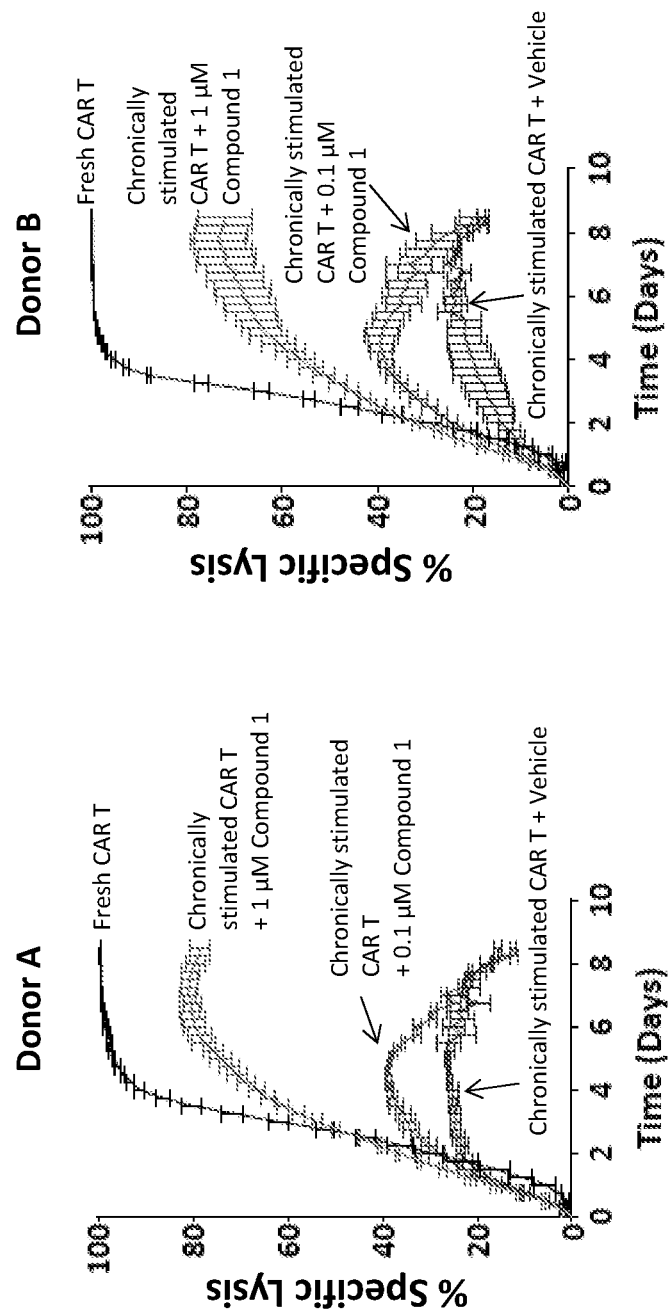

A representative image of A549 CD19+ spheroids following 9 days of co-culture with freshly thawed or chronically stimulated CAR T cells in which 3-(5-amino-2-methyl-4-oxo-4H-quinazolin-3-yl)-piperidine-2,6-dione (Compound 1) was given as a rescue treatment is shown in FIG. 43D. FIGS. 43E and 43F show the degree of antigen-specific cytolytic activity over time (FIG. 43E) and tumor volume reduction over time (FIG. 43F left panel), or after 9 days of co-culture (FIG. 13F right panel), observed in this study, for fresh CAR-T cells or chronically stimulated CAR-expressing T cells, in the presence of the indicated concentrations of Compound 1 or vehicle. As shown, presence of the compound was observed to restore antigen-specific cytokine production and tumor reduction by CAR-T cells having been subjected to chronic stimulation. FIG. 43G shows a dose response curve for this effect on tumor volume reduction in this study, consistent with an EC50 of Compound 1 for this effect of 0.1267 µM. FIG. 43H shows tumor volume in the assay at at various effector to target (E:T) ratios, in the presence of chronically stimulated CAR-T cells and either compound 1 or vehicle alone.

Figure 43J:
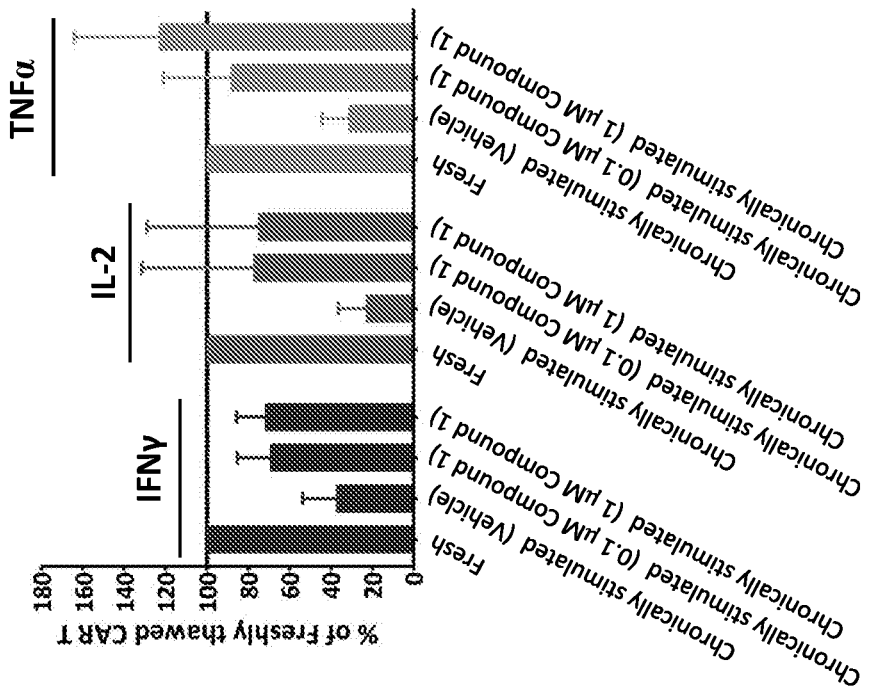
Figure 43I:
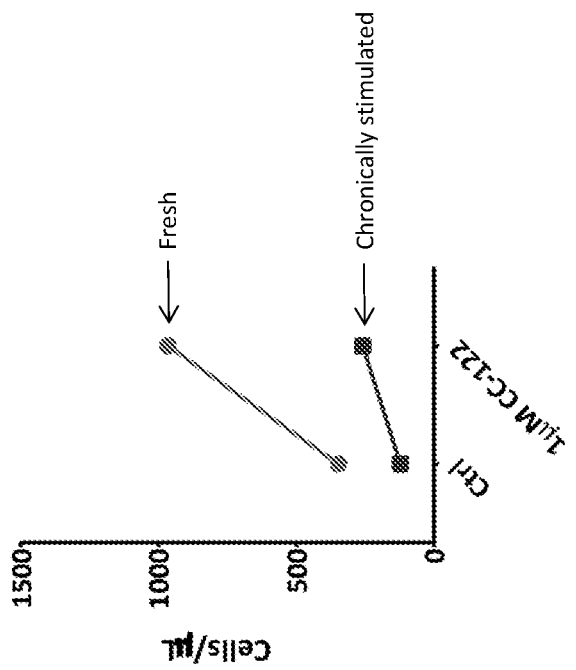

FIG. 43I shows numbers of CAR-T cells observed at day 5 of the assay, comparing results for cultures with chronically stimulated or freshly thawed CAR-T cells, in the presence of 1 µM Compound 1 or vehicle (ctrl). The results were consistent with that the ability of Compound 1 to increase expansion and/or survival of CAR-T cells under conditions involving CAR antigen exposure, in both fresh CAR-T cells and CAR-T cells that have been subjected to chronically stimulatory conditions resulting in an exhausted state.

Cytokine concentrations were determined from supernatants harvested at day 5 from co-cultures under the various conditions in this study. FIG. 43J depicts relative levels of cytokines of IFN-γ, IL-2, and TNF-α as compared to (normalized to) those observed for conditions involving freshly thawed CAR-expressing T cells. Mean values are shown for 5 healthy donors. In co-cultures containing long-term stimulated CAR-expressing T cells cultured with tumor spheroids in the presence of Compound 1, cytokine production was increased relative to co-cultures containing vehicle control. The results were consistent with that the ability of Compound 1 to restore the ability of chronically stimulated CAR-T cells exhibiting features of an exhausted phenotype to produce cytokines in response to CAR antigen exposure.

Gene expression analysis of CAR T cells sorted from tumor spheroids 5 days after co-culture was analyzed by RNA sequencing (RNA-seq) on the complementary DNA (cDNA) samples prepared from the RNA isolated from the long-term stimulated CAR-expressing T cells or on CAR-expressing T cells that had not undergone the long-term stimulation. Differential expression (DE, for RNA-seq) was calculated based on treatment effects with 0.1 µM and 1 µM Compound 1. Differential locus selection cut off was q≤0.05 and absolute log 2 fold change ≥0.5 for RNA-seq.

Figure 43K:
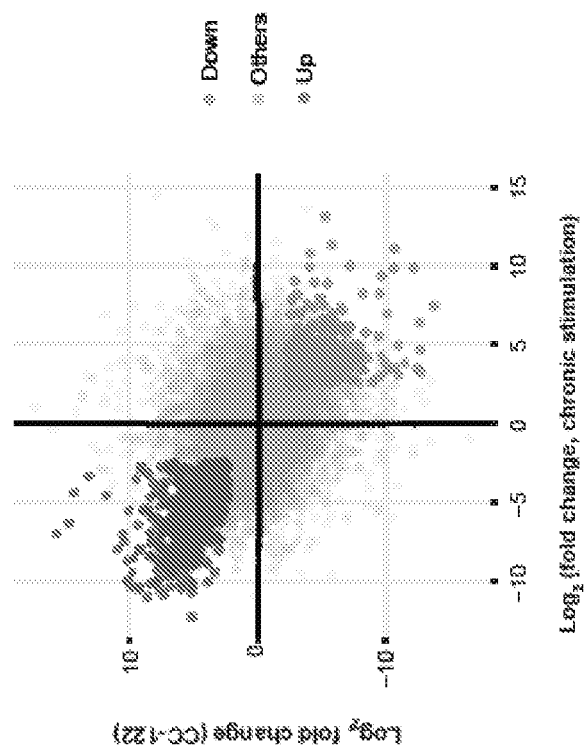
Figure 43L:
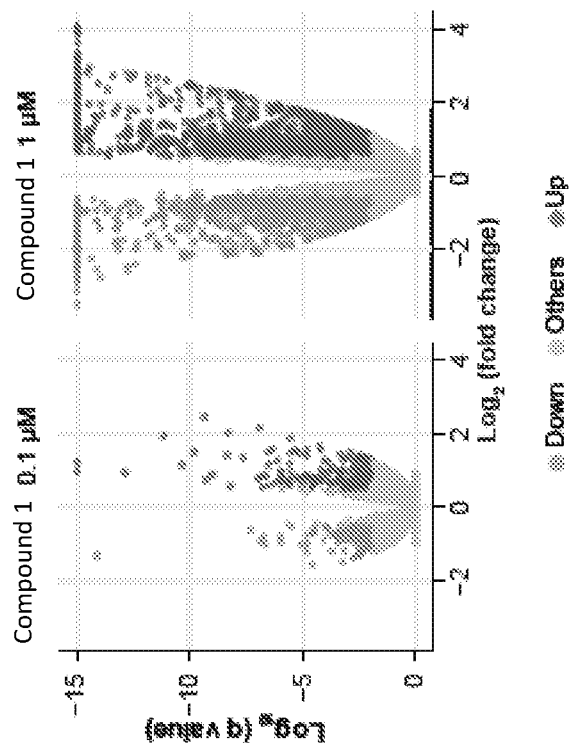
Figure 43M:
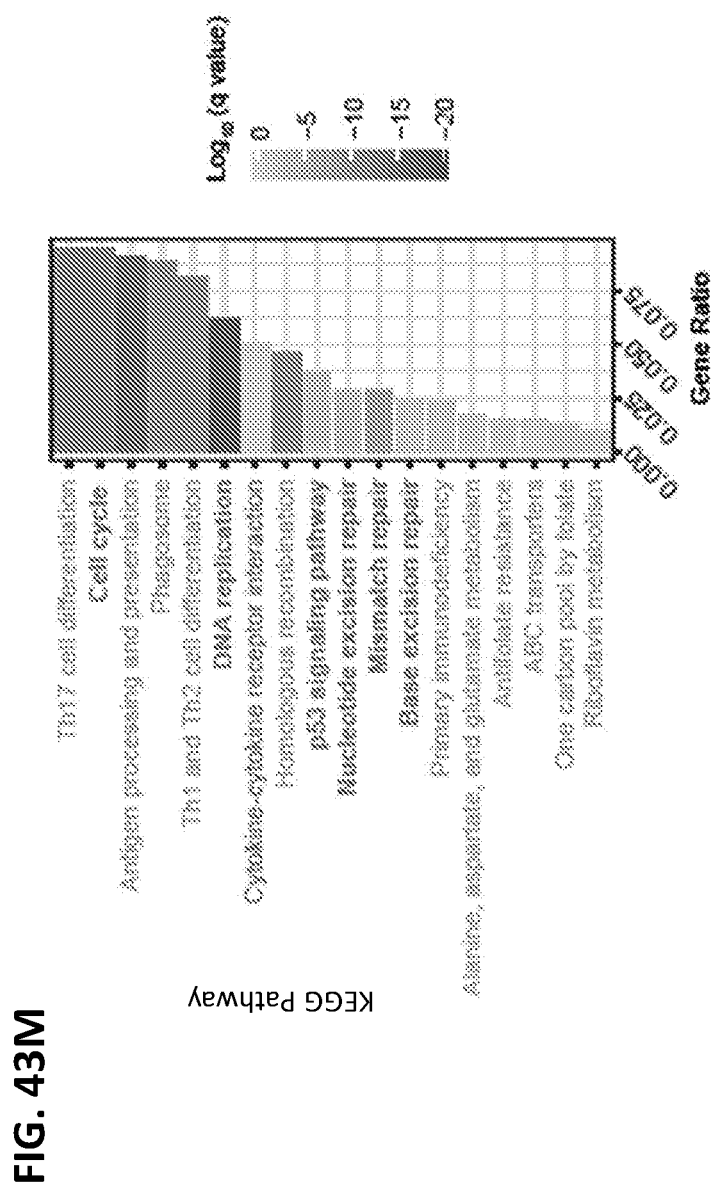

RNA-seq analysis demonstrated that treatment with Compound 1 after chronic stimulation resulted in a partial reversal of expressed genes in anti-CD19 CAR T cells associated with a hypofunctional, exhausted state. FIG. 43K shows plots of log 2 fold change (log 2FC) of gene expression in anti-CD19 CAR-T cells after both the long-term stimulation and subsequent incubation with Compound 1 relative to chronic stimulation control (y-axis), versus gene expression in anti-CD19 CAR+ T cells that that were chronically stimulated and compared to those had not been stimulated in the long-term stimulation assay (x-axis). As shown in FIG. 43L, the addition of Compound 1 following the long-term stimulation reversed the alteration in expression of some of the genes. Pathway analysis of CAR-T RNA-seq data using Kyoto Encyclopedia of Genes and Genomes (KEGG) revealed that pathways involved in T cell function are enriched following chronic stimulation conditions, and can be reversed after subsequent treatment with Compound 1 (FIG. 43M). Pathways that were altered among the set of enriched chronic-simulated-induced genes were specific cell proliferation pathways.

Together, the results were consistent with a conclusion that the presence of Compound 1 can restore or reverse an exhausted or chronically stimulated state in CAR T cells.

Example 21 Assessment of Gene Signature in CAR-T Cells Following Concurrent Long-Term Stimulation in the Presence of Compound 1 or Lenalidomide Anti-CD19 CAR-expressing T cells, produced as described in Example 14, were stimulated under conditions to induce chronic stimulation in the presence of 3-(5-amino-2-methyl-4-oxo-4H-quinazolin-3-yl)-piperidine-2,6-dione (Compound 1) or lenalidomide, or a vehicle control, or recombinant IL-2 (for comparison), under the chronic stimulatory conditions substantially as described in Example 20, except that Compound 1 or lenalidomide were present during (concurrent) the long-term stimulation. Gene expression was analyzed by RNA sequencing (RNA-seq) on the complementary DNA (cDNA) samples prepared from the RNA isolated from the long-term stimulated CAR-expressing T cells or on CAR-expressing T cells that had not undergone the long-term stimulation. Differential expression (DE, for RNA-seq) was calculated based on treatment effects (long-term stimulation vs. without long-term stimulation), for long-term stimulation in the presence of the compound (e.g. Compound 1 or lenalidomide) or IL-2, or a vehicle control. Differential locus selection cut off was q≤0.05 and log 2 fold change ≥0.5 for RNA-seq.

Figure 44A:
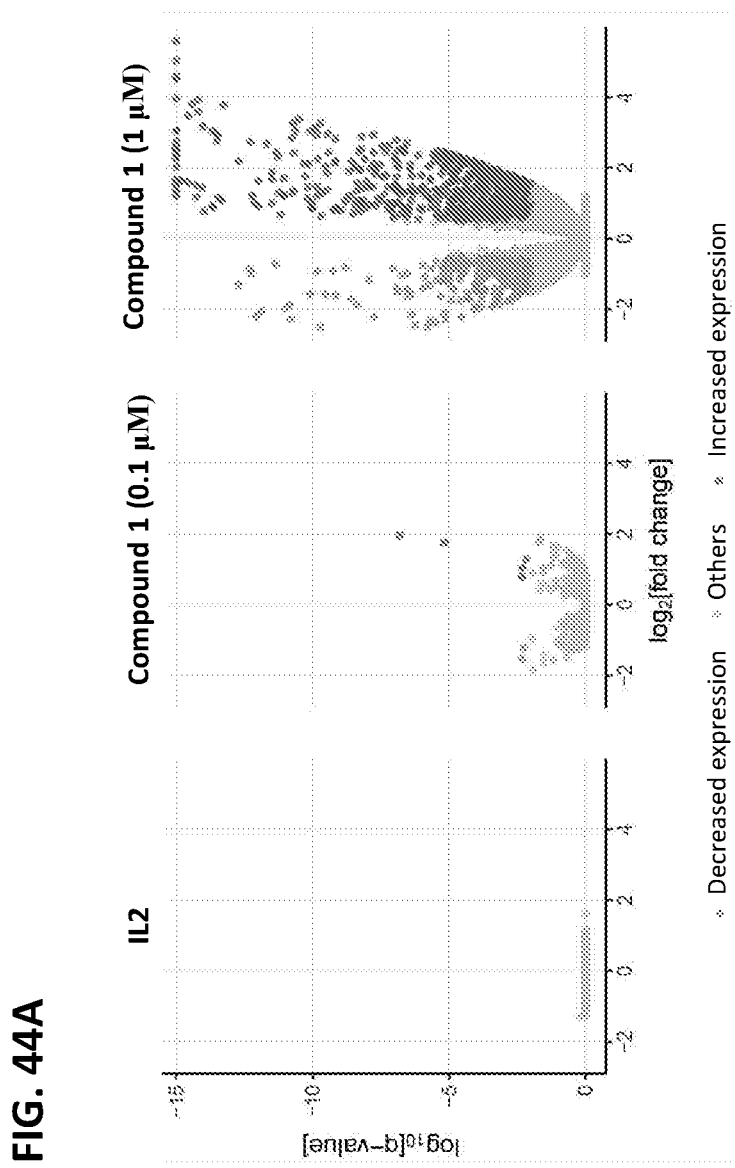
FIGS. 44A-44F show cytolytic function and analysis of gene expression in CAR-expressing T cells subjected to long-term stimulation in the presence of Compound 1 or lenalidomide, or a vehicle control, or IL-2 for comparison. Gene expression was analyzed by RNA-seq on the cDNA samples prepared from RNA isolated from the long-term stimulated CAR-expressing T cells, or on CAR-expressing T cells that had not undergone the long-term stimulation. Differential expression (DE) was calculated based on the treatment effects (long-term stimulation vs. without long-term stimulation), for long-term stimulation in the presence of the compound (e.g. Compound 1 or lenalidomide) or IL-2, or a vehicle control.
Figure 44B:
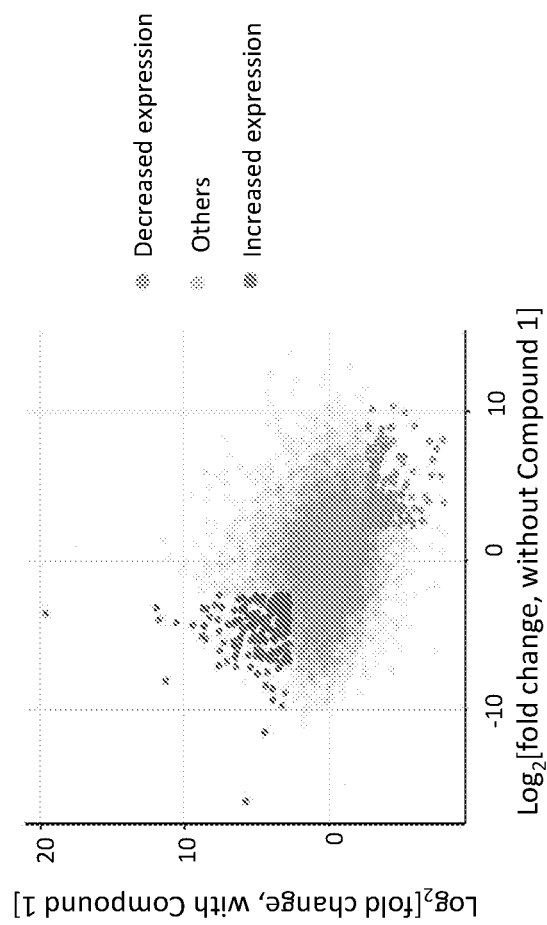
Figure 44C:
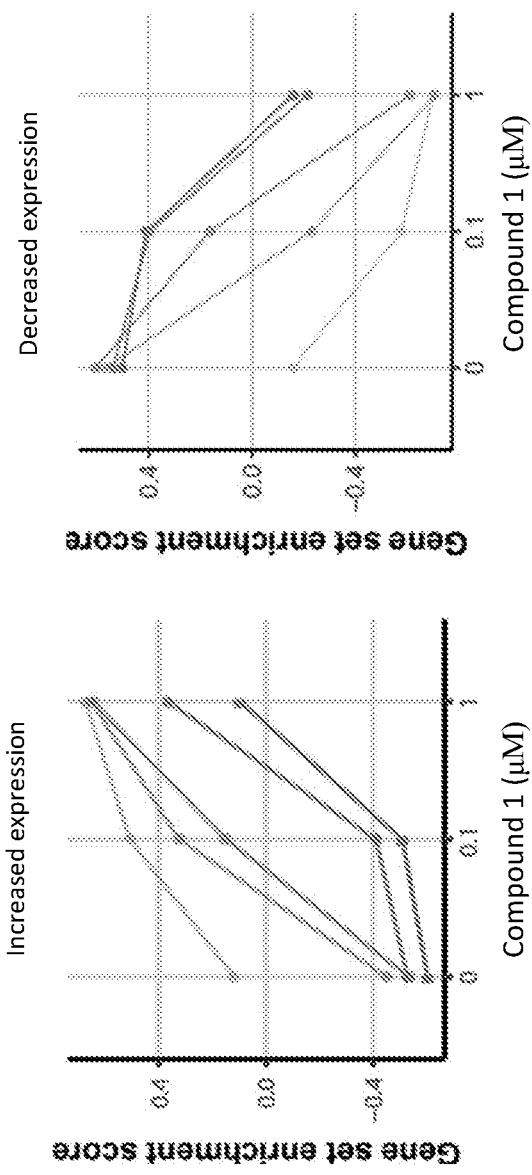
Figure 44D:
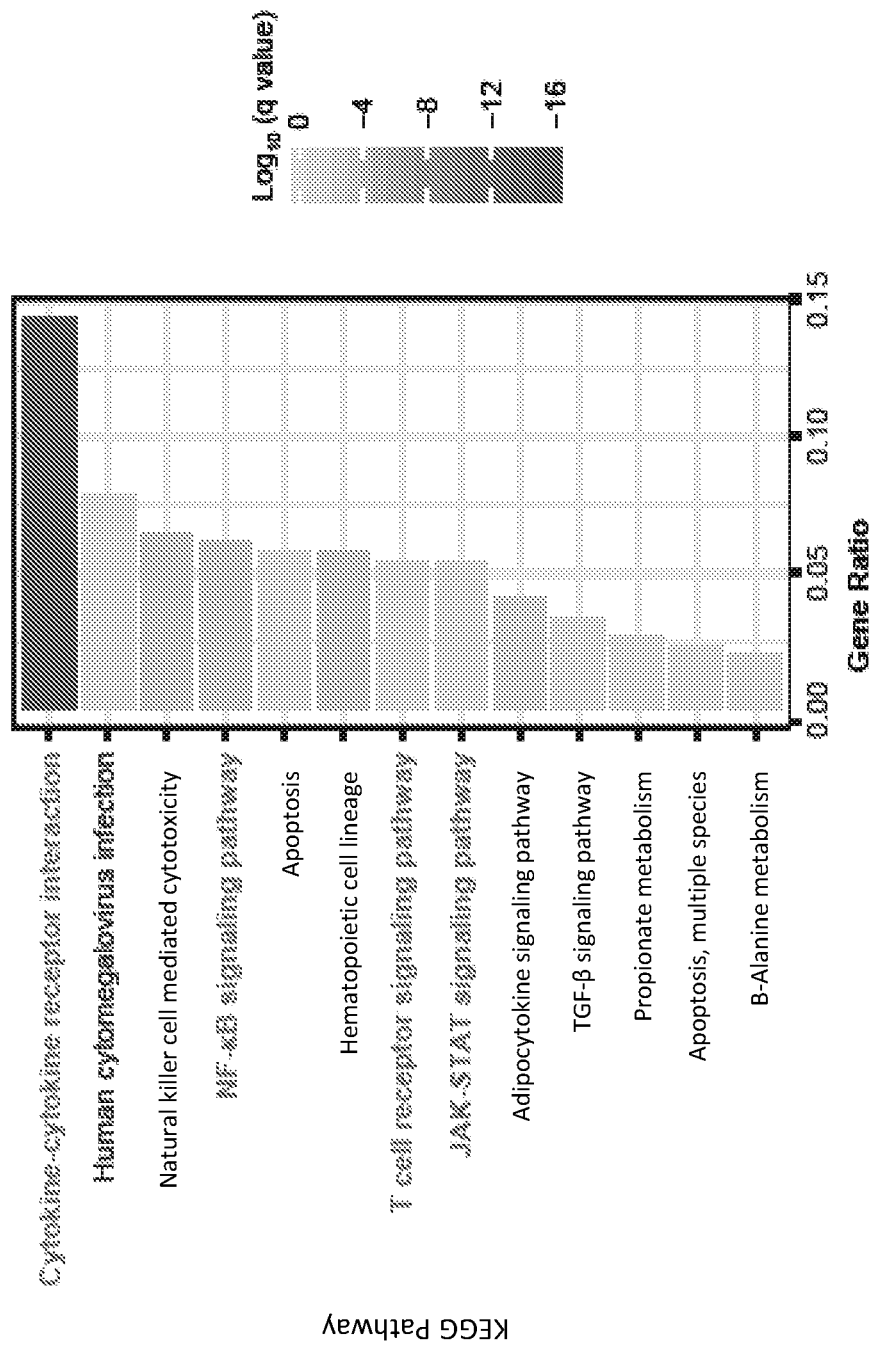

RNA-seq analysis demonstrated that treatment with Compound 1 or lenalidomide during chronic stimulation resulted in a partial reversal of expressed genes in anti-CD19 CAR T cells associated with a hypofunctional, exhausted state. FIG. 44A shows plots of log 2 fold change (log 2FC) of gene expression in anti-CD19 CAR-T cells after the long-term stimulation, in the presence of the compound or IL-2 relative to chronic stimulation control (y-axis), versus gene expression in anti-CD19 CAR+ T cells that that were chronically stimulated and compared to those had not been stimulated in the long-term stimulation assay (x-axis). As shown in FIG. 44A, the long-term stimulation resulted in altered (increased or decreased) expression of a number of genes. The presence of Compound 1 during the long-term stimulation reversed the alteration in expression of some of the genes (FIG. 44B). Similar results were observed with lenalidomide (data not shown). In contrast, incubation with IL-2 during the long-term stimulation assay did not impact the differential gene expression observed by the long-term stimulation in this assay (FIG. 44A). Similar results on gene expression were observed following long-term stimulation of CAR+ T cell expressing an anti-BCMA CAR carried out in the presence versus absence of lenalidomide. (data not shown). The gene set enrichment score for genes showing an increased or decreased expression in the presence of 0, 0.1, or 1 µM Compound 1 was also determined (FIG. 44C). Pathway analysis of CAR-T RNA-seq data using Kyoto Encyclopedia of Genes and Genomes (KEGG) showed enrichment of pathways involved in T cell function under chronic stimulation conditions, and can be prevented or reduced in the presence of concurrent treatment of Compound 1 (FIG. 44D). These results are consistent with a finding that concurrent treatment with Compound 1 during long-term stimulation can limit CAR T cell exhaustion as assessed by gene expression.

Example 22 Effect of Compound 1 on CAR T Function Following Concurrent Long-Term Stimulation in the Presence of Compound 1

Anti-CD19 CAR-expressing T cells, produced as described in Example 14, were stimulated under conditions to induce chronic stimulation in the presence of 3-(5-amino-2-methyl-4-oxo-4H-quinazolin-3-yl)-piperidine-2,6-dione (Compound 1) (0.1 µM and 1 µM), or a vehicle control, or recombinant IL-2 (for comparison), under the chronic stimulatory conditions substantially as described in Example 20, except that Compound 1 was present during the long-term stimulation (concurrent). Raji and Granta-519 tumor cells were co-cultured with CAR T cells at a 2.5:1 E:T ratio following the chronic stimulation and concurrent treatment with Compound 1.

Figure 44E:
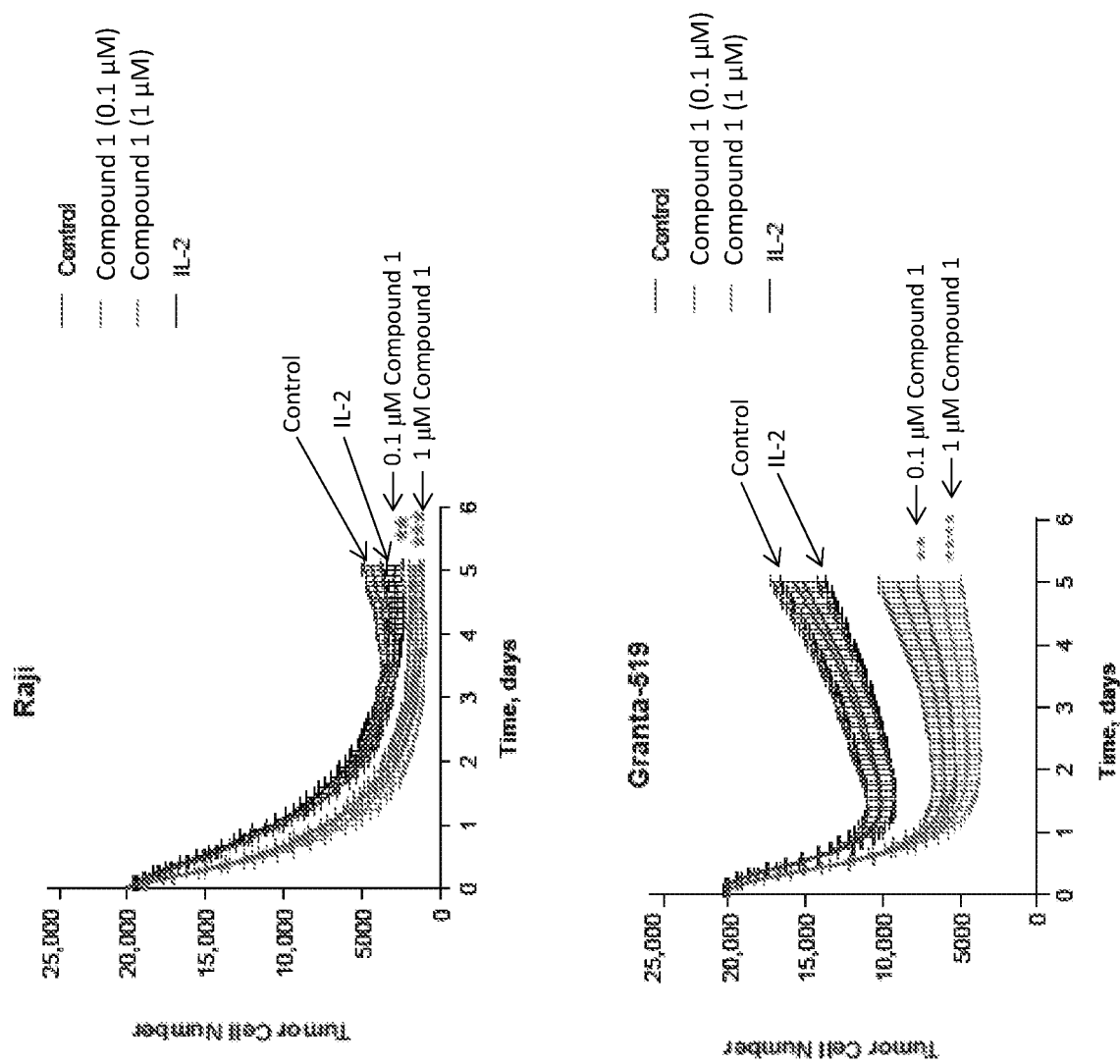
Figure 44F:
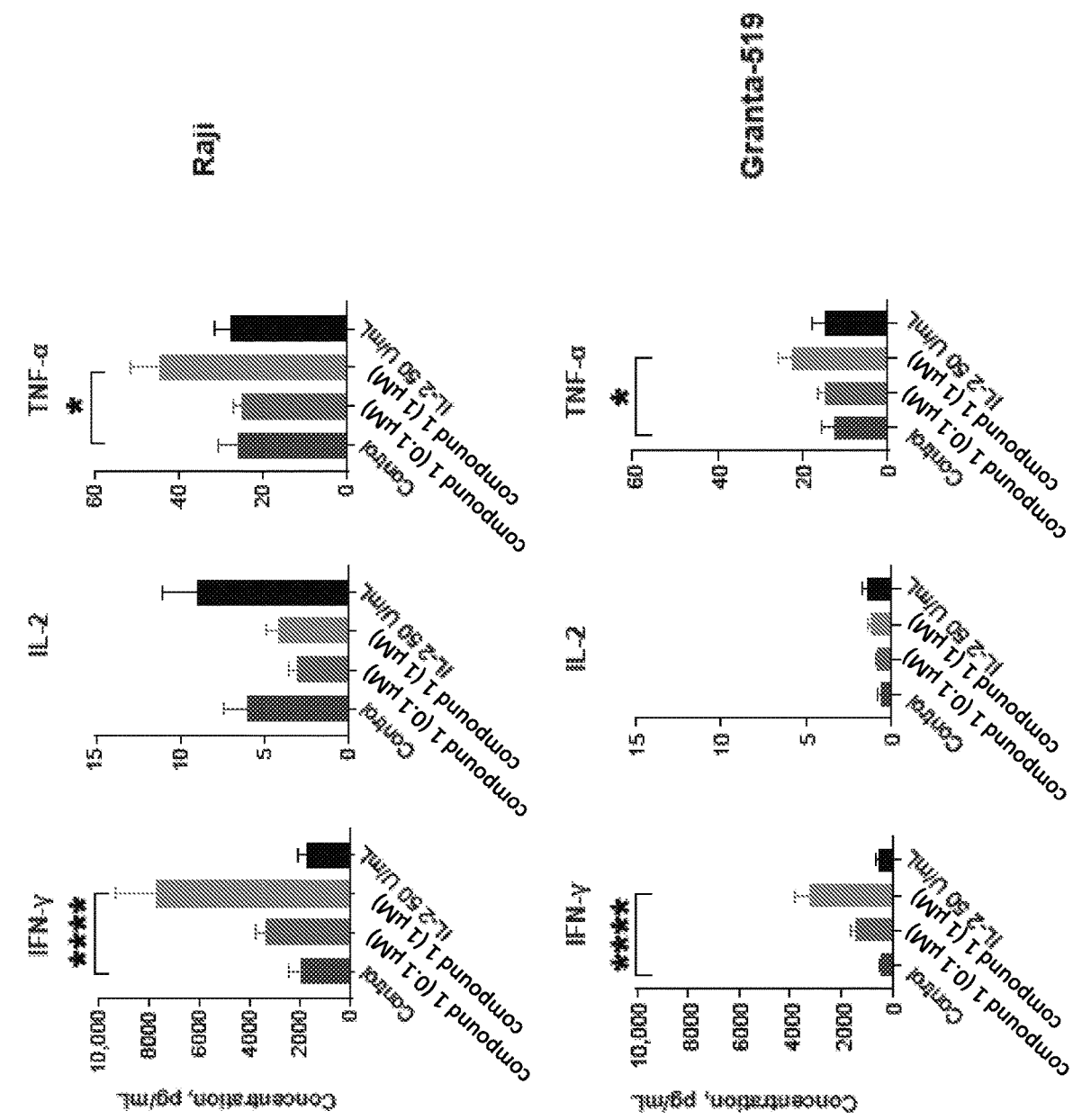

As shown in FIG. 44E, cytolytic activity, as measured by tumor cell number over time and normalized to time zero, was improved for chronically stimulated cells that had been incubated in the presence of 0.1 µM and 1 µM Compound 1 compared to cytolytic activity of chronically stimulated cells in the absence of the immunomodulatory compound (control). The improvement in cytolytic activity with the compound was greater than with IL-2. Supernatants from co-cultured cells were harvested after 24 hours and analyzed for cytokine production. As shown in FIG. 44F, IFN-γ and TNF-α production were increased relative to vehicle control following the concurrent treatment with 1 µM Compound 1 for both cell lines.

Together with the results in Example 21, these results demonstrate that Compound 1 can both enhance or increase T cell activity or function in response to CAR antigen, without resulting in or enhancing exhaustion during chronic stimulation and can reduce or prevent the development of an exhausted phenotype in response to chronic stimulation. The results are consistent with a finding that concurrent Compound 1 treatment during chronic stimulation improved CAR-T cell function, and can limit CAR T cell exhaustion.

Example 23 Comparison of Effect of Compound 1 on CAR-T Cell Function Following or Concurrent to Long-Term Stimulation Anti-CD19 CAR-expressing T cells from three donors, produced as described in Example 14, were stimulated under conditions to induce chronic stimulation either in the presence of (concurrent), or with subsequent treatment (rescue), with 0.1 µM and 1 µM 3-(5-amino-2-methyl-4-oxo-4H-quinazolin-3-yl)-piperidine-2,6-dione (Compound 1), or a vehicle control, or recombinant IL-2 (for comparison) under the chronic stimulatory conditions generally as described in Examples 20 and 21. The long-term stimulated anti-CD19 CAR-expressing T cells were co-cultured by incubation with Granta-519 tumor spheroids and cells were assessed at various time points for cytolytic function and cytokine function. During concurrent treatments Compound 1 was present during the long-term stimulation but was not present during the co-culture with target cells. During the rescue treatment Compound 1 was not present during the long-term stimulation but was present during the co-culture with target cells.

Averaged measurement of tumor spheroid size at day 9 following co-culture with CAR-T cells following long-term stimulation in the presence of Compound 1 as a concurrent treatment with long-term stimulation (FIG. 45A) or as a subsequent treatment with Compound 1 after long-term stimulation (FIG. 45B) showed a concentration dependent decrease in tumor volume. A more enhanced reduction was observed during the subsequent treatment with Compound 1.

Figure 45:
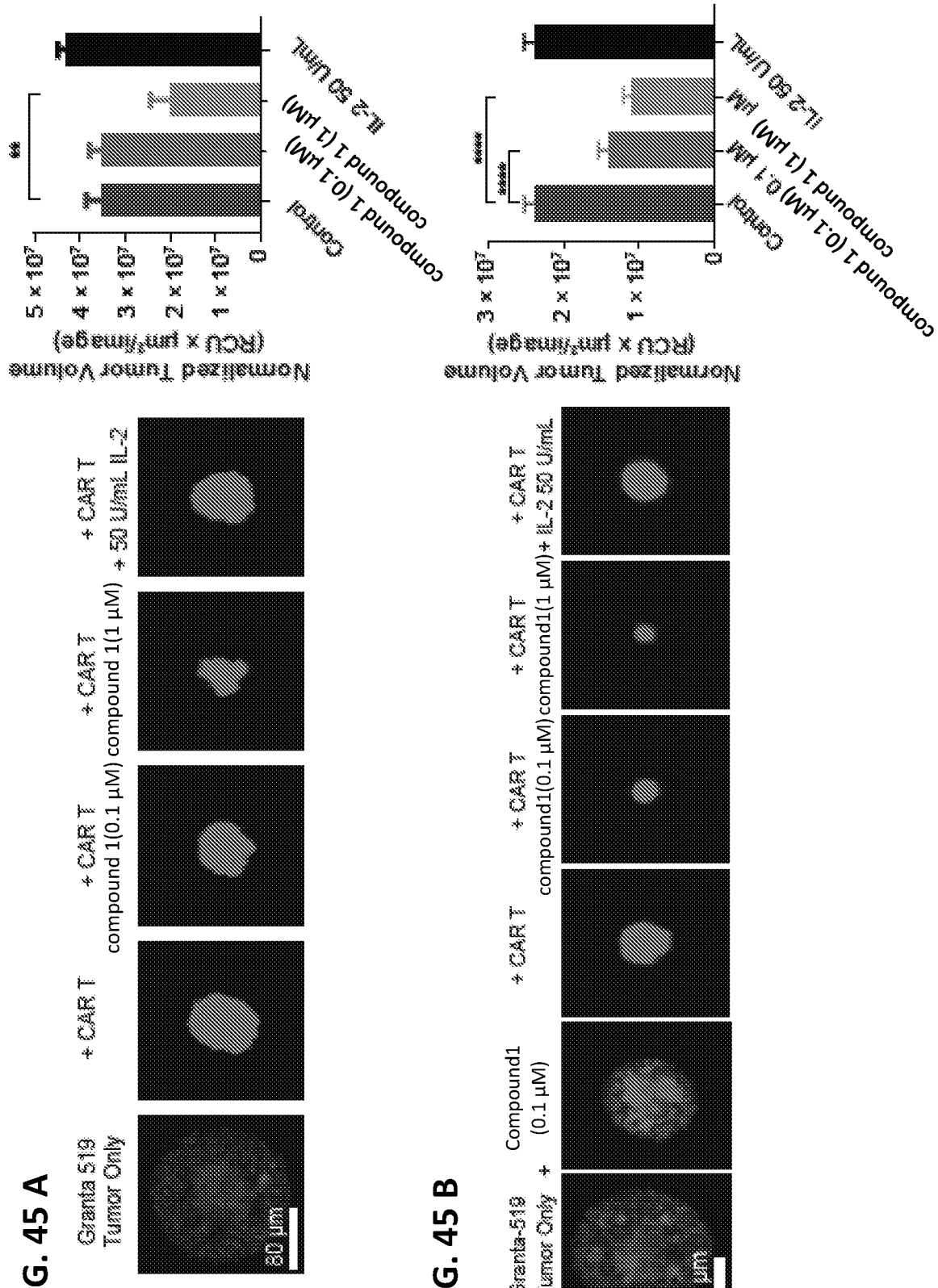
FIGS. 45A-45D show cytolytic function and cytokine production for anti-CD19 CAR-expressing T cells from three donors stimulated under conditions to induce chronic stimulation either in the presence of (concurrent), or with subsequent treatment (rescue), with, 0.1 µM and 1 µM Compound 1, or a vehicle control, or recombinant IL-2 (for comparison) co-cultured by incubation with Granta-519 tumor spheroids. Tumor spheroid size was measured at day 9 for T cells under concurrent (FIG. 45A) or subsequent (FIG. 45B) treatment with Compound 1, and cytokine concentrations from supernatants harvested at day 5 were measured for T cells under concurrent (FIG. 45C) or subsequent (FIG. 45D) treatment with Compound 1.
Figure 45:
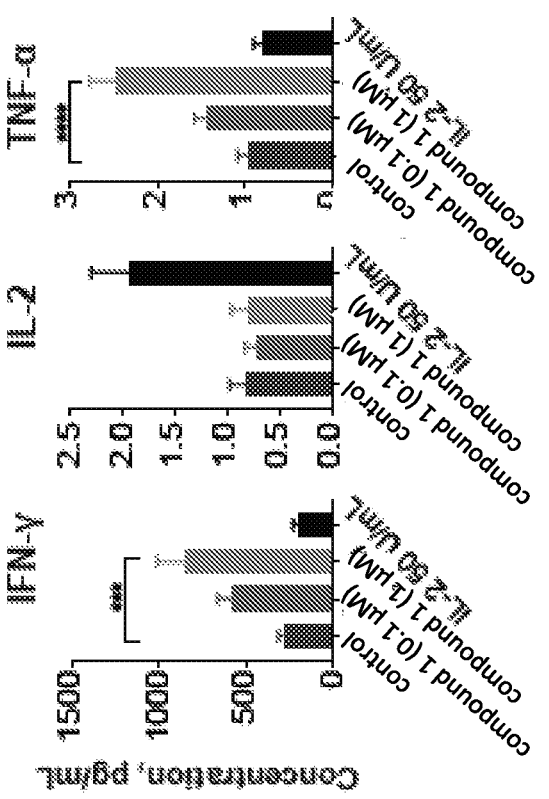
Figure 45:
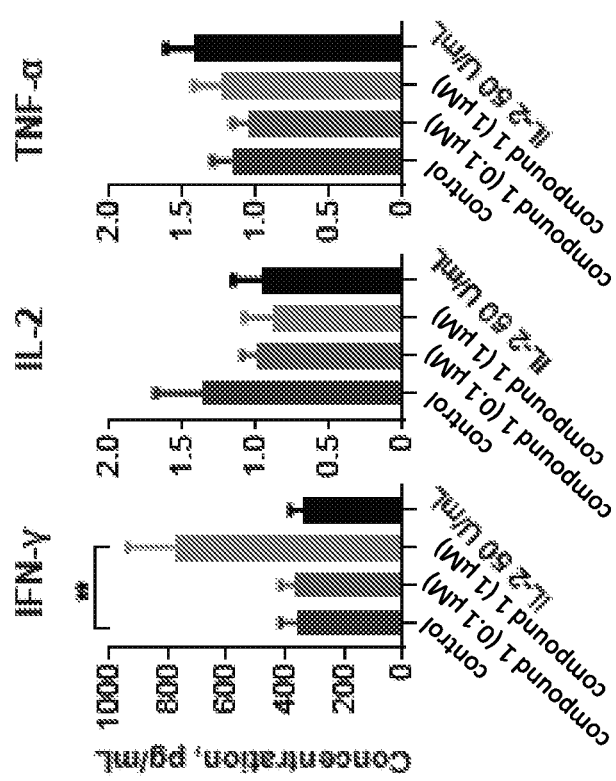

Cytokine concentrations were determined from supernatants harvested at day 5 from co-cultures under the above conditions of this study. FIGS. 45C and 45D depict relative levels of cytokines of IFN-γ, IL-2, and TNF-α for CAR-T cells in the presence of Compound 1 as a concurrent treatment with long-term stimulation (FIG. 45C) or as a subsequent treatment with Compound 1 after long-term stimulation (FIG. 45D). As shown in FIG. 45C, CAR-T cells stimulated with concurrent treatment with Compound 1 showed enhanced IFN-γ, while delayed treatment with 1 µM Compound 1 showed enhanced production of both IFN-γ and TNF-α (FIG. 45D).

Together, these results were consistent with a conclusion that delayed treatment with Compound 1 can enhance or increase T cell performance in response to CAR antigen, and can reduce or reverse an exhausted or chronically stimulated state in CAR T cells.

Example 24 Administration of Anti-CD19 CAR-Expressing Cells in Combination with Compound 1 to Subjects with Relapsed and Refractory Non-Hodgkin's Lymphoma (NHL)

Anti-CD19 CAR-expressing T cell compositions are produced substantially as described in Example 14, and generated $CD4^+$ CAR-expressing T cell compositions and CD8+ CAR-expressing T cell compositions are separately administered to subjects with relapsed/refractory (R/R) B cell non-Hodgkin lymphoma (NHL) in combination with subsequent administration with 3-(5-amino-2-methyl-4-oxo-4H-quinazolin-3-yl)-piperidine-2,6-dione (Compound 1). Groups of subjects selected for treatment include subjects with diffuse large B-cell lymphoma (DLBCL); de novo or transformed from indolent lymphoma (NOS); high-grade B-cell lymphoma, with MYC and BCL2 and/or BCL6 rearrangements with DLBCL histology (double/triple hit lymphoma); follicular lymphoma grade 3b (FLG3B); T cell/histiocyte-rich large B-cell lymphoma; EBV positive DLBCL, NOS; and primary mediastinal (thymic) large B-cell lymphoma. Subjects treated also include those that have relapsed following or are refractory to at least two prior lines of therapy, including a CD20-targeted agent and an anthracycline, and have an Eastern Cooperative Oncology Group (ECOG) score of less than or equal to 1 at screening.

Prior to CAR+ T cell infusion, subjects receive a lymphodepleting chemotherapy with fludarabine (flu, 30 mg/m$^2$/day) and cyclophosphamide (Cy, 300 mg/m$^2$/day) for three (3) days. The subjects receive CAR-expressing T cells 2-7 days after lymphodepletion. Subjects are administered a single dose of 1×10$^8$ CAR-expressing T cells (each single dose via separate infusions at a 1:1 ratio of CD4+ CAR-expressing T cells and CD8+ CAR-expressing T cells, respectively).

Compound 1 is administered orally to subjects beginning at day 29 (±7 days) post-CAR-T cell infusion at a dose of 1 mg, 2 mg or 3 mg on 5 consecutive days out of 7 days a week for 180 days.

Response to treatment is assessed based on radiographic tumor assessment by positron emission tomography (PET) and/or computed tomography (CT) or magnetic resonance imaging (MRI) scans at baseline prior to treatment and at various times following treatment (e.g. based on Lugano classification, see, e.g., Cheson et al., (2014) JCO 32(27): 3059-3067). The presence or absence of treatment-emergent adverse events (TEAE) following treatment also is assessed. Subjects also are assessed and monitored for neurotoxicity (neurological complications including symptoms of confusion, aphasia, encephalopathy, myoclonus seizures, convulsions, lethargy, and/or altered mental status), graded on a 1-5 scale, according to the National Cancer Institute—Common Toxicity Criteria (CTCAE) scale, version 4.03 (NCI-CTCAE v4.03). Common Toxicity Criteria (CTCAE) scale, version 4.03 (NCI-CTCAE v4.03). See Common Terminology for Adverse Events (CTCAE) Version 4, U.S. Department of Health and Human Services, Published: May 28, 2009 (v4.03: Jun. 14, 2010); and Guido Cavaletti & Paola Marmiroli *Nature Reviews Neurology* 6, 657-666 (December 2010). Cytokine release syndrome (CRS) also is determined and monitored, graded based on severity. See Lee et al, Blood. 2014; 124(2):188-95. Subjects also are assessed for pharmacokinetics (PK) of anti-CD19 CAR+ T cells pre- and post-treatment with Compound 1 and for PK of Compound 1.

The dosing of Compound 1 is stopped after Day 180 (6 months post CAR-T-cell infusion), unless the subject achieves a partial response (PR) in which case further administration of Compound 1 may continue until disease progression.

Example 25 Assessment of Pharmacodynamic Response of Aiolos and Ikaros Transcription Factor in Anti-CD19 CAR-Expressing T Cells in the Presence of Compound 1 and Compound 2

Anti-CD19 CAR-expressing T cell compositions (containing CD4+ and CD8+ T cells combined at a 1:1 ratio) were generated from five different healthy donors substantially as described in Example 14. Approximately 2.5×10$^5$ cells of the generated CAR+ T cell composition were stimulated overnight with 1 µg/ml of a CAR-specific anti-idiotypic antibody in the presence of 3-(5-amino-2-methyl-4-oxo-4H-quinazolin-3-yl)-piperidine-2,6-dione (Compound 1) or (S)-3-[4-(4-morpholin-4-ylmethyl-benzyloxy)-1-oxo-1,3-dihydro-isoindol-2-yl]-piperidine-2,6-dione (Compound 2) at concentrations ranging from 10 to 10000 nM or a vehicle control overnight at 37° C., 5% CO2. Following overnight incubation, anti-CD19 CAR-expressing T cells were stained with antibodies and analyzed by flow cytometry to assess intracellular levels of Ikaros and Aiolos in CD4+ CAR+ or CD8+ CAR+ cells, as measured by median fluorescence intensity (MFI). Median fluorescence intensity (MFI) values for Ikaros and Aiolos were normalized and calculated as a percentage relative to vehicle control.

Figure 46:
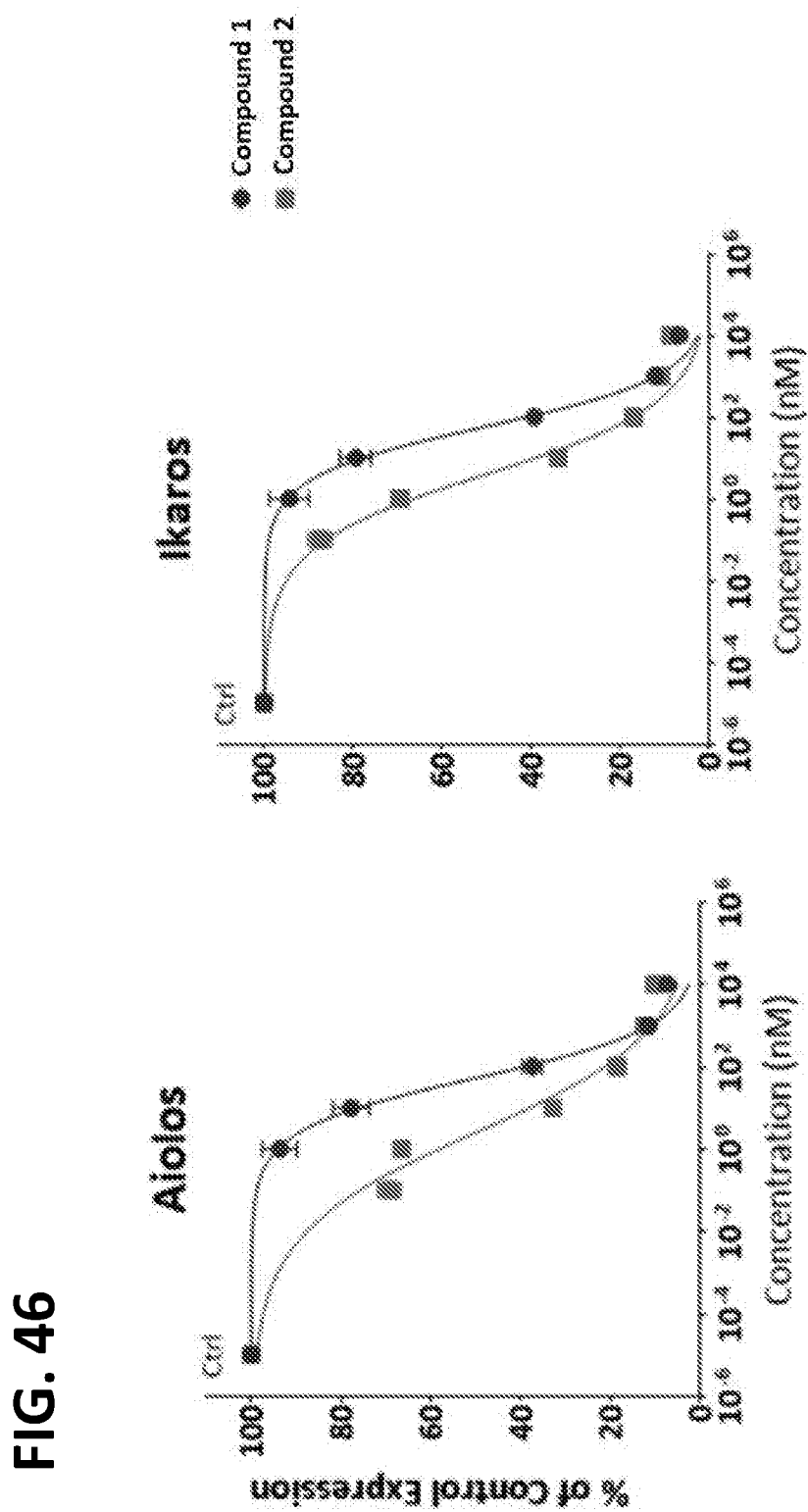
FIG. 46 shows intracellular Ikaros and Aiolos expression in anti-CD19 stimulated CAR-expressing T cells after incubation with varying concentrations of Compound 1 or Compound 2.

A concentration dependent decrease in intracellular Ikaros and Aiolos expression was observed in the anti-CD19 stimulated CAR-expressing T cells after incubation with either Compound 1 or Compound 2 (FIG. 46). The EC50 for reducing Aiolos and Ikaros expression was calculated as determined from the concentration of the inhibitor that reduced Aiolos or Ikaros MFI to 50% of its maximal MFI in the absence of the inhibitor. EC50 values for Compound 1 and Compound 2 are shown in Table E8, as an average of the 5 donors (range among donors is shown, based on a 95% confidence interval). The results show that Compound 2 is approximately 10-20 fold more potent than Compound 1 in the compound-mediated degradation of Ikaros and Aiolos in CAR-expressing T cells.

TABLE E8

Aiolos and Ikaros EC50 (nM) in CAR+ T cells.

| | Compound 1 | Compound 2 |
|---|---|---|
| Aiolos | 52.7 (41.7-66.5) | 2.5 (1.6-3.96) |
| Ikaros | 59.3 (47.6-74.1) | 4.0 (3.0-5.4) |

Example 26 Assessment of Immunomodulatory Compounds on CAR T Function Following Long-Term Stimulation Anti-CD19 CAR-expressing T cell compositions (containing CD4$^+$ and CD8$^+$ T cells combined at a 1:1 ratio) were generated from three different healthy donors substantially as described in Example 14. To subject cells to chronic stimulation conditions, the CAR+ T cells were incubated with 30 µg/mL plate-bound anti-idiotypic (anti-ID) antibody (see e.g. WO2018/023100), and incubated at 37° C. for a period of 6 days in the presence of a titrating amount of 3-(5-amino-2-methyl-4-oxo-4H-quinazolin-3-yl)-piperidine-2,6-dione (Compound 1) or (S)-3-[4-(4-morpholin-4-ylmethyl-benzyloxy)-1-oxo-1,3-dihydro-isoindol-2-yl]-piperidine-2,6-dione (Compound 2).

Figure 47A:
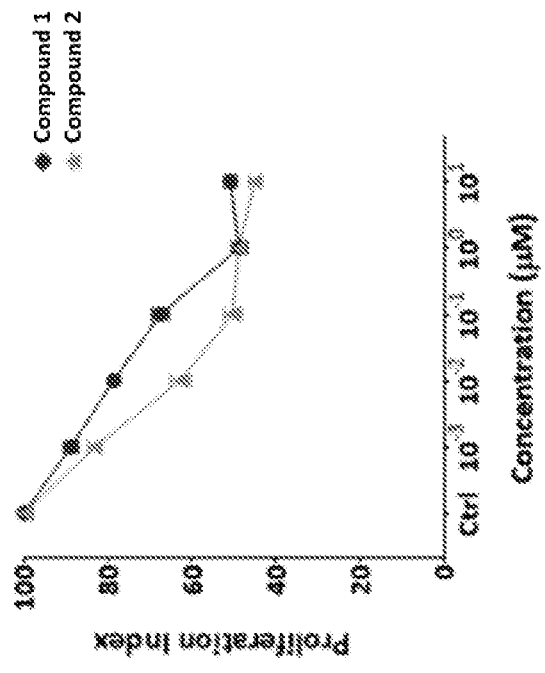
FIG. 47A shows the proliferation of anti-CD19 CAR T cell for three donors (mean±SEM) in the presence of varying concentrations of Compound 1 or Compound 2.
Figure 47B:
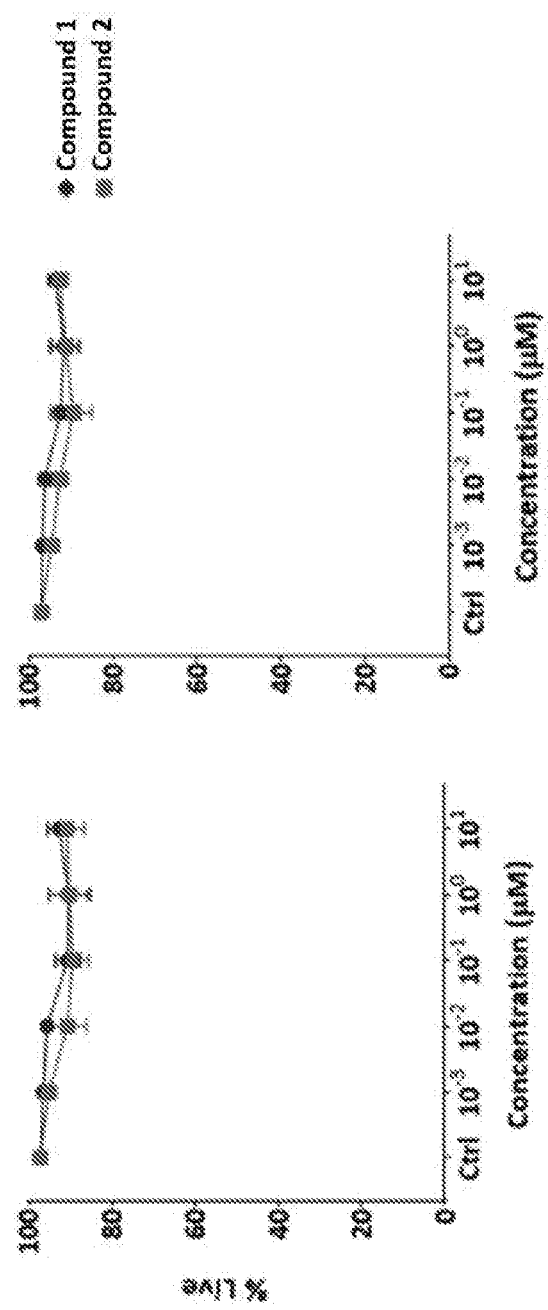
FIG. 47B shows the effect of varying concentrations of Compound 1 or Compound 2 on cell viability when the stimulation was carried out with 3 µg/mL anti-ID (left panel) or 30 µg/mL anti-ID (right panel).

Proliferation of T cells during the culture was assessed and is shown in FIG. 47A for the three donors (mean±SEM). As shown, the presence of the immunomodulatory compounds decreased CAR T cell count. Viability was assessed at Day 6 of treatment by flow cytometry using a live/dead dye. As shown in FIG. 47B (mean±SEM), the immunomodulatory compounds had no effect on cell viability when stimulation was carried out either with 3 µg/mL anti-ID (left panel) or 30 µg/mL anti-ID (right panel). Together, the results demonstrate an effect of the immunomodulatory compounds on cell doublings without impacting cell viability.

Figure 47C:
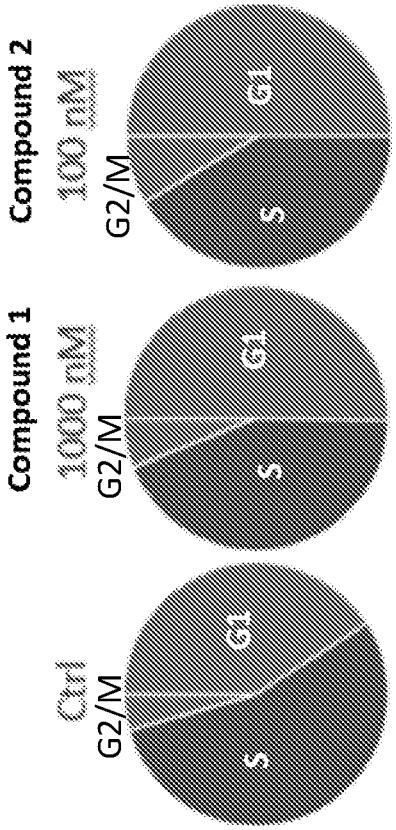
FIG. 47C shows the cell cycle analysis of the anti-CD19 CAR T cells after treatment with 1000 nM Compound 1 or 100 nM Compound 2.
Figure 47D:
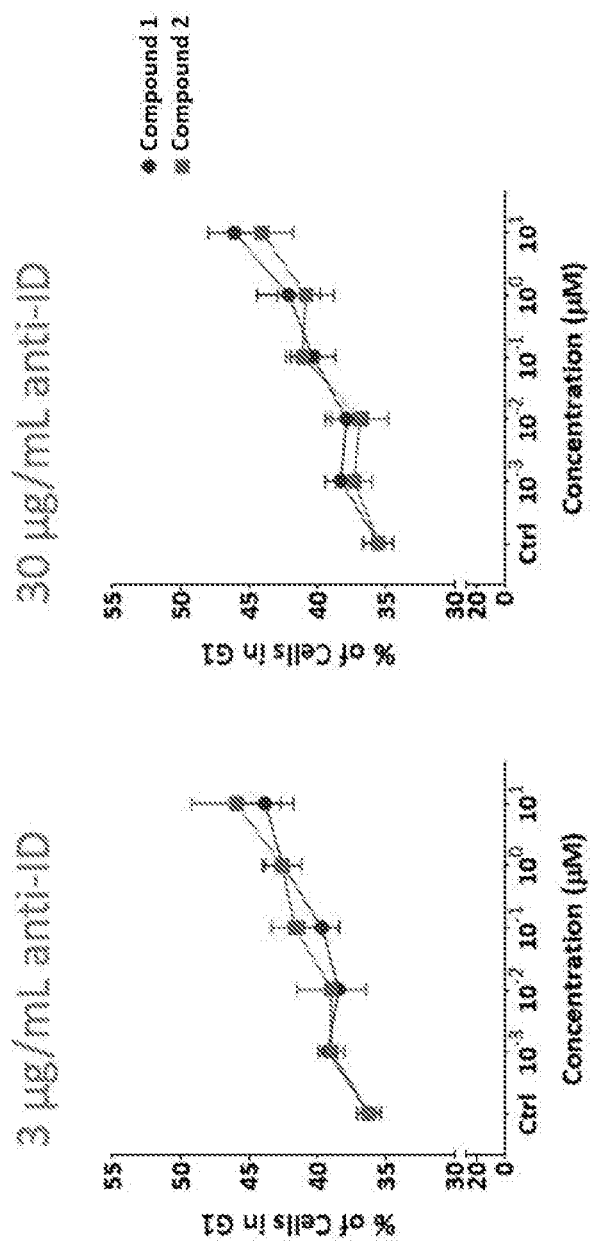
FIG. 47D shows the percentage of anti-CD19 CAR T cells in the G1 phase of the cell cycle when exposed to varying concentrations of Compound 1 or Compound 2.

To elucidate a possible effect on the cell cycle, cell cycle was determined using EDU incorporation for 2 hours after 3 days of stimulation and treatment with the immunomodulatory compound. The results in FIG. 47C shows that treatment with the immunomodulatory compounds increased the percentage of CAR T cells in G1 phase of the cell cycle. The percentage of cells in G1 phase of the cell cycle at increasing concentrations of immunomodulatory compounds is shown in FIG. 47D (left panel 3 μg/mL anti-ID, right panel 30 μg/mL anti-ID. Without wishing to be bound by theory, the accumulation of CAR T cells in G1 phase of the cell cycle when treated with immunomodulatory compounds may account for one of the mechanisms by which the immunomodulatory compounds to limit onset of exhaustion during chronic stimulation.

Figure 47E:
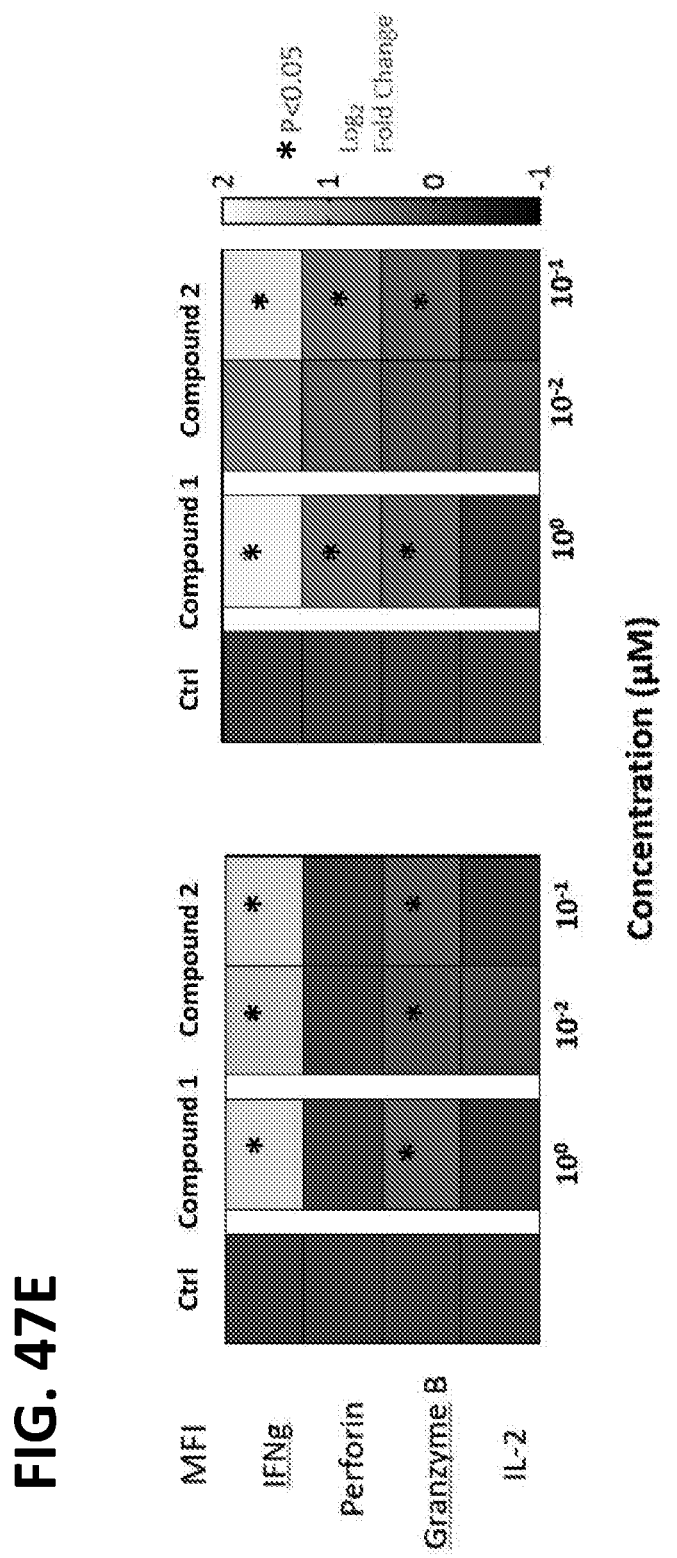
FIG. 47E shows the intracellular cytokine expression levels of IFNγ, perforin, granzyme B and IL-2 in anti-CD19 CAR T cells that have been stimulated for 24 hours or 72 hours with 30 µg/mL anti-ID and exposed to Compound 1 or Compound 2.

Intracellular cytokine levels in CAR T cells that had been stimulated for 24 hours or 72 hours with 30 μg/mL anti-ID was determined. T cells were cultured with anti-ID-conjugated beads for 4 hours in the presence of Golgi inhibitor. Intracellular cytokine levels of IFNγ, perforin, granzyme B and IL-2 was determined by flow cytometry. As shown in FIG. 47E, treatment of cells with the immunomodulatory compounds increased intracellular expression of effector cytokines (IFNγ, perforin, granzyme B), as determined by mean fluorescence intensity, but there was no significant changes in IL-2 production. Similar results were observed when measuring percentage of cells positive for the cytokines.

Example 27 Effect of Immunomodulatory Compounds on CAR T Function Following Concurrent Treatment During Long-Term Stimulation Anti-CD19 CAR-expressing T cells, produced as described in Example 14, were stimulated with 30 μg/mL plate-bound anti-idiotypic (anti-ID) antibody for 6 days in the presence of (S)-3-[4-(4-morpholin-4-ylmethyl-benzyloxy)-1-oxo-1,3-dihydro-isoindol-2-yl]-piperidine-2,6-dione (Compound 2) or a vehicle control, substantially as described in Example 22. After the long-term, chronic stimulation with concurrent treatment with Compound 2, CAR T cells were assessed for Ikaros expression or for CAR T function following rechallenge with CD19-expressing target cells.

A. Ikaros Expression

Figure 48A:
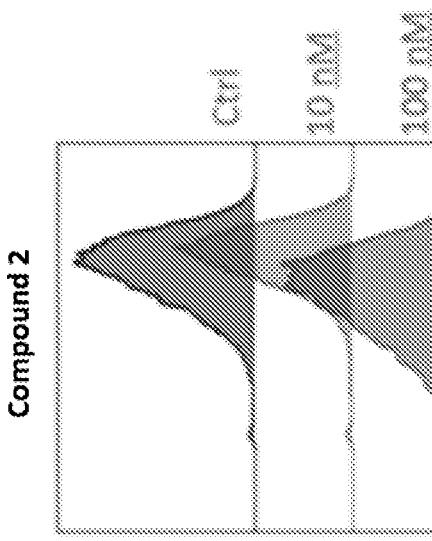
FIG. 48A shows the expression of Ikaros in anti-CD19 CAR T cells that had been subjected to chronic stimulation in the presence of Compound 2 (10 nM or 100 nM).

Expression of Ikaros in CAR T cells that had been subjected to chronic stimulation in the presence of Compound 2 (1 nM, 10 nM or 100 nM) was measured by intracellular flow cytometry analysis using an antibody to Ikaros. As shown in FIG. 48A, a reduction of Ikaros expression was maintained in chronically stimulated cells treated with 100 nM of Compound 2 but not 10 nM.

B. Cytolytic Activity

Figure 48B:
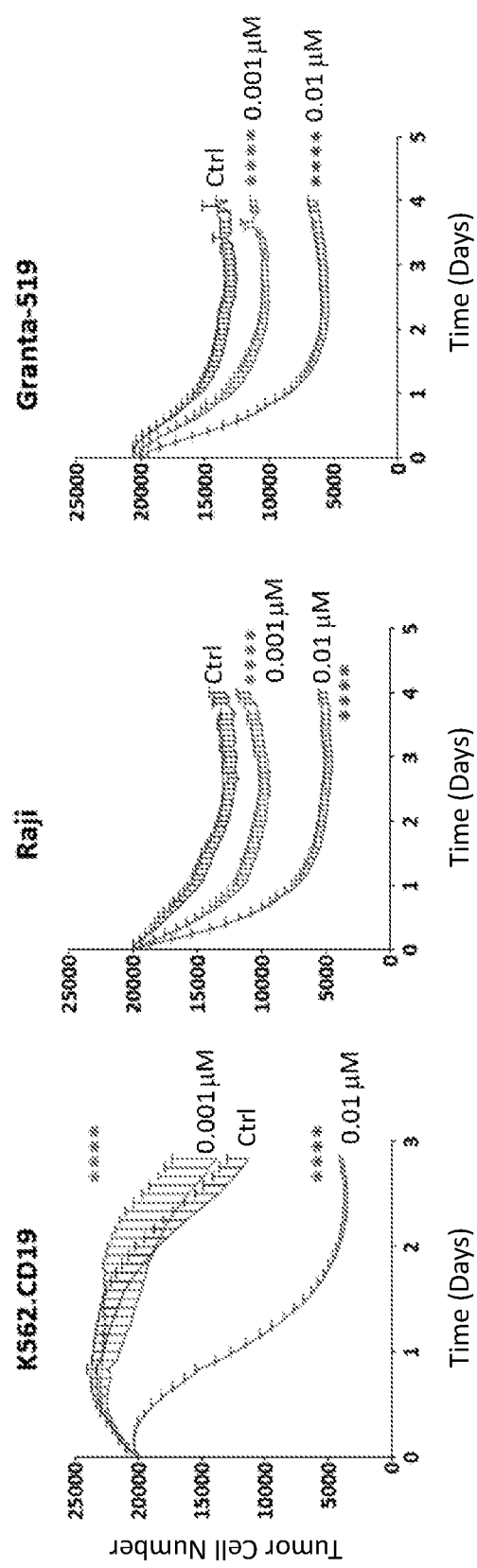
FIG. 48B shows the cytolytic activity, as measured by tumor cell number over time, for chronically stimulated cells that had been concurrently incubated in the presence of Compound 2 (0.001 µM or 0.01 µM) compared to absence of the compound (control) prior to rechallenge with CD19-expressing target cells.

CAR T cells that had been stimulated for 6 days with anti-ID concurrently in the presence of Compound 2 (0.001 μM or 0.01 μM) were washed free of compound and co-cultured with CD19+ tumor cells at an effector to target (E:T) ratio of 1:1 in the absence of Compound 2. The assessed CD19+ tumor cells included K562 cells transduced with CD19 (K562.CD19), Raji cells or Granta-519 cells. As shown in FIG. 48B, cytolytic activity, as measured by tumor cell number over time, was improved for chronically stimulated cells that had been concurrently incubated in the presence of Compound 2 compared to absence of the compound (control) prior to rechallenge with CD19-expressing target cells. These results are consistent with a finding that the immunomodulatory compound can reduce or prevent the development of an exhausted phenotype in response to chronic stimulation.

C. Spheroid Tumor Growth Assay

CAR T cells that had been stimulated for 6 days with anti-ID concurrently in the presence of Compound 2 (0.001 μM or 0.01 μM) were co-cultured with by incubation with Granta-519 tumor spheroids and CAR T cell cytolytic function and cytokine function were assessed at various time points. For comparison, cytolytic activity was also assessed for cells that had been similarly chronically stimulated with anti-ID in the presence of 1 μM or 0.1 μM Compound 1. Averaged measurement of tumor spheroid size at various times following co-culture with CAR-T cells was monitored. As shown in FIG. 48C, concurrent treatment of Compound 2 during chronic stimulation with anti-ID produced CAR T cells with improved cytolytic function to reduce Granta-519 spheroid growth. Average tumor volume after 9 days is shown in FIG. 48D, which demonstrates that Compound 2 significantly increased cytolytic function of CAR-T cells against Granta-519 tumor spheroids. The improvement in cytolytic function was greater with concurrent treatment with Compound 2 than Compound 1.

Figure 48E:
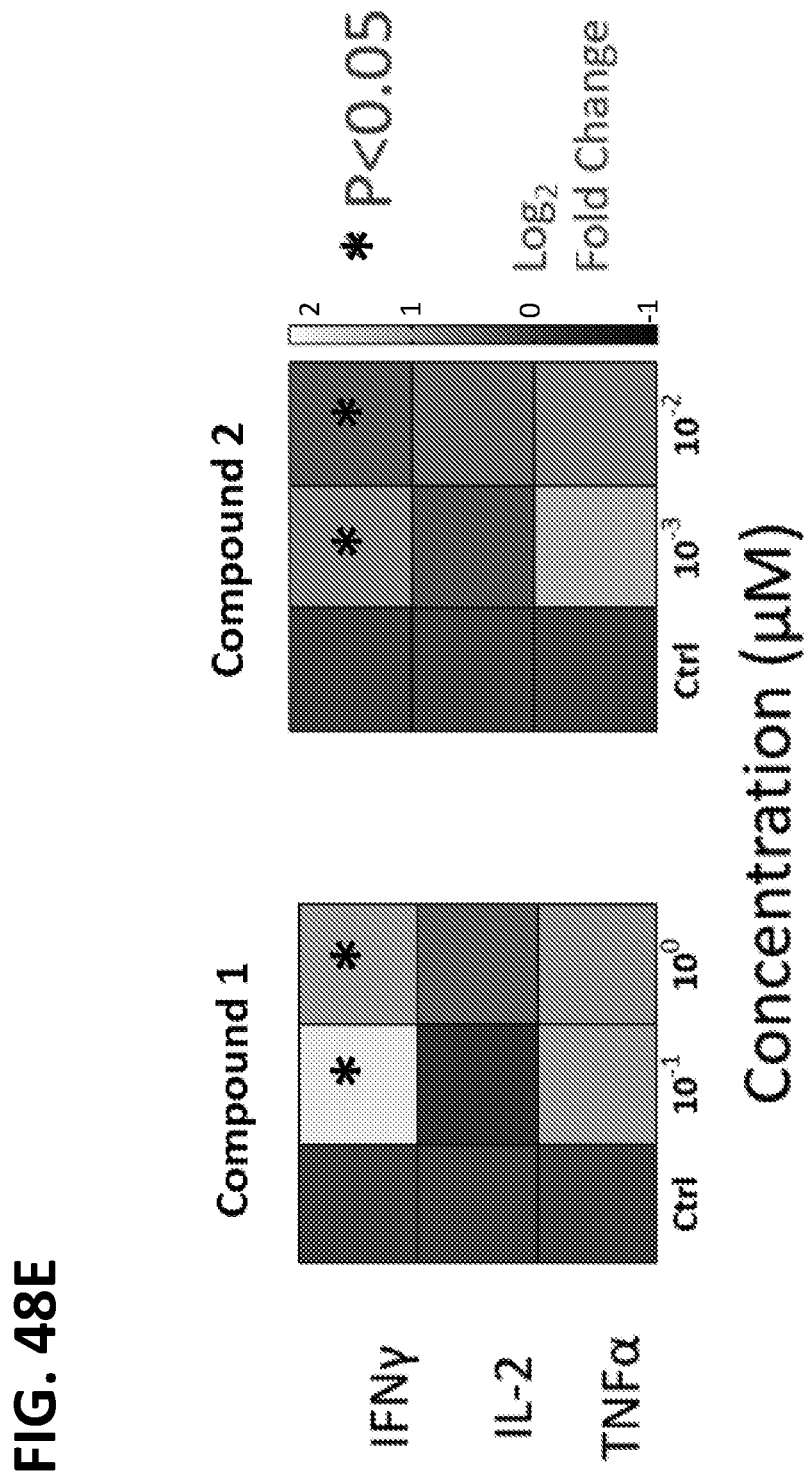
FIG. 48E shows the cytokine levels of IFNγ, IL-2 and TNFalpha measured from the supernatant of the chronically stimulated anti-CD19 CAR T cells that had been co-cultured for 5 days with CD19 tumor spheroids and treated with Compound 1 or Compound 2.

Cytokines (IFNγ, IL-2 and TNFalpha) were measured from supernatant of the chronically stimulated CAR T cells above that had been co-cultured for 5 days with CD19 tumor spheroids. The log 2 fold change compared to control cells (chronically stimulated cells that had not been concurrently treated with immunomodulatory compound) is shown in FIG. 48E. As shown, there was a statistically significant increase in IFNγ in cultures incubated with chronically stimulated cells that had been concurrently treated with Compound 2. The results further support that immunomodulatory compounds during conditions that can promote exhaustion, such as during chronic stimulation, can improve or preserve CAR T cell function and limit, reduce or prevent CAR T cell exhaustion. Together, the above results support the use of immunomodulatory compounds like Compound 2 to improve CAR T cell function, including under conditions that can potentially cause exhaustion, such as in response to CAR antigen. Such effects with Compound 2 may be superior to other immunomodulatory compounds, and also can be achieved at lower doses due to the 10-20 times potency of Compound 2 on Ikaros degradation.

Example 28 Effect of Immunomodulatory Compounds to Rescue CAR T Function after Long-Term Stimulation Anti-CD19 CAR-expressing T cells from three donors, produced as described in Example 14, were stimulated under conditions to induce chronic stimulation (to produce hypofunctional, exhausted CAR T cells), and then were subsequently treated (rescue) with (5)-3-[4-(4-morpholin-4-ylmethyl-benzyloxy)-1-oxo-1,3-dihydro-isoindol-2-yl]-piperidine-2,6-dione (Compound 2), or a vehicle control. Long-term, chronic stimulation was carried out by stimulation of CAR T cells with 30 μg/mL plate-bound anti-idiotypic (anti-ID) antibody for 6 days, substantially as described in Example 22. After the chronic stimulation, the CAR-T cells were rechallenged with CD19-expressing target cells in the presence of Compound 2, and cytolytic activity or cytokine production was assessed.

A. Cytolytic Activity

Figure 49A:
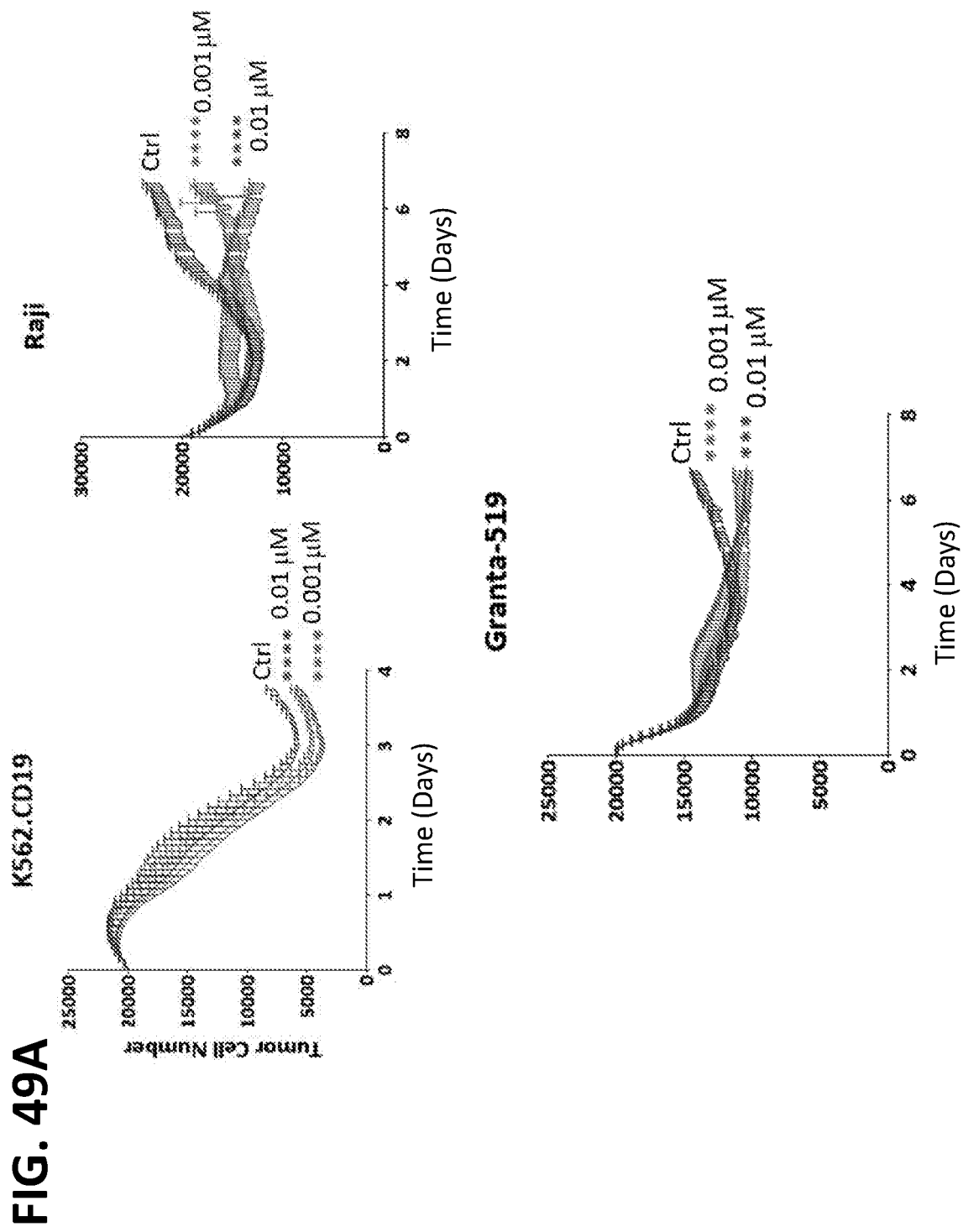
FIG. 49A shows the effect of Compound 2 (0.001 µM or 0.01 µM) on the cytolytic activity of K562 cells transduced with CD19 (K562.CD19), Raji cells or Granta-519 cells.

CAR T cells that had been stimulated for 6 days with anti-ID were co-cultured with CD19+ tumor cells at an effector to target (E:T) ratio of 1:1, in the presence of Compound 2 (0.001 µM or 0.01 µM). The assessed CD19+ tumor cells included K562 cells transduced with CD19 (K562.CD19), Raji cells or Granta-519 cells. As shown in FIG. 49A, there was a statistically significant improvement in cytolytic activity, as measured by tumor cell number over time, when chronically stimulated cells were re-challenged with CD19-expressing cells in the presence of Compound 2 compared to absence of the compound (control). These results are consistent with a finding that the immunomodulatory compound can rescue an exhausted phenotype caused by chronic stimulation.

B. Spheroid Tumor Growth Assay

Figure 49B:
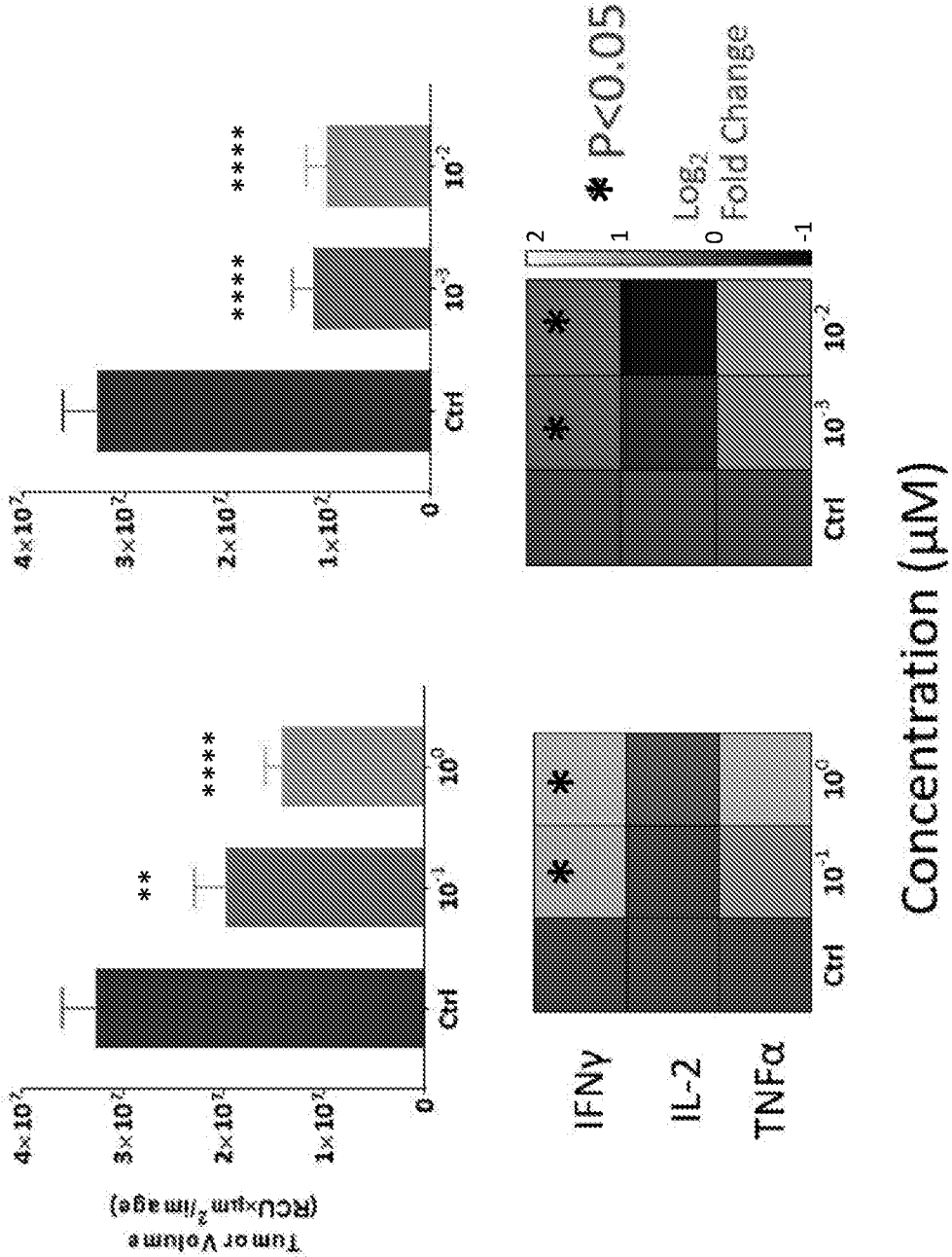
FIG. 49B shows the averaged measurement of the size of Granta-519 tumor spheroids at Day 9 following co-culture with CAR-T cells.
Figure 49C:
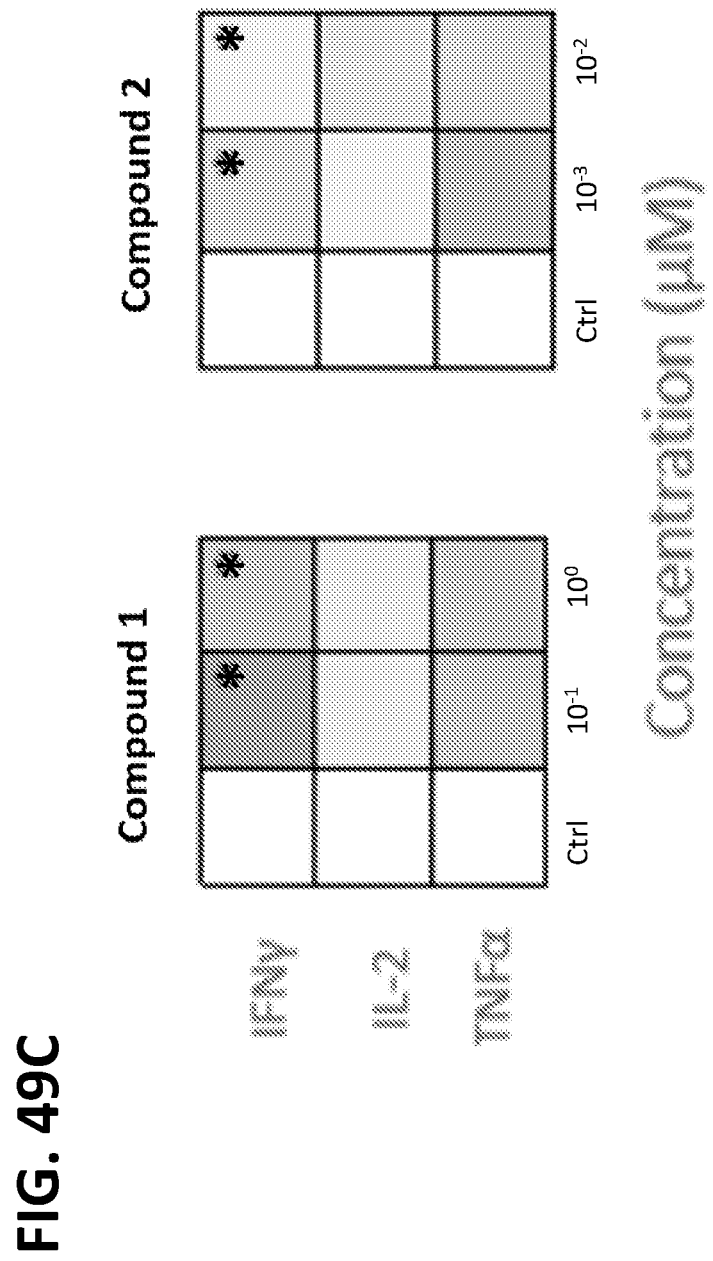
FIG. 49C shows the cytokine levels of IFNγ, IL-2 and TNFalpha measured from the supernatant of the chronically stimulated anti-CD19 CAR T cells that had been co-cultured for 5 days with CD19 tumor spheroids and treated with Compound 1 or Compound 2.

CAR T cells that had been stimulated for 6 days with anti-ID were co-cultured by incubation with Granta-519 tumor spheroids, in the presence of presence of Compound 2 (0.001 µM or 0.01 µM). Cells were assessed at various time points for cytolytic function and cytokine function. For comparison, cytolytic activity was also assessed for cells that had been similarly chronically stimulated with anti-ID, followed by co-culture in the presence of 1 uM or 0.1 uM Compound 1. Averaged measurement of tumor spheroid size at Day 9 following co-culture with CAR-T cells was assessed. As shown in FIG. 49B, rescue treatment with Compound 2 improved CAR T cell cytolytic to reduce Granta-519 spheroid growth. The improvement in cytolytic function was greater following rescue treatment with Compound 2 than Compound 1. Cytokines (IFNγ, IL-2 and TNFalpha) were measured from supernatant of the chronically stimulated CAR T cells above that had been co-cultured for 5 days with CD19 tumor spheroids. The log 2 fold change compared to control cells (chronically stimulated cells that had not been treated with immunomodulatory compound) is shown in FIG. 49C. As shown, there was a statistically significant increase in IFNγ in cultures incubated with chronically stimulated cells that had been subsequently treated with Compound 2 during rechallenge with CD19-expressing tumor spheroids.

Figure 50A:
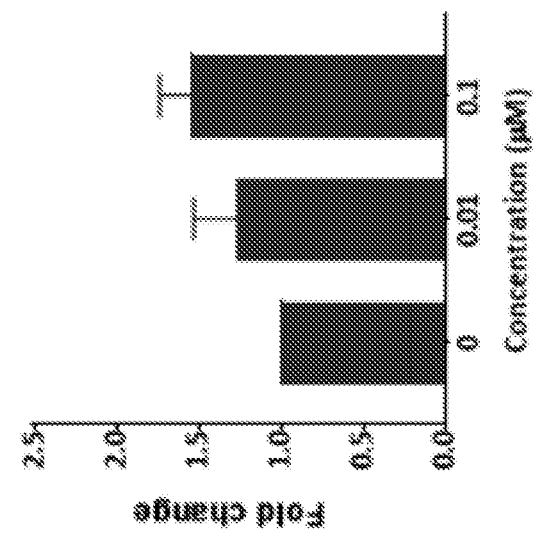
FIG. 50B shows the averaged measurement of the size of A549.CD19 tumor spheroids at Day 9 following co-culture with CAR-T cells in the presence of Compound 2 (0.001 µM, 0.01 µM, or 0.1 µM).
FIG. 50C shows the number of CAR T cells in co-cultures with A549.CD19 tumor spheroids, measured at day 5, with treatment with Compound 2 (0.01 µM or 0.1 µM).
Figure 50B:
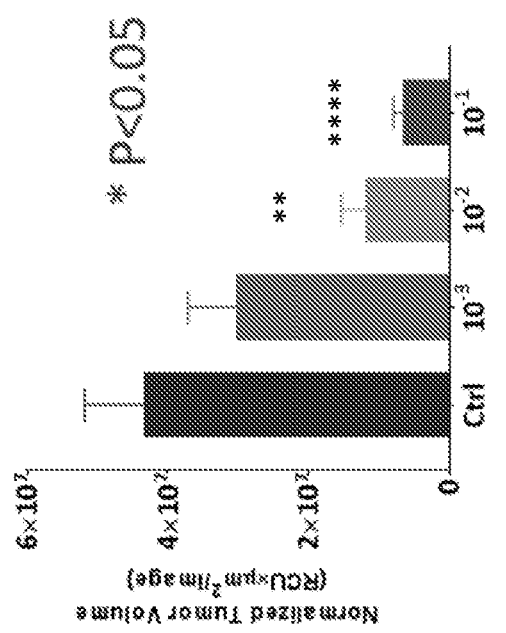
Figure 50C:
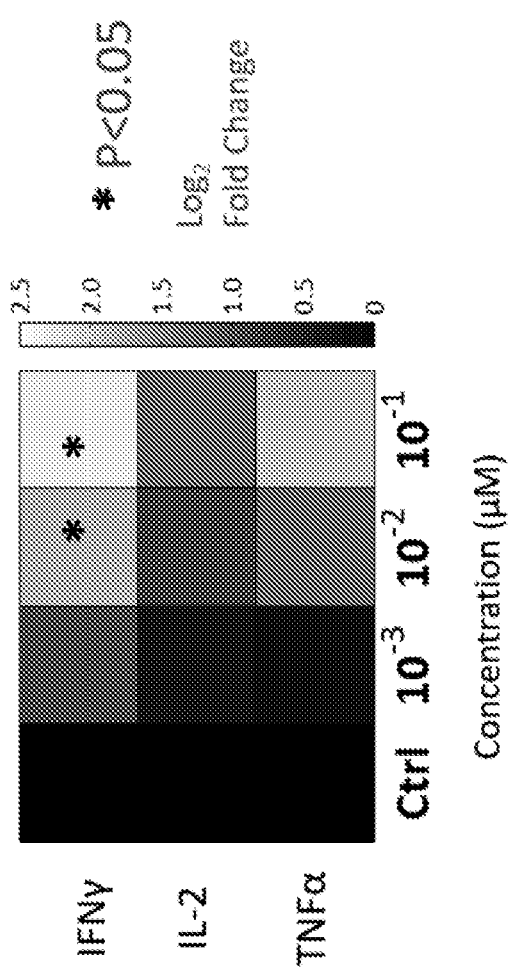

An A549.CD19 tumor spheroid model was further used to elucidate the T cell modulatory activity of the compounds. A549.CD19 tumor spheroid growth is insensitive to monotherapy treatment with the immunomodulatory compounds. CAR T cells that had been stimulated for 6 days with anti-ID were co-cultured by incubation with A549.CD19 tumor spheroids, in the presence of Compound 2 (0.001 µM, 0.01 µM, or 0.1 µM). Averaged measurement of tumor spheroid size at Day 9 following co-culture with CAR-T cells was assessed. As shown in FIG. 50A, rescue treatment with Compound 2 improved CAR T cell cytolytic to reduce A549.CD19 spheroid growth. Cytokines (IFNγ, IL-2 and TNFalpha) were measured from supernatant of the chronically stimulated CAR T cells above that had been co-cultured for 5 days with CD19 tumor spheroids. The log 2 fold change compared to control cells (chronically stimulated cells that had not been concurrently treated with immunomodulatory compound) is shown in FIG. 50B. As shown, there was a statistically significant increase in IFNγ in cultures incubated with chronically stimulated cells that had been subsequently treated with Compound 2 during rechallenge with CD19-expressing tumor spheroids. The number of CAR T cells in co-cultures with tumor spheroids, measured at day 5, were increased with treatment with Compound 2 (FIG. 50C).

These results further support that immunomodulatory compounds, such as Compound 2, can rescue or reverse CAR T cells that have become exhausted. This result was observed in a physiologically relevant 3D spheroid tumor culture model, both involving Granta spheroids known to be sensitive to the immunomodulatory compounds as well as A549.CD19 spheroids that are resistant to the immunomodulatory compounds. Although all assessed immunomodulatory compounds exhibit the ability to rescue CAR T cell function, Compound 2 exhibited a superior ability to rescue anti-tumor functionality compared to Compound 1 and was more potent as the effects were observed at much lower doses.

Example 29 Effect of Immunomodulatory Compounds on Anti-CD19 CAR T Cell Function in CAR T Cell Resistant Lines Because the cell immunomodulatory compounds are known to have anti-lymphoma activity, experiments were carried out to assess the anti-tumor combinatorial effect with sub-therapeutic effector ratios of anti-CD19 CAR T cells.

Anti-CD19 CAR T cells were co-cultured with RL CD19+ tumor cells at an effector to target (E:T) ratio of 1:1, in the presence of (S)-3-[4-(4-morpholin-4-ylmethyl-benzyloxy)-1-oxo-1,3-dihydro-isoindol-2-yl]-piperidine-2,6-dione (Compound 2) (0.001 µM, 0.01 µM or 0.1 µM). Acute cytolytic activity was measured by tumor cell number over time. As shown in FIG. 51A, the RL tumor cell line was sensitive to Compound 2 monotherapy at the 0.01 µM or 0.1 µM doses. Co-culture of CAR T cells with RL resistant tumor cells in the presence of Compound 2 improved cytolytic CAR T cell function, Cytolytic activity was also assessed in a spheroid model. About 5,000 RL cells were plated 48 hours prior to addition of 5,000 anti-CD19 CART cells (1:1 E:T ratio). Anti-CD19 CAR T cells were co-cultured with RL tumor spheroids, in the presence of Compound 1 (1 µM) or Compound 2 (0.001 µM, 0.01 µM or 0.1 µM). Tumor size was assessed at Day 4 post-incubation with CAR T cells FIG. 51B shows that the RL tumor spheroids were sensitive to the immunomodulatory compounds, particularly at 1 µM dose of Compound 1 or 0.01 µM or 0.1 µM doses of Compound 2. Reduction in tumor size was observed with the combination of anti-CD19 CAR T cells and immunomodulatory compound at all doses tested.

Figure 51C:
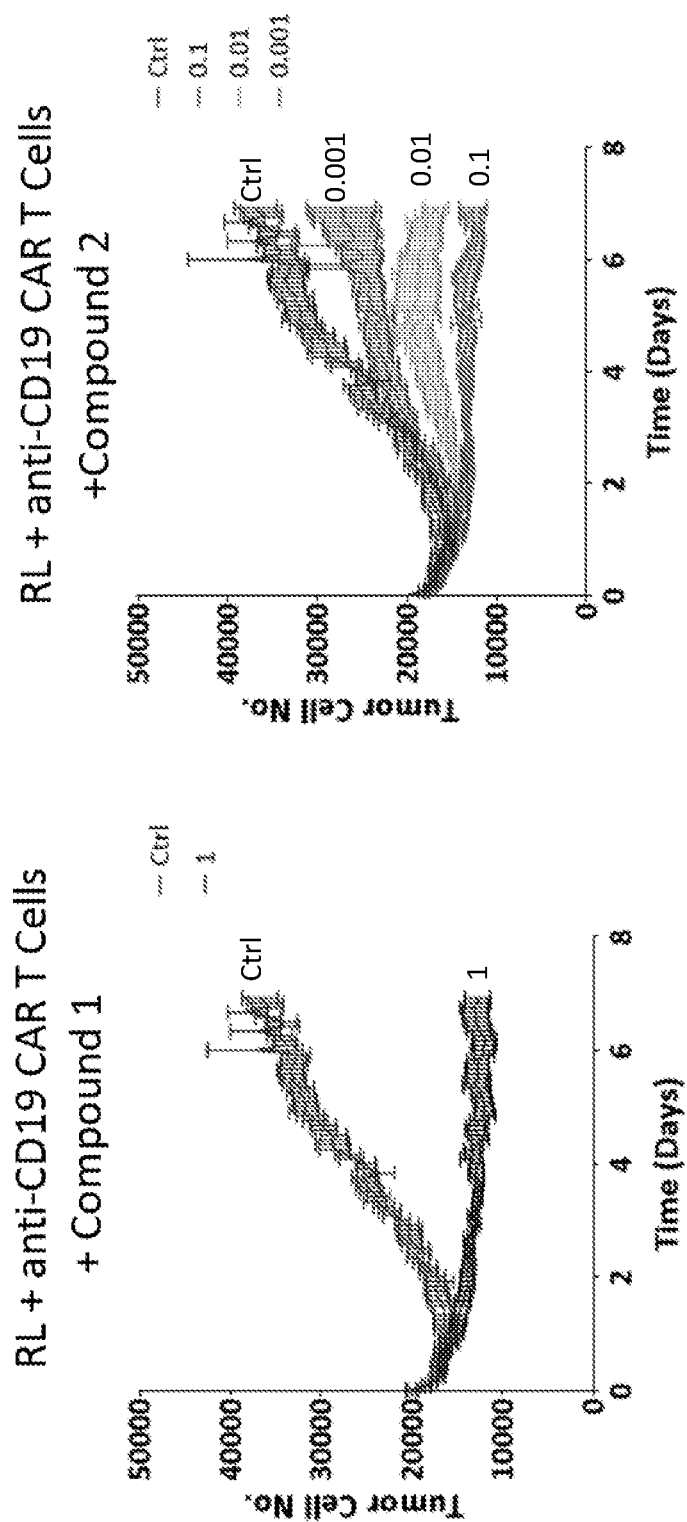
FIG. 51C shows tumor size of RL tumor spheroids cocultured with anti-CD19 CAR T cells in the presence of Compound 1 (1 µM) or Compound 2 (0.001 µM, 0.01 µM or 0.1 µM).

The RL cells were further used to assess the ability of immunomodulatory compounds to rescue or reverse the anti-CD19 CAR T cells from exhaustion. Anti-CD19 CAR-expressing T cells were stimulated under conditions to induce chronic stimulation and then were subsequently treated (rescue) with Compound 1 (1 µM) or Compound 2 (0.001 µM, 0.01 µM or 0.1 µM), or a vehicle control. Long-term, chronic stimulation was carried out by stimulation of CAR T cells with 30 µg/mL plate-bound anti-idiotypic (anti-ID) antibody for 6 days, substantially as described in Example 22. After the chronic stimulation, the CAR-T cells were cultured with RL cells in the presence of Compound 1 or Compound 2. Cytolytic activity was assessed over time by measuring tumor cell number in the culture. As shown in FIG. 51C rescue treatment with either Compound 1 or Compound 2 substantially improved CAR T cell cytolytic activity to reduce RLcell growth. These results demonstrated that the assessed immunomodulatory compounds can rescue chronically stimulated anti-CD19 CAR T cells to permit clearance of RL-resistant lines.

Example 30 Cytolytic Function and Cytokine Production of Chronically Stimulated Anti-BCMA CAR T Cells Against BCMA-Expressing MM Target Cells in the Presence of Cell Immunomodulatory Compound Cryofrozen anti-BCMA CAR T cells, produced substantially as described in Example 1 and formulated at a 1:1 ratio of CD4+ and CD8+ T cells, were thawed. Anti-BCMA CAR T cells were stimulated with BCMA conjugated beads (diameter about 4.5 µm from a 50 µg/ml BCMA-conjugated bead composition, generated as described in Example 9) at a ratio of T cells to beads of 1:1 in the presence or absence of lenalidomide (1000 nM), Compound 2 (0.1 nM, 1 nM or 10 nM) or DMSO vehicle control. The cells were then incubated at 37° C., 5% CO2 for 7 days.

Figure 52:
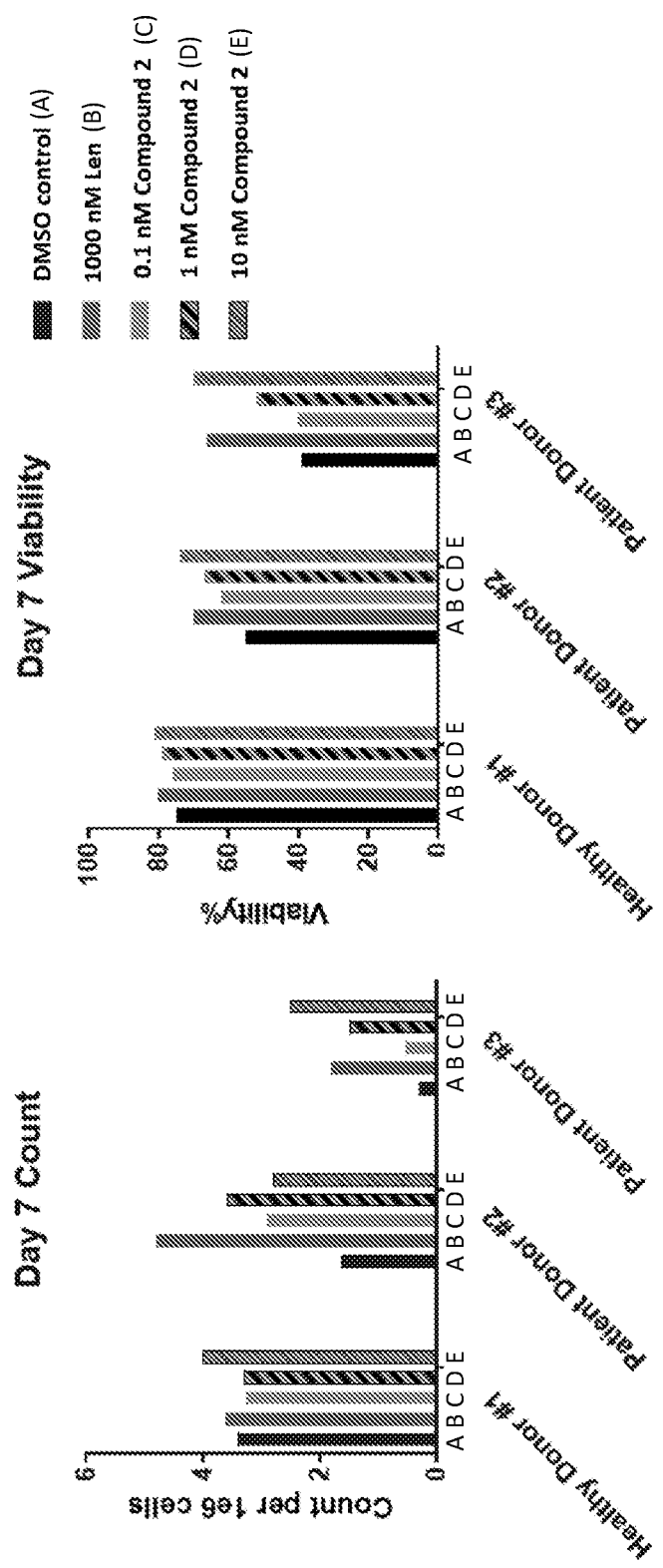
FIG. 52 shows the viability and count of anti-BCMA CAR T cells from three donors in the presence of lenalidomide (1000 nM) or Compound 2 (0.1 nM, 1 nM, or 10 nM) after 7 days.

At day 7, anti-BCMA CAR cells of all the samples were counted using a cellometer machine and stained for flow cytometric analysis. Cells were stained with a viability dye and analyzed by flow cytometry. As shown in FIG. 52, viability and count of anti-BCMA CAR T cells was increased in the presence of lenalidomide or Compound 2.

Cytolytic activity was assessed using OPM-2 and RPMI-8226 BCMA expressing target cells transduced with NucLight Red, a red fluorescent protein detectable by microscopy, to allow for measurement of target cell death. Anti-BCMA CAR T cells that had been stimulated for 7 days with BCMA-conjugated beads in the presence of the compounds were co-cultured with RPMI-8226 target cells at a 0.3:1 (effector:target) or 1:1 ratio. Cultures were incubated at 37° C., 5% CO2, and images were taken every 2 hours over 5-7 days with an Essen IncuCyte Zoom live-cell analysis system to track NucLightRed-positive target cells. When the long-term stimulation was carried out in the presence of lenalidomide or Compound 2, anti-BCMA CAR T cells showed increased cytolytic activity (FIG. 53A, results shown for 0.3:1 E:T ratio).

Figure 53C:
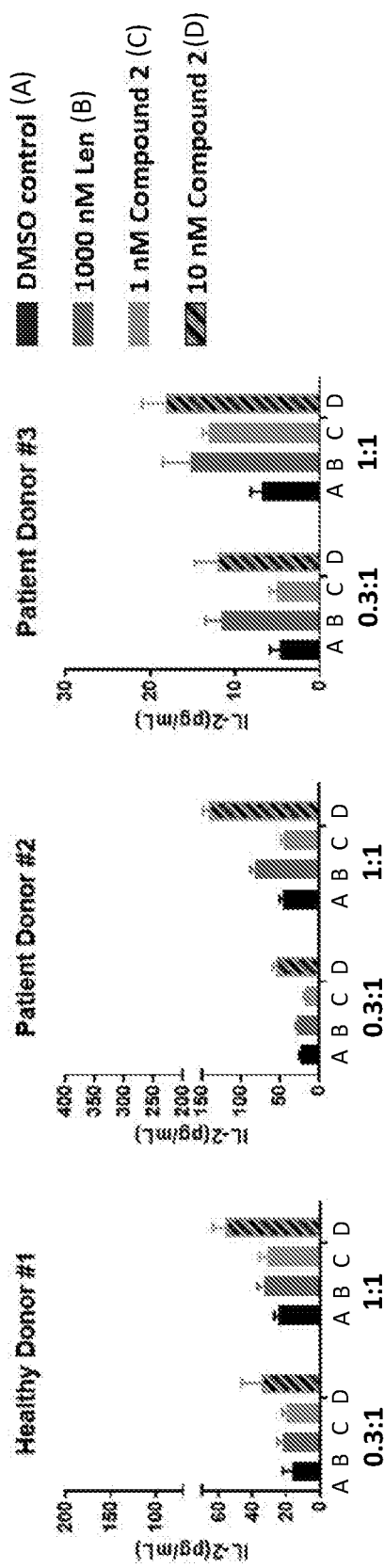
Figure 53D:
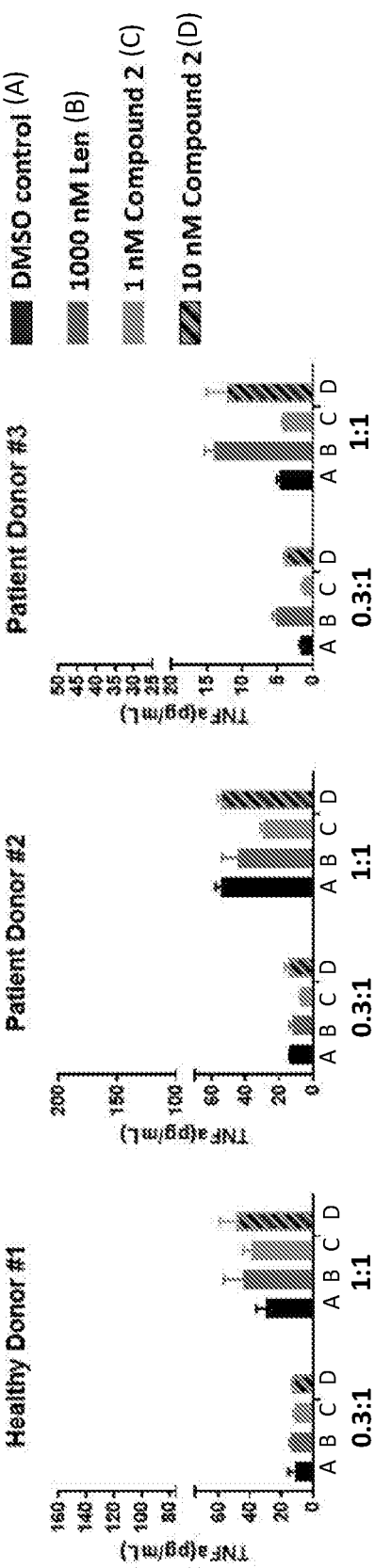

For cytokine measurements, cell-free supernatants were collected from the cytolytic assay described above 24 hours after plating. Cytokine levels were measured using IFNg, IL-2, and TNFalpha Meso Scale Discovery cytokine kit (Mesoscale) according to manufacturer instructions. The data was analyzed using GraphPad Prism to calculate absolute changes in cytokine relative to the DMSO vehicle control. As shown in FIG. 53B-D, when the long-term stimulation was carried out in the presence of lenalidomide or Compound 2, anti-BCMA CAR T cells showed increased production of IFN-gamma (FIG. 53B), IL-2 (FIG. 53C) or TNF-alpha (FIG. 53D).

These results demonstrate that lenalidomide or Compound 2 present during chronic stimulation increases anti-BCMA CAR T cell cytolytic activity and cytokine production following antigen rechallenge, and in the absence of the compound during rechallenge. These results further support the ability of cell immunomodulatory compounds, such as lenalidomide or Compound 2, to reduce or prevent the development of an exhausted phenotype in response to chronic stimulation, thereby improving CAR-T cell function and limiting CAR T cell exhaustion.

Example 31 Rescue of Cytolytic Function and Cytokine Production Following Chronic Stimulation of Anti-BCMA CAR T Cells by Cell Immunomodulatory Compound Studies were undertaken to determine whether Compound 2 rescued anti-BCMA CAR T cell function following chronic stimulation. To directly stimulate via CAR engagement to induce chronic stimulation of cells, anti-BCMA CAR T cells were stimulated with BCMA conjugated beads (diameter about 4.5 µm from a 50 µg/ml BCMA-conjugated bead composition, generated as described in Example 9) at a ratio of T cells to beads of 1:1. The cells were then incubated at 37° C., 5% CO2 for 7 days.

Figure 54A:
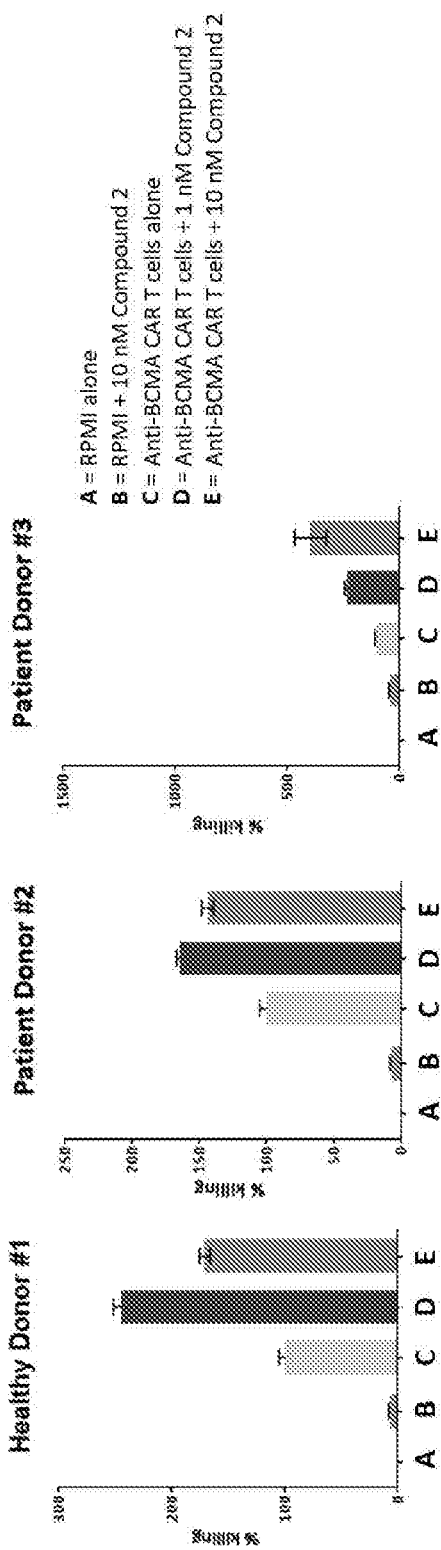
FIG. 54 shows cytolytic activity of anti-BCMA CAR T cells from three donors during chronic stimulation for 7 days with BCMA-conjugated beads and re-challenged with BCMA-expressing RPMI-8226 MM cells in the presence of Compound 2 (1 nM or 10 nM).
FIGS. 54B-D shows the production of IFN-gamma (FIG. 54B), IL-2 (FIG. 54C), and TNF-alpha (FIG. 54D) in anti-BCMA CAR T cells from three donors during chronic stimulation in the presence of Compound 2 (1 nM or 10 nM).
Figure 54B:
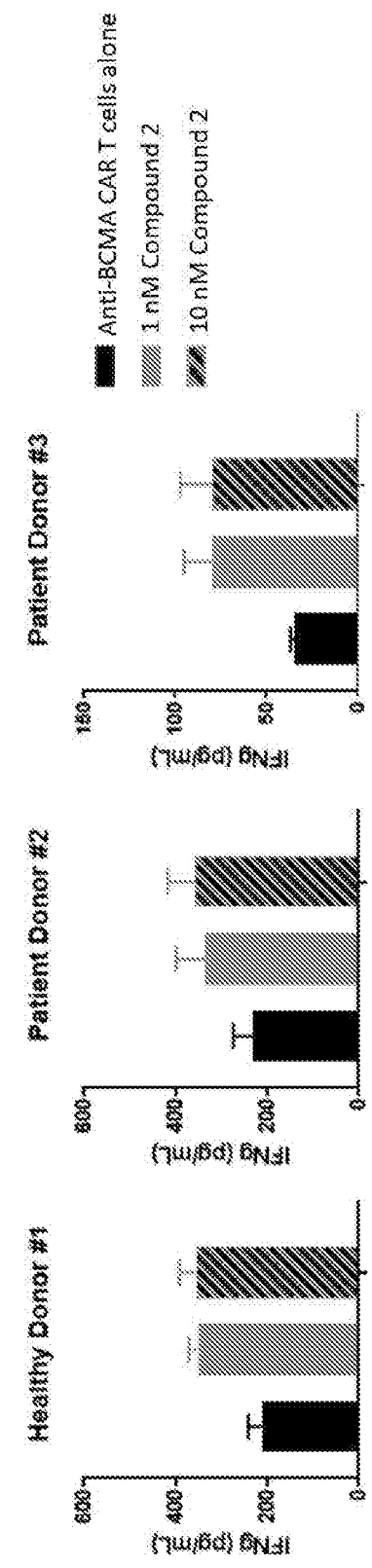
Figure 54C:
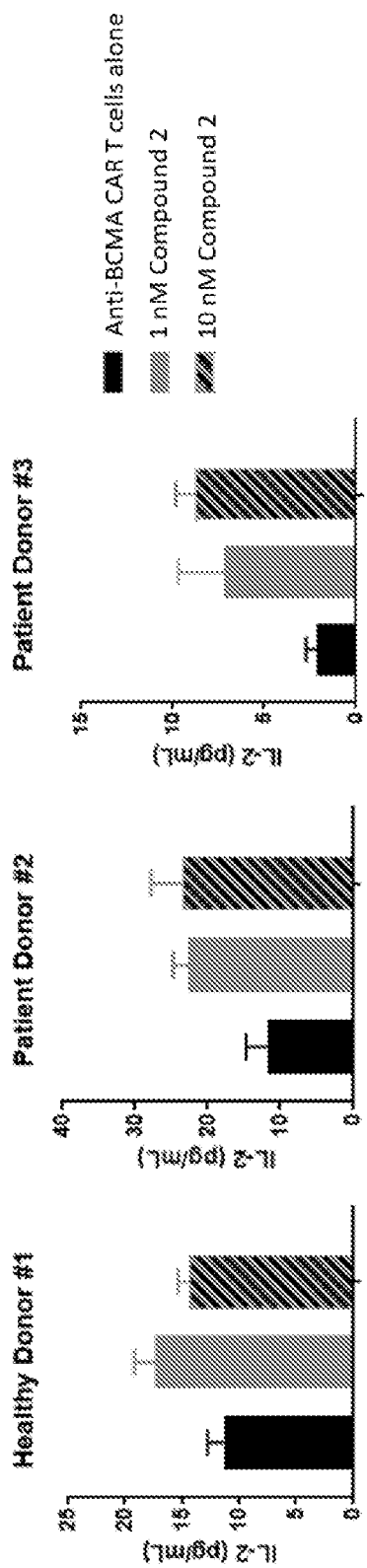
Figure 54D:
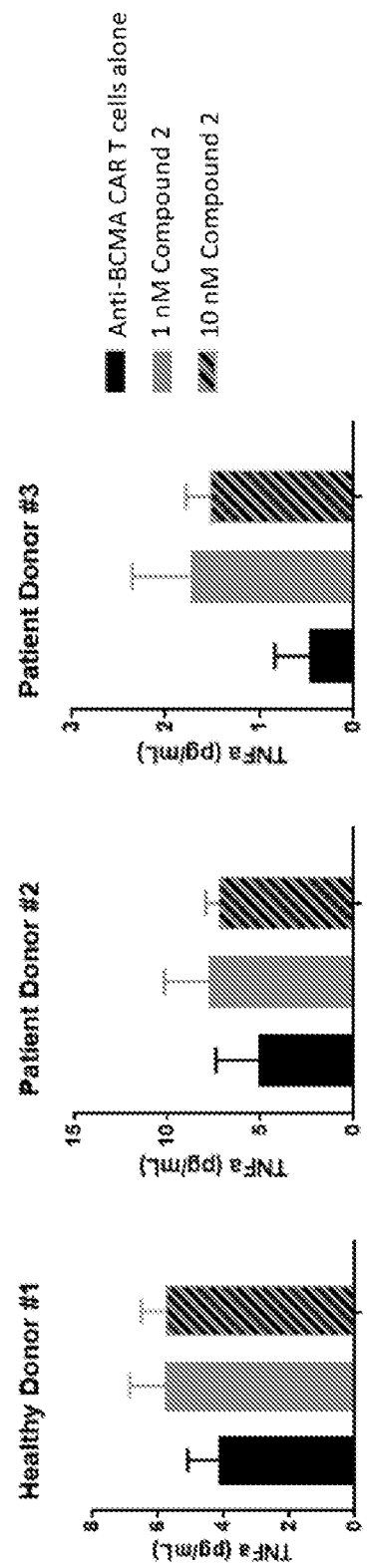

Anti-BCMA CAR T cells that had been stimulated for 7 days with BCMA-conjugated beads were re-challenged with BCMA-expressing RPMI-8226 MM cells at a 0.3:1 E:T ratio in the presence of Compound 2 (1 nm or 10 nM). Cultures were incubated at 37° C., 5% CO2, and images were taken every 2 hours over 5-7 days with an Essen IncuCyte Zoom live-cell analysis system to track NucLight-Red-positive target cells. As shown in FIG. 54A, there was an improvement in cytolytic activity when chronically stimulated cells were re-challenged with BCMA-expressing cells in the presence of Compound 2 compared to absence of the compound (control). Cell-free supernatants were collected from the cytolytic assay described above 24 hours after plating, and used to measure IFNg, IL-2, and TNF by MSD, as described in Example 30. As shown in FIG. 54B-D, anti-BCMA CAR T cells showed increased production of IFN-gamma (FIG. 54B), IL-2 (FIG. 54C) or TNF-alpha (FIG. 54D) when chronically stimulated cells were re-challenged with BCMA-expressing cells in the presence of Compound 2 compared to absence of the compound (control).

Figure 55C:
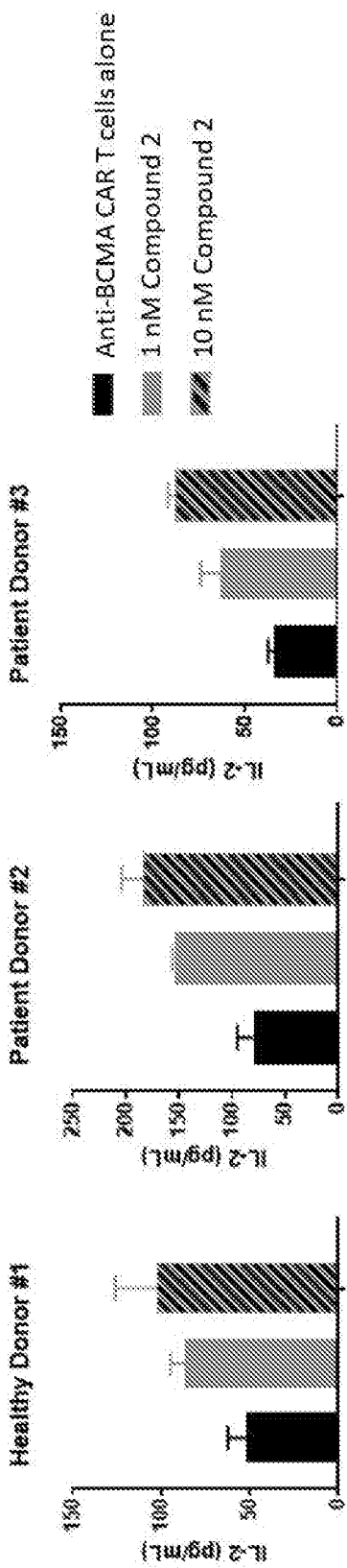
Figure 55D:
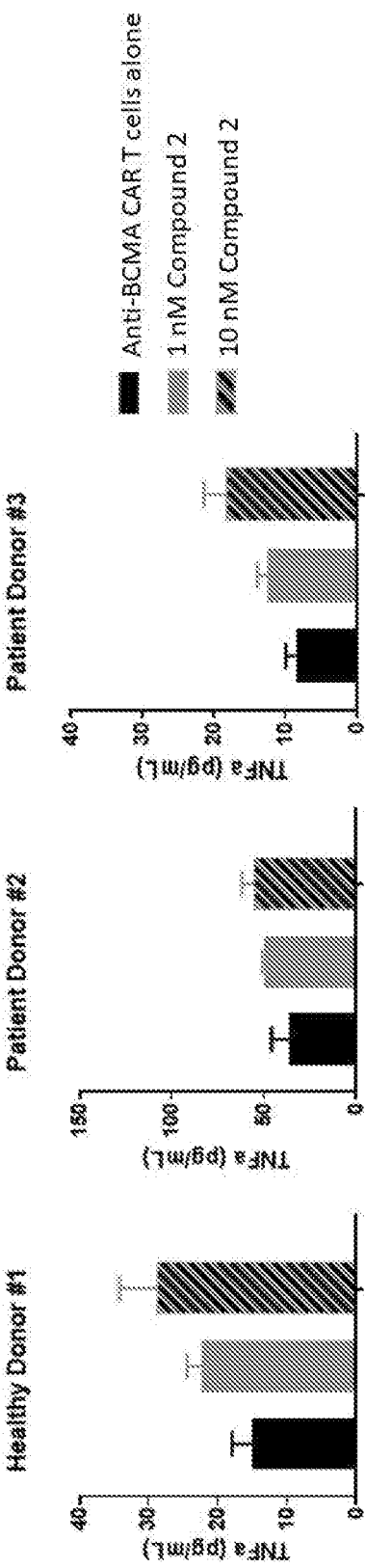

To further elucidate the role of Compound 2 on the target cells compared to the CAR T cell intrinsic effects, the IMiD/CELMoD resistant cell line DF-15R was also used to rechallenge anti-BCMA CAR T cells that had been chronically stimulated for 7 days. Cytolytic activity and cytokine production following the rechallenge were assessed as described above. Anti-BCMA CAR T cells showed both increased cytolytic activity (FIG. 55A) and cytokine production (FIG. 55B-D) in the presence of DF-15R, indicating a CAR T-intrinic increase in functionality.

These results further demonstrate that, following chronic stimulation, the addition of cell immunomodulatory compounds, such as Compound 2, during antigen rechallenge rescues exhausted anti-BCMA CAR T cells, as shown by increased cytolytic activity and cytokine production.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

| SEQ ID NO. | SEQUENCE | DESCRIPTION |
|---|---|---|
| 1 | ESKYGPPCPPCP | spacer (IgG4hinge) (aa)<br>*Homo sapiens* |
| 2 | GAATCTAAGTACGGACCGCCCTGCCCCCCTTGCCCT | spacer (IgG4hinge) (nt)<br>*Homo sapiens* |
| 3 | ESKYGPPCPPCPGQPREPQVYTLPPSQEEMTKNQVSLTCLVKGFYPSDIAVEWES<br>NGQPENNYKTTPPVLDSDGSFFLYSRLTVDKSRWQEGNVFSCSVMHEALHNHYTQ<br>KSLSLSLGK | Hinge-CH3 spacer<br>*Homo sapiens* |
| 4 | ESKYGPPCPPCPAPEFLGGPSVFLFPPKPKDTLMISRTPEVTCVVVDVSQEDPEV<br>QFNWYVDGVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSDIAVEWES<br>NGQPENNYKTTPPVLDSDGSFFLYSRLTVDKSRWQEGNVFSCSVMHEALHNHYTQ<br>KSLSLSLGK | Hinge-CH2-CH3 spacer<br>*Homo sapiens* |
| 5 | RWPESPKAQASSVPTAQPQAEGSLAKATTAPATTRNTGRGGEEKKKEKEKEEQEE<br>RETKTPECPSHTQPLGVYLLTPAVQDLWLRDKATFTCFVVGSDLKDAHLTWEVAG<br>KVPTGGVEEGLLERHSNGSQSQHSRLTLPRSL<br>WNAGTSVTCTLNHPSLPPQRLMALREPAAQAPVKLSLNLLASSDPPEAASWLLCE<br>VSGFSPPNILLMWLEDQREVNTSGFAPARPPPQPGSTTFWAWSVLRVPAPPSPQP<br>ATYTCVVSHEDSRTLLNASRSLEVSYVTDH | IgD-hinge-Fc<br>*Homo sapiens* |
| 6 | LEGGGEGRGSLLTCGDVEENPGPR | T2A<br>artificial |
| 7 | RKVCNGIGIGEFKDSLSINATNIKHFKNCTSISGDLHILPVAFRGDSFTHTPPLD<br>PQELDILKTVKEITGFLLIQAWPENRTDLHAFENLEIIRGRTKQHGQFSLAVVSL<br>NITSLGLRSLKEISDGDVIISGNKNLCYANTINWKKLFGTSGQKTKIISNRGENS<br>CKATGQVCHALCSPEGCWGPEPRDCVSCRNVSRGRECVDKCNLLEGEPREFVENS<br>ECIQCHPECLPQAMNITCTGRGPDNCIQCAHYIDGPHCVKTCPAGVMGENNTLVW<br>KYADAGHVCHLCHPNCTYGCTGPGLEGCPTNGPKIPSIATGMVGALLLLLVVALG<br>IGLFM | tEGFR<br>artificial |
| 8 | FWVLVVVGGVLACYSLLVTVAFIIFWV | CD28 (amino acids 153-179 of Accession No. P10747)<br>*Homo sapiens* |
| 9 | IEVMYPPPYLDNEKSNGTIIHVKGKHLCPSPLFPGPSKP<br>FWVLVVVGGVLACYSLLVTVAFIIFWV | CD28 (amino acids 114-179 of Accession No. P10747)<br>*Homo sapiens* |
| 10 | RSKRSRLLHSDYMNMTPRRPGPTRKHYQPYAPPRDFAAYRS | CD28 (amino acids 180-220 of P10747)<br>*Homo sapiens* |
| 11 | RSKRSRGGHSDYMNMTPRRPGPTRKHYQPYAPPRDFAAYRS | CD28 (LL to GG)<br>*Homo sapiens* |
| 12 | KRGRKKLLYIFKQPFMRPVQTTQEEDGCSCRFPEEEEGGCEL | 4-1BB (amino acids 214-255 of Q07011.1)<br>*Homo sapiens* |
| 13 | RVKFSRSADAPAYQQGQNQLYNELNLGRREEYDVLDKRRGRDPEMGGKPRRKNPQ<br>EGLYNELQKDKMAEAYSEIGMKGERRRGKGHDGLY<br>QGLSTATKDTYDALHMQALPPR | CD3 zeta<br>*Homo sapiens* |
| 14 | RVKFSRSAEPPAYQQGQNQLYNELNLGRREEYDVLDKRRGRDPEMGGKPRRKNPQ<br>EGLYNELQKDKMAEAYSEIGMKGERRRGKGHDGLY<br>QGLSTATKDTYDALHMQALPPR | CD3 zeta<br>*Homo sapiens* |
| 15 | RVKFSRSADAPAYKQGQNQLYNELNLGRREEYDVLDKRRGRDPEMGGKPRRKNPQ<br>EGLYNELQKDKMAEAYSEIGMKGERRRGKGHDGLY<br>QGLSTATKDTYDALHMQALP PR | CD3 zeta<br>*Homo sapiens* |
| 16 | PGGG-(SGGGG)5-P- wherein P is proline, G is glycine and S is serine | linker |

| SEQ ID NO. | SEQUENCE | DESCRIPTION |
|---|---|---|
| 17 | GSADDAKKDAAKKDGKS | Linker |
| 18 | MLQMAGQCSQNEYFDSLLHACIPCQLRCSSNTPPLTCQRYCNASVTNSVKGTNA | Extracellular domain of human BCMA (GenBank No. NP_001183.2) |
| 19 | GGGGS | Linker sequence |
| 20 | PKSSDKTHTCPPCPAPEAEGAPSVFLFPPKPKDTLMISRTPEVTCVVVDVSHEDP EVKFNWYVDGVEVHNAKTKPREEQYNSTYRVVSVLTVLHQDWLNGKEYKCKVSNK ALPSSIEKTISKAKGQPREPQVYTLPPSRDELTKNQVSLTCLVKGFYPSDIAVEW ESNGQPENNYKTTPPVLDSDGSFFLYSKLTVDKSRWQQGNVFSCSVMHEALHNHY TQKSLSLSPGK | Modified Human IgG1 Fc |
| 21 | MPLLLLLPLLWAGALA | CD33 Signal peptide |
| 22 | MPLLLLLPLLWAGALAMLQMAGQCSQNEYFDSLLHACIPCQLRCSSNTPPLTCQR YCNASVTNSVKGTNAGGGGSPKSSDKTHTCPPCPAPEAEGAPSVFLFPPKPKDTL MISRTPEVTCVVVDVSHEDPEVKFNWYVDGVEVHNAKTKPREEQYNSTYRVVSVL TVLHQDWLNGKEYKCKVSNKALPSSIEKTISKAKGQPREPQVYTLPPSRDELTKN QVSLTCLVKGFYPSDIAVEWESNGQPENNYKTTPPVLDSDGSFFLYSKLTVDKSR WQQGNVFSCSVMHEALHNHYTQKSLSLSPGK | BCMA-Fc construct |
| 23 | EGRGSLLTCGDVEENPGP | T2A |
| 24 | GSGATNFSLLKQAGDVEENPGP | P2A |
| 25 | ATNFSLLKQAGDVEENPGP | P2A |
| 26 | QCTNYALLKLAGDVESNPGP | E2A |
| 27 | VKQTLNFDLLKLAGDVESNPGP | F2A |
| 28 | RKVCNGIGIGEFKDSLSINATNIKHFKNCTSISGDLHILPVAFRGDSFTHTPPLD PQELDILKTVKEITGELLIQAWPENRTDLHAFENLEIIRGRTKQHGQFSLAVVSL NITSLGLRSLKEISDGDVIISGNKNLCYANTINWKKLFGTSGQKTKIISNRGENS CKATGQVCHALCSPEGCWGPEPRDCVSCRNVSRGRECVDKCNLLEGEPREFVENS ECIQCHPECLPQAMNITCTGRGPDNCIQCAHYIDGPHCVKTCPAGVMGENNTLVW KYADAGHVCHLCHPNCTYGCTGPGLEGCPTNGPKIPSIATGMVGALLLLLVVALG IGLFM | tEGFR artificial |
| 29 | ESKYGPPCPPCPAPPVAGPSVFLFPPKPKDTLMISRTPEVTCVVVDVSQEDPEVQ FNWYVDGVEVHNAKTKPREEQFQSTYRVVSVLTVLHQDWLNGKEYKCKVSNKGLP SSIEKTISKAKGQPREPQVYTLPPSQEEMTKNQVSLTCLVKGFYPSDIAVEWESN GQPENNYKTTPPVLDSDGSFFLYSRLTVDKSRWQEGNVFSCSVMHEALHNHYTQK SLSLSLGK | Hinge-CH2-CH3 spacer Homo sapiens |
| 30 | QIQLVQSGPELKKPGETVKISCKASGYTFTDYSINWVKRAPGKGLKWMGWINTET REPAYAYDFRGRFAFSLETSASTAYLQINNLKYEDTATYFCALDYSYAMDYWGQG TSVTVSS | Variable heavy (VH) Anti-BCMA |
| 31 | DIVLTQSPPSLAMSLGKRATISCRASESVTILGSHLIHWYQQKPGQPPTLLIQLA SNVQTGVPARFSGSGSRTDFTLTIDPVEEDDVAVYYCLQSRTIPRTFGGGTKLEI K | Variable light (VL) Anti-BCMA |
| 32 | QTQLVQSGPDLKKPGETVKLSCKASGYTFTNEGMNWVKQAPGKGEKWMAWINTYT GESYFADDFKGRFAFSVETSATTAYLQINNLKTEDTATYFCARGETYYGYDGGFA YWGQGTLVTVSA | Variable heavy (VH) Anti-BCMA |
| 33 | DVVMTQSHRFMSTSVGDRVSITCRASQDVNTAVSWYQQKPGQSPKLLIFSASYRY TGVPDRFTGSGSGADFTLTISSVQAEDLAVYYCQQHYSTPWTFGGGTKLDIK | Variable light (VL) Anti-BCMA |
| 34 | EVQLVQSGAEVKKPGESLKISCKGSGYSFTSYWIGWVRQMPGKGLEWMGIIYPGD SDTRYSPSFQGHVTISADKSISTAYLQWSSLKASDTAMYYCARYSGSFDNWGQGT LVTVSS | Variable heavy (VH) Anti-BCMA |
| 35 | SYELTQPPSASGTPGQRVTMSCSGTSSNIGSHSVNWYQQLPGTAPKLLIYTNNQR PSGVPDRFSGSKSGTSASLAISGLQSEDEADYYCAAWDGSLNGLVFGGGTKLTVL G | Variable light (VL) Anti-BCMA |

| SEQ ID NO. | SEQUENCE | DESCRIPTION |
|---|---|---|
| 36 | EVQLVQSGAEMKKPGASLKLSCKASGYTFIDYYVYWMRQAPGQGLESMGWINPNS GGTNYAQKFQGRVTMTRDTSISTAYMELSRLRSDDTAMYYCARSQRDGYMDYWGQ GTLVTVSS | Variable heavy (VH) Anti-BCMA |
| 37 | QSALTQPASVSASPGQSIAISCTGTSSDVGWYQQHPGKAPKLMIYEDSKRPSGVS NRFSGSKSGNTASLTISGLQAEDEADYYCSSNTRSSTLVFGGGTKLTVLG | Variable light (VL) Anti-BCMA |
| 38 | EVQLVQSGAEVKKPGSSVKVSCKASGGTFSSYAISWVRQAPGQGLEWMGRIIPIL GIANYAQKFQGRVTMTEDTSTDTAYMELSSLRSEDTAVYYCARSGYSKSIVSYMD YWGQGTLVTVSS | Variable heavy (VH) Anti-BCMA |
| 39 | LPVLTQPPSTSGTPGQRVTVSCSGSSSNIGSNVVFWYQQLPGTAPKLVIYRNNQR PSGVPDRFSVSKSGTSASLAISGLRSEDEADYYCAAWDDSLSGYVFGTGTKVTVL G | Variable light (VL) Anti-BCMA |
| 40 | QVQLVQSGAEVKKPGSSVKVSCKASGGTFSSYAISWVRQAPGQGLEWMGRIIpIL GTANYAQKFQGRVTITADESTSTAYMELSSLRSEDTAVYYCARSGYGSYRWEDSW GQGTLVTVSS | Variable heavy (VH) Anti-BCMA |
| 41 | QAVLTQPPSASGTPGQRVTISCSGSSSNIGSNYVFWYQQLPGTAPKLLIYSNNQR PSGVPDRFSGSKSGTSASLAISGLRSEDEADYYCAAWDDSLSASYVFGTGTKVTV LG | Variable light (VL) Anti-BCMA |
| 42 | QVQLVQSGAEVKKPGASVKVSCKASGYTFTDYYMHWVRQApGQRLEWMGWINPNS GGTNYAQKFQDRITVTRDTSSNTGYMELTRLRSDDTAVYYCARSPYSGVLDKWGQ GTLVTVSS | Variable heavy (VH) Anti-BCMA |
| 43 | QSVLTQPPSVSGAPGQRVTISCTGSSSNIGAGFDVHWYQQLPGTAPKLLIYGNSN RPSGVPDRFSGSKSGTSASLAITGLQAEDEADYYCQSYDSSLSGYVFGTGTKVTV LG | Variable light (VL) Anti-BCMA |
| 44 | DYGVS | FMC63 CDR H1 |
| 45 | VIWGSETTYYNSALKS | FMC63 CDR H2 |
| 46 | YAMDYWG | FMC63 CDR H3 |
| 47 | HYYYGGSYAMDY | FMC63 HC-CDR3 |
| 48 | RASQDISKYLN | FMC63 CDR L1 |
| 49 | SRLHSGV | FMC63 CDR L2 |
| 50 | HTSRLHS | FMC63 LC-CDR2 |
| 51 | GNTLPYTFG | FMC63 CDR L3 |
| 52 | QQGNTLPYT | FMC63 LC-CDR3 |
| 53 | EVKLQESGPGLVAPSQSLSVTCTVSGVSLPDYGVSWIRQPPRKGLEWLGVIWGSE TTYYNSALKSRLTIIKDNSKSQVFLKMNSLQTDDTAIYYCAKHYYYGGSYAMDYW GQGTSVTVSS | FMC63 VH |
| 54 | DIQMTQTTSSLSASLGDRVTISCRASQDISKYLNWYQQKPDGTVKLLIYHTSRLH SGVPSRFSGSGSGTDYSLTISNLEQEDIATYFCQQGNTLPYTFGGGTKLEIT | FMC63 VL |
| 55 | DIQMTQTTSSLSASLGDRVTISCRASQDISKYLNWYQQKPDGTVKLLIYHTSRLH SGVPSRFSGSGSGTDYSLTISNLEQEDIATYFCQQGNTLPYTFGGGTKLEITGST SGSGKPGSGEGSTKGEVKLQESGPGLVAPSQSLSVTCTVSGVSLPDYGVSWIRQP PRKGLEWLGVIWGSETTYYNSALKSRLTIIKDNSKSQVFLKMNSLQTDDTAIYYC AKHYYYGGSYAMDYWGQGTSVTVSS | FMC63 scFv |
| 56 | KASQNVGTNVA | SJ25C1 CDR L1 |
| 57 | SATYRNS | SJ25C1 CDR L2 |
| 58 | QQYNRYPYT | SJ25C1 CDR L3 |
| 59 | SYWMN | SJ25C1 CDR H1 |
| 60 | QIYPGDGDTNYNGKFKG | SJ25C1 CDR H2 |
| 61 | KTISSVVDFYFDY | SJ25C1 CDR H3 |

| SEQ ID NO. | SEQUENCE | DESCRIPTION |
|---|---|---|
| 62 | EVKLQQSGAELVRPGSSVKISCKASGYAFSSYWMNWVKQRPGQGLEWIGQIYPGD GDTNYNGKFKGQATLTADKSSSTAYMQLSGLTSEDSAVYFCARKTISSVVDFYFD YWGQGTTVTVSS | SJ25C1 VH |
| 63 | DIELTQSPKFMSTSVGDRVSVTCKASQNVGTNVAWYQQKPGQSPKPLIYSATYRN SGVPDRFTGSGSGTDFTLTITNVQSKDLADYFCQQYNRYPYTSGGGTKLEIKR | SJ25C1 VL |
| 64 | GGGGSGGGGSGGGGS | Linker |
| 65 | EVKLQQSGAELVRPGSSVKISCKASGYAFSSYWMNWVKQRPGQGLEWIGQIYPGD GDTNYNGKFKGQATLTADKSSSTAYMQLSGLTSEDSAVYFCARKTISSVVDFYFD YWGQGTTVTVSSGGGGSGGGGSGGGGSDIELTQSPKFMSTSVGDRVSVTCKASQN VGTNVAWYQQKPGQSPKPLIYSATYRNSGVPDRFTGSGSGTDFTLTITNVQSKDL ADYFCQQYNRYPYTSGGGTKLEIKR | SJ25C1 scFv |
| 66 | HYYYGGSYAMDY | FMC63 HC-CDR3 |
| 67 | HTSRLHS | FMC63 LC-CDR2 |
| 68 | QQGNTLPYT | FMC63 LC-CDR3 |
| 69 | gacatccagatgacccagaccacctccagcctgagcgccagcctgggcgaccggg tgaccatcagctgccgggccagccaggacatcagcaagtacctgaactggtatca gcagaagcccgacggcaccgtcaagctgctgatctaccacaccagccggctgcac agcggcgtgcccagccggtttagcggcagcggctccggcaccgactacagcctga ccatctccaacctggaacaggaagatatcgccacctactttttgccagcagggcaa cacactgccctacacctttggcggcggaacaaagctggaaatcaccggcagcacc tccggcagcggcaagcctggcagcggcgagggcagcaccaagggcagggtgaagc tgcaggaaagcggccctggcctggtgggccccagccagagcctgagcgtgacctg caccgtgagcggcgtgagcctgcccgactacggcgtgagctggatccggcagccc cccaggaagggcctggaatggctgggcgtgatctggggcagcgagaccacctact acaacagcccctgaagagccggctgaccatcatcaaggacaacagcaagagcca ggtgttcctgaagatgaacagcctgcagaccgacgacaccgccatctactactgc gccaagcactactactacggcggcagctacgccatggactactggggccagggca ccagcgtgaccgtgagcagc | Sequence encoding scFv |
| 70 | GSTSGSGKPGSGEGSTKG | Linker |
| 71 | GGGS | Linker |
| 72 | GGGGSGGGGSGGGGS | Linker |
| 73 | GSTSGSGKPGSGEGSTKG | Linker |
| 74 | SRGGGGSGGGGSGGGGSLEMA | Linker |
| 75 | MALPVTALLLPLALLLHAARP | CD8a signal peptide |
| 76 | METDTLLLWVLLLWVPGSTG | signal peptide |
| 77 | EVQLLESGGGLVQPGGSLRLSCAASGFTFSSYAMSWVRQAPGKGLEWVSAISGSG GSTYYADSVKGRFTISRDNSKNTLYLQMNSLRAEDTAVYYCARAEMGAVFDIWGQ GTMVTVSS | Variable heavy (VH) Anti-BCMA |
| 78 | EIVLTQSPATLSLSPGERATLSCRASQSVSRYLAWYQQKPGQAPRLLIYDASNRA TGIPARFSGSGSGTDFTLTISSLEPEDFAVYYCQQRISWPFTFGGGTKVEIK | Variable light (VL) Anti-BCMA |
| 79 | QVQLVESGGGVVQPGRSLRLSCAASGFTFSSYGMHWVRQAPGKGLEWVAVISYDG SNKYYADSVKGRFTISRDNSKNTLYLQMNSLRAEDTAVYYCARDGTYLGGLWYFD LWGRGTLVTVSS | Variable heavy (VH) Anti-BCMA |
| 80 | DIVMTQSPLSLPVTPGEPASISCRSSQSLLHSNGYNYLDWYLQKPGQSPQLLIYL GSNRASGVPDRFSGSGSGTDFTLKISRVEAEDVGVYYCMQGLGLPLTFGGGTKVE IK | Variable light (VL) Anti-BCMA |
| 81 | QVQLVQSGAEVKKPGASVKVSCKASGYTFTSYYMHWVRQAPGQGLEWMGIINPGG GSTSYAQKFQGRVTMTRDTSTSTVYMELSSLRSEDTAVYYCARESWPMDVWGQGT TVTVSS | Variable heavy (VH) Anti-BCMA |
| 82 | EIVMTQSPATLSVSPGERATLSCRASQSVSSNLAWYQQKPGQAPRLLIYGASTRA TGIPARFSGSGSGTEFTLTISSLQSEDFAVYYCQQYAAYPTFGGGTKVEIK | Variable light (VL) Anti-BCMA |

| SEQ ID NO. | SEQUENCE | DESCRIPTION |
|---|---|---|
| 83 | QLQLQESGPGLVKPSETLSLTCTVSGGSISSSSYYWGWIRQPPGKGLEWIGSISY SGSTYYNPSLKSRVTISVDTSKNQFSLKLSSVTAADTAVYYCARGRGYATSLAFD IWGQGTMVTVSS | Variable heavy (VH) Anti-BCMA |
| 84 | EIVLTQSPATLSLSPGERATLSCRASQSVSSYLAWYQQKPGQAPRLLIYDASNRA TGIPARFSGSGSGTDFTLTISSLEPEDFAVYYCQQRHVWPPTFGGGTKVEIK | Variable light (CL) Anti-BCMA |
| 85 | EVQLVESGGGLVQPGGSLRLSCAASGFTFSSYSMNWVRQAPGKGLEWVSTISSSS STIYYADSVKGRFTISRDNAKNSLYLQMNSLRAEDTAVYYCARGSQEHLIFDYWG QGTLVTVSS | Variable heavy (VH) Anti-BCMA |
| 86 | EIVLTQSPATLSLSPGERATLSCRASQSVSRYLAWYQQKPGQAPRLLIYDASNRA TGIPARFSGSGSGTDFTLTISSLEPEDFAVYYCQQRFYYPWTFGGGTKVEIK | Variable light (VL) Anti-BCMA |
| 87 | QVQLVESGGGVVQPGRSLRLSCAASGFTFSSYGMHWVRQAPGKGLEWVAVISYDG SNKYYADSVKGRFTISRDNSKNTLYLQMNSLRAEDTAVYYCARTDFWSGSPPGLD YWGQGTLVTVSS | Variable heavy (VH) Anti-BCMA |
| 88 | DIQLTQSPSSVSASVGDRVTITCRASQGISSWLAWYQQKPGKAPKLLIYGASSLQ SGVPSRFSGSGSGTDFTLTISSLQPEDFATYYCQQIYTFPFTFGGGTKVEIK | Variable light (VL) Anti-BCMA |
| 89 | QVQLVQSGAEVKKPGSSVKVSCKASGGTFSSYAISWVRQAPGQGLEWMGGIIPIF GTANYAQKFQGRVTITADESTSTAYMELSSLRSEDTAVYYCARTPEYSSSIWHYY YGMDVWGQGTTVTVSS | Variable heavy (VH) Anti-BCMA |
| 90 | DIVMTQSPDSLAVSLGERATINCKSSQSVLYSSNNKNYLAWYQQKPGQPPKLLIY WASTRESGVPDRFSGSGSGTDFTLTISSLQAEDVAVYYCQQFAHTPFTFGGGTKV EIK | Variable light (VL) Anti-BCMA |
| 91 | QVQLVESGGGVVQPGRSLRLSCAASGFTFSSYGMHWVRQAPGKGLEWVAVISYDG SNKYYADSVKGRFTISRDNSKNTLYLQMNSLRAEDTAVYYCVKGPLQEPPYDYGM DVWGQGTTVTVSS | Variable heavy (VH) Anti-BCMA |
| 92 | EIVMTQSPATLSVSPGERATLSCRASQSVSSNLAWYQQKPGQAPRLLIYSASTRA TGIPARFSGSGSGTEFTLTISSLQSEDFAVYYCQQHHVWPLTFGGGTKVEIK | Variable light (VL) Anti-BCMA |
| 93 | QVQLVQSGAEVKKPGSSVKVSCKASGGTFSSYAISWVRQAPGQGLEWMGRIIPIL GIANYAQKFQGRVTITADKSTSTAYMELSSLRSEDTAVYYCARGGYYSHDMWSED WGQGTLVTVSS | Variable heavy (VH) Anti-BCMA |
| 94 | LPVLTQPPSASGTPGQRVTISCSGRSSNIGSNSVNWYRQLPGAAPKLLIYSNNQR PPGVPVRFSGSKSGTSASLAISGLQSEDEATYYCATWDDNLNVHYVFGTGTKVTV LG | Variable light (VL) Anti-BCMA |
| 95 | QVQLVQSGSELKKPGASVKVSCKASGYTFTDYSINWVRQAPGQGLEWMGWINTET REPAYAYDFRGRFVFSLDTSVSTAYLQISSLKAEDTAVYYCARDYSYAMDYWGQG TLVTVSS | Variable heavy (VH) Anti-BCMA |
| 96 | DIVLTQSPASLAVSLGERATINCRASESVSVIGAHLIHWYQQKPGQPPKLLIYLA SNLETGVPARFSGSGSGTDFTLTISSLQAEDAAIYYCLQSRIFPRTFGQGTKLEI K | Variable light (VL) Anti-BCMA |
| 97 | EVQLVESGGGLVQPGGSLRLSCAVSGFALSNHGMSWVRRAPGKGLEWVSGIVYSG STYYAASVKGRFTISRDNSRNTLYLQMNSLRPEDTAIYYCSAHGGESDVWGQGTT VTVSS | Variable heavy (VH) Anti-BCMA |
| 98 | DIQLTQSPSSLSASVGDRVTITCRASQSISSYLNWYQQKPGKAPKLLIYAASSLQ SGVPSRFSGSGSGTDFTLTISSLQPEDFATYYCQQSYSTPYTFGQGTKVEIK | Variable light (VL) Anti-BCMA |
| 99 | QVQLVESGGGLVQPGRSLRLSCAASGFTFSNYAMSWVRQAPGKGLGWVSGISRSG ENTYYADSVKGRFTISRDNSKNTLYLQMNSLRDEDTAVYYCARSPAHYYGGMDVW GQGTTVTVSS | Variable heavy (VH) Anti-BCMA |
| 100 | DIVLTQSPGTLSLSPGERATLSCRASQSISSSFLAWYQQKPGQAPRLLIYGASRR ATGIPDRFSGSGSGTDFTLTISRLEPEDSAVYYCQQYHSSPSWTFGQGTKLEIK | Variable light (VL) Anti-BCMA |
| 101 | QVQLVESGGGLVQPGGSLRLSCAVSGFALSNHGMSWVRRAPGKGLEWVSGIVYSG STYYAASVKGRFTISRDNSRNTLYLQMNSLRPEDTAIYYCSAHGGESDVWGQGTT VTVSS | Variable heavy (VH) Anti-BCMA |
| 102 | DIRLTQSPSPLSASVGDRVTITCQASEDINKFLNWYHQTPGKAPKLLIYDASTLQ TGVPSRFSGSGSGTDFTLTINSLQPEDIGTYYCQQYESLPLTFGGGTKVEIK | Variable light (VL) Anti-BCMA |

| SEQ ID NO. | SEQUENCE | DESCRIPTION |
|---|---|---|
| 103 | EVQLVESGGGLVQPGGSLRLSCAVSGFALSNHGMSWVRRAPGKGLEWVSGIVYSGSTYYAASVKGRFTISRDNSRNTLYLQMNSLRPEDTAIYYCSAHGGESDVWGQGTTVTVSS | Variable heavy (VH) Anti-BCMA |
| 104 | EIVLTQSPGTLSLSPGERATLSCRASQSIGSSSLAWYQQKPGQAPRLLMYGASSRASGIPDRFSGSGSGTDFTLTISRLEPEDFAVYYCQQYAGSPPFTFGQGTKVEIK | Variable light (VL) Anti-BCMA |
| 105 | QIQLVQSGPELKKPGETVKISCKASGYTFRHYSMNWVKQAPGKGLKWMGRINTESGVPIYADDFKGRFAFSVETSASTAYLVINNLKDEDTASYFCSNDYLYSLDFWGQGTALTVSS | Variable heavy (VH) Anti-BCMA |
| 106 | DIVLTQSPPSLAMSLGKRATISCRASESVTILGSHLIYWYQQKPGQPPTLLTQLASNVQTGVPARFSGSGSRTDFTLTIDPVEEDDVAVYYCLQSRTIPRTFGGGTKLEIK | Variable light (VL) Anti-BCMA |
| 107 | QIQLVQSGPELKKPGETVKISCKASGYTFTHYSMNWVKQAPGKGLKWMGRINTETGEPLYADDFKGRFAFSLETSASTAYLVINNLKNEDTATFFCSNDYLYSCDYWGQGTTLTVSS | Variable heavy (VH) Anti-BCMA |
| 108 | DIVLTQSPASLAMSLGKRATISCRASESVSVIGAHLIHWYQQKPGQPPKLLIYLASNLETGVPARFSGSGSGTDFTLTIDPVEEDDVAIYSCLQSRIFPRTFGGGTKLEIK | Variable light (VL) Anti-BCMA |
| 109 | QVQLVQSGAEVKKPGASVKVSCKASGYSFPDYYINWVRQAPGQGLEWMGWIYFASGNSEYNQKFTGRVTMTRDTSINTAYMELSSLTSEDTAVYFCASLYDYDWYFDVWGQGTMVTVSS | Variable heavy (VH) Anti-BCMA |
| 110 | DIVMTQTPLSLSVTPGQPASISCKSSQSLVHSNGNTYLHWYLQKPGQSPQLLIYKVSNRFSGVPDRFSGSGSGTDFTLKISRVEAEDVGIYYCSQSSIYPWTFGQGTKLEIK | Variable light (VL) Anti-BCMA |
| 111 | QVQLVNQSGAEVKKPGASVKVSCKASGYSFPDYYINWVRQAPGQGLEWMGWYFASGNSEYNQKFTGRVTMTRDTSSSTAYMELSSLRSEDTAVYFCASLYDYDWYFDVWGQGTMVTVSS | Variable heavy (VH) Anti-BCMA |
| 112 | DIVMTQTPLSLSVTPGEPASISCKSSQSLVHSNGNTYLHWYLQKPGQSPQLLIYKVSNRFSGVPDRFSGSGSGADFTLKISRVEAEDVGVYYCAETSHVPWTFGQGTKLEIK | Variable light (VL) Anti-BCMA |
| 113 | QVQLVESGGGLVQPGGSLRLSCEASGFTLDYYAIGWFRQAPGKEREGVICISRSDGSTYYADSVKGRFTISRDNAKKTVYLQMISLKPEDTAAYYCAAGADCSGYLRDYEFRGQGTQVTVSS | Anti-BCMA sdAb |
| 114 | IEVMYPPPYLDNEKSNGTIIHVKGKHLCPSPLFPGPSKP | CD28 spacer |
| 115 | IYIWAPLAGTCGVLLLSLVITLYCN | CD8a TM |
| 116 | LDNEKSNGTIIHVKGKHLCPSPLFPGPSKP | CD28 spacer (truncated) |
| 117 | PTTTPAPRPPTPAPTIASQPLSLRPEACRPAAGGAVHTRGLDFACD | CD8a hinge |
| 118 | TTTPAPRPPTPAPTIASQPLSLRPEACRPAAGGAVHTRGLDFACD | CD8a hinge |
| 119 | FVPVFLPAKPTTTPAPRPPTPAPTIASQPLSLRPEACRPAAGGAVHTRGLDFACD | CD8a hinge |
| 120 | DTGLYICKVELMYPPPYYLGIGNGTQIYVIDPEPCPDSD | CTLA4 hinge |
| 121 | FLLWILAAVSSGLFFYSFLLTAVS | CTLA4 TM |
| 122 | QIKESLRAELRVTERRAEVPTAHPSPSPRPAGQFQTLV | PD-1 hinge |
| 123 | VGVVGGLLGSLVLLVWVLAVI | PD-1 TM |
| 124 | GLAVSTISSFFPPGYQ | FcγRIIIa hinge |
| 125 | EPKSPDKTHTCPPCPAPPVAGPSVFLFPPKPKDTLMIARTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | IgG1 hinge |

| SEQ ID NO. | SEQUENCE | DESCRIPTION |
|---|---|---|
| 126 | EVQLLESGGGLVQPGGSLRLSCAASGFTFSSYAMSWVRQAPGKGLEWVSAISGSG<br>GSTYYADSVKGRFTISRDNSKNTLYLQMNSLRAEDTAVYYCARAEMGAVFDIWGQ<br>GTMVTVSSGSTSGSGKPGSGEGSTKGEIVLTQSPATLSLSPGERATLSCRASQSV<br>SRYLAWYQQKPGQAPRLLIYDASNRATGIPARFSGSGSGTDFTLTISSLEPEDFA<br>VYYCQQRISWPFTFGGGTKVEIKRAAALDNEKSNGTIIHVKGKHLCPSPLFPGPS<br>KPFWVLVVVGGVLACYSLLVTVAFIIFWVRSKRSRLLHSDYMNMTPRRPGPTRKH<br>YQPYAPPRDFAAYRSRVKFSRSADAPAYQQGQNQLYNELNLGRREEYDVLDKRRG<br>RDPEMGGKPRRKNPQEGLYNELQKDKMAEAYSEIGMKGERRRGKGHDGLYQGLST<br>ATKDTYDALHMQALPPR | anti-BCMA CAR |
| 127 | EIVLTQSPATLSLSPGERATLSCRASQSVSRYLAWYQQKPGQAPRLLIYDASNRA<br>TGIPARFSGSGSGTDFTLTISSLEPEDFAVYYCQQRISWPFTFGGGTKVEIKRGS<br>TSGSGKPGSGEGSTKGEVQLLESGGGLVQPGGSLRLSCAASGFTFSSYAMSWVRQ<br>APGKGLEWVSAISGSGGSTYYADSVKGRFTISRDNSKNTLYLQMNSLRAEDTAVY<br>YCARAEMGAVFDIWGQGTMVTVSSAAALDNEKSNGTIIHVKGKHLCPSPLFPGPS<br>KPFWVLVVVGGVLACYSLLVTVAFIIFWVRSKRSRLLHSDYMNMTPRRPGPTRKH<br>YQPYAPPRDFAAYRSRVKFSRSADAPAYQQGQNQLYNELNLGRREEYDVLDKRRG<br>RDPEMGGKPRRKNPQEGLYNELQKDKMAEAYSEIGMKGERRRGKGHDGLYQGLST<br>ATKDTYDALHMQALPPR | anti-BCMA CAR |
| 128 | QVQLVESGGGVVQPGRSLRLSCAASGFTFSSYGMHWVRQAPGKGLEWVAVISYDG<br>SNKYYADSVKGRFTISRDNSKNTLYLQMNSLRAEDTAVYYCARDGTYLGGLWYFD<br>LWGRGTLVTVSSGSTSGSGKPGSGEGSTKGDIVMTQSPLSLPVTPGEPASISCRS<br>SQSLLHSNGYNYLDWYLQKPGQSPQLLIYLGSNRASGVPDRFSGSGSGTDFTLKI<br>SRVEAEDVGVYYCMQGLGLPLTFGGGTKVEIKRAAALDNEKSNGTIIHVKGKHLC<br>PSPLFPGPSKPFWVLVVVGGVLACYSLLVTVAFIIFWVRSKRSRLLHSDYMNMTP<br>RRPGPTRKHYQPYAPPRDFAAYRSRVKFSRSADAPAYQQGQNQLYNELNLGRREE<br>YDVLDKRRGRDPEMGGKPRRKNPQEGLYNELQKDKMAEAYSEIGMKGERRRGKGH<br>DGLYQGLSTATKDTYDALHMQALPPR | anti-BCMA CAR |
| 129 | DIVMTQSPLSLPVTPGEPASISCRSSQSLLHSNGYNYLDWYLQKPGQSPQLLIYL<br>GSNRASGVPDRFSGSGSGTDFTLKISRVEAEDVGVYYCMQGLGLPLTFGGGTKVE<br>IKRGSTSGSGKPGSGEGSTKGQVQLVESGGGVVQPGRSLRLSCAASGFTFSSYGM<br>HWVRQAPGKGLEWVAVISYDGSNKYYADSVKGRFTISRDNSKNTLYLQMNSLRAE<br>DTAVYYCARDGTYLGGLWYFDLWGRGTLVTVSSAAALDNEKSNGTIIHVKGKHLC<br>PSPLFPGPSKPFWVLVVVGGVLACYSLLVTVAFIIFWVRSKRSRLLHSDYMNMTP<br>RRPGPTRKHYQPYAPPRDFAAYRSRVKFSRSADAPAYQQGQNQLYNELNLGRREE<br>YDVLDKRRGRDPEMGGKPRRKNPQEGLYNELQKDKMAEAYSEIGMKGERRRGKGH<br>DGLYQGLSTATKDTYDALHMQALPPR | anti-BCMA CAR |
| 130 | QVQLVQSGAEVKKPGASVKVSCKASGYTFTSYYMHWVRQAPGQGLEWMGIINPGG<br>GSTSYAQKFQGRVTMTRDTSTSTVYMELSSLRSEDTAVYYCARESWPMDVWGQGT<br>TVTVSSGSTSGSGKPGSGEGSTKGEIVMTQSPATLSVSPGERATLSCRASQSVSS<br>NLAWYQQKPGQAPRLLIYGASTRATGIPARFSGSGSGTEFTLTISSLQSEDFAVY<br>YCQQYAAYPTFGGGTKVEIKRAAALDNEKSNGTIIHVKGKHLCPSPLFPGPSKPF<br>WVLVVVGGVLACYSLLVTVAFIIFWVRSKRSRLLHSDYMNMTPRRPGPTRKHYQP<br>YAPPRDFAAYRSRVKFSRSADAPAYQQGQNQLYNELNLGRREEYDVLDKRRGRDP<br>EMGGKPRRKNPQEGLYNELQKDKMAEAYSEIGMKGERRRGKGHDGLYQGLSTATK<br>DTYDALHMQALPPR | anti-BCMA CAR |
| 131 | EIVMTQSPATLSVSPGERATLSCRASQSVSSNLAWYQQKPGQAPRLLIYGASTRA<br>TGIPARFSGSGSGTEFTLTISSLQSEDFAVYYCQQYAAYPTFGGGTKVEIKRGST<br>SGSGKPGSGEGSTKGQVQLVQSGAEVKKPGASVKVSCKASGYTFTSYYMHWVRQA<br>PGQGLEWMGIINPGGGSTSYAQKFQGRVTMTRDTSTSTVYMELSSLRSEDTAVYY<br>CARESWPMDVWGQGTTVTVSSAAALDNEKSNGTIIHVKGKHLCPSPLFPGPSKPF<br>WVLVVVGGVLACYSLLVTVAFIIFWVRSKRSRLLHSDYMNMTPRRPGPTRKHYQP<br>YAPPRDFAAYRSRVKFSRSADAPAYQQGQNQLYNELNLGRREEYDVLDKRRGRDP<br>EMGGKPRRKNPQEGLYNELQKDKMAEAYSEIGMKGERRRGKGHDGLYQGLSTATK<br>DTYDALHMQALPPR | anti-BCMA CAR |
| 132 | QLQLQESGPGLVKPSETLSLTCTVSGGSISSSSYYWGWIRQPPGKGLEWIGSISY<br>SGSTYYNPSLKSRVTISVDTSKNQFSLKLSSVTAADTAVYYCARGRGYATSLAFD<br>IWGQGTMVTVSSGSTSGSGKPGSGEGSTKGEIVLTQSPATLSLSPGERATLSCRA<br>SQSVSSYLAWYQQKPGQAPRLLIYDASNRATGIPARFSGSGSGTDFTLTISSLEP<br>EDFAVYYCQQRHVWPPTFGGGTKVEIKRAAALDNEKSNGTIIHVKGKHLCPSPLF<br>PGPSKPFWVLVVVGGVLACYSLLVTVAFIIFWVRSKRSRLLHSDYMNMTPRRPGP<br>TRKHYQPYAPPRDFAAYRSRVKFSRSADAPAYQQGQNQLYNELNLGRREEYDVLD<br>KRRGRDPEMGGKPRRKNPQEGLYNELQKDKMAEAYSEIGMKGERRRGKGHDGLYQ<br>GLSTATKDTYDALHMQALPPR | anti-BCMA CAR |
| 133 | EIVLTQSPATLSLSPGERATLSCRASQSVSSYLAWYQQKPGQAPRLLIYDASNRA<br>TGIPARFSGSGSGTDFTLTISSLEPEDFAVYYCQQRHVWPPTFGGGTKVEIKRGS<br>TSGSGKPGSGEGSTKGQLQLQESGPGLVKPSETLSLTCTVSGGSISSSSYYWGWI | anti-BCMA CAR |

| SEQ ID NO. | SEQUENCE | DESCRIPTION |
|---|---|---|
| | RQPPGKGLEWIGSISYSGSTYYNPSLKSRVTISVDTSKNQFSLKLSSVTAADTAV YYCARGRGYATSLAFDIWGQGTMVTVSSAAALDNEKSNGTIIHVKGKHLCPSPLF PGPSKPFWVLVVVGGVLACYSLLVTVAFIIFWVRSKRSRLLHSDYMNMTPRRPGP TRKHYQPYAPPRDFAAYRSRVKFSRSADAPAYQQGQNQLYNELNLGRREEYDVLD KRRGRDPEMGGKPRRKNPQEGLYNELQKDKMAEAYSEIGMKGERRRGKGHDGLYQ GLSTATKDTYDALHMQALPPR | |
| 134 | EVQLVESGGGLVQPGGSLRLSCAASGFTFSSYSMNWVRQAPGKGLEWVSTISSSS STIYYADSVKGRFTISRDNAKNSLYLQMNSLRAEDTAVYYCARGSQEHLIFDYWG QGTLVTVSSGSTSGSGKPGSGEGSTKGEIVLTQSPATLSLSPGERATLSCRASQS VSRYLAWYQQKPGQAPRLLIYDASNRATGIPARFSGSGSGTDFTLTISSLEPEDF AVYYCQQRFYYPWTFGGGTKVEIKRAAALDNEKSNGTIIHVKGKHLCPSPLFPGP SKPFWVLVVVGGVLACYSLLVTVAFIIFWVRSKRSRLLHSDYMNMTPRRPGPTRK HYQPYAPPRDFAAYRSRVKFSRSADAPAYQQGQNQLYNELNLGRREEYDVLDKRR GRDPEMGGKPRRKNPQEGLYNELQKDKMAEAYSEIGMKGERRRGKGHDGLYQGLS TATKDTYDALHMQALPPR | anti-BCMA CAR |
| 135 | EIVLTQSPATLSLSPGERATLSCRASQSVSRYLAWYQQKPGQAPRLLIYDASNRA TGIPARFSGSGSGTDFTLTISSLEPEDFAVYYCQQRFYYPWTFGGGTKVEIKRGS TSGSGKPGSGEGSTKGEVQLVESGGGLVQPGGSLRLSCAASGFTFSSYSMNWVRQ APGKGLEWVSTISSSSSTIYYADSVKGRFTISRDNAKNSLYLQMNSLRAEDTAVY YCARGSQEHLIFDYWGQGTLVTVSSAAALDNEKSNGTIIHVKGKHLCPSPLFPGP SKPFWVLVVVGGVLACYSLLVTVAFIIFWVRSKRSRLLHSDYMNMTPRRPGPTRK HYQPYAPPRDFAAYRSRVKFSRSADAPAYQQGQNQLYNELNLGRREEYDVLDKRR GRDPEMGGKPRRKNPQEGLYNELQKDKMAEAYSEIGMKGERRRGKGHDGLYQGLS TATKDTYDALHMQALPPR | anti-BCMA CAR |
| 136 | QVQLVESGGGVVQPGRSLRLSCAASGFTFSSYGMHWVRQAPGKGLEWVAVISYDG SNKYYADSVKGRFTISRDNSKNTLYLQMNSLRAEDTAVYYCARTDFWSGSPPGLD YWGQGTLVTVSSGSTSGSGKPGSGEGSTKGDIQLTQSPSSVSASVGDRVTITCRA SQGISSWLAWYQQKPGKAPKLLIYGASSLQSGVPSRFSGSGSGTDFTLTISSLQP EDFATYYCQQIYTFPFTFGGGTKVEIKRAAALDNEKSNGTIIHVKGKHLCPSPLF PGPSKPFWVLVVVGGVLACYSLLVTVAFIIFWVRSKRSRLLHSDYMNMTPRRPGP TRKHYQPYAPPRDFAAYRSRVKFSRSADAPAYQQGQNQLYNELNLGRREEYDVLD KRRGRDPEMGGKPRRKNPQEGLYNELQKDKMAEAYSEIGMKGERRRGKGHDGLYQ GLSTATKDTYDALHMQALPPR | anti-BCMA CAR |
| 137 | DIQLTQSPSSVSASVGDRVTITCRASQGISSWLAWYQQKPGKAPKLLIYGASSLQ SGVPSRFSGSGSGTDFTLTISSLQPEDFATYYCQQIYTFPFTFGGGTKVEIKRGS TSGSGKPGSGEGSTKGQVQLVESGGGVVQPGRSLRLSCAASGFTFSSYGMHWVRQ APGKGLEWVAVISYDGSNKYYADSVKGRFTISRDNSKNTLYLQMNSLRAEDTAVY YCARTDFWSGSPPGLDYWGQGTLVTVSSAAALDNEKSNGTIIHVKGKHLCPSPLF PGPSKPFWVLVVVGGVLACYSLLVTVAFIIFWVRSKRSRLLHSDYMNMTPRRPGP TRKHYQPYAPPRDFAAYRSRVKFSRSADAPAYQQGQNQLYNELNLGRREEYDVLD KRRGRDPEMGGKPRRKNPQEGLYNELQKDKMAEAYSEIGMKGERRRGKGHDGLYQ GLSTATKDTYDALHMQALPPR | anti-BCMA CAR |
| 138 | QVQLVQSGAEVKKPGSSVKVSCKASGGTFSSYAISWVRQAPGQGLEWMGGIIPIF GTANYAQKFQGRVTITADESTSTAYMELSSLRSEDTAVYYCARTPEYSSSIWHYY YGMDVWGQGTTVTVSSGSTSGSGKPGSGEGSTKGDIVMTQSPDSLAVSLGERATI NCKSSQSVLYSSNNKNYLAWYQQKPGQPPKLLIYWASTRESGVPDRFSGSGSGTD FTLTISSLQAEDVAVYYCQQFAHTPFTFGGGTKVEIKRAAALDNEKSNGTIIHVK GKHLCPSPLFPGPSKPFWVLVVVGGVLACYSLLVTVAFIIFWVRSKRSRLLHSDY MNMTPRRPGPTRKHYQPYAPPRDFAAYRSRVKFSRSADAPAYQQGQNQLYNELNL GRREEYDVLDKRRGRDPEMGGKPRRKNPQEGLYNELQKDKMAEAYSEIGMKGERR RGKGHDGLYQGLSTATKDTYDALHMQALPPR | anti-BCMA CAR |
| 139 | DIVMTQSPDSLAVSLGERATINCKSSQSVLYSSNNKNYLAWYQQKPGQPPKLLIY WASTRESGVPDRFSGSGSGTDFTLTISSLQAEDVAVYYCQQFAHTPFTFGGGTKV EIKRGSTSGSGKPGSGEGSTKGQVQLVQSGAEVKKPGSSVKVSCKASGGTFSSYA ISWVRQAPGQGLEWMGGIIPIFGTANYAQKFQGRVTITADESTSTAYMELSSLRS EDTAVYYCARTPEYSSSIWHYYYGMDVWGQGTTVTVSSAAALDNEKSNGTIIHVK GKHLCPSPLFPGPSKPFWVLVVVGGVLACYSLLVTVAFIIFWVRSKRSRLLHSDY MNMTPRRPGPTRKHYQPYAPPRDFAAYRSRVKFSRSADAPAYQQGQNQLYNELNL GRREEYDVLDKRRGRDPEMGGKPRRKNPQEGLYNELQKDKMAEAYSEIGMKGERR RGKGHDGLYQGLSTATKDTYDALHMQALPPR | anti-BCMA CAR |
| 140 | QVQLVESGGGVVQPGRSLRLSCAASGFTFSSYGMHWVRQAPGKGLEWVAVISYDG SNKYYADSVKGRFTISRDNSKNTLYLQMNSLRAEDTAVYYCVKGPLQEPPYDYGM DVWGQGTTVTVSSGSTSGSGKPGSGEGSTKGEIVMTQSPATLSVSPGERATLSCR ASQSVSSNLAWYQQKPGQAPRLLIYSASTRATGIPARFSGSGSGTEFTLTISSLQ SEDFAVYYCQQHHVWPLTFGGGTKVEIKRAAALDNEKSNGTIIHVKGKHLCPSPL FPGPSKPFWVLVVVGGVLACYSLLVTVAFIIFWVRSKRSRLLHSDYMNMTPRRPG | anti-BCMA CAR |

| SEQ ID NO. | SEQUENCE | DESCRIPTION |
|---|---|---|
| | PTRKHYQPYAPPRDFAAYRSRVKFSRSADAPAYQQGQNQLYNELNLGRREEYDVL DKRRGRDPEMGGKPRRKNPQEGLYNELQKDKMAEAYSEIGMKGERRRGKGHDGLY QGLSTATKDTYDALHMQALPPR | |
| 141 | EIVMTQSPATLSVSPGERATLSCRASQSVSSNLAWYQQKPGQAPRLLIYSASTRA TGIPARFSGSGSGTEFTLTISSLQSEDFAVYYCQQHHVWPLTFGGGTKVEIKRGS TSGSGKPGSGEGSTKGQVQLVESGGGVVQPGRSLRLSCAASGFTFSSYGMHWVRQ APGKGLEWVAVISYDGSNKYYADSVKGRFTISRDNSKNTLYLQMNSLRAEDTAVY YCVKGPLQEPPYDYGMDVWGQGTTVTVSSAAALDNEKSNGTIIHVKGKHLCPSPL FPGPSKPFWVLVVVGGVLACYSLLVTVAFIIFWVRSKRSRLLHSDYMNMTPRRPG PTRKHYQPYAPPRDFAAYRSRVKFSRSADAPAYQQGQNQLYNELNLGRREEYDVL DKRRGRDPEMGGKPRRKNPQEGLYNELQKDKMAEAYSEIGMKGERRRGKGHDGLY QGLSTATKDTYDALHMQALPPR | anti-BCMA CAR |
| 142 | QSALTQPASVSASPGQSIAISCTGTSSDVGWYQQHPGKAPKLMIyEDSKRPSGVS NRFSGSKSGNTASLTISGLQAEDEADYYCSSNTRSSTLVFGGGTKLTVLGSRGGG GSGGGGSGGGGSLEMAEVQLVQSGAEMKKPGASLKLSCKASGYTFIDYYVYWMRQ APGQGLESMGWINPNSGGTNYAQKFQGRVTMTRDTSISTAYMELSRLRSDDTAMY YCARSQRDGYMDYWGQGTLVTVSSAAAIEVMYPPPYLDNEKSNGTIIHVKGKHLC PSPLFPGPSKPFWVLVVVGGVLACYSLLVTVAFIIFWVRSKRSRLLHSDYMNMTP RRPGPTRKHYQPYAPPRDFAAYRSRVKFSRSADAPAYQQGQNQLYNELNLGRREE YDVLDKRRGRDPEMGGKPRRKNPQEGLYNELQKDKMAEAYSEIGMKGERRRGKGH DGLYQGLSTATKDTYDALHMQALPPR | anti-BCMA CAR |
| 143 | QSVLTQPPSVSGAPGQRVTISCTGSSSNIGAGFDVHWYQQLPGTAPKLLIYGNSN RPSGVPDRFSGSKSGTSASLAITGLQAEDEADYYCQSYDSSLSGYVFGTGTKVTV LGSRGGGGSGGGGSGGGGSLEMAQVQLVQSGAEVKKPGASVKVSCKASGYTFTDY YMHWVRQAPGQRLEWMGWINPNSGGTNYAQKFQDRITVTRDTSSNTGYMELTRLR SDDTAVYYCARSPYSGVLDKWGQGTLVTVSSAAAIEVMYPPPYLDNEKSNGTIIH VKGKHLCPSPLFPGPSKPFWVLVVVGGVLACYSLLVTVAFIIFWVRSKRSRLLHS DYMNMTPRRPGPTRKHYQPYAPPRDFAAYRSRVKFSRSADAPAYQQGQNQLYNEL NLGRREEYDVLDKRRGRDPEMGGKPRRKNPQEGLYNELQKDKMAEAYSEIGMKGE RRRGKGHDGLYQGLSTATKDTYDALHMQALPPR | anti-BCMA CAR |
| 144 | SYELTQPPSASGTPGQRVTMSCSGTSSNIGSHSVNWYQQLPGTAPKLLIYTNNQR PSGVPDRFSGSKSGTSASLAISGLQSEDEADYYCAAWDGSLNGLVFGGGTKLTVL GSRGGGGSGGGGSGGGGSLEMAEVQLVQSGAEVKKPGESLKISCKGSGYSFTSYW IGWVRQMPGKGLEWMGIIYPGDSDTRYSPSFQGHVTISADKSISTAYLQWSSLKA SDTAMYYCARYSGSFDNWGQGTLVTVSSAAAIEVMYPPPYLDNEKSNGTIIHVKG KHLCPSPLFPGPSKPFWVLVVVGGVLACYSLLVTVAFIIFWVRSKRSRLLHSDYM NMTPRRPGPTRKHYQPYAPPRDFAAYRSRVKFSRSADAPAYQQGQNQLYNELNLG RREEYDVLDKRRGRDPEMGGKPRRKNPQEGLYNELQKDKMAEAYSEIGMKGERRR GKGHDGLYQGLSTATKDTYDALHMQALPPR | anti-BCMA CAR |
| 145 | LPVLTQPPSASGTPGQRVTISCSGRSSNIGSNSVNWYRQLPGAAPKLLIYSNNQR PPGVPVRFSGSKSGTSASLAISGLQSEDEATYYCATWDDNLNVHYVFGTGTKVTV LGSRGGGGSGGGGSGGGGSLEMAQVQLVQSGAEVKKPGSSVKVSCKASGGTFSSY AISWVRQAPGQGLEWMGRIIPILGIANYAQKFQGRVTITADKSTSTAYMELSSLR SEDTAVYYCARGGYYSHDMWSEDWGQGTLVTVSSAAAIEVMYPPPYLDNEKSNGT IIHVKGKHLCPSPLFPGPSKPFWVLVVVGGVLACYSLLVTVAFIIFWVRSKRSRL LHSDYMNMTPRRPGPTRKHYQPYAPPRDFAAYRSRVKFSRSADAPAYQQGQNQLY NELNLGRREEYDVLDKRRGRDPEMGGKPRRKNPQEGLYNELQKDKMAEAYSEIGM KGERRRGKGHDGLYQGLSTATKDTYDALHMQALPPR | anti-BCMA CAR |
| 146 | QAVLTQPPSASGTPGQRVTISCSGSSSNIGSNYVFWYQQLPGTAPKLLIYSNNQR PSGVPDRFSGSKSGTSASLAISGLRSEDEADYYCAAWDDSLSASYVFGTGTKVTV LGSRGGGGSGGGGSGGGGSLEMAQVQLVQSGAEVKKPGSSVKVSCKASGGTFSSY AISWVRQAPGQGLEWMGRIIPILGTANYAQKFQGRVTITADESTSTAYMELSSLR SEDTAVYYCARSGYGSYRWEDSWGQGTLVTVSSAAAIEVMYPPPYLDNEKSNGTI IHVKGKHLCPSPLFPGPSKPFWVLVVVGGVLACYSLLVTVAFIIFWVRSKRSRLL HSDYMNMTPRRPGPTRKHYQPYAPPRDFAAYRSRVKFSRSADAPAYQQGQNQLYN ELNLGRREEYDVLDKRRGRDPEMGGKPRRKNPQEGLYNELQKDKMAEAYSEIGMK GERRRGKGHDGLYQGLSTATKDTYDALHMQALPPR | anti-BCMA CAR |
| 147 | LPVLTQPPSASGTPGQRVTISCSGRSSNIGSNSVNWYRQLPGAAPKLLIYSNNQR PPGVPVRFSGSKSGTSASLAISGLQSEDEATYYCATWDDNLNVHYVFGTGTKVTV LGSRGGGGSGGGGSGGGGSLEMAQVQLVQSGAEVKKPGSSVKVSCKASGGTFSSY AISWVRQAPGQGLEWMGRIIPILGIANYAQKFQGRVTITADKSTSTAYMELSSLR SEDTAVYYCARGGYYSHDMWSEDWGQGTLVTVSSAAAPTTTPAPRPPTPAPTIAS QPLSLRPEACRPAAGGAVHTRGLDFACDIYIWAPLAGTCGVLLLSLVITLYCNKR GRKKLLYIFKQPFMRPVQTTQEEDGCSCRFPEEEEGGCELRVKFSRSAEPPAYQQ GQNQLYNELNLGRREEYDVLDKRRGRDPEMGGKPRRKNPQEGLYNELQKDKMAEA YSEIGMKGERRRGKGHDGLYQGLSTATKDTYDALHMQALPPR | anti-BCMA CAR |

| SEQ ID NO. | SEQUENCE | DESCRIPTION |
|---|---|---|
| 148 | SYELTQPPSASGTPGQRVTMSCSGTSSNIGSHSVNWYQQLPGTAPKLLIYTNNQR PSGVPDRFSGSKSGTSASLAISGLQSEDEADYYCAAWDGSLNGLVFGGGTKLTVL GSRGGGGSGGGGSGGGGSLEMAEVQLVQSGAEVKKPGESLKISCKGSGYSFTSYW IGWVRQMPGKGLEWMGIIYPGDSDTRYSPSFQGHVTISADKSISTAYLQWSSLKA SDTAMYYCARYSGSFDNWGQGTLVTVSSAAAPTTTPAPRPPTPAPTIASQPLSLR PEACRPAAGGAVHTRGLDFACDIYIWAPLAGTCGVLLLSLVITLYCNKRGRKKLL YIFKQPFMRPVQTTQEEDGCSCRFPEEEEGGCELRVKFSRSAEPPAYQQGQNQLY NELNLGRREEYDVLDKRRGRDPEMGGKPRRKNPQEGLYNELQKDKMAEAYSEIGM KGERRRGKGHDGLYQGLSTATKDTYDALHMQALPPR | anti-BCMA CAR |
| 149 | QAVLTQPPSASGTPGQRVTISCSGSSSNIGSNYVFWYQQLPGTAPKLLIYSNNQR PSGVPDRFSGSKSGTSASLAISGLRSEDEADYYCAAWDDSLSASYVFGTGTKVTV LGSRGGGGSGGGGSGGGGSLEMAQVQLVQSGAEVKKPGSSVKVSCKASGGTFSSY AISWVRQAPGQGLEWMGRIIPILGTANYAQKFQGRVTITADESTSTAYMELSSLR SEDTAVYYCARSGYGSYRWEDSWGQGTLVTVSSAAAPTTTPAPRPPTPAPTIASQ PLSLRPEACRPAAGGAVHTRGLDFACDIYIWAPLAGTCGVLLLSLVITLYCNKRG RKKLLYIFKQPFMRPVQTTQEEDGCSCRFPEEEEGGCELRVKFSRSAEPPAYQQG QNQLYNELNLGRREEYDVLDKRRGRDPEMGGKPRRKNPQEGLYNELQKDKMAEAY SEIGMKGERRRGKGHDGLYQGLSTATKDTYDALHMQALPPR | anti-BCMA CAR |
| 150 | QSVLTQPPSVSGAPGQRVTISCTGSSSNIGAGFDVHWYQQLPGTAPKLLIYGNSN RPSGVPDRFSGSKSGTSASLAITGLQAEDEADYYCQSYDSSLSGYVFGTGTKVTV LGSRGGGGSGGGGSGGGGSLEMAQVQLVQSGAEVKKPGASVKVSCKASGYTFTDY YMHWVRQAPGQRLEWMGWINPNSGGTNYAQKFQDRITVTRDTSSNTGYMELTRLR SDDTAVYYCARSPYSGVLDKWGQGTLVTVSSAAAPTTTPAPRPPTPAPTIASQPL SLRPEACRPAAGGAVHTRGLDFACDIYIWAPLAGTCGVLLLSLVITLYCNKRGRK KLLYIFKQPFMRPVQTTQEEDGCSCRFPEEEEGGCELRVKFSRSAEPPAYQQGQN QLYNELNLGRREEYDVLDKRRGRDPEMGGKPRRKNPQEGLYNELQKDKMAEAYSE IGMKGERRRGKGHDGLYQGLSTATKDTYDALHMQALPPR | anti-BCMA CAR |
| 151 | QSALTQPASVSASPGQSIAISCTGTSSDVGWYQQHPGKAPKLMIYEDSKRPSGVS NRFSGSKSGNTASLTISGLQAEDEADYYCSSNTRSSTLVFGGGTKLTVLGSRGGG GSGGGGSGGGGSLEMAEVQLVQSGAEMKKPGASLKLSCKASGYTFIDYYVYWMRQ APGQGLESMGWINPNSGGTNYAQKFQGRVTMTRDTSISTAYMELSRLRSDDTAMY YCARSQRDGYMDYWGQGTLVTVSSAAAPTTTPAPRPPTPAPTIASQPLSLRPEAC RPAAGGAVHTRGLDFACDIYIWAPLAGTCGVLLLSLVITLYCNKRGRKKLLYIFK QPFMRPVQTTQEEDGCSCRFPEEEEGGCELRVKFSRSAEPPAYQQGQNQLYNELN LGRREEYDVLDKRRGRDPEMGGKPRRKNPQEGLYNELQKDKMAEAYSEIGMKGER RRGKGHDGLYQGLSTATKDTYDALHMQALPPR | anti-BCMA CAR |
| 152 | DIVLTQSPPSLAMSLGKRATISCRASESVTILGSHLIHWYQQKPGQPPTLLIQLA SNVQTGVPARFSGSGSRTDFTLTIDPVEEDDVAVYYCLQSRTIPRTFGGGTKLEI KGSTSGSGKPGSGEGSTKGQIQLVQSGPELKKPGETVKISCKASGYTFTDYSINW VKRAPGKGLKWMGWINTETREPAYAYDFRGRFAFSLETSASTAYLQINNLKYEDT ATYFCALDYSYAMDYWGQGTSVTVSSAAATTTPAPRPPTPAPTIASQPLSLRPEA CRPAAGGAVHTRGLDFACDIYIWAPLAGTCGVLLLSLVITLYCKRGRKKLLYIFK QPFMRPVQTTQEEDGCSCRFPEEEEGGCELRVKFSRSADAPAYQQGQNQLYNELN LGRREEYDVLDKRRGRDPEMGGKPRRKNPQEGLYNELQKDKMAEAYSEIGMKGER RRGKGHDGLYQGLS TATKDTYDALHMQALPPR | anti-BCMA CAR |
| 153 | DIVLTQSPASLAVSLGERATINCRASESVSVIGAHLIHWYQQKPGQPPKLLIYLA SNLETGVPARFSGSGSGTDFTLTISSLQAEDAAIYYCLQSRIFPRTFGQGTKLEI KGSTSGSGKPGSGEGSTKGQVQLVQSGSELKKPGASVKVSCKASGYTFTDYSINW VRQAPGQGLEWMGWINTETREPAYAYDFRGRFVFSLDTSVSTAYLQISSLKAEDT AVYYCARDYSYAMDYWGQGTLVTVSSAAATTTPAPRPPTPAPTIASQPLSLRPEA CRPAAGGAVHTRGLDFACDIYIWAPLAGTCGVLLLSLVITLYCKRGRKKLLYIFK QPFMRPVQTTQEEDGCSCRFPEEEEGGCELRVKFSRSADAPAYQQGQNQLYNELN LGRREEYDVLDKRRGRDPEMGGKPRRKNPQEGLYNELQKDKMAEAYSEIGMKGER RRGKGHDGLYQGLSTATKDTYDALHMQALPPR | anti-BCMA CAR |
| 154 | DIVLTQSPASLAVSLGERATINCRASESVSVIGAHLIHWYQQKPGQPPKLLIYLA SNLETGVPARFSGSGSGTDFTLTISSLQAEDAAIYYCLQSRIFPRTFGQGTKLEI KGSTSGSGKPGSGEGSTKGQVQLVQSGSELKKPGASVKVSCKASGYTFTDYSINW VRQAPGQGLEWMGWINTETREPAYAYDFRGRFVFSLDTSVSTAYLQISSLKAEDT AVYYCARDYSYAMDYWGQGTLVTVSSAAADTGLYICKVELMYPPPYYLGIGNGTQ IYVIDPEPCPDSDFLLWILAAVSSGLFFYSFLLTAVSKRGRKKLLYIFKQPFMRP VQTTQEEDGCSCRFPEEEEGGCELRVKFSRSADAPAYQQGQNQLYNELNLGRREE YDVLDKRRGRDPEMGGKPRRKNPQEGLYNELQKDKMAEAYSEIGMKGERRRGKGH DGLYQGLSTATKDTYDALHMQALPPR | anti-BCMA CAR |
| 155 | DIVLTQSPASLAVSLGERATINCRASESVSVIGAHLIHWYQQKPGQPPKLLIYLA SNLETGVPARFSGSGSGTDFTLTISSLQAEDAAIYYCLQSRIFPRTFGQGTKLEI | anti-BCMA CAR |

| SEQ ID NO. | SEQUENCE | DESCRIPTION |
|---|---|---|
| | KGSTSGSGKPGSGEGSTKGQVQLVQSGSELKKPGASVKVSCKASGYTFTDYSINW VRQAPGQGLEWMGWINTETREPAYAYDFRGRFVFSLDTSVSTAYLQISSLKAEDT AVYYCARDYSYAMDYWGQGTLVTVSSAAAQIKESLRAELRVTERRAEVPTAHPSP SPRPAGQFQTLVVGVVGGLLGSLVLLVWVLAVICSKRGRKKLLYIFKQPFMRPVQ TTQEEDGCSCRFPEEEEGGCELRVKFSRSADAPAYQQGQNQLYNELNLGRREEYD VLDKRRGRDPEMGGKPRRKNPQEGLYNELQKDKMAEAYSEIGMKGERRRGKGHDG LYQGLSTATKDTYDALHMQALPPR | |
| 156 | EVQLVESGGGLVKPGGSLRLSCAASGFTFSDYYMSWIRQAPGKGLEWVSYISSSG STIYYADSVKGRFTISRDNAKNSLYLQMNSLRAEDTAVYYCAKVDGYTEDYWGQ GTLVTVSSGGGGSGGGGSGGGGSQSALTQPASVSGSPGQSITISCTGSSSDVGKY NLVSWYQQPPGKAPKLIIYDVNKRPSGVSNRFSGSKSGNTATLTISGLQGDDEAD YYCSSYGGSRSYVFGTGTKVTVLESKYGPPCPPCPAPPVAGPSVFLFPPKPKDTL MISRTPEVTCVVVDVSQEDPEVQFNWYVDGVEVHNAKTKPREEQFQSTYRVVSVL TVLHQDWLNGKEYKCKVSNKGLPSSIEKTISKAKGQPREPQVYTLPPSQEEMTKN QVSLTCLVKGFYPSDIAVEWESNGQPENNYKTTPPVLDSDGSFFLYSRLTVDKSR WQEGNVFSCSVMHEALHNHYTQKSLSLSLGKMFWVLVVVGGVLACYSLLVTVAFI IFWVKRGRKKLLYIFKQPFMRPVQTTQEEDGCSCRFPEEEEGGCELRVKFSRSAD APAYQQGQNQLYNELNLGRREEYDVLDKRRGRDPEMGGKPRRKNPQEGLYNELQK DKMAEAYSEIGMKGERRRGKGHDGLYQGLSTATKDTYDALHMQALPPR | anti-BCMA CAR |
| 157 | EVQLVQSGGGLVQPGRSLRLSCTASGFTFGDYAMSWFKQAPGKGLEWVGFIRSKA YGGTTEYAASVKGRFTISRDDKSIAYLQMNSLKTEDTAVYYCAAWSAPTDYWGQ GTLVTVSSGGGGSGGGGSGGGGSDIQMTQSPAFLSASVGDRVTVTCRASQGISNY LAWYQQKPGNAPRLLIYSASTLQSGVPSRFRGTGYGTEFSLTIDSLQPEDFATYY CQQSYTSRQTFGPGTRLDIKESKYGPPCPPCPAPPVAGPSVFLFPPKPKDTLMIS RTPEVTCVVVDVSQEDPEVQFNWYVDGVEVHNAKTKPREEQFQSTYRVVSVLTVL HQDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQE GNVFSCSVMHEALHNHYTQKSLSLSLGKMFWVLVVVGGVLACYSLLVTVAFIIFW VKRGRKKLLYIFKQPFMRPVQTTQEEDGCSCRFPEEEEGGCELRVKFSRSADAPA YQQGQNQLYNELNLGRREEYDVLDKRRGRDPEMGGKPRRKNPQEGLYNELQKDKM AEAYSEIGMKGERRRGKGHDGLYQGLSTATKDTYDALHMQALPPR | anti-BCMA CAR |
| 158 | EVQLVESGGGLVKPGGSLRLSCAASGFTFSDYYMSWIRQAPGKGLEWVSYISSSG STIYYADSVKGRFTISRDNAKNSLYLQMNSLRAEDTAVYYCAKVDGPPSFDIWGQ GTMVTVSSGGGGSGGGGSGGGGSSYVLTQPPSVSVAPGQTARITCGANNIGSKSV HWYQQKPGQAPMLVVYDDDDRPSGIPERFSGSNSGNTATLTISGVEAGDEADYFC HLWDRSRDHYVFGTGTKLTVLESKYGPPCPPCPAPPVAGPSVFLFPPKPKDTLMI SRTPEVTCVVVDVSQEDPEVQFNWYVDGVEVHNAKTKPREEQFQSTYRVVSVLTV LHQDWLNGKEYKCKVSNKGLPSSIEKTISKAKGQPREPQVYTLPPSQEEMTKNQV SLTCLVKGFYPSDIAVEWESNGQPENNYKTTPPVLDSDGSFFLYSRLTVDKSRWQ EGNVFSCSVMHEALHNHYTQKSLSLSLGKMFWVLVVVGGVLACYSLLVTVAFIIF WVKRGRKKLLYIFKQPFMRPVQTTQEEDGCSCRFPEEEEGGCELRVKFSRSADAP AYQQGQNQLYNELNLGRREEYDVLDKRRGRDPEMGGKPRRKNPQEGLYNELQKDK MAEAYSEIGMKGERRRGKGHDGLYQGLSTATKDTYDALHMQALPPR | anti-BCMA CAR |
| 159 | SYELTQPPSASGTPGQRVTMSCSGTSSNIGSHSVNWYQQLPGTAPKLLIYTNNQR PSGVPDRFSGSKSGTSASLAISGLQSEDEADYYCAAWDGSLNGLVFGGGTKLTVL GSRGGGGSGGGGSGGGGSLEMAEVQLVQSGAEVKKPGESLKISCKGSGYSFTSYW IGWVRQMPGKGLEWMGIIYPGDSDTRYSPSFQGHVTISADKSISTAYLQWSSLKA SDTAMYYCARYSGSFDNWGQGTLVTVSSESKYGPPCPPCPAPPVAGPSVFLFPPK PKDTLMISRTPEVTCVVVDVSQEDPEVQFNWYVDGVEVHNAKTKPREEQFQSTYR VVSVLTVLHQDWLNGKEYKCKVSNKGLPSSIEKTISKAKGQPREPQVYTLPPSQE EMTKNQVSLTCLVKGFYPSDIAVEWESNGQPENNYKTTPPVLDSDGSFFLYSRLT VDKSRWQEGNVFSCSVMHEALHNHYTQKSLSLSLGKMFWVLVVVGGVLACYSLLV TVAFIIFWVKRGRKKLLYIFKQPFMRPVQTTQEEDGCSCRFPEEEEGGCELRVKF SRSADAPAYQQGQNQLYNELNLGRREEYDVLDKRRGRDPEMGGKPRRKNPQEGLY NELQKDKMAEAYSEIGMKGERRRGKGHDGLYQGLSTATKDTYDALHMQALPPR | anti-BCMA CAR |
| 160 | QSALTQPASVSASPGQSIAISCTGTSSDVGWYQQHPGKAPKLMIYEDSKRPSGVS NRFSGSKSGNTASLTISGLQAEDEADYYCSSNTRSSTLVFGGGTKLTVLGSRGGG GSGGGGSGGGGSLEMAEVQLVQSGAEMKKPGASLKLSCKASGYTFIDYYVYWMRQ APGQGLESMGWINPNSGGTNYAQKFQGRVTMTRDTSISTAYMELSRLRSDDTAMY YCARSQRDGYMDYWGQGTLVTVSSESKYGPPCPPCPAPPVAGPSVFLFPPKPKDT LMISRTPEVTCVVVDVSQEDPEVQFNWYVDGVEVHNAKTKPREEQFQSTYRVVSV LTVLHQDWLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYSRLTVDKS RWQEGNVFSCSVMHEALHNHYTQKSLSLSLGKMFWVLVVVGGVLACYSLLVTVAF IIFWVKRGRKKLLYIFKQPFMRPVQTTQEEDGCSCRFPEEEEGGCELRVKFSRSA DAPAYQQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR | anti-BCMA CAR |

-continued

| SEQ ID NO. | SEQUENCE | DESCRIPTION |
|---|---|---|
| 161 | QSALTQPASVSASPGQSIAISCTGTSSDVGWYQQHPGKAPKLMIYEDSKRPSGVS NRFSGSKSGNTASLTISGLQAEDEADYYCSSNTRSSTLVFGGGTKLTVLGSRGGG GSGGGGSGGGGSLEMAEVQLVQSGAEMKKPGASLKLSCKASGYTFIDYYVYWMRQ APGQGLESMGWINPNSGGTNYAQKFQGRVTMTRDTSISTAYMELSRLRSDDTAMY YCARSQRDGYMDYWGQGTLVTVSSESKYGPPCPPCPAPPVAGPSVFLFPPKPKDT LMISRTPEVTCVVVDVSQEDPEVQFNWYVDGVEVHNAKTKPREEQFQSTYRVVSV LTVLHQDWLNGKEYKCKVSNKGLPSSIEKTISKAKGQPREPQVYTLPPSQEEMTK NQVSLTCLVKGFYPSDIAVEWESNGQPENNYKTTPPVLDSDGSFFLYSRLTVDKS RWQEGNVFSCSVMHEALHNHYTQKSLSLSLGKMFWVLVVVGGVLACYSLLVTVAF IIFWVRSKRSRLLHSDYMNMTPRRPGPTRKHYQPYAPPRDFAAYRSRVKFSRSAD APAYQQGQNQLYNELNLGRREEYDVLDKRRGRDPEMGGKPRRKNPQEGLYNELQK DKMAEAYSEIGMKGERRRGKGHDGLYQGLSTATKDTYDALHMQALPPR | anti-BCMA CAR |
| 162 | EVQLVESGGGLVQPGGSLRLSCAVSGFALSNHGMSWVRRAPGKGLEWVSGIVYSG STYYAASVKGRFTISRDNSRNTLYLQMNSLRPEDTAIYYCSAHGGESDVWGQGTT VTVSSASGGGGSGGGGRASGGGGSDIQLTQSPSSLSASVGDRVTITCRASQSISSYL NWYQQKPGKAPKLLIYAASSLQSGVPSRFSGSGSGTDFTLTISSLQPEDFATYYC QQSYSTPYTFGQGTKVEIKTTTPAPRPPTPAPTIASQPLSLRPEACRPAAGGAVH TRGLDFACDIYIWAPLAGTCGVLLLSLVITLYCKRGRKKLLYIFKQPFMRPVQTT QEEDGCSCRFPEEEEGGCELRVKFSRSADAPAYKQGQNQLYNELNLGRREEYDVL DKRRGRDPEMGGKPRRKNPQEGLYNELQKDKMAEAYSEIGMKGERRRGKGHDGLY QGLSTATKDTYDALHMQALPPR | anti-BCMA CAR |
| 163 | QVQLVESGGGLVQPGRSLRLSCAASGFTFSNYAMSWVRQAPGKGLGWVSGISRSG ENTYYADSVKGRFTISRDNSKNTLYLQMNSLRDEDTAVYYCARSPAHYYGGMDVW GQGTTVTVSSASGGGGSGGGRASGGGGSDIVLTQSPGTLSLSPGERATLSCRASQS ISSSFLAWYQQKPGQAPRLLIYGASRRATGIPDRFSGSGSGTDFTLTISRLEPED SAVYYCQQYHSSPSWTFGQGTKLEIKTTTPAPRPPTPAPTIASQPLSLRPEACRP AAGGAVHTRGLDFACDIYIWAPLAGTCGVLLLSLVITLYCKRGRKKLLYIFKQPF MRPVQTTQEEDGCSCRFPEEEEGGCELRVKFSRSADAPAYKQGQNQLYNELNLGR REEYDVLDKRRGRDPEMGGKPRRKNPQEGLYNELQKDKMAEAYSEIGMKGERRRG KGHDGLYQGLSTATKDTYDALHMQALPPR | anti-BCMA CAR |
| 164 | QVQLVESGGGLVQPGGSLRLSCAVSGFALSNHGMSWVRRAPGKGLEWVSGIVYSG STYYAASVKGRFTISRDNSRNTLYLQMNSLRPEDTAIYYCSAHGGESDVWGQGTT VTVSSASGGGGSGGRASGGGGSDIRLTQSPSPLSASVGDRVTITCQASEDINKFL NWYHQTPGKAPKLLIYDASTLQTGVPSRFSGSGSGTDFTLTINSLQPEDIGTYYC QQYESLPLTFGGGTKVEIKTTTPAPRPPTPAPTIASQPLSLRPEACRPAAGGAVH TRGLDFACDIYIWAPLAGTCGVLLLSLVITLYCKRGRKKLLYIFKQPFMRPVQTT QEEDGCSCRFPEEEEGGCELRVKFSRSADAPAYKQGQNQLYNELNLGRREEYDVL DKRRGRDPEMGGKPRRKNPQEGLYNELQKDKMAEAYSEIGMKGERRRGKGHDGLY QGLSTATKDTYDALHMQALPPR | anti-BCMA CAR |
| 165 | EVQLVESGGGLVQPGGSLRLSCAVSGFALSNHGMSWVRRAPGKGLEWVSGIVYSG STYYAASVKGRFTISRDNSRNTLYLQMNSLRPEDTAIYYCSAHGGESDVWGQGTT VTVSSASGGGGSGGGGSEIVLTQSPGTLSLSPGERATLSCRASQSIGSSS LAWYQQKPGQAPRLLMYGASSRASGIPDRFSGSGSGTDFTLTISRLEPEDFAVYY CQQYAGSPPFTFGQGTKVEIKTTTPAPRPPTPAPTIASQPLSLRPEACRPAAGGA VHTRGLDFACDIYIWAPLAGTCGVLLLSLVITLYCKRGRKKLLYIFKQPFMRPVQ TTQEEDGCSCRFPEEEEGGCELRVKFSRSADAPAYKQGQNQLYNELNLGRREEYD VLDKRRGRDPEMGGKPRRKNPQEGLYNELQKDKMAEAYSEIGMKGERRRGKGHDG LYQGLSTATKDTYDALHMQALPPR | anti-BCMA CAR |
| 166 | QIQLVQSGPDLKKPGETVKLSCKASGYTFTNFGMNWVKQAPGKGFKWMAWINTYT GESYFADDFKGRFAFSVETSATTAYLQINNLKTEDTATYFCARGEIYYGYDGGFA YWGQGTLVTVSAGGGGSGGGGSGGGGSDVVMTQSHRFMSTSVGDRVSITCRASQD VNTAVSWYQQKPGQSPKLLIFSASYRYTGVPDRFTGSGSGADFTLTISSVQAEDL AVYYCQQHYSTPWTFGGGTKLDIKTTTPAPRPPTPAPTIASQPLSLRPEACRPAA GGAVHTRGLDFACDIYIWAPLAGTCGVLLLSLVITLYCKRGRKKLLYIFKQPFMR PVQTTQEEDGCSCRFPEEEEGGCELRVKFSRSADAPAYKQGQNQLYNELNLGRRE EYDVLDKRRGRDPEMGGKPRRKNPQEGLYNELQKDKMAEAYSEIGMKGERRRGKG HDGLYQGLSTATKDTYDALHMQALPPR | anti-BCMA CAR |
| 167 | QIQLVQSGPELKKPGETVKISCKASGYTFTDYSINWVKRAPGKGLKWMGWINTET REPAYAYDFRGRFAFSLETSASTAYLQINNLKYEDTATYFCALDYSYAMDYWGQG TSVTVSSGGGGSGGGGSGGGGSQIQLVQSGPELKKPGETVKISCKASGYTFTDYS INWVKRAPGKGLKWMGWINTETREPAYAYDFRGRFAFSLETSASTAYLQINNLKY EDTATYFCALDYSYAMDYWGQGTSVTVSSTTTPAPRPPTPAPTIASQPLSLRPEA CRPAAGGAVHTRGLDFACDIYIWAPLAGTCGVLLLSLVITLYCKRGRKKLLYIFK QPFMRPVQTTQEEDGCSCRFPEEEEGGCELRVKFSRSADAPAYKQGQNQLYNELN LGRREEYDVLDKRRGRDPEMGGKPRRKNPQEGLYNELQKDKMAEAYSEIGMKGER RRGKGHDGLYQGLSTATKDTYDALHMQALPPR | anti-BCMA CAR |

| SEQ ID NO. | SEQUENCE | DESCRIPTION |
|---|---|---|
| 168 | QIQLVQSGPELKKPGETVKISCKASGYTFTDYSINWVKRAPGKGLKWMGWINTET REPAYAYDFRGRFAFSLETSASTAYLQINNLKYEDTATYFCALDYSYAMDYWGQG TSVTVSSGGGGSGGGGSGGGGSDIVLTQSPASLAMSLGKRATISCRASESVSVIG AHLIHWYQQKPGQPPKLLIYLASNLETGVPARFSGSGSGTDFTLTIDPVEEDDVA IYSCLQSRIFPRTFGGGTKLEIKTTTPAPRPPTPAPTIASQPLSLRPEACRPAAG GAVHTRGLDFACDIYIWAPLAGTCGVLLLSLVITLYCKRGRKKLLYIFKQPFMRP VQTTQEEDGCSCRFPEEEEGGCELRVKFSRSADAPAYKQGQNQLYNELNLGRREE YDVLDKRRGRDPEMGGKPRRKNPQEGLYNELQKDKMAEAYSEIGMKGERRRGKGH DGLYQGLSTATKDTYDALHMQALPPR | anti-BCMA CAR |
| 169 | QIQLVQSGPELKKPGETVKISCKASGYTFRHYSMNWVKQAPGKGLKWMGRINTES GVPIYADDFKGRFAFSVETSASTAYLVINNLKDEDTASYFCSNDYLYSLDFWGQG TALTVSSGGGGSGGGGSGGGGSDIVLTQSPPSLAMSLGKRATISCRASESVTILG SHLIYWYQQKPGQPPTLLIQLASNVQTGVPARFSGSGSRTDFTLTIDPVEEDDVA VYYCLQSRTIPRTFGGGTKLEIKTTTPAPRPPTPAPTIASQPLSLRPEACRPAAG GAVHTRGLDFACDIYIWAPLAGTCGVLLLSLVITLYCKRGRKKLLYIFKQPFMRP VQTTQEEDGCSCRFPEEEEGGCELRVKFSRSADAPAYKQGQNQLYNELNLGRREE YDVLDKRRGRDPEMGGKPRRKNPQEGLYNELQKDKMAEAYSEIGMKGERRRGKGH DGLYQGLSTATKDTYDALHMQALPPR | anti-BCMA CAR |
| 170 | QIQLVQSGPELKKPGETVKISCKASGYTFTHYSMNWVKQAPGKGLKWMGRINTET GEPLYADDFKGRFAFSLETSASTAYLVINNLKNEDTATFFCSNDYLYSCDYWGQG TTLTVSSGGGGSGGGGSGGGGSDIVLTQSPPSLAMSLGKRATISCRASESVTILG SHLIYWYQQKPGQPPTLLIQLASNVQTGVPARFSGSGSRTDFTLTIDPVEEDDVA VYYCLQSRTIPRTFGGGTKLEIKTTTPAPRPPTPAPTIASQPLSLRPEACRPAAG GAVHTRGLDFACDIYIWAPLAGTCGVLLLSLVITLYCKRGRKKLLYIFKQPFMRP VQTTQEEDGCSCRFPEEEEGGCELRVKFSRSADAPAYKQGQNQLYNELNLGRREE YDVLDKRRGRDPEMGGKPRRKNPQEGLYNELQKDKMAEAYSEIGMKGERRRGKGH DGLYQGLSTATKDTYDALHMQALPPR | anti-BCMA CAR |
| 171 | DIVLTQSPPSLAMSLGKRATISCRASESVTILGSHLIHWYQQKPGQPPTLLIQLA SNVQTGVPARFSGSGSRTDFTLTIDPVEEDDVAVYYCLQSRTIPRTFGGGTKLEI KGSTSGSGKPGSGEGSTKGQIQLVQSGPELKKPGETVKISCKASGYTFTDYSINW VKRAPGKGLKWMGWINTETREPAYAYDFRGRFAFSLETSASTAYLQINNLKYEDT ATYFCALDYSYAMDYWGQGTSVTVSSFVPVFLPAKPTTTPAPRPPTPAPTIASQP LSLRPEACRPAAGGAVHTRGLDFACDIYIWAPLAGTCGVLLLSLVITLYCNHRNR SKRSRLLHSDYMNMTPRRPGPTRKHYQPYAPPRDFAAYRSRVKFSRSADAPAYQQ GQNQLYNELNLGRREEYDVLDKRRGRDPEMGGKPRRKNPQEGLYNELQKDKMAEA YSEIGMKGERRRGKHDGLYQGLSTATKDTYDALHMQALPPR | anti-BCMA CAR |
| 172 | QVQINQSGAEVKKPGASVKVSCKASGYSFPDYYINWVRQAPGQGLEWMGWIYFAS GNSEYNQKFTGRVTMTRDTSINTAYMELSSLTSEDTAVYFCASLYDYDWYFDVWG QGTMVTVSSGGGGSGGGGSGGGGSDIVMTQTPLSLSVTPGQPASISCKSSQSLVH SNGNTYLHWYLQKPGQSPQLLIYKVSNRFSGVPDRFSGSGSGTDFTLKISRVEAE DVGIYYCSQSSIYPWTFGQGTKLEIKGLAVSTISSFFPPGYQIYIWAPLAGTCGV LLLSLVITLYCKRGRKKLLYIFKQPFMRPVQTTQEEDGCSCRFPEEEEGGCELRV KFSRSADAPAYQQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPR | anti-BCMA CAR |
| 173 | QVQLVQSGAEVKKPGASVKVSCKASGYSFPDYYINWVRQAPGQGLEWMGWIYFAS GNSEYNQKFTGRVTMTRDTSINTAYMELSSLTSEDTAVYFCASLYDYDWYFDVWG QGTMVTVSSGGGGSGGGGSGGGGSDIVMTQTPLSLSVTPGQPASISCKSSQSLVH SNGNTYLHWYLQKPGQSPQLLIYKVSNRFSGVPDRFSGSGSGTDFTLKISRVEAE DVGIYYCSQSSIYPWTFGQGTKLEIKTTTPAPRPPTPAPTIASQPLSLRPEACRP AAGGAVHTRGLDFACDIYIWAPLAGTCGVLLLSLVITLYCKRGRKKLLYIFKQPF MRPVQTTQEEDGCSCRFPEEEEGGCELRVKFSRSADAPAYQQGQNQLYNELNLGR REEYDVLDKRRGRDPEMGGKPRRKNPQEGLYNELQKDKMAEAYSEIGMKGERRRG KGHDGLYQGLSTATKDTYDALHMQALPPR | anti-BCMA CAR |
| 174 | QVQINQSGAEVKKPGASVKVSCKASGYSFPDYYINWVRQAPGQGLEWMGWIYFAS GNSEYNQKFTGRVTMTRDTSINTAYMELSSLTSEDTAVYFCASLYDYDWYFDVWG QGTMVTVSSGGGGSGGGGSGGGGSDIVMTQTPLSLSVTPGQPASISCKSSQSLVH SNGNTYLHWYLQKPGQSPQLLIYKVSNRFSGVPDRFSGSGSGTDFTLKISRVEAE DVGIYYCSQSSIYPWTFGQGTKLEIKEPKSPDKTHTCPPCPAPPVAGPSVFLFPP KPKDTLMIARTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFLYSKL TVDKSRWQQGNVFSCSVMHEALHNHYTQKSLSLSPGKIYIWAPLAGTCGVLLLSL VITLYCKRGRKKLLYIFKQPFMRPVQTTQEEDGCSCRFPEEEEGGCELRVKFSRS ADAPAYQQGQNQLYNELNLGRREEYDVLDKRRGRDPEMGGKPRRKNPQEGLYNEL QKDKMAEAYSEIGMKGERRRGKGHDGLYQGLSTATKDTYDALHMQALPPR | anti-BCMA CAR |

-continued

SEQUENCES

| SEQ ID NO. | SEQUENCE | DESCRIPTION |
|---|---|---|
| 175 | QVQLVQSGAEVKKPGASVKVSCKASGYSFPDYYINWVRQAPGQGLEWMGWIYFAS GNSEYNQKFTGRVTMTRDTSSSTAYMELSSLRSEDTAVYFCASLYDYDWYFDVWG QGTMVTVSSGGGGSGGGGSGGGGSDIVMTQTPLSLSVTPGEPASISCKSSQSLVH SNGNTYLHWYLQKPGQSPQLLIYKVSNRFSGVPDRFSGSGSGADFTLKISRVEAE DVGVYYCAETSHVPWTFGQGTKLEIKGLAVSTISSFFPPGYQIYIWAPLAGTCGV LLLSLVITLYCKRGRKKLLYIFKQPFMRPVQTTQEEDGCSCRFPEEEEGGCELRV KFSRSADAPAYQQGQNQLYNELNLGRREEYDVLDKRRGRDPEMGGKPRRKNPQEG LYNELQKDKMAEAYSEIGMKGERRRGKGHDGLYQGLSTATKDTYDALHMQALPPR | anti-BCMA CAR |
| 176 | QVQLVQSGAEVKKPGASVKVSCKASGYSFPDYYINWVRQAPGQGLEWMGWIYFAS GNSEYNQKFTGRVTMTRDTSSSTAYMELSSLRSEDTAVYFCASLYDYDWYFDVWG QGTMVTVSSGGGGSGGGGSGGGGSDIVMTQTPLSLSVTPGEPASISCKSSQSLVH SNGNTYLHWYLQKPGQSPQLLIYKVSNRFSGVPDRFSGSGSGADFTLKISRVEAE DVGVYYCAETSHVPWTFGQGTKLEIKTTTPAPRPPTPAPTIASQPLSLRPEACRP AAGGAVHTRGLDFACDIYIWAPLAGTCGVLLLSLVITLYCKRGRKKLLYIFKQPF MRPVQTTQEEDGCSCRFPEEEEGGCELRVKFSRSADAPAYQQGQNQLYNELNLGR REEYDVLDKRRGRDPEMGGKPRRKNPQEGLYNELQKDKMAEAYSEIGMKGERRRG KGHDGLYQGLSTATKDTYDALHMQALPPR | anti-BCMA CAR |
| 177 | QVQLVQSGAEVKKPGASVKVSCKASGYSFPDYYINWVRQAPGQGLEWMGWIYFAS GNSEYNQKFTGRVTMTRDTSSSTAYMELSSLRSEDTAVYFCASLYDYDWYFDVWG QGTMVTVSSGGGGSGGGGSGGGGSDIVMTQTPLSLSVTPGEPASISCKSSQSLVH SNGNTYLHWYLQKPGQSPQLLIYKVSNRFSGVPDRFSGSGSGADFTLKISRVEAE DVGVYYCAETSHVPWTFGQGTKLEIKEPKSPDKTHTCPPCPAPPVAGPSVFLFPP KPKDTLMIARTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSR DELTKNQVSLTCLVKGFYPSDIAVEWESNGQPENNYKTTPPVLDSDGSFFLYSKL TVDKSRWQQGNVFSCSVMHEALHNHYTQKSLSLSPGKIYIWAPLAGTCGVLLLSL VITLYCKRGRKKLLYIFKQPFMRPVQTTQEEDGCSCRFPEEEEGGCELRVKFSRS ADAPAYQQGQNQLYNELNLGRREEYDVLDKRRGRDPEMGGKPRRKNPQEGLYNEL QKDKMAEAYSEIGMKGERRRGKGHDGLYQGLSTATKDTYDALHMQALPPR | anti-BCMA CAR |
| 178 | IYIWAPLAGTCGVLLLSLVITLYCNHRN | CD8a TM |
| 179 | IYIWAPLAGTCGVLLLSLVIT | CD8a TM |
| 180 | RAAA | linking peptide |
| 181 | EVQLVESGGGLVKPGGSLRLSCAASGFTFSDYYMSWIRQAPGKGLEWVSYISSSG STIYYADSVKGRFTISRDNAKNSLYLQMNSLRAEDTAVYYCAKVDGDYTEDWGQ GTLVTVSS | Variable heavy (VH) Anti-BCMA |
| 182 | QSALTQPASVSGSPGQSITISCTGSSSDVGKYNLVSWYQQPPGKAPKLIIYDVNK RPSGVSNRFSGSKSGNTATLTISGLQGDDEADYYCSSYGGSRSYVFGTGTKVTVL | Variable light (VL) Anti-BCMA |
| 183 | EVQLVQSGGGLVQPGRSLRLSCTASGFTGDYAMSWFRQAPGKGLEWVGFIRSKA YGGTTEYAASVKGRFTISRDDSKSIAYLQMNSLKTEDTAVYYCAAWSAPTDYWGQ GTLVTVSS | Variable heavy (VH) Anti-BCMA |
| 184 | DIQMTQSPAFLSASVGDRVTVTCRASQGISNYLAWYQQKPGNAPRLLIYSASTLQ SGVPSRFRGTGYGTEFSLTIDSLQPEDFATYYCQQSYTSRQTFGPGTRLDIK | Variable light (VL) Anti-BCMA |
| 185 | EVQLVESGGGLVKPGGSLRLSCAASGFTFSDYYMSWIRQAPGKGLEWVSYISSSG STIYYADSVKGRFTISRDNAKNSLYLQMNSLRAEDTAVYYCAKVDGPPSFDIWGQ GTMVTVSS | Variable heavy (VH) Anti-BCMA |
| 186 | SYVLTQPPSVSVAPGQTARITCGANNIGSKSVHWYQQKPGQAPMLVVYDDDDRPS GIPERFSGSNSGNTATLTISGVEAGDEADYFCHLWDRSRDHYVFGTGTKLTVL | Variable light (VL) Anti-BCMA |
| 187 | EVQLVQSGAEVKKPGSSVKVSCKASGGTFSSYAISWVRQAPGQGLEWMGRIIPIL GIANYAQKFQGRVTMTEDTSTDTAYMELSSLRSEDTAVYYCARSGYSKSIVSYMD YWGQGTLVTVSS | Variable heavy (VH) Anti-BCMA |
| 188 | LPVLTQPPSTSGTPGQRVTVSCSGSSSNIGSNVVFWYQQLPGTAPKLVIYRNNQR PSGVPDRFSVSKSGTSASLAISGLRSEDEADYYCAAWDDSLSGYVFGTGTKVTVL G | Variable light (VL) Anti-BCMA |
| 189 | ASGGGGSGGRASGGGGS | Linker |

What is claimed:

1. A method of treatment, comprising:
   (a) administering a T cell therapy to a subject having a cancer, said T cell therapy comprising a dose of T cells expressing a recombinant antigen receptor that binds to a target antigen; and
   (b) administering to the subject an immunomodulatory compound, wherein the compound is (S) -3-[4-(4-morpholin-4-ylmethyl-benzyloxy)-1-oxo-1,3-dihydro-isoindol-2-yl]-piperidine-2,6-dione or a pharmaceutically acceptable salt, solvate, hydrate, co-crystal, clathrate, or polymorph thereof.

2. The method of claim 1, wherein the immunomodulatory compound is administered at a dose of from or from about 0.1 mg to 5 mg per day.

3. The method of claim 1, wherein the administration of the compound is initiated subsequently to initiation of administration of the T cell therapy.

4. The method of claim 3, wherein the administration of the compound is initiated within or within about 90 days after initiation of administration of the T cell therapy.

5. The method of claim 1, wherein the administration of the compound is initiated prior to administration of the T cell therapy.

6. The method of claim 5, wherein the compound is administered from or from about 0 to 30 days prior to initiation of the T cell therapy.

7. The method of claim 1, wherein the cancer is a B cell malignancy.

8. The method of claim 1, wherein the subject is or has been identified as having an Eastern Cooperative Oncology Group Performance Status (ECOG) status of less than or equal to 1.

9. The method of claim 1, wherein the target antigen is CD20, CD19, CD22, ROR1, CD45, CD21, CD5, CD33, Igkappa, Iglambda, CD79a, CD79b, or CD30.

10. The method of claim 1, wherein the cancer is a lymphoma.

11. The method of claim 1, wherein the target antigen is BCMA, G protein-coupled receptor class C group 5 member D (GPRC5D), CD38 (cyclic ADP ribose hydrolase), CD138 (syndecan-1, syndecan, SYN-1), CS-1 (CS1, CD2 subset 1, CRACC, SLAMF7, CD319, and 19A24), BAFF-R, TACI, or FcRH5.

12. The method of claim 1, wherein the cancer is a multiple myeloma.

13. The method of claim 1, wherein the administration of the compound continues for a period that is greater than one month.

14. The method of claim 1, wherein at the time of the initiation of the administration of the compound, the subject does not exhibit a severe toxicity following the administration of the T cell therapy.

15. The method of claim 1, wherein the compound is a pharmaceutically acceptable salt of(S)-3-[4-(4-morpholin-4-ylmethyl-benzyloxy)-1-oxo-1,3-dihydro-isoindol-2-yl]-piperidine-2,6-dione.

16. The method of claim 1, wherein the compound is (S)-3-[4-(4-morpholin-4-ylmethyl-benzyloxy)-1-oxo-1,3-dihydro-isoindol-2-yl]-piperidine-2,6-dione.

17. The method of claim 1, wherein the compound is administered orally.

18. The method of claim 1, wherein the administration of the compound comprises administration at an amount, frequency, and/or duration effective to:
(a) effect an increase in antigen-specific or antigen receptor-driven activity of naïve or non-exhausted T cells in the subject following exposure of the T cells to antigen or to an antigen receptor-specific agent as compared to the absence of said administration of said compound; or
(b) prevent, inhibit, or delay the onset of an exhaustion phenotype in naïve or non-exhausted T cells in the subject following exposure of the T cells to antigen or to an antigen receptor-specific agent, as compared to the absence of said administration of said compound; or
(c) reverse an exhaustion phenotype in exhausted T cells in the subject, as compared to the absence of said administration of said subject.

19. The method of claim 1, wherein the recombinant antigen receptor is a chimeric antigen receptor that specifically binds the target antigen.

20. The method of claim 1, wherein the dose of genetically engineered T cells comprises from or from about 1×105 to 5×108 total CAR-expressing T cells, inclusive.

21. The method of claim 1, wherein the dose of cells is administered parenterally.

22. The method of claim 1, wherein the T cells are primary T cells obtained from a subject.

23. The method of claim 1, wherein the T cells are autologous to the subject.

24. The method of claim 1, wherein the T cells are allogeneic to the subject.

25. The method of claim 1, further comprising, immediately prior to the administration of the T cell therapy, administering a lymphodepleting therapy to the subject.

26. A kit comprising:
(a) a T cell therapy comprising a dose of T cells expressing a recombinant antigen receptor that binds to a target antigen; and
(b) an immunomodulatory compound selected from the group consisting of: thalidomide analogs; thalidomide derivatives; compounds that interact with and/or bind to cereblon (CRBN) and/or one or more members of the CRBN E3 ubiquitin-ligase complex; inhibitors of Ikaros (IKZF1); inhibitors of Aiolos (IKZF3); and compounds that enhance or promote ubiquitination, depletion, and/or degradation of Ikaros (IKZF1) and/or Aiolos (IKZF3); and
(c) instructions for administering the compound and/or the T cell therapy according to the methods of claim 1.

27. The method of claim 1, wherein the immunomodulatory compound is administered in an effective amount of from about 0.1 mg to about 1 mg.

28. The method of claim 1, wherein the immunomodulatory compound is administered in an effective amount of about 0.4 mg, about 0.5 mg, about 0.7 mg, about 0.8 mg, and/or about 1.0 mg.

29. The method of claim 1, wherein the immunomodulatory compound is administered daily for a period of time in a cycling regimen.

30. The method of claim 1, wherein the immunomodulatory compound is administered once daily for 21 days over a 28-day treatment cycle.

31. The method of claim 1, wherein the administration of the immunomodulatory compound continues for a period that extends for at or greater than three months, four months, five months, or six months.

32. The method of claim 1, wherein the administration of the compound is initiated concurrently with initiation of administration of the T cell therapy.

33. The method of claim 25, wherein the lymphodepleting therapy comprises:
administration of cyclophosphamide at about 200-400 mg/m$^2$, inclusive, and/or fludarabine at about 20-40 mg/m$^2$, daily for 2-4 days;
administration of cyclophosphamide at about 500 mg/m$^2$; or
administration of bendamustine.

* * * * *